(12) United States Patent
June et al.

(10) Patent No.: US 11,161,907 B2
(45) Date of Patent: Nov. 2, 2021

(54) CAR-EXPRESSING CELLS AGAINST MULTIPLE TUMOR ANTIGENS AND USES THEREOF

(71) Applicants: Novartis AG, Basel (CH); The Trustees of the University of Pennsylvania, Philadelphia, PA (US)

(72) Inventors: Carl H. June, Merion Station, PA (US); Daniel J. Powell, Jr., Bala Cynwyd, PA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 55 days.

(21) Appl. No.: 15/548,202

(22) PCT Filed: Feb. 1, 2016

(86) PCT No.: PCT/US2016/015978
§ 371 (c)(1),
(2) Date: Aug. 2, 2017

(87) PCT Pub. No.: WO2016/126608
PCT Pub. Date: Aug. 11, 2016

(65) Prior Publication Data
US 2018/0044424 A1 Feb. 15, 2018

Related U.S. Application Data

(60) Provisional application No. 62/111,094, filed on Feb. 2, 2015.

(51) Int. Cl.
| | | |
|---|---|---|
| C07K 16/28 | (2006.01) | |
| C07K 16/32 | (2006.01) | |
| C07K 14/725 | (2006.01) | |
| A61K 39/395 | (2006.01) | |
| A61K 35/17 | (2015.01) | |
| C07K 14/705 | (2006.01) | |
| C07K 16/30 | (2006.01) | |
| C07K 14/54 | (2006.01) | |
| C07K 14/55 | (2006.01) | |
| A61K 39/00 | (2006.01) | |
| A61K 45/06 | (2006.01) | |
| C12N 15/113 | (2010.01) | |
| A61K 38/00 | (2006.01) | |

(52) U.S. Cl.
CPC .......... *C07K 16/2863* (2013.01); *A61K 35/17* (2013.01); *A61K 39/39558* (2013.01); *A61K 45/06* (2013.01); *C07K 14/54* (2013.01); *C07K 14/5418* (2013.01); *C07K 14/5443* (2013.01); *C07K 14/55* (2013.01); *C07K 14/7051* (2013.01); *C07K 14/70521* (2013.01); *C07K 14/70578* (2013.01); *C07K 16/28* (2013.01); *C07K 16/2803* (2013.01); *C07K 16/30* (2013.01); *C07K 16/32* (2013.01); *C12N 15/113* (2013.01); *A61K 38/00* (2013.01); *A61K 2039/505* (2013.01); *A61K 2039/507* (2013.01); *C07K 2317/22* (2013.01); *C07K 2317/31* (2013.01); *C07K 2317/55* (2013.01); *C07K 2317/565* (2013.01); *C07K 2317/569* (2013.01); *C07K 2317/622* (2013.01); *C07K 2317/76* (2013.01); *C07K 2317/92* (2013.01); *C07K 2319/00* (2013.01); *C07K 2319/02* (2013.01); *C07K 2319/03* (2013.01); *C12N 2310/14* (2013.01); *C12N 2310/531* (2013.01)

(58) Field of Classification Search
CPC ............ C07K 2319/00; C07K 2319/01; C07K 2319/03; C07K 14/7051
See application file for complete search history.

(56) References Cited

U.S. PATENT DOCUMENTS

| | | |
|---|---|---|
| 5,359,046 A | 10/1994 | Capon et al. |
| 5,686,281 A | 11/1997 | Roberts |
| 5,712,149 A | 1/1998 | Roberts |
| 5,874,240 A | 2/1999 | Ni et al. |
| 5,906,936 A | 5/1999 | Eshhar et al. |
| 6,103,521 A | 8/2000 | Capon et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |

(Continued)

FOREIGN PATENT DOCUMENTS

| | | |
|---|---|---|
| EP | 0574512 A1 | 12/1993 |
| EP | 0871495 A1 | 10/1998 |

(Continued)

OTHER PUBLICATIONS

Rudikoff et al. (PNAS USA, 1982, 79: 1979-1983) (Year: 1982).*
Coleman et al. (Research in Immunology, 1994; 145(1): 33-36) (Year: 1994).*
Ibragimova and Wade (Biophysical Journal, Oct. 1999, vol. 77, pp. 2191-2198) (Year: 1999).*
Prazma and Tedder (Immunology Letters 2008, 115: 1-8) (Year: 2008).*
Hornbach et al. (Methods Mol Biol. 2003, 207:365-81) (Year: 2003).*
Lanitis et al. (Cancer Immunol. Res. Apr. 7, 2013 1(1): 45-53) (Year: 2013).*

(Continued)

*Primary Examiner* — Peter J Reddig
(74) *Attorney, Agent, or Firm* — Lando & Anastasi, LLP

(57) ABSTRACT

The invention provides compositions and methods for treating cancer by using immune effector cells (e.g., T cells, NK cells) engineered to conditionally express an agent which enhances the immune effector response of an immune effector cell that expresses a Chimeric Antigen Receptor (CAR). The conditional agents described herein include agents that target a cancer associated antigen, e.g., a CAR, agents that inhibit one or more checkpoint inhibitors of the immune response, and a cytokine.

35 Claims, 62 Drawing Sheets

Specification includes a Sequence Listing.

(56) References Cited

U.S. PATENT DOCUMENTS

| | | |
|---|---|---|
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,655,461 B2 | 2/2010 | Finn et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 10,117,896 B2 * | 11/2018 | Powell, Jr. ............. A61K 35/17 |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0257994 A1 | 10/2009 | Jensen |
| 2011/0052554 A1 | 3/2011 | Zakrzewski et al. |
| 2012/0148552 A1 | 6/2012 | Jensen |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370045 A1 | 12/2014 | June et al. |
| 2015/0017141 A1 | 1/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0073423 A1 * | 3/2017 | Juillerat ................. C07K 16/30 |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |
| 2019/0388471 A1 | 12/2019 | June et al. |
| 2019/0389928 A1 | 12/2019 | Posey et al. |
| 2020/0048359 A1 | 2/2020 | Albelda et al. |
| 2020/0055948 A1 | 2/2020 | Daley et al. |
| 2020/0061113 A1 | 2/2020 | Kassim et al. |
| 2020/0085869 A1 | 3/2020 | Schuster et al. |
| 2020/0087376 A1 | 3/2020 | Fraietta et al. |

FOREIGN PATENT DOCUMENTS

| | | |
|---|---|---|
| EP | 1226244 A2 | 7/2002 |
| WO | 1992015322 A1 | 9/1992 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |
| WO | 9818809 A1 | 5/1998 |
| WO | 9900494 A2 | 1/1999 |
| WO | 9957268 A1 | 11/1999 |
| WO | 0014257 A1 | 3/2000 |
| WO | 2002033101 A1 | 4/2002 |
| WO | 02077029 A2 | 10/2002 |
| WO | 02088334 A1 | 11/2002 |
| WO | 2003057171 A2 | 7/2003 |
| WO | 2005019429 A2 | 3/2005 |
| WO | 2005044996 A2 | 5/2005 |
| WO | 2005/118788 A2 | 12/2005 |
| WO | 2006060878 A1 | 6/2006 |
| WO | 2008045437 A2 | 4/2008 |
| WO | 2010085660 A2 | 7/2010 |
| WO | 2011059836 A2 | 5/2011 |
| WO | 2011097477 A1 | 8/2011 |

(56) References Cited

FOREIGN PATENT DOCUMENTS

| | | | |
|---|---|---|---|
| WO | 2012058460 A2 | 5/2012 |
| WO | 2012079000 A1 | 6/2012 |
| WO | 2012082841 A2 | 6/2012 |
| WO | 2012/099973 A2 | 7/2012 |
| WO | 2012127464 A2 | 9/2012 |
| WO | 2012129514 A1 | 9/2012 |
| WO | 2012135854 A2 | 10/2012 |
| WO | 2012138858 A1 | 10/2012 |
| WO | 2013019615 A2 | 2/2013 |
| WO | 2013033626 A2 | 3/2013 |
| WO | 2013040371 A2 | 3/2013 |
| WO | 2013040557 A2 | 3/2013 |
| WO | 2013059593 A1 | 4/2013 |
| WO | 2013/126712 A1 | 8/2013 |
| WO | 2013126729 A1 | 8/2013 |
| WO | 2013126733 A1 | 8/2013 |
| WO | 2014/011984 A1 | 1/2014 |
| WO | 2014/011987 A1 | 1/2014 |
| WO | 2014/011993 A2 | 1/2014 |
| WO | 2014/012001 A2 | 1/2014 |
| WO | 2014011988 A2 | 1/2014 |
| WO | 2014011996 A1 | 1/2014 |
| WO | 2014031687 A1 | 2/2014 |
| WO | 2014039513 A2 | 3/2014 |
| WO | 2014/055442 A2 | 4/2014 |
| WO | 2014/055771 A1 | 4/2014 |
| WO | 2014055657 A1 | 4/2014 |
| WO | 2014130635 A1 | 8/2014 |
| WO | 2014130657 A1 | 8/2014 |
| WO | 2014/145252 A2 | 9/2014 |
| WO | 2015090229 A1 | 6/2015 |
| WO | 2015090230 A1 | 6/2015 |
| WO | 2015112626 A1 | 7/2015 |
| WO | 2015/142661 A1 | 9/2015 |
| WO | 2015142675 A2 | 9/2015 |
| WO | 2015157252 A1 | 10/2015 |
| WO | 2016014501 A1 | 1/2016 |
| WO | 2016014530 A1 | 1/2016 |
| WO | 2016014535 A1 | 1/2016 |
| WO | 2016014553 A1 | 1/2016 |
| WO | 2016014565 A2 | 1/2016 |
| WO | 2016014576 A1 | 1/2016 |
| WO | 2016019300 A1 | 2/2016 |
| WO | 2016025880 A1 | 2/2016 |
| WO | 2016028896 A1 | 2/2016 |
| WO | 2016044605 A1 | 3/2016 |
| WO | 2016/126608 A1 | 8/2016 |

OTHER PUBLICATIONS

Baeksgaard & Sorensen, "Acute tumor lysis syndrome in solid tumors—a case report and review of the literature" Cancer Chemotherapy Pharmacology (2003) vol. 51 pp. 187-192.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Acad Sci USA (2009) vol. 106 pp. 3360-3365.
Chmielewski et al. "IL-12 Release by Engineered T Cells Expressing Chimeric Antigen Receptors Can Effectively Muster an Antigen-Independent Macrophage Response on Tumor Cells That Have Shut Down Tumor Antigen Expression" Cancer Research (2011) vol. 71, No. 17, pp. 5697-5706.
Chmielewski et al. "Of CARs and TRUCKs: Chimeric antigen receptor (CAR) T cells engineered with an inducible cytokine to modulate the tumor stroma" Imunological Reviews (2014) vol. 257, pp. 83-90.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.

(56) References Cited

OTHER PUBLICATIONS

Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International Application No. PCT/US2016/015978 dated May 19, 2016.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH), Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
MacAllan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody—and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.

(56) References Cited

OTHER PUBLICATIONS

Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Jang et al., "Human 4-1BB (CD137) Signals Are Mediated by TRAF2 and Activate Nuclear Factor-KB" Biochemical and Biophysical Research Communications (1998) vol. 242 pp. 613-620.
Irving et al., "Functional Characterization of a Signal Transducing Motif Present in the T Cell Antigen Receptor Chain" The Rockefeller University Press (1993) vol. 177 pp. 1093-1103.
Abate-Daga et al. "Development of a T Cell Receptor Targeting an HLAA* 0201 Restricted Epitope from the Cancer-Testis Antigen SSX2 for Adoptive Immunotherapy of Cancer" PLOS One (2014) vol. 9, No. 3, e93321, pp. 1-12.
Aggen et al. "Single-Chain V?V? T Cell Receptors Function Without Mispairing With Endogenous TCR Chains" Gene Therapy (2012) vol. 19, No. 4, pp. 365-374.
Cornish-Bowden "Nomenclature for incompletely specified bases in nucleic acid sequences: recommendations 1984" Nucleic Acids Research (1985) vol. 13, No. 9, pp. 3021-3030.
Gattinoni et al. "Adoptive immunotherapy for cancer: building on success" Nat Rev Immunol (2006) vol. 6, No. 5, pp. 383-393.
Kershaw et al. "Gene-engineered T cells for cancer therapy" Nature Reviews Cancer (2013) vol. 13, pp. 525-541.
Lanitis et al. "A Human ErbB2-Specific T-Cell Receptor Confers Potent Antitumor Effector Functions in Genetically Engineered Primary Cytotoxic Lymphocytes" Human Gene Therapy (2014) vol. 25 pp. 730-739.
Willemsen et al. "Grafting primary human T lymphocytes with cancerspecific chimeric single chain and two chain TCR" Gene Therapy (2000) vol. 7, pp. 1369-1377.
Zhang et al. "Transgenic TCR expression: comparison of single chain with full-length receptor constructs for T-cell function" Cancer Gene Therapy (2004) vol. 11, pp. 487-496.

\* cited by examiner

SEQUENCE LISTING

```
<160> NUMBER OF SEQ ID NOS: 425

<210> SEQ ID NO 1
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt ttcccgaggg tgggggagaa ccgtatataa     180
gtgcagtagt cgccgtgaac gttcttttc gcaacgggtt tgccgccaga acacaggtaa      240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagcccttc gcctcgtgct tgagttgagg      420
cctggcctgg gcgctggggc cgccgcgtgc gaatctggtg gcaccttcgc gcctgtctcg     480
ctgctttcga taagtctcta gccatttaaa atttttgatg acctgctgcg acgctttttt     540
tctggcaaga tagtcttgta aatgcgggcc aagatctgca cactggtatt tcggttttg     600 gggccgcggg cggcgacggg gcccgtgcgt cccagcgcac atgttcggcg aggcggggcc     660
tgcgagcgcg gccaccgaga atcggacggg ggtagtctca agctggccgg cctgctctgg     720
tgcctggcct cgcgccgccg tgtatcgccc cgccctgggc ggcaaggctg gcccggtcgg     780
caccagttgc gtgagcggaa agatggccgc ttcccggccc tgctgcaggg agctcaaaat     840
ggaggacgcg gcgctcggga gagcgggcgg gtgagtcacc cacacaaagg aaaagggcct     900
ttccgtcctc agccgtcgct tcatgtgact ccacggagta ccgggcgccg tccaggcacc     960
tcgattagtt ctcgagcttt tggagtacgt cgtctttagg ttgggggag gggttttatg     1020 cgatggagtt tccccacact gagtgggtgg agactgaagt taggccagct tggcacttga    1080
tgtaattctc cttggaattt gccctttttg agtttggatc ttggttcatt ctcaagcctc    1140
agacagtggt tcaaagtttt tttcttccat ttcaggtgtc gtga                     1184

<210> SEQ ID NO 2
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Met Ala Leu Pro Val Thr Ala Leu Leu Leu Pro Leu Ala Leu Leu Leu
1               5                   10                  15

His Ala Ala Arg Pro
            20
```

<210> SEQ ID NO 3
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
atggccctgc ctgtgacagc cctgctgctg cctctggctc tgctgctgca tgccgctaga    60
ccc                                                                  63

<210> SEQ ID NO 4
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
accacgacgc cagcgccgcg accaccaaca ccggcgccca ccatcgcgtc gcagcccctg    60
tccctgcgcc agaggcgtg ccggccagcg gcggggggcg cagtgcacac gaggggggctg   120 gacttcgcct gtgat                                                    135

<210> SEQ ID NO 6
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

| Glu | Val | His | Asn | Ala | Lys | Thr | Lys | Pro | Arg | Glu | Gln | Phe | Asn | Ser |
| --- | --- | --- | --- | --- | --- | --- | --- | --- | --- | --- | --- | --- | --- | --- |
| 65 | | | | 70 | | | | | 75 | | | | | 80 |

| Thr | Tyr | Arg | Val | Val | Ser | Val | Leu | Thr | Val | Leu | His | Gln | Asp | Trp | Leu |
| --- | --- | --- | --- | --- | --- | --- | --- | --- | --- | --- | --- | --- | --- | --- | --- |
| | | | | 85 | | | | | 90 | | | | | 95 | |

| Asn | Gly | Lys | Glu | Tyr | Lys | Cys | Lys | Val | Ser | Asn | Lys | Gly | Leu | Pro | Ser |
| --- | --- | --- | --- | --- | --- | --- | --- | --- | --- | --- | --- | --- | --- | --- | --- |
| | | | 100 | | | | | 105 | | | | | 110 | | |

| Ser | Ile | Glu | Lys | Thr | Ile | Ser | Lys | Ala | Lys | Gly | Gln | Pro | Arg | Glu | Pro |
| --- | --- | --- | --- | --- | --- | --- | --- | --- | --- | --- | --- | --- | --- | --- | --- |
| | | | 115 | | | | | 120 | | | | | 125 | | |

| Gln | Val | Tyr | Thr | Leu | Pro | Pro | Ser | Gln | Glu | Glu | Met | Thr | Lys | Asn | Gln |
| --- | --- | --- | --- | --- | --- | --- | --- | --- | --- | --- | --- | --- | --- | --- | --- |
| 130 | | | | | 135 | | | | | 140 | | | | | |

| Val | Ser | Leu | Thr | Cys | Leu | Val | Lys | Gly | Phe | Tyr | Pro | Ser | Asp | Ile | Ala |
| --- | --- | --- | --- | --- | --- | --- | --- | --- | --- | --- | --- | --- | --- | --- | --- |
| 145 | | | | | 150 | | | | | 155 | | | | | 160 |

| Val | Glu | Trp | Glu | Ser | Asn | Gly | Gln | Pro | Glu | Asn | Asn | Tyr | Lys | Thr | Thr |
| --- | --- | --- | --- | --- | --- | --- | --- | --- | --- | --- | --- | --- | --- | --- | --- |
| | | | | 165 | | | | | 170 | | | | | 175 | |

| Pro | Pro | Val | Leu | Asp | Ser | Asp | Gly | Ser | Phe | Phe | Leu | Tyr | Ser | Arg | Leu |
| --- | --- | --- | --- | --- | --- | --- | --- | --- | --- | --- | --- | --- | --- | --- | --- |
| | | | 180 | | | | | 185 | | | | | 190 | | |

| Thr | Val | Asp | Lys | Ser | Arg | Trp | Gln | Glu | Gly | Asn | Val | Phe | Ser | Cys | Ser |
| --- | --- | --- | --- | --- | --- | --- | --- | --- | --- | --- | --- | --- | --- | --- | --- |
| | | | 195 | | | | | 200 | | | | | 205 | | |

| Val | Met | His | Glu | Ala | Leu | His | Asn | His | Tyr | Thr | Gln | Lys | Ser | Leu | Ser |
| --- | --- | --- | --- | --- | --- | --- | --- | --- | --- | --- | --- | --- | --- | --- | --- |
| 210 | | | | | 215 | | | | | 220 | | | | | |

| Leu | Ser | Leu | Gly | Lys | Met |
| --- | --- | --- | --- | --- | --- |
| 225 | | | | 230 | |

<210> SEQ ID NO 7
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic polynucleotide"

<400> SEQUENCE: 7

```
gagagcaagt acggccctcc ctgccccect tgccctgccc ccgagttcct gggcggaccc    60
agcgtgttcc tgttcccccc caagcccaag acaccctga tgatcagccg accccccgag   120
gtgacctgtg tggtggtgga cgtgtcccag gaggaccccg aggtccagtt caactggtac   180
gtggacggcg tggaggtgca caacgccaag accaagcccc gggaggagca gttcaatagc   240
acctaccggg tggtgtccgt gctgaccgtg ctgcaccagg actggctgaa cggcaaggaa   300
tacaagtgta aggtgtccaa cagggcctg cccagcagca tcgagaaaac catcagcaag   360
gccaagggcc agcctcggga gccccaggtg tacaccctgc cccctagcca agaggagatg   420
accaagaacc aggtgtccct gacctgcctg gtgaagggct tctacccag cgacatcgcc   480
gtggagtggg agagcaacgg ccagcccgag aacaactaca gaccaccccc ccctgtgctg   540
gacagcgacg gcagcttctt cctgtacagc cggctgaccg tggacaagag ccggtggcag   600
gagggcaacg tctttagctg ctccgtgatg cacgaggccc tgcacaacca ctacacccag   660
aagagcctga gcctgtccct gggcaagatg                                   690
```

<210> SEQ ID NO 8
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence:
  Synthetic polypeptide"

<400> SEQUENCE: 8

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Lys Lys Lys Glu Lys
        35                  40                  45

Glu Lys Glu Glu Gln Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 9
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
aggtggcccg aaagtcccaa ggcccaggca tctagtgttc ctactgcaca gccccaggca     60
gaaggcagcc tagccaaagc tactactgca cctgccacta cgcgcaatac tggccgtggc    120
ggggaggaga agaaaaagga gaaagagaaa gaagaacagg aagagaggga gaccaagacc    180
cctgaatgtc catcccatac ccagccgctg ggcgtctatc tcttgactcc cgcagtacag    240
gacttgtggc ttagagataa ggccaccttt acatgtttcg tcgtgggctc tgacctgaag    300

| | | |
|---|---|---|
| gatgcccatt tgacttggga ggttgccgga aagtacccca cagggggggt tgaggaaggg | 360 | |
| ttgctggagc gccattccaa tggctctcag agccagcact caagactcac ccttccgaga | 420 | |
| tccctgtgga acgccgggac ctctgtcaca tgtactctaa atcatcctag cctgccccca | 480 | |
| cagcgtctga tggcccttag agagccagcc gcccaggcac cagttaagct tagcctgaat | 540 | |
| ctgctcgcca gtagtgatcc cccagaggcc gccagctggc tcttatgcga agtgtccggc | 600 | |
| tttagcccgc caacatctt gctcatgtgg ctggaggacc agcgagaagt gaacaccagc | 660 | |
| ggcttcgctc cagcccggcc cccacccag ccgggttcta ccacattctg ggcctggagt | 720 | |
| gtcttaaggg tcccagcacc acctagcccc cagccagcca catacacctg tgttgtgtcc | 780 | |
| catgaagata gcaggaccct gctaaatgct tctaggagtc tggaggtttc ctacgtgact | 840 | |
| gaccatt | 847 | |

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Ser Gly Gly Gly Gly Ser
1               5                   10

<210> SEQ ID NO 11
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ggtggcggag gttctggagg tggaggttcc                                      30

<210> SEQ ID NO 12
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 13
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13

```
atctacatct gggcgcccTT ggccgggact tgtggggtcc ttctcctgtc actggttatc    60
acccTTtact gc                                                        72
```

<210> SEQ ID NO 14
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 15
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 16
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 17
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
``` tcc                                                                      123

<210> SEQ ID NO 18
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240 cggagggggca aggggcacga tggcctttac cagggtctca gtacagccac caaggacacc     300
tacgacgccc ttcacatgca ggccctgccc cctcgc                               336

<210> SEQ ID NO 20
<211> LENGTH: 112
<212> TYPE: PRT
<213> ORGANISM: Homo sapiens

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 336
<212> TYPE: DNA
<213> ORGANISM: Homo sapiens

<400> SEQUENCE: 21
agagtgaagt tcagcaggag cgcagacgcc cccgcgtacc agcagggcca gaaccagctc    60
tataacgagc tcaatctagg acgaagagag gagtacgatg tttTggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                            336

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Gly Gly Gly Ser
1               5

<210> SEQ ID NO 23
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ggtggcggag gttctggagg tggaggttcc                                    30

<210> SEQ ID NO 24
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

```
Arg Met Ser Pro Ser Asn Gln Thr Asp Lys Leu Ala Ala Phe Pro Glu
         50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150
```

<210> SEQ ID NO 25
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25

```
cccggatggt ttctggactc tccggatcgc ccgtggaatc ccccaacctt ctcaccggca      60
ctcttggttg tgactgaggg cgataatgcg accttcacgt gctcgttctc caacacctcc     120
gaatcattcg tgctgaactg gtaccgcatg agcccgtcaa accagaccga caagctcgcc     180
gcgtttccgg aagatcggtc gcaaccggga caggattgtc ggttccgcgt gactcaactg     240
ccgaatggca gagacttcca catgagcgtg gtccgcgcta ggcgaaacga ctccgggacc     300
tacctgtgcg gagccatctc gctggcgcct aaggcccaaa tcaaagagag cttgagggcc     360
gaactgagag tgaccgagcg cagagctgag gtgccaactg cacatccatc cccatcgcct     420
cggcctgcgg ggcagtttca gaccctggtc                                     450
```

<210> SEQ ID NO 26
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Met Ala Leu Pro Val Thr Ala Leu Leu Leu Pro Leu Ala Leu Leu Leu
 1               5                  10                  15

His Ala Ala Arg Pro Pro Gly Trp Phe Leu Asp Ser Pro Asp Arg Pro
             20                  25                  30

Trp Asn Pro Pro Thr Phe Ser Pro Ala Leu Leu Val Val Thr Glu Gly
         35                  40                  45

Asp Asn Ala Thr Phe Thr Cys Ser Phe Ser Asn Thr Ser Glu Ser Phe
     50                  55                  60

Val Leu Asn Trp Tyr Arg Met Ser Pro Ser Asn Gln Thr Asp Lys Leu
 65                  70                  75                  80

Ala Ala Phe Pro Glu Asp Arg Ser Gln Pro Gly Gln Asp Cys Arg Phe
                 85                  90                  95
```

Arg Val Thr Gln Leu Pro Asn Gly Arg Asp Phe His Met Ser Val Val
             100                 105                 110

Arg Ala Arg Arg Asn Asp Ser Gly Thr Tyr Leu Cys Gly Ala Ile Ser
         115                 120                 125

Leu Ala Pro Lys Ala Gln Ile Lys Glu Ser Leu Arg Ala Glu Leu Arg
     130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                 165                 170                 175

Pro Arg Pro Pro Thr Pro Ala Pro Thr Ile Ala Ser Gln Pro Leu Ser
             180                 185                 190

Leu Arg Pro Glu Ala Cys Arg Pro Ala Ala Gly Gly Ala Val His Thr
         195                 200                 205

Arg Gly Leu Asp Phe Ala Cys Asp Ile Tyr Ile Trp Ala Pro Leu Ala
     210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                 245                 250                 255

Arg Pro Val Gln Thr Thr Gln Glu Glu Asp Gly Cys Ser Cys Arg Phe
             260                 265                 270

Pro Glu Glu Glu Glu Gly Gly Cys Glu Leu Arg Val Lys Phe Ser Arg
         275                 280                 285

Ser Ala Asp Ala Pro Ala Tyr Lys Gln Gly Gln Asn Gln Leu Tyr Asn
     290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                 325                 330                 335

Gln Glu Gly Leu Tyr Asn Glu Leu Gln Lys Asp Lys Met Ala Glu Ala
             340                 345                 350

Tyr Ser Glu Ile Gly Met Lys Gly Glu Arg Arg Arg Gly Lys Gly His
         355                 360                 365

Asp Gly Leu Tyr Gln Gly Leu Ser Thr Ala Thr Lys Asp Thr Tyr Asp
     370                 375                 380

Ala Leu His Met Gln Ala Leu Pro Pro Arg
385                 390

<210> SEQ ID NO 27
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
atggccctcc ctgtcactgc cctgcttctc ccctcgcac tcctgctcca cgccgctaga      60
ccacccggat ggtttctgga ctctccggat cgcccgtgga atccccaac cttctcaccg     120 gcactcttgg ttgtgactga gggcgataat gcgaccttca cgtgctcgtt ctccaacacc    180
tccgaatcat tcgtgctgaa ctggtaccgc atgagcccgt caaaccagac cgacaagctc    240
gccgcgtttc cggaagatcg gtcgcaaccg ggacaggatt gtcggttccg cgtgactcaa    300

```
ctgccgaatg gcagagactt ccacatgagc gtggtccgcg ctaggcgaaa cgactccggg    360
acctacctgt gcggagccat ctcgctggcg cctaaggccc aaatcaaaga gagcttgagg    420
gccgaactga gagtgaccga gcgcagagct gaggtgccaa ctgcacatcc atccccatcg    480
cctcggcctg cggggcagtt tcagaccctg gtcacgacca ctccggcgcc gcgcccaccg    540
actccggccc caactatcgc gagccagccc ctgtcgctga ggccggaagc atgccgccct    600
gccgccggag gtgctgtgca tacccgggga ttggacttcg catgcgacat ctacatttgg    660
gctcctctcg ccggaacttg tggcgtgctc cttctgtccc tggtcatcac cctgtactgc    720
aagcggggtc ggaaaaagct tctgtacatt ttcaagcagc ccttcatgag gcccgtgcaa    780
accacccagg aggaggacgg ttgctcctgc cggttccccg aagaggaaga aggaggttgc    840
gagctgcgcg tgaagttctc ccggagcgcc gacgcccccg cctataagca gggccagaac    900
cagctgtaca cgaactgaa cctgggacgg cgggaagagt acgatgtgct ggacaagcgg    960
cgcggccggg accccgaaat gggcgggaag cctagaagaa agaaccctca ggaaggcctg    1020
tataacgagc tgcagaagga caagatggcc gaggcctact ccgaaattgg gatgaaggga    1080
gagcggcgga ggggaaaggg gcacgacggc ctgtaccaag gactgtccac cgccaccaag    1140
gacacatacg atgccctgca catgcaggcc cttccccctc gc                      1182
```

<210> SEQ ID NO 28
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(40)
<223> OTHER INFORMATION: /note="This sequence may encompass 1-10 'Gly
      Gly Gly Ser' repeating units"

<400> SEQUENCE: 28

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 29
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Gly Gly Gly Ser Gly Gly Gly Gly Ser Gly Gly Gly Gly Ser Gly
1               5                   10                  15

Gly Gly Gly Ser
            20

<210> SEQ ID NO 30
<211> LENGTH: 15
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Gly Gly Ser
1

<210> SEQ ID NO 32
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(2000)
<223> OTHER INFORMATION: /note="This sequence may encompass 50-2000
      nucleotides"

<400> SEQUENCE: 32
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
```

```
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa                                                2000

<210> SEQ ID NO 33
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa                                     150

<210> SEQ ID NO 34
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides"

<400> SEQUENCE: 34
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
```

```
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
```

| | |
|---|---|
| aaaaaaaaaa aaaaaaaaaa aaaaaaaaaa aaaaaaaaaa aaaaaaaaaa aaaaaaaaaa | 2820 |
| aaaaaaaaaa aaaaaaaaaa aaaaaaaaaa aaaaaaaaaa aaaaaaaaaa aaaaaaaaaa | 2880 |
| aaaaaaaaaa aaaaaaaaaa aaaaaaaaaa aaaaaaaaaa aaaaaaaaaa aaaaaaaaaa | 2940 |
| aaaaaaaaaa aaaaaaaaaa aaaaaaaaaa aaaaaaaaaa aaaaaaaaaa aaaaaaaaaa | 3000 |
| aaaaaaaaaa aaaaaaaaaa aaaaaaaaaa aaaaaaaaaa aaaaaaaaaa aaaaaaaaaa | 3060 |
| aaaaaaaaaa aaaaaaaaaa aaaaaaaaaa aaaaaaaaaa aaaaaaaaaa aaaaaaaaaa | 3120 |
| aaaaaaaaaa aaaaaaaaaa aaaaaaaaaa aaaaaaaaaa aaaaaaaaaa aaaaaaaaaa | 3180 |
| aaaaaaaaaa aaaaaaaaaa aaaaaaaaaa aaaaaaaaaa aaaaaaaaaa aaaaaaaaaa | 3240 |
| aaaaaaaaaa aaaaaaaaaa aaaaaaaaaa aaaaaaaaaa aaaaaaaaaa aaaaaaaaaa | 3300 |
| aaaaaaaaaa aaaaaaaaaa aaaaaaaaaa aaaaaaaaaa aaaaaaaaaa aaaaaaaaaa | 3360 |
| aaaaaaaaaa aaaaaaaaaa aaaaaaaaaa aaaaaaaaaa aaaaaaaaaa aaaaaaaaaa | 3420 |
| aaaaaaaaaa aaaaaaaaaa aaaaaaaaaa aaaaaaaaaa aaaaaaaaaa aaaaaaaaaa | 3480 |
| aaaaaaaaaa aaaaaaaaaa aaaaaaaaaa aaaaaaaaaa aaaaaaaaaa aaaaaaaaaa | 3540 |
| aaaaaaaaaa aaaaaaaaaa aaaaaaaaaa aaaaaaaaaa aaaaaaaaaa aaaaaaaaaa | 3600 |
| aaaaaaaaaa aaaaaaaaaa aaaaaaaaaa aaaaaaaaaa aaaaaaaaaa aaaaaaaaaa | 3660 |
| aaaaaaaaaa aaaaaaaaaa aaaaaaaaaa aaaaaaaaaa aaaaaaaaaa aaaaaaaaaa | 3720 |
| aaaaaaaaaa aaaaaaaaaa aaaaaaaaaa aaaaaaaaaa aaaaaaaaaa aaaaaaaaaa | 3780 |
| aaaaaaaaaa aaaaaaaaaa aaaaaaaaaa aaaaaaaaaa aaaaaaaaaa aaaaaaaaaa | 3840 |
| aaaaaaaaaa aaaaaaaaaa aaaaaaaaaa aaaaaaaaaa aaaaaaaaaa aaaaaaaaaa | 3900 |
| aaaaaaaaaa aaaaaaaaaa aaaaaaaaaa aaaaaaaaaa aaaaaaaaaa aaaaaaaaaa | 3960 |
| aaaaaaaaaa aaaaaaaaaa aaaaaaaaaa aaaaaaaaaa aaaaaaaaaa aaaaaaaaaa | 4020 |
| aaaaaaaaaa aaaaaaaaaa aaaaaaaaaa aaaaaaaaaa aaaaaaaaaa aaaaaaaaaa | 4080 |
| aaaaaaaaaa aaaaaaaaaa aaaaaaaaaa aaaaaaaaaa aaaaaaaaaa aaaaaaaaaa | 4140 |
| aaaaaaaaaa aaaaaaaaaa aaaaaaaaaa aaaaaaaaaa aaaaaaaaaa aaaaaaaaaa | 4200 |
| aaaaaaaaaa aaaaaaaaaa aaaaaaaaaa aaaaaaaaaa aaaaaaaaaa aaaaaaaaaa | 4260 |
| aaaaaaaaaa aaaaaaaaaa aaaaaaaaaa aaaaaaaaaa aaaaaaaaaa aaaaaaaaaa | 4320 |
| aaaaaaaaaa aaaaaaaaaa aaaaaaaaaa aaaaaaaaaa aaaaaaaaaa aaaaaaaaaa | 4380 |
| aaaaaaaaaa aaaaaaaaaa aaaaaaaaaa aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaaaaaa aaaaaaaaaa aaaaaaaaaa aaaaaaaaaa aaaaaaaaaa aaaaaaaaaa | 4560 |
| aaaaaaaaaa aaaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaaa aaaaaaaaaa aaaaaaaaaa aaaaaaaaaa aaaaaaaaaa aaaaaaaaaa | 4740 |
| aaaaaaaaaa aaaaaaaaaa aaaaaaaaaa aaaaaaaaaa aaaaaaaaaa aaaaaaaaaa | 4800 |
| aaaaaaaaaa aaaaaaaaaa aaaaaaaaaa aaaaaaaaaa aaaaaaaaaa aaaaaaaaaa | 4860 |
| aaaaaaaaaa aaaaaaaaaa aaaaaaaaaa aaaaaaaaaa aaaaaaaaaa aaaaaaaaaa | 4920 |
| aaaaaaaaaa aaaaaaaaaa aaaaaaaaaa aaaaaaaaaa aaaaaaaaaa aaaaaaaaaa | 4980 |
| aaaaaaaaaa aaaaaaaaaa | 5000 |

<210> SEQ ID NO 35

```
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
tttttttttt tttttttttt tttttttttt tttttttttt tttttttttt tttttttttt    60
tttttttttt tttttttttt tttttttttt tttttttttt                         100

<210> SEQ ID NO 36
<211> LENGTH: 500
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
tttttttttt tttttttttt tttttttttt tttttttttt tttttttttt tttttttttt    60
tttttttttt tttttttttt tttttttttt tttttttttt tttttttttt tttttttttt   120
tttttttttt tttttttttt tttttttttt tttttttttt tttttttttt tttttttttt   180
tttttttttt tttttttttt tttttttttt tttttttttt tttttttttt tttttttttt   240
tttttttttt tttttttttt tttttttttt tttttttttt tttttttttt tttttttttt   300
tttttttttt tttttttttt tttttttttt tttttttttt tttttttttt tttttttttt   360
tttttttttt tttttttttt tttttttttt tttttttttt tttttttttt tttttttttt   420
tttttttttt tttttttttt tttttttttt tttttttttt tttttttttt tttttttttt   480
tttttttttt tttttttttt                                                500

<210> SEQ ID NO 37
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
aaaaaaaaaa aaaaaaaaaa aaaaaaaaaa aaaaaaaaaa aaaaaaaaaa aaaaaaaaaa    60
aaaa                                                                 64

<210> SEQ ID NO 38
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(400)
<223> OTHER INFORMATION: /note="This sequence may encompass 100-400
      nucleotides"

<400> SEQUENCE: 38
aaaaaaaaaa aaaaaaaaaa aaaaaaaaaa aaaaaaaaaa aaaaaaaaaa aaaaaaaaaa    60
```

| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa aaaaaaaaaa aaaaaaaaaa aaaaaaaaaa | 180 |
| aaaaaaaaaa aaaaaaaaaa aaaaaaaaaa aaaaaaaaaa aaaaaaaaaa aaaaaaaaaa | 240 |
| aaaaaaaaaa aaaaaaaaaa aaaaaaaaaa aaaaaaaaaa aaaaaaaaaa aaaaaaaaaa | 300 |
| aaaaaaaaaa aaaaaaaaaa aaaaaaaaaa aaaaaaaaaa aaaaaaaaaa aaaaaaaaaa | 360 |
| aaaaaaaaaa aaaaaaaaaa aaaaaaaaaa aaaaaaaaaa | 400 |

```
<210> SEQ ID NO 39
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
```

```
                290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370

<210> SEQ ID NO 40
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 41
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
acaaaaaaga agtattcatc cagtgtgcac gaccctaacg gtgaatacat gttcatgaga      60
gcagtgaaca cagccaaaaa atccagactc acagatgtga cccta                    105

<210> SEQ ID NO 42
<211> LENGTH: 69
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Leu
        35                  40                  45

Pro Ile Gly Cys Ala Ala Phe Val Val Cys Ile Leu Gly Cys Ile
    50                  55                  60

Leu Ile Cys Trp Leu
```

<210> SEQ ID NO 43
<211> LENGTH: 207
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

```
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgatttctg gttacccata ggatgtgcag cctttgttgt agtctgcatt    180
ttgggatgca tacttatttg ttggctt                                         207
```

<210> SEQ ID NO 44
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 45
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                   123
```

<210> SEQ ID NO 46
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30
```

```
Thr Met Asn Trp Val Lys Gln Ser His Gly Lys Ser Leu Glu Trp Ile
         35                  40                  45

Gly Leu Ile Thr Pro Tyr Asn Gly Ala Ser Ser Tyr Asn Gln Lys Phe
 50                  55                  60

Arg Gly Lys Ala Thr Leu Thr Val Asp Lys Ser Ser Ser Thr Ala Tyr
 65                  70                  75                  80

Met Asp Leu Leu Ser Leu Thr Ser Glu Asp Ser Ala Val Tyr Phe Cys
             85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Gly Gly Ser Gly Gly Gly
            115                 120                 125

Ser Gly Gly Gly Ser Asp Ile Glu Leu Thr Gln Ser Pro Ala Ile
        130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Gly Arg Phe Ser Gly Ser Gly Ser Gly Asn Ser Tyr Ser Leu Thr Ile
            195                 200                 205

Ser Ser Val Glu Ala Glu Asp Ala Thr Tyr Tyr Cys Gln Gln Trp
        210                 215                 220

Ser Gly Tyr Pro Leu Thr Phe Gly Ala Gly Thr Lys Leu Glu Ile
225                 230                 235
```

<210> SEQ ID NO 47
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Gln Val Gln Leu Gln Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Arg Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Glu Asp Thr Ala Val Tyr Tyr Cys
             85                  90                  95

Ala Arg Gly Arg Tyr Tyr Gly Met Asp Val Trp Gly Gln Gly Thr Met
            100                 105                 110

Val Thr Val Ser Ser Gly Gly Gly Gly Ser Gly Gly Gly Ser Gly
            115                 120                 125

Gly Gly Ser Gly Gly Gly Ser Glu Ile Val Leu Thr Gln Ser
        130                 135                 140

Pro Ala Thr Leu Ser Leu Ser Pro Gly Glu Arg Ala Thr Ile Ser Cys
```

```
                145                 150                 155                 160
Arg Ala Ser Gln Ser Val Ser Ser Asn Phe Ala Trp Tyr Gln Gln Arg
                    165                 170                 175

Pro Gly Gln Ala Pro Arg Leu Leu Ile Tyr Asp Ala Ser Asn Arg Ala
                180                 185                 190

Thr Gly Ile Pro Pro Arg Phe Ser Gly Ser Gly Ser Gly Thr Asp Phe
            195                 200                 205

Thr Leu Thr Ile Ser Ser Leu Glu Pro Glu Asp Phe Ala Ala Tyr Tyr
        210                 215                 220

Cys His Gln Arg Ser Asn Trp Leu Tyr Thr Phe Gly Gln Gly Thr Lys
225                 230                 235                 240

Val Asp Ile Lys

<210> SEQ ID NO 48
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Arg Arg Thr Val Val Thr Pro Arg Ala Tyr Tyr Gly
            100                 105                 110

Met Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Leu Thr Gln Ser Pro Ser Thr Leu Ser Ala Ser
145                 150                 155                 160

Val Gly Asp Arg Val Thr Ile Thr Cys Gln Ala Ser Gln Asp Ile Ser
                165                 170                 175

Asn Ser Leu Asn Trp Tyr Gln Gln Lys Ala Gly Lys Ala Pro Lys Leu
            180                 185                 190

Leu Ile Tyr Asp Ala Ser Thr Leu Glu Thr Gly Val Pro Ser Arg Phe
        195                 200                 205

Ser Gly Ser Gly Ser Gly Thr Asp Phe Ser Phe Thr Ile Ser Ser Leu
    210                 215                 220

Gln Pro Glu Asp Ile Ala Thr Tyr Tyr Cys Gln Gln His Asp Asn Leu
225                 230                 235                 240

Pro Leu Thr Phe Gly Gln Gly Thr Lys Val Glu Ile Lys
                245                 250
```

-continued

```
<210> SEQ ID NO 49
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Trp Asp Gly Ser Tyr Tyr Tyr Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Val Leu
    130                 135                 140

Thr Gln Thr Pro Ser Ser Leu Ser Ala Ser Val Gly Asp Arg Val Thr
145                 150                 155                 160

Ile Thr Cys Arg Ala Ser Gln Ser Ile Asn Thr Tyr Leu Asn Trp Tyr
                165                 170                 175

Gln His Lys Pro Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Phe Ser Pro Leu Thr Phe Gly Gly Gly
225                 230                 235                 240

Thr Lys Leu Glu Ile Lys
                245

<210> SEQ ID NO 50
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met His Trp Val Arg Gln Val Pro Gly Lys Gly Leu Val Trp Val
```

```
                35                  40                  45
Ser Arg Ile Asn Thr Asp Gly Ser Thr Thr Tyr Ala Asp Ser Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Arg Asp Asp Thr Ala Val Tyr Tyr Cys
                 85                  90                  95

Val Gly Gly His Trp Ala Val Trp Gly Gln Gly Thr Thr Val Thr Val
            100                 105                 110

Ser Ser Gly Gly Gly Gly Ser Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Val Gly Asp Arg Val Thr Ile Thr Cys Arg Ala Ser
145                 150                 155                 160

Gln Ser Ile Ser Asp Arg Leu Ala Trp Tyr Gln Gln Lys Pro Gly Lys
                165                 170                 175

Ala Pro Lys Leu Leu Ile Tyr Lys Ala Ser Ser Leu Glu Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Val Tyr Tyr Cys Gln Gln
    210                 215                 220

Tyr Gly His Leu Pro Met Tyr Thr Phe Gly Gln Gly Thr Lys Val Glu
225                 230                 235                 240

Ile Lys

<210> SEQ ID NO 51
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Val Gln Leu Val Gln Ser Gly Ala Glu Val Glu Lys Pro Gly Ala
 1               5                  10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140
```

```
Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
            165                 170                 175

Lys Ala Pro Lys Leu Leu Ile Tyr Thr Ala Ser Ile Leu Gln Asn Gly
        180                 185                 190

Val Pro Ser Arg Phe Ser Gly Ser Gly Ser Gly Thr Asp Phe Thr Leu
    195                 200                 205

Thr Ile Ser Ser Leu Gln Pro Glu Asp Phe Ala Thr Tyr Tyr Cys Leu
210                 215                 220

Gln Thr Tyr Thr Thr Pro Asp Phe Gly Pro Gly Thr Lys Val Glu Ile
225                 230                 235                 240

Lys
```

<210> SEQ ID NO 52
<211> LENGTH: 252
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Arg Leu Ile Ala Val Ala Gly Asp Tyr Tyr Tyr Tyr Gly
            100                 105                 110

Met Asp Val Trp Gly Gln Gly Thr Met Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Met Thr Gln Ser Pro Ser Ser Val Ala Ser Val
145                 150                 155                 160

Gly Asp Arg Val Thr Ile Thr Cys Arg Ala Ser Gln Gly Val Gly Arg
                165                 170                 175

Trp Leu Ala Trp Tyr Gln Gln Lys Pro Gly Thr Ala Pro Lys Leu Leu
            180                 185                 190

Ile Tyr Ala Ala Ser Thr Leu Gln Ser Gly Val Pro Ser Arg Phe Ser
        195                 200                 205

Gly Ser Gly Ser Gly Thr Asp Phe Thr Leu Thr Ile Asn Asn Leu Gln
    210                 215                 220

Pro Glu Asp Phe Ala Thr Tyr Tyr Cys Gln Gln Ala Asn Ser Phe Pro
225                 230                 235                 240

Leu Thr Phe Gly Gly Gly Thr Arg Leu Glu Ile Lys
                245                 250
```

<210> SEQ ID NO 53
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Lys Val Ser Ser Ser Pro Ala Phe Asp Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
            165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
            210                 215                 220

Phe Ala Val Tyr Tyr Cys Gln His Tyr Gly Gly Ser Pro Leu Ile Thr
225                 230                 235                 240

Phe Gly Gln Gly Thr Arg Leu Glu Ile Lys
                245                 250
```

<210> SEQ ID NO 54
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Pro Phe Thr Gly Tyr
            20                  25                  30
```

Ser Leu His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Asp His Tyr Gly Gly Asn Ser Leu Phe Tyr Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Asp Ile Gln Leu Thr
    130                 135                 140

Gln Ser Pro Ser Ser Ile Ser Ala Ser Val Gly Asp Thr Val Ser Ile
145                 150                 155                 160

Thr Cys Arg Ala Ser Gln Asp Ser Gly Thr Trp Leu Ala Trp Tyr Gln
                165                 170                 175

Gln Lys Pro Gly Lys Ala Pro Asn Leu Leu Met Tyr Asp Ala Ser Thr
                180                 185                 190

Leu Glu Asp Gly Val Pro Ser Arg Phe Ser Gly Ser Ala Ser Gly Thr
            195                 200                 205

Glu Phe Thr Leu Thr Val Asn Arg Leu Gln Pro Glu Asp Ser Ala Thr
210                 215                 220

Tyr Tyr Cys Gln Gln Tyr Asn Ser Tyr Pro Leu Thr Phe Gly Gly Gly
225                 230                 235                 240

Thr Lys Val Asp Ile Lys
            245

<210> SEQ ID NO 55
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Gly Tyr Ala Gln Lys Phe
 50                  55                  60

Gln Gly Arg Val Thr Met Thr Arg Asp Thr Ser Thr Ser Thr Val His
 65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Ser Asp Ala Phe Asp Ile Trp Gly
                100                 105                 110

Gln Gly Thr Met Val Thr Val Ser Ser Gly Gly Gly Ser Gly Gly
            115                 120                 125

Gly Gly Ser Gly Gly Gly Gly Ser Gly Gly Gly Gly Ser Asp Ile Gln

```
            130                 135                 140
Met Thr Gln Ser Pro Pro Ser Leu Ser Ala Ser Val Gly Asp Arg Val
145                 150                 155                 160

Thr Ile Thr Cys Arg Ala Ser Gln Asp Ile Ser Ser Ala Leu Ala Trp
                165                 170                 175

Tyr Gln Gln Lys Pro Gly Thr Pro Lys Leu Leu Ile Tyr Asp Ala
            180                 185                 190

Ser Ser Leu Glu Ser Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Phe Ser Ser Tyr Pro Leu Thr Phe Gly
225                 230                 235                 240

Gly Gly Thr Arg Leu Glu Ile Lys
                245
```

<210> SEQ ID NO 56
<211> LENGTH: 255
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Gly Gly Ile Tyr Tyr Tyr Gly Met Asp Val Trp
            100                 105                 110

Gly Gln Gly Thr Thr Ile Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Val Met Thr Gln Thr Pro Asp Ser Leu Ala Val Ser Leu Gly Glu Arg
145                 150                 155                 160

Ala Thr Ile Ser Cys Lys Ser Ser His Ser Val Leu Tyr Asn Arg Asn
                165                 170                 175

Asn Lys Asn Tyr Leu Ala Trp Tyr Gln Gln Lys Pro Gly Gln Pro Pro
            180                 185                 190

Lys Leu Leu Phe Tyr Trp Ala Ser Thr Arg Lys Ser Gly Val Pro Asp
        195                 200                 205

Arg Phe Ser Gly Ser Gly Ser Gly Thr Asp Phe Thr Leu Thr Ile Ser
    210                 215                 220

Ser Leu Gln Pro Glu Asp Phe Ala Thr Tyr Phe Cys Gln Gln Thr Gln
225                 230                 235                 240
```

```
Thr Phe Pro Leu Thr Phe Gly Gln Gly Thr Arg Leu Glu Ile Asn
                245                 250                 255

<210> SEQ ID NO 57
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Gly Gly Gly Gly Ser Gly Gly Gly Gly Ser Gly Gly Gly Gly
        115                 120                 125

Gly Ser Gly Gly Gly Ser Asp Ile Arg Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys

<210> SEQ ID NO 58
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
```

```
                    20                  25                  30

Tyr Met His Trp Val Arg Gln Ala Pro Gly Gln Gly Leu Glu Trp Met
             35                  40                  45

Gly Arg Ile Asn Pro Asn Ser Gly Gly Thr Asn Tyr Ala Gln Lys Phe
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Thr Thr Thr Ser Tyr Ala Phe Asp Ile Trp Gly Gln Gly Thr
             100                 105                 110

Met Val Thr Val Ser Ser Gly Gly Gly Gly Ser Gly Gly Gly Gly Ser
             115                 120                 125

Gly Gly Gly Gly Ser Gly Gly Gly Ser Asp Ile Gln Leu Thr Gln
             130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Thr Trp Leu Ala Trp Tyr Gln Gln
                 165                 170                 175

Lys Pro Gly Lys Ala Pro Asn Leu Leu Ile Tyr Lys Ala Ser Thr Leu
             180                 185                 190

Glu Ser Gly Val Pro Ser Arg Phe Ser Gly Ser Gly Ser Gly Thr Glu
             195                 200                 205

Phe Thr Leu Thr Ile Ser Ser Leu Gln Pro Asp Asp Phe Ala Thr Tyr
             210                 215                 220

Tyr Cys Gln Gln Tyr Asn Thr Tyr Ser Pro Tyr Thr Phe Gly Gln Gly
225                 230                 235                 240

Thr Lys Leu Glu Ile Lys
                 245

<210> SEQ ID NO 59
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Gln Val Gln Leu Val Gln Ser Gly Gly Gly Leu Val Lys Pro Gly Gly
 1               5                  10                  15

Ser Leu Arg Leu Ser Cys Glu Ala Ser Gly Phe Ile Phe Ser Asp Tyr
             20                  25                  30

Tyr Met Gly Trp Ile Arg Gln Ala Pro Gly Lys Gly Leu Glu Trp Val
             35                  40                  45

Ser Tyr Ile Gly Arg Ser Gly Ser Ser Met Tyr Tyr Ala Asp Ser Val
             50                  55                  60

Lys Gly Arg Phe Thr Phe Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Ala Ser Pro Val Val Ala Ala Thr Glu Asp Phe Gln His Trp Gly
             100                 105                 110

Gln Gly Thr Leu Val Thr Val Ser Ser Gly Gly Gly Gly Ser Gly Gly
             115                 120                 125
```

Gly Gly Ser Gly Gly Gly Ser Gly Gly Gly Ser Asp Ile Val
            130                 135                 140

Met Thr Gln Thr Pro Ala Thr Leu Ser Leu Ser Pro Gly Glu Arg Ala
145                 150                 155                 160

Thr Leu Ser Cys Arg Ala Ser Gln Ser Val Thr Ser Asn Tyr Leu Ala
                165                 170                 175

Trp Tyr Gln Gln Lys Pro Gly Gln Ala Pro Arg Leu Leu Phe Gly
                180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
    210                 215                 220

Phe Ala Met Tyr Tyr Cys Gln Gln Tyr Gly Ser Ala Pro Val Thr Phe
225                 230                 235                 240

Gly Gln Gly Thr Lys Leu Glu Ile Lys
                245

<210> SEQ ID NO 60
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Gln Val Gln Leu Val Gln Ser Gly Ala Glu Val Arg Ala Pro Gly Ala
1               5                   10                  15

Ser Val Lys Ile Ser Cys Lys Ala Ser Gly Phe Thr Phe Arg Gly Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Arg Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Met Tyr Tyr Cys
                85                  90                  95

Ala Arg Thr Ala Ser Cys Gly Gly Asp Cys Tyr Tyr Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Gly Gly Gly Ser Asp Ile
    130                 135                 140

Gln Met Thr Gln Ser Pro Pro Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
                180                 185                 190

Ser Ser Ser Leu Ala Ser Gly Val Pro Ser Arg Phe Ser Gly Ser Gly
            195                 200                 205

Ser Gly Ala Glu Phe Thr Leu Thr Ile Ser Ser Leu Gln Pro Asp Asp
    210                 215                 220

```
Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
            245
```

<210> SEQ ID NO 61
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

```
Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Ser Trp Ser Trp Gly Tyr Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Ser Glu Leu Thr Gln Asp
    130                 135                 140

Pro Ala Val Ser Val Ala Leu Gly Gln Thr Val Arg Thr Thr Cys Gln
145                 150                 155                 160

Gly Asp Ala Leu Arg Ser Tyr Tyr Ala Ser Trp Tyr Gln Gln Lys Pro
                165                 170                 175

Gly Gln Ala Pro Met Leu Val Ile Tyr Gly Lys Asn Asn Arg Pro Ser
            180                 185                 190

Gly Ile Pro Asp Arg Phe Ser Gly Ser Asp Ser Gly Asp Thr Ala Ser
        195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Tyr Pro Val Phe Gly Thr Gly Thr Lys
225                 230                 235                 240

Val Thr Val Leu
```

<210> SEQ ID NO 62
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

```
Glu Val Gln Leu Val Glu Ser Gly Gly Gly Leu Val Gln Pro Gly Arg
1               5                   10                  15
```

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Thr Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
            85                  90                  95

Ala Lys Asp Ser Ser Ser Trp Tyr Gly Gly Ser Ala Phe Asp Ile
            100                 105                 110

Trp Gly Gln Gly Thr Met Val Thr Val Ser Ser Gly Gly Gly Gly Ser
            115                 120                 125

Gly Gly Gly Gly Ser Gly Gly Gly Ser Ser Glu Leu Thr Gln
 130                 135                 140

Glu Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
            165                 170                 175

Pro Gly Gln Ala Pro Val Leu Val Ile Phe Gly Arg Ser Arg Arg Pro
            180                 185                 190

Ser Gly Ile Pro Asp Arg Phe Ser Gly Ser Ser Ser Gly Asn Thr Ala
            195                 200                 205

Ser Leu Ile Ile Thr Gly Ala Gln Ala Glu Asp Glu Ala Asp Tyr Tyr
            210                 215                 220

Cys Asn Ser Arg Asp Asn Thr Ala Asn His Tyr Val Phe Gly Thr Gly
225                 230                 235                 240

Thr Lys Leu Thr Val Leu
            245

<210> SEQ ID NO 63
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Thr Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
            85                  90                  95

Ala Lys Asp Ser Ser Ser Trp Tyr Gly Gly Ser Ala Phe Asp Ile
            100                 105                 110

```
Trp Gly Gln Gly Thr Met Val Thr Val Ser Ser Gly Gly Gly Ser
            115                 120                 125

Gly Gly Gly Gly Ser Gly Gly Gly Ser Ser Glu Leu Thr Gln
        130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Tyr Gly Lys Asn Asn Arg Pro
            180                 185                 190

Ser Gly Ile Pro Asp Arg Phe Ser Gly Ser Ser Ser Gly Asn Thr Ala
        195                 200                 205

Ser Leu Thr Ile Thr Gly Ala Gln Ala Glu Asp Glu Ala Asp Tyr Tyr
210                 215                 220

Cys Asn Ser Arg Gly Ser Ser Gly Asn His Tyr Val Phe Gly Thr Gly
225                 230                 235                 240

Thr Lys Val Thr Val Leu
            245

<210> SEQ ID NO 64
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Thr Gly Trp Val Gly Ser Tyr Tyr Tyr Met Asp Val Trp
            100                 105                 110

Gly Lys Gly Thr Thr Val Thr Val Ser Ser Gly Gly Gly Gly Ser Gly
        115                 120                 125

Gly Gly Gly Ser Gly Gly Gly Ser Gly Gly Gly Ser Glu Ile
        130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Ser Val Ser Ser Asn Tyr Leu
                165                 170                 175

Ala Trp Tyr Gln Gln Lys Pro Gly Gln Pro Arg Leu Leu Ile Tyr
            180                 185                 190

Asp Val Ser Thr Arg Ala Thr Gly Ile Pro Ala Arg Phe Ser Gly Gly
        195                 200                 205

Gly Ser Gly Thr Asp Phe Thr Leu Thr Ile Ser Ser Leu Glu Pro Glu
```

```
                210                 215                 220
Asp Phe Ala Val Tyr Tyr Cys Gln Gln Arg Ser Asn Trp Pro Pro Trp
225                 230                 235                 240

Thr Phe Gly Gln Gly Thr Lys Val Glu Ile Lys
                245                 250

<210> SEQ ID NO 65
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Ser Arg Tyr Tyr Tyr Gly Met Asp Val Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Gly Gly Gly Ser Glu Ile Val
        130                 135                 140

Met Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
    210                 215                 220

Phe Ala Val Tyr Tyr Cys Gln His Tyr Gly Gly Ser Pro Leu Ile Thr
225                 230                 235                 240

Phe Gly Gln Gly Thr Lys Val Asp Ile Lys
                245                 250

<210> SEQ ID NO 66
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66
```

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Ala Ala Ala Gly His Asp Trp Tyr Phe Asp Leu Trp
            100                 105                 110

Gly Arg Gly Thr Leu Val Thr Val Ser Ser Gly Gly Gly Gly Ser Gly
            115                 120                 125

Gly Gly Gly Ser Gly Gly Gly Gly Ser Gly Gly Gly Gly Ser Asp Ile
        130                 135                 140

Arg Val Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Ile Pro Leu Thr Phe
225                 230                 235                 240

Gly Gln Gly Thr Lys Val Glu Ile Lys
                245

<210> SEQ ID NO 67
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Val Gln Leu Val Gln Ser Trp Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

```
Ala Arg Ser Pro Arg Val Thr Thr Gly Tyr Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Gly Gly Gly Ser Asp Ile Gln Leu
    130                 135                 140

Thr Gln Ser Pro Ser Thr Leu Ser Ala Ser Val Gly Asp Arg Val Thr
145                 150                 155                 160

Ile Thr Cys Arg Ala Ser Gln Ser Ile Ser Ser Trp Leu Ala Trp Tyr
                165                 170                 175

Gln Gln Lys Pro Gly Lys Ala Pro Lys Leu Leu Ile Tyr Lys Ala Ser
            180                 185                 190

Ser Leu Glu Ser Gly Val Pro Ser Arg Phe Ser Gly Ser Gly Ser Gly
        195                 200                 205

Thr Glu Phe Thr Leu Thr Ile Ser Ser Leu Gln Pro Asp Asp Phe Ala
    210                 215                 220

Thr Tyr Tyr Cys Gln Gln Tyr Ser Ser Tyr Pro Leu Thr Phe Gly Gly
225                 230                 235                 240

Gly Thr Arg Leu Glu Ile Lys
                245

<210> SEQ ID NO 68
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Gln Val Gln Leu Val Gln Ser Gly Ala Glu Val Arg Arg Pro Gly Ala
1               5                   10                  15

Ser Val Lys Ile Ser Cys Arg Ala Ser Gly Asp Thr Ser Thr Arg His
            20                  25                  30

Tyr Ile His Trp Leu Arg Gln Ala Pro Gly Gln Gly Pro Glu Trp Met
        35                  40                  45

Gly Val Ile Asn Pro Thr Thr Gly Pro Ala Thr Gly Ser Pro Ala Tyr
    50                  55                  60

Ala Gln Met Leu Gln Gly Arg Val Thr Met Thr Arg Asp Thr Ser Thr
65                  70                  75                  80

Arg Thr Val Tyr Met Glu Leu Arg Ser Leu Arg Phe Glu Asp Thr Ala
                85                  90                  95

Val Tyr Tyr Cys Ala Arg Ser Val Val Gly Arg Ser Ala Pro Tyr Tyr
            100                 105                 110

Phe Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Gly Ile Ser
                165                 170                 175

Asp Tyr Ser Ala Trp Tyr Gln Gln Lys Pro Gly Lys Ala Pro Lys Leu
            180                 185                 190

Leu Ile Tyr Ala Ala Ser Thr Leu Gln Ser Gly Val Pro Ser Arg Phe
```

```
            195                 200                 205
Ser Gly Ser Gly Ser Gly Thr Asp Phe Thr Leu Thr Ile Ser Tyr Leu
    210                 215                 220

Gln Ser Glu Asp Phe Ala Thr Tyr Tyr Cys Gln Gln Tyr Tyr Ser Tyr
225                 230                 235                 240

Pro Leu Thr Phe Gly Gly Gly Thr Lys Val Asp Ile Lys
                245                 250
```

<210> SEQ ID NO 69
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Tyr Thr Thr Tyr Ala Gln Lys Phe
        50                  55                  60

Gln Gly Arg Leu Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Arg Ser Cys Gly Gly Asp Cys Tyr Tyr Phe Asp Asn Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Leu Thr Gln Ser Pro Ser Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
        195                 200                 205

Ser Gly Ala Glu Phe Thr Leu Thr Ile Ser Ser Leu Gln Pro Asp Asp
    210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
                245
```

<210> SEQ ID NO 70
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 70

Gln Ile Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Val His Val Gly Trp Ile Arg Gln Pro Pro Gly Lys Ala Leu Glu
        35                  40                  45

Trp Leu Ala Leu Ile Ser Trp Ala Asp Asp Lys Arg Tyr Arg Pro Ser
    50                  55                  60

Leu Arg Ser Arg Leu Asp Ile Thr Arg Val Thr Ser Lys Asp Gln Val
65                  70                  75                  80

Val Leu Ser Met Thr Asn Met Gln Pro Glu Asp Thr Ala Thr Tyr Tyr
                85                  90                  95

Cys Ala Leu Gln Gly Phe Asp Gly Tyr Glu Ala Asn Trp Gly Pro Gly
            100                 105                 110

Thr Leu Val Thr Val Ser Ser Gly Gly Gly Ser Gly Gly Gly Gly
            115                 120                 125

Ser Gly Gly Gly Gly Ser Gly Gly Gly Gly Ser Asp Ile Val Met Thr
    130                 135                 140

Gln Ser Pro Ser Ser Leu Ser Ala Ser Ala Gly Asp Arg Val Thr Ile
145                 150                 155                 160

Thr Cys Arg Ala Ser Arg Gly Ile Ser Ser Ala Leu Ala Trp Tyr Gln
                165                 170                 175

Gln Lys Pro Gly Lys Pro Pro Lys Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205

Asp Phe Thr Leu Thr Ile Asp Ser Leu Glu Pro Glu Asp Phe Ala Thr
    210                 215                 220

Tyr Tyr Cys Gln Gln Ser Tyr Ser Thr Pro Trp Thr Phe Gly Gln Gly
225                 230                 235                 240

Thr Lys Val Asp Ile Lys
                245

<210> SEQ ID NO 71
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
caagtccaac tgcagcagtc aggagcggaa gtgaagaaac caggagcgtc agtcaaagtg      60
tcgtgcaagg ctagcggcta caccttcacc ggctactaca tgcactgggt tcgacaggct     120
ccagggcagg gtctggagtg gatgggccgc atcaacccga attccggtgg gactaactac     180
gcccagaagt tccagggaag agtgaccatg actaggggaca cgtcgatcag cactgcgtac     240
atggaactga gccgcctgcg gtccgaggat actgccgtct actactgcgc acgcggaagg     300
tactatggaa tggacgtgtg gggccaaggg actatggtga ctgtgagctc gggaggggga     360
ggctccggtg gcgggggatc aggaggagga ggatcagggg gaggaggttc cgaaattgtc     420
ctcacccaga gccggcaac cctctcactt tccccgggag agcgcgcaac catctcttgc      480

```
cgggctagcc aatccgtgtc gtccaatttc gcctggtacc agcaacggcc gggacaagcc      540
cctagactcc tgatctacga cgccagcaac agagcgactg gaattcctcc acgcttttcg      600
ggatcaggct ccggtaccga cttcaccctg actatctcgt cgctcgaacc cgaggatttc      660
gccgcctact actgtcatca gcggtcgaac tggttgtata cgtttggcca gggcaccaag      720
gtggatatca ag                                                          732
```

<210> SEQ ID NO 72
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72

```
caagtccaac tcgtccagtc aggagcagaa gtcaagaaac caggtgctag cgtgaaagtg       60
tcgtgcaagg cgtcgggata cactttcacc ggatactaca tgcactgggt ccgccaggcc      120
cccggacaag gactggaatg gatgggctgg atcaacccga atagcggggg aactaattac      180
gcccagaagt ttcagggacg agtgaccatg acccgcgata cctctatctc gaccgcctac      240
atggagctct ccagactgcg ctccgacgat actgcagtgt actactgcgc ccgggacctg      300
aggcggactg tggttactcc tcgcgcctat tatggcatgg acgtgtgggg ccaaggaact      360
actgtgactg tgagctcggg aggcggtggg tcaggcggag gagggtcggg cggtggtggc      420
tcgggagggg gaggaagcga cattcaactt acgcagagcc cgtcaaccct gtcagcgtca      480
gtgggagatc gggtgaccat cacgtgtcag gccagccagg atatctccaa ctcgctcaac      540
tggtaccagc aaaaggcggg taaagctccg aagctgctga tctacgacgc ttccacccte      600 gagactggag tcccatccag attttccggg tcaggaagcg gcaccgattt ctccttcacc      660
atttcgtcct tgcaaccgga ggacatcgca acctactact gccagcagca tgacaacttg      720
cctctgacgt tcgggcaggg caccaaggtg gaaatcaag                             759
```

<210> SEQ ID NO 73
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 73

```
caagtccaac tcgtccaatc aggagcggaa gtcaaaaagc ccggagctcc agtgaaagtg       60
tcatgcaagg cctccggcta caccttcacc ggttactata tgcactgggt gcggcaggcc      120
ccgggccagg ggttggaatg gatgggatgg atcaatccaa actcgggtgg gactaactac      180
gcccagaagt tccaaggacg ggtgaccatg actagggaca cctcgatctc caccgcatac      240
atggagctta gcagactccg ctccgacgat accgcagtct actattgcgc gcggggagag      300
tgggacggat cgtactacta cgattactgg ggccaggaa ctctggtgac tgtttcctcg       360
ggtggaggag gttcaggcgg aggcggctcg ggcgggggag gatctggagg aggagggtcc      420
gacattgtgc tgacccaaac tccttcgtcc ctgtcggcca gcgtgggcga ccgcgtgacg      480
attacgtgca gagctagcca atccatcaat acttacctca ctggtaccag gcataagccg      540
```

```
gggaaagcac caaagctgct gatctacgcc gcctcatcct tgcagagcgg tgtgccttca    600
cgctttagcg gatcgggatc gggaacggat tcaccctga ctatcagctc cctccagccg     660
gaggattttg cgacctacta ctgtcagcag agcttctcac cgctgacttt cggcggcggg   720
accaagctgg aaatcaag                                                  738
```

```
<210> SEQ ID NO 74
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
caagtgcaac tcgttgaatc aggtggaggt ttggtgcaac ccggaggatc tctcagactg     60
tcgtgtgcgg cgtccggtt caccttttcg tcctactgga tgcactgggt gcgccaggtg   120
ccgggaaaag gactggtgtg ggtgtccaga atcaacaccg acgggtcaac gactacctac   180
gcagatagcg tggaaggtcg gttcaccatt tcgcgggaca cgctaaaaa cactctgtac    240 cttcagatga attcactgcg cgatgacgac accgcagtct actactgcgt cggtggacac   300
tgggcggtct ggggacaggg aactacggtg actgtgtcca gcggcggggg aggaagcggc   360
ggagggggga gcggaggcgg aggatcagga ggaggcggct ccgatatcca gatgacccag   420
tcgccatcga ccctctccgc tagcgtgggg gatagggtca ctatcacttg ccgagccagc   480
caatccatta gcgaccggct tgcctggtac aacagaaac ctggaaaggc cccgaagctg    540
ctcatctaca aggcctcgtc actggagtcg ggagtcccgt cccgcttttc cggctcgggc   600
tcaggcaccg agttcactct gaccatctcg agcctgcagc cggacgattt cgccgtgtat    660
tactgccagc aatacggaca tctcccaatg tacacgttcg gtcagggcac caaggtcgaa   720
atcaag                                                              726
```

```
<210> SEQ ID NO 75
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
caagtccaac tcgttcaatc aggcgcagaa gtcgaaaagc ccggagcatc agtcaaagtc     60
tcttgcaagg cttccggcta caccttcacg gactactaca tgcactgggt gcgccaggct    120
ccaggccagg gactggagtg gatgggatgg atcaacccga attccggggg aactaactac    180
gcccagaagt tcagggccg ggtgactatg actcgcgata cctcgatctc gactgcgtac    240
atggagctca gccgcctccg gtcggacgat accgccgtgt actattgtgc gtcgggatgg   300
gacttcgact actgggggca gggcactctg gtcactgtgt caagcggagg aggtggatca    360
ggtggaggtg gaagcggggg aggaggttcc ggcggcggag gatcagatat cgtgatgacg    420
caatcgcctt cctcgttgtc cgcatccgtg ggagacaggg tgaccattac ttgcagagcg   480
tcccagtcca ttcggtacta cctgtcgtgg taccagcaga agccggggaa agccccaaaa    540
ctgcttatct atactgcctc gatcctccaa aacggcgtgc catcaagatt cagcggttcg   600
ggcagcggga ccgactttac cctgactatc agcagcctgc agccggaaga tttcgccacg    660
```

```
tactactgcc tgcaaaccta caccaccccg gacttcggac ctggaaccaa ggtggagatc    720
aag                                                                 723

<210> SEQ ID NO 76
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
caagtgcaac tcgtccagtc aggtgcagaa gtgaagaaac ccggagcgtc agtcaaagtg     60
tcatgcaagg cgtcaggcta caccttcacc agctactaca tgcactgggt gcggcaggcc    120
ccaggccaag gcttggagtg gatgggaatc attaacccgt caggaggctc cacctcctac    180
gcccagaagt tcagggaag agtgacgatg actcgggata cgtcgacctc gaccgtgtac    240
atggaactga gctcgctgcg ctccgaggac actgctgtgt actactgcgc acggtacaga    300
ctcattgccg tggcaggaga ctactactac tatggcatgg acgtctgggg cagggcact    360 atggtcactg tgtcgtccgg cggaggaggc tcgggtggag gaggtagcgg aggagggga    420 agcggagggg ggggctccga tatccagatg actcagtcgc cttcctccgt gtcggcctcg    480
gttggagatc gcgtcaccat cacttgtcga gcttcccaag gagtcggtag gtggctggcg    540
tggtaccagc aaaagccggg aactgccccg aagctcctga tctacgcggc tagcaccctg    600
cagtcgggag tgccatcccg cttcagcgga tctgggtcag gtaccgactt cacccttacg    660
atcaacaatc tccagccgga ggactttgcc acctattact gccaacaggc caacagcttc    720
cctctgactt tcggaggggg cactcgcctg gaaatcaag                          759

<210> SEQ ID NO 77
<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77
caagtgcaat tggttcaatc aggaggagga gtggtgcaac ctggaagatc tctcagactg     60
tcgtgtgcgg catcgggatt cactttctca tcatacgcaa tgcactgggt ccgccaggcc    120
ccgggcaaag gcttggaatg ggtggcggtc atttcatacg acggctcgaa caagtactac    180
gctgacagcg tgaagggacg ctttactatt tcccgggaca attcgaagaa cactctgtac    240
ctccagatga actcccttag ggctgaggac accgccgtct actactgcgc acgctggaaa    300
gtgtcgtcca gctccccagc ttttgactac tggggacagg gaacccttgt gaccgtgtcg    360
tccggtggag ggggaagcgg cggagggga tcaggtggcg gcggatcggg aggcggggga    420
tcagaaatcg tgctgactca gtccccggcc acgctgtctc tcagcccggg agagagagcg    480
atcctgtcct gccgcgcctc gcagagcgtg tacactaagt acctgggtg gtaccagcag    540 aaaccgggtc aagcgcctcg gctgctgatc tacgatgcct ccacccgggc caccggaatc    600
cccgatcggt tctccggcag cggctcggga actgatttca cgctgaccat caatcgcctg    660
gagccggaag atttcgccgt ctattactgc cagcattacg gcgggagccc actcatcacc    720
```

```
ttcggtcaag gaacccgact cgaaatcaag                                         750
```

<210> SEQ ID NO 78
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 78

```
caagtccaac tccagcagtc aggtgcagaa gtcaaaaagc caggagcatc cgtgaaggtt         60
tcgtgcaaga cttccggcta ccctttacc gggtactccc tccattgggt gagacaagca        120
ccgggccagg gactggagtg gatgggatgg atcaacccaa attcggcgg caccaactat        180
gcgcagaagt tccaggacg ggtgaccatg actcgcgaca cttcgatctc cactgcctac        240
atggagctgt cccgcttgag atctgacgac acggccgtct actactgcgc ccgggatcac        300
tacggaggta attcgctgtt ctactgggg cagggaaccc ttgtgactgt gtcctcgggt        360
ggtggagggt caggaggcgg aggctcaggg ggaggaggta gcggaggagg cggatcagac        420
atccaactga cccagtcacc atcctccatc tcggctagcg tcggagacac cgtgtcgatt        480
acttgtaggg cctcccaaga ctcagggacg tggctggcgt ggtatcagca aaaaccgggc        540
aaagctccga acctgttgat gtacgacgcc agcaccctcg aagatggagt gcctagccgc        600
ttcagcggaa gcgcctcggg cactgaattc acgctgactg tgaatcggct ccagccggag        660
gattcggcga cctactactg ccagcagtac aacagctacc ccctgacctt tggaggcggg        720
accaaggtgg atatcaag                                                      738
```

<210> SEQ ID NO 79
<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

```
caagtgcaac tcgtccagtc aggtgcagaa gtgaagaaac caggagcgtc cgtcgaagtg         60
tcgtgtaagg cgtccggcta cactttcacc tcgtactaca tgcactgggt gcggcaggcc        120
ccgggacaag gcctcgaatg gatgggaatc atcaacccga gcggaggctc gactggttac        180
gcccagaagt tccagggaag ggtgacgatg acccgcgata cctcgacttc gaccgttcat        240
atggagctct cgtccctgcg gagcgaggac actgctgtct actattgcgc gcggggagga        300
tactctagct cctccgatgc atttgacatt tggggccagg gaactatggt gaccgtgtca        360
tcaggcggag gtggatcagg aggaggaggg tcggagggg gaggcagcgg cggggtgggg        420
tcggacattc agatgacgca gtcccctcct agcctgagcg cctcggtggg tgacagagtg        480
accatcactt gcagagcctc gcaagacatc tcctccgcat ggcttggta ccagcaaaag        540
ccgggcactc cgccgaaact gctcatctac gatgcctcct cactggagtc aggagtccca        600
tctcgcttct cggggtcagg aagcggcacc gattttaccc ttaccatctc cagcctgcag        660
cccgaggact cgccacgta ctactgccaa cagttcagct cctacccact gaccttcggg        720
ggcggaactc gcctggaaat caag                                               744
```

<210> SEQ ID NO 80
<211> LENGTH: 765
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80

```
caagtgcaac tcgtccagag cggagcagaa gtcaagaagc caggagcgtc agtgaaagtg      60
tcatgcaagg ccagcggcta tacctttact tcgtatggga tctcctgggt gcggcaggca     120
ccgggccaag gactggagtg gatgggatgg atctcagcct acaacggtaa caccaactac     180
gcccagaagc tgcaaggacg cgtgaccatg actactgata cgagcacctc cactgcctac     240
atggaattgc ggtcccttcg gtcggacgat actgctgtgt actactgcgc aagagtcgcc     300
ggagggatct actactacta cggcatggac gtctggggac agggaaccac cattacggtg     360
tcgagcggag gggaggctc gggggggagga ggaagcggag gtggcggctc cggggcggc     420
ggatcggaca ttgtgatgac ccagactcct gactccctgg ctgtttcgtt gggagagcgc     480
gcgactatct cgtgtaagtc cagccactca gtcctgtaca atcgcaataa caagaactac     540
ctcgcgtggt accagcaaaa accgggtcag ccgcctaaac tcctgttcta ctgggcctcc     600
accagaaaga gcggggtgcc agatcgattc tctggatcag gatcaggtac cgactttacg     660
ctgaccatct cgtccctgca gccggaggat ttcgcgactt acttctgcca gcagactcag     720
actttcccc tcaccttcgg tcaaggcacc aggctggaaa tcaat            765
```

<210> SEQ ID NO 81
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
caagtccaat tgcagcagag cggagcagaa gtgaagaagc caggagcgtc agtcaaagtg      60
tcgtgtaagg cgtcaggata caccttcacg ggatactaca tgcactgggt gcgccaggcc     120
ccgggccaag gactcgagtg gatgggctgg atcaaccta actctggagg caccaactac     180
gcccagaatt ccaaggcag agtgaccatg acccgggaca cctccatctc gactgcctat     240
atggaactgc ggcggctgcg ctcggacgat actgctgtgt attactgcgc cagcggctgg     300
gactttgact actggggaca gggtactctg gtgactgttt cctcgggagg aggcggatcg     360
ggtggaggag gtagcggggg aggggggtcg ggaggcggag gcagcgatat tgcatgact     420
caatcgccgt cctccctgag cgctagcgtg ggagatcgag tcaccatcac ttgcagagcg     480
tcacagtcga ttcgctacta cctgtcctgg taccagcaga accgggaaa ggcaccaaag     540
cttctgatct acacggcctc catcctgcaa aatggtgtcc catcaaggtt ctccgggtca     600
gggagcggca ctgacttcac tctcaccatc tcctcactcc agcccgagga ctttgcaacc     660
tactactgcc tccagacgta caccaccccg gatttcggtc ctggaaccaa ggtggaaatc     720
aaa            723
```

<210> SEQ ID NO 82
<211> LENGTH: 738
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 82

```
caagtccaac tcgtccaaag cggagcagaa gtcaaaaagc caggagcgtc ggtgaaagtg      60
tcttgcaaag ccagcggcta caccttcacg ggttactaca tgcactgggt gcgccaggcg     120
ccgggccagg ggctggagtg gatgggccgg attaaccecta acageggggg aactaattac     180
gctcagaagt tccagggtag agtcaccatg actacggaca cttccacttc caccgcctat     240
atggaactgc gctccctccg ctcagatgat actgccgtgt attactgcgc gcggactacc     300
acgtcatacg catttgacat ctggggccag ggaactatgg tgaccgtgag ctcgggcgga     360
ggcggttcag ggggaggagg aagcggagga ggaggatcgg gaggaggtgg ctccgatatc     420
cagctgactc agtccccgag caccctgtcg gcgtcggtgg gggacagggt taccatcacc     480
tgtagagctt cccaatccat ttcgacttgg ctggcctggt accagcaaaa gccgggaaag     540
gccectaatt tgcttatcta caaggcatcg accctcgaaa gcggtgtgcc ctcccggttt     600
tcgggatcag gatcagggac cgagttcacc ctgaccatct catccctcca gccggacgac     660
ttcgccactt actactgcca gcagtacaac acctactcgc catacacttt cggccaaggc     720
accaagctgg agatcaag                                                    738
```

<210> SEQ ID NO 83
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

```
caagttcaac tcgtgcaatc aggtggagga ctcgtcaaac ccggaggatc attgagactg      60
tcatgcgaag cgagcggttt tatcttctcc gattactata tgggatggat tcggcaggcc     120
ccgggaaagg gactcgaatg ggtgtcatac atcggaaggt caggctcgtc catgtactac     180
gcagactcgg tgaaaggcag attcaccttt agcegggaca cgccaagaa ttccctctac     240
ttgcagatga acagcctgcg agccgaggat actgctgtct actactgtgc cgcgtcgccg     300
gtggtggcag ctactgaaga tttccagcac tggggacagg gaactctggt cacggtgtcg     360
agcggtgggg gcggaagcgg aggcggagga tcgggcggcg gaggttcggg ggggggaggg     420
tctgacatcg tgatgaccca aaccccagcc acctgagcc tctccctgg agagcgcgcg     480
actctttcgt gccgcgcttc ccagtcagtg accagcaatt acttggcttg gtaccaacag     540
aagccgggac aggcgccacg gctgctgctt tttggtgcca gcactcgcgc caccggaatc     600
ccggatcgct tctcgggctc agggtccggg acggacttca ccctgactat caaccggctg     660
gaacctgagg acttcgcgat gtactactgc cagcagtacg gctccgcacc agtcactttc     720
ggacaaggca ccaagctgga gatcaag                                          747
```

<210> SEQ ID NO 84
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 84

```
caagtccaac tcgtccagtc gggagcagaa gttagagcac caggagcgtc agtgaaaatc      60
tcatgcaagg cctcgggctt cacgttccgc ggatactaca tccactgggt gcgccaagcc     120
ccgggtcagg gattggagtg gatgggaatc attaacccat caggagggag ccgggcttac     180
gcgcagaagt tccagggacg cgtcactatg acccgagata cttccacctc gactgtgtac     240
atggaactct cgtccctgag gtccgacgac actgcgatgt attactgtgc tcggactgcc     300
agctgcggtg gggactgtta ctacctcgat tactggggcc agggaactct ggtgaccgtg     360
tccagcggag gtggcgggtc agggggtggc ggaagcggag gcggcggttc aggcggagga     420
ggctcggaca tccaaatgac gcaatcgccg cctaccctga gcgcttccgt gggagatcgg     480
gtgaccatta cttgcagagc atccgagaac gtcaatatct ggctggcctg gtaccaacag     540
aagccgggga aggcccctaa actgctgatc tacaagtcga gcagccttgc ctctggagtg     600
ccctcccgct tctcgggctc gggatcagga gcggaattca ccctcaccat ctcctccctg     660
cagccagatg actttgccac ctactactgc cagcagtacc agagctatcc gttgaccttt     720
gggggaggca ctaaagtgga catcaag                                          747
```

<210> SEQ ID NO 85
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 85

```
caagttcaac tcgttcaatc aggtggagga ctcgtgcaac caggaagatc actcagactc      60
agctgcgccg cgtcgggatt cactttcgat gactacgcaa tgcactgggt gcggcaggcc     120
ccgggcaaag gactggaatg ggtgagcgga attagctgga actcggggtc catcgggtac     180
gccgactcgg tgaagggacg ctttacgatc tcccgggaca atgccaagaa ctccctgtat     240
ttgcagatga actccttgag ggctgaggac accgccgtgt actactgcgc taaagatgga     300
tcatcgtcct ggtcctgggg atacttcgat tactggggcc agggcactct ggtgaccgtg     360
tcgtcaggcg gtggagggtc gggcggagga ggtagcggag gcggagggag cagctctgaa     420
ctgacccaag accggcggt gtcggtcgcc cttggtcaga ctgtgcggac tacctgtcag     480
ggggacgcgc tgcgctcgta ctacgcttca tggtaccagc agaagcccgg acaggcacct     540
atgctggtca tctacggaaa gaataaccgc ccatccggca tccgggatcg cttctcgggt     600
tcggacagcg gcgacaccgc atccctgacg atcactggag cgcaggccga ggatgaagcc     660
gactactact gcaattcccg agattcaagc ggctaccctg tgtttgggac cggaactaag     720
gtcaccgtcc tg                                                          732
```

<210> SEQ ID NO 86
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 86

```
gaagtgcaac tcgtggaatc tggtggagga cttgtgcaac ctggaagatc gttgagactc    60
tcatgtgctg cctccgggtt cacctttgac gactacgcca tgcactgggt gcgccaggca   120
ccaggaaagg gtctggagtg ggtttcgggt atctcgtgga actccgggag cactggctac   180
gctgattcgg tgaaaggccg gtttaccatc tcccgagaca tgcgaagaa ttccctctat    240
ctgcagatga acagcctccg ggccgaggat actgccctgt actactgcgc caaggatagc   300
tcatcatggt acggaggtgg atcggctttc gatatctggg gccagggcac gatggtcacc   360
gtgtcctcgg ggggcggagg ctccggggga ggaggtagcg gaggaggagg atcgagctca   420
gagttgactc aagaacccgc agtgtccgtg gcactgggcc aaaccgtcag gatcacttgc   480
cagggagaca gcctgaggtc gtactacgcg tcctggtacc agcagaagcc gggacaggcc   540
ccggtcctgg tcattttcgg acgctcaaga cgcccatcgg gcatcccgga ccggttcagc   600
ggaagctcct cgggaaacac cgcgtcactt atcattaccg gcgcacaggc tgaggacgaa   660
gcggattact actgcaactc ccgcgacaat actgccaacc attacgtgtt cgggaccgga   720
acgaaactga ctgtcctg                                                738
```

<210> SEQ ID NO 87
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
gaagttcaat tggtggaatc tggaggagga cttgtgcaac ccggtagatc tctgagactg    60
tcctgtgcgg catcgggatt cacctttgac gactacgcta tgcactgggt gagacaagcc   120
cctggaaaag gactggagtg ggtgtcaggc atctcctgga atagcgggtc cactggatac   180
gccgattcgg tcaagggtcg cttcaccatt tcccgggaca tgccaagaa ctccctgtac    240
cttcaaatga actccctccg ggccgaggat accgccctct actactgcgc caaagacagc   300
tcgtcatggt atggcggagg gtcggcattt gacatctggg gacagggaac tatggtgact   360
gtgtcatcag gaggcggcgg aagcggcggc ggcgggtccg gcggaggagg gtcgtccagc   420
gaactcaccc aagatccagc agtgagcgtc gcgctgggcc agaccgtcag gatcacgtgc   480
cagggagatt cactgcgctc atactacgcg tcctggtacc agcagaagcc ggggcaggcc   540
ccggtcctcg tgatctacgg aaagaacaac cgcccgtcgg gtatcccaga ccgcttttcg   600
ggtagctcca gcggaaatac ggctagcctg accatcactg gagcacaggc tgaggatgaa   660
gcggactact actgcaattc gcggggctca tcggggaacc attacgtgtt cggaactggt   720
accaaggtga ctgtcctg                                                738
```

<210> SEQ ID NO 88
<211> LENGTH: 753
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
caagtgcagc tcgttcaatc aggcggagga ctcgttcaac caggaggatc attgcgactc    60
```

```
tcatgtgcgg cctctggatt cacgtttagc tcatattgga tgcactgggt gcggcaggcg    120
ccggggaaag gtctggtgtg ggtcagccgc atcaactcag acggctcctc gacttcgtac    180
gccgactccg tgaagggacg ctttaccatt tcccgcgaca acgccaagaa tacccttac     240 cttcagatga actccctccg cgctgaggat accgccgtgt actactgcgt gaggactggc    300
tgggtcggca gctactacta ctacatggac gtgtggggca aggaactac tgtcaccgtg     360 tcaagcggcg gtggaggttc cggcggggga ggatcggggg gggcggatc gggtggcgga     420 ggatcggaga tcgtgttgac ccagtcgccg gaaccctgt cgctgtcgcc tggggagaga     480
gcaactctgt cctgccgggc ttcccagtcg gtgtcgagca attacctggc atggtaccaa    540
cagaagccgg acagccgcc acgcctgctg atctatgacg tgtcaactcg gcaactgga     600 atccctgcgc ggttcagcgg cggagggagc ggtaccgatt tcaccctgac tatttcctcc    660
ctcgaaccag aagatttcgc cgtctactac tgccagcaga aagcaactg ccgccctgg     720 acgttcggac aaggaaccaa ggtcgaaatc aag                                 753

<210> SEQ ID NO 89
<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
caagtgcaat tggttcaatc aggaggagga gtcgtgcagc ccggaagatc gttgagactg    60
tcatgtgccg cgagcggctt tactttctca agctacggaa tgcattgggt gcgacaggct    120
ccgggaaaag gactggaatg ggtcgcagtg atctcatacg acggctcgaa caagtactac    180
gccgactccg tcaagggtcg gttcacgatt tcgcgcgata attccaagaa cactctgtac    240
ctccaaatga acagcctccg ggcagaggac accgccgtct actactgcgc taagggatac    300
tcgcgctact actactatgg aatggatgtg tggggccagg gaactaccgt gacggtgtcg    360
tccggcggcg gtgggtcggg cggaggcgga tcaggtggag gtggaagcgg aggaggaggg    420
agcgaaatcg tcatgactca gtcccctgct acccttctc tgtcgccggg agaaagagcc    480
atcctgagct gccgggcctc ccagagcgtg tacaccaaat acctgggatg gtaccagcag    540
aagccggggc aggcaccaag gctcctgatc tacgatgcgt ccacccgcgc gactggtatc    600
ccagaccgct tttccggctc ggggtcaggg actgacttca cccttactat caatcggctc    660
gagcctgagg atttcgccgt gtattactgc cagcactacg gagggtcccc gctgattacc    720
ttcggccaag gcaccaaagt ggacatcaag                                     750

<210> SEQ ID NO 90
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
caagtgcaac ttgttcaatc aggaggagga ctcgttcaac ccggaggatc actgcgactc    60
tcatgtgcag cgtcggggtt caccttctcc agctacgcaa tgtcctgggt gcgccaagcc    120
```

```
cctggaaaag gcctggagtg ggtgtcggcc atctctggga gcggggatc aacttactac      180 gctgactccg tcaagggccg ctttaccatc tcccgggaca acagcaagaa cactctctat      240
ctccagatga actcgctgag agccgaagat accgctgtct actactgcgc gaagagagaa      300
gctgccgcag gcacgattg gtacttcgac ttgtggggca gggcaccct tgtgaccgtg        360 tcctccggtg gaggcggatc aggaggtggg ggatcgggtg gaggaggaag cggaggcggc      420
ggttcggaca ttcgcgtcac ccagtcaccg agctccctca gcgcatcggt gggcgaccgg      480
gtcactatca cttgccgggc gtcccagtcg atctcatcgt atctgaattg gtaccagcag      540
aaaccgggaa aggcgccgaa gctgttgatc tacgctgcca gctccctgca gtcgggtgtg      600
ccatcacgct tttccggctc gggatcggga accgatttca ctctgacgat ctctagcctg      660
cagccagaag atttcgccac ttactactgc cagcagtcct acagcatccc tctgactttc      720
ggacaaggga cgaaagtgga gattaag                                          747

<210> SEQ ID NO 91
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
caagtccaac tcgttcagtc atgggcagaa gtcaagaaac ccggtgcaag cgtcaaagtg      60
tcgtgtaagg cctccggcta cactttcact tcctactaca tgcactgggt gcgccaagcc      120
ccgggacagg gccttgaatg gatgggcatc atcaacccat caggaggttc cacgagctac      180
gcgcagaagt tccaggggag agtgacgatg actagagata cctccacgag caccgtctac      240
atggagctgt cgaatctgcg gtcagaggac actgctgtgt attactgcgc gcgctccccg      300
cgggtgacca ctggctactt tgactactgg ggacaaggga ccctggtgac cgtcagctcg      360
ggaggcggag gatcgggagg tggagggtcc ggtggaggcg gctctggagg aggcgggtcg      420
gacattcaat tgacccagag cccatccacc ctctcagcct cggtggggga tagggtgact      480
atcacttgcc gggcctccca gtcaatttcc agctggctgg cttggtacca gcaaaagcct      540
ggaaaggcac cgaagctcct gatctacaag gcctcatctc tggaatcagg agtgccttcg      600
cgcttcagcg gaagcggctc gggaactgag tttaccctga ccatctcgag cctgcagcca      660
gatgacttcg cgacctatta ctgccagcag tactcgtcct acccgttgac tttcggagga      720
ggtacccgcc tcgaaatcaa a                                                741

<210> SEQ ID NO 92
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92
caagtccaac tcgtccagtc cggtgcagaa gtcagaaggc caggagcaag cgtgaagatc      60
tcgtgtagag cgtcaggaga caccagcact cgccattaca tccactggct gcgccaggct      120
ccgggccaag gccggagtg gatgggtgtg atcaacccga ctacgggacc ggctaccgga      180
agccctgcgt acgcacagat gctgcaggga cgggtgacta tgacccgcga tactagcact      240
```

```
aggaccgtgt acatggaact ccgctcgttg cggttcgaag ataccgccgt ctactactgc    300
gcccggtccg tggtgggccg aagcgcccct tactacttcg attactgggg acagggcact    360
ctggtgaccg ttagctccgg tgggggaggc tcgggtggag gcggatcggg aggaggaggc    420
agcggtggag ggggatcgga cattcagatg acccagtcac cctcctccct ctcagcctcg    480
gtcggggacc gggtgaccat tacgtgcaga gcctcacaag ggatctcgga ctactccgcc    540
tggtaccagc agaaaccggg aaaagcgcca aagctcctga tctacgccgc gagcaccctg    600
caatcaggag tgccatcgcg ctttctgga tcgggctcag ggactgactt cacgctgact    660
atctcctacc ttcagtccga ggatttcgct acctactact gccaacagta ttactcctat    720
cccctgacct tggcggagg cactaaggtg gacatcaag                           759
```

<210> SEQ ID NO 93
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
caagtccaac tccagcaatc gggagcagaa gtcaagaaac caggcgcatc ggtgaaagtg     60
tcgtgtaagg cgtcagggta caccttcacc aactactata tgcactgggt gcgccaggct    120
ccaggccagg ggttggagtg gatggggatc atcaatccgt caggtggcta caccacttac    180
gctcagaagt tccaggacg cctcactatg actcgcgata ctagcacctc cacggtgtac    240
atggaactgt catcgctgag gtccgaagat accgccgtct actactgcgc acggatcaga    300
tcctgcggag gagattgtta ctactttgac aactggggac agggcaccct tgttactgtg    360
tcatcgggag gaggggggaag cggaggaggt ggatcaggcg gcggtggcag cgggggcgga    420
ggatcggaca ttcagctgac tcagtccccc tccactttgt cggccagcgt gggagacaga    480
gtgaccatca cttgccgggc gtccgagaac gtcaatatct ggctggcctg gtaccagcaa    540
aagcctggaa aagccccgaa gctgctcatc tataagtcat ccagcctggc gtctggtgtg    600
ccgtcgcggt tctccggcag cgggagcgga gccgagttca ctctcaccat ttcgagcctt    660
caaccggacg atttcgccac ctactactgc cagcagtacc aatcctaccc tctgacgttt    720
ggaggtggaa ccaaggtgga catcaag                                        747
```

<210> SEQ ID NO 94
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
caaatcactc tgaaagaatc tggaccggcc ctggttaagc cgactcaaac gctcacccct     60
acttgcacct tcagcggatt ctcactcagc actgctggtg tgcacgtcgg atggattaga    120
cagccgcctg gaaaggccct ggaatggctc gccctcatct cctgggccga tgacaagaga    180
tacaggcccc gcttcgatc ccggttggac attacccggg tgacctcgaa agatcaggtg    240
gtgctctcaa tgaccaatat gcagccggag gacaccgcta cgtactactg cgcactgcaa    300
```

```
ggatttgacg gctacgaggc taactgggga ccaggtactc tggtcaccgt gagctccggc    360
gggggaggat caggcggggg ggggtcagga ggcggaggct ccgtggagg aggatcggat      420 atcgtcatga cccagtcccc aagctcgctg agcgcgtcag cgggcgaccg cgtgactatc    480
acttgccggg ccagccgcgg catctcctcc gcactggcgt ggtaccagca gaagcctgga    540
aaaccgccaa agctcctgat ctatgatgcc tccagcctgg agtcaggtgt ccccagccgc    600
ttctcgggtt cgggctcggg aaccgacttc actttgacca tcgactcgct ggaaccggaa    660
gatttcgcaa cctactactg tcagcagtcc tactcgaccc cttggacttt tggacaaggg    720
acgaaggtgg acatcaag                                                    738
```

<210> SEQ ID NO 95
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95

```
caagtccagc tccagcagtc gggcccagag ttggagaagc ctggggcgag cgtgaagatc     60
tcatgcaaag cctcaggcta ctcctttact ggatacacga tgaattgggt gaaacagtcg    120 catgaaagt cactggaatg gatcggtctg attacgccct acaacggcgc ctccagctac    180
aaccagaagt tcaggggaaa ggcgacccct actgtcgaca agtcgtcaag caccgcctac    240
atggacctcc tgtccctgac ctccgaagat agcgcggtct actttgtgc acgcggaggt    300 tacgatggac ggggattcga ctactggggc cagggaacca ctgtcaccgt gtcgagcgga    360
ggcggaggga gcgaggagg aggcagcgga ggtgagggt cggatatcga actcactcag    420
tccccagcaa tcatgtccgc ttcaccggga gaaaaggtga ccatgacttg ctcggcctcc    480
tcgtccgtgt catacatgca ctggtaccaa caaaaatcgg gacctcccc taagagatgg    540 atctacgata ccagcaaact ggcttcaggc gtgccgggac gcttctcggg ttcggggagc    600
ggaaattcgt attcgttgac catttcgtcc gtggaagccg aggacgacgc aacttattac    660
tgccaacagt ggtcaggcta cccgctcact ttcggagccg gcactaagct ggagatc      717
```

<210> SEQ ID NO 96
<211> LENGTH: 256
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

```
Ser Arg Ala Ala Gln Pro Ala Met Ala Gln Val Gln Leu Gln Gln Ser
1               5                   10                  15

Gly Ala Glu Leu Val Lys Pro Gly Ala Ser Val Lys Ile Ser Cys Lys
            20                  25                  30

Ala Ser Gly Tyr Ser Phe Thr Gly Tyr Phe Met Asn Trp Val Lys Gln
        35                  40                  45

Ser His Gly Lys Ser Leu Glu Trp Ile Gly Arg Ile His Pro Tyr Asp
    50                  55                  60

Gly Asp Thr Phe Tyr Asn Gln Asn Phe Lys Asp Lys Ala Thr Leu Thr
65                  70                  75                  80
```

Val Asp Lys Ser Ser Asn Thr Ala His Met Glu Leu Leu Ser Leu Thr
            85                  90                  95

Ser Glu Asp Phe Ala Val Tyr Tyr Cys Thr Arg Tyr Asp Gly Ser Arg
            100                 105                 110

Ala Met Asp Tyr Trp Gly Gln Gly Thr Thr Val Thr Val Ser Ser Gly
            115                 120                 125

Gly Gly Gly Ser Gly Gly Gly Gly Ser Gly Gly Gly Gly Ser Asp Ile
130                 135                 140

Glu Leu Thr Gln Ser Pro Ala Ser Leu Ala Val Ser Leu Gly Gln Arg
145                 150                 155                 160

Ala Ile Ile Ser Cys Lys Ala Ser Gln Ser Val Ser Phe Ala Gly Thr
            165                 170                 175

Ser Leu Met His Trp Tyr His Gln Lys Pro Gly Gln Gln Pro Lys Leu
            180                 185                 190

Leu Ile Tyr Arg Ala Ser Asn Leu Glu Ala Gly Val Pro Thr Arg Phe
            195                 200                 205

Ser Gly Ser Gly Ser Lys Thr Asp Phe Thr Leu Asn Ile His Pro Val
            210                 215                 220

Glu Glu Glu Asp Ala Ala Thr Tyr Tyr Cys Gln Gln Ser Arg Glu Tyr
225                 230                 235                 240

Pro Tyr Thr Phe Gly Gly Gly Thr Lys Leu Glu Ile Lys Arg Ala Ala
            245                 250                 255

<210> SEQ ID NO 97
<211> LENGTH: 768
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
tctagagcgg cccagccggc catggcccag gtgcagctgc agcagtctgg agctgagctg      60
gtgaagcctg ggcttcagt gaagatatcc tgcaaggctt ctggttactc atttactggc     120
tactttatga actgggtgaa gcagagccat ggaaagagcc ttagtggat tggacgtatt     180 catccttacg atggtgatac tttctacaac cagaacttca aggacaaggc cacattgact     240
gtagacaaat cctctaacac agcccacatg agctcctga cctgacatc tgaggacttt     300 gcagtctatt attgtacaag atacgacggt agtcgggcta tggactactg gggccaaggg     360
accacggtca ccgtctcctc aggtggaggc ggttcaggcg gaggtggctc tggcggtggc     420
ggatcggaca tcgagctcac tcagtctcca gcttctttgg ctgtgtctct agggcagagg     480
gccatcatct cctgcaaggc cagccaaagt gtcagttttg ctggtactag tttaatgcac     540
tggtaccacc agaaaccagg acagcaaccc aaactcctca tctatcgtgc atccaaccta     600
gaagctgggg ttcctaccag gtttagtggc agtgggtcta agacagactt cacccctcaat     660 atccatcctg tggaggagga ggatgctgca acctattact gtcagcaaag tagggaatat     720
ccgtacacgt tcggagggg gacaaagttg gaaataaaac gggcggcc                  768

<210> SEQ ID NO 98
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 98

```
Gln Leu Val Glu Ser Gly Gly Gly Leu Val Gln Pro Gly Arg Ser Leu
1               5                   10                  15
Arg Leu Ser Cys Thr Thr Ser Gly Phe Thr Phe Gly Asp Tyr Ala Met
            20                  25                  30
Ile Trp Ala Arg Gln Ala Pro Gly Lys Gly Leu Glu Trp Val Ser Ser
        35                  40                  45
Ile Ser Ser Ser Ser Tyr Ile Tyr Tyr Ala Asp Ser Val Lys Gly
    50                  55                  60
Arg Phe Thr Ile Ser Arg Asp Asn Ala Lys Asn Ser Leu Tyr Leu Gln
65                  70                  75                  80
Met Asn Ser Leu Arg Ala Glu Asp Thr Ala Val Tyr Tyr Cys Ala Arg
                85                  90                  95
Glu Arg Tyr Asp Phe Trp Ser Gly Met Asp Val Trp Gly Lys Gly Thr
            100                 105                 110
Thr Val Thr Val Ser Ser Gly Gly Gly Gly Ser Gly Gly Gly Gly Ser
        115                 120                 125
Gly Gly Ser Ala Gln Ser Ala Leu Thr Gln Pro Ala Ser Val Ser Gly
    130                 135                 140
Ser Pro Gly Gln Ser Ile Thr Ile Ser Cys Thr Gly Thr Ser Ser Asp
145                 150                 155                 160
Val Gly Ser Tyr Asn Leu Val Ser Trp Tyr Gln Gln His Pro Gly Lys
                165                 170                 175
Ala Pro Lys Leu Met Ile Tyr Glu Gly Ser Lys Arg Pro Ser Gly Val
            180                 185                 190
Ser Asn Arg Phe Ser Gly Ser Lys Ser Gly Asn Ala Ala Ser Leu Thr
        195                 200                 205
Ile Ser Gly Leu Gln Ala Glu Asp Glu Ala Asp Tyr Tyr Cys Gln Ser
    210                 215                 220
Tyr Asp Ser Ser Leu Ser Val Val Phe Gly Gly Gly Thr Lys Leu Thr
225                 230                 235                 240
Val Leu Gly
```

<210> SEQ ID NO 99
<211> LENGTH: 729
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

```
cagctggtgg agtctggggg aggcttggta cagccagggc ggtccctgag actctcctgc    60
acaacttctg gattcacttt tggtgattat gctatgatct gggcccgcca ggctccaggg   120
aaggggctgg agtgggtctc atccattagt agtagtagta gttacatata ctacgcagac   180
tcagtgaagg gccgattcac catctccaga gacaacgcca agaactcact gtatctgcaa   240
atgaacagcc tgagagccga ggacacggct gtgtattact gtgcgagaga acgatacgat   300
ttttggagtg gaatggacgt ctggggcaaa gggaccacgg tcaccgtctc gagtggtgga   360
ggcggttcag gcgagggtgg ctctggcggt agtgcacagt ctgccctgac tcagcctgcc   420
tccgtgtctg ggtctcctgg acagtcgatc accatctcct gcactggaac cagcagtgat   480
```

```
gttgggagtt ataaccttgt ctcctggtac aacagcacc caggcaaagc ccccaaactc     540
atgatttatg agggcagtaa gcggccctca ggggtttcta atcgcttctc tggctccaag     600
tctggcaacg cggcctccct gacaatctct gggctccagg ctgaggacga ggctgattat     660
tactgccagt cctatgacag cagcctgagt gtggtattcg gcggagggac caagctgacc     720
gtcctaggt                                                             729
```

<210> SEQ ID NO 100
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 100

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Arg Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Glu Asp Thr
            100                 105                 110

Ala Val Tyr Tyr Cys Ala Arg Gly Arg Tyr Tyr Gly Met Asp Val Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Ser Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Ile Ser Cys Arg Ala Ser Gln Ser Val Ser Ser Asn Phe Ala
            180                 185                 190

Trp Tyr Gln Gln Arg Pro Gly Gln Ala Pro Arg Leu Leu Ile Tyr Asp
        195                 200                 205

Ala Ser Asn Arg Ala Thr Gly Ile Pro Pro Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Ala Tyr Tyr Cys His Gln Arg Ser Asn Trp Leu Tyr Thr Phe
                245                 250                 255

Gly Gln Gly Thr Lys Val Asp Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300
```

Leu Asp Phe Ala Cys Asp Ile Tyr Ile Trp Ala Pro Leu Ala Gly Thr
305                 310                 315                 320

Cys Gly Val Leu Leu Ser Leu Val Ile Thr Leu Tyr Cys Lys Arg
            325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 101
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp Leu Arg Arg Thr Val Val Thr Pro
        115                 120                 125

Arg Ala Tyr Tyr Gly Met Asp Val Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Gln Leu Thr Gln Ser Pro Ser

```
                    165                 170                 175

Thr Leu Ser Ala Ser Val Gly Asp Arg Val Thr Ile Thr Cys Gln Ala
                180                 185                 190

Ser Gln Asp Ile Ser Asn Ser Leu Asn Trp Tyr Gln Gln Lys Ala Gly
            195                 200                 205

Lys Ala Pro Lys Leu Leu Ile Tyr Asp Ala Ser Thr Leu Glu Thr Gly
        210                 215                 220

Val Pro Ser Arg Phe Ser Gly Ser Gly Ser Gly Thr Asp Phe Ser Phe
225                 230                 235                 240

Thr Ile Ser Ser Leu Gln Pro Glu Asp Ile Ala Thr Tyr Tyr Cys Gln
                245                 250                 255

Gln His Asp Asn Leu Pro Leu Thr Phe Gly Gln Gly Thr Lys Val Glu
                260                 265                 270

Ile Lys Thr Thr Thr Pro Ala Pro Arg Pro Pro Thr Pro Ala Pro Thr
            275                 280                 285

Ile Ala Ser Gln Pro Leu Ser Leu Arg Pro Glu Ala Cys Arg Pro Ala
        290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
                340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
        370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Gly Arg Asp Pro Glu Met Gly Gly
                420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 102
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Met Ala Leu Pro Val Thr Ala Leu Leu Leu Pro Leu Ala Leu Leu Leu
1               5                   10                  15
```

```
His Ala Ala Arg Pro Gln Val Gln Leu Val Gln Ser Gly Ala Glu Val
             20                  25                  30
Lys Lys Pro Gly Ala Pro Val Lys Val Ser Cys Lys Ala Ser Gly Tyr
         35                  40                  45
Thr Phe Thr Gly Tyr Tyr Met His Trp Val Arg Gln Ala Pro Gly Gln
     50                  55                  60
Gly Leu Glu Trp Met Gly Trp Ile Asn Pro Asn Ser Gly Gly Thr Asn
 65                  70                  75                  80
Tyr Ala Gln Lys Phe Gln Gly Arg Val Thr Met Thr Arg Asp Thr Ser
                 85                  90                  95
Ile Ser Thr Ala Tyr Met Glu Leu Ser Arg Leu Arg Ser Asp Asp Thr
            100                 105                 110
Ala Val Tyr Tyr Cys Ala Arg Gly Glu Trp Asp Gly Ser Tyr Tyr Tyr
        115                 120                 125
Asp Tyr Trp Gly Gln Gly Thr Leu Val Thr Val Ser Ser Gly Gly Gly
    130                 135                 140
Gly Ser Gly Gly Gly Gly Ser Gly Gly Gly Gly Ser Gly Gly Gly Gly
145                 150                 155                 160
Ser Asp Ile Val Leu Thr Gln Thr Pro Ser Ser Leu Ser Ala Ser Val
                165                 170                 175
Gly Asp Arg Val Thr Ile Thr Cys Arg Ala Ser Gln Ser Ile Asn Thr
            180                 185                 190
Tyr Leu Asn Trp Tyr Gln His Lys Pro Gly Lys Ala Pro Lys Leu Leu
        195                 200                 205
Ile Tyr Ala Ala Ser Ser Leu Gln Ser Gly Val Pro Ser Arg Phe Ser
    210                 215                 220
Gly Ser Gly Ser Gly Thr Asp Phe Thr Leu Thr Ile Ser Ser Leu Gln
225                 230                 235                 240
Pro Glu Asp Phe Ala Thr Tyr Tyr Cys Gln Gln Ser Phe Ser Pro Leu
                245                 250                 255
Thr Phe Gly Gly Gly Thr Lys Leu Glu Ile Lys Thr Thr Thr Pro Ala
            260                 265                 270
Pro Arg Pro Pro Thr Pro Ala Pro Thr Ile Ala Ser Gln Pro Leu Ser
        275                 280                 285
Leu Arg Pro Glu Ala Cys Arg Pro Ala Ala Gly Gly Ala Val His Thr
    290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Lys Arg Gly Arg Lys Lys Leu Leu Tyr Ile Phe Lys Gln Pro Phe Met
            340                 345                 350
Arg Pro Val Gln Thr Thr Gln Glu Glu Asp Gly Cys Ser Cys Arg Phe
        355                 360                 365
Pro Glu Glu Glu Glu Gly Gly Cys Glu Leu Arg Val Lys Phe Ser Arg
    370                 375                 380
Ser Ala Asp Ala Pro Ala Tyr Lys Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
            420                 425                 430
Gln Glu Gly Leu Tyr Asn Glu Leu Gln Lys Asp Lys Met Ala Glu Ala
```

```
                435                 440                 445
Tyr Ser Glu Ile Gly Met Lys Gly Glu Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 103
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Trp Met His Trp Val Arg Gln Val Pro Gly Lys
    50                  55                  60

Gly Leu Val Trp Val Ser Arg Ile Asn Thr Asp Gly Ser Thr Thr Thr
65                  70                  75                  80

Tyr Ala Asp Ser Val Glu Gly Arg Phe Thr Ile Ser Arg Asp Asn Ala
                85                  90                  95

Lys Asn Thr Leu Tyr Leu Gln Met Asn Ser Leu Arg Asp Asp Asp Thr
            100                 105                 110

Ala Val Tyr Tyr Cys Val Gly Gly His Trp Ala Val Trp Gly Gln Gly
        115                 120                 125

Thr Thr Val Thr Val Ser Ser Gly Gly Gly Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Thr Leu Ser Ala Ser Val Gly Asp Arg Val Thr Ile
                165                 170                 175

Thr Cys Arg Ala Ser Gln Ser Ile Ser Asp Arg Leu Ala Trp Tyr Gln
            180                 185                 190

Gln Lys Pro Gly Lys Ala Pro Lys Leu Leu Ile Tyr Lys Ala Ser Ser
        195                 200                 205

Leu Glu Ser Gly Val Pro Ser Arg Phe Ser Gly Ser Gly Ser Gly Thr
    210                 215                 220

Glu Phe Thr Leu Thr Ile Ser Ser Leu Gln Pro Asp Asp Phe Ala Val
225                 230                 235                 240

Tyr Tyr Cys Gln Gln Tyr Gly His Leu Pro Met Tyr Thr Phe Gly Gln
                245                 250                 255

Gly Thr Lys Val Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300
```

```
Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 104
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Glu Lys Pro Gly Ala Ser Val Lys Val Ser Cys Lys Ala Ser Gly Tyr
        35                  40                  45

Thr Phe Thr Asp Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Ser Gly Trp Asp Phe Asp Tyr Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Gly Gly Gly Gly Ser Asp Ile Val Met
145                 150                 155                 160
```

Thr Gln Ser Pro Ser Ser Leu Ser Ala Ser Val Gly Asp Arg Val Thr
                165                 170                 175

Ile Thr Cys Arg Ala Ser Gln Ser Ile Arg Tyr Tyr Leu Ser Trp Tyr
            180                 185                 190

Gln Gln Lys Pro Gly Lys Ala Pro Lys Leu Leu Ile Tyr Thr Ala Ser
        195                 200                 205

Ile Leu Gln Asn Gly Val Pro Ser Arg Phe Ser Gly Ser Gly Ser Gly
    210                 215                 220

Thr Asp Phe Thr Leu Thr Ile Ser Ser Leu Gln Pro Glu Asp Phe Ala
225                 230                 235                 240

Thr Tyr Tyr Cys Leu Gln Thr Tyr Thr Thr Pro Asp Phe Gly Pro Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 105
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val

-continued

Lys Lys Pro Gly Ala Ser Val Lys Val Ser Cys Lys Ala Ser Gly Tyr
            20                  25                  30
Thr Phe Thr Ser Tyr Tyr Met His Trp Val Arg Gln Ala Pro Gly Gln
    35                  40                  45
Gly Leu Glu Trp Met Gly Ile Ile Asn Pro Ser Gly Gly Ser Thr Ser
65                  70                  75                  80
Tyr Ala Gln Lys Phe Gln Gly Arg Val Thr Met Thr Arg Asp Thr Ser
                85                  90                  95
Thr Ser Thr Val Tyr Met Glu Leu Ser Ser Leu Arg Ser Glu Asp Thr
            100                 105                 110
Ala Val Tyr Tyr Cys Ala Arg Tyr Arg Leu Ile Ala Val Ala Gly Asp
        115                 120                 125
Tyr Tyr Tyr Tyr Gly Met Asp Val Trp Gly Gln Gly Thr Met Val Thr
    130                 135                 140
Val Ser Ser Gly Gly Gly Gly Ser Gly Gly Gly Gly Ser Gly Gly Gly
145                 150                 155                 160
Gly Ser Gly Gly Gly Gly Ser Asp Ile Gln Met Thr Gln Ser Pro Ser
                165                 170                 175
Ser Val Ser Ala Ser Val Gly Asp Arg Val Thr Ile Thr Cys Arg Ala
            180                 185                 190
Ser Gln Gly Val Gly Arg Trp Leu Ala Trp Tyr Gln Gln Lys Pro Gly
        195                 200                 205
Thr Ala Pro Lys Leu Leu Ile Tyr Ala Ala Ser Thr Leu Gln Ser Gly
    210                 215                 220
Val Pro Ser Arg Phe Ser Gly Ser Gly Ser Gly Thr Asp Phe Thr Leu
225                 230                 235                 240
Thr Ile Asn Asn Leu Gln Pro Glu Asp Phe Ala Thr Tyr Tyr Cys Gln
                245                 250                 255
Gln Ala Asn Ser Phe Pro Leu Thr Phe Gly Gly Gly Thr Arg Leu Glu
            260                 265                 270
Ile Lys Thr Thr Thr Pro Ala Pro Arg Pro Pro Thr Pro Ala Pro Thr
        275                 280                 285
Ile Ala Ser Gln Pro Leu Ser Leu Arg Pro Glu Ala Cys Arg Pro Ala
    290                 295                 300
Ala Gly Gly Ala Val His Thr Arg Gly Leu Asp Phe Ala Cys Asp Ile
305                 310                 315                 320
Tyr Ile Trp Ala Pro Leu Ala Gly Thr Cys Gly Val Leu Leu Leu Ser
                325                 330                 335
Leu Val Ile Thr Leu Tyr Cys Lys Arg Gly Arg Lys Lys Leu Leu Tyr
            340                 345                 350
Ile Phe Lys Gln Pro Phe Met Arg Pro Val Gln Thr Thr Gln Glu Glu
        355                 360                 365
Asp Gly Cys Ser Cys Arg Phe Pro Glu Glu Glu Glu Gly Gly Cys Glu
    370                 375                 380
Leu Arg Val Lys Phe Ser Arg Ser Ala Asp Ala Pro Ala Tyr Lys Gln
385                 390                 395                 400
Gly Gln Asn Gln Leu Tyr Asn Glu Leu Asn Leu Gly Arg Arg Glu Glu
                405                 410                 415
Tyr Asp Val Leu Asp Lys Arg Arg Gly Arg Asp Pro Glu Met Gly Gly
            420                 425                 430
Lys Pro Arg Arg Lys Asn Pro Gln Glu Gly Leu Tyr Asn Glu Leu Gln
        435                 440                 445

```
Lys Asp Lys Met Ala Glu Ala Tyr Ser Glu Ile Gly Met Lys Gly Glu
            450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 106
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Ala Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Trp Lys Val Ser Ser Ser Ser Pro Ala
        115                 120                 125

Phe Asp Tyr Trp Gly Gln Gly Thr Leu Val Thr Val Ser Ser Gly Gly
130                 135                 140

Gly Gly Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Ile Leu Ser Cys Arg Ala Ser Gln Ser Val Tyr
            180                 185                 190

Thr Lys Tyr Leu Gly Trp Tyr Gln Gln Lys Pro Gly Gln Ala Pro Arg
        195                 200                 205

Leu Leu Ile Tyr Asp Ala Ser Thr Arg Ala Thr Gly Ile Pro Asp Arg
210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Val Tyr Tyr Cys Gln His Tyr Gly Gly
                245                 250                 255

Ser Pro Leu Ile Thr Phe Gly Gln Gly Thr Arg Leu Glu Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
```

```
                290                 295                 300
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Ser Leu Val Ile
                325                 330                 335

Thr Leu Tyr Cys Lys Arg Gly Arg Lys Leu Leu Tyr Ile Phe Lys
                340                 345                 350

Gln Pro Phe Met Arg Pro Val Gln Thr Thr Gln Glu Glu Asp Gly Cys
            355                 360                 365

Ser Cys Arg Phe Pro Glu Glu Glu Glu Gly Gly Cys Glu Leu Arg Val
        370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 107
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
                20                  25                  30

Lys Lys Pro Gly Ala Ser Val Lys Val Ser Cys Lys Thr Ser Gly Tyr
            35                  40                  45

Pro Phe Thr Gly Tyr Ser Leu His Trp Val Arg Gln Ala Pro Gly Gln
        50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
                100                 105                 110

Ala Val Tyr Tyr Cys Ala Arg Asp His Tyr Gly Gly Asn Ser Leu Phe
            115                 120                 125

Tyr Trp Gly Gln Gly Thr Leu Val Thr Val Ser Ser Gly Gly Gly Gly
        130                 135                 140

Ser Gly Gly Gly Gly Ser Gly Gly Gly Gly Ser Gly Gly Gly Gly Ser
145                 150                 155                 160
```

-continued

Asp Ile Gln Leu Thr Gln Ser Pro Ser Ser Ile Ser Ala Ser Val Gly
                165                 170                 175

Asp Thr Val Ser Ile Thr Cys Arg Ala Ser Gln Asp Ser Gly Thr Trp
            180                 185                 190

Leu Ala Trp Tyr Gln Gln Lys Pro Gly Lys Ala Pro Asn Leu Leu Met
        195                 200                 205

Tyr Asp Ala Ser Thr Leu Glu Asp Gly Val Pro Ser Arg Phe Ser Gly
    210                 215                 220

Ser Ala Ser Gly Thr Glu Phe Thr Leu Thr Val Asn Arg Leu Gln Pro
225                 230                 235                 240

Glu Asp Ser Ala Thr Tyr Tyr Cys Gln Gln Tyr Asn Ser Tyr Pro Leu
                245                 250                 255

Thr Phe Gly Gly Gly Thr Lys Val Asp Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 108
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Met Ala Leu Pro Val Thr Ala Leu Leu Leu Pro Leu Ala Leu Leu Leu
1               5                   10                  15

-continued

His Ala Ala Arg Pro Gln Val Gln Leu Val Gln Ser Gly Ala Glu Val
             20                  25                  30

Lys Lys Pro Gly Ala Ser Val Glu Val Ser Cys Lys Ala Ser Gly Tyr
         35                  40                  45

Thr Phe Thr Ser Tyr Tyr Met His Trp Val Arg Gln Ala Pro Gly Gln
     50                  55                  60

Gly Leu Glu Trp Met Gly Ile Ile Asn Pro Ser Gly Gly Ser Thr Gly
65                  70                  75                  80

Tyr Ala Gln Lys Phe Gln Gly Arg Val Thr Met Thr Arg Asp Thr Ser
                 85                  90                  95

Thr Ser Thr Val His Met Glu Leu Ser Ser Leu Arg Ser Glu Asp Thr
             100                 105                 110

Ala Val Tyr Tyr Cys Ala Arg Gly Gly Tyr Ser Ser Ser Asp Ala
         115                 120                 125

Phe Asp Ile Trp Gly Gln Gly Thr Met Val Thr Val Ser Ser Gly Gly
     130                 135                 140

Gly Gly Ser Gly Gly Gly Gly Ser Gly Gly Gly Gly Ser Gly Gly Gly
145                 150                 155                 160

Gly Ser Asp Ile Gln Met Thr Gln Ser Pro Pro Ser Leu Ser Ala Ser
                 165                 170                 175

Val Gly Asp Arg Val Thr Ile Thr Cys Arg Ala Ser Gln Asp Ile Ser
             180                 185                 190

Ser Ala Leu Ala Trp Tyr Gln Gln Lys Pro Gly Thr Pro Pro Lys Leu
         195                 200                 205

Leu Ile Tyr Asp Ala Ser Ser Leu Glu Ser Gly Val Pro Ser Arg Phe
     210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Phe Ser Ser Tyr
                 245                 250                 255

Pro Leu Thr Phe Gly Gly Gly Thr Arg Leu Glu Ile Lys Thr Thr Thr
             260                 265                 270

Pro Ala Pro Arg Pro Pro Thr Pro Ala Pro Thr Ile Ala Ser Gln Pro
         275                 280                 285

Leu Ser Leu Arg Pro Glu Ala Cys Arg Pro Ala Ala Gly Gly Ala Val
     290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                 325                 330                 335

Tyr Cys Lys Arg Gly Arg Lys Lys Leu Leu Tyr Ile Phe Lys Gln Pro
             340                 345                 350

Phe Met Arg Pro Val Gln Thr Thr Gln Glu Glu Asp Gly Cys Ser Cys
         355                 360                 365

Arg Phe Pro Glu Glu Glu Gly Gly Cys Glu Leu Arg Val Lys Phe
     370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                 405                 410                 415

Lys Arg Arg Gly Arg Asp Pro Glu Met Gly Gly Lys Pro Arg Arg Lys
             420                 425                 430

Asn Pro Gln Glu Gly Leu Tyr Asn Glu Leu Gln Lys Asp Lys Met Ala

```
                    435                 440                 445
Glu Ala Tyr Ser Glu Ile Gly Met Lys Gly Glu Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 109
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Ser Tyr Gly Ile Ser Trp Val Arg Gln Ala Pro Gly Gln
        50                  55                  60

Gly Leu Glu Trp Met Gly Trp Ile Ser Ala Tyr Asn Gly Asn Thr Asn
65                  70                  75                  80

Tyr Ala Gln Lys Leu Gln Gly Arg Val Thr Met Thr Thr Asp Thr Ser
                85                  90                  95

Thr Ser Thr Ala Tyr Met Glu Leu Arg Ser Leu Arg Ser Asp Asp Thr
            100                 105                 110

Ala Val Tyr Tyr Cys Ala Arg Val Ala Gly Gly Ile Tyr Tyr Tyr Tyr
        115                 120                 125

Gly Met Asp Val Trp Gly Gln Gly Thr Thr Ile Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Val Met Thr Gln Thr Pro Asp Ser Leu Ala Val
                165                 170                 175

Ser Leu Gly Glu Arg Ala Thr Ile Ser Cys Lys Ser Ser His Ser Val
            180                 185                 190

Leu Tyr Asn Arg Asn Asn Lys Asn Tyr Leu Ala Trp Tyr Gln Gln Lys
        195                 200                 205

Pro Gly Gln Pro Pro Lys Leu Leu Phe Tyr Trp Ala Ser Thr Arg Lys
    210                 215                 220

Ser Gly Val Pro Asp Arg Phe Ser Gly Ser Gly Ser Gly Thr Asp Phe
225                 230                 235                 240

Thr Leu Thr Ile Ser Ser Leu Gln Pro Glu Asp Phe Ala Thr Tyr Phe
                245                 250                 255

Cys Gln Gln Thr Gln Thr Phe Pro Leu Thr Phe Gly Gly Gly Thr Arg
            260                 265                 270

Leu Glu Ile Asn Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300
```

```
Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
            325                 330                 335

Leu Ser Leu Val Ile Thr Leu Tyr Cys Lys Arg Gly Arg Lys Lys Leu
        340                 345                 350

Leu Tyr Ile Phe Lys Gln Pro Phe Met Arg Pro Val Gln Thr Thr Gln
            355                 360                 365

Glu Glu Asp Gly Cys Ser Cys Arg Phe Pro Glu Glu Glu Glu Gly Gly
        370                 375                 380

Cys Glu Leu Arg Val Lys Phe Ser Arg Ser Ala Asp Ala Pro Ala Tyr
385                 390                 395                 400

Lys Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 110
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Gly Tyr Tyr Met His Trp Val Arg Gln Ala Pro Gly Gln
        50                  55                  60

Gly Leu Glu Trp Met Gly Trp Ile Asn Pro Asn Ser Gly Gly Thr Asn
65                  70                  75                  80

Tyr Ala Gln Asn Phe Gln Gly Arg Val Thr Met Thr Arg Asp Thr Ser
                85                  90                  95

Ile Ser Thr Ala Tyr Met Glu Leu Arg Arg Leu Arg Ser Asp Asp Thr
            100                 105                 110

Ala Val Tyr Tyr Cys Ala Ser Gly Trp Asp Phe Asp Tyr Trp Gly Gln
        115                 120                 125

Gly Thr Leu Val Thr Val Ser Ser Gly Gly Gly Ser Gly Gly Gly Gly
    130                 135                 140

Gly Ser Gly Gly Gly Gly Ser Gly Gly Gly Gly Ser Asp Ile Arg Met
```

```
            145                 150                 155                 160
Thr Gln Ser Pro Ser Ser Leu Ser Ala Ser Val Gly Asp Arg Val Thr
                165                 170                 175
Ile Thr Cys Arg Ala Ser Gln Ser Ile Arg Tyr Tyr Leu Ser Trp Tyr
                180                 185                 190
Gln Gln Lys Pro Gly Lys Ala Pro Lys Leu Leu Ile Tyr Thr Ala Ser
                195                 200                 205
Ile Leu Gln Asn Gly Val Pro Ser Arg Phe Ser Gly Ser Gly Ser Gly
                210                 215                 220
Thr Asp Phe Thr Leu Thr Ile Ser Ser Leu Gln Pro Glu Asp Phe Ala
225                 230                 235                 240
Thr Tyr Tyr Cys Leu Gln Thr Tyr Thr Thr Pro Asp Phe Gly Pro Gly
                245                 250                 255
Thr Lys Val Glu Ile Lys Thr Thr Thr Pro Ala Pro Arg Pro Pro Thr
                260                 265                 270
Pro Ala Pro Thr Ile Ala Ser Gln Pro Leu Ser Leu Arg Pro Glu Ala
                275                 280                 285
Cys Arg Pro Ala Ala Gly Gly Ala Val His Thr Arg Gly Leu Asp Phe
                290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Lys Arg Gly Arg Lys
                325                 330                 335
Lys Leu Leu Tyr Ile Phe Lys Gln Pro Phe Met Arg Pro Val Gln Thr
                340                 345                 350
Thr Gln Glu Glu Asp Gly Cys Ser Cys Arg Phe Pro Glu Glu Glu Glu
                355                 360                 365
Gly Gly Cys Glu Leu Arg Val Lys Phe Ser Arg Ser Ala Asp Ala Pro
                370                 375                 380
Ala Tyr Lys Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
                405                 410                 415
Glu Met Gly Gly Lys Pro Arg Arg Lys Asn Pro Gln Glu Gly Leu Tyr
                420                 425                 430
Asn Glu Leu Gln Lys Asp Lys Met Ala Glu Ala Tyr Ser Glu Ile Gly
                435                 440                 445
Met Lys Gly Glu Arg Arg Arg Gly Lys Gly His Asp Gly Leu Tyr Gln
                450                 455                 460
Gly Leu Ser Thr Ala Thr Lys Asp Thr Tyr Asp Ala Leu His Met Gln
465                 470                 475                 480
Ala Leu Pro Pro Arg
                485

<210> SEQ ID NO 111
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Met Ala Leu Pro Val Thr Ala Leu Leu Leu Pro Leu Ala Leu Leu Leu
1               5                   10                  15
```

His Ala Ala Arg Pro Gln Val Gln Leu Val Gln Ser Gly Ala Glu Val
                20                  25                  30
Lys Lys Pro Gly Ala Ser Val Lys Val Ser Cys Lys Ala Ser Gly Tyr
                35                  40                  45
Thr Phe Thr Gly Tyr Tyr Met His Trp Val Arg Gln Ala Pro Gly Gln
 50                  55                  60
Gly Leu Glu Trp Met Gly Arg Ile Asn Pro Asn Ser Gly Gly Thr Asn
 65                  70                  75                  80
Tyr Ala Gln Lys Phe Gln Gly Arg Val Thr Met Thr Thr Asp Thr Ser
                 85                  90                  95
Thr Ser Thr Ala Tyr Met Glu Leu Arg Ser Leu Arg Ser Asp Asp Thr
                100                 105                 110
Ala Val Tyr Tyr Cys Ala Arg Thr Thr Thr Ser Tyr Ala Phe Asp Ile
                115                 120                 125
Trp Gly Gln Gly Thr Met Val Thr Val Ser Ser Gly Gly Gly Gly Ser
130                 135                 140
Gly Gly Gly Gly Ser Gly Gly Gly Ser Gly Gly Gly Gly Ser Asp
145                 150                 155                 160
Ile Gln Leu Thr Gln Ser Pro Ser Thr Leu Ser Ala Ser Val Gly Asp
                165                 170                 175
Arg Val Thr Ile Thr Cys Arg Ala Ser Gln Ser Ile Ser Thr Trp Leu
                180                 185                 190
Ala Trp Tyr Gln Gln Lys Pro Gly Lys Ala Pro Asn Leu Leu Ile Tyr
                195                 200                 205
Lys Ala Ser Thr Leu Glu Ser Gly Val Pro Ser Arg Phe Ser Gly Ser
                210                 215                 220
Gly Ser Gly Thr Glu Phe Thr Leu Thr Ile Ser Ser Leu Gln Pro Asp
225                 230                 235                 240
Asp Phe Ala Thr Tyr Tyr Cys Gln Gln Tyr Asn Thr Tyr Ser Pro Tyr
                245                 250                 255
Thr Phe Gly Gln Gly Thr Lys Leu Glu Ile Lys Thr Thr Thr Pro Ala
                260                 265                 270
Pro Arg Pro Pro Thr Pro Ala Pro Thr Ile Ala Ser Gln Pro Leu Ser
                275                 280                 285
Leu Arg Pro Glu Ala Cys Arg Pro Ala Ala Gly Gly Ala Val His Thr
                290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Lys Arg Gly Arg Lys Lys Leu Leu Tyr Ile Phe Lys Gln Pro Phe Met
                340                 345                 350
Arg Pro Val Gln Thr Thr Gln Glu Glu Asp Gly Cys Ser Cys Arg Phe
                355                 360                 365
Pro Glu Glu Glu Glu Gly Gly Cys Glu Leu Arg Val Lys Phe Ser Arg
                370                 375                 380
Ser Ala Asp Ala Pro Ala Tyr Lys Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
                420                 425                 430

-continued

```
Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 112
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Lys Pro Gly Gly Ser Leu Arg Leu Ser Cys Glu Ala Ser Gly Phe
        35                  40                  45

Ile Phe Ser Asp Tyr Tyr Met Gly Trp Ile Arg Gln Ala Pro Gly Lys
    50                  55                  60

Gly Leu Glu Trp Val Ser Tyr Ile Gly Arg Ser Gly Ser Ser Met Tyr
65                  70                  75                  80

Tyr Ala Asp Ser Val Lys Gly Arg Phe Thr Phe Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Ala Ser Pro Val Val Ala Thr Glu Asp
        115                 120                 125

Phe Gln His Trp Gly Gln Gly Thr Leu Val Thr Val Ser Ser Gly Gly
    130                 135                 140

Gly Gly Ser Gly Gly Gly Gly Ser Gly Gly Gly Ser Gly Gly Gly
145                 150                 155                 160

Gly Ser Asp Ile Val Met Thr Gln Thr Pro Ala Thr Leu Ser Leu Ser
                165                 170                 175

Pro Gly Glu Arg Ala Thr Leu Ser Cys Arg Ala Ser Gln Ser Val Thr
            180                 185                 190

Ser Asn Tyr Leu Ala Trp Tyr Gln Gln Lys Pro Gly Gln Ala Pro Arg
        195                 200                 205

Leu Leu Leu Phe Gly Ala Ser Thr Arg Ala Thr Gly Ile Pro Asp Arg
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Met Tyr Tyr Cys Gln Gln Tyr Gly Ser
                245                 250                 255

Ala Pro Val Thr Phe Gly Gln Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
```

```
            290                 295                 300
Val His Thr Arg Gly Leu Asp Phe Ala Cys Asp Ile Tyr Ile Trp Ala
305                 310                 315                 320

Pro Leu Ala Gly Thr Cys Gly Val Leu Leu Ser Leu Val Ile Thr
            325                 330                 335

Leu Tyr Cys Lys Arg Gly Arg Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 113
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Arg Ala Pro Gly Ala Ser Val Lys Ile Ser Cys Lys Ala Ser Gly Phe
        35                  40                  45

Thr Phe Arg Gly Tyr Tyr Ile His Trp Val Arg Gln Ala Pro Gly Gln
    50                  55                  60

Gly Leu Glu Trp Met Gly Ile Ile Asn Pro Ser Gly Gly Ser Arg Ala
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Asp Asp Thr
            100                 105                 110

Ala Met Tyr Tyr Cys Ala Arg Thr Ala Ser Cys Gly Gly Asp Cys Tyr
        115                 120                 125

Tyr Leu Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160
```

Gly Gly Ser Asp Ile Gln Met Thr Gln Ser Pro Thr Leu Ser Ala
            165                 170                 175

Ser Val Gly Asp Arg Val Thr Ile Thr Cys Arg Ala Ser Glu Asn Val
        180                 185                 190

Asn Ile Trp Leu Ala Trp Tyr Gln Gln Lys Pro Gly Lys Ala Pro Lys
    195                 200                 205

Leu Leu Ile Tyr Lys Ser Ser Leu Ala Ser Gly Val Pro Ser Arg
210                 215                 220

Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
                245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 114
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 114

Met Ala Leu Pro Val Thr Ala Leu Leu Leu Pro Leu Ala Leu Leu Leu
1               5                   10                  15

-continued

His Ala Ala Arg Pro Gln Val Gln Leu Val Gln Ser Gly Gly Leu
            20                  25                  30
Val Gln Pro Gly Arg Ser Leu Arg Leu Ser Cys Ala Ala Ser Gly Phe
        35                  40                  45
Thr Phe Asp Asp Tyr Ala Met His Trp Val Arg Gln Ala Pro Gly Lys
    50                  55                  60
Gly Leu Glu Trp Val Ser Gly Ile Ser Trp Asn Ser Gly Ser Ile Gly
65                  70                  75                  80
Tyr Ala Asp Ser Val Lys Gly Arg Phe Thr Ile Ser Arg Asp Asn Ala
                85                  90                  95
Lys Asn Ser Leu Tyr Leu Gln Met Asn Ser Leu Arg Ala Glu Asp Thr
            100                 105                 110
Ala Val Tyr Tyr Cys Ala Lys Asp Gly Ser Ser Ser Trp Ser Trp Gly
        115                 120                 125
Tyr Phe Asp Tyr Trp Gly Gln Gly Thr Leu Val Thr Val Ser Ser Gly
    130                 135                 140
Gly Gly Gly Ser Gly Gly Gly Ser Gly Gly Gly Ser Ser
145                 150                 155                 160
Glu Leu Thr Gln Asp Pro Ala Val Ser Val Ala Leu Gly Gln Thr Val
                165                 170                 175
Arg Thr Thr Cys Gln Gly Asp Ala Leu Arg Ser Tyr Tyr Ala Ser Trp
            180                 185                 190
Tyr Gln Gln Lys Pro Gly Gln Ala Pro Met Leu Val Ile Tyr Gly Lys
        195                 200                 205
Asn Asn Arg Pro Ser Gly Ile Pro Asp Arg Phe Ser Gly Ser Asp Ser
    210                 215                 220
Gly Asp Thr Ala Ser Leu Thr Ile Thr Gly Ala Gln Ala Glu Asp Glu
225                 230                 235                 240
Ala Asp Tyr Tyr Cys Asn Ser Arg Asp Ser Ser Gly Tyr Pro Val Phe
                245                 250                 255
Gly Thr Gly Thr Lys Val Thr Val Leu Thr Thr Thr Pro Ala Pro Arg
            260                 265                 270
Pro Pro Thr Pro Ala Pro Thr Ile Ala Ser Gln Pro Leu Ser Leu Arg
        275                 280                 285
Pro Glu Ala Cys Arg Pro Ala Ala Gly Gly Ala Val His Thr Arg Gly
    290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Leu Tyr Cys Lys Arg
                325                 330                 335
Gly Arg Lys Lys Leu Leu Tyr Ile Phe Lys Gln Pro Phe Met Arg Pro
            340                 345                 350
Val Gln Thr Thr Gln Glu Glu Asp Gly Cys Ser Cys Arg Phe Pro Glu
        355                 360                 365
Glu Glu Glu Gly Gly Cys Glu Leu Arg Val Lys Phe Ser Arg Ser Ala
    370                 375                 380
Asp Ala Pro Ala Tyr Lys Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser

```
                435                 440                 445
Glu Ile Gly Met Lys Gly Glu Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 115
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Thr Gly
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Leu Tyr Tyr Cys Ala Lys Asp Ser Ser Ser Trp Tyr Gly Gly Gly
        115                 120                 125

Ser Ala Phe Asp Ile Trp Gly Gln Gly Thr Met Val Thr Val Ser Ser
    130                 135                 140

Gly Gly Gly Gly Ser Gly Gly Gly Ser Gly Gly Gly Ser Ser
145                 150                 155                 160

Ser Glu Leu Thr Gln Glu Pro Ala Val Ser Val Ala Leu Gly Gln Thr
                165                 170                 175

Val Arg Ile Thr Cys Gln Gly Asp Ser Leu Arg Ser Tyr Tyr Ala Ser
            180                 185                 190

Trp Tyr Gln Gln Lys Pro Gly Gln Ala Pro Val Leu Val Ile Phe Gly
        195                 200                 205

Arg Ser Arg Arg Pro Ser Gly Ile Pro Asp Arg Phe Ser Gly Ser Ser
    210                 215                 220

Ser Gly Asn Thr Ala Ser Leu Ile Ile Thr Gly Ala Gln Ala Glu Asp
225                 230                 235                 240

Glu Ala Asp Tyr Tyr Cys Asn Ser Arg Asp Asn Thr Ala Asn His Tyr
                245                 250                 255

Val Phe Gly Thr Gly Thr Lys Leu Thr Val Leu Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300
```

-continued

```
Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
            325                 330                 335

Lys Arg Gly Arg Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
        370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 116
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Thr Gly
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Leu Tyr Tyr Cys Ala Lys Asp Ser Ser Ser Trp Tyr Gly Gly Gly
        115                 120                 125

Ser Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Ser
145                 150                 155                 160
```

Ser Glu Leu Thr Gln Asp Pro Ala Val Ser Val Ala Leu Gly Gln Thr
            165                 170                 175

Val Arg Ile Thr Cys Gln Gly Asp Ser Leu Arg Ser Tyr Tyr Ala Ser
        180                 185                 190

Trp Tyr Gln Gln Lys Pro Gly Gln Ala Pro Val Leu Val Ile Tyr Gly
            195                 200                 205

Lys Asn Asn Arg Pro Ser Gly Ile Pro Asp Arg Phe Ser Gly Ser Ser
210                 215                 220

Ser Gly Asn Thr Ala Ser Leu Thr Ile Thr Gly Ala Gln Ala Glu Asp
225                 230                 235                 240

Glu Ala Asp Tyr Tyr Cys Asn Ser Arg Gly Ser Ser Gly Asn His Tyr
                245                 250                 255

Val Phe Gly Thr Gly Thr Lys Val Thr Val Leu Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
        290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 117
<211> LENGTH: 495
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu

-continued

```
               20                  25                  30
Val Gln Pro Gly Gly Ser Leu Arg Leu Ser Cys Ala Ala Ser Gly Phe
            35                  40                  45

Thr Phe Ser Ser Tyr Trp Met His Trp Val Arg Gln Ala Pro Gly Lys
 50                  55                  60

Gly Leu Val Trp Val Ser Arg Ile Asn Ser Asp Gly Ser Ser Thr Ser
 65                  70                  75                  80

Tyr Ala Asp Ser Val Lys Gly Arg Phe Thr Ile Ser Arg Asp Asn Ala
                 85                  90                  95

Lys Asn Thr Leu Tyr Leu Gln Met Asn Ser Leu Arg Ala Glu Asp Thr
               100                 105                 110

Ala Val Tyr Tyr Cys Val Arg Thr Gly Trp Val Gly Ser Tyr Tyr Tyr
           115                 120                 125

Tyr Met Asp Val Trp Gly Lys Gly Thr Thr Val Thr Val Ser Ser Gly
       130                 135                 140

Gly Gly Gly Ser Gly Gly Gly Ser Gly Gly Gly Ser Gly Gly Gly Gly
145                 150                 155                 160

Gly Gly Ser Glu Ile Val Leu Thr Gln Ser Pro Gly Thr Leu Ser Leu
               165                 170                 175

Ser Pro Gly Glu Arg Ala Thr Leu Ser Cys Arg Ala Ser Gln Ser Val
           180                 185                 190

Ser Ser Asn Tyr Leu Ala Trp Tyr Gln Gln Lys Pro Gly Gln Pro Pro
       195                 200                 205

Arg Leu Leu Ile Tyr Asp Val Ser Thr Arg Ala Thr Gly Ile Pro Ala
   210                 215                 220

Arg Phe Ser Gly Gly Gly Ser Gly Thr Asp Phe Thr Leu Thr Ile Ser
225                 230                 235                 240

Ser Leu Glu Pro Glu Asp Phe Ala Val Tyr Tyr Cys Gln Gln Arg Ser
               245                 250                 255

Asn Trp Pro Pro Trp Thr Phe Gly Gln Gly Thr Lys Val Glu Ile Lys
           260                 265                 270

Thr Thr Thr Pro Ala Pro Arg Pro Pro Thr Pro Ala Pro Thr Ile Ala
       275                 280                 285

Ser Gln Pro Leu Ser Leu Arg Pro Glu Ala Cys Arg Pro Ala Ala Gly
   290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
               325                 330                 335

Ile Thr Leu Tyr Cys Lys Arg Gly Arg Lys Lys Leu Leu Tyr Ile Phe
           340                 345                 350

Lys Gln Pro Phe Met Arg Pro Val Gln Thr Thr Gln Glu Glu Asp Gly
       355                 360                 365

Cys Ser Cys Arg Phe Pro Glu Glu Glu Glu Gly Gly Cys Glu Leu Arg
   370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
               405                 410                 415

Val Leu Asp Lys Arg Arg Gly Arg Asp Pro Glu Met Gly Gly Lys Pro
           420                 425                 430

Arg Arg Lys Asn Pro Gln Glu Gly Leu Tyr Asn Glu Leu Gln Lys Asp
       435                 440                 445
```

```
Lys Met Ala Glu Ala Tyr Ser Glu Ile Gly Met Lys Gly Glu Arg Arg
        450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 118
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Gly Tyr Ser Arg Tyr Tyr Tyr Tyr Gly
        115                 120                 125

Met Asp Val Trp Gly Gln Gly Thr Thr Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Leu Ser
                165                 170                 175

Pro Gly Glu Arg Ala Ile Leu Ser Cys Arg Ala Ser Gln Ser Val Tyr
            180                 185                 190

Thr Lys Tyr Leu Gly Trp Tyr Gln Gln Lys Pro Gly Gln Ala Pro Arg
        195                 200                 205

Leu Leu Ile Tyr Asp Ala Ser Thr Arg Ala Thr Gly Ile Pro Asp Arg
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Val Tyr Tyr Cys Gln His Tyr Gly Gly
                245                 250                 255

Ser Pro Leu Ile Thr Phe Gly Gln Gly Thr Lys Val Asp Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300
```

```
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Ser Leu Val Ile
            325                 330                 335

Thr Leu Tyr Cys Lys Arg Gly Arg Lys Lys Leu Leu Tyr Ile Phe Lys
        340                 345                 350

Gln Pro Phe Met Arg Pro Val Gln Thr Thr Gln Glu Glu Asp Gly Cys
    355                 360                 365

Ser Cys Arg Phe Pro Glu Glu Glu Gly Gly Cys Glu Leu Arg Val
370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490

<210> SEQ ID NO 119
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Arg Glu Ala Ala Gly His Asp Trp
        115                 120                 125

Tyr Phe Asp Leu Trp Gly Arg Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Arg Val Thr Gln Ser Pro Ser Ser Leu Ser Ala
```

```
                    165                 170                 175
Ser Val Gly Asp Arg Val Thr Ile Thr Cys Arg Ala Ser Gln Ser Ile
                180                 185                 190

Ser Ser Tyr Leu Asn Trp Tyr Gln Gln Lys Pro Gly Lys Ala Pro Lys
            195                 200                 205

Leu Leu Ile Tyr Ala Ala Ser Ser Leu Gln Ser Gly Val Pro Ser Arg
        210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Tyr Cys Gln Gln Ser Tyr Ser
                245                 250                 255

Ile Pro Leu Thr Phe Gly Gln Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 120
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Trp Ala Glu Val
            20                  25                  30
```

-continued

```
Lys Lys Pro Gly Ala Ser Val Lys Val Ser Cys Lys Ala Ser Gly Tyr
        35                  40                  45
Thr Phe Thr Ser Tyr Tyr Met His Trp Val Arg Gln Ala Pro Gly Gln
    50                  55                  60
Gly Leu Glu Trp Met Gly Ile Ile Asn Pro Ser Gly Gly Ser Thr Ser
65                  70                  75                  80
Tyr Ala Gln Lys Phe Gln Gly Arg Val Thr Met Thr Arg Asp Thr Ser
                85                  90                  95
Thr Ser Thr Val Tyr Met Glu Leu Ser Asn Leu Arg Ser Glu Asp Thr
                100                 105                 110
Ala Val Tyr Tyr Cys Ala Arg Ser Pro Arg Val Thr Thr Gly Tyr Phe
                115                 120                 125
Asp Tyr Trp Gly Gln Gly Thr Leu Val Thr Val Ser Ser Gly Gly Gly
    130                 135                 140
Gly Ser Gly Gly Gly Gly Ser Gly Gly Gly Gly Ser Gly Gly Gly Gly
145                 150                 155                 160
Ser Asp Ile Gln Leu Thr Gln Ser Pro Ser Thr Leu Ser Ala Ser Val
                165                 170                 175
Gly Asp Arg Val Thr Ile Thr Cys Arg Ala Ser Gln Ser Ile Ser Ser
                180                 185                 190
Trp Leu Ala Trp Tyr Gln Gln Lys Pro Gly Lys Ala Pro Lys Leu Leu
    195                 200                 205
Ile Tyr Lys Ala Ser Ser Leu Glu Ser Gly Val Pro Ser Arg Phe Ser
    210                 215                 220
Gly Ser Gly Ser Gly Thr Glu Phe Thr Leu Thr Ile Ser Ser Leu Gln
225                 230                 235                 240
Pro Asp Asp Phe Ala Thr Tyr Tyr Cys Gln Gln Tyr Ser Ser Tyr Pro
                245                 250                 255
Leu Thr Phe Gly Gly Gly Thr Arg Leu Glu Ile Lys Thr Thr Thr Pro
                260                 265                 270
Ala Pro Arg Pro Pro Thr Pro Ala Pro Thr Ile Ala Ser Gln Pro Leu
    275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Lys Arg Gly Arg Lys Lys Leu Leu Tyr Ile Phe Lys Gln Pro Phe
                340                 345                 350
Met Arg Pro Val Gln Thr Thr Gln Glu Glu Asp Gly Cys Ser Cys Arg
    355                 360                 365
Phe Pro Glu Glu Glu Glu Gly Gly Cys Glu Leu Arg Val Lys Phe Ser
    370                 375                 380
Arg Ser Ala Asp Ala Pro Ala Tyr Lys Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
                420                 425                 430
Pro Gln Glu Gly Leu Tyr Asn Glu Leu Gln Lys Asp Lys Met Ala Glu
    435                 440                 445
```

```
Ala Tyr Ser Glu Ile Gly Met Lys Gly Glu Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 121
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Arg Arg Pro Gly Ala Ser Val Lys Ile Ser Cys Arg Ala Ser Gly Asp
            35                  40                  45

Thr Ser Thr Arg His Tyr Ile His Trp Leu Arg Gln Ala Pro Gly Gln
    50                  55                  60

Gly Pro Glu Trp Met Gly Val Ile Asn Pro Thr Thr Gly Pro Ala Thr
65              70                  75                  80

Gly Ser Pro Ala Tyr Ala Gln Met Leu Gln Gly Arg Val Thr Met Thr
                85                  90                  95

Arg Asp Thr Ser Thr Arg Thr Val Tyr Met Glu Leu Arg Ser Leu Arg
            100                 105                 110

Phe Glu Asp Thr Ala Val Tyr Tyr Cys Ala Arg Ser Val Val Gly Arg
        115                 120                 125

Ser Ala Pro Tyr Tyr Phe Asp Tyr Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Gln Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Gly Ile Ser Asp Tyr Ser Ala Trp Tyr Gln Gln Lys Pro Gly
        195                 200                 205

Lys Ala Pro Lys Leu Leu Ile Tyr Ala Ala Ser Thr Leu Gln Ser Gly
    210                 215                 220

Val Pro Ser Arg Phe Ser Gly Ser Gly Ser Gly Thr Asp Phe Thr Leu
225                 230                 235                 240

Thr Ile Ser Tyr Leu Gln Ser Glu Asp Phe Ala Thr Tyr Tyr Cys Gln
                245                 250                 255

Gln Tyr Tyr Ser Tyr Pro Leu Thr Phe Gly Gly Gly Thr Lys Val Asp
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
```

```
            305                 310                 315                 320
        Tyr Ile Trp Ala Pro Leu Ala Gly Thr Cys Gly Val Leu Leu Leu Ser
                        325                 330                 335
        Leu Val Ile Thr Leu Tyr Cys Lys Arg Gly Arg Lys Leu Leu Tyr
                        340                 345                 350
        Ile Phe Lys Gln Pro Phe Met Arg Pro Val Gln Thr Thr Gln Glu Glu
                        355                 360                 365
        Asp Gly Cys Ser Cys Arg Phe Pro Glu Glu Glu Gly Gly Cys Glu
                    370                 375                 380
        Leu Arg Val Lys Phe Ser Arg Ser Ala Asp Ala Pro Ala Tyr Lys Gln
        385                 390                 395                 400
        Gly Gln Asn Gln Leu Tyr Asn Glu Leu Asn Leu Gly Arg Arg Glu Glu
                        405                 410                 415
        Tyr Asp Val Leu Asp Lys Arg Arg Gly Arg Asp Pro Glu Met Gly Gly
                    420                 425                 430
        Lys Pro Arg Arg Lys Asn Pro Gln Glu Gly Leu Tyr Asn Glu Leu Gln
                    435                 440                 445
        Lys Asp Lys Met Ala Glu Ala Tyr Ser Glu Ile Gly Met Lys Gly Glu
                450                 455                 460
        Arg Arg Arg Gly Lys Gly His Asp Gly Leu Tyr Gln Gly Leu Ser Thr
        465                 470                 475                 480
        Ala Thr Lys Asp Thr Tyr Asp Ala Leu His Met Gln Ala Leu Pro Pro
                        485                 490                 495
        Arg

<210> SEQ ID NO 122
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Met Ala Leu Pro Val Thr Ala Leu Leu Leu Pro Leu Ala Leu Leu Leu
        1               5                   10                  15
        His Ala Ala Arg Pro Gln Val Gln Leu Gln Gln Ser Gly Ala Glu Val
                        20                  25                  30
        Lys Lys Pro Gly Ala Ser Val Lys Val Ser Cys Lys Ala Ser Gly Tyr
                    35                  40                  45
        Thr Phe Thr Asn Tyr Tyr Met His Trp Val Arg Gln Ala Pro Gly Gln
                50                  55                  60
        Gly Leu Glu Trp Met Gly Ile Ile Asn Pro Ser Gly Gly Tyr Thr Thr
        65                  70                  75                  80
        Tyr Ala Gln Lys Phe Gln Gly Arg Leu Thr Met Thr Arg Asp Thr Ser
                        85                  90                  95
        Thr Ser Thr Val Tyr Met Glu Leu Ser Ser Leu Arg Ser Glu Asp Thr
                        100                 105                 110
        Ala Val Tyr Tyr Cys Ala Arg Ile Arg Ser Cys Gly Gly Asp Cys Tyr
                    115                 120                 125
        Tyr Phe Asp Asn Trp Gly Gln Gly Thr Leu Val Thr Val Ser Ser Gly
                130                 135                 140
        Gly Gly Gly Ser Gly Gly Gly Gly Ser Gly Gly Gly Gly Ser Gly Gly
        145                 150                 155                 160
```

Gly Gly Ser Asp Ile Gln Leu Thr Gln Ser Pro Ser Thr Leu Ser Ala
            165                 170                 175

Ser Val Gly Asp Arg Val Thr Ile Thr Cys Arg Ala Ser Glu Asn Val
        180                 185                 190

Asn Ile Trp Leu Ala Trp Tyr Gln Gln Lys Pro Gly Lys Ala Pro Lys
    195                 200                 205

Leu Leu Ile Tyr Lys Ser Ser Leu Ala Ser Gly Val Pro Ser Arg
210                 215                 220

Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
            245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
        370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
        450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 123
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Met Ala Leu Pro Val Thr Ala Leu Leu Leu Pro Leu Ala Leu Leu Leu
1               5                   10                  15

His Ala Ala Arg Pro Gln Ile Thr Leu Lys Glu Ser Gly Pro Ala Leu

-continued

```
             20                  25                  30
Val Lys Pro Thr Gln Thr Leu Thr Leu Thr Cys Thr Phe Ser Gly Phe
             35                  40                  45
Ser Leu Ser Thr Ala Gly Val His Val Gly Trp Ile Arg Gln Pro Pro
             50                  55                  60
Gly Lys Ala Leu Glu Trp Leu Ala Leu Ile Ser Trp Ala Asp Asp Lys
 65                  70                  75                  80
Arg Tyr Arg Pro Ser Leu Arg Ser Arg Leu Asp Ile Thr Arg Val Thr
                     85                  90                  95
Ser Lys Asp Gln Val Val Leu Ser Met Thr Asn Met Gln Pro Glu Asp
                    100                 105                 110
Thr Ala Thr Tyr Tyr Cys Ala Leu Gln Gly Phe Asp Gly Tyr Glu Ala
                    115                 120                 125
Asn Trp Gly Pro Gly Thr Leu Val Thr Val Ser Ser Gly Gly Gly Gly
                    130                 135                 140
Ser Gly Gly Gly Gly Ser Gly Gly Gly Gly Ser Gly Gly Gly Gly Ser
145                 150                 155                 160
Asp Ile Val Met Thr Gln Ser Pro Ser Ser Leu Ser Ala Ser Ala Gly
                    165                 170                 175
Asp Arg Val Thr Ile Thr Cys Arg Ala Ser Arg Gly Ile Ser Ser Ala
                    180                 185                 190
Leu Ala Trp Tyr Gln Gln Lys Pro Gly Lys Pro Pro Lys Leu Leu Ile
                    195                 200                 205
Tyr Asp Ala Ser Ser Leu Glu Ser Gly Val Pro Ser Arg Phe Ser Gly
                    210                 215                 220
Ser Gly Ser Gly Thr Asp Phe Thr Leu Thr Ile Asp Ser Leu Glu Pro
225                 230                 235                 240
Glu Asp Phe Ala Thr Tyr Tyr Cys Gln Gln Ser Tyr Ser Thr Pro Trp
                    245                 250                 255
Thr Phe Gly Gln Gly Thr Lys Val Asp Ile Lys Thr Thr Thr Pro Ala
                    260                 265                 270
Pro Arg Pro Pro Thr Pro Ala Pro Thr Ile Ala Ser Gln Pro Leu Ser
                    275                 280                 285
Leu Arg Pro Glu Ala Cys Arg Pro Ala Ala Gly Gly Ala Val His Thr
                    290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                    325                 330                 335
Lys Arg Gly Arg Lys Lys Leu Leu Tyr Ile Phe Lys Gln Pro Phe Met
                    340                 345                 350
Arg Pro Val Gln Thr Thr Gln Glu Glu Asp Gly Cys Ser Cys Arg Phe
                    355                 360                 365
Pro Glu Glu Glu Glu Gly Gly Cys Glu Leu Arg Val Lys Phe Ser Arg
                    370                 375                 380
Ser Ala Asp Ala Pro Ala Tyr Lys Gln Gly Gln Asn Gln Leu Tyr Asn
385                 390                 395                 400
Glu Leu Asn Leu Gly Arg Arg Glu Glu Tyr Asp Val Leu Asp Lys Arg
                    405                 410                 415
Arg Gly Arg Asp Pro Glu Met Gly Gly Lys Pro Arg Arg Lys Asn Pro
                    420                 425                 430
Gln Glu Gly Leu Tyr Asn Glu Leu Gln Lys Asp Lys Met Ala Glu Ala
                    435                 440                 445
```

```
Tyr Ser Glu Ile Gly Met Lys Gly Glu Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
            485                 490

<210> SEQ ID NO 124
<211> LENGTH: 383
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Glu Lys Pro Gly Ala Ser Val Lys Ile Ser Cys Lys Ala Ser Gly Tyr
        35                  40                  45

Ser Phe Thr Gly Tyr Thr Met Asn Trp Val Lys Gln Ser His Gly Lys
50                  55                  60

Ser Leu Glu Trp Ile Gly Leu Ile Thr Pro Tyr Asn Gly Ala Ser Ser
65                  70                  75                  80

Tyr Asn Gln Lys Phe Arg Gly Lys Ala Thr Leu Thr Val Asp Lys Ser
                85                  90                  95

Ser Ser Thr Ala Tyr Met Asp Leu Leu Ser Leu Thr Ser Glu Asp Ser
            100                 105                 110

Ala Val Tyr Phe Cys Ala Arg Gly Gly Tyr Asp Gly Arg Gly Phe Asp
        115                 120                 125

Tyr Trp Gly Gln Gly Thr Thr Val Thr Val Ser Ser Gly Gly Gly Gly
130                 135                 140

Ser Gly Gly Gly Gly Ser Gly Gly Gly Gly Ser Asp Ile Glu Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met His Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Gly Arg Phe Ser Gly Ser Gly Ser Gly Asn Ser
210                 215                 220

Tyr Ser Leu Thr Ile Ser Ser Val Glu Ala Glu Asp Ala Thr Tyr
225                 230                 235                 240

Tyr Cys Gln Gln Trp Ser Gly Tyr Pro Leu Thr Phe Gly Ala Gly Thr
                245                 250                 255

Lys Leu Glu Ile Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
290                 295                 300
```

```
Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
            325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Gly Gly
        355                 360                 365

Cys Glu Leu Arg Val Lys Phe Ser Arg Ser Ala Asp Ala Pro Ala
    370                 375                 380

<210> SEQ ID NO 125
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 125
atggccctcc ctgtcaccgc cctgctgctt ccgctggctc ttctgctcca cgccgctcgg     60
ccccaagtcc aactgcagca gtcaggagcg gaagtgaaga accaggagc gtcagtcaaa    120 gtgtcgtgca aggctagcgg ctacaccttc accggctact acatgcactg ggttcgacag    180
gctccagggc agggtctgga gtggatgggc cgcatcaacc cgaattccgg tgggactaac    240
tacgcccaga gttccagggg aagagtgacc atgactaggg acacgtcgat cagcactgcg    300
tacatggaac tgagccgcct gcggtccgag gatactgccg tctactactg cgcacgcgga    360
aggtactatg gaatggacgt gtggggccaa gggactatgg tgactgtgag ctcgggaggg    420
ggaggctccg gtggcggggg atcaggagga ggaggatcag ggggaggagg ttccgaaatt    480
gtcctcaccc agagcccggc aaccctctca ctttccccgg gagagcgcgc aaccatctct    540
tgccgggcta gccaatccgt gtcgtccaat ttcgcctggt accagcaacg gccgggacaa    600
gcccctagac tcctgatcta cgacgccagc aacagagcga ctggaattcc tccacgcttt    660
tcgggatcag gctccggtac cgacttcacc ctgactatct cgtcgctcga acccgaggat    720
ttcgccgcct actactgtca tcagcggtcg aactggttgt atacgtttgg ccagggcacc    780
aaggtggata tcaagaccac taccccagca ccgaggccac ccaccccggc tcctaccatc    840
gcctcccagc tctgtccct gcgtccggag gcatgtagac ccgcagctgg tggggccgtg    900
catacccggg gtcttgactt cgcctgcgat atctacattt gggcccctct ggctggtact    960
tgcggggtcc tgctgctttc actcgtgatc actctttact gtaagcgcgg tcggaagaag   1020
ctgctgtaca tctttaagca accttcatg aggcctgtgc agactactca agaggaggac   1080
ggctgttcat gccggttccc agaggaggag gaaggcggct gcgaactgcg cgtgaaattc   1140
agccgcagcg cagatgctcc agcctacaag caggggcaga accagctcta caacgaactc   1200
aatcttggtc ggagagagga gtacgacgtg ctggacaagc ggagaggacg ggacccagaa   1260
atgggcggga agccgcgcag aaagaatccc caagagggcc tgtacaacga gctccaaaag   1320
gataagatgg cagaagccta tagcgagatt ggtatgaaag ggaacgcag aagaggcaaa   1380 ggccacgacg gactgtacca gggactcagc accgccacca aggacaccta tgacgctctt   1440
cacatgcagg ccctgccgcc tcgg                                         1464

<210> SEQ ID NO 126
```

<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 126

```
atggccctcc ctgtcaccgc cctgctgctt ccgctggctc ttctgctcca cgccgctcgg    60
ccccaagtcc aactcgtcca gtcaggagca gaagtcaaga aaccaggtgc tagcgtgaaa   120
gtgtcgtgca aggcgtcggg atacactttc accggatact acatgcactg ggtccgccag   180
gcccccggac aaggactgga atggatgggc tggatcaacc cgaatagcgg gggaactaat   240
tacgcccaga gtttcagggg acgagtgacc atgacccgcg atacctctat ctcgaccgcc   300
tacatggagc tctccagact gcgctccgac gatactgcag tgtactactg cgcccgggac   360
ctgaggcgga ctgtggttac tcctcgcgcc tattatggca tggacgtgtg gggccaagga   420
actactgtga ctgtgagctc ggggaggcggt gggtcaggcg gaggagggtc gggcggtggt   480
ggctcgggag gggaggaag cgacattcaa cttacgcaga gccgtcaac cctgtcagcg   540
tcagtgggag atcgggtgac catcacgtgt caggccagcc aggatatctc caactcgctc   600
aactggtacc agcaaaaggc gggtaaagct ccgaagctgc tgatctacga cgcttccacc   660
ctcgagactg gagtcccatc cagatttccc gggtcaggaa gcggcaccga tttctccttc   720
accatttcgt ccttgcaacc ggaggacatc gcaacctact actgccagca gcatgacaac   780
ttgcctctga cgttcgggca gggcaccaag gtggaaatca agaccactac cccagcaccg   840
aggccaccca ccccggctcc taccatcgcc tcccagcctc tgtccctgcg tccggaggca   900
tgtagacccg cagctggtgg ggccgtgcat acccggggtc ttgacttcgc ctgcgatatc   960
tacatttggg cccctctggc tggtacttgc ggggtcctgc tgctttcact cgtgatcact  1020
ctttactgta gcgcggtcg gaagaagctg ctgtacatct ttaagcaacc cttcatgagg  1080
cctgtgcaga ctactcaaga ggaggacggc tgttcatgcc ggttcccaga ggaggaggaa  1140
ggcggctgcg aactgcgcgt gaaattcagc cgcagcgcag atgctccagc ctacaagcag  1200
gggcagaacc agctctacaa cgaactcaat cttggtcgga gagaggagta cgacgtgctg  1260
gacaagcgga gaggacggga cccagaaatg ggcgggaagc cgcgcagaaa gaatccccaa  1320
gagggcctgt acaacgagct ccaaaaggat aagatggcag aagcctatag cgagattggt  1380
atgaaagggg aacgcagaag aggcaaaggc cacgacggac tgtaccaggg actcagcacc  1440
gccaccaagg acacctatga cgctcttcac atgcaggccc tgccgcctcg g           1491
```

<210> SEQ ID NO 127
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127

```
atggccctcc ctgtcaccgc cctgctgctt ccgctggctc ttctgctcca cgccgctcgg    60
ccccaagtcc aactcgtcca atcaggagcg gaagtcaaaa agcccggagc tccagtgaaa   120
gtgtcatgca aggcctccgg ctacaccttc accggttact atatgcactg ggtgcggcag   180
gccccgggcc aggggttgga atggatggga tggatcaatc caaactcggg tggactaac   240
```

```
tacgcccaga agttccaagg acgggtgacc atgactaggg acacctcgat ctccaccgca      300
tacatggagc ttagcagact ccgctccgac gataccgcag tctactattg cgcgcgggga      360
gagtgggacg gatcgtacta ctacgattac tggggccagg gaactctggt gactgtttcc      420
tcgggtggag gaggttcagg cggaggcggc tcgggcgggg gaggatctgg aggaggaggg      480
tccgacattg tgctgaccca aactccttcg tccctgtcgg ccagcgtggg cgaccgcgtg      540
acgattacgt gcagagctag ccaatccatc aatacttacc tcaactggta ccagcataag      600
ccggggaaag caccaaagct gctgatctac gccgcctcat ccttgcagag cggtgtgcct      660
tcacgcttta gcggatcggg atcgggaacg gatttcaccc tgactatcag ctccctccag      720
ccggaggatt ttgcgaccta ctactgtcag cagagcttct caccgctgac tttcggcggc      780
gggaccaagc tggaaatcaa gaccactacc ccagcaccga ggccacccac ccggctcct       840 accatcgcct cccagcctct gtccctgcgt ccggaggcat gtagacccgc agctggtggg      900
gccgtgcata cccgggggtct tgacttcgcc tgcgatatct acatttgggc ccctctggct     960
ggtacttgcg gggtcctgct gctttcactc gtgatcactc tttactgtaa gcgcggtcgg     1020
aagaagctgc tgtacatctt taagcaaccc ttcatgaggc ctgtgcagac tactcaagag     1080
gaggacggct gttcatgccg gttcccagag gaggaggaag gcggctgcga actgcgcgtg     1140
aaattcagcc gcagcgcaga tgctccagcc tacaagcagg gcagaaccag ctctacaac     1200 gaactcaatc ttggtcggag agaggagtac gacgtgctgg acaagcggag aggacgggac     1260
ccagaaatgg gcgggaagcc gcgcagaaag aatccccaag agggcctgta caacgagctc     1320
caaaaggata agatggcaga agcctatagc gagattggta tgaaggggga acgcagaaga     1380
ggcaaaggcc acgacggact gtaccaggga ctcagcaccg ccaccaagga cacctatgac     1440
gctcttcaca tgcaggccct gccgcctcgg                                      1470
```

<210> SEQ ID NO 128
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 128

```
atggccctcc ctgtcaccgc cctgctgctt ccgctggctc ttctgctcca cgccgctcgg       60
ccccaagtgc aactcgttga atcaggtgga ggtttggtgc aacccggagg atctctcaga      120
ctgtcgtgtg cggcgtccgg gttcaccttt tcgtcctact ggatgcactg ggtgcgccag      180
gtgccgggaa aaggactggt gtgggtgtcc agaatcaaca ccgacgggtc aacgactacc      240
tacgcagata gcgtggaagg tcggttcacc atttcgcggg acaacgctaa aaacactctg      300
taccttcaga tgaattcact gcgcgatgac gacaccgcag tctactactg cgtcggtgga      360
cactgggcgg tctggggaca gggaactacg gtgactgtgt ccagcggcgg gggaggaagc      420
ggcggagggg ggagcggagg cggaggatca ggaggaggcg gctccgatat ccagatgacc      480
cagtcgccat cgaccctctc cgctagcgtg gggataggg tcactatcac ttgccgagcc      540
agccaatcca ttagcgaccg gcttgcctgg taccaacaga aacctggaaa ggccccgaag      600
ctgctcatct acaaggcctc gtcactggag tcggagtcc cgtccgctt tccggctcg       660 ggctcaggca ccgagttcac tctgaccatc tcgagcctgc agccggacga tttcgccgtg      720
```

```
tattactgcc agcaatacgg acatctccca atgtacacgt tcggtcaggg caccaaggtc    780
gaaatcaaga ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta agcaaccctt catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggaccc  agaaatgggc   1260
gggaagccgc gcagaaagaa tccccaagag ggcctgtaca cgagctcca  aaaggataag   1320
atggcagaag cctatagcga gattggtatg aaagggaac  gcagaagagg caaaggccac   1380
gacggactgt accagggact cagcaccgcc accaaggaca cctatgacgc tcttcacatg   1440
caggccctgc cgcctcgg                                                 1458

<210> SEQ ID NO 129
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129
atggccctcc ctgtcaccgc cctgctgctt ccgctggctc ttctgctcca cgccgctcgg     60
ccccaagtcc aactcgttca atcaggcgca gaagtcgaaa agcccggagc atcagtcaaa    120
gtctcttgca aggcttccgg ctacaccttc acggactact acatgcactg ggtgcgccag    180
gctccaggcc agggactgga gtggatggga tggatcaacc cgaattccgg gggaactaac    240
tacgcccaga gtttcagggg ccgggtgact atgactcgcg atacctcgat ctcgactgcg    300
tacatggagc tcagccgcct ccggtcgac  gataccgccg tgtactattg tgcgtcggga    360
tgggacttcg actactgggg gcagggcact ctggtcactg tgtcaagcgg aggaggtgga    420
tcaggtggag gtggaagcgg gggaggaggt tccggcggcg gaggatcaga tatcgtgatg    480
acgcaatcgc cttcctcgtt gtccgcatcc gtgggagaca gggtgaccat tacttgcaga    540
gcgtcccagt ccattcggta ctacctgtcg tggtaccagc agaagccggg aaagccccca    600
aaactgctta tctatactgc ctcgatcctc caaaacggcg tgccatcaag attcagcggt    660
tcgggcagcg gaccgacttt accctgact  atcagcagcc tgcagccgga agatttcgcc    720
acgtactact gcctgcaaac ctacaccacc ccggacttcg gacctggaac caaggtggag    780
atcaagacca ctaccccagc accgaggcca cccaccccgg ctcctaccat cgcctcccag    840
cctctgtccc tgcgtccgga ggcatgtaga cccgcagctg tggggccgt  gcatacccgg    900
ggtcttgact tcgcctgcga tatctacatt tgggcccctc tggctggtac ttgcggggtc    960
ctgctgcttt cactcgtgat cactctttac tgtaagcgcg gtcggaagaa gctgctgtac   1020
atctttaagc aacccttcat gaggcctgtg cagactactc aagaggagga cggctgttca   1080
tgccggttcc cagaggagga ggaaggcggc tgcgaactgc gcgtgaaatt cagccgcagc   1140
gcagatgctc cagcctacaa gcaggggcag aaccagctct acaacgaact caatcttggt   1200
cggagagagg agtacgacgt gctggacaag cggagaggac gggacccaga aatgggcggg   1260
```

```
aagccgcgca gaaagaatcc ccaagagggc ctgtacaacg agctccaaaa ggataagatg      1320
gcagaagcct atagcgagat tggtatgaaa ggggaacgga gaagaggcaa aggccacgac      1380
ggactgtacc agggactcag caccgccacc aaggacacct atgacgctct tcacatgcag      1440
gccctgccgc ctcgg                                                       1455

<210> SEQ ID NO 130
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
atggccctcc ctgtcaccgc cctgctgctt ccgctggctc ttctgctcca cgccgctcgg        60
ccccaagtgc aactcgtcca gtcaggtgca gaagtgaaga acccggagc gtcagtcaaa       120 gtgtcatgca aggcgtcagg ctacaccttc accagctact acatgcactg ggtgcggcag      180
gccccaggcc aaggcttgga gtggatggga atcattaacc cgtcaggagg ctccacctcc      240
tacgcccaga gtttcagggg aagagtgacg atgactcggg atacgtcgac ctcgaccgtg      300
tacatggaac tgagctcgct gcgctccgag gacactgctg tgtactactg cgcacggtac      360
agactcattg ccgtggcagg agactactac tactatggca tggacgtctg ggggcagggc      420
actatggtca ctgtgtcgtc cggcggagga ggctcgggtg gaggaggtag cggaggaggg      480
ggaagcggag gggggggctc cgatatccag atgactcagt cgccttcctc cgtgtcggcc      540
tcggttggag atcgcgtcac catcacttgt cgagcttccc aaggagtcgg taggtggctg      600
gcgtggtacc agcaaaagcc gggaactgcc ccgaagctcc tgatctacgc ggctagcacc      660
ctgcagtcgg gagtgccatc ccgcttcagc ggatctgggt caggtaccga cttcaccctt      720
acgatcaaca atctccagcc ggaggacttt gccacctatt actgccaaca ggccaacagc      780
ttccctctga ctttcggagg gggcactcgc ctggaaatca agaccactac cccagcaccg      840
aggccaccca ccccggctcc taccatcgcc tcccagcctc tgtccctgcg tccggaggca      900
tgtagacccg cagctggtgg ggccgtgcat acccggggtc ttgacttcgc ctgcgatatc      960
tacatttggg cccctctggc tggtacttgc ggggtcctgc tgctttcact cgtgatcact     1020
ctttactgta gcgcggtcg gaagaagctg ctgtacatct taagcaacc cttcatgagg     1080 cctgtgcaga ctactcaaga ggaggacggc tgttcatgcc ggttcccaga ggaggaggaa     1140
ggcggctgcg aactgcgcgt gaaattcagc cgcagcgcag atgctccagc ctacaagcag     1200
gggcagaacc agctctacaa cgaactcaat cttggtcgga gagaggagta cgacgtgctg     1260
gacaagcgga gaggacggga cccagaaatg ggcgggaagc cgcgcagaaa gaatccccaa     1320
gagggcctgt acaacgagct ccaaaaggat aagatggcag aagcctatag cgagattggt     1380
atgaaagggg aacgcagaag aggcaaaggc cacgacggac tgtaccaggg actcagcacc     1440
gccaccaagg acacctatga cgctcttcac atgcaggccc tgccgcctcg g              1491

<210> SEQ ID NO 131
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 131

```
atggccctcc ctgtcaccgc cctgctgctt ccgctggctc ttctgctcca cgccgctcgg      60
ccccaagtgc aattggttca atcaggagga ggagtggtgc aacctggaag atctctcaga     120
ctgtcgtgtg cggcatcggg attcactttc tcatcatacg caatgcactg ggtccgccag     180
gccccgggca aaggcttgga atgggtggcg gtcatttcat acgacggctc gaacaagtac     240
tacgctgaca gcgtgaaggg acgctttact atttcccggg acaattcgaa gaacactctg     300
tacctccaga tgaactccct tagggctgag gacaccgccg tctactactg cgcacgctgg     360
aaagtgtcgt ccagctcccc agcttttgac tactgggac agggaaccct tgtgaccgtg      420
tcgtccggtg gagggggaag cggcggaggg ggatcaggtg cggcggatc gggaggcggg      480
ggatcagaaa tcgtgctgac tcagtccccg gccacgctgt ctctcagccc gggagagaga     540
gcgatcctgt cctgccgcgc ctcgcagagc gtgtacacta agtacctggg gtggtaccag     600
cagaaaccgg gtcaagcgcc tcggctgctg atctacgatg cctccacccg gccaccgga     660
atccccgatc ggttctccgg cagcggctcg ggaactgatt tcacgctgac catcaatcgc     720
ctggagccgg aagatttcgc cgtctattac tgccagcatt acggcgggag cccactcatc     780
accttcggtc aaggaacccg actcgaaatc aagaccacta ccccagcacc gaggccaccc     840
accccggctc ctaccatcgc ctcccagcct ctgtccctgc gtccggaggc atgtagaccc     900
gcagctggtg gggccgtgca tacccggggt cttgacttcg cctgcgatat ctacatttgg     960
gcccctctgg ctggtacttg cggggtcctg ctgctttcac tcgtgatcac tctttactgt    1020
aagcgcggtc ggaagaagct gctgtacatc tttaagcaac ccttcatgag gcctgtgcag    1080
actactcaag aggaggacgg ctgttcatgc cggttcccag aggaggagga aggcggctgc    1140
gaactgcgcg tgaaattcag ccgcagcgca gatgctccag cctacaagca ggggcagaac    1200
cagctctaca cgaactcaa tcttggtcgg agagaggagt acgacgtgct ggacaagcgg    1260
agaggacggg acccagaaat gggcgggaag ccgcgcagaa agaatcccca gagggcctg    1320
tacaacgagc tccaaaagga taagatggca gaagcctata gcgagattgg tatgaaaggg    1380
gaacgcagaa gaggcaaagg ccacgacgga ctgtaccagg gactcagcac cgccaccaag    1440
gacacctatg acgctcttca catgcaggcc ctgccgcctc gg                       1482
```

<210> SEQ ID NO 132
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132

```
atggccctcc ctgtcaccgc cctgctgctt ccgctggctc ttctgctcca cgccgctcgg      60
ccccaagtcc aactccagca gtcaggtgca gaagtcaaaa agccaggagc atccgtgaag     120
gtttcgtgca agacttccgg ctacccttt accgggtact ccctccattg ggtgagacaa      180
gcaccgggcc agggactgga gtggatggga tggatcaacc caaattcggg cggcaccaac    240
tatgcgcaga agttccaggg acgggtgacc atgactcgcg acacttcgat ctccactgcc    300
tacatggagc tgtcccgctt gagatctgac gacacgccg tctactactg cgcccgggat    360
cactacggag gtaattcgct gttctactgg gggcagggaa cccttgtgac tgtgtcctcg    420
```

```
ggtggtggag ggtcaggagg cggaggctca gggggaggag gtagcggagg aggcggatca    480
gacatccaac tgacccagtc accatcctcc atctcggcta gcgtcggaga caccgtgtcg    540
attacttgta gggcctccca agactcaggg acgtggctgg cgtggtatca gcaaaaaccg    600
ggcaaagctc cgaacctgtt gatgtacgac gccagcaccc tcgaagatgg agtgcctagc    660
cgcttcagcg gaagcgcctc gggcactgaa ttcacgctga ctgtgaatcg gctccagccg    720
gaggattcgg cgacctacta ctgccagcag tacaacagct accccctgac ctttggaggc    780
gggaccaagg tggatatcaa gaccactacc ccagcaccga ggccacccac cccggctcct    840
accatcgcct cccagcctct gtccctgcgt ccggaggcat gtagacccgc agctggtggg    900
gccgtgcata cccggggtct tgacttcgcc tgcgatatct acatttgggc ccctctggct    960
ggtacttgcg gggtcctgct gctttcactc gtgatcactc tttactgtaa gcgcggtcgg   1020
aagaagctgc tgtacatctt taagcaaccc ttcatgaggc ctgtgcagac tactcaagag   1080
gaggacggct gttcatgccg gttcccagag gaggaggaag cggctgcga actgcgcgtg    1140 aaattcagcc gcagcgcaga tgctccagcc tacaagcagg ggcagaacca gctctacaac   1200
gaactcaatc ttggtcggag agaggagtac gacgtgctgg acaagcggag aggacgggac   1260
ccagaaatgg gcgggaagcc gcgcagaaag aatccccaag agggcctgta caacgagctc   1320
caaaaggata gatggcaga agcctatagc gagattggta tgaaagggga acgcagaaga    1380
ggcaaaggcc acgacggact gtaccaggga ctcagcaccg ccaccaagga cacctatgac   1440
gctcttcaca tgcaggccct gccgcctcgg                                    1470
```

<210> SEQ ID NO 133
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133

```
atggccctcc ctgtcaccgc cctgctgctt ccgctggctc ttctgctcca cgccgctcgg     60
ccccaagtgc aactcgtcca gtcaggtgca gaagtgaaga aaccaggagc gtccgtcgaa    120
gtgtcgtgta aggcgtccgg ctacactttc acctcgtact acatgcactg ggtgcggcag    180
gccccgggac aaggcctcga atggatggga atcatcaacc cgagcggagg ctcgactggt    240
tacgcccaga gttccagggg aagggtgacg atgacccgcg atacctcgac ttcgaccgtt    300
catatggagc tctcgtccct gcggagcgag gacactgctg tctactattg cgcgcgggga    360
ggatactcta gctcctccga tgcatttgac atttggggcc aggaactat ggtgaccgtg     420 tcatcaggcg gaggtggatc aggaggagga gggtcggag gggaggcag cggcggggt      480 gggtcggaca ttcagatgac gcagtcccct cctagcctga cgcctcggt gggtgacaga    540 gtgaccatca cttgcagagc ctcgcaagac atctcctccg cattggcttg gtaccagcaa   600
aagccgggca ctccgccgaa actgctcatc tacgatgcct cctcactgga gtcaggagtc   660
ccatctcgct tctcggggtc aggaagcggc accgatttta cccttaccat ctccagcctg   720
cagcccgagg acttcgccac gtactactgc caacagttca gctcctaccc actgaccttc   780
gggggcggaa ctgcctggaa aatcaagacc actaccccag caccgaggcc acccaccccg    840
gctcctacca tcgcctccca gcctctgtcc ctgcgtccgg aggcatgtag acccgcagct    900
```

| | |
|---|---|
| ggtgggccg tgcatacccg gggtcttgac ttcgcctgcg atatctacat ttgggcccct | 960 |
| ctggctggta cttgcggggt cctgctgctt tcactcgtga tcactcttta ctgtaagcgc | 1020 |
| ggtcggaaga agctgctgta catctttaag caacccttca tgaggcctgt gcagactact | 1080 |
| caagaggagg acggctgttc atgccggttc cagaggagg aggaaggcgg ctgcgaactg | 1140 |
| cgcgtgaaat tcagccgcag cgcagatgct ccagcctaca agcagggca gaaccagctc | 1200 |
| tacaacgaac tcaatcttgg tcggagagag gagtacgacg tgctggacaa gcggagagga | 1260 |
| cgggacccag aaatgggcgg gaagccgcgc agaaagaatc cccaagaggg cctgtacaac | 1320 |
| gagctccaaa aggataagat ggcagaagcc tatagcgaga ttggtatgaa aggggaacgc | 1380 |
| agaagaggca aaggccacga cggactgtac cagggactca gcaccgccac caaggacacc | 1440 |
| tatgacgctc ttcacatgca ggccctgccg cctcgg | 1476 |

<210> SEQ ID NO 134
<211> LENGTH: 1497
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 134

| | |
|---|---|
| atggccctcc ctgtcaccgc cctgctgctt ccgctggctc ttctgctcca cgccgctcgg | 60 |
| ccccaagtgc aactcgtcca gagcggagca gaagtcaaga agccaggagc gtcagtgaaa | 120 |
| gtgtcatgca aggccagcgg ctataccttt acttcgtatg ggatctcctg ggtgcggcag | 180 |
| gcaccgggcc aaggactgga gtggatggga tggatctcag cctacaacgg taacaccaac | 240 |
| tacgcccaga agctgcaagg acgcgtgacc atgactactg atacgagcac ctccactgcc | 300 |
| tacatggaat tgcggtccct tcggtcggac gatactgctg tgtactactg cgcaagagtc | 360 |
| gccggaggga tctactacta ctacggcatg gacgtctggg gacagggaac caccattacg | 420 |
| gtgtcgagcg gaggggagg ctcggggga ggaggaagcg gaggtggcgg ctccggggc | 480 |
| ggcggatcgg acattgtgat gacccagact cctgactccc tggctgtttc gttgggagag | 540 |
| cgcgcgacta tctcgtgtaa gtccagccac tcagtcctgt acaatcgcaa taacaagaac | 600 |
| tacctcgcgt ggtaccagca aaaaccgggt cagccgccta aactcctgtt ctactgggcc | 660 |
| tccaccagaa agagcggggt gccagatcga ttctctggat caggatcagg taccgacttt | 720 |
| acgctgacca tctcgtccct gcagccgag gatttcgcga cttacttctg ccagcagact | 780 |
| cagactttcc ccctcaccct cggtcaaggc accaggctgg aaatcaatac cactaccca | 840 |
| gcaccgaggc cacccacccc ggctcctacc atcgcctccc agcctctgtc cctgcgtccg | 900 |
| gaggcatgta gacccgcagc tggtggggcc gtgcataccc ggggtcttga cttcgcctgc | 960 |
| gatatctaca tttgggcccc tctggctggt acttgcgggg tcctgctgct ttcactcgtg | 1020 |
| atcactcttt actgtaagcg cggtcggaag aagctgctgt acatctttaa gcaacccttc | 1080 |
| atgaggcctg tgcagactac tcaagaggag gacggctgtt catgccggtt cccagaggag | 1140 |
| gaggaaggcg gctgcgaact gcgcgtgaaa ttcagccgca gcgcagatgc tccagcctac | 1200 |
| aagcagggc agaaccagct ctacaacgaa ctcaatcttg gtcggagaga ggagtacgac | 1260 |
| gtgctggaca gcggagagg acgggaccca gaaatgggcg ggaagccgcg cagaaagaat | 1320 |
| ccccaagagg gcctgtacaa cgagctccaa aaggataaga tggcagaagc ctatagcgag | 1380 |
| attggtatga aggggaacg cagaagaggc aaaggccacg acggactgta ccagggactc | 1440 |

```
agcaccgcca ccaaggacac ctatgacgct cttcacatgc aggccctgcc gcctcgg      1497
```

<210> SEQ ID NO 135
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135

```
atggccctcc ctgtcaccgc cctgctgctt ccgctggctc ttctgctcca cgccgctcgg      60
ccccaagtcc aattgcagca gagcggagca gaagtgaaga agccaggagc gtcagtcaaa     120
gtgtcgtgta aggcgtcagg atacaccttc acgggatact acatgcactg ggtgcgccag     180
gccccgggcc aaggactcga gtggatgggc tggatcaacc ctaactctgg aggcaccaac     240
tacgcccaga atttccaagg cagagtgacc atgacccggg acacctccat ctcgactgcc     300
tatatggaac tgcggcggct gcgctcggac gatactgctg tgtattactg cgccagcggc     360
tgggactttg actactgggg acagggtact ctggtgactg tttcctcggg aggaggcgga     420
tcgggtggag gaggtagcgg gggagggggg tcgggaggcg gaggcagcga tattcgcatg     480
actcaatcgc cgtcctccct gagcgctagc gtgggagatc gagtcaccat cacttgcaga     540
gcgtcacagt cgattcgcta ctacctgtcc tggtaccagc agaaaccggg aaaggcacca     600
aagcttctga tctacacggc ctccatcctg caaaatggtg tcccatcaag gttctccggg     660
tcagggagcg gcactgactt cactctcacc atctcctcac tccagcccga ggactttgca     720
acctactact gctcccagac gtacaccacc ccggatttcg gtcctggaac caaggtggaa     780
atcaaaacca ctaccccagc accgaggcca cccaccccgg ctcctaccat cgcctcccag     840
cctctgtccc tgcgtccgga ggcatgtaga cccgcagctg gtggggccgt gcataccggg     900
ggtcttgact tcgcctgcga tatctacatt tgggcccctc tggctggtac ttgcggggtc     960
ctgctgcttt cactcgtgat cactctttac tgtaagcgcg gtcggaagaa gctgctgtac    1020
atctttaagc aaccccttcat gaggcctgtg cagactactc aagaggagga cggctgttca    1080
tgccggttcc cagaggagga ggaaggcggc tgcgaactgc gcgtgaaatt cagccgcagc    1140
gcagatgctc cagcctacaa gcaggggcag aaccagctct acaacgaact caatcttggt    1200
cggagagagg agtacgacgt gctggacaag cggagaggac gggacccaga aatgggcggg    1260
aagccgcgca gaaagaatcc ccaagagggc ctgtacaacg agctccaaaa ggataagatg    1320
gcagaagcct atagcgagat tggtatgaaa ggggaacgca gaagaggcaa aggccacgac    1380
ggactgtacc agggactcag caccgccacc aaggacacct atgacgctct tcacatgcag    1440
gccctgccgc ctcgg                                                    1455
```

<210> SEQ ID NO 136
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136

```
atggccctcc ctgtcaccgc cctgctgctt ccgctggctc ttctgctcca cgccgctcgg      60
```

-continued

| | |
|---|---|
| ccccaagtcc aactcgtcca aagcggagca gaagtcaaaa agccaggagc gtcggtgaaa | 120 |
| gtgtcttgca aagccagcgg ctacaccttc acgggttact acatgcactg ggtgcgccag | 180 |
| gcgccgggcc aggggctgga gtggatgggc cggattaacc ctaacagcgg gggaactaat | 240 |
| tacgctcaga agttccaggg tagagtcacc atgactacgg acacttccac ttccaccgcc | 300 |
| tatatggaac tgcgctccct ccgctcagat gatactgccg tgtattactg cgcgcggact | 360 |
| accacgtcat acgcatttga catctgggc cagggaacta tggtgaccgt gagctcgggc | 420 |
| ggaggcggtt caggggagg aggaagcgga ggaggaggat cgggaggagg tggctccgat | 480 |
| atccagctga ctcagtcccc gagcaccctg tcggcgtcgg tggggacag ggttaccatc | 540 |
| acctgtagag cttcccaatc catttcgact tggctggcct ggtaccagca aaagccggga | 600 |
| aaggccccta atttgcttat ctacaaggca tcgaccctcg aaagcggtgt gccctcccgg | 660 |
| ttttcgggat caggatcagg gaccgagttc accctgacca tctcatccct ccagccggac | 720 |
| gacttcgcca cttactactg ccagcagtac aacacctact cgccatacac tttcggccaa | 780 |
| ggcaccaagc tggagatcaa gaccactacc ccagcaccga ggccacccac cccggctcct | 840 |
| accatcgcct cccagcctct gtccctgcgt ccggaggcat gtagacccgc agctggtggg | 900 |
| gccgtgcata cccggggtct tgacttcgcc tgcgatatct acatttgggc ccctctggct | 960 |
| ggtacttgcg gggtcctgct gctttcactc gtgatcactc tttactgtaa gcgcggtcgg | 1020 |
| aagaagctgc tgtacatctt taagcaaccc ttcatgaggc ctgtgcagac tactcaagag | 1080 |
| gaggacggct gttcatgccg gttcccagag gaggaggaag gcggctgcga actgcgcgtg | 1140 |
| aaattcagcc gcagcgcaga tgctccagcc tacaagcagg gcagaaacca gctctacaac | 1200 |
| gaactcaatc ttggtcggag agaggagtac gacgtgctgg acaagcggag aggacgggac | 1260 |
| ccagaaatgg gcgggaagcc gcgcagaaag aatccccaag agggcctgta caacgagctc | 1320 |
| caaaaggata agatggcaga agcctatagc gagattggta tgaaagggga acgcagaaga | 1380 |
| ggcaaaggcc acgacggact gtaccaggga ctcagcaccg ccaccaagga cacctatgac | 1440 |
| gctcttcaca tgcaggccct gccgcctcgg | 1470 |

<210> SEQ ID NO 137
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 137

| | |
|---|---|
| atggccctcc ctgtcaccgc cctgctgctt ccgctggctc ttctgctcca cgccgctcgg | 60 |
| ccccaagttc aactcgtgca atcaggtgga ggactcgtca acccggagg atcattgaga | 120 |
| ctgtcatgcg aagcgagcgg ttttatcttc tccgattact atatgggatg gattcggcag | 180 |
| gccccgggaa agggactcga atgggtgtca tacatcggaa ggtcaggctc gtccatgtac | 240 |
| tacgcagact cggtgaaagg cagattcacc tttagccggg acaacgccaa gaattccctc | 300 |
| tacttgcaga tgaacagcct gcgagccgag gatactgctg tctactactg tgccgcgtcg | 360 |
| ccggtggtgg cagctactga agatttccag cactggggac agggaactct ggtcacggtg | 420 |
| tcgagcggtg ggggcggaag cggaggcgga ggatcgggcg gcggaggttc ggggggggga | 480 |
| gggtctgaca tcgtgatgac ccaaacccca gccaccctga gctctctccc ggagagcgc | 540 |
| gcgactcttt cgtgccgcgc ttcccagtca gtgaccagca attacttggc ttggtaccaa | 600 |

```
cagaagccgg gacaggcgcc acggctgctg cttttttggtg ccagcactcg cgccaccgga      660
atcccggatc gcttctcggg ctcagggtcc gggacggact tcaccctgac tatcaaccgg      720
ctggaacctg aggacttcgc gatgtactac tgccagcagt acggctccgc accagtcact      780
ttcggacaag gcaccaagct ggagatcaag accactaccc cagcaccgag gccacccacc      840
ccggctccta ccatcgcctc ccagcctctg tccctgcgtc cggaggcatg tagacccgca      900
gctggtgggg ccgtgcatac ccggggtctt gacttcgcct gcgatatcta catttgggcc      960
cctctggctg gtacttgcgg ggtcctgctg ctttcactcg tgatcactct ttactgtaag     1020
cgcggtcgga agaagctgct gtacatcttt aagcaaccct tcatgaggcc tgtgcagact     1080
actcaagagg aggacggctg ttcatgccgg ttcccagagg aggaggaagg cggctgcgaa     1140
ctgcgcgtga aattcagccg cagcgcagat gctccagcct acaagcaggg gcagaaccag     1200
ctctacaacg aactcaatct tggtcggaga gaggagtacg acgtgctgga caagcggaga     1260
ggacgggacc cagaaatggg cgggaagccg cgcagaaaga tccccaaga gggcctgtac      1320 aacgagctcc aaaaggataa gatggcagaa gcctatagcg agattggtat gaaaggggaa     1380
cgcagaagag gcaaaggcca cgacggactg taccagggac tcagcaccgc caccaaggac     1440
acctatgacg ctcttcacat gcaggccctg ccgcctcgg                            1479
```

<210> SEQ ID NO 138
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 138

```
atggccctcc ctgtcaccgc cctgctgctt ccgctggctc ttctgctcca cgccgctcgg       60
ccccaagtcc aactcgtcca gtcgggagca gaagttagag caccaggagc gtcagtgaaa      120
atctcatgca aggcctcggg cttcacgttc gcgggatact acatccactg ggtgcgccaa      180
gccccgggtc agggattgga gtggatggga atcattaacc catcaggagg gagccgggct      240
tacgcgcaga gttccagggg acgcgtcact atgacccgag atacttccac ctcgactgtg      300
tacatggaac tctcgtccct gaggtccgac gacactgcga tgtattactg tgctcggact      360
gccagctgcg gtggggactg ttactacctc gattactggg gccagggaac tctggtgacc      420
gtgtccagcg gaggtggcgg gtcaggggt ggcggaagcg gaggcggcgg ttcaggcgga       480
ggaggctcgg acatccaaat gacgcaatcg ccgcctaccc tgagcgcttc cgtgggagat      540
cgggtgacca ttacttgcag agcatccgag aacgtcaata tctggctggc ctggtaccaa      600
cagaagccgg ggaaggcccc taaactgctg atctacaagt cgagcagcct tgcctctgga      660
gtgccctccc gcttctcggg ctcgggatca ggagcggaat tcaccctcac catctcctcc      720
ctgcagccag atgactttgc cacctactac tgccagcagt accagagcta tccgttgacc      780
tttgggggag gcactaaagt ggacatcaag accactaccc cagcaccgag gccacccacc      840
ccggctccta ccatcgcctc ccagcctctg tccctgcgtc cggaggcatg tagacccgca      900
gctggtgggg ccgtgcatac ccggggtctt gacttcgcct gcgatatcta catttgggcc      960
cctctggctg gtacttgcgg ggtcctgctg ctttcactcg tgatcactct ttactgtaag     1020
cgcggtcgga agaagctgct gtacatcttt aagcaaccct tcatgaggcc tgtgcagact     1080
```

| | |
|---|---|
| actcaagagg aggacggctg ttcatgccgg ttcccagagg aggaggaagg cggctgcgaa | 1140 |
| ctgcgcgtga aattcagccg cagcgcagat gctccagcct acaagcaggg gcagaaccag | 1200 |
| ctctacaacg aactcaatct tggtcggaga gaggagtacg acgtgctgga caagcggaga | 1260 |
| ggacgggacc cagaaatggg cgggaagccg cgcagaaaga atccccaaga gggcctgtac | 1320 |
| aacgagctcc aaaaggataa gatggcagaa gcctatagcg agattggtat gaaaggggaa | 1380 |
| cgcagaagag gcaaaggcca cgacggactg taccagggac tcagcaccgc caccaaggac | 1440 |
| acctatgacg ctcttcacat gcaggccctg ccgcctcgg | 1479 |

<210> SEQ ID NO 139
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic polynucleotide"

<400> SEQUENCE: 139

| | |
|---|---|
| atggccctcc ctgtcaccgc cctgctgctt ccgctggctc ttctgctcca cgccgctcgg | 60 |
| ccccaagttc aactcgttca atcaggtgga ggactcgtgc aaccaggaag atcactcaga | 120 |
| ctcagctgcg ccgcgtcggg attcactttc gatgactacg caatgcactg ggtgcggcag | 180 |
| gccccgggca aggactgga atgggtgagc ggaattagct ggaactcggg gtccatcggg | 240 |
| tacgccgact cggtgaaggg acgctttacg atctcccggg acaatgccaa gaactccctg | 300 |
| tatttgcaga tgaactcctt gagggctgag gacaccgccg tgtactactg cgctaaagat | 360 |
| ggatcatcgt cctggtcctg gggatacttc gattactggg gccagggcac tctggtgacc | 420 |
| gtgtcgtcag gcggtggagg gtcggccgga ggaggtagcg gaggcggagg gagcagctct | 480 |
| gaactgaccc aagacccggc ggtgtcggtc gcccttggtc agactgtgcg gactacctgt | 540 |
| caggggacg cgctgcgctc gtactacgct tcatggtacc agcagaagcc cggacaggca | 600 |
| cctatgctgg tcatctacgg aaagaataac cgcccatccg gcatcccgga tcgcttctcg | 660 |
| ggttcggaca gcggcgacac cgcatccctg acgatcactg gagcgcaggc cgaggatgaa | 720 |
| gccgactact actgcaattc ccgagattca gcggctacc ctgtgtttgg gaccggaact | 780 |
| aaggtcaccg tcctgaccac taccccagca ccgaggccac ccaccccggc tcctaccatc | 840 |
| gcctcccagc ctctgtccct gcgtccggag gcatgtagac ccgcagctgg tggggccgtg | 900 |
| cataccccggg gtcttgactt cgcctgcgat atctacattt gggcccctct ggctggtact | 960 |
| tgcgggggtcc tgctgctttc actcgtgatc actctttact gtaagcgcgg tcggaagaag | 1020 |
| ctgctgtaca tctttaagca accccttcatg aggcctgtgc agactactca agaggaggac | 1080 |
| ggctgttcat gccggttccc agaggaggag gaaggcggct gcgaactgcg cgtgaaattc | 1140 |
| agccgcagcg cagatgctcc agcctacaag caggggcaga accagctcta caacgaactc | 1200 |
| aatcttggtc ggagagagga gtacgacgtg ctggacaagc ggagaggacg ggacccagaa | 1260 |
| atgggcggga agccgcgcag aaagaatccc caagagggcc tgtacaacga gctccaaaag | 1320 |
| gataagatgg cagaagccta tagcgagatt ggtatgaaag gggaacgcag aagaggcaaa | 1380 |
| ggccacgacg gactgtacca gggactcagc accgccacca ggacaccta tgacgctctt | 1440 |
| cacatgcagg ccctgccgcc tcgg | 1464 |

<210> SEQ ID NO 140
<211> LENGTH: 1470

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 140
atggccctcc ctgtcaccgc cctgctgctt ccgctggctc ttctgctcca cgccgctcgg      60
cccgaagtgc aactcgtgga atctggtgga ggacttgtgc aacctggaag atcgttgaga     120
ctctcatgtg ctgcctccgg gttcaccttt gacgactacg ccatgcactg ggtgcgccag     180
gcaccaggaa agggtctgga gtgggtttcg ggtatctcgt ggaactccgg gagcactggc     240
tacgctgatt cggtgaaagg ccggtttacc atctcccgag acaatgcgaa gaattccctc     300
tatctgcaga tgaacagcct ccgggccgag gatactgccc tgtactactg cgccaaggat     360
agctcatcat ggtacggagg tggatcggct ttcgatatct ggggccaggg cacgatggtc     420
accgtgtcct cggggggcgg aggctccggg ggaggaggta gcgaggagga ggatcgagc      480
tcagagttga ctcaagaacc cgcagtgtcc gtggcactgg ccaaaccgt caggatcact      540
tgccagggag acagcctgag gtcgtactac gcgtcctggt accagcagaa gccgggacag     600
gccccggtcc tggtcatttt cggacgctca agacgcccat cgggcatccc ggaccggttc     660
agcggaagct cctcgggaaa caccgcgtca cttatcatta ccggcgcaca ggctgaggac     720
gaagcggatt actactgcaa ctcccgcgac aatactgcca accattacgt gttcgggacc     780
ggaacgaaac tgactgtcct gaccactacc ccagcaccga ggccacccac cccggctcct     840
accatcgcct cccagcctct gtccctgcgt ccggaggcat gtagacccgc agctggtggg     900
gccgtgcata cccggggtct tgacttcgcc tgcgatatct catttgggc cctctggct       960
ggtacttgcg gggtcctgct gctttcactc gtgatcactc tttactgtaa gcgcggtcgg    1020
aagaagctgc tgtacatctt taagcaaccc ttcatgaggc ctgtgcagac tactcaagag    1080
gaggacggct gttcatgccg gttcccagag gaggaggaag gcggctgcga actgcgcgtg    1140
aaattcagcc gcagcgcaga tgctccagcc tacaagcagg gcagaaacca gctctacaac    1200
gaactcaatc ttggtcggag agaggagtac gacgtgctgg acaagcggag aggacgggac    1260
ccagaaatgg gcgggaagcc gcgcagaaag aatccccaag agggcctgta caacgagctc    1320
caaaaggata gatggcaga agcctatagc gagattggta tgaaagggga acgcagaaga    1380
ggcaaaggcc acgacggact gtaccaggga ctcagcaccg ccaccaagga cacctatgac    1440
gctcttcaca tgcaggccct gccgcctcgg                                    1470

<210> SEQ ID NO 141
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 141
atggccctcc ctgtcaccgc cctgctgctt ccgctggctc ttctgctcca cgccgctcgg      60
cccgaagttc aattggtgga atctggagga ggacttgtgc aacccggtag atctctgaga     120
ctgtcctgtg cggcatcggg attcaccttc gacgactacg ctatgcactg ggtgagacaa     180
gcccctggaa aaggactgga gtgggtgtca ggcatctcct ggaatagcgg gtccactgga     240
```

```
tacgccgatt cggtcaaggg tcgcttcacc atttcccggg acaatgccaa gaactccctg    300
taccttcaaa tgaactccct ccgggccgag gataccgccc tctactactg cgccaaagac   360
agctcgtcat ggtatggcgg agggtcggca tttgacatct ggggacaggg aactatggtg   420
actgtgtcat caggaggcgg cggaagcggc ggcggcgggt ccggcggagg agggtcgtcc   480
agcgaactca cccaagatcc agcagtgagc gtcgcgctgg gccagaccgt caggatcacg   540
tgccagggag attcactgcg ctcatactac gcgtcctggt accagcagaa gccggggcag   600
gccccggtcc tcgtgatcta cggaaagaac aaccgcccgt cgggtatccc agaccgcttt   660
tcgggtagct ccagcggaaa tacggctagc ctgaccatca ctggagcaca ggctgaggat   720
gaagcggact actactgcaa ttcgcgggc tcatcgggga accattacgt gttcggaact   780
ggtaccaagg tgactgtcct gaccactacc ccagcaccga ggccacccac cccggctcct   840
accatcgcct cccagcctct gtccctgcgt ccggaggcat gtagacccgc agctggtggg   900
gccgtgcata cccggggtct tgacttcgcc tgcgatatct acatttgggc ccctctggct   960
ggtacttgcg gggtcctgct gctttcactc gtgatcactc tttactgtaa gcgcggtcgg   1020
aagaagctgc tgtacatctt taagcaaccc ttcatgaggc ctgtgcagac tactcaagag   1080
gaggacggct gttcatgccg gttcccagag gaggaggaag cggctgcga actgcgcgtg   1140 aaattcagcc gcagcgcaga tgctccagcc tacaagcagg ggcagaacca gctctacaac   1200
gaactcaatc ttggtcggag agaggagtac gacgtgctgg acaagcggag aggacgggac   1260
ccagaaatgg gcgggaagcc gcgcagaaag aatccccaag agggcctgta caacgagctc   1320
caaaaggata gatggcaga agcctatagc gagattggta tgaaagggga acgcagaaga   1380
ggcaaaggcc acgacggact gtaccaggga ctcagcaccg ccaccaagga cacctatgac   1440
gctcttcaca tgcaggccct gccgcctcgg                                   1470
```

<210> SEQ ID NO 142
<211> LENGTH: 1485
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 142

```
atggccctcc ctgtcaccgc cctgctgctt ccgctggctc ttctgctcca cgccgctcgg    60
ccccaagtgc agctcgttca atcaggcgga ggactcgttc aaccaggagg atcattgcga   120
ctctcatgtg cggcctctgg attcacgttt agctcatatt ggatgcactg ggtgcggcag   180
gcgccgggga aaggtctggt gtgggtcagc gcatcaact cagacggctc ctcgacttcg   240
tacgccgact ccgtgaaggg acgctttacc atttcccgcg acaacgccaa gaatacccit   300 taccttcaga tgaactccct ccgcgctgag gataccgccg tgtactactg cgtgaggact   360
ggctgggtcg gcagctacta ctactacatg gacgtgtggg gcaaaggaac tactgtcacc   420
gtgtcaagcg gcggtggagg ttccggcggg ggaggatcgg ggggggcgg atcgggtggc   480 ggaggatcgg agatcgtgtt gacccagtcg ccgggaaccc tgtcgctgtc gcctggggag   540
agagcaactc tgtcctgccg ggcttcccag tcggtgtcga gcaattacct ggcatggtac   600
caacagaagc cgggacagcc gccacgcctc ctgatctatg acgtgtcaac tcgggcaact   660
ggaatccctg cgcggttcag cggcggaggg agcggtaccg atttcaccct gactatttcc   720
tccctcgaac cagaagattt cgccgtctac tactgccagc agagaagcaa ctggccgccc   780
```

```
tggacgttcg gacaaggaac caaggtcgaa atcaagacca ctaccccagc accgaggcca     840 cccacccgg ctcctaccat cgcctcccag cctctgtccc tgcgtccgga ggcatgtaga      900
cccgcagctg gtgggccgt gcatacccgg ggtcttgact tcgcctgcga tatctacatt     960
tgggcccctc tggctggtac ttgcggggtc ctgctgcttt cactcgtgat cactctttac    1020
tgtaagcgcg gtcggaagaa gctgctgtac atctttaagc aacccttcat gaggcctgtg    1080
cagactactc aagaggagga cggctgttca tgccggttcc cagaggagga ggaaggcggc    1140
tgcgaactgc gcgtgaaatt cagccgcagc gcagatgctc cagcctacaa gcaggggcag    1200
aaccagctct acaacgaact caatcttggt cggagagagg agtacgacgt gctggacaag    1260
cggagaggac gggacccaga atgggcggg aagccgcgca gaaagaatcc ccaagagggc     1320
ctgtacaacg agctccaaaa ggataagatg gcagaagcct atagcgagat tggtatgaaa    1380
ggggaacgca agagggcaa aggccacgac ggactgtacc agggactcag caccgccacc     1440
aaggacacct atgacgctct tcacatgcag gccctgccgc ctcgg                    1485
```

<210> SEQ ID NO 143
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 143

```
atggccctcc ctgtcaccgc cctgctgctt ccgctggctc ttctgctcca cgccgctcgg     60
ccccaagtgc aattggttca atcaggagga ggagtcgtgc agcccggaag atcgttgaga    120
ctgtcatgtg ccgcgagcgg ctttactttc tcaagctacg gaatgcattg ggtgcgacag    180
gctccgggaa aaggactgga atgggtcgca gtgatctcat acgacggctc gaacaagtac    240
tacgccgact ccgtcaaggg tcggttcacg atttcgcgcg ataattccaa gaacactctg    300
tacctccaaa tgaacagcct ccgggcagag acaccgccg tctactactg cgctaaggga    360
tactcgcgct actactacta tggaatggat gtgtggggcc agggaactac cgtgacggtg    420
tcgtccggcg gcggtgggtc gggcggaggc ggatcaggtg gaggtggaag cggaggagga    480
gggagcgaaa tcgtcatgac tcagtcccct gctaccctt ctctgtcgcc gggagaaaga    540
gccatcctga gctgccgggc ctcccagagc gtgtacacca aatacctggg atggtaccag    600
cagaagccgg gcaggcacc aaggctcctg atctacgatg cgtccacccg cgcgactggt    660
atcccagacc gcttttccgg ctcggggtca gggactgact tcaccttac tatcaatcgg    720 ctcgagcctg aggatttcgc cgtgtattac tgccagcact acgagggtc cccgctgatt    780 accttcggcc aaggcaccaa agtggacatc aagaccacta ccccagcacc gaggccaccc    840
acccgggctc ctaccatcgc ctcccagcct cgtccctgc gtccggaggc atgtagacccc    900 gcagctggtg gggccgtgca tacccgggt cttgacttcg cctgcgatat ctacatttgg    960
gcccctctgg ctggtacttg cggggtcctg ctgctttcac tcgtgatcac tctttactgt    1020
aagcgcggtc ggaagaagct gctgtacatc tttaagcaac ccttcatgag gcctgtgcag    1080
actactcaag aggacgg ctgttcatgc cggttcccag aggaggag aggcggctgc          1140 gaactgcgcg tgaaattcag ccgcagcgca gatgctccag cctacaagca ggggcagaac    1200
cagctctaca acgaactcaa tcttggtcgg agagaggagt acgacgtgct ggacaagcgg    1260
```

| | |
|---|---|
| agaggacggg acccagaaat gggcgggaag ccgcgcagaa agaatcccca agagggcctg | 1320 |
| tacaacgagc tccaaaagga taagatggca gaagcctata gcgagattgg tatgaaaggg | 1380 |
| gaacgcagaa gaggcaaagg ccacgacgga ctgtaccagg gactcagcac cgccaccaag | 1440 |
| gacacctatg acgctcttca catgcaggcc ctgccgcctc gg | 1482 |

<210> SEQ ID NO 144
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144

| | |
|---|---|
| atggccctcc ctgtcaccgc cctgctgctt ccgctggctc ttctgctcca cgccgctcgg | 60 |
| ccccaagtgc aacttgttca atcaggagga ggactcgttc aacccggagg atcactgcga | 120 |
| ctctcatgtg cagcgtcggg gttcaccttc tccagctacg caatgtcctg ggtgcgccaa | 180 |
| gcccctggaa aaggcctgga gtgggtgtcg gccatctctg ggagcggggg atcaacttac | 240 |
| tacgctgact ccgtcaaggg ccgctttacc atctcccggg acaacagcaa gaacactctc | 300 |
| tatctccaga tgaactcgct gagagccgaa gataccgctg tctactactg cgcgaagaga | 360 |
| gaagctgccg cagggcacga ttggtacttc gacttgtggg gcaggggcac ccttgtgacc | 420 |
| gtgtcctccg gtggaggcgg atcaggaggt gggggatcgg gtggaggagg aagcggaggc | 480 |
| ggcggttcgg acattgcgt cacccagtca ccgagctccc tcagcgcatc ggtgggcgac | 540 |
| cgggtcacta tcacttgccg ggcgtcccag tcgatctcat cgtatctgaa ttggtaccag | 600 |
| cagaaaccgg gaaaggcgcc gaagctgttg atctacgctg ccagctccct gcagtcgggt | 660 |
| gtgccatcac gcttttccgg ctcgggatcg ggaaccgatt tcactctgac gatctctagc | 720 |
| ctgcagccag aagatttcgc cacttactac tgccagcagt cctacagcat ccctctgact | 780 |
| ttcggacaag ggacgaaagt ggagattaag accactaccc cagcaccgag gccacccacc | 840 |
| ccggctccta ccatcgcctc ccagcctctg tccctgcgtc cggaggcatg tagacccgca | 900 |
| gctggtgggg ccgtgcatac ccgggggtctt gacttcgcct gcgatatcta catttgggcc | 960 |
| cctctggctg gtacttgcgg ggtcctgctg ctttcactcg tgatcactct ttactgtaag | 1020 |
| cgcggtcgga agaagctgct gtacatcttt aagcaacccct tcatgaggcc tgtgcagact | 1080 |
| actcaagagg aggacggctg ttcatgccgg ttcccagagg aggaggaagg cggctgcgaa | 1140 |
| ctgcgcgtga aattcagccg cagcgcagat gctccagcct acaagcaggg gcagaaccag | 1200 |
| ctctacaacg aactcaatct tggtcggaga gaggagtacg acgtgctgga caagcggaga | 1260 |
| ggacgggacc cagaaatggg cgggaagccg cgcagaaaga tccccaaga gggcctgtac | 1320 |
| aacgagctcc aaaaggataa gatggcagaa gcctatagcg agattggtat gaagggggaa | 1380 |
| cgcagaagag gcaaaggcca cgacggactg taccagggac tcagcaccgc caccaaggac | 1440 |
| acctatgacg ctcttcacat gcaggccctg ccgcctcgg | 1479 |

<210> SEQ ID NO 145
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 145

```
atggccctcc ctgtcaccgc cctgctgctt ccgctggctc ttctgctcca cgccgctcgg      60
ccccaagtcc aactcgttca gtcatgggca gaagtcaaga acccggtgc aagcgtcaaa     120
gtgtcgtgta aggcctccgg ctacactttc acttcctact acatgcactg ggtgcgccaa    180
gccccgggac agggccttga atggatgggc atcatcaacc catcaggagg ttccacgagc    240
tacgcgcaga agttccaggg gagagtgacg atgactagaa tacctccac gagcaccgtc    300
tacatggagc tgtcgaatct gcggtcagag gacactgctg tgtattactg cgcgcgctcc    360
ccgcgggtga ccactggcta ctttgactac tggggacaag ggaccctggt gaccgtcagc    420
tcgggaggcg gaggatcggg aggtggaggg tccggtggag gcggctctgg aggaggcggg    480
tcggacattc aattgaccca gagcccatcc accctctcag cctcggtggg ggataggggtg   540
actatcactt gccgggcctc ccagtcaatt tccagctggc tggcttggta ccagcaaaag    600
cctggaaagg caccgaagct cctgatctac aaggcctcat ctctggaatc aggagtgcct    660
tcgcgcttca gcggaagcgg ctcgggaact gagtttaccc tgaccatctc gagcctgcag    720
ccagatgact tcgcgaccta ttactgccag cagtactcgt cctacccgtt gactttcgga    780
ggaggtaccc gcctcgaaat caaaaccact accccagcac cgaggccacc caccccggct    840
cctaccatcg cctcccagcc tctgtccctg cgtccggagg catgtagacc cgcagctggt    900
ggggccgtgc atacccgggg tcttgacttc gcctgcgata tctacatttg gcccctctg    960
gctggtactt gcggggtcct gctgctttca ctcgtgatca ctctttactg taagcgcggt   1020
cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
aacgaactca atcttggtcg gagagaggag tacgacgtgc tggacaagcg agaggacgg    1260
gacccagaaa tgggcgggaa gccgcgcaga aagaatcccc aagagggcct gtacaacgag   1320
ctccaaaagg ataagatggc agaagcctat agcgagattg gtatgaaagg gaacgcaga    1380
agaggcaaag gccacgacgg actgtaccag ggactcagca ccgccaccaa ggacacctat   1440
gacgctcttc acatgcaggc cctgccgcct cgg                                1473
```

<210> SEQ ID NO 146
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 146

```
atggccctcc ctgtcaccgc cctgctgctt ccgctggctc ttctgctcca cgccgctcgg      60
ccccaagtcc aactcgtcca gtccggtgca gaagtcagaa ggccaggagc aagcgtgaag    120
atctcgtgta gagcgtcagg agacaccagc actcgccatt acatccactg gctgcgccag    180
gctccgggcc aagggccgga gtggatgggt gtgatcaacc cgactacggg accggctacc    240
ggaagccctg cgtacgcaca gatgctgcag ggacgggtga ctatgacccg cgatactagc    300
actaggaccg tgtacatgga actccgctcg ttgcggttcg aagataccgc cgtctactac    360
tgcgcccggt ccgtggtggg ccgaagcgcc ccttactact cgattactg gggacagggc    420
```

```
actctggtga ccgttagctc cggtggggga ggctcgggtg gaggcggatc gggaggagga      480
ggcagcggtg gaggggggatc ggacattcag atgacccagt caccctcctc cctctcagcc    540
tcggtcgggg accgggtgac cattacgtgc agagcctcac aagggatctc ggactactcc     600
gcctggtacc agcagaaacc gggaaaagcg ccaaagctcc tgatctacgc cgcgagcacc     660
ctgcaatcag gagtgccatc gcgcttttct ggatcgggct cagggactga cttcacgctg     720
actatctcct accttcagtc cgaggatttc gctacctact actgccaaca gtattactcc     780
tatcccctga cctttggcgg aggcactaag gtggacatca gaccactac cccagcaccg      840
aggccaccca ccccggctcc taccatcgcc tcccagcctc tgtccctgcg tccgaggca     900
tgtagacccg cagctggtgg ggccgtgcat acccgggtc ttgacttcgc ctgcgatatc     960
tacatttggg cccctctggc tggtacttgc ggggtcctgc tgctttcact cgtgatcact    1020
ctttactgta agcgcggtcg aagaagctg ctgtacatct ttaagcaacc cttcatgagg    1080
cctgtgcaga ctactcaaga ggaggacggc tgttcatgcc ggttcccaga ggaggaggaa    1140
ggcggctgcg aactgcgcgt gaaattcagc cgcagcgcag atgctccagc ctacaagcag   1200
gggcagaacc agctctacaa cgaactcaat cttggtcgga gagaggagta cgacgtgctg   1260
gacaagcgga gaggacggga cccagaaatg ggcgggaagc cgcgcagaaa gaatccccaa   1320
gagggcctgt acaacgagct ccaaaaggat aagatggcag aagcctatag cgagattggt   1380
atgaaagggg aacgcagaag aggcaaaggc cacgacggac tgtaccaggg actcagcacc   1440
gccaccaagg acacctatga cgctcttcac atgcaggccc tgccgcctcg g             1491
```

<210> SEQ ID NO 147
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 147

```
atggccctcc ctgtcaccgc cctgctgctt ccgctggctc ttctgctcca cgccgctcgg      60
ccccaagtcc aactccagca tcgggagca gaagtcaaga accaggcgc atcggtgaaa      120
gtgtcgtgta aggcgtcagg gtacaccttc accaactact atatgcactg ggtgcgccag   180
gctccaggcc aggggttgga gtggatgggg atcatcaatc cgtcaggtgg ctacaccact   240
tacgctcaga gttccagggg acgcctcact atgactcgcg atactagcac ctccacggtg   300
tacatggaac tgtcatcgct gaggtccgaa gataccgccg tctactactg cgcacggatc   360
agatcctgcg gaggagattg ttactacttt gacaactggg gacagggcac ccttgttact   420
gtgtcatcgg gaggaggggg aagcggagga ggtggatcag gcggcggtgg cagcggggc    480
ggaggatcgg acattcagct gactcagtcc ccctccactt tgtcggccag cgtgggagac   540
agagtgacca tcacttgccg ggcgtccgag aacgtcaata tctggctggc ctggtaccag   600
caaaagcctg gaaaagcccc gaagctgctc atctataagt catccagcct ggcgtctggt   660
gtgccgtcgc ggttctccgg cagcgggagc ggagccgagt tcactctcac catttcgagc   720
cttcaaccgg acgatttcgc cacctactac tgccagcagt accaatccta ccctctgacg   780
tttggaggtg gaaccaaggt ggacatcaag accactaccc cagcaccgag gccacccacc   840
ccggctccta ccatcgcctc ccagcctctg tccctgcgtc cggaggcatg tagacccgca   900
gctggtgggg ccgtgcatac ccggggtctt gacttcgcct gcgatatcta catttgggcc   960
```

```
cctctggctg gtacttgcgg ggtcctgctg ctttcactcg tgatcactct ttactgtaag    1020
cgcggtcgga agaagctgct gtacatcttt aagcaaccct tcatgaggcc tgtgcagact    1080
actcaagagg aggacggctg ttcatgccgg ttcccagagg aggaggaagg cggctgcgaa    1140
ctgcgcgtga aattcagccg cagcgcagat gctccagcct acaagcaggg gcagaaccag    1200
ctctacaacg aactcaatct tggtcggaga gaggagtacg acgtgctgga caagcggaga    1260
ggacgggacc cagaaatggg cgggaagccc gcagaaaga atccccaaga gggcctgtac    1320
aacgagctcc aaaaggataa gatggcagaa gcctatagcg agattggtat gaaaggggaa    1380
cgcagaagag gcaaaggcca cgacggactg taccagggac tcagcaccgc caccaaggac    1440
acctatgacg ctcttcacat gcaggccctg ccgcctcgg                            1479
```

<210> SEQ ID NO 148
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 148

```
atggccctcc ctgtcaccgc cctgctgctt ccgctggctc ttctgctcca cgccgctcgg    60
ccccaaatca ctctgaaaga atctggaccg gccctggtta agccgactca aacgctcacc    120
cttacttgca ccttcagcgg attctcactc agcactgctg gtgtgcacgt cggatggatt    180
agacagccgc ctggaaaggc cctggaatgg ctcgccctca tctcctgggc cgatgacaag    240
agatacaggc cctcgcttcg atcccggttg gacattaccc gggtgacctc gaaagatcag    300
gtggtgctct caatgaccaa tatgcagccg gaggacaccg ctacgtacta ctgcgcactg    360
caaggatttg acggctacga ggctaactgg ggaccaggta ctctggtcac cgtgagctcc    420
ggcgggggag gatcaggcgg ggggggtca ggaggcggag gctccggtgg aggaggatcg    480
gatatcgtca tgacccagtc cccaagctcg ctgagcgcgt cagcgggcga ccgcgtgact    540
atcacttgcc gggccagccg cggcatctcc tccgcactgg cgtggtacca gcagaagcct    600
ggaaaaccgc caaagctcct gatctatgat gcctccagcc tggagtcagg tgtccccagc    660
cgcttctcgg gttcgggctc gggaaccgac ttcactttga ccatcgactc gctggaaccg    720
gaagatttcg caacctacta ctgtcagcag tcctactcga ccccttggac ttttggacaa    780
gggacgaagg tggacatcaa gaccactacc ccagcaccga gccacccac cccggctcct    840 accatcgcct cccagcctct gtccctgcgt ccggaggcat gtagaccgc agctggtggg    900 gccgtgcata cccggggtct tgacttcgcc tgcgatatct acatttgggc ccctctggct    960
ggtacttgcg ggtcctgct gctttcactc gtgatcactc tttactgtaa gcgcggtcgg    1020
aagaagctgc tgtacatctt taagcaaccc ttcatgaggc ctgtgcagac tactcaagag    1080
gaggacggct gttcatgccg gttcccagag gaggaggaag gcggctgcga actgcgcgtg    1140
aaattcagcc gcagcgcaga tgctccagcc tacaagcagg ggcagaacca gctctacaac    1200
gaactcaatc ttggtcggag agaggagtac gacgtgctgg acaagcggag aggacgggac    1260
ccagaaatgg gcgggaagcc gcgcagaaag aatccccaag agggcctgta caacgagctc    1320
caaaaggata agatggcaga agcctatagc gagattggta tgaaagggga acgcagaaga    1380
ggcaaaggcc acgacggact gtaccaggga ctcagcaccg ccaccaagga cacctatgac    1440
```

-continued

```
gctcttcaca tgcaggccct gccgcctcgg                              1470
```

<210> SEQ ID NO 149
<211> LENGTH: 1149
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 149

```
atggccctcc ctgtcaccgc cctgctgctt ccgctggctc ttctgctcca cgccgctcgg    60
ccccaagtcc agctccagca gtcgggccca gagttggaga agcctggggc gagcgtgaag   120
atctcatgca aagcctcagg ctactccttt actggataca cgatgaattg ggtgaaacag   180
tcgcatggaa agtcactgga atggatcggt ctgattacgc cctacaacgg cgcctccagc   240
tacaaccaga agttcagggg aaaggcgacc cttactgtcg acaagtcgtc aagcaccgcc   300
tacatggacc tcctgtccct gacctccgaa gatagcgcgg tctactttg tgcacgcgga   360
ggttacgatg gacggggatt cgactactgg ggccagggaa ccactgtcac cgtgtcgagc   420
ggaggcggag ggagcggagg aggaggcagc ggaggtggag ggtcggatat cgaactcact   480
cagtccccag caatcatgtc cgcttcaccg ggagaaaagg tgaccatgac ttgctcggcc   540
tcctcgtccg tgtcatacat gcactggtac caacaaaaat cggggaccct ccctaagaga   600
tggatctacg ataccagcaa actggcttca ggcgtgccgg acgcttctc gggttcgggg   660
agcggaaatt cgtattcgtt gaccatttcg tccgtggaag ccgaggacga cgcaacttat   720
tactgccaac agtggtcagg ctacccgctc actttcggag ccggcactaa gctggagatc   780
accactaccc cagcaccgag gccacccacc ccggctccta ccatcgcctc ccagcctctg   840
tccctgcgtc cggaggcatg tagacccgca gctggtgggg ccgtgcatac ccggggtctt   900
gacttcgcct gcgatatcta catttgggcc cctctggctg gtacttgcgg ggtcctgctg   960
ctttcactcg tgatcactct ttactgtaag cgcggtcgga agaagctgct gtacatcttt  1020
aagcaacccct tcatgaggcc tgtgcagact actcaagagg aggacggctg ttcatgccgg  1080
ttcccagagg aggaggaagg cggctgcgaa ctgcgcgtga aattcagccg cagcgcagat  1140
gctccagcc                                                          1149
```

<210> SEQ ID NO 150
<211> LENGTH: 504
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 150

```
Met Ala Leu Pro Val Thr Ala Leu Leu Leu Pro Leu Ala Leu Leu
1               5                   10                  15

His Ala Ala Arg Pro Gly Ser Ser Arg Ala Ala Gln Pro Ala Met Ala
            20                  25                  30

Gln Val Gln Leu Gln Gln Ser Gly Ala Glu Leu Val Lys Pro Gly Ala
        35                  40                  45

Ser Val Lys Ile Ser Cys Lys Ala Ser Gly Tyr Ser Phe Thr Gly Tyr
    50                  55                  60

Phe Met Asn Trp Val Lys Gln Ser His Gly Lys Ser Leu Glu Trp Ile
```

```
                65                  70                  75                  80
Gly Arg Ile His Pro Tyr Asp Gly Asp Thr Phe Tyr Asn Gln Asn Phe
                    85                  90                  95

Lys Asp Lys Ala Thr Leu Thr Val Asp Lys Ser Ser Asn Thr Ala His
                100                 105                 110

Met Glu Leu Leu Ser Leu Thr Ser Glu Asp Phe Ala Val Tyr Tyr Cys
                115                 120                 125

Thr Arg Tyr Asp Gly Ser Arg Ala Met Asp Tyr Trp Gly Gln Gly Thr
    130                 135                 140

Thr Val Thr Val Ser Ser Gly Gly Gly Ser Gly Gly Gly Gly Ser
145                 150                 155                 160

Gly Gly Gly Gly Ser Asp Ile Glu Leu Thr Gln Ser Pro Ala Ser Leu
                165                 170                 175

Ala Val Ser Leu Gly Gln Arg Ala Ile Ile Ser Cys Lys Ala Ser Gln
                180                 185                 190

Ser Val Ser Phe Ala Gly Thr Ser Leu Met His Trp Tyr His Gln Lys
            195                 200                 205

Pro Gly Gln Gln Pro Lys Leu Leu Ile Tyr Arg Ala Ser Asn Leu Glu
    210                 215                 220

Ala Gly Val Pro Thr Arg Phe Ser Gly Ser Gly Ser Lys Thr Asp Phe
225                 230                 235                 240

Thr Leu Asn Ile His Pro Val Glu Glu Asp Ala Ala Thr Tyr Tyr
                245                 250                 255

Cys Gln Gln Ser Arg Glu Tyr Pro Tyr Thr Phe Gly Gly Gly Thr Lys
                260                 265                 270

Leu Glu Ile Lys Arg Ala Ala Ala Ser Thr Thr Thr Pro Ala Pro Arg
        275                 280                 285

Pro Pro Thr Pro Ala Pro Thr Ile Ala Ser Gln Pro Leu Ser Leu Arg
        290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
                340                 345                 350

Gly Arg Lys Lys Leu Leu Tyr Ile Phe Lys Gln Pro Phe Met Arg Pro
            355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Lys Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
    435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495
```

His Met Gln Ala Leu Pro Pro Arg
            500

<210> SEQ ID NO 151
<211> LENGTH: 9228
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 151

| | | | | | |
|---|---|---|---|---|---|
| atggccttac | cagtgaccgc | cttgctcctg | ccgctggcct | tgctgctcca | cgccgccagg | 60 |
| ccgggatcct | ctagagcggc | ccagccggcc | atggcccagg | tgcagctgca | gcagtctgga | 120 |
| gctgagctgg | tgaagcctgg | ggcttcagtg | aagatatcct | gcaaggcttc | tggttactca | 180 |
| tttactggct | actttatgaa | ctgggtgaag | cagagccatg | gaaagagcct | tgagtggatt | 240 |
| ggacgtattc | atcctacga | tggtgatact | ttctacaacc | agaacttcaa | ggacaaggcc | 300 |
| acattgactg | tagacaaatc | ctctaacaca | gcccacatgg | agctcctgag | cctgacatct | 360 |
| gaggactttg | cagtctatta | ttgtacaaga | tacgacggta | gtcgggctat | ggactactgg | 420 |
| ggccaaggga | ccacggtcac | cgtctcctca | ggtggaggcg | gttcaggcgg | aggtggctct | 480 |
| ggcggtggcg | gatcggacat | cgagctcact | cagtctccag | cttctttggc | tgtgtctcta | 540 |
| gggcagaggg | ccatcatctc | ctgcaaggcc | agccaaagtg | tcagttttgc | tggtactagt | 600 |
| ttaatgcact | ggtaccacca | gaaaccagga | cagcaaccca | aactcctcat | ctatcgtgca | 660 |
| tccaacctag | aagctggggt | tcctaccagg | tttagtggca | gtgggtctaa | gacagacttc | 720 |
| accctcaata | tccatcctgt | ggaggaggag | gatgctgcaa | cctattactg | tcagcaaagt | 780 |
| agggaatatc | cgtacacgtt | cggaggggggg | acaaagttgg | aaataaaacg | ggcggccgct | 840 |
| agcaccacga | cgccagcgcc | gcgaccacca | acaccggcgc | ccaccatcgc | gtcgcagccc | 900 |
| ctgtccctgc | gcccagaggc | gtgccggcca | gcggcggggg | gcgcagtgca | cacgaggggg | 960 |
| ctggacttcg | cctgtgatat | ctacatctgg | gcgcccttgg | ccgggacttg | tggggtcctt | 1020 |
| ctcctgtcac | tggttatcac | cctttactgc | aaacggggca | gaaagaaact | cctgtatata | 1080 |
| ttcaaacaac | catttatgag | accagtacaa | actactcaag | aggaagatgg | ctgtagctgc | 1140 |
| cgatttccag | aagaagaaga | aggaggatgt | gaactgagag | tgaagttcag | caggagcgca | 1200 |
| gacgccccccg | cgtacaagca | gggccagaac | cagctctata | acgagctcaa | tctaggacga | 1260 |
| agagaggagt | acgatgtttt | ggacaagaga | cgtggccggg | accctgagat | ggggggaaag | 1320 |
| ccgagaagga | agaaccctca | ggaaggcctg | tacaatgaac | tgcagaaaga | taagatggcg | 1380 |
| gaggcctaca | gtgagattgg | gatgaaaggc | gagcgccgga | ggggcaaggg | gcacgatggc | 1440 |
| ctttaccagg | tctcagtac | agccaccaag | gacacctacg | acgcccttca | catgcaggcc | 1500 |
| ctgccccctc | gctaagtcga | ctcgacaatc | aacctctgga | ttacaaaatt | tgtgaaagat | 1560 |
| tgactggtat | tcttaactat | gttgctcctt | ttacgctatg | tggatacgct | gctttaatgc | 1620 |
| ctttgtatca | tgctattgct | tcccgtatgg | ctttcatttt | ctcctccttg | tataaatcct | 1680 |
| ggttgctgtc | tctttatgag | gagttgtggc | ccgttgtcag | gcaacgtggc | gtggtgtgca | 1740 |
| ctgtgtttgc | tgacgcaacc | cccactggtt | ggggcattgc | caccacctgt | cagctccttt | 1800 |
| ccgggacttt | cgctttcccc | ctccctattg | ccacggcgga | actcatcgcc | gcctgccttg | 1860 |
| cccgctgctg | gacaggggct | cggctgttgg | gcactgacaa | ttccgtggtg | ttgtcgggga | 1920 |

```
agctgacgtc ctttccatgg ctgctcgcct gtgttgccac ctggattctg cgcgggacgt   1980
ccttctgcta cgtcccttcg gccctcaatc cagcggacct tccttcccgc ggcctgctgc   2040
cggctctgcg gcctcttccg cgtcttcgcc ttcgccctca gacgagtcgg atctcccttt   2100
gggccgcctc cccgcctgga attcgagctc ggtacctta agaccaatga cttacaaggc    2160
agctgtagat cttagccact ttttaaaaga aaggggggga ctggaagggc taattcactc   2220
ccaacgaaga caagatctgc tttttgcttg tactgggtct ctctggttag accagatctg   2280
agcctgggag ctctctggct aactagggaa cccactgctt aagcctcaat aaagcttgcc   2340
ttgagtgctt caagtagtgt gtgcccgtct gttgtgtgac tctggtaact agagatccct   2400
cagacccttt tagtcagtgt ggaaaatctc tagcagtagt agttcatgtc atcttattat   2460
tcagtattta aacttgcaa agaaatgaat atcagagagt gagaggaact tgtttattgc    2520
agcttataat ggttacaaat aaagcaatag catcacaaat ttcacaaata aagcattttt   2580
ttcactgcat tctagttgtg gtttgtccaa actcatcaat gtatcttatc atgtctggct   2640
ctagctatcc cgcccctaac tccgcccagt tccgcccatt ctccgcccca tggctgacta   2700
atttttttta tttatgcaga ggccgaggcc gcctcggcct ctgagctatt ccagaagtag   2760
tgaggaggct ttttttggagg cctaggcttt tgcgtcgaga cgtacccaat tcgccctata   2820
gtgagtcgta ttacgcgcgc tcactggccg tcgttttaca acgtcgtgac tgggaaaacc   2880
ctggcgttac ccaacttaat cgccttgcag cacatccccc tttcgccagc tggcgtaata   2940
gcgaagaggc ccgcaccgat cgcccttccc aacagttgcg cagcctgaat ggcgaatggc   3000
gcgacgcgcc ctgtagcggc gcattaagcg cggcgggtgt ggtggttacg cgcagcgtga   3060
ccgctacact tgccagcgcc ctagcgcccg ctcctttcgc tttcttccct tcctttctcg   3120
ccacgttcgc cggctttccc cgtcaagctc taaatcgggg gctcccttta gggttccgat   3180
ttagtgcttt acggcacctc gaccccaaaa aacttgatta gggtgatggt tcacgtagtg   3240
ggccatcgcc ctgatagacg gttttttcgcc ctttgacgtt ggagtccacg ttctttaata  3300
gtggactctt gttccaaact ggaacaacac tcaaccctat ctcggtctat tcttttgatt   3360
tataagggat tttgccgatt tcggcctatt ggttaaaaaa tgagctgatt taacaaaaat   3420
ttaacgcgaa ttttaacaaa atattaacgt ttacaatttc ccaggtggca cttttcgggg   3480
aaatgtgcgc ggaacccta tttgtttatt tttctaaata cattcaaata tgtatccgct    3540
catgagacaa taaccctgat aaatgcttca ataatattga aaaggaaga gtatgagtat    3600
tcaacatttc cgtgtcgccc ttattccctt ttttgcggca ttttgccttc ctgttttgc    3660
tcacccagaa acgctggtga aagtaaaaga tgctgaagat cagttgggtg cacgagtggg   3720
ttacatcgaa ctggatctca acagcggtaa gatccttgag agttttcgcc ccgaagaacg   3780
ttttccaatg atgagcactt ttaaagttct gctatgtggc gcggtattat cccgtattga   3840
cgccgggcaa gagcaactcg gtcgccgcat acactattct cagaatgact tggttgagta   3900
ctcaccagtc acagaaaagc atcttacgga tggcatgaca gtaagagaat tatgcagtgc   3960
tgccataacc atgagtgata acactgcggc caacttactt ctgacaacga tcggaggacc   4020
gaaggagcta accgcttttt tgcacaacat ggggatcat gtaactcgcc ttgatcgttg    4080
ggaaccggag ctgaatgaag ccataccaaa cgacgagcgt gacaccacga tgcctgtagc   4140
aatggcaaca acgttgcgca aactattaac tggcgaacta cttactctag cttcccggca   4200
acaattaata gactggatgg aggcggataa agttgcagga ccacttctgc gctcggccct   4260
```

```
tccggctggc tggtttattg ctgataaatc tggagccggt gagcgtgggt ctcgcggtat    4320
cattgcagca ctggggccag atggtaagcc ctcccgtatc gtagttatct acacgacggg    4380
gagtcaggca actatggatg aacgaaatag acagatcgct gagataggtg cctcactgat    4440
taagcattgg taactgtcag accaagttta ctcatatata ctttagattg atttaaaact    4500
tcatttttaa tttaaaagga tctaggtgaa gatcctttt gataatctca tgaccaaaat     4560
cccttaacgt gagttttcgt tccactgagc gtcagacccc gtagaaaaga tcaaaggatc    4620
ttcttgagat ccttttttc tgcgcgtaat ctgctgcttg caaacaaaaa aaccaccgct     4680
accagcggtg tttgtttgc cggatcaaga gctaccaact ctttttccga aggtaactgg     4740
cttcagcaga gcgcagatac caaatactgt ccttctagtg tagccgtagt taggccacca    4800
cttcaagaac tctgtagcac cgcctacata cctcgctctg ctaatcctgt taccagtggc    4860
tgctgccagt ggcgataagt cgtgtcttac cgggttggac tcaagacgat agttaccgga    4920
taaggcgcag cggtcgggct gaacgggggg ttcgtgcaca cagcccagct tggagcgaac    4980
gacctacacc gaactgagat acctacagcg tgagctatga gaaagcgcca cgcttcccga    5040
agggagaaag gcggacaggt atccggtaag cggcagggtc ggaacaggag agcgcacgag    5100
ggagcttcca gggggaaacg cctggtatct ttatagtcct gtcgggtttc gccacctctg    5160
acttgagcgt cgatttttgt gatgctcgtc aggggggcgg agcctatgga aaaacgccag    5220
caacgcggcc ttttacggt tcctggcctt ttgctggcct tttgctcaca tgttctttcc     5280
tgcgttatcc cctgattctg tggataaccg tattaccgcc tttgagtgag ctgataccgc    5340
tcgccgcagc cgaacgaccg agcgcagcga gtcagtgagc gaggaagcgg aagagcgccc    5400
aatacgcaaa ccgcctctcc ccgcgcgttg gccgattcat taatgcagct ggcacgacag    5460
gtttcccgac tggaaagcgg gcagtgagcg caacgcaatt aatgtgagtt agctcactca    5520
ttaggcaccc caggctttac actttatgct tccggctcgt atgttgtgtg gaattgtgag    5580
cggataacaa tttcacacag gaaacagcta tgaccatgat tacgccaagc gcgcaattaa    5640
ccctcactaa agggaacaaa agctggagct gcaagcttaa tgtagtctta tgcaatactc    5700
ttgtagtctt gcaacatggt aacgatgagt tagcaacatg ccttacaagg agagaaaaag    5760
caccgtgcat gccgattggt ggaagtaagg tggtacgatc gtgccttatt aggaaggcaa    5820
cagacgggtc tgacatggat tggacgaacc actgaattgc cgcattgcag agatattgta    5880
tttaagtgcc tagctcgata caataaacgg gtctctctgg ttagaccaga tctgagcctg    5940
ggagctctct ggctaactag gaacccact gcttaagcct caataaagct tgccttgagt     6000
gcttcaagta gtgtgtgccc gtctgttgtg tgactctggt aactagagat ccctcagacc    6060
cttttagtca gtgtggaaaa tctctagcag tggcgcccga acaggaccct gaaagcgaaa    6120
gggaaaccag agctctctcg acgcaggact cggcttgctg aagcgcgcac ggcaagaggc    6180
gaggggcggc gactggtgag tacgccaaaa attttgacta gcggaggcta aaggagaga    6240
gatgggtgcg agagcgtcag tattaagcgg gggagaatta gatcgcgatg gaaaaaatt     6300
cggttaaggc caggggaaa gaaaaaatat aaattaaaac atatagtatg ggcaagcagg     6360
gagctagaac gattcgcagt taatcctggc ctgttagaaa catcagaagg ctgtagacaa    6420
atactgggac agctacaacc atcccttcag acaggatcag aagaacttag atcattatat    6480
aatacagtag caacctctca ttgtgtgcat caaaggatag agataaaaga caccaaggaa    6540
gctttagaca agatagaga agagcaaaac aaaagtaaga ccaccgcaca gcaagcggcc    6600
gctgatcttc agacctggag gaggagatat gagggacaat tggagaagtg aattatataa    6660
```

```
atataaagta gtaaaaattg aaccattagg agtagcaccc accaaggcaa agagaagagt   6720
ggtgcagaga gaaaaagag cagtgggaat aggagctttg ttccttgggt tcttgggagc    6780
agcaggaagc actatgggcg cagcctcaat gacgctgacg gtacaggcca gacaattatt   6840
gtctggtata gtgcagcagc agaacaattt gctgagggct attgaggcgc aacagcatct   6900
gttgcaactc acagtctggg gcatcaagca gctccaggca agaatcctgg ctgtggaaag   6960
atacctaaag gatcaacagc tcctggggat ttggggttgc tctggaaaac tcatttgcac   7020
cactgctgtg ccttggaatg ctagttggag taataaatct ctggaacaga ttggaatcac   7080
acgacctgga tggagtggga cagagaaatt aacaattaca caagcttaat acactcctta   7140
attgaagaat cgcaaaacca gcaagaaaag aatgaacaag aattattgga attagataaa   7200
tgggcaagtt tgtggaattg gtttaacata acaaattggc tgtggtatat aaaattattc   7260
ataatgatag taggaggctt ggtaggttta agaatagttt ttgctgtact ttctatagtg   7320
aatagagtta ggcagggata ttcaccatta tcgtttcaga cccacctccc aaccccgagg   7380
ggacccgaca ggcccgaagg aatagaagaa gaaggtggag agagagacag agacagatcc   7440
attcgattag tgaacggatc tcgacggtat cgattagact gtagcccagg aatatggcag   7500
ctagattgta cacatttaga aggaaaagtt atcttggtag cagttcatgt agccagtgga   7560
tatatagaag cagaagtaat tccagcagag acagggcaag aaacagcata cttcctctta   7620
aaattagcag gaagatggcc agtaaaaaca gtacatacag acaatggcag caatttcacc   7680
agtactacag ttaaggccgc ctgttggtgg gcggggatca agcaggaatt tggcattccc   7740
tacaatcccc aaagtcaagg agtaatagaa tctatgaata agaattaaa gaaaattata    7800 ggacaggtaa gagatcaggc tgaacatctt aagacagcag tacaaatggc agtattcatc   7860
cacaatttta aaagaaaagg ggggattggg gggtacagtg caggggaaag aatagtagac   7920
ataatagcaa cagacataca aactaaagaa ttacaaaaac aaattacaaa aattcaaaat   7980
tttcgggttt attacaggga cagcagagat ccagtttggc tgcatacgcg tcgtgaggct   8040
ccggtgcccg tcagtgggca gagcgcacat cgcccacagt ccccgagaag ttgggggag    8100 gggtcggcaa ttgaaccggt gcctagagaa ggtggcgcgg ggtaaactgg gaaagtgatg   8160
tcgtgtactg gctccgcctt tttcccgagg gtgggggaga accgtatata agtgcagtag   8220
tcgccgtgaa cgttcttttt cgcaacgggt ttgccgccag aacacaggta agtgccgtgt   8280
gtggttcccg cgggcctggc ctctttacgg gttatggccc ttgcgtgcct tgaattactt   8340
ccacctggct gcagtacgtg attcttgatc ccgagcttcg ggttggaagt gggtgggaga   8400
gttcgaggcc ttgcgcttaa ggagccccct cgcctcgtgc ttgagttgag gcctggcctg   8460
ggcgctgggc ccgccgcgtg cgaatctggt ggcaccttcg cgcctgtctc gctgctttcg   8520
ataagtctct agccatttaa aatttttgat gacctgctgc gacgcttttt ttctggcaag   8580
atagtcttgt aaatgcgggc caagatctgc acactggtat ttcggttttt ggggccgcgg   8640
gcggcgacgg ggcccgtgcg tcccagcgca catgttcggc gaggcggggc ctgcgagcgc   8700
ggccaccgag aatcggacgg gggtagtctc aagctggccg gcctgctctg gtgcctggcc   8760
tcgcgccgcc gtgtatcgcc ccgccctggg cggcaaggct ggcccggtcg caccagttg    8820 cgtgagcgga agatggccg cttcccggcc ctgctgcagg gagctcaaaa tggaggacgc    8880
ggcgctcggg agagcgggcg ggtgagtcac ccacacaaag gaaaagggcc tttcgtcct    8940 cagccgtcgc ttcatgtgac tccacggagt accgggcgcc gtccaggcac ctcgattagt   9000
```

```
tctcgagctt tggagtacg tcgtctttag gttgggggga ggggttttat gcgatggagt    9060
ttccccacac tgagtgggtg gagactgaag ttaggccagc ttggcacttg atgtaattct    9120
ccttggaatt tgccctttt gagtttggat cttggttcat tctcaagcct cagacagtgg    9180
ttcaaagttt ttttcttcca tttcaggtgt cgtgagctag ctctagag                9228
```

<210> SEQ ID NO 152
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 152

```
Met Ala Leu Pro Val Thr Ala Leu Leu Leu Pro Leu Ala Leu Leu Leu
1               5                   10                  15

His Ala Ala Arg Pro Gly Ser Gln Leu Val Glu Ser Gly Gly Gly Leu
            20                  25                  30

Val Gln Pro Gly Arg Ser Leu Arg Leu Ser Cys Thr Thr Ser Gly Phe
        35                  40                  45

Thr Phe Gly Asp Tyr Ala Met Ile Trp Ala Arg Gln Ala Pro Gly Lys
    50                  55                  60

Gly Leu Glu Trp Val Ser Ser Ile Ser Ser Ser Ser Tyr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Glu Arg Tyr Asp Phe Trp Ser Gly Met
        115                 120                 125

Asp Val Trp Gly Lys Gly Thr Thr Val Thr Val Ser Ser Gly Gly Gly
    130                 135                 140

Gly Ser Gly Gly Gly Ser Gly Gly Ser Ala Gln Ser Ala Leu Thr
145                 150                 155                 160

Gln Pro Ala Ser Val Ser Gly Ser Pro Gly Gln Ser Ile Thr Ile Ser
                165                 170                 175

Cys Thr Gly Thr Ser Ser Asp Val Gly Ser Tyr Asn Leu Val Ser Trp
            180                 185                 190

Tyr Gln Gln His Pro Gly Lys Ala Pro Lys Leu Met Ile Tyr Glu Gly
        195                 200                 205

Ser Lys Arg Pro Ser Gly Val Ser Asn Arg Phe Ser Gly Ser Lys Ser
    210                 215                 220

Gly Asn Ala Ala Ser Leu Thr Ile Ser Gly Leu Gln Ala Glu Asp Glu
225                 230                 235                 240

Ala Asp Tyr Tyr Cys Gln Ser Tyr Asp Ser Ser Leu Ser Val Val Phe
                245                 250                 255

Gly Gly Gly Thr Lys Leu Thr Val Leu Gly Ala Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320
```

```
Ala Gly Thr Cys Gly Val Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
            485                 490

<210> SEQ ID NO 153
<211> LENGTH: 9189
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 153 atggcttac cagtgaccgc cttgctcctg ccgctggcct tgctgctcca cgccgccagg      60
ccgggatccc agctggtgga gtctggggga ggcttggtac agccagggcg gtccctgaga    120
ctctcctgca caacttctgg attcactttt ggtgattatg ctatgatctg ggcccgccag    180
gctccaggga aggggctgga gtgggtctca tccattagta gtagtagtag ttacatatac    240
tacgcagact cagtgaaggg ccgattcacc atctccagag acaacgccaa gaactcactg    300
tatctgcaaa tgaacagcct gagagccgag gacacggctg tgtattactg tgcgagagaa    360
cgatacgatt tttggagtgg aatggacgtc tggggcaaag ggaccacggt caccgtctcg    420
agtggtggag gcggttcagg cggaggtggc tctggcggta gtgcacagtc tgccctgact    480
cagcctgcct ccgtgtctgg gtctcctgga cagtcgatca ccatctcctg cactggaacc    540
agcagtgatg ttgggagtta taaccttgtc cctggtacc aacagcaccc aggcaaagcc    600
cccaaactca tgatttatga gggcagtaag cggccctcag gggtttctaa tcgcttctct    660
ggctccaagt ctggcaacgc ggcctccctg acaatctctg gctccaggc tgaggacgag    720 gctgattatt actgccagtc ctatgacagc agcctgagtg tggtattcgg cggagggacc    780
aagctgaccg tcctaggtgc tagcaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg ggcgcccttg    960
gccgggactt gtggggtcct tctcctgtca ctggttatca cccttactg caaacggggc   1020
```

```
agaaagaaac tcctgtatat attcaaacaa ccatttatga gaccagtaca aactactcaa    1080
gaggaagatg gctgtagctg ccgatttcca gaagaagaag aaggaggatg tgaactgaga    1140
gtgaagttca gcaggagcgc agacgccccc gcgtacaagc agggccagaa ccagctctat    1200
aacgagctca atctaggacg aagagaggag tacgatgttt tggacaagag acgtggccgg    1260
gaccctgaga tgggggggaaa gccgagaagg aagaaccctc aggaaggcct gtacaatgaa    1320
ctgcagaaag ataagatggc ggaggcctac agtgagattg ggatgaaagg cgagcgccgg    1380
aggggcaagg ggcacgatgg cctttaccag ggtctcagta cagccaccaa ggacacctac    1440
gacgccttc acatgcaggc cctgccccct cgctaagtcg actcgacaat caacctctgg    1500
attacaaaat tgtgaaaga ttgactggta ttcttaacta tgttgctcct tttacgctat    1560
gtggatacgc tgctttaatg cctttgtatc atgctattgc ttcccgtatg gctttcattt    1620
tctcctcctt gtataaatcc tggttgctgt ctctttatga ggagttgtgg cccgttgtca    1680
ggcaacgtgg cgtggtgtgc actgtgtttg ctgacgcaac ccccactggt tggggcattg    1740
ccaccacctg tcagctcctt tccgggactt tcgctttccc cctccctatt gccacggcgg    1800
aactcatcgc cgcctgcctt gcccgctgct ggacagggc tcggctgttg ggcactgaca    1860
attccgtggt gttgtcgggg aagctgacgt cctttccatg gctgctcgcc tgtgttgcca    1920
cctggattct gcgcgggacg tccttctgct acgtcccttc ggcccttcaat ccagcggacc    1980
ttccttcccg cggcctgctg ccggctctgc ggcctcttcc gcgtcttcgc cttcgccctc    2040
agacgagtcg gatctcccttt tgggccgcct ccccgcctgg aattcgagct cggtaccttt    2100
aagaccaatg acttacaagg cagctgtaga tcttagccac ttttttaaaag aaagggggg    2160
actggaaggg ctaattcact cccaacgaag acaagatctg cttttttgctt gtactgggtc    2220
tctctggtta gaccagatct gagcctggga gctctctggc taactaggga acccactgct    2280
taagcctcaa taaagcttgc cttgagtgct tcaagtagtg tgtgcccgtc tgttgtgtga    2340
ctctggtaac tagagatccc tcagacccct ttagtcagtg tggaaaatct ctagcagtag    2400
tagttcatgt catcttatta ttcagtattt ataacttgca aagaaatgaa tatcagagag    2460
tgagaggaac ttgtttattg cagcttataa tggttacaaa taaagcaata gcatcacaaa    2520
tttcacaaat aaagcatttt tttcactgca ttctagttgt ggtttgtcca aactcatcaa    2580
tgtatcttat catgtctggc tctagctatc ccgcccctaa ctccgcccag ttccgcccat    2640
tctccgcccc atggctgact aattttttt atttatgcag aggccgaggc cgcctcggcc    2700
tctgagctat tccagaagta gtgaggaggc ttttttggag gcctaggctt ttgcgtcgag    2760
acgtacccaa ttcgccctat agtgagtcgt attacgcgcg ctcactggcc gtcgttttac    2820
aacgtcgtga ctgggaaaac cctggcgtta cccaacttaa tcgccttgca gcacatcccc    2880
ctttcgccag ctggcgtaat agcgaagagg cccgcaccga tcgcccttcc caacagttgc    2940
gcagcctgaa tggcgaatgg cgcgacgcgc cctgtagcgg cgcattaagc gcggcgggtg    3000
tggtggttac gcgcagcgtg accgctacac ttgccagcgc cctagcgccc gctcctttcg    3060
ctttcttccc ttcctttctc gccacgttcg ccggctttcc ccgtcaagct ctaaatcggg    3120
ggctcccttt agggttccga tttagtgctt tacggcacct cgaccccaaa aaacttgatt    3180
agggtgatgg ttcacgtagt gggccatcgc cctgatagac ggtttttcgc cctttgacgt    3240
tggagtccac gttctttaat agtggactct tgttccaaac tggaacaaca ctcaacccta    3300
tctcggtcta ttcttttgat ttataaggga ttttgccgat ttcggcctat tggttaaaaa    3360
```

```
atgagctgat ttaacaaaaa tttaacgcga attttaacaa aatattaacg tttacaatttt    3420 cccaggtggc acttttcggg gaaatgtgcg cggaacccct atttgtttat ttttctaaat    3480
acattcaaat atgtatccgc tcatgagaca ataaccctga taaatgcttc aataatattg    3540
aaaaaggaag agtatgagta ttcaacattt ccgtgtcgcc cttattccct tttttgcggc    3600
attttgcctt cctgtttttg ctcacccaga aacgctggtg aaagtaaaag atgctgaaga    3660
tcagttgggt gcacgagtgg gttacatcga actggatctc aacagcggta agatccttga    3720
gagttttcgc cccgaagaac gttttccaat gatgagcact tttaaagttc tgctatgtgg    3780
cgcggtatta tcccgtattg acgccgggca agagcaactc ggtcgccgca tacactattc    3840
tcagaatgac ttggttgagt actcaccagt cacagaaaag catcttacgg atggcatgac    3900
agtaagagaa ttatgcagtg ctgccataac catgagtgat aacactgcgg ccaacttact    3960
tctgacaacg atcggaggac cgaaggagct aaccgctttt ttgcacaaca tgggggatca    4020
tgtaactcgc cttgatcgtt gggaaccgga gctgaatgaa gccataccaa acgacgagcg    4080
tgacaccacg atgcctgtag caatggcaac aacgttgcgc aaactattaa ctggcgaact    4140
acttactcta gcttcccggc aacaattaat agactggatg gaggcggata aagttgcagg    4200
accacttctg cgctcggccc ttccggctgg ctggtttatt gctgataaat ctggagccgg    4260
tgagcgtggg tctcgcggta tcattgcagc actggggcca gatggtaagc cctcccgtat    4320
cgtagttatc tacacgacgg ggagtcaggc aactatggat gaacgaaata gacagatcgc    4380
tgagataggt gcctcactga ttaagcattg gtaactgtca gaccaagttt actcatatat    4440
actttagatt gatttaaaac ttcattttta atttaaaagg atctaggtga agatcctttt    4500
tgataatctc atgaccaaaa tcccttaacg tgagttttcg ttccactgag cgtcagaccc    4560
cgtagaaaag atcaaaggat cttcttgaga tccttttttt ctgcgcgtaa tctgctgctt    4620
gcaaacaaaa aaaccaccgc taccagcggt ggtttgtttg ccggatcaag agctaccaac    4680 tcttttccg aaggtaactg gcttcagcag agcgcagata ccaaatactg tccttctagt    4740
gtagccgtag ttaggccacc acttcaagaa ctctgtagca ccgcctacat acctcgctct    4800
gctaatcctg ttaccagtgg ctgctgccag tggcgataag tcgtgtctta ccgggttgga    4860
ctcaagacga tagttaccgg ataaggcgca gcggtcgggc tgaacggggg gttcgtgcac    4920
acagcccagc ttggagcgaa cgacctacac cgaactgaga tacctacagc gtgagctatg    4980
agaaagcgcc acgcttcccg aagggagaaa ggcggacagg tatccggtaa gcggcagggt    5040
cggaacagga gagcgcacga gggagcttcc agggggaaac gcctggtatc tttatagtcc    5100
tgtcgggttt cgccacctct gacttgagcg tcgatttttg tgatgctcgt cagggggggcg    5160 gagcctatgg aaaaacgcca gcaacgcggc ctttttacgg ttcctggcct tttgctggcc    5220
ttttgctcac atgttctttc ctgcgttatc ccctgattct gtggataacc gtattaccgc    5280
ctttgagtga gctgataccg ctcgccgcag ccgaacgacc gagcgcagcg agtcagtgag    5340
cgaggaagcg gaagagcgcc caatacgcaa accgcctctc cccgcgcgtt ggccgattca    5400
ttaatgcagc tggcacgaca ggtttcccga ctggaaagcg ggcagtgagc gcaacgcaat    5460
taatgtgagt tagctcactc attaggcacc ccaggcttta cactttatgc ttccggctcg    5520
tatgttgtgt ggaattgtga gcggataaca atttcacaca ggaaacagct atgaccatga    5580
ttacgccaag cgcgcaatta accctcacta aagggaacaa aagctggagc tgcaagctta    5640
atgtagtctt atgcaatact cttgtagtct tgcaacatgg taacgatgag ttagcaacat    5700
gccttacaag gagagaaaaa gcaccgtgca tgccgattgg tggaagtaag gtggtacgat    5760
```

```
cgtgccttat taggaaggca acagacgggt ctgacatgga ttggacgaac cactgaattg   5820
ccgcattgca gagatattgt atttaagtgc ctagctcgat acaataaacg ggtctctctg   5880
gttagaccag atctgagcct gggagctctc tggctaacta gggaacccac tgcttaagcc   5940
tcaataaagc ttgccttgag tgcttcaagt agtgtgtgcc cgtctgttgt gtgactctgg   6000
taactagaga tccctcagac ccttttagtc agtgtggaaa atctctagca gtggcgcccg   6060
aacagggacc tgaaagcgaa agggaaacca gagctctctc gacgcaggac tcggcttgct   6120
gaagcgcgca cggcaagagg cgaggggcgg cgactggtga gtacgccaaa aattttgact   6180
agcggaggct agaaggagag atgggtgc gagagcgtca gtattaagcg gggagaatt     6240
agatcgcgat gggaaaaaat tcggttaagg ccaggggggaa agaaaaaata taaattaaaa   6300
catatagtat gggcaagcag ggagctgaaa cgattcgcag ttaatcctgg cctgttagaa   6360
acatcagaag gctgtagaca atactggga cagctacaac catcccttca gacaggatca    6420
gaagaactta gatcattata taatacagta gcaaccctct attgtgtgca tcaaaggata   6480
gagataaaag acaccaagga agctttagac aagatagagg aagagcaaaa caaaagtaag   6540
accaccgcac agcaagcggc cgctgatctt cagacctgga ggaggagata tgagggacaa   6600
ttggagaagt gaattatata aatataaagt agtaaaaatt gaaccattag gagtagcacc   6660
caccaaggca aagagaagag tggtgcagag agaaaaaaga gcagtgggaa taggagcttt   6720
gttccttggg ttcttgggag cagcaggaag cactatgggc gcagcctcaa tgacgctgac   6780
ggtacaggcc agacaattat tgtctggtat agtgcagcag cagaacaatt tgctgagggc   6840
tattgaggcg caacagcatc tgttgcaact cacagtctgg ggcatcaagc agctccaggc   6900
aagaatcctg gctgtggaaa gatacctaaa ggatcaacag ctcctgggga tttgggttg    6960
ctctggaaaa ctcatttgca ccactgctgt gccttggaat gctagttgga gtaataaatc   7020
tctggaacag attggaatca cacgacctgg atggagtggg acagagaaat taacaattac   7080
acaagcttaa tacactcctt aattgaagaa tcgcaaaacc agcaagaaaa gaatgaacaa   7140
gaattattgg aattagataa atgggcaagt ttgtggaatt ggtttaacat aacaaattgg   7200
ctgtggtata taaaattatt cataatgata gtaggaggct tggtaggttt aagaatagtt   7260
tttgctgtac tttctatagt gaatagagtt aggcagggat attcaccatt atcgtttcag   7320
acccacctcc caaccccgag gggacccgac aggcccgaag gaatagaaga agaaggtgga   7380
gagagagaca gagacagatc cattcgatta gtgaacggat ctcgacggta tcgattagac   7440
tgtagcccag gaatatggca gctagattgt acacatttag aaggaaaagt tatcttggta   7500
gcagttcatg tagccagtgg atatatagaa gcagaagtaa ttccagcaga gacagggcaa   7560
gaaacagcat acttcctctt aaaattagca ggaagatggc cagtaaaaac agtacataca   7620
gacaatggca gcaatttcac cagtactaca gttaaggccg cctgttggtg gcggggatc    7680
aagcaggaat ttggcattcc ctacaatccc caaagtcaag gagtaataga atctatgaat   7740
aaagaattaa agaaaattat aggacaggta agagatcagg ctgaacatct taagacagca   7800
gtacaaatgg cagtattcat ccacaatttt aaaagaaaag gggggattgg ggggtacagt   7860
gcagggggaaa gaatagtaga cataatagca acagacatac aaactaaaga attacaaaaa   7920
caaattacaa aaattcaaaa ttttcggggtt tattacaggg acagcagaga tccagtttgg   7980
ctgcatacgc gtcgtgaggc tccggtgccc gtcagtgggc agagcgcaca tcgcccacag   8040
tccccgagaa gttgggggga ggggtcggca attgaaccgg tgcctagaga aggtggcgcg   8100
```

```
gggtaaactg gaaaagtgat gtcgtgtact ggctccgcct ttttcccgag ggtgggggag      8160
aaccgtatat aagtgcagta gtcgccgtga acgttctttt tcgcaacggg tttgccgcca      8220
gaacacaggt aagtgccgtg tgtggttccc gcgggcctgg cctctttacg ggttatggcc      8280
cttgcgtgcc ttgaattact tccacctggc tgcagtacgt gattcttgat cccgagcttc      8340
gggttggaag tgggtgggag agttcgaggc cttgcgctta aggagcccct tcgcctcgtg      8400
cttgagttga ggcctggcct gggcgctggg gccgccgcgt gcgaatctgg tggcaccttc      8460
gcgcctgtct cgctgctttc gataagtctc tagccatttta aaattttga tgacctgctg      8520 cgacgctttt tttctggcaa gatagtcttg taaatgcggg ccaagatctg cacactggta      8580
tttcggtttt tggggccgcg ggcggcgacg gggcccgtgc gtcccagcgc acatgttcgg      8640
cgaggcgggg cctgcgagcg cggccaccga gaatcggacg ggggtagtct caagctggcc      8700
ggcctgctct ggtgcctggc ctcgcgccgc cgtgtatcgc cccgccctgg gcggcaaggc      8760
tggcccggtc ggcaccagtt gcgtgagcgg aaagatggcc gcttcccggc cctgctgcag      8820
ggagctcaaa atggaggacg cggcgctcgg gagagcgggc gggtgagtca cccacacaaa      8880
ggaaaagggc ctttccgtcc tcagccgtcg cttcatgtga ctccacggag taccgggcgc      8940
cgtccaggca cctcgattag ttctcgagct tttggagtac gtcgtcttta ggttgggggg      9000 aggggttttta tgcgatggag tttccccaca ctgagtgggt ggagactgaa gttaggccag      9060
cttggcactt gatgtaattc tccttggaat ttgccctttt tgagtttgga tcttggttca      9120
ttctcaagcc tcagacagtg gttcaaagtt ttttcttcc atttcaggtg tcgtgagcta      9180
gctctagag                                                             9189

<210> SEQ ID NO 154
<211> LENGTH: 521
<212> TYPE: DNA
<213> ORGANISM: Unknown
<220> FEATURE:
<221> NAME/KEY: source
<223> OTHER INFORMATION: /note="Description of Unknown:
      Phosphoglycerate kinase (PGK) promoter polynucleotide"

<400> SEQUENCE: 154
acccctctct ccagccacta agccagttgc tccctcggct gacggctgca cgcgaggcct        60
ccgaacgtct tacgccttgt ggcgcgcccg tccttgtccc gggtgtgatg gcggggtgtg       120
gggcggaggg cgtggcgggg aagggccggc gacgagagcc gcgcgggacg actcgtcggc       180
gataaccggt gtcgggtagc gccagccgcg cgacggtaac gagggaccgc gacaggcaga       240
cgctcccatg atcactctgc acgccgaagg caaatagtgc aggccgtgcg gcgcttggcg       300
ttccttggaa gggctgaatc cccgcctcgt ccttcgcagc ggccccccgg gtgttcccat       360
cgccgcttct aggcccactg cgacgcttgc ctgcacttct tacacgctct gggtcccagc       420
cgcggcgacg caaagggcct tggtgcgggt ctcgtcggcg cagggacgcg tttgggtccc       480
gacggaacct tttccgcgtt ggggttgggg caccataagc t                          521

<210> SEQ ID NO 155
<211> LENGTH: 118
<212> TYPE: DNA
<213> ORGANISM: Unknown
<220> FEATURE:
<221> NAME/KEY: source
<223> OTHER INFORMATION: /note="Description of Unknown:
      Phosphoglycerate kinase (PGK) promoter polynucleotide"

<400> SEQUENCE: 155
```

-continued

```
acccctctct ccagccacta agccagttgc tccctcggct gacggctgca cgcgaggcct     60
ccgaacgtct tacgccttgt ggcgcgcccg tccttgtccc gggtgtgatg gcggggtg     118
```

<210> SEQ ID NO 156
<211> LENGTH: 221
<212> TYPE: DNA
<213> ORGANISM: Unknown
<220> FEATURE:
<221> NAME/KEY: source
<223> OTHER INFORMATION: /note="Description of Unknown:
      Phosphoglycerate kinase (PGK) promoter polynucleotide"

<400> SEQUENCE: 156

```
acccctctct ccagccacta agccagttgc tccctcggct gacggctgca cgcgaggcct     60
ccgaacgtct tacgccttgt ggcgcgcccg tccttgtccc gggtgtgatg gcggggtgtg    120
gggcggaggg cgtggcgggg aagggccggc gacgagagcc gcgcgggacg actcgtcggc    180
gataaccggt gtcgggtagc gccagccgcg cgacggtaac g                       221
```

<210> SEQ ID NO 157
<211> LENGTH: 324
<212> TYPE: DNA
<213> ORGANISM: Unknown
<220> FEATURE:
<221> NAME/KEY: source
<223> OTHER INFORMATION: /note="Description of Unknown:
      Phosphoglycerate kinase (PGK) promoter polynucleotide"

<400> SEQUENCE: 157

```
acccctctct ccagccacta agccagttgc tccctcggct gacggctgca cgcgaggcct     60
ccgaacgtct tacgccttgt ggcgcgcccg tccttgtccc gggtgtgatg gcggggtgtg    120
gggcggaggg cgtggcgggg aagggccggc gacgagagcc gcgcgggacg actcgtcggc    180
gataaccggt gtcgggtagc gccagccgcg cgacggtaac gagggaccgc gacaggcaga    240
cgctcccatg atcactctgc acgccgaagg caaatagtgc aggccgtgcg gcgcttggcg    300
ttccttggaa gggctgaatc cccg                                          324
```

<210> SEQ ID NO 158
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Phosphoglycerate kinase (PGK) promoter polynucleotide"

<400> SEQUENCE: 158

```
acccctctct ccagccacta agccagttgc tccctcggct gacggctgca cgcgaggcct     60
ccgaacgtct tacgccttgt ggcgcgcccg tccttgtccc gggtgtgatg gcggggtgtg    120
gggcggaggg cgtggcgggg aagggccggc gacgagagcc gcgcgggacg actcgtcggc    180
gataaccggt gtcgggtagc gccagccgcg cgacggtaac gagggaccgc gacaggcaga    240
cgctcccatg atcactctgc acgccgaagg caaatagtgc aggccgtgcg gcgcttggcg    300
ttccttggaa gggctgaatc cccgcctcgt ccttcgcagc ggcccccgg gtgttcccat     360 cgccgcttct aggcccactg cgacgcttgc ctgcacttct tacacgctct gggtcccagc    420
cg                                                                  422
```

<210> SEQ ID NO 159

```
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(21)
<223> OTHER INFORMATION: /note="Variant residues given in the sequence
      have no preference with respect to those in the annotations for
      variant positions"

<400> SEQUENCE: 159

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 160
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(22)
<223> OTHER INFORMATION: /note="Variant residues given in the sequence
      have no preference with respect to those in the annotations for
      variant positions"

<400> SEQUENCE: 160

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 161
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(23)
<223> OTHER INFORMATION: /note="Variant residues given in the sequence
      have no preference with respect to those in the annotations for
      variant positions"

<400> SEQUENCE: 161

Gly Ser Gly Gln Cys Thr Asn Tyr Ala Leu Leu Lys Leu Ala Gly Asp
1               5                   10                  15
```

```
Val Glu Ser Asn Pro Gly Pro
            20
```

<210> SEQ ID NO 162
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(25)
<223> OTHER INFORMATION: /note="Variant residues given in the sequence
      have no preference with respect to those in the annotations for
      variant positions"

<400> SEQUENCE: 162

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 163
<211> LENGTH: 1132
<212> TYPE: PRT
<213> ORGANISM: Homo sapiens

<400> SEQUENCE: 163

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
```

```
              210                 215                 220
Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Glu Ala Thr Ser Leu Glu Gly Ala
                275                 280                 285

Leu Ser Gly Thr Arg His Ser His Pro Ser Val Gly Arg Gln His His
290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
                355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
                450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Gly Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
                530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
625                 630                 635                 640
```

```
Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050
```

| Met | Ser | Leu | Gly | Ala | Lys | Gly | Ala | Ala | Gly | Pro | Leu | Pro | Ser | Glu |
|---|---|---|---|---|---|---|---|---|---|---|---|---|---|---|
| | 1055 | | | | 1060 | | | | 1065 | | | | | |

Ala Val Gln Trp Leu Cys His Gln Ala Phe Leu Leu Lys Leu Thr
     1070            1075              1080

Arg His Arg Val Thr Tyr Val Pro Leu Leu Gly Ser Leu Arg Thr
     1085            1090              1095

Ala Gln Thr Gln Leu Ser Arg Lys Leu Pro Gly Thr Thr Leu Thr
     1100            1105              1110

Ala Leu Glu Ala Ala Ala Asn Pro Ala Leu Pro Ser Asp Phe Lys
     1115            1120              1125

Thr Ile Leu Asp
     1130

```
<210> SEQ ID NO 164
<211> LENGTH: 4027
<212> TYPE: DNA
<213> ORGANISM: Homo sapiens

<400> SEQUENCE: 164
caggcagcgt ggtcctgctg cgcacgtggg aagccctggc cccggccacc cccgcgatgc    60
cgcgcgctcc ccgctgccga ccgtgcgct  ccctgctgcg cagccactac cgcgaggtgc   120
tgccgctggc cacgttcgtg cggcgcctgg ggccccaggg ctggcggctg gtgcagcgcg   180
gggaccggc ggctttccgc cgcgctggtgg cccagtgcct ggtgtgcgtg ccctgggacg   240
cacggccgcc cccgccgcc cctccttcc gccaggtgtc ctgcctgaag gagctggtgg   300
cccgagtgct gcagaggctg tgcgagcgcg cgcgaagaa cgtgctggcc ttcggcttcg   360
cgctgctgga cggggcccgc gggggccccc cgaggccttt caccaccagc gtgcgcagct   420
acctgcccaa cacggtgacc gacgcactgc ggggagcgg ggcgtggggg ctgctgttgc   480
gccgcgtggg cgacgacgtg ctggttcacc tgctggcacg ctgcgcgctc tttgtgctgg   540
tggctcccag ctgcgcctac caggtgtgcg ggccgccgct gtaccagctc ggcgctgcca   600
ctcaggcccg gcccccgcca cacgctagtg gaccccgaag gcgtctggga tgcgaacggg   660
cctggaacca tagcgtcagg gaggccgggg tccccctggg cctgccagcc ccgggtgcga   720
ggaggcgcgg gggcagtgcc agccgaagtc tgccgttgcc caagaggccc aggcgtggcg   780
ctgcccctga gccggagcgg acgcccgttg gcaggggtc ctgggcccac ccgggcagga   840
cgcgtggacc gagtgaccgt ggtttctgtg tggtgtcacc tgccagaccc gccgaagaag   900
ccacctcttt ggagggtgcg ctctctggca cgcgccactc ccaccatcc gtgggccgcc    960
agcaccacgc gggcccccca tccacatcgc ggccaccacg tccctgggac acgccttgtc  1020
cccggtgta cgccgagacc aagcacttcc tctactcctc aggcgacaag gagcagctgc  1080
ggccctcctt cctactcagc tctctgaggc ccagcctgac tggcgctcgg aggctcgtgg  1140
agaccatctt tctgggttcc aggccctgga tgccagggac tccccgcagg ttgccccgcc  1200
tgccccagcg ctactggcaa atgcggcccc tgtttctgga gctgcttggg aaccacgcgc  1260
agtgccccta cggggtgctc ctcaagacgc actgcccgct gcgagctgcg gtcaccccag  1320
cagccggtgt ctgtgcccgg gagaagcccc agggctctgt ggcggccccc gaggaggagg  1380
acacagaccc ccgtcgcctg gtgcagctgc tccgccagca cagcagcccc tggcaggtgt  1440
acggcttcgt gcgggcctgc ctgcgccggc tggtgccccc aggcctctgg ggctccaggc  1500
acaacgaacg ccgcttcctc aggaacacca agaagttcat ctcccctgggg aagcatgcca  1560
agctctcgct gcaggagctg acgtggaaga tgagcgtgcg gggctgcgct tggctgcgca  1620
```

```
ggagcccagg ggttggctgt gttccggccg cagagcaccg tctgcgtgag gagatcctgg    1680
ccaagttcct gcactggctg atgagtgtgt acgtcgtcga gctgctcagg tctttctttt    1740
atgtcacgga gaccacgttt caaaagaaca ggctcttttt ctaccggaag agtgtctgga    1800
gcaagttgca aagcattgga atcagacagc acttgaagag ggtgcagctg cgggagctgt    1860
cggaagcaga ggtcaggcag catcgggaag ccaggcccgc cctgctgacg tccagactcc    1920
gcttcatccc caagcctgac gggctgcggc cgattgtgaa catggactac gtcgtgggag    1980
ccagaacgtt ccgcagagaa aagagggccg agcgtctcac ctcgagggtg aaggcactgt    2040
tcagcgtgct caactacgag cgggcgcggc gccccggcct cctgggcgcc tctgtgctgg    2100
gcctggacga tatccacagg gcctggcgca ccttcgtgct gcgtgtgcgg gcccaggacc    2160
cgccgcctga gctgtacttt gtcaaggtgg atgtgacggg cgcgtacgac accatccccc    2220
aggacaggct cacggaggtc atcgccagca tcatcaaacc ccagaacacg tactgcgtgc    2280
gtcggtatgc cgtggtccag aaggccgccc atgggcacgt ccgcaaggcc ttcaagagcc    2340
acgtctctac cttgacagac ctccagccgt acatgcgaca gttcgtggct cacctgcagg    2400
agaccagccc gctgagggat gccgtcgtca tcgagcagag ctcctccctg aatgaggcca    2460
gcagtggcct cttcgacgtc ttcctacgct tcatgtgcca ccacgccgtg cgcatcaggg    2520
gcaagtccta cgtccagtgc caggggatcc cgcagggctc catcctctcc acgtgctct    2580 gcagcctgtg ctacggcgac atggagaaca agctgtttgc ggggattcgg cgggacgggc    2640
tgctcctgcg tttggtggat gatttcttgt tggtgacacc tcacctcacc cacgcgaaaa    2700
ccttcctcag gaccctggtc cgaggtgtcc ctgagtatgg ctgcgtggtg aacttgcgga    2760
agacagtggt gaacttccct gtagaagacg aggccctggg tggcacggct tttgttcaga    2820
tgccggccca cggcctattc ccctggtgcg gcctgctgct ggatacccgg accctggagg    2880
tgcagagcga ctactccagc tatgcccgga cctccatcag agccagtctc accttcaacc    2940
gcggcttcaa ggctgggagg aacatgcgtc gcaaactctt tggggtcttg cggctgaagt    3000
gtcacagcct gtttctggat ttgcaggtga acagcctcca gacggtgtgc accaacatct    3060
acaagatcct cctgctgcag gcgtacaggt ttcacgcatg tgtgctgcag ctcccatttc    3120
atcagcaagt ttggaagaac cccacatttt tcctgcgcgt catctctgac acggcctccc    3180
tctgctactc catcctgaaa gccaagaacg cagggatgtc gctgggggcc aagggcgccg    3240
ccggccctct gccctccgag gccgtgcagt ggctgtgcca ccaagcattc ctgctcaagc    3300
tgactcgaca ccgtgtcacc tacgtgccac tcctgggggtc actcaggaca gcccagacgc    3360
agctgagtcg gaagctcccg gggacgacgc tgactgccct ggaggccgca gccaacccgg    3420
cactgccctc agacttcaag accatcctgg actgatggcc acccgccac agccaggccg    3480 agagcagaca ccagcagccc tgtcacgccg ggctctacgt cccagggagg gagggcggc    3540 ccacacccag gcccgcaccg ctgggagtct gaggcctgag tgagtgtttg gccgaggcct    3600
gcatgtccgg ctgaaggctg agtgtccggc tgaggcctga gcgagtgtcc agccaagggc    3660
tgagtgtcca gcacacctgc cgtcttcact tccccacagg ctggcgctcg gctccacccc    3720
agggccagct tttcctcacc aggagcccgg cttccactcc ccacatagga atagtccatc    3780
cccagattcg ccattgttca ccctcgccc tgccctcctt tgccttccac cccaccatc    3840 caggtggaga ccctgagaag gaccctggga gctctgggaa tttggagtga ccaaaggtgt    3900
gccctgtaca caggcgagga ccctgcacct ggatggggt ccctgtgggt caaattgggg    3960
```

```
ggaggtgctg tgggagtaaa atactgaata tatgagtttt tcagttttga aaaaaaaaaa    4020
aaaaaaa                                                              4027
```

<210> SEQ ID NO 165
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165

```
ggaggtccct caccttcta                                                   19
```

<210> SEQ ID NO 166
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166

```
cggaggatct tatgctgaa                                                   19
```

<210> SEQ ID NO 167
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167

```
cccgcttcca gatcataca                                                   19
```

<210> SEQ ID NO 168
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168

```
ggagacctca acaagatat                                                   19
```

<210> SEQ ID NO 169
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169

```
aaggcatggt cattggtat                                                   19
```

<210> SEQ ID NO 170
<211> LENGTH: 19
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 170
gcatggtcat tggtatcat                                               19

<210> SEQ ID NO 171
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
ggtcattggt atcatgagt                                               19

<210> SEQ ID NO 172
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
cctagtgggt atccctgta                                               19

<210> SEQ ID NO 173
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gaggatggac attgttctt                                               19

<210> SEQ ID NO 174
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gcatgcaggc tacagttca                                               19

<210> SEQ ID NO 175
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
ccagcacatg cactgttga                                               19
```

```
<210> SEQ ID NO 176
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
cacatgcact gttgagtga                                                    19

<210> SEQ ID NO 177
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
ctggaggtcc ctcaccttct a                                                 21

<210> SEQ ID NO 178
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gtcggaggat cttatgctga a                                                 21

<210> SEQ ID NO 179
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
tgcccgcttc cagatcatac a                                                 21

<210> SEQ ID NO 180
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
ctggagacct caacaagata t                                                 21

<210> SEQ ID NO 181
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 181
tcaaggcatg gtcattggta t                                              21

<210> SEQ ID NO 182
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
aggcatggtc attggtatca t                                              21

<210> SEQ ID NO 183
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
atggtcattg gtatcatgag t                                              21

<210> SEQ ID NO 184
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gccctagtgg gtatccctgt a                                              21

<210> SEQ ID NO 185
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
atgaggatgg acattgttct t                                              21

<210> SEQ ID NO 186
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gagcatgcag gctacagttc a                                              21

<210> SEQ ID NO 187
<211> LENGTH: 21
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
ttccagcaca tgcactgttg a                                              21

<210> SEQ ID NO 188
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
agcacatgca ctgttgagtg a                                              21

<210> SEQ ID NO 189
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
tagaaggtga gggacctcca g                                              21

<210> SEQ ID NO 190
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
ttcagcataa gatcctccga c                                              21

<210> SEQ ID NO 191
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
tgtatgatct ggaagcgggc a                                              21

<210> SEQ ID NO 192
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
atatcttgtt gaggtctcca g                                              21
```

<210> SEQ ID NO 193
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
ataccaatga ccatgccttg a                                             21

<210> SEQ ID NO 194
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
atgataccaa tgaccatgcc t                                             21

<210> SEQ ID NO 195
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
atggtcattg gtatcatgag t                                             21

<210> SEQ ID NO 196
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
gccctagtgg gtatccctgt a                                             21

<210> SEQ ID NO 197
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
atgaggatgg acattgttct t                                             21

<210> SEQ ID NO 198
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 198
gagcatgcag gctacagttc a                                    21

<210> SEQ ID NO 199
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ttccagcaca tgcactgttg a                                    21

<210> SEQ ID NO 200
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
agcacatgca ctgttgagtg a                                    21

<210> SEQ ID NO 201
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
tagaaggtga gggacctcc                                       19

<210> SEQ ID NO 202
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
ttcagcataa gatcctccg                                       19

<210> SEQ ID NO 203
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
tgtatgatct ggaagcggg                                       19

<210> SEQ ID NO 204
<211> LENGTH: 19

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
atatcttgtt gaggtctcc                                                  19

<210> SEQ ID NO 205
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
ataccaatga ccatgcctt                                                  19

<210> SEQ ID NO 206
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
atgataccaa tgaccatgc                                                  19

<210> SEQ ID NO 207
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
atggtcattg gtatcatga                                                  19

<210> SEQ ID NO 208
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
gccctagtgg gtatccctg                                                  19

<210> SEQ ID NO 209
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
```

```
atgaggatgg acattgttc                                                19
```

<210> SEQ ID NO 210
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210

```
gagcatgcag gctacagtt                                                19
```

<210> SEQ ID NO 211
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211

```
ttccagcaca tgcactgtt                                                19
```

<210> SEQ ID NO 212
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212

```
agcacatgca ctgttgagt                                                19
```

<210> SEQ ID NO 213
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213

```
ggccaggatg gttcttaga                                                19
```

<210> SEQ ID NO 214
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214

```
gcttcgtgct aaactggta                                                19
```

<210> SEQ ID NO 215
<211> LENGTH: 19
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 215
gggcgtgact tccacatga                                                  19

<210> SEQ ID NO 216
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
caggcctaga gaagtttca                                                  19

<210> SEQ ID NO 217
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
cttggaaccc attcctgaa                                                  19

<210> SEQ ID NO 218
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
ggaacccatt cctgaaatt                                                  19

<210> SEQ ID NO 219
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
gaacccattc ctgaaatta                                                  19

<210> SEQ ID NO 220
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
aacccattcc tgaaattat                                                  19

<210> SEQ ID NO 221
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
acccattcct gaaattatt                                                    19

<210> SEQ ID NO 222
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
cccattcctg aaattattt                                                    19

<210> SEQ ID NO 223
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
ctgtggttct attatatta                                                    19

<210> SEQ ID NO 224
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
tctaagaacc atcctggcc                                                    19

<210> SEQ ID NO 225
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
taccagttta gcacgaagc                                                    19

<210> SEQ ID NO 226
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
```

```
tcatgtggaa gtcacgccc                                              19

<210> SEQ ID NO 227
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
tgaaacttct ctaggcctg                                              19

<210> SEQ ID NO 228
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
ttcaggaatg ggttccaag                                              19

<210> SEQ ID NO 229
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
aatttcagga atgggttcc                                              19

<210> SEQ ID NO 230
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
taatttcagg aatgggttc                                              19

<210> SEQ ID NO 231
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
ataatttcag gaatgggtt                                              19

<210> SEQ ID NO 232
<211> LENGTH: 19
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 232
aataatttca ggaatgggt                                                    19

<210> SEQ ID NO 233
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
aaataatttc aggaatggg                                                    19

<210> SEQ ID NO 234
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
taatataata gaaccacag                                                    19

<210> SEQ ID NO 235
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
gcggccagga tggttcttag a                                                 21

<210> SEQ ID NO 236
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
gagcttcgtg ctaaactggt a                                                 21

<210> SEQ ID NO 237
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
acgggcgtga cttccacatg a                                                 21
```

```
<210> SEQ ID NO 238
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
tgcaggccta gagaagtttc a                                            21

<210> SEQ ID NO 239
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
tccttggaac ccattcctga a                                            21

<210> SEQ ID NO 240
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
ttggaaccca ttcctgaaat t                                            21

<210> SEQ ID NO 241
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
tggaacccat tcctgaaatt a                                            21

<210> SEQ ID NO 242
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
ggaacccatt cctgaaatta t                                            21

<210> SEQ ID NO 243
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 243
gaacccattc ctgaaattat t                                        21

<210> SEQ ID NO 244
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
aacccattcc tgaaattatt t                                        21

<210> SEQ ID NO 245
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ccctgtggtt ctattatatt a                                        21

<210> SEQ ID NO 246
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
tctaagaacc atcctggccg c                                        21

<210> SEQ ID NO 247
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
taccagttta gcacgaagct c                                        21

<210> SEQ ID NO 248
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
tcatgtggaa gtcacgcccg t                                        21

<210> SEQ ID NO 249
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 249
tgaaacttct ctaggcctgc a                                              21

<210> SEQ ID NO 250
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
ttcaggaatg ggttccaagg a                                              21

<210> SEQ ID NO 251
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
aatttcagga atgggttcca a                                              21

<210> SEQ ID NO 252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
taatttcagg aatgggttcc a                                              21

<210> SEQ ID NO 253
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
ataatttcag gaatgggttc c                                              21

<210> SEQ ID NO 254
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
aataatttca ggaatgggtt c                                              21
```

<210> SEQ ID NO 255
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
aaataatttc aggaatgggt t                                              21

<210> SEQ ID NO 256
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
taatataata gaaccacagg g                                              21

<210> SEQ ID NO 257
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
aaatatgaga gcatgctaa                                                 19

<210> SEQ ID NO 258
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
ttagcatgct ctcatattt                                                 19

<210> SEQ ID NO 259
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
ttaaatatga gagcatgcta a                                              21

<210> SEQ ID NO 260
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

<400> SEQUENCE: 260
ttagcatgct ctcatattta a                                              21

<210> SEQ ID NO 261
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 261 wggaaanhn                                                             9

<210> SEQ ID NO 262
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
agcttggatc caagaggaaa atttgtttca tacagaaggc gttaagagga aaatttgttt    60
catacagaag gcgttaagag gaaaatttgt ttcatacaga aggcgttcaa gcttgtcgac   120

<210> SEQ ID NO 263
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 263
ataggatccc agctggtgga gtctggggga ggc                                 33

<210> SEQ ID NO 264
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 264
atagctagca cctaggacgg tcagcttggt ccc                                 33

<210> SEQ ID NO 265
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 265

```
atggacttcc aggttcagat cttttcgttc ctgctgatca gcgcctctgt tatcatgtcg      60
cgcggcgaca tccagatgac ccagtcccct tcctccctct ctgcctctgt gggagaccgc     120
gttaccatca catgccgagc ttcccaggac gtgaacacag ccgtggcctg gtaccagcag     180
aagcccggga aggcacccaa actcctcatc tactccgcct ccttcctata cagtggcgtg     240
ccttcccgat tctccggctc caggagtggc acggacttta cgctcaccat tagtagcctg     300
cagcccgaag acttcgcgac ctactattgt cagcaacact acacgacgcc accaactttc     360
ggccagggta ccaaggtcga gattaagcga accggcagta ccagtgggtc tggcaagccc     420
ggcagcggcg agggatccga ggtccagctg gtcgagtccg gcggggggcct ggtgcagccg     480
ggcggctcgc tgaggttatc ttgcgccgcc agtggcttca acatcaagga tacttacatc     540
cactgggtga ggcaggctcc gggcaagggc ctggaatggg tggctaggat ctaccctact     600
aacgggtaca cacgctacgc agattcggtg aaggccgct tcactatctc cgccgacacc     660
tcgaagaaca ctgcttacct gcagatgaac tccctcaggg ccgaagatac tgcagtctac     720
tactgctccc gctggggtgg ggacggcttc tacgccatgg acgtgtgggg tcagggcact     780
ctagttacag tgtcatccac cacgacgcca gcgccgcgac caccaacacc ggcgcccacc     840
atcgcgtcgc agcccctgtc cctgcgccca gaggcgtgcc ggccagcggc ggggggcgca     900
gtgcacacga gggggctgga cttcgcctgt gatatctaca tctgggcgcc cttggccggg     960
acttgtgggg tccttctcct gtcactggtt atcacccttt actgcaaacg ggcagaaagg    1020
aaactcctgt atatattcaa acaaccattt atgagaccag tacaaactac tcaagaggaa    1080
gatggctgta gctgccgatt ccagaagaa gaagaaggag gatgtgaact gagagtgaag    1140
ttcagcagga gcgcagacgc ccccgcgtac aagcagggcc agaaccagct ctataacgag    1200
ctcaatctag gacgaagaga ggagtacgac gttttggaca gagacgtgg ccgggaccct    1260
gagatggggg gaaagccgag aaggaagaac cctcaggaag gcctgtacaa tgaactgcag    1320
aaagataaga tggcggaggc ctacagtgag attgggatga aggcgagcg ccggaggggc    1380
aaggggcacg atggccttta ccagggtctc agtacagcca ccaaggacac ctacgacgcc    1440
cttcacatgc aggccctgcc ccctcgctaa                                     1470
```

<210> SEQ ID NO 266
<211> LENGTH: 2268
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 266

```
atggacttcc aggttcagat cttttcgttc ctgctgatca gcgcctctgt tatcatgtcg      60
cgcggcgaca tccagatgac ccagtcccct tcctccctct ctgcctctgt gggagaccgc     120
gttaccatca catgccgagc ttcccaggac gtgaacacag ccgtggcctg gtaccagcag     180
aagcccggga aggcacccaa actcctcatc tactccgcct ccttcctaga gagtggcgtg     240
ccttcccgat tctccggctc cggcagtggc acggacttta cgctcaccat tagtagcctg     300
cagcccgaag acttcgcgac ctactattgt cagcaacact acacgacgcc accaactttc     360
ggccagggta ccaaggtcga gattaagcga accggcagta ccagtgggtc tggcaagccc     420
```

```
ggcagcggcg agggatccga ggtccagctg gtcgagtccg gcgggggcct ggtgcagccg    480
ggcggctcgc tgaggttatc ttgcgccgcc agtggcttca acatcaagga tacttacatc    540
cactgggtga ggcaggctcc gggcaagggc ctggaatggg tggctaggat ctaccctact    600
aacgggtaca cacgctacgc agattcggtg aaaggccgct tcactatctc cagggacgac    660
tcgaagaaca ctctgtacct gcagatgaac tccctcaggg ccgaagatac tgcagtctac    720
tactgcgccc gctggggtgg ggacggcttc gtagccatgg acgtgtgggg tcagggcact    780
ctagttacag tgtcatccac cacgacgcca gcgccgcgac caccaacacc ggcgcccacc    840
atcgcgtcgc agcccctgtc cctgcgccca gaggcgtgcc ggccagcggc gggggcgca    900
gtgcacacga gggggctgga cttcgcctgt gatatctaca tctgggcgcc cttggccggg    960
acttgtgggg tccttctcct gtcactggtt atcacccttt actgcaaacg gggcagaaag   1020
aaactcctgt atatattcaa acaaccattt atgagaccag tacaaactac tcaagaggaa   1080
gatggctgta gctgccgatt ccagaagaa gaagaaggag gatgtgaact gagaatggac    1140
ttccaggttc agatcttttc gttcctgctg atcagcgcct ctgttatcat gtcgcgcggc   1200
gacatccaga tgacccagtc cccttcctcc ctctctgcct ctgtgggaga ccgcgttacc   1260
atcacatgcc gagcttccca ggacgtgaac acagccgtgg cctggtacca gcagaagccc   1320
gggaaggcac ccaaactcct catctactcc gcctccttcc tagagagtgg cgtgccttcc   1380
cgattctccg gctccggcag tggcacggac tttacgctca ccattagtag cctgcagccc   1440
gaagacttcg cgacctacta ttgtcagcaa cactacacga cgccaccaac tttcggccag   1500
ggtaccaagg tcgagattaa gcgaaccggc agtaccagtg ggtctggcaa gcccggcagc   1560
ggcgagggat ccgaggtcca gctggtcgag tccggcgggg gcctggtgca gccgggcggc   1620
tcgctgaggt tatcttgcgc cgccagtggc ttcaacatca aggatactta catccactgg   1680
gtgaggcagg ctccgggcaa gggcctggaa tgggtggcta ggatctaccc tactaacggg   1740
tacacacgct acgcagattc ggtgaaaggc cgcttcacta tctccaggga cgactcgaag   1800
aacactctgt acctgcagat gaactccctc agggccgaag atactgcagt ctactactgc   1860
gcccgctggg gtggggacgg cttcgtagcc atggacgtgt ggggtcaggg cactctagtt   1920
acagtgtcat ccgtgaagtt cagcaggagc gcagacgccc ccgcgtacaa gcagggccag   1980
aaccagctct ataacgagct caatctagga cgaagagagg agtacgacgt tttggacaag   2040
agacgtggcc gggaccctga gatggggga aagccgagaa ggaagaaccc tcaggaaggc   2100
ctgtacaatg aactgcagaa agataagatg gcggaggcct acagtgagat tgggatgaaa   2160
ggcgagcgcc ggaggggcaa ggggcacgat ggcctttacc agggtctcag tacagccacc   2220
aaggacacct acgacgccct tcacatgcag gccctgcccc ctcgctaa               2268
```

<210> SEQ ID NO 267
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 267

```
accacgacgc cagcgccgcg accaccaaca ccggcgccca ccatcgcgtc gcagcccctg     60
tccctgcgcc cagaggcgtg ccggccagcg gcgggggggcg cagtgcacac gagggggctg    120
```

```
gacttcgcct gtgatatcta catctgggcg cccttggccg ggacttgtgg ggtccttctc      180
ctgtcactgg ttatcaccct ttactgcaaa cggggcagaa agaaactcct gtatatattc      240
aaacaaccat ttatgagacc agtacaaact actcaagagg aagatggctg tagctgccga      300
tttccagaag aagaaatgga cttccaggtt cagatctttt cgttcctgct gatcagcgcc      360
tctgttatca tgtcgcgcgg cgacatccag atgacccagt ccccttcctc cctctctgcc      420
tctgtgggag accgcgttac catcacatgc cgagcttccc aggacgtgaa cacagccgtg      480
gcctggtacc agcagaagcc cgggaaggca cccaaactcc tcatctactc cgcctccttc      540
ctagagagtg gcgtgccttc ccgattctcc ggctccggca gtggcacgga ctttacgctc      600
accattagta gcctgcagcc cgaagacttc gcgacctact attgtcagca acactacacg      660
acgccaccaa ctttcggcca gggtaccaag gtcgagatta agcgaaccgg cagtaccagt      720
gggtctggca agcccggcag cggcgaggga tccgaggtcc agctggtcga gtccggcggg      780
ggcctggtgc agccgggcgg ctcgctgagg ttatcttgcg ccgccagtgg cttcaacatc      840
aaggatactt acatccactg ggtgaggcag gctccgggca agggcctgga atgggtggct      900
aggatctacc ctactaacgg gtacacacgc tacgcagatt cggtgaaagg ccgcttcact      960
atctccgccg acacctcgaa gaacactgct tacctgcaga tgaactccct cagggccgaa     1020
gatactgcag tctactactg ctcccgctgg ggtggggacg gcttcgtagc catggacgtg     1080
tggggtcagg gcactctagt tacagtgtca tccgaaggag gatgtgaact gagagtgaag     1140
ttcagcagga gcgcagacgc ccccgcgtac aagcagggcc agaaccagct ctataacgag     1200
ctcaatctag gacgaagaga ggagtacgac gttttggaca agagacgtgg ccgggaccct     1260
gagatggggg gaaagccgag aaggaagaac cctcaggaag gcctgtacaa tgaactgcag     1320
aaagataaga tggcggaggc ctacagtgag attgggatga aggcgagcg ccggaggggc      1380
aaggggcacg atggccttta ccagggtctc agtacagcca ccaaggacac ctacgacgcc     1440
cttcacatgc aggccctgcc ccctcgctaa                                      1470
```

<210> SEQ ID NO 268
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 268

```
atggacttcc aggttcagat cttttcgttc ctgctgatca gcgcctctgt tatcatgtcg       60
cgcggcgaca tccagatgac ccagtcccct tcctccctct ctgcctctgt gggagaccgc      120
gttaccatca catgccgagc ttcccaggac gtgaacacag ccgtggcctg gtaccagcag      180
aagcccggga aggcacccaa actcctcatc tactccgcct ccttcctaga gagtggcgtg      240
ccttcccgat tctccggctc caggagtggc acggacttta cgctcaccat tagtagcctg      300
cagcccgaag acttcgcgac ctactattgt cagcaacact acacgacgcc accaactttc      360
ggccagggta ccaaggtcga gattaagcga accggcagta ccagtgggtc tggcaagccc      420
ggcagcggcg agggatccga ggtccagctg gtcgagtccg gcggggggcct ggtgcagccg      480
ggcggctcgc tgaggttatc ttgcgccgcc agtggcttca acatcaagga tacttacatc      540
cactgggtga ggcaggctcc gggcaagggc ctggaatggg tggctaggat ctaccctact      600
aacgggtaca cacgctacgc agattcggtg aaaggccgct tcactatctc cgccgacacc      660
```

```
tcgaagaaca ctgcttacct gcagatgaac tccctcaggg ccgaagatac tgcagtctac    720
tactgctccc gctggggtgg ggacggcttc gtagccatgg acgtgtgggg tcagggcact    780
ctagttacag tgtcatccac cacgacgcca gcgccgcgac caccaacacc ggcgcccacc    840
atcgcgtcgc agcccctgtc cctgcgccca gaggcgtgcc ggccagcggc gggggcgca     900 gtgcacacga gggggctgga cttcgcctgt gatatctaca tctgggcgcc cttggccggg    960
acttgtgggg tccttctcct gtcactggtt atcacccttt actgcaaacg gggcagaaag    1020
aaactcctgt atatattcaa caaccatttt atgagaccag tacaaactac tcaagaggaa    1080
gatggctgta gctgccgatt ccagaagaa gaagaaggag gatgtgaact gagagtgaag     1140
ttcagcagga gcgcagacgc ccccgcgtac aagcagggcc agaaccagct ctataacgag    1200
ctcaatctag gacgaagaga ggagtacgac gttttggaca agagacgtgg ccgggaccct    1260
gagatggggg gaaagccgag aaggaagaac cctcaggaag gcctgtacaa tgaactgcag    1320
aaagataaga tggcggaggc ctacagtgag attgggatga aggcgagcg ccggagggc      1380 aaggggcacg atggcctttta ccagggtctc agtacagcca ccaaggacac ctacgacgcc   1440
cttcacatgc aggccctgcc ccctcgctaa                                    1470
```

<210> SEQ ID NO 269
<211> LENGTH: 1392
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 269

```
atggacttcc aggttcagat cttttcgttc ctgctgatca gcgcctctgt tatcatgtcg     60
cgcggcgaca tccagatgac ccagtcccct tcctccctct ctgcctctgt gggagaccgc    120
gttaccatca catgccgagc ttcccaggac gtgaacacag ccgtggcctg gtaccagcag    180
aagcccggga aggcacccaa actcctcatc tactccgcct ccttcctaga gagtggcgtg    240
ccttcccgat tctccggctc caggagtggc acggacttta cgctcaccat tagtagcctg    300
cagcccgaag acttcgcgac ctactattgt cagcaacact acacgacgcc accaactttc    360
ggccagggta ccaaggtcga gattaagcga accggcagta ccagtgggtc tggcaagccc    420
ggcagcggcg agggatccga ggtccagctg gtcgagtccg gcggggggcct ggtgcagccg    480 ggcggctcgc tgaggttatc ttgcgccgcc agtggcttca acatcaagga tacttacatc    540
cactgggtga ggcaggctcc gggcaagggc ctggaatggg tggctaggat ctaccctact    600
aacgggtaca cacgctacgc agattcggtg aaaggccgct tcactatctc cgccgacacc    660
tcgaagaaca ctgcttacct gcagatgaac tccctcaggg ccgaagatac tgcagtctac    720
accacgacgc cagcgccgcg accaccaaca ccggcgccca ccatcgcgtc gcagcccctg    780
tccctgcgcc cagaggcgtg ccggccagcg gcgggggggcg cagtgcacac gagggggctg    840
gacttcgcct gtgatatcta catctgggcg cccttggccg ggacttgtgg ggtccttctc    900
ctgtcactgg ttatcaccct ttactgcaaa cggggcagaa gaaactcct gtatatattc     960 aaacaaccat ttatgagacc agtacaaact actcaagagg aagatggctg tagctgccga    1020
tttccagaag aagaagaagg aggatgtgaa ctgagagtga agttcagcag gagcgcagac    1080
gcccccgcgt acaagcaggg ccagaaccag ctctataacg agctcaatct aggacgaaga    1140
```

```
gaggagtacg acgttttgga caagagacgt ggccgggacc ctgagatggg gggaaagccg  1200
agaaggaaga accctcagga aggcctgtac aatgaactgc agaaagataa gatggcggag  1260
gcctacagtg agattgggat gaaaggcgag cgccggaggg gcaaggggca cgatggcctt  1320
taccagggtc tcagtacagc caccaaggac acctacgacg cccttcacat gcaggccctg  1380 cccectcgct aa                                                     1392
```

<210> SEQ ID NO 270
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 270

```
atgggttggt cgtgcattat cctcttcctc gtcgcaaccg ctaccggcgt tcactcggat   60
tacaaggatg acgacgacaa agaggtacag ctggtgcaga gcggggccga ggttaagaag  120
cccgggtctt ccgtaaaggt gtcctgcaag gcctcggggg gcacattctc atcgtacgca  180
atatcgtggg tgcggcaggc ccccgggcag gggctggaat ggatgggcgg aattatccca  240
atcttcggga ccgccaacta tgcccagaag tttcagggtc gtgtgaccat tactgccgac  300
gagtccacca gtacggccta catggagctg agtagtctgc gtagcgagga tactgccgtt  360
tattattgcg cccgggaaga gggaccgtac tgctcgtcga cctcatgtta cggcgccttc  420
gacatctggg gccaaggcac cctggtgacg gtgtcctccg gtggtggcgg aagtggcggc  480 gggggtccg gcggggcgg ttcacagtcc gtcctgaccc aggatcccgc ggtgtcggtc  540
gcgctgggtc agacagtaaa gataacatgc cagggcgatt ctctgcgcag ttatttcgcc  600
tcgtggtacc agcagaaacc cggccaggct cctacccttg ttatgtacgc gcgcaatgac  660
agacccgcgg gcgtgcccga ccgcttctcc ggctcaaaga gcgggaccte cgcctccctg  720 gccatctccg ggctccagtc tgaggatgag gccgattact actgcgctgc ttgggacgac  780
tccctcaatg gctatctgtt tggcgcaggc acaaagctga ccgtgctcac cacgacgcca  840
gcgccgcgac caccaacacc ggcgcccacc atcgcgtcgc agcccctgtc cctgcgccca  900
gaggcgtgcc ggccagcggc gggggcgca gtgcacacga gggggctgga cttcgcctgt  960
gatatctaca tctgggcgcc cttggccggg acttgtgggg tccttctcct gtcactggtt  1020 atcaccecttt actgcaaacg gggcagaaag aaactcctgt atatattcaa acaaccattt  1080
atgagaccag tacaaactac tcaagaggaa gatggctgta gctgccgatt ccagaagaa  1140 gaagaaggag gatgtgaact gagagtgaag ttcagcagga gcgcagacgc ccccgcgtac  1200
aagcagggcc agaaccagct ctataacgag ctcaatctag gacgaagaga ggagtacgac  1260
gttttggaca gagacgtggg ccgggaccet gagatggggg gaaagccgag aaggaagaac  1320
cctcaggaag gcctgtacaa tgaactgcag aaagataaga tggcggaggc ctacagtgag  1380
attgggatga aaggcgagcg ccggaggggc aaggggcacg atggccttta ccagggtctc  1440
agtacagcca ccaaggacac ctacgacgcc cttcacatgc aggccctgcc cctcgctaa  1500
```

<210> SEQ ID NO 271
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 271

```
atgggttggt cgtgcattat cctcttcctc gtcgcaaccg ctaccggcgt tcactcggat    60
tacaaggatg acgacgacaa agaggtacag ctggtgcaga gcggggccga ggttaagaag   120
cccgggtctt ccgtaaaggt gtcctgcaag gcctcggggg gcacattctc atcgtacgca   180
ataggttggg tgcggcaggc ccccgggcag gggctggaat ggatgggcgg aattatccca   240
atcttcggga tcgccaacta tgcccagaag tttcagggtc gtgtgaccat tactgccgac   300
gagtccacca gtagtgccta catggagctg agtagtctgc gtagcgagga tactgccgtt   360
tattattgcg cccgggaaga gggaccgtac tgctcgtcga cctcatgtta cgcagccttc   420
gacatctggg gccaaggcac cctggtgacg gtgtcctccg gtggtggcgg aagtggcggc   480
gggggtccg gcggggcgg ttcacagtcc gtcctgaccc aggatcccgc ggtgtcggtc   540
gcgctgggtc agacagtaaa gataacatgc agggcgatt ctctgcgcag ttatttcgcc   600
tcgtggtacc agcagaaacc cggccaggct cctacccttg ttatgtacgc gcgcaatgac   660
agacccgcgg gcgtgcccga ccgcttctcc ggctcaaaga gcgggacctc cgcctccctg   720
gccatctccg ggctccagcc cgaggatgag gccgattact actgcgctgc ttgggacgac   780
tccctcaatg ctatctgtt tggcgcaggc acaaagctga ccgtgctcac cacgacgcca   840
gcgccgcgac caccaacacc ggcgcccacc atcgcgtcgc agcccctgtc cctgcgccca   900
gaggcgtgcc ggccagcggc gggggcgca gtgcacacga gggggctgga cttcgcctgt   960
gatatctaca tctgggcgcc cttggccggg acttgtgggg tccttctcct gtcactggtt  1020
atcaccctt actgcaaacg gggcagaaag aaactcctgt atatattcaa acaaccattt  1080
atgagaccag tacaaactac tcaagaggaa gatggctgta gctgccgatt ccagaagaa  1140
gaagaaggag gatgtgaact gagagtgaag ttcagcagga gcgcagacgc cccgcgtac  1200
aagcagggcc agaaccagct ctataacgag ctcaatctag acgaagaga ggagtacgac  1260
gttttggaca gagacgtgg ccgggaccct gagatggggg gaaagccgag aaggaagaac  1320
cctcaggaag gcctgtacaa tgaactgcag aaagataaga tggcggaggc ctacagtgag  1380
attgggatga aggcgagcg ccggagggc aaggggcacg atggccttta ccagggtctc  1440
agtacagcca ccaaggacac ctacgacgcc cttcacatgc aggccctgcc ccctcgctaa  1500
```

<210> SEQ ID NO 272
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 272

```
atgggttggt cgtgcattat cctcttcctc gtcgcaaccg ctaccggcgt tcactcggat    60
tacaaggatg acgacgacaa agaggtacag ctggtgcaga gcggggccga ggttaagaag   120
cccgggtctt ccgtaaaggt gtcctgcaag gcctcggggg gcacattctc atcgtacgca   180
atatcgtggg tgcggcaggc ccccgggcag gggctggaat gggtcggcgg aattatccca   240
atcttcggga ccgccaacta tgcccagaag tttcagggtc gtgtgaagat tactgccgac   300
gagtccgcaa gtacggccta catggagctg agtagtctgc gtagcgagga tactgccgtt   360
```

```
tattattgcg cccgggaaga gggaccgtac tgctcgtcga cctcatgtta cgcagccttc    420
gacatctggg gccaaggcac cctggtgacg gtgtcctccg gtggtggcgg aagtggcggc    480 gggggtccg gcggggcgg ttcacagtcc gtcctgaccc aggatcccgc ggtgtcggtc    540
gcgctgggtc agacagtaaa gataacatgc cagggcgatt ctctgcgcag ttatctggcc    600
tcgtggtacc agcagaaacc cggccaggct cctacccttg ttacctacgc gcgcaatgac    660
agacccgcgg gcgtgcccga ccgcttctcc ggctcaaaga gcgggacctc cgcctccctg    720
gccatctccg ggctccagtc tgaggatgag gccgattact actgcgctgc ttgggacgac    780
tccctcaatg gctatctgtt tggcgcaggc acaaagctga ccgtgctcac cacgacgcca    840
gcgccgcgac caccaacacc ggcgcccacc atcgcgtcgc agccctgtc cctgcgccca    900 gaggcgtgcc ggccagcggc gggggcgca gtgcacacga gggggctgga cttcgcctgt    960
gatatctaca tctgggcgcc cttggccggg acttgtgggg tccttctcct gtcactggtt   1020
atcacccttt actgcaaacg gggcagaaag aaactcctgt atatattcaa acaaccattt   1080
atgagaccag tacaaactac tcaagaggaa gatggctgta gctgccgatt ccagaagaa   1140 gaagaaggag gatgtgaact gagagtgaag ttcagcagga gcgcagacgc ccccgcgtac   1200
aagcagggcc agaaccagct ctataacgag ctcaatctag gacgaagaga ggagtacgac   1260
gttttggaca gagacgtggg ccgggaccct gagatggggg gaaagccgag aaggaagaac   1320
cctcaggaag gcctgtacaa tgaactgcag aaagataaga tggcggaggc ctacagtgag   1380
attgggatga aggcgagcg ccggaggggc aaggggcacg atggccttta ccagggtctc   1440
agtacagcca ccaaggacac ctacgacgcc cttcacatgc aggccctgcc ccctcgctaa   1500
```

<210> SEQ ID NO 273
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 273

```
atgggttggt cgtgcattat cctcttcctc gtcgcaaccg ctaccggcgt tcactcggat     60
tacaaggatg acgacgacaa agaggtacag ctggtgcaga gcggggccga ggttaagaag    120
cccgggtctt ccgtaaaggt gtcctgcaag gcctcggggg gcacattctc atcgtacgca    180
atatcgtggg tgcggcaggc ccccgggcag gggctggaat gggtcggcgg aattatccca    240
atcttcggga ccgccaacta tgcccagaag tttcagggtc gtgtgaagat tactgccgac    300
gagtccgcaa gtacggccta catggagctg agtagtctgc gtagcgagga tactgccgtt    360
tattattgcg cccgggaaga gggaccgtac tgctcgtcga cctcatgtta cggcgccttc    420
gacatctggg gccaaggcac cctggtgacg gtgtcctccg gtggtggcgg aagtggcggc    480 gggggtccg gcggggcgg ttcacagtcc gtcctgaccc aggatcccgc ggtgtcggtc    540
gcgctgggtc agacagtaaa gataacatgc cagggcgatt ctctgcgcag ttatctggcc    600
tcgtggtacc agcagaaacc cggccaggct cctacccttg ttacctacgc gcgcaatgac    660
agacccgcgg gcgtgcccga ccgcttctcc ggctcaaaga gcgggacctc cgcctccctg    720
gccatctccg ggctccagtc tgaggatgag gccgattact actgcgctgc ttgggacgac    780
tccctcaatg gctatctgtt tggcgcaggc acaaagctga ccgtgctcac cacgacgcca    840
gcgccgcgac caccaacacc ggcgcccacc atcgcgtcgc agccctgtc cctgcgccca    900
```

```
gaggcgtgcc ggccagcggc ggggggcgca gtgcacacga ggggctgga cttcgcctgt    960
gatatctaca tctgggcgcc cttggccggg acttgtgggg tccttctcct gtcactggtt   1020
atcacccttt actgcaaacg gggcagaaag aaactcctgt atatattcaa acaaccattt   1080
atgagaccag tacaaactac tcaagaggaa gatggctgta gctgccgatt tccagaagaa   1140
gaagaaggag gatgtgaact gagagtgaag ttcagcagga gcgcagacgc ccccgcgtac   1200
aagcagggcc agaaccagct ctataacgag ctcaatctag gacgaagaga ggagtacgac   1260
gttttggaca agagacgtgg ccgggaccct gagatggggg gaaagccgag aaggaagaac   1320
cctcaggaag gcctgtacaa tgaactgcag aaagataaga tggcggaggc ctacagtgag   1380
attgggatga aaggcgagcg ccggagggc aaggggcacg atggcctta ccagggtctc     1440
agtacagcca ccaaggacac ctacgacgcc cttcacatgc aggccctgcc ccctcgctaa   1500
```

<210> SEQ ID NO 274
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 274

```
atgggttggt cgtgcattat cctcttcctc gtcgcaaccg ctaccggcgt tcactcggat    60
tacaaggatg acgacgacaa agaggtacag ctggtgcaga gcggggccga ggttaagaag   120
cccgggtctt ccgtaaaggt gtcctgcaag gcctcggggg gcacattctc atcgtacgca   180
atatcgtggg tgcggcaggc ccccgggcag gggctggaat ggatgggcgg aattatccca   240
atcttcggga ccgccaacta tgcccagaag tttcagggtc gtgtgaccat tactgccgac   300
gagtccacca gtacggccta catggagctg agtagtctgc gtagcgagga tactgccgtt   360
tattattgcg cccgggaaga gggaccgtac tgctcgtcga cctcatgtta cgcagccttc   420
gacatctggg gccaaggcac cctggtgacg gtgtcctccg gtggtggcgg aagtggcggc   480
ggggggtccg gcggggggcgg ttcacagtcc gtcctgaccc aggatcccgc ggcatcggtc   540
gcgctgggtc agacagtaaa gataacatgc cagggcgatt ctctgcgcag ttatttcgcc   600
tcgtggtacc agcagaaacc cggccaggct cctacccttg ttatgtacgc gcgcaatgac   660
agacccgcgg gcgtgcccga ccgcttctcc ggctcaaaga gcgggacctc cgcctccctg   720
gccatctccg gctccagtc tgaggatgag gccgattact actgcgctgc ttgggacgac   780
tccctcaatg gctatctgtt tggcgcaggc acaaagctga ccgtgctcac cacgacgcca   840
gcgccgcgac caccaacacc ggcgcccacc atcgcgtcgc agcccctgtc cctgcgccca   900
gaggcgtgcc ggccagcggc ggggggcgca gtgcacacga ggggctgga cttcgcctgt   960
gatatctaca tctgggcgcc cttggccggg acttgtgggg tccttctcct gtcactggtt   1020
atcacccttt actgcaaacg gggcagaaag aaactcctgt atatattcaa acaaccattt   1080
atgagaccag tacaaactac tcaagaggaa gatggctgta gctgccgatt tccagaagaa   1140
gaagaaggag gatgtgaact gagagtgaag ttcagcagga gcgcagacgc ccccgcgtac   1200
aagcagggcc agaaccagct ctataacgag ctcaatctag gacgaagaga ggagtacgac   1260
gttttggaca agagacgtgg ccgggaccct gagatggggg gaaagccgag aaggaagaac   1320
cctcaggaag gcctgtacaa tgaactgcag aaagataaga tggcggaggc ctacagtgag   1380
```

```
attgggatga aaggcgagcg ccggaggggc aagggggcacg atggccttta ccagggtctc   1440
agtacagcca ccaaggacac ctacgacgcc cttcacatgc aggccctgcc ccctcgctaa   1500
```

<210> SEQ ID NO 275
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Gly Tyr Thr Phe Thr Gly Tyr Tyr Met His
1               5                   10

<210> SEQ ID NO 276
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Gly Phe Thr Phe Ser Ser Tyr Trp Met His
1               5                   10

<210> SEQ ID NO 277
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Gly Tyr Thr Phe Thr Asp Tyr Tyr Met His
1               5                   10

<210> SEQ ID NO 278
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Gly Tyr Thr Phe Thr Ser Tyr Tyr Met His
1               5                   10

<210> SEQ ID NO 279
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Gly Phe Thr Phe Ser Ser Tyr Ala Met His
1               5                   10

<210> SEQ ID NO 280
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Gly Tyr Pro Phe Thr Gly Tyr Ser Leu His
1               5                   10

<210> SEQ ID NO 281
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Gly Tyr Thr Phe Thr Ser Tyr Tyr Met His
1               5                   10

<210> SEQ ID NO 282
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Gly Tyr Thr Phe Thr Ser Tyr Gly Ile Ser
1               5                   10

<210> SEQ ID NO 283
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Gly Tyr Thr Phe Thr Gly Tyr Tyr Met His
1               5                   10

<210> SEQ ID NO 284
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Gly Phe Ile Phe Ser Asp Tyr Tyr Met Gly
1               5                   10

<210> SEQ ID NO 285
<211> LENGTH: 10
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Gly Phe Thr Phe Arg Gly Tyr Tyr Ile His
1               5                   10

<210> SEQ ID NO 286
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Gly Phe Thr Phe Asp Asp Tyr Ala Met His
1               5                   10

<210> SEQ ID NO 287
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Gly Phe Thr Phe Ser Ser Tyr Trp Met His
1               5                   10

<210> SEQ ID NO 288
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Gly Phe Thr Phe Ser Ser Tyr Gly Met His
1               5                   10

<210> SEQ ID NO 289
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Gly Phe Thr Phe Ser Ser Tyr Ala Met Ser
1               5                   10

<210> SEQ ID NO 290
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 290

Gly Tyr Thr Phe Thr Ser Tyr Tyr Met His
1               5                   10

<210> SEQ ID NO 291
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Gly Asp Thr Ser Thr Arg His Tyr Ile His
1               5                   10

<210> SEQ ID NO 292
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Gly Tyr Thr Phe Thr Asn Tyr Tyr Met His
1               5                   10

<210> SEQ ID NO 293
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Gly Phe Ser Leu Ser Thr Ala Gly Val His Val Gly
1               5                   10

<210> SEQ ID NO 294
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Gly Tyr Ser Phe Thr Gly Tyr Thr Met Asn
1               5                   10

<210> SEQ ID NO 295
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

```
Arg Ile Asn Pro Asn Ser Gly Gly Thr Asn Tyr Ala Gln Lys Phe Gln
1               5                   10                  15

Gly

<210> SEQ ID NO 296
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Trp Ile Asn Pro Asn Ser Gly Gly Thr Asn Tyr Ala Gln Lys Phe Gln
1               5                   10                  15

Gly

<210> SEQ ID NO 297
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Arg Ile Asn Thr Asp Gly Ser Thr Thr Thr Tyr Ala Asp Ser Val Glu
1               5                   10                  15

Gly

<210> SEQ ID NO 298
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Val Ile Ser Tyr Asp Gly Ser Asn Lys Tyr Tyr Ala Asp Ser Val Lys
1               5                   10                  15

Gly

<210> SEQ ID NO 299
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Trp Ile Asn Pro Asn Ser Gly Gly Thr Asn Tyr Ala Gln Lys Phe Gln
1               5                   10                  15

Gly

<210> SEQ ID NO 300
<211> LENGTH: 17
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 300

Ile Ile Asn Pro Ser Gly Gly Ser Thr Gly Tyr Ala Gln Lys Phe Gln
1               5                   10                  15

Gly

<210> SEQ ID NO 301
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Trp Ile Ser Ala Tyr Asn Gly Asn Thr Asn Tyr Ala Gln Lys Leu Gln
1               5                   10                  15

<210> SEQ ID NO 302
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Trp Ile Asn Pro Asn Ser Gly Gly Thr Asn Tyr Ala Gln Asn Phe Gln
1               5                   10                  15

Gly

<210> SEQ ID NO 303
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Arg Ile Asn Pro Asn Ser Gly Gly Thr Asn Tyr Ala Gln Lys Phe Gln
1               5                   10                  15

Gly

<210> SEQ ID NO 304
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Tyr Ile Gly Arg Ser Gly Ser Ser Met Tyr Tyr Ala Asp Ser Val Lys
1               5                   10                  15

Gly

<210> SEQ ID NO 305
```

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Ile Ile Asn Pro Ser Gly Gly Ser Arg Ala Tyr Ala Gln Lys Phe Gln
1               5                   10                  15

Gly

<210> SEQ ID NO 306
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Gly Ile Ser Trp Asn Ser Gly Ser Ile Gly Tyr Ala Asp Ser Val Lys
1               5                   10                  15

<210> SEQ ID NO 307
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Gly Ile Ser Trp Asn Ser Gly Ser Thr Gly Tyr Ala Asp Ser Val Lys
1               5                   10                  15

Gly

<210> SEQ ID NO 308
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Gly Ile Ser Trp Asn Ser Gly Ser Thr Gly Tyr Ala Asp Ser Val Lys
1               5                   10                  15

Gly

<210> SEQ ID NO 309
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Arg Ile Asn Ser Asp Gly Ser Ser Thr Ser Tyr Ala Asp Ser Val Lys
1               5                   10                  15
```

Gly

<210> SEQ ID NO 310
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Val Ile Ser Tyr Asp Gly Ser Asn Lys Tyr Tyr Ala Asp Ser Val Lys
1               5                   10                  15

Gly

<210> SEQ ID NO 311
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ala Ile Ser Gly Ser Gly Gly Ser Thr Tyr Tyr Ala Asp Ser Val Lys
1               5                   10                  15

Gly

<210> SEQ ID NO 312
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Ile Ile Asn Pro Ser Gly Gly Ser Thr Ser Tyr Ala Gln Lys Phe Gln
1               5                   10                  15

Gly

<210> SEQ ID NO 313
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Val Ile Asn Pro Thr Thr Gly Pro Ala Thr Gly Ser Pro Ala Tyr Ala
1               5                   10                  15

Gln Met Leu Gln Gly
            20

<210> SEQ ID NO 314
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 314

Ile Ile Asn Pro Ser Gly Gly Tyr Thr Thr Tyr Ala Gln Lys Phe Gln
1               5                   10                  15

Gly

<210> SEQ ID NO 315
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Leu Ile Ser Trp Ala Asp Asp Lys Arg Tyr Arg Pro Ser Leu Arg Ser
1               5                   10                  15

<210> SEQ ID NO 316
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Leu Ile Thr Pro Tyr Asn Gly Ala Ser Ser Tyr Asn Gln Lys Phe Arg
1               5                   10                  15

Gly

<210> SEQ ID NO 317
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Gly Arg Tyr Tyr Gly Met Asp Val
1               5

<210> SEQ ID NO 318
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Asp Leu Arg Arg Thr Val Val Thr Pro Arg Ala Tyr Tyr Gly Met Asp
1               5                   10                  15

Val

<210> SEQ ID NO 319
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 319

Gly Glu Trp Asp Gly Ser Tyr Tyr Asp Tyr
1               5                   10

<210> SEQ ID NO 320
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Gly His Trp Ala Val
1               5

<210> SEQ ID NO 321
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Gly Trp Asp Phe Asp Tyr
1               5

<210> SEQ ID NO 322
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Tyr Arg Leu Ile Ala Val Ala Gly Asp Tyr Tyr Tyr Gly Met Asp
1               5                   10                  15

Val

<210> SEQ ID NO 323
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Trp Lys Val Ser Ser Ser Ser Pro Ala Phe Asp Tyr
1               5                   10

<210> SEQ ID NO 324
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 324

Asp His Tyr Gly Gly Asn Ser Leu Phe Tyr
1               5                   10

<210> SEQ ID NO 325
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Gly Gly Tyr Ser Ser Ser Ser Asp Ala Phe Asp Ile
1               5                   10

<210> SEQ ID NO 326
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Val Ala Gly Gly Ile Tyr Tyr Tyr Tyr Gly Met Asp Val
1               5                   10

<210> SEQ ID NO 327
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Gly Trp Asp Phe Asp Tyr
1               5

<210> SEQ ID NO 328
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Thr Thr Thr Ser Tyr Ala Phe Asp Ile
1               5

<210> SEQ ID NO 329
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Ser Pro Val Val Ala Ala Thr Glu Asp Phe Gln His
1               5                   10

<210> SEQ ID NO 330
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Thr Ala Ser Cys Gly Gly Asp Cys Tyr Tyr Leu Asp Tyr
1               5                   10

<210> SEQ ID NO 331
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Asp Gly Ser Ser Ser Trp Ser Trp Gly Tyr Phe Asp Tyr
1               5                   10

<210> SEQ ID NO 332
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Asp Ser Ser Ser Trp Tyr Gly Gly Gly Ser Ala Phe Asp Ile
1               5                   10

<210> SEQ ID NO 333
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Asp Ser Ser Ser Trp Tyr Gly Gly Gly Ser Ala Phe Asp Ile
1               5                   10

<210> SEQ ID NO 334
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Thr Gly Trp Val Gly Ser Tyr Tyr Tyr Tyr Met Asp Val
1               5                   10

```
<210> SEQ ID NO 335
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Gly Tyr Ser Arg Tyr Tyr Tyr Tyr Gly Met Asp Val
1               5                   10

<210> SEQ ID NO 336
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Arg Glu Ala Ala Ala Gly His Asp Trp Tyr Phe Asp Leu
1               5                   10

<210> SEQ ID NO 337
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Ser Pro Arg Val Thr Thr Gly Tyr Phe Asp Tyr
1               5                   10

<210> SEQ ID NO 338
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

Ser Val Val Gly Arg Ser Ala Pro Tyr Tyr Phe Asp Tyr
1               5                   10

<210> SEQ ID NO 339
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Ile Arg Ser Cys Gly Gly Asp Cys Tyr Tyr Phe Asp Asn
1               5                   10

<210> SEQ ID NO 340
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 340

Gln Gly Phe Asp Gly Tyr Glu Ala Asn
1               5

<210> SEQ ID NO 341
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Gly Gly Tyr Asp Gly Arg Gly Phe Asp Tyr
1               5                   10

<210> SEQ ID NO 342
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Arg Ala Ser Gln Ser Val Ser Ser Asn Phe Ala
1               5                   10

<210> SEQ ID NO 343
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Gln Ala Ser Gln Asp Ile Ser Asn Ser Leu Asn
1               5                   10

<210> SEQ ID NO 344
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Arg Ala Ser Gln Ser Ile Asn Thr Tyr Leu Asn
1               5                   10

<210> SEQ ID NO 345
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 345

Arg Ala Ser Gln Ser Ile Ser Asp Arg Leu Ala
1               5                   10

<210> SEQ ID NO 346
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Arg Ala Ser Gln Ser Ile Arg Tyr Tyr Leu Ser
1               5                   10

<210> SEQ ID NO 347
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Arg Ala Ser Gln Gly Val Gly Arg Trp Leu Ala
1               5                   10

<210> SEQ ID NO 348
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Arg Ala Ser Gln Ser Val Tyr Thr Lys Tyr Leu Gly
1               5                   10

<210> SEQ ID NO 349
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Arg Ala Ser Gln Asp Ser Gly Thr Trp Leu Ala
1               5                   10

<210> SEQ ID NO 350
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Arg Ala Ser Gln Asp Ile Ser Ser Ala Leu Ala

<210> SEQ ID NO 351
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Lys Ser Ser His Ser Val Leu Tyr Asn Arg Asn Asn Lys Asn Tyr Leu
1               5                   10                  15

Ala

<210> SEQ ID NO 352
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Arg Ala Ser Gln Ser Ile Arg Tyr Tyr Leu Ser
1               5                   10

<210> SEQ ID NO 353
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Arg Ala Ser Gln Ser Ile Ser Thr Trp Leu Ala
1               5                   10

<210> SEQ ID NO 354
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Arg Ala Ser Gln Ser Val Thr Ser Asn Tyr Leu Ala
1               5                   10

<210> SEQ ID NO 355
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Arg Ala Ser Glu Asn Val Asn Ile Trp Leu Ala
1               5                   10

<210> SEQ ID NO 356
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Gln Gly Asp Ala Leu Arg Ser Tyr Tyr Ala Ser
1               5                   10

<210> SEQ ID NO 357
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

Gln Gly Asp Ser Leu Arg Ser Tyr Tyr Ala Ser
1               5                   10

<210> SEQ ID NO 358
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Gln Gly Asp Ser Leu Arg Ser Tyr Tyr Ala Ser
1               5                   10

<210> SEQ ID NO 359
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Arg Ala Ser Gln Ser Val Ser Ser Asn Tyr Leu Ala
1               5                   10

<210> SEQ ID NO 360
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Arg Ala Ser Gln Ser Val Tyr Thr Lys Tyr Leu Gly
1               5                   10

<210> SEQ ID NO 361
<211> LENGTH: 11
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Arg Ala Ser Gln Ser Ile Ser Ser Tyr Leu Asn
1               5                   10

<210> SEQ ID NO 362
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Arg Ala Ser Gln Ser Ile Ser Ser Trp Leu Ala
1               5                   10

<210> SEQ ID NO 363
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Arg Ala Ser Gln Gly Ile Ser Asp Tyr Ser
1               5                   10

<210> SEQ ID NO 364
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Arg Ala Ser Glu Asn Val Asn Ile Trp Leu Ala
1               5                   10

<210> SEQ ID NO 365
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Arg Ala Ser Arg Gly Ile Ser Ser Ala Leu Ala
1               5                   10

<210> SEQ ID NO 366
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                        Synthetic peptide"

<400> SEQUENCE: 366

Ser Ala Ser Ser Ser Val Ser Tyr Met His
1               5                   10

<210> SEQ ID NO 367
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Asp Ala Ser Asn Arg Ala Thr
1               5

<210> SEQ ID NO 368
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Asp Ala Ser Thr Leu Glu Thr
1               5

<210> SEQ ID NO 369
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Ala Ala Ser Ser Leu Gln Ser
1               5

<210> SEQ ID NO 370
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Lys Ala Ser Ser Leu Glu Ser
1               5

<210> SEQ ID NO 371
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371
```

```
Thr Ala Ser Ile Leu Gln Asn
1               5

<210> SEQ ID NO 372
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Ala Ala Ser Thr Leu Gln Ser
1               5

<210> SEQ ID NO 373
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Asp Ala Ser Thr Arg Ala Thr
1               5

<210> SEQ ID NO 374
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Asp Ala Ser Thr Leu Glu Asp
1               5

<210> SEQ ID NO 375
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Asp Ala Ser Ser Leu Glu Ser
1               5

<210> SEQ ID NO 376
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Trp Ala Ser Thr Arg Lys Ser
1               5
```

```
<210> SEQ ID NO 377
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Thr Ala Ser Ile Leu Gln Asn
1               5

<210> SEQ ID NO 378
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Lys Ala Ser Thr Leu Glu Ser
1               5

<210> SEQ ID NO 379
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Gly Ala Ser Thr Arg Ala Thr
1               5

<210> SEQ ID NO 380
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Lys Ser Ser Ser Leu Ala Ser
1               5

<210> SEQ ID NO 381
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Gly Lys Asn Asn Arg Pro Ser
1               5

<210> SEQ ID NO 382
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 382

Gly Arg Ser Arg Arg Pro Ser
1               5

<210> SEQ ID NO 383
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Gly Lys Asn Asn Arg Pro Ser
1               5

<210> SEQ ID NO 384
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Asp Val Ser Thr Arg Ala Thr
1               5

<210> SEQ ID NO 385
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385

Asp Ala Ser Thr Arg Ala Thr
1               5

<210> SEQ ID NO 386
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386

Ala Ala Ser Ser Leu Gln Ser
1               5

<210> SEQ ID NO 387
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 387

Lys Ala Ser Ser Leu Glu Ser
1               5

<210> SEQ ID NO 388
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Ala Ala Ser Thr Leu Gln Ser
1               5

<210> SEQ ID NO 389
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 389

Lys Ser Ser Ser Leu Ala Ser
1               5

<210> SEQ ID NO 390
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Asp Ala Ser Ser Leu Glu Ser
1               5

<210> SEQ ID NO 391
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Asp Thr Ser Lys Leu Ala Ser
1               5

<210> SEQ ID NO 392
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

His Gln Arg Ser Asn Trp Leu Tyr Thr
```

```
1               5
```

<210> SEQ ID NO 393
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

```
Gln Gln His Asp Asn Leu Pro Leu Thr
1               5
```

<210> SEQ ID NO 394
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

```
Gln Gln Ser Phe Ser Pro Leu Thr
1               5
```

<210> SEQ ID NO 395
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

```
Gln Gln Tyr Gly His Leu Pro Met Tyr Thr
1               5                   10
```

<210> SEQ ID NO 396
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

```
Leu Gln Thr Tyr Thr Thr Pro Asp
1               5
```

<210> SEQ ID NO 397
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

```
Gln Gln Ala Asn Ser Phe Pro Leu Thr
1               5
```

<210> SEQ ID NO 398

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Gln His Tyr Gly Gly Ser Pro Leu Ile Thr
1               5                   10

<210> SEQ ID NO 399
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

Gln Gln Tyr Asn Ser Tyr Pro Leu Thr
1               5

<210> SEQ ID NO 400
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Gln Gln Phe Ser Ser Tyr Pro Leu Thr
1               5

<210> SEQ ID NO 401
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 401

Gln Gln Thr Gln Thr Phe Pro Leu Thr
1               5

<210> SEQ ID NO 402
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Leu Gln Thr Tyr Thr Thr Pro Asp
1               5

<210> SEQ ID NO 403
<211> LENGTH: 10
<212> TYPE: PRT
<213> ORGANISM: Artificial Sequence
<220> FEATURE:
```

<220> FEATURE:
<221> NAME/KEY: source
<223> OTHER INFORMATION: /note="Description of Artificial Sequence:
      Synthetic peptide"

<400> SEQUENCE: 403

Gln Gln Tyr Asn Thr Tyr Ser Pro Tyr Thr
1               5                   10

<210> SEQ ID NO 404
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 404

Gln Gln Tyr Gly Ser Ala Pro Val Thr
1               5

<210> SEQ ID NO 405
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 405

Gln Gln Tyr Gln Ser Tyr Pro Leu Thr
1               5

<210> SEQ ID NO 406
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

Asn Ser Arg Asp Ser Ser Gly Tyr Pro Val
1               5                   10

<210> SEQ ID NO 407
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

Asn Ser Arg Asp Asn Thr Ala Asn His Tyr Val
1               5                   10

<210> SEQ ID NO 408
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 408

Asn Ser Arg Gly Ser Ser Gly Asn His Tyr Val
1               5                   10

<210> SEQ ID NO 409
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

Gln Gln Arg Ser Asn Trp Pro Pro Trp Thr
1               5                   10

<210> SEQ ID NO 410
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

Gln His Tyr Gly Gly Ser Pro Leu Ile Thr
1               5                   10

<210> SEQ ID NO 411
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Gln Gln Ser Tyr Ser Ile Pro Leu Thr
1               5

<210> SEQ ID NO 412
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Gln Gln Tyr Ser Ser Tyr Pro Leu Thr
1               5

<210> SEQ ID NO 413
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

Gln Gln Tyr Tyr Ser Tyr Pro Leu Thr
1               5
```

```
<210> SEQ ID NO 414
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

Gln Gln Tyr Gln Ser Tyr Pro Leu Thr
1               5

<210> SEQ ID NO 415
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 415

Gln Gln Ser Tyr Ser Thr Pro Trp Thr
1               5

<210> SEQ ID NO 416
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 416

Gln Gln Trp Ser Gly Tyr Pro Leu Thr
1               5

<210> SEQ ID NO 417
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 1-6 'Gly Gly
      Gly Gly Ser' repeating units"
<220> FEATURE:
<223> OTHER INFORMATION: /note="See specification as filed for detailed
      description of substitutions and preferred embodiments"

<400> SEQUENCE: 417

Gly Gly Gly Gly Ser Gly Gly Gly Gly Ser Gly Gly Gly Gly Ser
1               5                   10                  15

Gly Gly Gly Ser Gly Gly Gly Gly Ser Gly Gly Gly Gly Ser
            20                  25                  30

<210> SEQ ID NO 418
<211> LENGTH: 20
<212> TYPE: DNA
<213> ORGANISM: Artificial Sequence
<220> FEATURE:
<221> NAME/KEY: source
```

<223> OTHER INFORMATION: /note="Description of Artificial Sequence:
    Synthetic primer"

<400> SEQUENCE: 418
gcctccactt caaccacagt                                              20

<210> SEQ ID NO 419
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"
<220> FEATURE:
<221> NAME/KEY: misc_feature
<222> LOCATION: (1)..(1)
<223> OTHER INFORMATION: /note="5'-FAM modified"

<400> SEQUENCE: 419
cagtgcagct cacagatg                                                18

<210> SEQ ID NO 420
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: MISC_FEATURE
<222> LOCATION: (1)..(50)
<223> OTHER INFORMATION: /note="This sequence may encompass 1-10 'Gly
    Gly Gly Gly Ser' repeating units"

<400> SEQUENCE: 420

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 421
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: misc_feature
<222> LOCATION: (1)..(5000)
<223> OTHER INFORMATION: /note="This sequence may encompass 50-5000
    nucleotides"

<400> SEQUENCE: 421
tttttttttt tttttttttt tttttttttt tttttttttt tttttttttt tttttttttt    60
tttttttttt tttttttttt tttttttttt tttttttttt tttttttttt tttttttttt   120
tttttttttt tttttttttt tttttttttt tttttttttt tttttttttt tttttttttt   180
tttttttttt tttttttttt tttttttttt tttttttttt tttttttttt tttttttttt   240

-continued

| | | | | | | |
|---|---|---|---|---|---|---|
| tttttttttt | tttttttttt | tttttttttt | tttttttttt | tttttttttt | tttttttttt | 300 |
| tttttttttt | tttttttttt | tttttttttt | tttttttttt | tttttttttt | tttttttttt | 360 |
| tttttttttt | tttttttttt | tttttttttt | tttttttttt | tttttttttt | tttttttttt | 420 |
| tttttttttt | tttttttttt | tttttttttt | tttttttttt | tttttttttt | tttttttttt | 480 |
| tttttttttt | tttttttttt | tttttttttt | tttttttttt | tttttttttt | tttttttttt | 540 |
| tttttttttt | tttttttttt | tttttttttt | tttttttttt | tttttttttt | tttttttttt | 600 |
| tttttttttt | tttttttttt | tttttttttt | tttttttttt | tttttttttt | tttttttttt | 660 |
| tttttttttt | tttttttttt | tttttttttt | tttttttttt | tttttttttt | tttttttttt | 720 |
| tttttttttt | tttttttttt | tttttttttt | tttttttttt | tttttttttt | tttttttttt | 780 |
| tttttttttt | tttttttttt | tttttttttt | tttttttttt | tttttttttt | tttttttttt | 840 |
| tttttttttt | tttttttttt | tttttttttt | tttttttttt | tttttttttt | tttttttttt | 900 |
| tttttttttt | tttttttttt | tttttttttt | tttttttttt | tttttttttt | tttttttttt | 960 |
| tttttttttt | tttttttttt | tttttttttt | tttttttttt | tttttttttt | tttttttttt | 1020 |
| tttttttttt | tttttttttt | tttttttttt | tttttttttt | tttttttttt | tttttttttt | 1080 |
| tttttttttt | tttttttttt | tttttttttt | tttttttttt | tttttttttt | tttttttttt | 1140 |
| tttttttttt | tttttttttt | tttttttttt | tttttttttt | tttttttttt | tttttttttt | 1200 |
| tttttttttt | tttttttttt | tttttttttt | tttttttttt | tttttttttt | tttttttttt | 1260 |
| tttttttttt | tttttttttt | tttttttttt | tttttttttt | tttttttttt | tttttttttt | 1320 |
| tttttttttt | tttttttttt | tttttttttt | tttttttttt | tttttttttt | tttttttttt | 1380 |
| tttttttttt | tttttttttt | tttttttttt | tttttttttt | tttttttttt | tttttttttt | 1440 |
| tttttttttt | tttttttttt | tttttttttt | tttttttttt | tttttttttt | tttttttttt | 1500 |
| tttttttttt | tttttttttt | tttttttttt | tttttttttt | tttttttttt | tttttttttt | 1560 |
| tttttttttt | tttttttttt | tttttttttt | tttttttttt | tttttttttt | tttttttttt | 1620 |
| tttttttttt | tttttttttt | tttttttttt | tttttttttt | tttttttttt | tttttttttt | 1680 |
| tttttttttt | tttttttttt | tttttttttt | tttttttttt | tttttttttt | tttttttttt | 1740 |
| tttttttttt | tttttttttt | tttttttttt | tttttttttt | tttttttttt | tttttttttt | 1800 |
| tttttttttt | tttttttttt | tttttttttt | tttttttttt | tttttttttt | tttttttttt | 1860 |
| tttttttttt | tttttttttt | tttttttttt | tttttttttt | tttttttttt | tttttttttt | 1920 |
| tttttttttt | tttttttttt | tttttttttt | tttttttttt | tttttttttt | tttttttttt | 1980 |
| tttttttttt | tttttttttt | tttttttttt | tttttttttt | tttttttttt | tttttttttt | 2040 |
| tttttttttt | tttttttttt | tttttttttt | tttttttttt | tttttttttt | tttttttttt | 2100 |
| tttttttttt | tttttttttt | tttttttttt | tttttttttt | tttttttttt | tttttttttt | 2160 |
| tttttttttt | tttttttttt | tttttttttt | tttttttttt | tttttttttt | tttttttttt | 2220 |
| tttttttttt | tttttttttt | tttttttttt | tttttttttt | tttttttttt | tttttttttt | 2280 |
| tttttttttt | tttttttttt | tttttttttt | tttttttttt | tttttttttt | tttttttttt | 2340 |
| tttttttttt | tttttttttt | tttttttttt | tttttttttt | tttttttttt | tttttttttt | 2400 |
| tttttttttt | tttttttttt | tttttttttt | tttttttttt | tttttttttt | tttttttttt | 2460 |
| tttttttttt | tttttttttt | tttttttttt | tttttttttt | tttttttttt | tttttttttt | 2520 |
| tttttttttt | tttttttttt | tttttttttt | tttttttttt | tttttttttt | tttttttttt | 2580 |
| tttttttttt | tttttttttt | tttttttttt | tttttttttt | tttttttttt | tttttttttt | 2640 |

| | | | | | |
|---|---|---|---|---|---|
| tttttttttt | tttttttttt | tttttttttt | tttttttttt | tttttttttt | tttttttttt | 2700 |
| tttttttttt | tttttttttt | tttttttttt | tttttttttt | tttttttttt | tttttttttt | 2760 |
| tttttttttt | tttttttttt | tttttttttt | tttttttttt | tttttttttt | tttttttttt | 2820 |
| tttttttttt | tttttttttt | tttttttttt | tttttttttt | tttttttttt | tttttttttt | 2880 |
| tttttttttt | tttttttttt | tttttttttt | tttttttttt | tttttttttt | tttttttttt | 2940 |
| tttttttttt | tttttttttt | tttttttttt | tttttttttt | tttttttttt | tttttttttt | 3000 |
| tttttttttt | tttttttttt | tttttttttt | tttttttttt | tttttttttt | tttttttttt | 3060 |
| tttttttttt | tttttttttt | tttttttttt | tttttttttt | tttttttttt | tttttttttt | 3120 |
| tttttttttt | tttttttttt | tttttttttt | tttttttttt | tttttttttt | tttttttttt | 3180 |
| tttttttttt | tttttttttt | tttttttttt | tttttttttt | tttttttttt | tttttttttt | 3240 |
| tttttttttt | tttttttttt | tttttttttt | tttttttttt | tttttttttt | tttttttttt | 3300 |
| tttttttttt | tttttttttt | tttttttttt | tttttttttt | tttttttttt | tttttttttt | 3360 |
| tttttttttt | tttttttttt | tttttttttt | tttttttttt | tttttttttt | tttttttttt | 3420 |
| tttttttttt | tttttttttt | tttttttttt | tttttttttt | tttttttttt | tttttttttt | 3480 |
| tttttttttt | tttttttttt | tttttttttt | tttttttttt | tttttttttt | tttttttttt | 3540 |
| tttttttttt | tttttttttt | tttttttttt | tttttttttt | tttttttttt | tttttttttt | 3600 |
| tttttttttt | tttttttttt | tttttttttt | tttttttttt | tttttttttt | tttttttttt | 3660 |
| tttttttttt | tttttttttt | tttttttttt | tttttttttt | tttttttttt | tttttttttt | 3720 |
| tttttttttt | tttttttttt | tttttttttt | tttttttttt | tttttttttt | tttttttttt | 3780 |
| tttttttttt | tttttttttt | tttttttttt | tttttttttt | tttttttttt | tttttttttt | 3840 |
| tttttttttt | tttttttttt | tttttttttt | tttttttttt | tttttttttt | tttttttttt | 3900 |
| tttttttttt | tttttttttt | tttttttttt | tttttttttt | tttttttttt | tttttttttt | 3960 |
| tttttttttt | tttttttttt | tttttttttt | tttttttttt | tttttttttt | tttttttttt | 4020 |
| tttttttttt | tttttttttt | tttttttttt | tttttttttt | tttttttttt | tttttttttt | 4080 |
| tttttttttt | tttttttttt | tttttttttt | tttttttttt | tttttttttt | tttttttttt | 4140 |
| tttttttttt | tttttttttt | tttttttttt | tttttttttt | tttttttttt | tttttttttt | 4200 |
| tttttttttt | tttttttttt | tttttttttt | tttttttttt | tttttttttt | tttttttttt | 4260 |
| tttttttttt | tttttttttt | tttttttttt | tttttttttt | tttttttttt | tttttttttt | 4320 |
| tttttttttt | tttttttttt | tttttttttt | tttttttttt | tttttttttt | tttttttttt | 4380 |
| tttttttttt | tttttttttt | tttttttttt | tttttttttt | tttttttttt | tttttttttt | 4440 |
| tttttttttt | tttttttttt | tttttttttt | tttttttttt | tttttttttt | tttttttttt | 4500 |
| tttttttttt | tttttttttt | tttttttttt | tttttttttt | tttttttttt | tttttttttt | 4560 |
| tttttttttt | tttttttttt | tttttttttt | tttttttttt | tttttttttt | tttttttttt | 4620 |
| tttttttttt | tttttttttt | tttttttttt | tttttttttt | tttttttttt | tttttttttt | 4680 |
| tttttttttt | tttttttttt | tttttttttt | tttttttttt | tttttttttt | tttttttttt | 4740 |
| tttttttttt | tttttttttt | tttttttttt | tttttttttt | tttttttttt | tttttttttt | 4800 |
| tttttttttt | tttttttttt | tttttttttt | tttttttttt | tttttttttt | tttttttttt | 4860 |
| tttttttttt | tttttttttt | tttttttttt | tttttttttt | tttttttttt | tttttttttt | 4920 |
| tttttttttt | tttttttttt | tttttttttt | tttttttttt | tttttttttt | tttttttttt | 4980 | tttttttttt tttttttttt                                                          5000

<210> SEQ ID NO 422
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 100-5000
      nucleotides"

<400> SEQUENCE: 422
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800

-continued

```
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa aaaaaaaaaa aaaaaaaaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa    2160
aaaaaaaaaa aaaaaaaaaa aaaaaaaaaa aaaaaaaaaa aaaaaaaaaa aaaaaaaaaa    2220
aaaaaaaaaa aaaaaaaaaa aaaaaaaaaa aaaaaaaaaa aaaaaaaaaa aaaaaaaaaa    2280
aaaaaaaaaa aaaaaaaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
aaaaaaaaaa aaaaaaaaaa aaaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaaaaaaaa    2520
aaaaaaaaaa aaaaaaaaaa aaaaaaaaaa aaaaaaaaaa aaaaaaaaaa aaaaaaaaaa    2580
aaaaaaaaaa aaaaaaaaaa aaaaaaaaaa aaaaaaaaaa aaaaaaaaaa aaaaaaaaaa    2640
aaaaaaaaaa aaaaaaaaaa aaaaaaaaaa aaaaaaaaaa aaaaaaaaaa aaaaaaaaaa    2700
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
```

```
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 423
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Arg Gly Asp Ser
1

<210> SEQ ID NO 424
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 424

Ile Ile Asn Pro Ser Gly Gly Ser Thr Ser Tyr Ala Gln Lys Phe Gln
1               5                   10                  15

<210> SEQ ID NO 425
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 425
tcaaacgtgt ctgtgttgta ggt                                               23
```

CAR-EXPRESSING CELLS AGAINST MULTIPLE TUMOR ANTIGENS AND USES THEREOF

RELATED APPLICATIONS

This application is a U.S. National Stage Application under 35 U.S.C. § 371 of International Application No. PCT/US2016/015978, filed Feb. 1, 2016, which claims priority to U.S. Provisional Application No. 62/111,094, filed Feb. 2, 2015. The entire contents of the aforesaid applications are hereby incorporated herein by reference.

SEQUENCE LISTING

The instant application contains a Sequence Listing which has been submitted electronically in ASCII format and is hereby incorporated by reference in its entirety. Said ASCII copy, created on Apr. 12, 2016, is named N2067-7084WO SL .txt and is 457,421 bytes in size.

FIELD OF THE INVENTION

The present invention relates generally to the use of immune effector cells (e.g., T cells, NK cells) engineered to conditionally express an agent which enhances the immune effector response, e.g., a Chimeric Antigen Receptor (CAR), to treat a disease associated with expression of a tumor antigen.

BACKGROUND OF THE INVENTION

Adoptive cell transfer (ACT) therapy with autologous T-cells, especially with T-cells transduced with Chimeric Antigen Receptors (CARs), has shown promise in hematologic cancer trials. However, there exists an urgent need for improved methods of CAR therapy for increased therapeutic efficacy and treatment of other cancers.

SUMMARY OF THE INVENTION

The present disclosure relates to, in part, compositions and methods for treating cancer, e.g., a cancer described herein, in a subject using an immune effector cell that constitutively expresses a chimeric antigen receptor (CAR) (referred to herein as a nonconditional CAR) and conditionally expresses another agent useful for treating cancer. In such embodiments, the conditionally expressed agent is expressed upon activation of the immune effector cell, e.g., the binding of the nonconditional CAR to its target, e.g., a cancer associated antigen described herein. In one embodiment, the conditionally expressed agent is a CAR (referred to herein as a conditional CAR). In another embodiment, the conditionally expressed agent inhibits a checkpoint inhibitor of the immune response. In another embodiment, the conditionally expressed agent improves or enhances the efficacy of a CAR, and can include a cytokine. Compositions, including nucleic acids encoding the nonconditional CAR and conditional agent, e.g., conditional CAR, and cells expressing nonconditional CAR and conditional agent, e.g., conditional CAR (referred to herein as CAR-expressing cells), are also provided herein. Methods for generating the CAR-expressing cell and using a CAR-expressing cell, or CAR-expressing cell population, for treatment of cancer are also described herein.

In one aspect, the present disclosure features, a nucleic acid, e.g., an isolated nucleic acid, comprising:

(a) a nucleotide sequence encoding an agent, e.g., polypeptide or nucleic acid, that enhances the immune response against a target cell, e.g., a cancer cell;

(b) a first activation-conditional control region operatively linked to (a).

In one embodiment, the nucleic acid further comprises:

(c) a nucleotide sequence encoding a second agent, e.g., polypeptide or nucleic acid, that enhances the immune response against a target cell, e.g., a cancer cell; and, (d) a second control region operatively linked to (c), wherein the second control region is other than an activation-conditional control region, e.g., the second control region comprises a constitutive control region, e.g., elongation factor 1 alpha (EF1a) control region.

In another aspect, the present disclosure features, a nucleic acid, e.g., an isolated nucleic acid, comprising:

(a) a nucleotide sequence encoding a first CAR comprising an antigen binding domain, a transmembrane domain, and an intracellular signaling domain;

(b) a first activation-conditional control region operatively linked to (a);

(c) a nucleotide sequence encoding a second CAR comprising an antigen binding domain, a transmembrane domain, and an intracellular signaling domain; and (d) a second control region operatively linked to (c), wherein the second control region is other than an activation-conditional control region, e.g., the second control region comprises a constitutive control region.

In one embodiment, the second control region comprises a constitutive control region, e.g., an elongation factor 1 alpha (EF1a) control region as described herein. The second CAR operatively linked to a second control region comprising a constitutive control region is also referred to herein as a nonconditional CAR.

In one embodiment, the second CAR (e.g., nonconditional CAR) comprises an antigen binding domain, a transmembrane domain, and an intracellular signaling domain, and wherein the antigen binding domain binds to a cancer associated antigen selected from the group consisting of: mesothelin, EGFRvIII, TSHR, CD19, CD123, CD22, CD30, CD171, CS-1, CLL-1, CD33, GD2, GD3, BCMA, Tn Ag, prostate specific membrane antigen (PSMA), ROR1, FLT3, FAP, TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha (FRa), ERBB2 (Her2/neu), MUC1, epidermal growth factor receptor (EGFR), NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In one embodiment, the antigen binding domain of the second CAR binds to mesothelin. Examples of mesothelin binding domains suitable for use in a CAR are further described herein. In one embodiment, the mesothelin binding domain is a provided in Table 2.

In one embodiment, the antigen binding domain of the second CAR binds to EGFRvIII.

Conditionally Expressed Agents that Enhance Anti-Tumor Immune Response

The present disclosure relates to conditional expression of agents that enhance the anti-tumor immune response, e.g., the anti-tumor effect of an immune effector cell, e.g., a CAR-expressing cell. The conditionally expressed agents include: a CAR, e.g., targeting a different antigen, e.g., cancer associated antigen described herein, than the nonconditional CAR, an agent that inhibits a checkpoint inhibitor of the immune response, or a cytokine.

In any of the nucleic acids described herein, the nucleic acid comprises, e.g., in (a), a sequence encoding a first CAR operatively linked to a first activation-conditional control region. The first CAR operatively linked to a first activation-conditional control region is also referred to herein as a conditional CAR.

In any of the nucleic acids described herein, the first CAR (e.g., the conditional CAR) comprises a first antigen binding domain that binds a first antigen; and the second CAR (e.g., the nonconditional CAR) comprises a second antigen binding domain that binds a second antigen. In one embodiment, the first antigen is different from the second antigen. In one embodiment, the first antigen and the second antigen are co-expressed on a cancer cell. In one embodiment, the first antigen is expressed on a first population of cancer cells and the second antigen is expressed on a second population of cancer cells. In one embodiment, the second antigen is expressed on a cancer cell and wherein the first antigen is not expressed on the cancer cell.

In any of the nucleic acids described herein, the first antigen, e.g., recognized by the antigen of the first CAR, is selected from the group consisting of: Folate receptor alpha (FRa), ERBB2 (Her2/neu), EphA2, IL-13Ra2, epidermal growth factor receptor (EGFR), Mesothelin, TSHR, CD19, CD123, CD22, CD30, CD171, CS-1, CLL-1, CD33, EGFRvIII, GD2, GD3, BCMA, Tn Ag, prostate specific membrane antigen (PSMA), ROR1, FLT3, FAP, TAG72, CD38, CD44v6, CEA, EPCAM, B7H3, KIT, interleukin-11 receptor a (IL-11Ra), PSCA, PRSS21, VEGFR2, LewisY, CD24, platelet-derived growth factor receptor-beta (PDGFR-beta), SSEA-4, CD20, MUC1, NCAM, Prostase, PAP, ELF2M, Ephrin B2, IGF-I receptor, CAIX, LMP2, gp100, bcr-abl, tyrosinase, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In any of the nucleic acids described herein, the second antigen, e.g., recognized by the antigen of the second CAR, is selected from the group consisting of: mesothelin, EGFRvIII, TSHR, CD19, CD123, CD22, CD30, CD171, CS-1, CLL-1, CD33, EGFRvIII, GD2, GD3, BCMA, Tn Ag, prostate specific membrane antigen (PSMA), ROR1, FLT3, FAP, TAG72, CD38, CD44v6, CEA, EPCAM, B7H3, KIT, interleukin-11 receptor a (IL-11Ra), PSCA, PRSS21, VEGFR2, LewisY, CD24, platelet-derived growth factor receptor-beta (PDGFR-beta), SSEA-4, CD20, MUC1, NCAM, Prostase, PAP, ELF2M, Ephrin B2, IGF-I receptor, CAIX, LMP2, gp100, bcr-abl, tyrosinase, Fucosyl GM1, sLe, GM3, TGS5, HMWMAA, o-acetyl-GD2, Folate receptor alpha (FRa), ERBB2 (Her2/neu), EphA2, IL-13Ra2, epidermal growth factor receptor (EGFR), Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In any of the nucleic acids described herein where the second antigen recognized by the antigen binding domain of the second CAR (nonconditional CAR) is EGFRvIII, the first antigen, e.g., recognized by the antigen binding domain of the first CAR (conditional CAR) is an antigen expressed on an EGFRvIII-expressing tumor, e.g., EGFR or a different variant thereof, EphA2, ErbB2 (Her2/neu), or IL-13Ra2.

In any of the nucleic acids described herein where the second antigen recognized by the antigen binding domain of the second CAR (nonconditional CAR) mesothelin, the first antigen, e.g., recognized by the antigen binding domain of the first CAR (conditional CAR), is an antigen expressed on a mesothelin-expressing tumor, e.g., is FRa or ErbB2 (Her2/neu).

In one embodiment, the antigen binding domain of the first CAR binds to folate receptor alpha (FRa). Examples of FRa binding domains suitable for use in a CAR are further described herein. In one embodiment, the FRa binding domain is a provided in Table 5.

Additional embodiments of the first CAR (conditional CAR) and/or the second CAR (nonconditional CAR) are provided below: In any of the nucleic acids described herein, the transmembrane domain of the first and/or second CAR comprises a transmembrane domain from a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises the amino acid sequence of SEQ ID NO: 12; an amino acid sequence comprises at least one, two or three modifications but not more than 20, 10 or 5 modifications of the amino acid sequence of SEQ ID NO: 12, or a sequence with 95-99% identity to the amino acid sequence of SEQ ID NO: 12. In one embodiment, the transmembrane domain comprises the nucleic acid sequence of SEQ ID NO: 13, or a sequence with 95-99% identity to the nucleic acid sequence of SEQ ID NO: 13.

In any of the nucleic acids described herein, the antigen binding domain of the first and/or second CAR is connected to the transmembrane domain by a hinge region. In one embodiment, the hinge region comprises SEQ ID NO:4, SEQ ID NO: 6, SEQ ID NO: 8, or SEQ ID NO: 10 or a sequence with 95-99% identity thereof. In one embodiment, the hinge region comprises the nucleic acid sequence of SEQ ID NO: 5, SEQ ID NO: 7, SEQ ID NO: 9, or SEQ ID NO: 11, or a sequence with 95-99% identity to the nucleic acid sequence of SEQ ID NO: 5, SEQ ID NO: 7, SEQ ID NO: 9, or SEQ ID NO: 11.

In any of the nucleic acids described herein, the intracellular signaling domain of the first and/or second CAR comprises a costimulatory signaling domain comprising a functional signaling domain obtained from a protein selected from the group consisting of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one embodiment, the intracellular signaling domain comprises a functional signaling domain of 4-1BB and/or a functional signaling domain of CD3 zeta. In one embodiment, the intracellular signaling domain comprises a functional signaling domain of CD27 and/or a functional signaling domain of CD3 zeta. In one embodiment, the intracellular signaling domain comprises a functional signaling domain of ICOS and/or a functional signaling domain of CD3 zeta. In one embodiment, the intracellular signaling domain comprises a functional signaling domain of CD28 and/or a functional signaling domain of CD3 zeta.

In one embodiment, the costimulatory domain, e.g., a signaling domain of 4-1BB, CD27, ICOS, or CD28, comprises the amino acid sequence of SEQ ID NO: 14, SEQ ID NO: 16, SEQ ID NO: 40, or SEQ ID NO: 44, or an amino acid sequence having at least one, two or three modifications but not more than 20, 10 or 5 modifications of the amino acid sequence of SEQ ID NO:14, SEQ ID NO: 16, SEQ ID NO: 40, or SEQ ID NO: 44, or an amino acid sequence with 95-99% identity to the amino acid sequence of SEQ ID NO: 14, SEQ ID NO: 16, SEQ ID NO: 40, or SEQ ID NO: 44. In one embodiment, the costimulatory domain comprises the nucleic acid sequence of SEQ ID NO:15, SEQ ID NO: 17, SEQ ID NO: 41, or SEQ ID NO: 45, or a sequence having 95-99% sequence identity to SEQ ID NO:15, SEQ ID NO: 17, SEQ ID NO: 41, or SEQ ID NO: 4.

In one embodiment, the intracellular signaling domain comprises the amino acid sequence of SEQ ID NO:14, SEQ ID NO: 16, SEQ ID NO: 40, or SEQ ID NO: 44, and/or the amino acid sequence of SEQ ID NO: 18 or SEQ ID NO:20; or an amino acid sequence having at least one, two or three modifications but not more than 20, 10 or 5 modifications of the amino acid sequence of SEQ ID NO:14, SEQ ID NO: 16, SEQ ID NO: 40, or SEQ ID NO: 44, and/or the amino acid sequence of SEQ ID NO:18 or SEQ ID NO:20; or an amino acid sequence with 95-99% identity to the amino acid sequence of SEQ ID NO: 14, SEQ ID NO: 16, SEQ ID NO: 40, or SEQ ID NO: 44, and/or the amino acid sequence of SEQ ID NO:18 or SEQ ID NO:20. In one embodiment, the intracellular signaling domain comprises the nucleic acid sequence of SEQ ID NO:15, SEQ ID NO: 17, SEQ ID NO: 41, or SEQ ID NO: 45, and/or the nucleic acid sequence of SEQ ID NO: 19 or SEQ ID NO: 21; or a sequence having 95-99% sequence identity to SEQ ID NO:15, SEQ ID NO: 17, SEQ ID NO: 41, or SEQ ID NO: 4, and/or the nucleic acid sequence of SEQ ID NO: 19 or SEQ ID NO: 21.

In one embodiment, the intracellular signaling domain comprises the amino acid sequence of SEQ ID NO:14 and the amino acid sequence of SEQ ID NO:18 or SEQ ID NO:20, wherein the amino acid sequences comprising the intracellular signaling domain are expressed in the same frame and as a single polypeptide chain.

In any of the nucleic acids described herein, the first and/or second CAR further comprises a leader sequence comprising the amino acid sequence of SEQ ID NO:2. In one embodiment, the leader sequence comprises the nucleic acid sequence of SEQ ID NO:3, or a sequence having 95-99% sequence identity to SEQ ID NO: 3.

In any of the nucleic acids described herein, the first CAR can comprise an amino acid or nucleic acid sequence of a FRa CAR described herein, e.g., as provided in Table 7. In any of the nucleic acids described herein, the first CAR can comprise an amino acid or nucleic acid sequence of a ErbB2 (Her2/neu) CAR described herein.

In any of the nucleic acids described herein, the second CAR can comprise an amino acid or nucleic acid sequence of a mesothelin CAR described herein, e.g., as provided in Table 6. In any of the nucleic acids described herein, the second CAR can comprise an amino acid or nucleic acid sequence of an EGFRvIII CAR described herein.

In any of the nucleic acids described herein, the nucleic acid comprises, e.g., in (a), a sequence encoding a nucleotide sequence encoding an inhibitor of a checkpoint inhibitor of the immune response. In one embodiment, the checkpoint inhibitor of the immune response is selected from the group consisting of: PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the nucleotide sequence encodes an RNA-based inhibitor, e.g., an shRNA, of a checkpoint inhibitor. Exemplary shRNAs directed to PD-1 are provided herein. In another embodiment, the nucleotide sequence encodes an antibody molecule, e.g., an antibody or fragment thereof, that inhibits or decreases the activity of a checkpoint inhibitor. Exemplary antibodies that inhibit or decrease the activity of a checkpoint inhibitor are provided herein.

In any of the nucleic acids described herein, the nucleic acid comprises, e.g., in (a), a sequence encoding a nucleotide sequence encoding a cytokine. In one embodiment, the cytokine comprises IL-2, IL-7, IL-15, or IL-21.

In any of the nucleic acids described herein, the activation-conditional control region comprises a nucleotide sequence that induces expression of (a) upon immune effector cell activation. In one embodiment, the activation-conditional control region comprises a promoter of a gene that is induced upon immune effector cell activation. In one embodiment, the activation-conditional control region comprises a nuclear factor of activated T cells (NFAT) promoter, an NF-kB promoter, an IL-2 promoter, or an IL-2 receptor (IL-2R) promoter. In one embodiment, the activation-conditional control region comprises one or more binding sites for a transcription modulator, e.g., a transcription factor, that induces gene expression upon immune effector cell activation. In one embodiment, the activation-conditional control region comprises one or more NFAT binding sides.

In any of the nucleic acids described herein, the second control region that is other than an activation-conditional control region is a constitutive control region. In one embodiment, the constitutive control region comprises a constitutive promoter. In one embodiment, the constitutive promoter is an EF1alpha promoter, e.g., comprises the nucleic acid sequence of SEQ ID NO: 1.

Nucleic Acid Constructs, Vectors, and Cells

In any of the nucleic acids described herein, (a), the nucleotide sequence encoding an agent, e.g., polypeptide or nucleic acid, that enhances the immune response against a target cell, e.g., a cancer cell; and (b), the first activation-conditional control region operatively linked to (a), are disposed on a single nucleic acid molecule, e.g., a viral vector, e.g., a lentivirus vector.

In any of the nucleic acids described herein, (a) the nucleotide sequence encoding an agent, e.g., polypeptide or nucleic acid, that enhances the immune response against a target cell, e.g., a cancer cell, and (c), the nucleotide sequence encoding a second agent, e.g., polypeptide or nucleic acid, that enhances the immune response against a target cell, e.g., a cancer cell, are disposed on a single nucleic acid molecule, e.g., a viral vector, e.g., a lentivirus vector.

In any of the nucleic acids described herein, (a), (b), (c) and (d) are all disposed on a single nucleic acid molecule, e.g., a viral vector, e.g., a lentivirus vector, and (a) comprises the nucleotide sequence encoding the first CAR;

(b) comprises the activation-conditional control region operatively linked to (a);

(c) comprises the sequence encoding the second CAR; and, (d) comprises the second control region operatively linked to (c), wherein the second control region comprises a constitutive control region.

In one embodiment, any of the nucleic acids described herein comprises a bicistronic viral vector, e.g., a bicistronic lentiviral vector.

In any of the nucleic acids described herein, (a) is translated as a first RNA and (c) is translated as a second RNA.

In any of the nucleic acids described herein, (a) is disposed on a first nucleic acid molecule, e.g., a first viral vector, e.g., a first lentivirus vector; and (c) is disposed on a second nucleic acid molecule, e.g., a second viral vector, e.g., a second lentivirus vector.

In any of the nucleic acids described herein, (a) and (b) are disposed on a first nucleic acid molecule, e.g., a first viral vector, e.g., a first lentivirus vector; and (c) and (d) are disposed on a second nucleic acid molecule, e.g., a second viral vector, e.g., a second lentivirus vector; wherein:

(a) comprises the nucleotide sequence encoding the first CAR, and (b) comprises the activation-conditional control region operatively linked to (a), and (c) comprises the nucleotide sequence encoding the second CAR, and, (d) comprises the second control region operatively linked to (c), wherein the second control region comprises a constitutive control region.

In another aspect, the present disclosure features a vector system, e.g., a vector system comprising one or more vectors, comprising any of the nucleic acids described herein.

In another aspect, the present disclosure features a cell, e.g., an immune effector cell, e.g., a T cell or NK cell, comprising: a nucleic acid as described herein, or a vector system comprising nucleic acid described herein.

In another aspect, the present disclosure features a method of making a cell described herein, e.g., a CAR-expressing cell, comprising introducing into a cell, a nucleic acid described herein; or a vector system comprising a nucleic acid described herein.

Compositions and Methods for Treating Cancer

In another aspect, the present disclosure features a composition comprising an immune effector cell (e.g., a population of immune effector cells) described herein comprising a chimeric antigen receptor (CAR) molecule for use in the treatment of a subject having a cancer. In one embodiment, the immune effector cell comprises a nonconditional CAR as described herein. In one embodiment, the immune effector cell further comprises one or more of, a conditionally expressed agent, e.g., a conditional CAR as described herein, an agent that inhibits a checkpoint inhibitor, or a cytokine.

In another aspect, the present disclosure features a method of treating a subject having a cancer, e.g., a method of providing an anti-tumor immunity in a subject. In one embodiment, the method includes administering to the subject an effective amount of an immune effector cell (e.g., a population of immune effector cells) comprising a CAR molecule as described herein. In one embodiment, the immune effector cell comprises a nonconditional CAR as described herein. In one embodiment, the immune effector cell further comprises one or more of, a conditionally expressed agent, e.g., a conditional CAR as described herein, an agent that inhibits a checkpoint inhibitor, or a cytokine.

In embodiments of any of the methods and compositions described herein, the cell, e.g., the immune effector cell, comprises any nucleic acid or vector described herein.

In embodiments of any of the methods and compositions described herein, the cell is a human cell.

In embodiments of any of the methods and compositions described herein, the cell is a T cell. In one embodiment, the T cell is an autologous or allogeneic T cell.

In embodiments of any of the methods and compositions described herein, the cell is a NK cell. In one embodiment, the NK cell is an autologous or allogeneic NK cell.

In embodiments of any of the methods and compositions described herein, the cancer is associated with expression of a cancer associated antigen selected from the group consisting of Mesothelin, TSHR, CD19, CD123, CD22, CD30, CD171, CS-1, CLL-1, CD33, EGFRvIII, GD2, GD3, BCMA, Tn Ag, prostate specific membrane antigen (PSMA), ROR1, FLT3, FAP, TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha, ERBB2 (Her2/neu), MUC1, epidermal growth factor receptor (EGFR), NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In embodiments of any of the methods and compositions described herein, the cancer is a solid cancer selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

In embodiments of any of the methods and compositions described herein, the cancer is a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or preleukemia.

In embodiments of any of the methods and compositions described herein, the cell comprises a second CAR under control of a constitutive control region, and a first CAR under control of an activation-conditional control region, wherein the first CAR is expressed upon binding of the second CAR to a cancer associated antigen expressed on a cancer cell.

In embodiments of any of the methods and compositions described herein, the second CAR comprises an antigen binding domain that binds to mesothelin. In such embodiments, the first CAR comprises an antigen binding domain that binds to an antigen that is expressed on mesothelin-expressing cancer cells, or expressed on cells in the tumor microenvironment of a mesothelin-expressing cancer/tumor, e.g., FRa or ErbB2 (Her2/neu).

In embodiments of any of the methods and compositions described herein, the second CAR comprises an antigen binding domain that binds to EGFRvIII. In such embodiments, the first CAR comprises an antigen binding domain that binds to an antigen that is expressed on EGFRvIII-expressing cancer cells or expressed on cells in the tumor microenvironment of a mesothelin-expressing cancer/tumor, e.g., EGFR or other variants thereof, ErbB2 (Her2/neu), EphA2, or IL-13Ra2.

In embodiments of any of the methods and compositions described herein, the method of treating a subject having cancer further comprises administering an additional therapeutic agent, e.g., an anti-cancer agent, or a low-dose of an mTOR inhibitor.

In another aspect, the present disclosure features, a method of providing a cell, e.g., a CAR cell, described herein, comprising providing an immune effector cell, e.g., a T cell from a human, to a recipient entity, e.g., a laboratory or hospital; and receiving from said entity, a cell described herein, e.g., a CAR cell, derived from said immune effector cell, or a daughter cell thereof. In an embodiment the entity inserted a nucleic acid described herein, into said immune effector cell or a daughter cell thereof. In an embodiment the method further comprises administering the cell to a human.

In another aspect, the present disclosure features, a CAR cell, described herein, comprising: receiving from an entity, e.g., a health care provider, an immune effector cell, e.g., a T cell, from a human; inserting a nucleic acid described herein, into said immune effector cell, or a daughter cell thereof, to form a the cell; and, optionally, providing the cell to the entity.

BRIEF DESCRIPTION OF THE DRAWINGS

FIG. 22B depicts NFAT inducible promoter driven luciferase activity of a PD1 RCAR which include PD1-ECD-TM-FRB and FKBP-4 1BB-CD3 zeta as compared to the control treatment by IgG1-Fc.

(FIG. 33A) Schematic representation of C4 based CAR constructs containing the CD3ζ cytosolic domain alone (C4-z) or in combination with the CD27 costimulatory module (C4-27z). The murine anti-human FRA MOv19-27z CAR is also shown. (FIG. 33B) Transduced T cells consisted of CD4- and CD8-positive cells with both subsets expressing C4 CARs. C4 CAR expression (open histograms) was detected via biotin-labeled rabbit anti-human IgG (H+L) staining followed by streptavidin-phycoerythrin after transduction with lentivirus compared to untransduced (UNT) T cells (filled gray histograms). Transduction efficiencies are indicated with the percentage of CAR expression in parentheses. ScFv, single-chain antibody variable fragment L, linker; C4, anti-FRA scFv; VH, variable H chain; VL, variable L chain; TM, transmembrane region.

(FIG. 34A) C4 and MOv19 CARs expression on primary human T cells can be detected via biotin-labeled recombinant FRA protein followed by SA-PE. As shown, both CD8+ T and CD8− (CD4+) cells can efficiently express CARs as measured by flow cytometry. (FIG. 34B) C4 and MOv19 CARs-transduced T cells showed lytic function in a bioluminescence killing assay. CAR-T cells killed FR+ SKOV3 and A1847 at the indicated E/T ratio more than 20 hours. Untransduced T cells served as negative controls. Mean and SD of triplicate wells from 1 of at least 3 independent experiments is shown. (FIG. 34C) C4 or MOv19 CAR T cells were co-cultured with FRA+ target cells (SKOV3, A1847 and T47D) and FRA− (C30) at a 1:1 E:T ratio. (FIG. 34D) C4 or MOv19 CAR T cells were stimulated with SKOV3 cells for 5-hour in the presence of Golgi inhibitor and analyzed by flow cytometry for intracellular IFN-g, TNF-a and IL-2. (FIG. 34E) IFN-g release assay of C4 and MOv19 CAR T cells after overnight co-culture with FRA+ tumor cells (at 1:10, 1:3, 1:1, 3:1 and 10:1 ratios).

(FIG. 35A) Tumor regression mediated by C4-27z and MOv19-27z CAR T cells. NSG mice bearing established subcutaneous tumor were treated with i.v. injections of $1\times10^7$ C4-27z and MOv19-27z CAR+ T cells or control CD19-27z and UNT T cells or saline on day 40 and 45. Tumor growth was assessed by caliper measurement. Tumors treated with C4-27z CAR or MOv19 CAR T cells (~60% CAR expression) regressed (arrows indicate days of T cell infusion); tumors treated with saline, UNT or CD19-27z CAR T cells did not regress 3 weeks post-first T cell dose. (FIG. 35B) SKOV3 fLuc+ bioluminescence signal was decreased in C4-27z and MOv19-27z CAR T cells treated mice compared with the CD19-27z and the control treatment groups 3 weeks after the first T cell dose. (FIG. 35C) Macroscopic evaluation of resected tumor specimens following T cell therapy. Tumors were harvested from mice at the time of euthanasia, nearly 45 days after first T cell injection. (FIG. 35D) Stable persistence of C4 CAR and MOv19 CAR T cells in vivo. Peripheral blood was collected 3 weeks after the first T cell infusion and quantified for the absolute number of human CD4+ and CD8+ T cells/μl of blood. Mean cell count±SEM is shown with n=5 for all groups.

(FIG. 36A) Human embryonic kidney 293T cells and normal epithelial ovarian cell line IOSE6 express very low level of FRA.SKOV3 and C30 served as positive and negative controls, respectively. (FIG. 36B) C4-27z CAR T cells secret minimal amount of IFN-γ following overnight incubation with normal 293T cells and IOSE 6 cell lines expressing low levels of surface FRA compared to MOv19-27z CAR T cells. (FIG. 36C) C4 and MOv19 CAR T cells were stimulated with 293T or IOSE6 cells for 5-hour in the presence of Golgi inhibitor and analyzed by flow cytometry for intracellular IFN-g and TNF-a.

(FIG. 37A) Lentiviral titers (transduction units, TU) were determined using SupT1 cells based on 3-fold serial dilution of concentrated virus from 1:3 to a final dilution of 1:6,561.C4 CAR-encoding lentivirus has a higher titer when Compared to the titer of MOv19 CAR encoding lentivirus, following the same production and concentration protocols in parallel. (FIG. 37B) Primary human T cells were infected with C4 CAR or MOv19 CAR encoding lentivirus at a multiplicity of infection (MOI) of 1, 2 or 5. These data represent one of at least three independent experiments.

FIG. 47A shows day 0 PK following the first dose of RAD001. FIG. 47B shows Day 14 PK following the final RAD001 dose. Diamonds denote the 10 mg/kg dose of RAD001; squares denote the 1 mg/kg dose of RAD001; triangles denote the 3 mg/kg dose of RAD001; and x's denote the 10 mg/kg dose of RAD001.

FIG. 48A shows CD4$^+$ CAR T cells; FIG. 48B shows CD8$^+$ CAR T cells. Circles denote PBS; squares denote huCTL019; triangles denote huCTL019 with 3 mg/kg RAD001; inverted triangles denote huCTL019 with 0.3 mg/kg RAD001; diamonds denote huCTL019 with 0.03 mg/kg RAD001; and circles denote huCTL019 with 0.003 mg/kg RAD001.

DETAILED DESCRIPTION

Definitions

Figure 1:
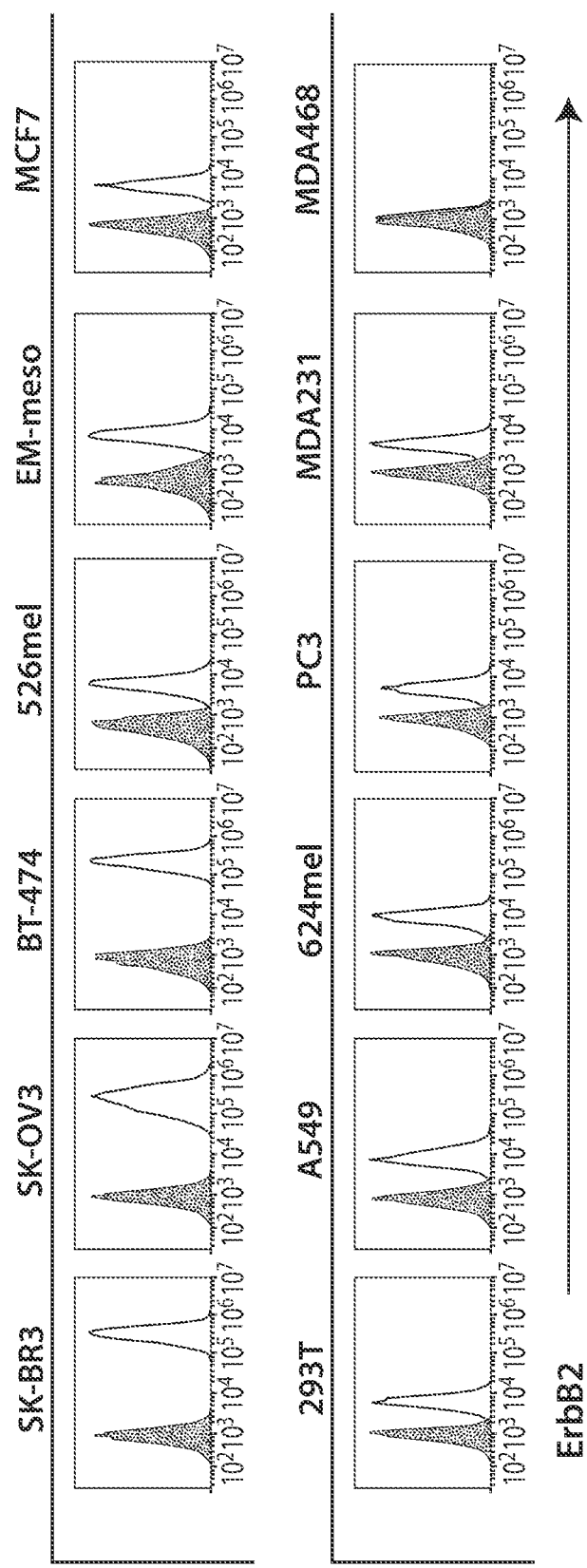
FIG. 1: Flow cytometry detection of ErbB2 surface expression on tumors and cell lines. Cells were stained with anti-ErbB2 Affibody-biotin and detected with streptavidin-allophycocyanin (APC) (open histograms); cells incubated with APC alone indicate background (grey histograms).
Figures 2A, 2B, 2C:
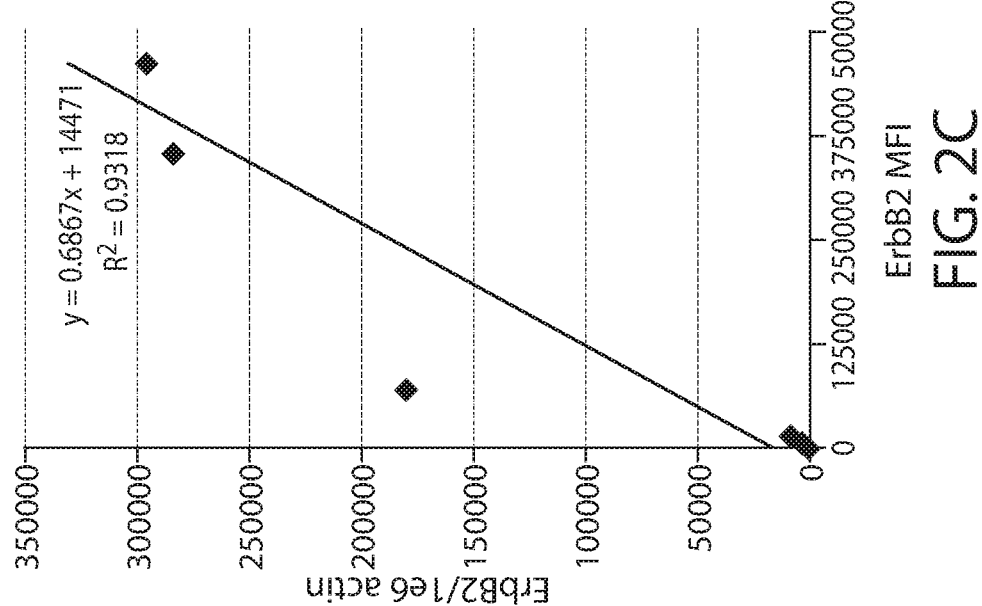
FIGS. 2A, 2B, and 2C: Correlation of ErbB2 detection by flow cytometry and quantitative PCR. Copy numbers of ErbB2 detected by quantitative PCR (ErbB2/1E6 actin) (FIG. 2A). ErbB2 mean fluorescence intensity (ErbB2 MFI) as shown in the histograms in FIG. 1 (FIG. 2B). The correlation is plotted between the ErbB2 expression detected by flow cytometry (MFI, x-axis) and quantitative PCR (y-axis). The forward and reverse primers and probe used for ErbB2 quantitative PCR are as follows: ErbB2-1F, GCCTC-CACTTCAACCACAGT (SEQ ID NO: 418); ErbB2-1R, TCAAACGTGTCTGTGTTGTAGGT; ErbB2-1M2, FAM-CAGTGCAGCTCACAGATG (SEQ ID NO: 419).

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein.

In one aspect, the stimulatory molecule is the zeta chain associated with the T cell receptor complex. In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27, ICOS, and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen recognition domain (e.g., a scFv) during cellular processing and localization of the CAR to the cellular membrane.

A CAR that comprises an antigen binding domain (e.g., a scFv, or TCR) that targets, e.g., binds to, a specific antigen X, such as those described herein, is also referred to as XCAR. For example, a CAR that comprises an antigen binding domain that targets, e.g., binds to, mesothelin is referred to as mesothelin CAR.

The term "activation-conditional control region", as used herein refers to one or more nucleic acid sequences that mediates, e.g., induces, the transcription and/or expression of a sequence under its control, e.g., a sequence encoding a CAR upon activation of the immune effector cell (e.g., a T cell) in which it is disposed. In an embodiment, activation of the immune effector cell, e.g., a CAR-expressing cell, can comprise one or more of the following: binding of the CAR-expressing cell to a cell expressing a tumor antigen recognized by the CAR, e.g., via the binding of a CAR not under the control of the activation conditional control region to a targeted tumor antigen, e.g., the non-conditional CAR; clustering/association of a CAR not under the control of the activation-conditional control region; upregulation of a signaling pathway associated with activation; induction of NFAT, ATF2, or NF-κB expression or activity. In an embodiment, the activation-conditional control region comprises a promoter operably linked to a CAR. In an embodiment, the promoter comprises a nucleic acid sequence of a gene that is upregulated during activation of an immune effector cell, e.g., in an immune response. Examples of such promoters are provided herein, and include the promoter for endogenous IL-2. In embodiments, the activation-conditional control region comprises a promoter operably linked to a CAR and further comprises one or more, e.g., 2, 3, 4, 5, 6, or more, other regulatory elements that mediates activity of the promoter operably linked to the CAR, e.g., to increase or induce expression of the CAR. For example, the promoter comprises nucleic acid sequence that recruits a transcription factor, whose expression or activity is dependent upon activation of the CAR-expressing immune effector cell. In an embodiment, the promoter comprises a binding site recognized by a member of the nuclear factor of activated T cells (NFAT) family. In an embodiment, the activation-conditional control region comprises an IL-2 promoter and 3 or 6 NFAT binding sites. The activation-conditional control region can be located proximal or distal to the 5' or 3' of the nucleic acid sequence under its control, e.g., a sequence encoding the CAR, or within an intronic sequence of the nucleic acid sequence under its control.

The term "signaling domain" refers to the functional portion of a protein which acts by transmitting information within the cell to regulate cellular activity via defined signaling pathways by generating second messengers or functioning as effectors by responding to such messengers. In some aspects, the signaling domain of the CAR described herein is derived from a stimulatory molecule or co-stimulatory molecule described herein, or is a synthesized or engineered signaling domain.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The portion of the CAR of the invention comprising an antibody or antibody fragment thereof may exist in a variety of forms where the antigen binding domain is expressed as part of a contiguous polypeptide chain including, for example, scFv antibody fragments, linear antibodies, single domain antibodies such as sdAb (either VL or VH), camelid VHH domains, a humanized antibody, a bispecific antibody, an antibody conjugate (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR of the invention comprises an antibody fragment. In a further aspect, the CAR comprises an antibody fragment that comprises a scFv.

As used herein, the term "binding domain" or "antibody molecule" (also referred to herein as "anti-target (e.g., CD123) binding domain") refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated or can be derived from a biological sample, or might be macromolecule besides a polypeptide. Such a biological sample can include, but is not limited to a tissue sample, a tumor sample, a cell or a fluid with other biological components.

The terms "anti-cancer effect" or "anti-cancer activity" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "apheresis" as used herein refers to an extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "cancer" refers to a disease characterized by the uncontrolled growth of aberrant cells. Cancer includes all types of cancerous growths or oncogenic processes, metastatic tissues or malignantly transformed cells, tissues or organs irrespective of the histopathologic type or stage of invasiveness. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of a cancer associated antigen or tumor antigen as described herein" includes, but is not limited to, a disease associated with expression of a cancer associated antigen or tumor antigen as described herein or condition associated with cells which express a tumor antigen as described herein including, e.g., proliferative diseases such as a cancer or malignancy or a precancerous condition such as a myelodysplasia, a myelodysplastic syndrome or a preleukemia; or a noncancer related indication associated with cells which express a cancer associated antigen or tumor antigen as described herein. In one aspect, a cancer associated with expression of a cancer associated antigen or tumor antigen as described herein is a hematological cancer. In one aspect, a cancer associated with expression of a cancer associated antigen or tumor antigen as described herein is a solid cancer. Further diseases associated with expression of a tumor antigen described herein include, but not limited to, e.g., atypical and/or non-classical cancers, malignancies, precancerous conditions or proliferative diseases associated with expression of a cancer associated antigen or tumor antigen as described herein. Non-cancer related indications associated with expression of a tumor antigen as described herein include, but are not limited to, e.g., autoimmune disease, (e.g., lupus), inflammatory disorders (allergy and asthma) and transplantation.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules, such as downregulation of TGF-β, and/or reorganization of cytoskeletal structures, and the like.

The term "stimulatory molecule," refers to a molecule expressed by an immune effector cell (e.g., a T cell, NK cell, B cell) that provides the cytoplasmic signaling sequence(s) that regulate activation of the immune effector cell in a stimulatory way for at least some aspect of the immune effector cell signaling pathway, e.g., the T cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from CD3 zeta, common FcR gamma (FCER1G), Fc gamma RIIa, FcR beta (Fc epsilon R1b), CD3 gamma, CD3 delta, CD3 epsilon, CD5, CD22, CD79a, CD79b, CD278 (also known as "ICOS"), FcεRI, DAP10, DAP12, and CD66d. In a specific CAR of the invention, the intracellular signaling domain in any one or more CARs of the invention comprises an intracellular signaling sequence, e.g., a primary signaling sequence of CD3-zeta. In a specific CAR of the invention, the primary signaling sequence of CD3-zeta is the sequence provided as SEQ ID NO: 18, or the equivalent residues from a non-human species, e.g., mouse, rodent, monkey, ape and the like. In a specific CAR of the invention, the primary signaling sequence of CD3-zeta is the sequence as provided in SEQ ID NO:20, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR-expressing cell, e.g., a CART cell or CAR-expressing NK cell. Examples of immune effector function, e.g., in a CART cell or CAR-expressing NK cell, include cytolytic activity and helper activity, including the secretion of cytokines. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. In an embodiment, the intracellular signaling domain is synthesized or engineered. For example, in the case of a CAR-expressing immune effector cell, e.g., CART cell or CAR-expressing NK cell, a primary intracellular signaling domain can comprise a cytoplasmic sequence of a T cell receptor, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta, CD3 gamma, CD3 delta, CD3 epsilon, CD5, CD22, CD79a, CD79b, CD278 ("ICOS"), FcεRI CD66d, DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO: 18. In one aspect, the "zeta stimulatory domain" or a "CD3-zeta stimulatory domain" is the sequence provided as SEQ ID NO:20.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO: 14 or the equivalent residues from a non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "immune effector cell," as used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NK-T) cells, mast cells, and myeloic-derived phagocytes. "Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence, e.g., a polynucleotide sequence that is operably linked to the promoter.

The term "control region" refers to a nucleic acid sequence which is required for expression of a gene product operably linked to the control region sequence. In some instances, this sequence may be the core promoter sequence and in other instances, this sequence may also include an enhancer sequence and other regulatory elements, e.g., transcription factor binding sites, which modulate or are required for expression of the gene product. The control region sequence may, for example, be one which expresses the gene product in an inducible manner, e.g., after immune effector cell activation or in a tissue-specific manner. Alternatively, the control region sequence can be one which expresses the gene product in a constitutive manner, e.g., under most or all physiological conditions of the cell. In one embodiment, the control region is a constitutive control region comprising a constitutive promoter. In one embodiment, the control region is an activation-conditional control region, comprising an inducible promoter, and optionally, one or more additional regulatory elements, in which transcription of the gene product operably linked to the activation-conditional control region is initiated upon activation of the immune effector cell.

The term "constitutive promoter" refers to a nucleotide sequence which, when operably linked with a polynucleotide which encodes or specifies a gene product, causes the gene product to be produced in a cell under most or all physiological conditions of the cell.

The term "inducible promoter" refers to a nucleotide sequence which, when operably linked with a polynucleotide which encodes or specifies a gene product, causes the gene product to be produced in a cell substantially only under certain conditions, e.g., after a specific event or in the presence of an inducer which corresponds to the inducible promoter. In one embodiment, transcription under the control of an inducible promoter occurs in response to activation of the immune effector cell or activation of a CAR molecule described herein. In one embodiment, the inducible promoter is a promoter for any gene that is activated, e.g., upregulated, upon immune effector cell activation or T cell receptor signaling (e.g., CD3 signaling). The activation-conditional control regions described herein can include one or more inducible promoters, and/or one or more sequences associated with the inducible promoter, e.g., transcription factor binding sites.

The term "tissue-specific promoter" refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library. The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1. For example, n=1, n=2, n=3, n=4, n=5, n=6, n=7, n=8, n=9 and n=10 (SEQ ID NO:28). In one embodiment, the flexible polypeptide linkers include, but are not limited to, (Gly4 Ser)4 (SEQ ID NO:29) or (Gly4 Ser)3 (SEQ ID NO:30). In another embodiment, the linkers include multiple repeats of (Gly2Ser), (GlySer) or (Gly3Ser) (SEQ ID NO:31). Also included within the scope of the invention are linkers described in WO2012/138475, incorporated herein by reference.

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 34), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (e.g., a stimulatory and/or costimulatory molecule present on a T cell or a cancer associated antigen present on the surface of a target cancer cell) protein present in a sample, but which antibody or ligand, does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with regulatable intracellular signal generation. In some embodiments, an RCAR comprises at least an extracellular antigen binding domain, a transmembrane and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as "RCARX cell"). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$ increased CD27+, decreased KLRG1, and increased BCL2;

wherein any of the changes described above occurs, e.g., at least transiently, e.g., as compared to a non-treated subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Description

Provided herein are compositions of matter and methods of use for the treatment of a disease such as cancer using immune effector cells (e.g., T cells, NK cells) engineered as described herein. The engineered immune effector cells described herein comprise an agent that enhances the immune response, also referred to herein as an immune-response enhancer, that is expressed by the cell in a conditional manner to increase therapeutic efficacy in treatment of a cancer, e.g., a cancer described herein. The agents that enhance the immune response described herein are expressed by the cell upon activation the immune effector cell.

Conditional Expression of Immune-Response Enhancers

Disclosed herein are compositions and methods for enhancing the therapeutic efficacy of a CAR-expressing immune effector cell, by conditionally expressing a polypeptide or nucleic acid that enhances the immune response once the immune effector cell has been activated.

In embodiments, an immune effector cell is engineered to express a CAR (referred to herein as a CAR-expressing cell) that targets a cancer associated antigen or tumor antigen as described herein, whereby the expression of the CAR is non-conditional (also referred to herein as the non-conditional CAR-expressing cell, and wherein the a polypeptide or nucleic acid that enhances the immune response, e.g., a CAR, that is constitutively expressed is also referred to herein as the non-conditional CAR). In such embodiments, non-conditional expression of the CAR is achieved through use of a constitutive promoter that results in expression, e.g., transcription, of the CAR under most or all physiological conditions of the cell. In an embodiment, the constitutive promoter is EF1alpha, or comprises SEQ ID NO: 1. Other constitutive promoters suitable for use herein include, but are not limited to, a CMV IE gene promoter, an ubiquitin C promoter, or a phosphoglycerate kinase (PGK) promoter, or variants thereof.

In embodiments, the non-conditional CAR-expressing cell is further engineered to conditionally express an agent, e.g., a polypeptide or nucleic acid, that enhances, e.g., promotes or increases, the immune response. In an embodiment, the agent that enhances the immune response is only substantially expressed when the non-conditional CAR-expressing cell is activated. In an embodiment, the conditional expression of the agent that enhances the immune response is achieved through the use of a control region that is responsive to, e.g., induced by, activation of the non-conditional CAR-expressing cell. Activation of the non-conditional CAR-expressing cell can be achieved by recognition and binding of the antigen binding domain of the non-conditional CAR to its cognate antigen, e.g., the tumor antigen targeted by the antigen binding domain, or by signaling through the non-conditional CAR. Suitable control regions that induce expression only upon activation of the non-conditional CAR-expressing cell are provided herein.

The agent that enhances the immune response of an immune effector cell comprises one or more of the following characteristics: 1) targets an additional tumor antigen, e.g., a different tumor antigen targeted by the constitutively expressed, e.g., nonconditional, CAR; 2) inhibits the expression or activity of an inhibitory molecule; and/or 3) activates the expression and/or secretion of a component that enhances immune response or immune effector cell activation. Exemplary agents that enhance the immune response of the non-conditional CAR-expressing cell are further described herein.

Conditional expression of an agent that enhances the immune response as described herein provides several advantages.

Without wishing to be bound by theory, it is believed that a therapeutic agent that can target more than one tumor antigen, e.g., 2, 3, 4, or more different tumor antigens, may have increased therapeutic efficacy by resulting in the targeting of a greater proportion of the cancer cells. Additionally or alternatively, and without wishing to be bound by theory, it is believed that cancer recurrences can occur due to antigen escape following treatment with a tumor antigen-specific CAR therapy. Initial attack by the tumor antigen-specific CAR-expressing cells can result in exclusive elimination of the tumor cells expressing the targeted tumor antigen and may initially result in tumor regression. However, cancer cells that do not express the targeted tumor antigen continue to proliferate, which can progress to tumor recurrence in which the initial CAR therapy has no effect. Thus, without wishing to be bound by theory, it is believed that sequential targeting of two or more different tumor antigens allows the potentiation of anti-tumor immunity by targeting multiple tumor antigens, and increased therapeutic efficacy.

Additionally or alternatively, without wishing to be bound by theory, inducible expression of a second therapeutic agent, e.g., a conditional CAR described herein, provides the added potency of additional targeting, and thereby targets additional populations of cancer cells. Additionally or alternatively, without wishing to be bound by theory, an inducible expression system allows the utilization of a second therapeutic agent, e.g., a conditional CAR described herein, that binds to an antigen that is present on both normal and cancer cells. Thus, inducible expression of such a CAR allows targeted or limited ablation of normal cells that express the antigen recognized by the conditional CAR, where the activity of the conditional CAR is spatially limited to the tumor microenvironment. This allows increased therapeutic efficacy by minimizing side effects of the CAR therapy, with the increased potency of targeting additional cancer cells.

Agents that Target Another Tumor Antigen

In embodiments, the agent that enhances the immune response of an immune effector cell targets an additional tumor antigen, such as a different tumor antigen that that targeted by the non-conditional CAR. In embodiments, the immune effector cell can express more than one, e.g., 2, 3, 4, or 5 or more, agents that target different tumor antigens, where each agent targets a different tumor antigen than that targeted by the non-conditional CAR or any of the other agents. The agent(s) that target additional tumor antigens also comprise domains that induce or activate signaling that can result in proliferation, survival, and/or cytotoxic activity of the cell.

In embodiments, the agent that enhances the immune response of an immune effector cell is a CAR that targets a different tumor antigen than the tumor antigen targeted by the non-conditional CAR. The conditionally expressed CAR is referred to herein as the conditional CAR. Expression, e.g., transcription and/or translation, of the conditional CAR occurs only when the cell comprising a non-conditional CAR cell is activated, e.g., when the non-conditional CAR binds to its target tumor antigen, e.g., a cancer associated antigen described herein. The domains and arrangement of such domains, of the conditional CAR can be any of those described herein in the section titled "Chimeric Antigen Receptors".

In other embodiments, the agent that enhances the immune response of an immune effector cell is a TCR or a TCR-based molecule. In some embodiments, the TCR or TCR-based molecule functions on its own to induce tumor-killing activity, while in other aspects, the TCR-based molecule can be part of a chimeric molecule (e.g., a TCR-CAR) that induces tumor-killing activity.

In embodiments, the TCR or TCR-based molecule is capable of binding specifically to a short target peptide (as opposed to, or in addition to, a target sequence that is part of a full-length protein). In embodiments, the TCR or TCR-based molecule is capable of binding to a target that is typically intracellular. In embodiments, the TCR or TCR-based molecule is capable of binding to a peptide that is simultaneously bound by an MHC.

In embodiments, the TCR-based molecule has homology to, a T cell receptor (TCR). TCRs, in their endogenous context, are found on the surface of T cells and can specifically recognize antigens presented by MHC proteins. A T cell receptor is typically a heterodimer, and may comprise (i) and alpha and a beta chain or (ii) a gamma and a delta chain. Like antibodies, T cell receptors typically contain six complementarity-determining regions (CDRs) which determine their target specificity. Generally, three CDRs are situated in one chain (e.g., the alpha chain) and three CDRs are situated in a second chain (e.g., the beta chain). The CDRs are typically part of the TCR's variable domain. An endogenous TCR also comprises a constant region, a transmembrane region which anchors the TCR to the cell membrane, and a cytoplasmic region.

In embodiments, the TCR-based molecule is recombinant. In embodiments, the TCR-based molecule may comprise one or more TCR CDRs, e.g., 2, 3, 4, 5, or 6 CDRs. The TCR-based molecule may comprise one or two TCR variable domains. In embodiments, the two variable domains are linked (e.g., fused) together. The alpha domain may be N-terminal or C-terminal to the beta domain. The TCR-based molecule may comprise a single-chain TCR or a single chain comprising portions of a TCR, e.g., as described in (Willemsen R A et al, Gene Therapy 2000; 7: 1369-1377; Zhang T et al, Cancer Gene Ther 2004; 11: 487-496; Aggen et al, Gene Ther. 2012 April; 19(4):365-74). In embodiments, the molecule comprises two TCR extracellular domains fused together. In embodiments, the TCR-based molecule comprises a TCR alpha chain fused to a TCR beta chain which is fused to a TCR constant region (e.g., the TCR beta chain constant region). In embodiments, the constant region comprises a Ser57Cys mutation.

Many TCRs specific to proteins of interest are known in the art, and selected examples are described below. It is also possible to generate a TCR specific to a desired antigen, e.g., by isolating T cells from a subject that received a cancer vaccine, through a process as described in Lanitis et al., "A Human ErbB2-Specific T-Cell Receptor Confers Potent Antitumor Effector Functions in Genetically Engineered Primary Cytotoxic Lymphocytes" HUMAN GENE THERAPY 25:730-739 (August 2014). A TCR can be designed taking into account the type of HLA receptor expressed by the cancer, as described in Lanitis et al.

In an embodiment, the TCR or TCR-based molecule recognizes ERBB2 (HER2/neu), e.g., residues 369-377 of ERBB2. An example of such a construct is described in Lanitis et al., HUMAN GENE THERAPY 25:730-739 (August 2014). The construct may comprise a TCR alpha domain and a TCR beta domain, optionally linked together, e.g., with a 2A peptide linker.

In embodiments, the TCR or TCR-based molecule recognizes MART1, tyrosinase, GP100 (also called PMEL), NYESO1, a member of the MAGE family of proteins e.g., MAGEA4, a HPV-16 protein, CEA, a HBV protein, WT1, AURKA, HA1, HA2, HMMR, RCC antigen, survivin, MDM2, or p53. See, e.g., Kershaw et al., Nature Reviews: Cancer, Vol. 13, August 2003, p. 525 doi:10.1038/nrc3565, (e.g., Box 2).

In an embodiment, the TCR is specific for SSX2, e.g., when bound to HLA-A2. The TCR-based molecule may have a geometry of, e.g., TCR alpha chain-optional linker- TCR beta chain. The linker may be, e.g., a 2A linker. See, e.g., Abate-Daga et al., PLOS ONE, March 2014, Volume 9, Issue 3, e93321.

In embodiments, the TCR-based molecule comprises an antigen-binding domain that is based on, or has homology to, a TCR, and is linked to an intracellular signaling domain as described herein, e.g., in a CAR, to form a TCR-CAR. A TCR-CAR can comprise an antigen-binding domain of a TCR, as an alternative to (or in addition to) an antibody-based antigen-binding domain. Accordingly, one embodiment, the TCR-CAR molecule comprises a TCR-based antigen binding domain, a transmembrane domain (e.g., as described herein), and an intracellular signaling domain (e.g., an intracellular signaling domain comprising a costimulatory domain and/or a primary signaling domain). The TCR-based molecule may be N-terminal or C-terminal to the hinge domain and/or transmembrane domain.

The TCR-based antigen-binding domain may comprise one or more TCR CDRs, or one or two TCR variable domains, e.g., may comprise a TCR-based molecule as described in the previous section. In embodiments, the TCR-based antigen-binding domain lacks one or more of (e.g., all of) a TCR constant region, a TCR transmembrane region, and a TCR cytoplasmic region.

Certain chimeric TCRs have been described in the art, and selected examples are summarized herein.

In some embodiments, a TCR-CAR comprises a TCR-based antigen binding domain specific for MAGE-A1. In two-chain systems, the extracellular domains of TCR alpha and beta chains may be fused in-frame to an intracellular domain, e.g., an intracellular signaling domain such as CD3-zeta or costimulatory domain, to induce the recombinant TCR chains to pair with each other rather than a patient's endogenous TCR chains. The one-chain system may comprise two TCR variable domains fused to each other, e.g., with a linker disposed therebetween. The transmembrane domain may comprise, e.g., the CD3-zeta transmembrane domain. The chimeric TCR may involve a single-chain or two-chain chimeric TCR that comprises one or more of a CD3-zeta element, a transmembrane region, a short portion of the CD3-zeta extracellular region, and a TCR-based antigen-binding domain, e.g., one that is specific for MAGE-A1 (a melanoma antigen) and HLA-A1. See, e.g., For instance, Willemsen et al. Gene Therapy (2000) 7, 1369-1377.

In embodiments, a TCR-CAR comprises stabilized Vα/Vβ single-chain TCR (scTv). This scTv can be linked, e.g., fused, to one or more intracellular domains, such as domains from Lck, CD3-zeta, and CD28. The scTv may recognize, e.g., a SIY peptide. The scTv may have a geometry of, e.g., optional leader sequence-alpha chain-linker-beta chain. A hinge and/or transmembrane region may be linked to the beta chain. See, e.g., Aggen et al., Gene Ther. 2012 April; 19(4): 365-374.

In embodiments, a TCR-CAR comprises a Vα chain and a Vβ chain, optionally joined by a linker, and may optionally also comprise a TCR constant region, e.g., a beta chain constant region. The construct may comprise a transduction domain (e.g., comprising CD8, CD3-zeta, p56$^{Lck}$ and/or CD28 domains), e.g., fused C-terminally to the TCR-based antigen-binding domain. A transmembrane domain may be disposed between the antigen binding domain and the transduction domain. See, e.g., Zhang et al., Cancer Gene Therapy (2004) 11, 487-496.

In embodiments, the TCR-CAR recognizes the antigen MUC1. It may comprise a signaling domain, e.g., of CD3-zeta, and/or a transmembrane domain, e.g., of CD3-zeta. In embodiments, the geometry of the TCR-based antigen-binding domain is: optional TCR leader-TCR variable alpha chain-optional linker-TCR variable beta chain-constant region e.g., from TCR beta chain. See, e.g., U.S. Pat. No. 7,655,461.

Agents that Inhibit a Checkpoint Inhibitor

In one embodiment, the agent that enhances the immune response of an immune effector cell can be an agent which inhibits a molecule that modulates or regulates, e.g., inhibits, immune effector cell function. In some embodiments, the molecule that modulates or regulates immune effector cell function, e.g., T cell function, is an inhibitory molecule, or also referred to herein as a checkpoint inhibitor. Inhibitory molecules (or checkpoint inhibitors), e.g., Programmed Death 1 (PD-1 or PD1), can, in some embodiments, decrease the ability of a CAR-expressing cell to mount an immune effector response. Examples of inhibitory molecules or checkpoint inhibitors include: PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of a molecule that modulates or regulates, e.g., inhibits, T cell function, e.g., by inhibition at the DNA, RNA or protein level, can optimize a CAR-expressing cell performance.

In embodiments, the agent that inhibits a checkpoint inhibitor as described herein can be a peptide, a recombinant or fusion protein, or an antibody or fragment thereof that inhibits the expression or function of a checkpoint inhibitor as described herein. For example, the agent that inhibits a checkpoint inhibitor can be an antibody molecule, e.g., an antibody or a fragment thereof, that inhibits one or more of PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, as described further herein. Examples of inhibitors of checkpoint inhibitors, e.g., antibodies or fragments thereof that inhibit checkpoint inhibitors, are also provided in the section titled "Combination Therapies", in the subsection titled "Inhibitors of Checkpoint Inhibitors".

In one embodiment, the agent that inhibits a checkpoint inhibitor is an anti-PD-1 antibody or fragment thereof as described in US 2015/0210769, entitled "Antibody Molecules to PD-1 and Uses Thereof," incorporated by reference in its entirety. In one embodiment, the agent that inhibits a checkpoint inhibitor is an antibody or fragment thereof chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769.

In one embodiment, the agent that inhibits a checkpoint inhibitor is an anti-TIM3 antibody of fragment thereof as described in US 2015/0218274, entitled "Antibody Molecules to TIM3 and Uses Thereof," incorporated by reference in its entirety. In one embodiment, the agent that inhibits a checkpoint inhibitor is an antibody or fragment thereof chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274.

In one embodiment, the agent that inhibits a checkpoint inhibitor is an anti-LAG3 antibody or fragment thereof as described in US 2015/0259420, entitled "Antibody Molecules to LAG3 and Uses Thereof," incorporated by reference in its entirety. In one embodiment, the agent that inhibits a checkpoint inhibitor is an antibody or fragment thereof chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420.

In embodiments, the agent that inhibits checkpoint inhibitor as described herein a comprises an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA. In an embodiment, the agent that modulates or regulates, e.g., inhibits, T-cell function is inhibited within a CAR-expressing cell. In these embodiments, a dsRNA molecule that inhibits expression of a molecule that modulates or regulates, e.g., inhibits, T-cell function is linked to the nucleic acid that encodes a component, e.g., all of the components, of the CAR. In an embodiment, a nucleic acid molecule that encodes a dsRNA molecule that inhibits expression of the molecule that modulates or regulates, e.g., inhibits, T-cell function is operably linked to an activation-conditional control region described herein such that the dsRNA molecule that inhibits expression of the molecule that modulates or regulates, e.g., inhibits, T-cell function is expressed, e.g., is expressed within a CAR-expressing cell upon activation. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. FIGS. 44A-44E depicts examples of vectors for expressing a component, e.g., all of the components, of the CAR with a dsRNA molecule that inhibits expression of the molecule that modulates or regulates, e.g., inhibits, T-cell function.

Examples of dsRNA molecules useful for inhibiting expression of a molecule that modulates or regulates, e.g., inhibits, T-cell function, wherein the molecule that modulates or regulates, e.g., inhibits, T-cell function is PD-1 are provided below.

Provided in Table 8 below are the names of PDCD1 (PD1) RNAi agents (derived from their position in the mouse PDCD1 gene sequence NM_008798.2), along with the SEQ ID NOs: 165-212 representing the DNA sequence. Both sense (S) and antisense (AS) sequences are presented as 19mer and 21mer sequences are in this table. Also note that the position (PoS, e.g., 176) is derived from the position number in the mouse PDCD1 gene sequence NM_008798.2. SEQ ID NOs are indicated in groups of 12 that correspond with "sense 19" SEQ ID NOs: 165-176; "sense 21" SEQ ID NOs: 177-188; "asense 21" SEQ ID NOs: 189-200; "asense 19" SEQ ID NOs: 201-212.

TABLE 8

| Mouse PDCD1 (PD1) shRNA sequences | | | | | |
| --- | --- | --- | --- | --- | --- |
| Position on NM_008798.2 | Target region | Sense19 | Sense21 | Asense21 | Asense19 |
| 176 | CDS | GGAGGTCCCTCACCTTCTA (SEQ ID NO: 165) | CTGGAGGTCCCTCACCTTCTA (SEQ ID NO: 177) | TAGAAGGTGAGGACCTCCAG (SEQ ID NO: 189) | TAGAAGGTGAGGACCTCC (SEQ ID NO: 201) |

TABLE 8-continued

Mouse PDCD1 (PD1) shRNA sequences

| Position on NM_008798.2 | Target region | Sense19 | Sense21 | Asense21 | Asense19 |
|---|---|---|---|---|---|
| 260 | CDS | CGGAGGATCTTATGCTGAA (SEQ ID NO: 166) | GTCGGAGGATCTTATGCTGAA (SEQ ID NO: 178) | TTCAGCATAAGATCCTCCGAC (SEQ ID NO: 190) | TTCAGCATAAGATCCTCCG (SEQ ID NO: 202) |
| 359 | CDS | CCCGCTTCCAGATCATACA (SEQ ID NO: 167) | TGCCCGCTTCCAGATCATACA (SEQ ID NO: 179) | TGTATGATCTGGAAGCGGGCA (SEQ ID NO: 191) | TGTATGATCTGGAAGCGGG (SEQ ID NO: 203) |
| 528 | CDS | GGAGACCTCAACAAGATAT (SEQ ID NO: 168) | CTGGAGACCTCAACAAGATAT (SEQ ID NO: 180) | ATATCTTGTTGAGGTCTCCAG (SEQ ID NO: 192) | ATATCTTGTTGAGGTCTCC (SEQ ID NO: 204) |
| 581 | CDS | AAGGCATGGTCATTGGTAT (SEQ ID NO: 169) | TCAAGGCATGGTCATTGGTAT (SEQ ID NO: 181) | ATACCAATGACCATGCCTTGA (SEQ ID NO: 193) | ATACCAATGACCATGCCTT (SEQ ID NO: 205) |
| 584 | CDS | GCATGGTCATTGGTATCAT (SEQ ID NO: 170) | AGGCATGGTCATTGGTATCAT (SEQ ID NO: 182) | ATGATACCAATGACCATGCCT (SEQ ID NO: 194) | ATGATACCAATGACCATGC (SEQ ID NO: 206) |
| 588 | CDS | GGTCATTGGTATCATGAGT (SEQ ID NO: 171) | ATGGTCATTGGTATCATGAGT (SEQ ID NO: 183) | ATGGTCATTGGTATCATGAGT (SEQ ID NO: 195) | ATGGTCATTGGTATCATGA (SEQ ID NO: 207) |
| 609 | CDS | CCTAGTGGGTATCCCTGTA (SEQ ID NO: 172) | GCCCTAGTGGGTATCCCTGTA (SEQ ID NO: 184) | GCCCTAGTGGGTATCCCTGTA (SEQ ID NO: 196) | GCCCTAGTGGGTATCCCTG (SEQ ID NO: 208) |
| 919 | CDS | GAGGATGGACATTGTTCTT (SEQ ID NO: 173) | ATGAGGATGGACATTGTTCTT (SEQ ID NO: 185) | ATGAGGATGGACATTGTTCTT (SEQ ID NO: 197) | ATGAGGATGGACATTGTTC (SEQ ID NO: 209) |
| 1021 | 3'UTR | GCATGCAGGCTACAGTTCA (SEQ ID NO: 174) | GAGCATGCAGGCTACAGTTCA (SEQ ID NO: 186) | GAGCATGCAGGCTACAGTTCA (SEQ ID NO: 198) | GAGCATGCAGGCTACAGTT (SEQ ID NO: 210) |
| 1097 | 3'UTR | CCAGCACATGCACTGTTGA (SEQ ID NO: 175) | TTCCAGCACATGCACTGTTGA (SEQ ID NO: 187) | TTCCAGCACATGCACTGTTGA (SEQ ID NO: 199) | TTCCAGCACATGCACTGTT (SEQ ID NO: 211) |
| 1101 | 3'UTR | CACATGCACTGTTGAGTGA (SEQ ID NO: 176) | AGCACATGCACTGTTGAGTGA (SEQ ID NO: 188) | AGCACATGCACTGTTGAGTGA (SEQ ID NO: 200) | AGCACATGCACTGTTGAGT (SEQ ID NO: 212) |

Provided in Table 9 below are the names of PDCD1 (PD1) RNAi agents (derived from their position in the human PDCD1 gene sequence, along with the SEQ ID NOs. 213-260 representing the DNA sequence. Both sense (S) and antisense (AS) sequences are presented as 19mer and 21mer sequences. SEQ ID NOs are indicated in groups of 12 that correspond with "sense 19" SEQ ID NOs: 213-223, 257; "sense 21" SEQ ID NOs: 224-234, 258; "asense 21" SEQ ID NOs: 235-245, 259; "asense 19" SEQ ID NOs: 246-256, 260.

TABLE 9

Human PDCD1 (PD1) shRNA sequences

| Position on NM_005018.2 | Target region | Sense19 | Asense19 | Sense21 | Asense21 |
|---|---|---|---|---|---|
| 145 | CDS | GGCCAGGATGGTTCTTAGA (SEQ ID NO: 213) | TCTAAGAACCATCCTGGCC (SEQ ID NO: 224) | GCGGCCAGGATGGTTCTTAGA (SEQ ID NO: 235) | TCTAAGAACCATCCTGGCCGC (SEQ ID NO: 246) |
| 271 | CDS | GCTTCGTGCTAAACTGGTA (SEQ ID NO: 214) | TACCAGTTTAGCACGAAGC (SEQ ID NO: 225) | GAGCTTCGTGCTAAACTGGTA (SEQ ID NO: 236) | TACCAGTTTAGCACGAAGCTC (SEQ ID NO: 247) |
| 393 | CDS | GGGCGTGACTTCCACATGA (SEQ ID NO: 215) | TCATGTGGAAGTCACGCCC (SEQ ID NO: 226) | ACGGGCGTGACTTCCACATGA (SEQ ID NO: 237) | TCATGTGGAAGTCACGCCCGT (SEQ ID NO: 248) |

TABLE 9-continued

Human PDCD1 (PD1) shRNA sequences

| Position on NM_005018.2 | Target region | Sense19 | Asense19 | Sense21 | Asense21 |
|---|---|---|---|---|---|
| 1497 | 3'UTR | CAGGCCTAGAG AAGTTTCA (SEQ ID NO: 216) | TGAAACTTCTC TAGGCCTG (SEQ ID NO: 227) | TGCAGGCCTAG AGAAGTTTCA (SEQ ID NO: 238) | TGAAACTTCTC TAGGCCTGCA (SEQ ID NO: 249) |
| 1863 | 3'UTR | CTTGGAACCCA TTCCTGAA (SEQ ID NO: 217) | TTCAGGAATGG GTTCCAAG (SEQ ID NO: 228) | TCCTTGGAACC CATTCCTGAA (SEQ ID NO: 239) | TTCAGGAATGG GTTCCAAGGA (SEQ ID NO: 250) |
| 1866 | 3'UTR | GGAACCCATTC CTGAAATT (SEQ ID NO: 218) | AATTTCAGGAA TGGGTTCC (SEQ ID NO: 229) | TTGGAACCCAT TCCTGAAATT (SEQ ID NO: 240) | AATTTCAGGAA TGGGTTCCAA (SEQ ID NO: 251) |
| 1867 | 3'UTR | GAACCCATTCC TGAAATTA (SEQ ID NO: 219) | TAATTTCAGGA ATGGGTTC (SEQ ID NO: 230) | TGGAACCCATT CCTGAAATTA (SEQ ID NO: 241) | TAATTTCAGGA ATGGGTTCCA (SEQ ID NO: 252) |
| 1868 | 3'UTR | AACCCATTCCT GAAATTAT (SEQ ID NO: 220) | ATAATTTCAGG AATGGGTT (SEQ ID NO: 231) | GGAACCCATTC CTGAAATTAT (SEQ ID NO: 242) | ATAATTTCAGG AATGGGTTCC (SEQ ID NO: 253) |
| 1869 | 3'UTR | ACCCATTCCTG AAATTATT (SEQ ID NO: 221) | AATAATTTCAG GAATGGGT (SEQ ID NO: 232) | GAACCCATTCC TGAAATTATT (SEQ ID NO: 243) | AATAATTTCAG GAATGGGTTC (SEQ ID NO: 254) |
| 1870 | 3'UTR | CCCATTCCTGA AATTATTT (SEQ ID NO: 222) | AAATAATTTCA GGAATGGG (SEQ ID NO: 233) | AACCCATTCCT GAAATTATTT (SEQ ID NO: 244) | AAATAATTTCA GGAATGGGTT (SEQ ID NO: 255) |
| 2079 | 3'UTR | CTGTGGTTCTA TTATATTA (SEQ ID NO: 223) | TAATATAATAGA ACCACAG (SEQ ID NO: 234) | CCCTGTGGTTC TATTATATTA (SEQ ID NO: 245) | TAATATAATAGA ACCACAGGG (SEQ ID NO: 256) |
| 2109 | 3'UTR | AAATATGAGAG CATGCTAA (SEQ ID NO: 257) | TTAGCATGCTC TCATATTT (SEQ ID NO: 258) | TTAAATATGAG AGCATGCTAA (SEQ ID NO: 259) | TTAGCATGCTC TCATATTTAA (SEQ ID NO: 260) |

Agents that Activate the Expression and/or Secretion of a Component that Enhances Immune Response In embodiments, the agent that enhances immune response is an agent that activates, e.g., increases or induces, the expression and/or secretion of a component that enhances immune response. For example, the agent can be a component that increases or induces the expression and/or secretion of a cytokine.

In another embodiment, the agent that enhances the immune response is a cytokine. Cytokines that enhance, e.g., increase, the differentiation, proliferation, survival, and/or cytotoxic activity of an immune effector cell are known in the art. In one embodiment, the cytokine is IL-2, IL-7, IL-15, or IL-21.

Control Regions Induced by Immune Effector Cell Activation

The activation-conditional control regions described herein are operatively linked to control the expression, e.g., transcription, of an agent that enhances the immune response of the cells described herein. The activation-conditional control regions can be constructed such that expression, e.g., transcription, of the immune response enhancer agent described herein only occurs once the cell has been activated, e.g., by binding of the non-conditional CAR to its target antigen, e.g., a cancer associated antigen described herein. In an embodiment, the activation-conditional control region comprises an inducible promoter sequence, wherein the promoter can initiate expression of the immune response enhancer only upon activation of the immune effector cell. In another embodiment, the activation-conditional control region further comprises a regulatory sequence, e.g., an enhancer sequence or a transcription factor binding site, that facilitates or initiates expression at the promoter or initiates the expression of the immune response enhancer upon activation of the immune effector cell.

In embodiments, the activation-conditional control region that is induced upon immune effector cell activation comprises one or more, e.g., 1, 2, 3, 4, 5, 6, or more, NFAT binding sites. In embodiments, the NFAT-binding sequence in the promoter comprises (5'-GGAAA-3'), optionally situated in a longer consensus sequence of 5' (A/T)GGAAA(A/N)(A/T/C)N 3' (SEQ ID NO: 261). In embodiments, the NFAT-binding sequence is a κb-like sequence such as GGGACT. (See, Gibson et al., The Journal of Immunology, 2007, 179: 3831-3840.) In one embodiment, the activation-conditional control region comprises the sequence of AGCTTGGATCCAAGAGGAAAATTTGTTTCATA-CAGAAGGCGTTAAGAGGAAAATT TGTTTCATA-CAGAAGGCGTTAAGAGGAAAATTTGTTTCATA-CAGAAGGCGTTCAAG CTTGTCGAC (SEQ ID NO: 262).

NFAT-responsive elements may be located in the promoter region, but can also be located distal to it, e.g., 5' of the proximal promoter, within intronic regions, or 3' of the gene. (See, Hogan et al., Genes & Dev. 2003. 17: 2205-2232.)

Numerous NFAT-controlled promoters are known in the art. For instance, the CD40 ligand (CD40L) promoter contains NFAT binding motifs and drives expression in activated T cells. (See, Tsytsykova et al., J. Biol. Chem. 2011

286: 44126-44133.) The CD3γ promoter contains three NFAT binding motifs. (See, Badran et al., Dec. 6, 2002 The Journal of Biological Chemistry, 277, 47136-47148.) A promoter comprising a minimal IL-2 promoter and 3 or 6 NFAT binding sites is capable of driving activation-induced expression of a reporter gene in human T cells. (See, Hooijberg E, Bakker A Q, Ruizendaal J J, Spits H. NFAT-controlled expression of GFP permits visualization and isolation of antigen-stimulated primary human T cells. Blood. 2000; 96:459-466.) An NFAT-responsive composite promoter containing binding motifs for NFAT drives IL-12 expression upon the recognition of tumor-specific antigen mediated by a T cell receptor (TCR) that was engineered into the same lymphocytes, as described in Zhang L, Kerkar S P, Yu Z, Zheng Z, Yang S, Restifo N P, Rosenberg S A, Morgan R A. Improving adoptive T cell therapy by targeting and controlling IL-12 expression to the tumor environment. Mol Ther. 2011; 19:751-759. In embodiments, the NFAT-responsive promoter is the promoter of a cytokine or cytokine receptor, e.g., including IL-2, IL-2 receptor (IL-2R), IL-3, GM-CSF, IL-4, IL-10, and IFN-γ. In embodiments the NFAT-responsive promoter is the promoter of a calcineurin-regulated gene. (See, Hogan et al., Genes & Dev. 2003. 17: 2205-2232.)

In other embodiments, the activation-conditional control region comprises other promoters or regulatory elements responsive to transcription factors whose expression is activated, e.g., induced, upon activation of an immune effector cell. For example, other transcription factors induced upon activation of an immune effector cell, in addition to the NFAT family, include, but are not limited to ATF2 (activating transcription factor 2), NF-κB (nuclear factor-κB), IL-2, and IL-2 receptor (IL-2R). In an embodiment, the activation-conditional control region that is induced upon immune effector cell activation comprises one or more, e.g., 1, 2, 3, 4, 5, 6, or more, ATF2 binding sites, and/or an ATF2 promoter. In an embodiment, the activation-conditional control region that is induced upon immune effector cell activation comprises one or more, e.g., 1, 2, 3, 4, 5, 6, or more, NF-κB binding sites and/or an NF-kB promoter. In an embodiment, the activation-conditional control region that is induced upon immune effector cell activation comprises a combination of one or more, e.g., 1, 2, 3, 4, 5, 6, or more, NFAT, ATF2, and/or NF-κB binding sites. In an embodiment, the activation-conditional control region that is induced upon immune effector cell activation comprises a NFAT, ATF2, and/or NF-κB promoter sequence. In one embodiment, the activation conditional control region comprises an IL-2 promoter or an IL-2R promoter.

More broadly, in embodiments, the promoter comprises a sequence from a promoter of a gene that is activated or upregulated during immune effector cell activation, e.g., T cell activation, or signaling, e.g., CD3 signaling. In the art, a variety of genes are known to be upregulated during T cell activation. Exemplary genes in this category are listed, for example, in Mao et al., Genomics. 2004 June; 83(6):989-99; Teague et al. PNAS Oct. 26, 1999 vol. 96 no. 22 12691-12696 (see, e.g., Table 3), which publications are incorporated by reference herein in their entirety, including the tables. In embodiments, the gene that is upregulated during T-cell activation is a regulator of T-cell activation, e.g., CD2, CD276, CD47, DPP4, CD3D, CD3E, CD3G, CD4, CD7, CD80, CD86, CD8A, CD8B, FOXP3, ICOSLG, IRF4, LAG3, LCK, MAP3K7 (TAK1), MICB, NCK1, TNFSF14, or VAV1. In embodiments, the gene that is upregulated during T-cell activation is a gene involved in T-cell proliferation, e.g., CD28, CD3E, ICOSLG, IL1B, IL10, IL12B, IL18, NCK1, RIPK2, or TNFSF14. In embodiments, the gene that is upregulated during T-cell activation is a gene involved in T-cell differentiation, e.g., ADA, APC, BCL2, BLM, CD1D, CD2, CD27 (TNFRSF7), CD4, CD80, CD86, EGR1, IL12B, IL15, IL2, IRF4, NOS2 (iNOS), PTPRC, or SOCS1. In embodiments, the gene that is upregulated during T-cell activation is a gene involved in T-cell polarization, e.g., CCL3, CCR1, CCR2, CCR3, CCR4, CCR5, CD274, CD28, CD4, CD40LG (TNFSF5), CSF2 (GM-CSF), CXCR3, CXCR4, IFNG, IL12A, IL12RB1, IL12RB2, IL18R1, IL2, IL4, IL4R, IL5, or TGFB1. In embodiments, the gene that is upregulated during T-cell activation is regulators of Th1 or Th2 Development, e.g., CD2, CD40 (TNFRSF5), CD5, CD7, CSF2 (GM-CSF), IFNG, IL10, IL12A, IL13, IL3, IL4, IL5, TLR2, TLR4, or TLR9. In embodiments, the gene that is upregulated during T-cell activation is a gene involved in Th1 or Th2 Differentiation, e.g., CD28, CD40 (TNFRSF5), CD40LG (TNFSF5), CD86, IFNG, IL12A, IL12B, IL12RB1, IL12RB2, IL18, IL18R1, IL2, IL2RA, IL4, IL4R, or IL6.

In embodiments, the gene that is upregulated during immune effector cell activation is a gene involved in natural killer cell activation, e.g., CD2, IL12A, IL12B, or IL2.

In any of the embodiments described herein, the promoter sequence can be modified or altered to decrease the size, e.g., in nucleotides, while retaining promoter activity, increase or decrease transcriptional activity, or responsiveness to immune effector cell activation signals. For example, the promoter is an IL-2 promoter that has been modified to generate a minimal IL-2 promoter (comprising positions −60 to −6, as described in Fiering et al., Genes Dev. 1990, 4:1823).

In an embodiment, the control region comprises one or more, e.g., 1, 2, 3, 4, 5, 6, or more, NFAT binding sites, e.g., 3 or 6 NFAT binding sites, and a minimal IL-2 promoter.

Cancer Associated Antigens

The present invention provides immune effector cells (e.g., T cells, NK cells) that are engineered to contain one or more CARs that direct the immune effector cells to a cancer cell. This is achieved through an antigen binding domain on the CAR that is specific for, e.g., binds to, a cancer associated antigen. In one embodiment, the non-conditional CAR comprises an antigen binding domain that binds to a cancer-associated antigen described herein. In another embodiment, the conditional CAR comprises an antigen binding domain that binds to a cancer associated antigen described herein.

There are two classes of cancer associated antigens (tumor antigens) that can be targeted by the CARs of the instant invention: (1) cancer associated antigens that are expressed on the surface of cancer cells; and (2) cancer associated antigens that are localized intracellularly, however, a fragment of such antigen (e.g., a peptide) is presented on the surface of the cancer cells, e.g., by MHC (major histocompatibility complex).

Accordingly, the present invention provides CARs that target the following cancer associated antigens (tumor antigens): CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6,E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In one embodiment, the cancer associated antigen recognized by the antigen binding domain of the nonconditional CAR and/or the conditional CAR is associated with a solid tumor.

In one embodiment, the cancer associated antigen recognized by the antigen binding domain of the nonconditional CAR and/or the conditional CAR is primarily expressed on cancer cells, e.g., the cancer associated antigen is not expressed, or is not substantially expressed, on normal cells.

Chimeric Antigen Receptor

The present invention encompasses CAR molecules, wherein the CAR comprises an antigen binding domain (e.g., antibody or antibody fragment, TCR or TCR fragment) that binds specifically to a cancer associated antigen described herein, wherein the sequence of the antigen binding domain is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule. In one embodiment, a CAR molecule is constitutively expressed (also referred to herein as the nonconditional CAR). In another embodiment, a CAR molecule is expressed in a conditional manner (the conditional CAR), e.g., the CAR molecule is expressed upon activation of the immune effector cell in which the CAR is disposed. In such embodiments, the nonconditional CAR and the conditional CAR comprises components and properties as further discussed herein.

Sequences of examples of various components of CARs of the instant invention is listed in Table 1, where aa stands for amino acids, and na stands for nucleic acids that encode the corresponding peptide.

TABLE 1

Sequences of various components of CAR
(aa - amino acids, na - nucleic acid that encodes the corresponding protein)

| SEQ ID NO | Description | Sequence |
| --- | --- | --- |
| 1 | EF-1 promoter (na) | CGTGAGGCTCCGGTGCCCGTCAGTGGGCAGAGCGCACATCGCCC ACAGTCCCCGAGAAGTTGGGGGGAGGGGTCGGCAATTGAACCG GTGCCTAGAGAAGGTGGCGCGGGGTAAACTGGGAAAGTGATGT CGTGTACTGGCTCCGCCTTTTTCCCGAGGGTGGGGGAGAACCGT ATATAAGTGCAGTAGTCGCCGTGAACGTTCTTTTTCGCAACGGGT TTGCCGCCAGAACACAGGTAAGTGCCGTGTGTGGTTCCCGCGGG CCTGGCCTCTTTACGGGTTATGGCCCTTGCGTGCCTTGAATTACT TCCACCTGGCTGCAGTACGTGATTCTTGATCCCGAGCTTCGGGTT GGAAGTGGGTGGGAGAGTTCGAGGCCTTGCGCTTAAGGAGCCCC TTCGCCTCGTGCTTGAGTTGAGGCCTGGCCTGGGCGCTGGGGCC GCCGCGTGCGAATCTGGTGGCACCTTCGCGCCTGTCTCGCTGCTT TCGATAAGTCTCTAGCCATTTAAAATTTTTGATGACCTGCTGCGA CGCTTTTTTTCTGGCAAGATAGTCTTGTAAATGCGGGCCAAGATC TGCACACTGGTATTTCGGTTTTTGGGGCCGCGGGCGGCGACGGG GCCCGTGCGTCCCAGCGCACATGTTCGGCGAGGCGGGGCCTGCG AGCGCGGCCACCGAGAATCGGACGGGGGTAGTCTCAAGCTGGCC GGCCTGCTCTGGTGCCTGGCCTCGCGCCGCCGTGTATCGCCCCGC CCTGGGCGGCAAGGCTGGCCCGGTCGGCACCAGTTGCGTGAGCG GAAAGATGGCCGCTTCCCGGCCCTGCTGCAGGGAGCTCAAAATG GAGGACGCGGCGCTCGGGAGAGCGGGCGGGTGAGTCACCCACA CAAAGGAAAAGGGCCTTTCCGTCCTCAGCCGTCGCTTCATGTGA CTCCACGGAGTACCGGGCGCCGTCCAGGCACCTCGATTAGTTCT CGAGCTTTTGGAGTACGTCGTCTTTAGGTTGGGGGGAGGGGTTTT ATGCGATGGAGTTTCCCCACACTGAGTGGGTGGAGACTGAAGTT AGGCCAGCTTGGCACTTGATGTAATTCTCCTTGGAATTTGCCCTT TTTGAGTTTGGATCTTGGTTCATTCTCAAGCCTCAGACAGTGGTT CAAAGTTTTTTTCTTCCATTTCAGGTGTCGTGA |
| 2 | Leader (aa) | MALPVTALLLPLALLLHAARP |
| 3 | Leader (na) | ATGGCCCTGCCTGTGACAGCCCTGCTGCTGCCTCTGGCTCTGCTG CTGCATGCCGCTAGACCC |
| 4 | CD 8 hinge (aa) | TTTPAPRPPTPAPTIASQPLSLRPEACRPAAGGAVHTRGLDFACD |
| 5 | CD8 hinge (na) | ACCACGACGCCAGCGCCGCGACCACCAACACCGGCGCCCACCAT CGCGTCGCAGCCCCTGTCCCTGCGCCCAGAGGCGTGCCGGCCAG CGGCGGGGGGCGCAGTGCACACGAGGGGGCTGGACTTCGCCTGT GAT |

TABLE 1-continued

Sequences of various components of CAR
(aa - amino acids, na - nucleic acid that
encodes the corresponding protein)

| SEQ ID NO | Description | Sequence |
|---|---|---|
| 6 | Ig4 hinge (aa) | ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKM |
| 7 | Ig4 hinge (na) | GAGAGCAAGTACGGCCCTCCCTGCCCCCCTTGCCCTGCCCCCGAGTTCCTGGGCGGACCCAGCGTGTTCCTGTTCCCCCCCAAGCCCAAGGACACCCTGATGATCAGCCGGACCCCCGAGGTGACCTGTGTGGTGGTGGACGTGTCCCAGGAGGACCCCGAGGTCCAGTTCAACTGGTACGTGGACGGCGTGGAGGTGCACAACGCCAAGACCAAGCCCCGGGAGGAGCAGTTCAATAGCACCTACCGGGTGGTGTCCGTGCTGACCGTGCTGCACCAGGACTGGCTGAACGGCAAGGAATACAAGTGTAAGGTGTCCAACAAGGGCCTGCCCAGCAGCATCGAGAAAACCATCAGCAAGGCCAAGGGCCAGCCTCGGGAGCCCCAGGTGTACACCCTGCCCCCTAGCCAAGAGGAGATGACCAAGAACCAGGTGTCCCTGACCTGCCTGGTGAAGGGCTTCTACCCCAGCGACATCGCCGTGGAGTGGGAGAGCAACGGCCAGCCCGAGAACAACTACAAGACCACCCCCCCTGTGCTGGACAGCGACGGCAGCTTCTTCCTGTACAGCCGGCTGACCGTGGACAAGAGCCGGTGGCAGGAGGGCAACGTCTTTAGCTGCTCCGTGATGCACGAGGCCCTGCACAACCACTACACCCAGAAGAGCCTGAGCCTGTCCCTGGGCAAGATG |
| 8 | IgD hinge (aa) | RWPESPKAQASSVPTAQPQAEGSLAKATTAPATTRNTGRGGEEKKKEKEKEEQEERETKTPECPSHTQPLGVYLLTPAVQDLWLRDKATFTCFVVGSDLKDAHLTWEVAGKVPTGGVEEGLLERHSNGSQSQHSRLTLPRSLWNAGTSVTCTLNHPSLPPQRLMALREPAAQAPVKLSLNLLASSDPPEAASWLLCEVSGFSPPNILLMWLEDQREVNTSGFAPARPPPQPGSTTFWAWSVLRVPAPPSPQPATYTCVVSHEDSRTLLNASRSLEVSYVTDH |
| 9 | IgD hinge (na) | AGGTGGCCCGAAAGTCCCAAGGCCCAGGCATCTAGTGTTCCTACTGCACAGCCCCAGGCAGAAGGCAGCCTAGCCAAAGCTACTACTGCACCTGCCACTACGCGCAATACTGGCCGTGGCGGGGAGGAGAAGAAAAAGGAGAAAGAGAAAGAAGAACAGGAAGAGAGGGAGACCAAGACCCCTGAATGTCCATCCCATACCCAGCCGCTGGGCGTCTATCTCTTGACTCCCGCAGTACAGGACTTGTGGCTTAGAGATAAGGCCACCTTTACATGTTTCGTCGTGGGCTCTGACCTGAAGGATGCCCATTTGACTTGGGAGGTTGCCGGAAAGGTACCCACAGGGGGGGTTGAGGAAGGGTTGCTGGAGCGCATTCCAATGGCTCTCAGAGCCAGCACTCAAGACTCACCCTTCCGAGATCCCTGTGGAACGCCGGACCTCTGTCACATGTACTCTAAATCATCCTAGCCTGCCCCCACAGCGTCTGATGGCCCTTAGAGAGCCAGCCGCCCAGGCACCAGTTAAGCTTAGCCTGAATCTGCTCGCCAGTAGTGATCCCCCAGAGGCCGCCAGCTGGCTCTTATGCGAAGTGTCCGGCTTTAGCCCGCCCAACATCTTGCTCATGTGGCTGGAGGACCAGCGAGAAGTGAACACCAGCGGCTTCGCTCCAGCCCGGCCCCCACCCCAGCCGGGTTCTACCACATTCTGGGCCTGGAGTGTCTTAAGGGTCCCAGCACCACCTAGCCCCCAGCCAGCCACATACACCTGTGTTGTGTCCCATGAAGATAGCAGGACCCTGCTAAATGCTTCTAGGAGTCTGGAGGTTTCCTACGTGACTGACCATT |
| 10 | GS hinge/linker (aa) | GGGGSGGGGS |
| 11 | GS hinge/linker (na) | GGTGGCGGAGGTTCTGGAGGTGGAGGTTCC |
| 12 | CD8TM (aa) | IYIWAPLAGTCGVLLLSLVITLYC |
| 13 | CD8 TM (na) | ATCTACATCTGGGCGCCCTTGGCCGGGACTTGTGGGGTCCTTCTCCTGTCACTGGTTATCACCCTTTACTGC |
| 14 | 4-1BB intracellular domain (aa) | KRGRKKLLYIFKQPFMRPVQTTQEEDGCSCRFPEEEEGGCEL |

TABLE 1-continued

Sequences of various components of CAR
(aa - amino acids, na - nucleic acid that
encodes the corresponding protein)

| SEQ ID NO | Description | Sequence |
|---|---|---|
| 15 | 4-1BB intracellular domain (na) | AAACGGGGCAGAAAGAAACTCCTGTATATATTCAAACAACCATT TATGAGACCAGTACAAACTACTCAAGAGGAAGATGGCTGTAGCT GCCGATTTCCAGAAGAAGAAGAAGGAGGATGTGAACTG |
| 16 | CD27 (aa) | QRRKYRSNKGESPVEPAEPCRYSCPREEEGSTIPIQEDYRKPEPACSP |
| 17 | CD27 (na) | AGGAGTAAGAGGAGCAGGCTCCTGCACAGTGACTACATGAACAT GACTCCCCGCCGCCCCGGGCCCACCCGCAAGCATTACCAGCCCT ATGCCCCACCACGCGACTTCGCAGCCTATCGCTCC |
| 18 | CD3-zeta (aa) | RVKFSRSADAPAYKQGQNQLYNELNLGRREEYDVLDKRRGRDPE MGGKPRRKNPQEGLYNELQKDKMAEAYSEIGMKGERRRGKGHDG LYQGLSTATKDTYDALHMQALPPR |
| 19 | CD3-zeta (na) | AGAGTGAAGTTCAGCAGGAGCGCAGACGCCCCCGCGTACAAGC AGGGCCAGAACCAGCTCTATAACGAGCTCAATCTAGGACGAAGA GAGGAGTACGATGTTTTGGACAAGAGACGTGGCCGGGACCCTGA GATGGGGGGAAAGCCGAGAAGGAAGAACCCTCAGGAAGGCCTG TACAATGAACTGCAGAAAGATAAGATGGCGGAGGCCTACAGTG AGATTGGGATGAAAGGCGAGCGCCGGAGGGGCAAGGGGCACGA TGGCCTTTACCAGGGTCTCAGTACAGCCACCAAGGACACCTACG ACGCCCTTCACATGCAGGCCCTGCCCCCTCGC |
| 20 | CD3-zeta (aa) | RVKFSRSADAPAYQQGQNQLYNELNLGRREEYDVLDKRRGRDPE MGGKPRRKNPQEGLYNELQKDKMAEAYSEIGMKGERRRGKGHDG LYQGLSTATKDTYDALHMQALPPR |
| 21 | CD3-zeta (na) | AGAGTGAAGTTCAGCAGGAGCGCAGACGCCCCCGCGTACCAGC AGGGCCAGAACCAGCTCTATAACGAGCTCAATCTAGGACGAAG AGAGGAGTACGATGTTTTGGACAAGAGACGTGGCCGGGACCCT GAGATGGGGGGAAAGCCGAGAAGGAAGAACCCTCAGGAAGGCC TGTACAATGAACTGCAGAAAGATAAGATGGCGGAGGCCTACAG TGAGATTGGGATGAAAGGCGAGCGCCGGAGGGGCAAGGGCAC GATGGCCTTTACCAGGGTCTCAGTACAGCCACCAAGGACACCT ACGACGCCCTTCACATGCAGGCCCTGCCCCCTCGC |
| 22 | linker | GGGGS |
| 23 | linker | GGTGGCGGAGGTTCTGGAGGTGGAGGTTCC |
| 24 | PD-1 extracellular domain (aa) | Pgwfldspdrpwnpptfspallvvtegdnatftcsfsntsesfy lnwyrmspsnqtdklaafpedrsqpgqdcrfrvtqlpngrdfhm svvrarrndsgtylcgaislapkaqikeslraelryterraevp tahpspsprpaggfqtlv |
| 25 | PD-1 extracellular domain (na) | Cccgggatggtttctggactctccggatcgcccgtggaatccccc aaccttctcaccggcactcttggttgtgactgagggcgataatg cgaccttcacgtgctcgttctccaacacctccgaatcattcgtg ctgaactggtaccgcatgagcccgtcaaaccagaccgacaagct cgccgcgtttccggaagatcggtcgcaacccgggacaggattgtc ggttccgcgtgactcaactgccgaatggcagagacttccacatg agcgtggtccgcgctaggcgaaacgactccgggacctacctgtg cggagccatctcgctggcgcctaaggcccaaatcaaagagagct tgagggccgaactgagagtgaccgagcgcagagctgaggtgcca actgcacatccatcccatcgcctcggcctgcggggcagtttca gaccctggtc |
| 26 | PD-1 CAR (aa) with signal | Malpvtalllplalllhaarppgwfldspdrpwnpptfspallv vtegdnatftcsfsntsesfylnwyrmspsnqtdklaafpedrs qpgqdcrfrvtqlpngrdfhmsvvrarrndsgtylcgaislapk aqikeslraelryterraevptahpspsprpaggfqtivtapap rpptpaptiasqplslrpeacrpaaggavhtrgldfacdiyiwa plagtcgvlllslvitlyckrgrkkllyiflcqpfmrpvqttqe edgcscrfpeeeeggcelrvkfsrsadapaykqgqnqlynelnl grreeydvldkagrdpemggkprrknpqeglynelqkdkmaeay seigmkgerrrgkghdglyqglstatkdtydalhmqalppr |
| 27 | PD-1 CAR (na) | Atggccctccctgtcactgccctgcttctcccccctcgcactcct gctccacgcgctagaccacccggatggtttctggactctccgg atcgcccgtggaatccccaaccttctcaccggcactcttggtt gtgactgagggcgataatgcgaccttcacgtgctcgttctccaa |

TABLE 1-continued

Sequences of various components of CAR
(aa - amino acids, na - nucleic acid that encodes the corresponding protein)

| SEQ ID NO | Description | Sequence |
|---|---|---|
| | | cacctccgaatcattcgtgctgaactggtaccgcatgagcccgt caaaccagaccgacaagctcgccgcgtttccggaagatcggtcg caaccgggacaggattgtcggttccgcgtgactcaactgccgaa tggcagagacttccacatgagcgtggtccgcgctaggcgaaacg actccgggacctacctgtgcggagccatctcgctggcgcctaag gcccaaatcaaagagagcttgagggccgaactgagagtgaccga gcgcagagctgaggtgccaactgcacatccatcccatcgcctc ggcctgcggggcagtttcagaccctggtcacgaccactccggcg ccgcgcccaccgactccggccccaactatcgcgagccagcccct gtcgctgaggccgaagcatgccgccctgccgccggaggtgctg tgcatacccggggattggacttcgcatgcgacatctacatttgg gctcctctcgccgaacttgtggcgtgctccttctgtccctggt catcaccctgtactgcaagcggggtcggaaaaagcttctgtaca ttttcaagcagcccttcatgaggcccgtgcaaaccacccaggag gaggacggttgctcctgccggttccccgaagaggaagaaggagg ttgcgagctgcgcgtgaagttctcccggagcgccgacgcccccg cctataagcagggccagaaccagctgtacaacgaactgaacctg ggacggcgggaagagtacgatgtgctggacaagcggcgcggccg ggaccccgaaatgggcgggaagcctagaagaaagaaccctcagg aaggcctgtataacgagctgcagaaggacaagatggccgaggcc tactccgaaattgggatgaagggagagcggcggaggggaaggg gcacgacggcctgtaccaaggactgtccaccgccaccaaggaca catacgatgccctgcacatgcaggcccttccccctcgc |
| 28 | linker | (Gly-Gly-Gly-Ser)n, where n = 1-10 |
| 29 | linker | (Gly₄Ser)₄ |
| 30 | linker | (Gly₄Ser)3 |
| 31 | linker | (Gly₃Ser) |
| 32 | polyA (2000 A's) | [a]₂₀₀₀ |
| 33 | polyA (150 A's) | [a]₁₅₀ |
| 34 | polyA (5000 A's) | [a]₅₀₀₀ |
| 35 | polyA (100 T's) | [t]₁₀₀ |
| 36 | polyA (500 T's) | [t]₅₀₀ |
| 37 | polyA (64 A's) | [a]₆₄ |
| 38 | polyA (400 A's) | [a]₄₀₀ |
| 39 | PD1 CAR (aa) | Pqwfldspdrpwnppt fspallvvteqdnatftcsfsntsesfy lnwyrmspsnqtdklaafpedrsqpgqdcrfrvtqlpngrdfhm svvrarrndsqtylcgaislapkaqikeslraelryterraevp tahpspsprpaggfqtlvtttpaprpptpaptiasqplslrpea crpaaggavhtrgldfacdiyiwaplagtcgvllslvitlyck rgrkkllyifkqpfmrpvqttqeedgcscrfpeeeeggcelrvk fsrsadapaykqgqnqlynelnlgrreeydvldlargrdpemgg kprrknpqeglynelqkdkmaeayseigmkgerrrgkghdglyq glstatkdtydalhmqalppr |
| 40 | ICOS ICD domain (aa) | T K K K Y S S S V H D P N G E Y M F M R A V N T A K K S P L T D V T L |
| 41 | ICOS ICD domain (na) | ACAAAAAAGAAGTATTCATCCAGTGTGCACGACCCTAACGGTGAATACAT GTTCATGAGAGCAGTGAACACAGCCAAAAAATCCAGACTCACAGATGTGA CCCTA |

TABLE 1-continued

Sequences of various components of CAR
(aa - amino acids, na - nucleic acid that
encodes the corresponding protein)

| SEQ ID NO | Description | Sequence |
|---|---|---|
| 42 | ICOS TM domain (aa) | T T T P A P R P P T P A P T I A S Q P L S L R P E A C R P A A G G A V H T R G L D F A C D F W L P I G C A A F V V V C I L G C I L I C W L |
| 43 | ICOS TM domain (na) | ACCACGACGCCAGCGCCGCGACCACCAACACCGGCGCCCACCATCGCGTC GCAGCCCCTGTCCCTGCGCCCAGAGGCGTGCCGGCCAGCGGCGGGGGCG CAGTGCACACGAGGGGGCTGGACTTCGCCTGTGATTTCTGGTTACCCATA GGATGTGCAGCCTTTGTTGTAGTCTGCATTTTGGGATGCATACTTATTTG TTGGCTT |
| 44 | CD28 domain (aa) | RSKRSRLLHSDYMNMTPRRPGPTRKHYQPYAPPRDFAAYRS |
| 45 | CD28 domain (na) | AGGAGTAAGAGGAGCAGGCTCCTGCACAGTGACTACATGAACATGACTCC CCGCCGCCCCGGGCCCACCCGCAAGCATTACCAGCCCTATGCCCCACCAC GCGACTTCGCAGCCTATCGCTCC |

In specific aspects, a CAR construct of the invention comprises a scFv domain, wherein the scFv may be preceded by an optional leader sequence such as provided in SEQ ID NO: 2, and followed by an optional hinge sequence such as provided in SEQ ID NO:4 or SEQ ID NO:6 or SEQ ID NO:8 or SEQ ID NO:10, a transmembrane region such as provided in SEQ ID NO:12, an intracellular signalling domain that includes SEQ ID NO:14, SEQ ID NO:16, SEQ ID NO: 40, or SEQ ID NO: 44, and a CD3 zeta sequence that includes SEQ ID NO:18 or SEQ ID NO:20, e.g., wherein the domains are contiguous with and in the same reading frame to form a single fusion protein.

In one aspect, an exemplary CAR constructs comprise an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

An exemplary leader sequence is provided as SEQ ID NO: 2. An exemplary hinge/spacer sequence is provided as SEQ ID NO: 4 or SEQ ID NO:6 or SEQ ID NO:8 or SEQ ID NO: 10. An exemplary transmembrane domain sequence is provided as SEQ ID NO: 12. An exemplary sequence of the intracellular signaling domain of the 4-1BB protein is provided as SEQ ID NO: 14. An exemplary sequence of the intracellular signaling domain of CD27 is provided as SEQ ID NO: 16. An exemplary sequence of the intracellular signaling domain of ICOS is provided as SEQ ID NO: 40. An exemplary sequence of the intracellular signaling domain of CD28 is provided as SEQ ID NO: 44. An exemplary CD3zeta domain sequence is provided as SEQ ID NO: 18 or SEQ ID NO:20.

In one aspect, the present invention encompasses a recombinant nucleic acid construct comprising a nucleic acid molecule encoding a CAR, wherein the nucleic acid molecule comprises the nucleic acid sequence encoding an antigen binding domain, e.g., described herein, that is contiguous with and in the same reading frame as a nucleic acid sequence encoding an intracellular signaling domain.

In one aspect, the present invention encompasses a recombinant nucleic acid construct comprising a nucleic acid molecule encoding a CAR, wherein the nucleic acid molecule comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, CD27, 4-1BB, ICOS, and the like. In some instances, the CAR can comprise any combination of CD3-zeta, CD27, CD28, 4-1BB, ICOS, and the like.

The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR") (e.g., a 3' and/or 5' UTR described herein), a 5' cap (e.g., a 5' cap described herein) and/or Internal Ribosome Entry Site (IRES) (e.g., an IRES described herein), the nucleic acid to be expressed, and a polyA tail, typically 50-2000 bases in length (SEQ ID NO:32). RNA so produced can efficiently transfect different kinds of cells. In one embodiment, the template includes sequences for the CAR. In an embodiment, an RNA CAR vector is transduced into a cell, e.g., a T cell or a NK cell, by electroporation.

Antigen Binding Domain

In one aspect, the CAR of the invention, e.g., the nonconditional CAR or the conditional CAR, comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the portion of the CAR comprising the antigen binding domain comprises an antigen binding domain that targets a tumor antigen, e.g., a tumor antigen described herein.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In embodiments, the nonconditional or the conditional CAR described herein comprises an antigen binding domain against a cancer associated antigen described herein, as described further below.

In one embodiment, the CAR described herein, e.g., a nonconditional CAR or a conditional CAR, includes an antigen-binding domain against mesothelin, which is an antigen binding portion, e.g., CDRs, VL and/or VH or scFv of an antibody, antigen-binding fragment or CAR described in, e.g., PCT publication WO2015/090230. In other embodiments the nonconditional CAR or the conditional CAR described herein includes an antigen-binding domain against mesothelin, which is an antigen binding portion, e.g., CDRs, VL and/or VH or scFv, of an antibody, antigen-binding fragment, or CAR described in, e.g., PCT publications WO1997/025068, WO1999/028471, WO2005/014652, WO2006/099141, WO2009/045957, WO2009/068204, WO2009/120769, WO2013/142034, WO2013/040557, or WO2013/063419, the contents of which are incorporated by reference herein in their entireties.

In an embodiment, the antigen binding domain is a murine scFv domain that binds to human mesothelin, e.g., SS1 or SEQ ID NO: 46. In an embodiment, the antigen binding domain is a humanized antibody or antibody fragment, e.g., scFv domain, derived from the murine SS1 scFv. In an embodiment, the antigen binding domain is a human antibody or antibody fragment that binds to human mesothelin. Exemplary human scFv domains (and their sequences) and the murine SS1 scFv that bind to mesothelin are provided in Table 2. CDR sequences are underlined. The scFv domain sequences provided in Table 2 include a light chain variable region (VL) and a heavy chain variable region (VH). The VL and VH are attached by a linker comprising the sequence GGGGSGGGGSGGGGS (SEQ ID NO: 30) (e.g., as shown in SS1 scFv domains) or GGGGSGGGGSGGGGSGGGGS (SEQ ID NO: 29) (e.g., as shown in M1, M2, M3, M4, M5, M6, M7, M8, M9, M10, M11, M12, M13, M14, M15, M16, M17, M18, M19, M20, M21, M22, M23, or M24 scFv domains). The scFv domains listed in Table 2 are in the following orientation: VL-linker-VH.

TABLE 2

Antigen binding domains that bind to mesothelin
(aa - amino acids, na - nucleic acid
that encodes the corresponding polypeptide)

| Name | Sequence | SEQ ID NO: |
|---|---|---|
| M5 (human) (aa) | QVQLVQSGAEVEKPGASVKVSCKAS<u>GYTFTDYYMH</u>WVRQAPGQGLEWMG<u>WINPNSGGTNY AQKFQG</u>RVTMTRDTSISTAYMELSRLRSDDTAVYYCAS<u>GWDFDY</u>WGQGTLVTVSSGGGGS GGGGSGGGGSGGGGSDIVMTQSPSSLSASVGDRVTITC<u>RASQSIRYYLS</u>WYQQKPGKAPK LLIY<u>TASILQN</u>GVPSRFSGSGSGTDFTLTISSLQPEDFATYYC<u>LQTYTTPDF</u>GPGTKVEI K | 51 |
| M11 (human) (aa) | QVQLQQSGAEVKKPGASVKVSCKAS<u>GYTFTGYYMH</u>WVRQAPGQGLEWMG<u>WINPNSGGTNY AQNFQG</u>RVTMTRDTSISTAYMELRRLRSDDTAVYYCAS<u>GWDFDY</u>WGQGTLVTVSSGGGGS GGGGSGGGGSGGGGSDIRMTQSPSSLSASVGDRVTITC<u>RASQSIRYYLS</u>WYQQKPGKAPK LLIY<u>TASILQN</u>GVPSRFSGSGSGTDFTLTISSLQPEDFATYYC<u>LQTYTTPDF</u>GPGTKVEI K | 57 |
| ss1 (murine) (aa) | Q V Q L Q Q S G P E L E K P G A S V K I S C K A S G Y S F T G Y T M N W V K Q S H G K S L E W I G L I T P Y N G A S S Y N Q K F R G K A T L T V D K S S S T A Y M D L L S L T S E D S A V Y F C A R G G Y D G R G F D Y W G Q G T T V T V S S G G G S G G G G S G G G G S D I E L T Q S P A I M S A S P G E K V T M T C S A S S S V S Y M H W Y Q Q K S G T S P K R W I Y D T S K L A S G V P G R F S G S G S G N S Y S L T I S S V E A E D D A T Y Y C Q Q W S G Y P L T F G A G T K L E I | 46 |

TABLE 2-continued

Antigen binding domains that bind to mesothelin
(aa - amino acids, na - nucleic acid
that encodes the corresponding polypeptide)

| Name | Sequence | SEQ ID NO: |
|---|---|---|
| M1 (human) (aa) | QVQLQQSGAEVKKPGASVKVSCKAS<u>GYTFTGYYMH</u>WVRQAPGQGLEWMG<u>RINPNSGGTNY AQKFQG</u>RVTMTRDTSISTAYMELSRLRSEDTAVYYCAR<u>GRYYGMDV</u>WGQGTMVTVSSGGG GSGGGGSGGGGSGGGGSEIVLTQSPATLSLSPGERATISC<u>RASQSVSSNFA</u>WYQQRPGQA PRLLIY<u>DASNRAT</u>GIPPRFSGSGSGTDFTLTISSLEPEDFAAYYC<u>HQRSNWLYT</u>FGQGTK VDIK | 47 |
| M2 (human) (aa) | QVQLVQSGAEVKKPGASVKVSCKAS<u>GYTFTGYYMH</u>WVRQAPGQGLEWMG<u>WINPNSGGTNY AQKFQG</u>RVTMTRDTSISTAYMELSRLRSDDTAVYYCARD<u>LRRTVVTPRAYYGMDV</u>WGQGT TVTVSSGGGGSGGGGSGGGGSGGGGSDIQLTQSPSTLSASVGDRVTITC<u>QASQDISNSLN</u> WYQQKAGKAPKLLIY<u>DASTLET</u>GVPSRFSGSGSGTDFSFTISSLQPEDIATYYC<u>QQHDNL PLT</u>FGQGTKVEIK | 48 |
| M3 (human) (aa) | QVQLVQSGAEVKKPGAPVKVSCKAS<u>GYTFTGYYMH</u>WVRQAPGQGLEWMG<u>WINPNSGGTNY AQKFQG</u>RVTMTRDTSISTAYMELSRLRSDDTAVYYCAR<u>GEWDGSYYYDY</u>WGQGTLVTVSS GGGGSGGGGSGGGGSGGGGSDIVLTQTPSSLSASVGDRVTITC<u>RASQSINTYLN</u>WYQHKP GKAPKLLIY<u>AASSLQS</u>GVPSRFSGSGSGTDFTLTISSLQPEDFATYYC<u>QQSFSPLT</u>FGGG TKLEIK | 49 |
| M4 (human) (aa) | QVQLVESGGGLVQPGGSLRLSCAAS<u>GTFSSYWMH</u>WVRQVPGKGLVWVS<u>RINTDGSTTTY ADSVEG</u>RFTISRDNAKNTLYLQMNSLRDDDTAVYYCVG<u>GHWAV</u>WGQGTTVTVSSGGGGSG GGGSGGGGSGGGGSDIQMTQSPSTLSASVGDRVTITC<u>RASQSISDRLA</u>WYQQKPGKAPKL LIY<u>KASSLES</u>GVPSRFSGSGSGTEFTLTISSLQPDDFAVYYC<u>QQYGHLPMYT</u>FGQGTKVE IK | 50 |
| M6 (human) (aa) | QVQLVQSGAEVKKPGASVKVSCKAS<u>GYTFTSYYMH</u>WVRQAPGQGLEWMG<u>IINPSGGSTSY AQKFQG</u>RVTMTRDTSTSTVYMELSSLRSEDTAVYYCAR<u>YRLIAVAGDYYYYGMDV</u>WGQGT MVTVSSGGGGSGGGGSGGGGSGGGGSDIQMTQSPSSVASVGDRVTITC<u>RASQVGRWLA</u>W YQQKPGTAPKLLIY<u>AASTLQS</u>GVPSRFSGSGSGTDFTLTINNLQPEDFATYYC<u>QQANSFP LT</u>FGGGTRLEIK | 52 |
| M7 (human) (aa) | QVQLVQSGGGVVQPGRSLRLSCAAS<u>GTFSSYAMH</u>WVRQAPGKGLEWVA<u>VISYDGSNKYY ADSVKG</u>RFTISRDNSKNTLYLQMNSLRAEDTAVYYCAR<u>WKVSSSSPAFDY</u>WGQGTLVTVS SGGGGSGGGGSGGGGSGGGGSEIVLTQSPATLSLSPGERAILSC<u>RASQSVYTKYLG</u>WYQQ KPGQAPRLLIY<u>DASTRAT</u>GIPDRFSGSGSGTDFTLTINRLEPEDFAVYYC<u>QHYGGSPLIT</u> FGQGTRLEIK | 53 |
| M8 (human) (aa) | QVQLQQSGAEVKKPGASVKVSCKTS<u>GYPFTGYSLH</u>WVRQAPGQGLEWMG<u>WINPNSGGTNY AQKFQG</u>RVTMTRDTSISTAYMELSRLRSDDTAVYYCARD<u>HYGGNSLFY</u>WGQGTLVTVSSG GGGSGGGGSGGGGSGGGGSDIQLTQSPSSISASVGDTVSITC<u>RASQDSGTWLA</u>WYQQKPG KAPNLLMY<u>DASTLED</u>GVPSRFSGSASGTEFTLTVNRLQPEDSATYYC<u>QQYNSYPLT</u>FGGG TKVDIK | 54 |
| M9 (human) (aa) | QVQLVQSGAEVKKPGASVEVSCKAS<u>GYTFTSYYMH</u>WVRQAPGQGLEWMG<u>IINPSGGSTGY AQKFQG</u>RVTMTRDTSTSTVHMELSSLRSEDTAVYYCAR<u>GGYSSSSDAFDI</u>WGQGTMVTVS SGGGGSGGGGSGGGGSGGGGSDIQMTQSPPSLSASVGDRVTITC<u>RASQDISSALA</u>WYQQK PGTPPKLLIY<u>DASSLES</u>GVPSRFSGSGSGTDFTLTISSLQPEDFATYYC<u>QQFSSYPLT</u>FG GGTRLEIK | 55 |
| M10 (human) (aa) | QVQLVQSGAEVKKPGASVKVSCKAS<u>GYTFTSYGIS</u>WVRQAPGQGLEWMG<u>WISAYNGNTNY AQKLQG</u>RVTMTTDTSTSTAYMELRSLRSDDTAVYYCARV<u>AGGIYYYYGMDV</u>WGQGTTITV SSGGGGSGGGGSGGGGSGGGGSDIVMTQTPDSLAVSLGERATISC<u>KSSHSVLYNRNNKNY LA</u>WYQQKPGQPPKLLFY<u>WASTRKS</u>GVPDRFSGSGSGTDFTLTISSLQPEDFATYFC<u>QQTQ TFPLT</u>FGQGTRLEIN | 56 |
| M12 (human) (aa) | QVQLVQSGAEVKKPGASVKVSCKAS<u>GYTFTGYYMH</u>WVRQAPGQGLEWMG<u>RINPNSGGTNY AQKFQG</u>RVTMTTDTSTSTAYMELRSLRSDDTAVYYCAR<u>TTTSYAFDI</u>WGQGTMVTVSSGG GGSGGGGSGGGGSGGGGSDIQLTQSPSTLSASVGDRVTITC<u>RASQSISTWLA</u>WYQQKPGK APNLLIY<u>KASTLES</u>GVPSRFSGSGSGTEFTLTISSLQPDDFATYYC<u>QQYNTYSPYT</u>FGQG TKLEIK | 58 |
| M13 (human) (aa) | QVQLVQSGGGLVKPGGSLRLSCEAS<u>GFIFSDYYMG</u>WIRQAPGKGLEWVS<u>YIGRSGSSMYY ADSVKG</u>RFTFSRDNAKNSLYLQMNSLRAEDTAVYYCAAS<u>PVVAATEDFQH</u>WGQGTLVTVS SGGGGSGGGGSGGGGSGGGGSDIVMTQTPATLSLSPGERATLSC<u>RASQSVTSNYLA</u>WYQQ KPGQAPRLLLF<u>GASTRAT</u>GIPDRFSGSGSGTDFTLTINRLEPEDFAMYYC<u>QQYGSAPVT</u>F GQGTKLEIK | 59 |
| M14 (human) (aa) | QVQLVQSGAEVRAPGASVKISCKAS<u>GFTFRGYYIH</u>WVRQAPGQGLEWMG<u>IINPSGGSRAY AQKFQG</u>RVTMTRDTSTSTVYMELSSLRSEDTAMYYCAR<u>TASCGGDCYYLDY</u>WGQGTLVTV SSGGGGSGGGGSGGGGSGGGGSDIQMTQSPPTLSASVGDRVTITC<u>RASENVNIWLA</u>WYQQ KPGKAPKLLIY<u>KSSSLAS</u>GVPSRFSGSGSGAEFTLTISSLQPDDFATYYC<u>QQYQSYPLT</u>F GGGTKVDIK | 60 |

TABLE 2-continued

Antigen binding domains that bind to mesothelin
(aa - amino acids, na - nucleic acid
that encodes the corresponding polypeptide)

| Name | Sequence | SEQ ID NO: |
|---|---|---|
| M15<br>(human)<br>(aa) | QVQLVQSGGGLVQPGRSLRLSCAASGFTFDDYAMHWVRQAPGKGLEWVSGISWNSGSIGY<br>ADSVKGRFTISRDNAKNSLYLQMNSLRAEDTAVYYCAKDGSSSWSWGYFDYWGQGTLVTV<br>SSGGGGSGGGGSGGGGSSSELTQDPAVSVALGQTVRTTCQGDALRSYYASWYQQKPGQAP<br>MLVIYGKNNRPSGIPDRFSGSDSGDTASLTITGAQAEDEADYYCNSRDSSGYPVFGTGTK<br>VTVL | 61 |
| M16<br>(human)<br>(aa) | EVQLVESGGGLVQPGRSLRLSCAASGFTFDDYAMHWVRQAPGKGLEWVSGISWNSGSTGY<br>ADSVKGRFTISRDNAKNSLYLQMNSLRAEDTALYYCAKDSSSWYGGGSAFDIWGQGTMVT<br>VSSGGGGSGGGGSGGGGSSSELTQEPAVSVALGQTVRITCQGDSLRSYYASWYQQKPGQA<br>PVLVIFGRSRRPSGIPDRFSGSSSGNTASLIITGAQAEDEADYYCNSRDNTANHYVFGTG<br>TKLTVL | 62 |
| M17<br>(human)<br>(aa) | EVQLVESGGGLVQPGRSLRLSCAASGFTFDDYAMHWVRQAPGKGLEWVSGISWNSGSTGY<br>ADSVKGRFTISRDNAKNSLYLQMNSLRAEDTALYYCAKDSSSWYGGGSAFDIWGQGTMVT<br>VSSGGGGSGGGGSGGGGSSSELTQDPAVSVALGQTVRITCQGDSLRSYYASWYQQKPGQA<br>PVLVIYGKNNRPSGIPDRFSGSSSGNTASLTITGAQAEDEADYYCNSRGSSGNHYVFGTG<br>TKVTVL | 63 |
| M18<br>(human)<br>(aa) | QVQLVQSGGGLVQPGGSLRLSCAASGFTFSSYWMHWVRQAPGKGLVWVSRINSDGSSTSY<br>ADSVKGRFTISRDNAKNTLYLQMNSLRAEDTAVYYCVRTGWVGSYYYYMDVWGKGTTVTV<br>SSGGGGSGGGGSGGGGSGGGGSEIVLTQSPGTLSLSPGERATLSCRASQSVSSNYLAWYQ<br>QKPGQPPRLLIYDVSTRATGIPARFSGGGSGTDFTLTISSLEPEDFAVYYCQQRSNWPPW<br>TFGQGTKVEIK | 64 |
| M19<br>(human)<br>(aa) | QVQLVQSGGGVVQPGRSLRLSCAASGFTFSSYGMHWVRQAPGKGLEWVAVISYDGSNKYY<br>ADSVKGRFTISRDNSKNTLYLQMNSLRAEDTAVYYCAKGYSRYYYYGMDVWGQGTTVTVS<br>SGGGGSGGGGSGGGGSGGGGSEIVMTQSPATLSLSPGERAILSCRASQSVYTKYLGWYQQ<br>KPGQAPRLLIYDASTRATGIPDRFSGSGSGTDFTLTINRLEPEDFAVYYCQHYGGSPLIT<br>FGQGTKVDIK | 65 |
| M20<br>(human)<br>(aa) | QVQLVQSGGGLVQPGGSLRLSCAASGFTFSSYAMSWVRQAPGKGLEWVSAISGSGGSTYY<br>ADSVKGRFTISRDNSKNTLYLQMNSLRAEDTAVYYCAKREAAAGHDWYFDLWGRGTLVTV<br>SSGGGGSGGGGSGGGGSGGGGSDIRVTQSPSSLSASVGDRVTITCRASQSISSYLNWYQQ<br>KPGKAPKLLIYAASSLQSGVPSRFSGSGSGTDFTLTISSLQPEDFATYYCQQSYSIPLTF<br>GQGTKVEIK | 66 |
| M21<br>(human)<br>(aa) | QVQLVQSWAEVKKPGASVKVSCKASGYTFTSYYMHWVRQAPGQGLEWMGIINPSGGSTSY<br>AQKFQGRVTMTRDTSTSTVYMELSNLRSEDTAVYYCARSPRVTTGYFDYWGQGTLVTVSS<br>GGGGSGGGGSGGGGSGGGGSDIQLTQSPSTLSASVGDRVTITCRASQSISSWLAWYQQKP<br>GKAPKLLIYKASSLESGVPSRFSGSGSGTEFTLTISSLQPDDFATYYCQQYSSYPLTFGG<br>GTRLEIK | 67 |
| M22<br>(human)<br>(aa) | QVQLVQSGAEVRRPGASVKISCRASGDTSTRHYIHWLRQAPGQGPEWMGVINPTTGPATG<br>SPAYAQMLQGRVTMTRDTSTRTVYMELRSLRFEDTAVYYCARSVVGRSAPYYFDYWGQGT<br>LVTVSSGGGGSGGGGSGGGGSGGGGSDIQMTQSPSSLSASVGDRVTITCRASQGISDYSA<br>WYQQKPGKAPKLLIYAASTLQSGVPSRFSGSGSGTDFTLTISYLQSEDFATYYCQQYYSY<br>PLTFGGGTKVDIK | 68 |
| M23<br>(human)<br>(aa) | QVQLQQSGAEVKKPGASVKVSCKASGYTFTNYYMHWVRQAPGQGLEWMGIINPSGGYTTY<br>AQKFQGRLTMTRDTSTSTVYMELSSLRSEDTAVYYCARIRSCGGDCYYFDNWGQGTLVTV<br>SSGGGGSGGGGSGGGGSGGGGSDIQLTQSPSTLSASVGDRVTITCRASENVNIWLAWYQQ<br>KPGKAPKLLIYKSSSLASGVPSRFSGSGSGAEFTLTISSLQPDDFATYYCQQYQSYPLTF<br>GGGTKVDIK | 69 |
| M24<br>(human)<br>(aa) | QITLKESGPALVKPTQTLTLTCTFSGFSLSTAGVHVGWIRQPPGKALEWLALISWADDKR<br>YRPSLRSRLDITRVTSKDQVVLSMTNMQPEDTATYYCALQGFDGYEANWGPGTLVTVSSG<br>GGGSGGGGSGGGGSGGGGSDIVMTQSPSSLSASAGDRVTITCRASRGISSALAWYQQKPG<br>KPPKLLIYDASSLESGVPSRFSGSGSGTDFTLTIDSLEPEDFATYYCQQSYSTPWTFGQG<br>TKVDIK | 70 |
| M1<br>(na) | CAAGTCCAACTGCAGCAGTCAGGAGCGGAAGTGAAGAAACCAGGAGCGTCAGTCAAAGTG<br>TCGTGCAAGGCTAGCGGCTACACCTTCACCGGCTACTACATGCACTGGGTTCGACAGGCT<br>CCAGGGCAGGGTCTGGAGTGGATGGGCCGCATCAACCCGAATTCCGGTGGGACTAACT<br>ACGCCCAGAAGTTCCAGGGAAGAGTGACCATGACTAGGGACACGTCGATCAGCACTGCGT<br>ACATGGAACTGAGCCGCCTGCGGTCCGAGGATACTGCCGTCTACTACTGCGCACGCGGAA<br>GGTACTATGGAATGGACGTGTGGGGCCAAGGGACTATGGTGACTGTGAGCTCGGGAGGGG<br>GAGGCTCCGGTGGCGGGGGATCAGGAGGAGGAGGATCAGGGGGAGGAGGTTCCGAAATTG<br>TCCTCACCCAGAGCCCGGCAACCCTCTCACTTTCCCCGGGAGAGCGCGCAACCATCTCTT<br>GCCGGGCTAGCCAATCCGTGTCGTCCAATTTCGCCTGGTACCAGCAACGGCCGGGACAAG<br>CCCCTAGACTCCTGATCTACGACGCCAGCAACAGAGCGACTGGAATTCCTCCACGCTTTT<br>CGGGATCAGGCTCCGGTACCGACTTCACCCTGACTATCTCGTCGCTCGAACCCGAGGATT<br>TCGCCGCCTACTACTGTCATCAGCGGTCGAACTGGTTGTATACGTTTGGCCAGGGCACCA<br>AGGTGGATATCAAG | 71 |

TABLE 2-continued

Antigen binding domains that bind to mesothelin
(aa - amino acids, na - nucleic acid
that encodes the corresponding polypeptide)

| Name | Sequence | SEQ ID NO: |
|---|---|---|
| M2 (na) | CAAGTCCAACTCGTCCAGTCAGGAGCAGAAGTCAAGAAACCAGGTGCTAGCGTGAAAGTG<br>TCGTGCAAGGCGTCGGGATACACTTTCACCGGATACTACATGCACTGGGTCCGCCAGGCC<br>CCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTA<br>CATGGAGCTCTCCAGACTGCGCTCCGACGATACTGCAGTGTACTACTGCGCCCGGGACCT<br>GAGGCGGACTGTGGTTACTCCTCGCGCCTATTATGGCATGGACGTGTGGGGCCAAGGAAC<br>TACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTC<br>AGTGGGAGATCGGGTGACCATCACGTGTCAGGCCAGCCAGGATATCTCCAACTCGCTCAA<br>CTGGTACCAGCAAAAGGCGGGTAAAGCTCCGAAGCTGCTGATCTACGACGCTTCCACCCT<br>CGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTT<br>GCCTCTGACGTTCGGGCAGGGCACCAAGGTGGAAATCAAG | 72 |
| M3 (na) | CAAGTCCAACTCGTCCAATCAGGAGCGGAAGTCAAAAAGCCCGGAGCTCCAGTGAAAGTG<br>TCATGCAAGGCCTCCGGCTACACCTTCACCGGTTACTATATGCACTGGGTGCGGCAGGCC<br>CCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCAT<br>ACATGGAGCTTAGCAGACTCCGCTCCGACGATACCGCAGTCTACTATTGCGCGCGGGGAG<br>AGTGGGACGGATCGTACTACTACGATTACTGGGGCCAGGGAACTCTGGTGACTGTTTCCT<br>CGGGTGGAGGAGGTTCAGGCGGAGGCGGCTCGGGCGGGGGAGGATCTGGAGGAGGAGGGT<br>CCGACATTGTGCTGACCCAAACTCCTTCGTCCCTGTCGGCCAGCGTGGGCGACCGCGTGA<br>CGATTACGTGCAGAGCTAGCCAATCCATCAATACTTACCTCAACTGGTACCAGCATAAGC<br>CGGGGAAAGCACCAAAGCTGCTGATCTACGCCGCCTCATCCTTGCAGAGCGGTGTGCCTT<br>CACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCG<br>GGACCAAGCTGGAAATCAAG | 73 |
| M4 (na) | CAAGTGCAACTCGTTGAATCAGGTGGAGGTTTGGTGCAACCCGGAGGATCTCTCAGACTG<br>TCGTGTGCGGCGTCCGGGTTCACCTTTTCGTCCTACTGGATGCACTGGGTGCGCCAGGTG<br>CCGGGAAAAGGACTGGTGTGGGTGTCCAGAATCAACACCGACGGGTCAACGACTACCT<br>ACGCAGATAGCGTGGAAGGTCGGTTCACCATTTCGCGGGACAACGCTAAAAACACTCTGT<br>ACCTTCAGATGAATTCACTGCGCGATGACGACACCGCAGTCTACTACTGCGTCGGTGGAC<br>ACTGGGCGGTCTGGGGACAGGGAACTACGGTGACTGTGTCCAGCGGCGGGGGAGGAAGCG<br>GCGGAGGGGGGAGCGGAGGCGGAGGATCAGGAGGAGGCGGCTCCGATATCCAGATGACCC<br>AGTCGCCATCGACCCTCTCCGCTAGCGTGGGGGATAGGGTCACTATCACTTGCCGAGCCA<br>GCCAATCCATTAGCGACCGGCTTGCCTGGTACCAACAGAAACCTGGAAAGGCCCCGAAGC<br>TGCTCATCTACAAGGCCTCGTCACTGGAGTCGGGAGTCCCGTCCCGCTTTTCCGGCTCGG<br>GCTCAGGCACCGAGTTCACTCTGACCATCTCGAGCCTGCAGCCGGACGATTTCGCCGTGT<br>ATTACTGCCAGCAATACGGACATCTCCCAATGTACACGTTCGGTCAGGGCACCAAGGTCG<br>AAATCAAG | 74 |
| M5 (na) | CAAGTCCAACTCGTTCAATCAGGCGCAGAAGTCGAAAAGCCCGGAGCATCAGTCAAAGTC<br>TCTTGCAAGGCTTCCGGCTACACCTTCACGGACTACTACATGCACTGGGTGCGCCAGGCT<br>CCAGGCCAGGGACTGGAGTGGATGGGATGGATCAACCCGAATTCCGGGGGAACTAACTA<br>CGCCCAGAAGTTTCAGGGCCGGGTGACTATGACTCGCGATACCTCGATCTCGACTGCGTA<br>CATGGAGCTCAGCCGCCTCCGGTCGGACGATACCGCCGTGTACTATTGTGCGTCGGGATG<br>GGACTTCGACTACTGGGGGCAGGGCACTCTGGTCACTGTGTCAAGCGGAGGAGGTGGATC<br>AGGTGGAGGTGGAAGCGGGGGAGGAGGTTCCGGCGGCGGAGGATCAGATATCGTGATGAC<br>GCAATCGCCTTCCTCGTTGTCCGCATCCGTGGGAGACAGGGTGACCATTACTTGCAGAGC<br>GTCCCAGTCCATTCGGTACTACCTGTCGTGGTACCAGCAGAAGCCGGGGAAAGCCCCAAA<br>ACTGCTTATCTATACTGCCTCGATCCTCCAAAACGGCGTGCCATCAAGATTCAGCGGTTC<br>GGGCAGCGGGACCGACTTTACCCTGACTATCAGCAGCCTGCAGCCGGAAGATTTCGCCAC<br>GTACTACTGCCTGCAAACCTACACCACCCCGGACTTCGGACCTGGAACCAAGGTGGAGAT<br>CAAG | 75 |
| M6 (na) | CAAGTGCAACTCGTCCAGTCAGGTGCAGAAGTGAAGAAACCCGGAGCGTCAGTCAAAGTG<br>TCATGCAAGGCGTCAGGCTACACCTTCACCAGCTACTACATGCACTGGGTGCGGCAGGCC<br>CCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTA<br>CATGGAACTGAGCTCGCTGCGCTCCGAGGACACTGCTGTGTACTACTGCGCACGGTACAG<br>ACTCATTGCCGTGGCAGGAGACTACTACTACTATGGCATGGACGTCTGGGGGCAGGGCAC<br>TATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTC<br>GGTTGGAGATCGCGTCACCATCACTTGTCGAGCTTCCCAAGGAGTCGGTAGGTGGCTGGC<br>GTGGTACCAGCAAAAGCCGGGAACTGCCCCGAAGCTCCTGATCTACGCGGCTAGCACCCT<br>GCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTT<br>CCCTCTGACTTTCGGAGGGGGCACTCGCCTGGAAATCAAG | 76 |
| M7 (na) | CAAGTGCAATTGGTTCAATCAGGAGGAGGAGTGGTGCAACCTGGAAGATCTCTCAGACTG<br>TCGTGTGCGGCATCGGGATTCACTTTCTCATCATACGCAATGCACTGGGTCCGCCAGGCC | 77 |

TABLE 2-continued

Antigen binding domains that bind to mesothelin
(aa - amino acids, na - nucleic acid
that encodes the corresponding polypeptide)

| Name | Sequence | SEQ ID NO: |
|---|---|---|
| | CCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGT<br>ACCTCCAGATGAACTCCCTTAGGGCTGAGGACACCGCCGTCTACTACTGCGCACGCTGGA<br>AAGTGTCGTCCAGCTCCCCAGCTTTTGACTACTGGGGACAGGGAACCCTTGTGACCGTGT<br>CGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAGAGAG<br>CGATCCTGTCCTGCCGCGCCTCGCAGAGCGTGTACACTAAGTACCTGGGGTGGTACCAGC<br>AGAAACCGGGTCAAGCGCCTCGGCTGCTGATCTACGATGCCTCCACCCGGGCCACCGGAA<br>TCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCA<br>CCTTCGGTCAAGGAACCCGACTCGAAATCAAG | |
| M8<br>(na) | CAAGTCCAACTCCAGCAGTCAGGTGCAGAAGTCAAAAAGCCAGGAGCATCCGTGAAGGTT<br>TCGTGCAAGACTTCCGGCTACCCTTTTACCGGGTACTCCCTCCATTGGGTGAGACAAGCA<br>CCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCT<br>ACATGGAGCTGTCCCGCTTGAGATCTGACGACACGGCCGTCTACTACTGCGCCCGGGATC<br>ACTACGGAGGTAATTCGCTGTTCTACTGGGGGCAGGGAACCCTTGTGACTGTGTCCTCGG<br>GTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGA<br>TTACTTGTAGGGCCTCCCAAGACTCAGGGACGTGGCTGGCGTGGTATCAGCAAAAACCGG<br>GCAAAGCTCCGAACCTGTTGATGTACGACGCCAGCACCCTCGAAGATGGAGTGCCTAGCC<br>GCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCG<br>GGACCAAGGTGGATATCAAG | 78 |
| M9<br>(na) | CAAGTGCAACTCGTCCAGTCAGGTGCAGAAGTGAAGAAACCAGGAGCGTCCGTCGAAGTG<br>TCGTGTAAGGCGTCCGGCTACACTTTCACCTCGTACTACATGCACTGGGTGCGGCAGGCC<br>CCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTC<br>ATATGGAGCTCTCGTCCCTGCGGAGCGAGGACACTGCTGTCTACTATTGCGCGCGGGGAG<br>GATACTCTAGCTCCTCCGATGCATTTGACATTTGGGGCCAGGGAACTATGGTGACCGTGT<br>CATCAGGCGGAGGTGGATCAGGAGGAGGAGGGTCGGGAGGGGGAGGCAGCGGCGGGGGTG<br>GGTCGGACATTCAGATGACGCAGTCCCCTCCTAGCCTGAGCGCCTCGGTGGGTGACAGAG<br>TGACCATCACTTGCAGAGCCTCGCAAGACATCTCCTCCGCATTGGCTTGGTACCAGCAAA<br>AGCCGGGCACTCCGCCGAAACTGCTCATCTACGATGCCTCCTCACTGGAGTCAGGAGTCC<br>CATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCG<br>GGGGCGGAACTCGCCTGGAAATCAAG | 79 |
| M10<br>(na) | CAAGTGCAACTCGTCCAGAGCGGAGCAGAAGTCAAGAAGCCAGGAGCGTCAGTGAAAGTG<br>TCATGCAAGGCCAGCGGCTATACCTTTACTTCGTATGGGATCTCCTGGGTGCGGCAGGCA<br>CCGGGCCAAGGACTGGAGTGGATGGGATGGATCTCAGCCTACAACGGTAACACCAACTAC<br>GCCCAGAAGCTGCAAGGACGCGTGACCATGACTACTGATACGAGCACCTCCACTGCCTAC<br>ATGGAATTGCGGTCCCTTCGGTCGGACGATACTGCTGTGTACTACTGCGCAAGAGTCGCC<br>GGAGGGATCTACTACTACTACGGCATGGACGTCTGGGGACAGGGAACCACCATTACGGTG<br>TCGAGCGGAGGGGGAGGCTCGGGGGGAGGAGGAAGCGGAGGTGGCGGCTCCGGGGGCGGC<br>GGATCGGACATTGTGATGACCCAGACTCCTGACTCCCTGGCTGTTTCGTTGGGAGAGCGC<br>GCGACTATCTCGTGTAAGTCCAGCCACTCAGTCCTGTACAATCGCAATAACAAGAACTAC<br>CTCGCGTGGTACCAGCAAAAACCGGGTCAGCCGCCTAAACTCCTGTTCTACTGGGCCTCC<br>ACCAGAAAGAGCGGGGTGCCAGATCGATTCTCTGGATCAGGATCAGGTACCGACTTTACG<br>CTGACCATCTCGTCCCTGCAGCCGGAGGATTTCGCGACTTACTTCTGCCAGCAGACTCAG<br>ACTTTCCCCCTCACCTTCGGTCAAGGCACCAGGCTGGAAATCAAT | 80 |
| M11<br>(na) | CAAGTCCAATTGCAGCAGAGCGGAGCAGAAGTGAAGAAGCCAGGAGCGTCAGTCAAAGTG<br>TCGTGTAAGGCGTCAGGATACACCTTCACGGGATACTACATGCACTGGGTGCGCCAGGCC<br>CCGGGCCAAGGACTCGAGTGGATGGGCTGGATCAACCCTAACTCTGGAGGCACCAACTAC<br>GCCCAGAATTTCCAAGGCAGAGTGACCATGACCCGGGACACCTCCATCTCGACTGCCTAT<br>ATGGAACTGCGGCGGCTGCGCTCGGACGATACTGCTGTGTATTACTGCGCCAGCGGCTGG<br>GACTTTGACTACTGGGGACAGGGTACTCTGGTGACTGTTTCCTCGGGAGGAGGCGGATCG<br>GGTGGAGGAGGTAGCGGGGGAGGGGGGTCGGGAGGCGGAGGCAGCGATATTCGCATGACT<br>CAATCGCCGTCCTCCCTGAGCGCTAGCGTGGGAGATCGAGTCACCATCACTTGCAGAGCG<br>TCACAGTCGATTCGCTACTACCTGTCCTGGTACCAGCAGAAACCGGGAAAGGCACCAAAG<br>CTTCTGATCTACACGGCCTCCATCCTGCAAAATGGTGTCCCATCAAGGTTCTCCGGGTCA<br>GGGAGCGGCACTGACTTCACTCTCACCATCTCCTCACTCCAGCCCGAGGACTTTGCAACC<br>TACTACTGCCTCCAGACGTACACCACCCCGGATTTCGGTCCTGGAACCAAGGTGGAAATC<br>AAA | 81 |
| M12<br>(na) | CAAGTCCAACTCGTCCAAAGCGGAGCAGAAGTCAAAAAGCCAGGAGCGTCGGTGAAAGTG<br>TCTTGCAAAGCCAGCGGCTACACCTTCACGGGTTACTACATGCACTGGGTGCGCCAGGCG<br>CCGGGCCAGGGGCTGGAGTGGATGGGCCGGATTAACCCTAACAGCGGGGGAACTAATTAC<br>GCTCAGAAGTTCCAGGGTAGAGTCACCATGACTACGGACACTTCCACTTCCACCGCCTAT<br>ATGGAACTGCGCTCCCTCCGCTCAGATGATACTGCCGTGTATTACTGCGCGCGGACTACC | 82 |

TABLE 2-continued

Antigen binding domains that bind to mesothelin
(aa - amino acids, na - nucleic acid
that encodes the corresponding polypeptide)

| Name | Sequence | SEQ ID NO: |
|---|---|---|
| | ACGTCATACGCATTTGACATCTGGGGCCAGGGAACTATGGTGACCGTGAGCTCGGGCGGA GGCGGTTCAGGGGGAGGAGGAAGCGGAGGAGGAGGATCGGGAGGAGGTGGCTCCGATATC CAGCTGACTCAGTCCCCGAGCACCCTGTCGGCGTCGGTGGGGACAGGGTTACCATCACC TGTAGAGCTTCCCAATCCATTTCGACTTGGCTGGCCTGGTACCAGCAAAAGCCGGGAAAG GCCCCTAATTTGCTTATCTACAAGGCATCGACCCTCGAAAGCGGTGTGCCCTCCCGGTTT TCGGGATCAGGATCAGGGACCGAGTTCACCCTGACCATCTCATCCCTCCAGCCGGACGAC TTCGCCACTTACTACTGCCAGCAGTACAACACCTACTCGCCATACACTTTCGGCCAAGGC ACCAAGCTGGAGATCAAG | |
| M13 (na) | CAAGTTCAACTCGTGCAATCAGGTGGAGGACTCGTCAAACCCGGAGGATCATTGAGACTG TCATGCGAAGCGAGCGGTTTTATCTTCTCCGATTACTATATGGGATGGATTCGGCAGGCC CCGGGAAAGGGACTCGAATGGGTGTCATACATCGGAAGGTCAGGCTCGTCCATGTACTAC GCAGACTCGGTGAAAGGCAGATTCACCTTTAGCCGGGACAACGCCAAGAATTCCCTCTAC TTGCAGATGAACAGCCTGCGAGCCGAGGATACTGCTGTCTACTACTGTGCCGCGTCGCCG GTGGTGGCAGCTACTGAAGATTTCCAGCACTGGGGACAGGGAACTCTGGTCACGGTGTCG AGCGGTGGGGCGGAAGCGGAGGCGGAGGATCGGGCGGCGGAGGTTCGGGGGGGGAGGG TCTGACATCGTGATGACCCAAACCCCAGCCACCCTGAGCCTCTCCCCTGGAGAGCGCGCG ACTCTTTCGTGCCGCGCTTCCCAGTCAGTGACCAGCAATTACTTGGCTTGGTACCAACAG AAGCCGGGACAGGCGCCACGGCTGCTGCTTTTTGGTGCCAGCACTCGCGCCACCGGAATC CCGGATCGCTTCTCGGGCTCAGGGTCCGGGACGGACTTCACCCTGACTATCAACCGGCTG GAACCTGAGGACTTCGCGATGTACTACTGCCAGCAGTACGGCTCCGCACCAGTCACTTTC GGACAAGGCACCAAGCTGGAGATCAAG | 83 |
| M14 (na) | CAAGTCCAACTCGTCCAGTCGGGAGCAGAAGTTAGAGCACCAGGAGCGTCAGTGAAAATC TCATGCAAGGCCTCGGGCTTCACGTTCCGCGGATACTACATCCACTGGGTGCGCCAAGCC CCGGGTCAGGGATTGGAGTGGATGGGAATCATTAACCCATCAGGAGGGAGCCGGGCTTAC GCGCAGAAGTTCCAGGGACGCGTCACTATGACCCGAGATACTTCCACCTCGACTGTGTAC ATGGAACTCTCGTCCCTGAGGTCCGACGACACTGCGATGTATTACTGTGCTCGGACTGCC AGCTGCGGTGGGGACTGTTACTACCTGATTACTGGGGCCAGGGAACTCTGGTGACCGTG TCCAGCGGAGGTGGCGGGTCAGGGGGTGGCGGAAGCGGAGGCGGCGGTTCAGGCGGAGG AGGCTCGGACATCCAAATGACGCAATCGCCGCCTACCCTGAGCGCTTCCGTGGGAGATCG GGTGACCATTACTTGCAGAGCATCCGAGAACGTCAATATCTGGCTGGCCTGGTACCAACA GAAGCCGGGAAGGCCCCTAAACTGCTGATCTACAAGTCGAGCAGCCTTGCCTCTGGAGT GCCCTCCCGCTTCTCGGGCTCGGGATCAGGAGCGGAATTCACCCTCACCATCTCCTCCCT GCAGCCAGATGACTTTGCCACCTACTACTGCCAGCAGTACCAGAGCTATCCGTTGACCTT TGGGGGAGGCACTAAAGTGGACATCAAG | 84 |
| M15 (na) | CAAGTTCAACTCGTTCAATCAGGTGGAGGACTCGTGCAACCAGGAAGATCACTCAGACTC AGCTGCGCCGCGTCGGGATTCACTTTCGATGACTACGCAATGCACTGGGTGCGGCAGGCC CCGGGCAAAGGACTGGAATGGGTGAGCGGAATTAGCTGGAACTCGGGGTCCATCGGGTAC GCCGACTCGGTGAAGGGACGCTTTACGATCTCCCGGGACAATGCCAAGAACTCCCTGTAT TTGCAGATGAACTCCTTGAGGGCTGAGGACACCGCCGTGTACTACTGCGCTAAAGATGGA TCATCGTCCTGGTCCTGGGGATACTTCGATTACTGGGGCCAGGGCACTCTGGTGACCGTG TCGTCAGGCGGTGGAGGGTCGGGCGGAGGAGGTAGCGGAGGCGGAGGGAGCAGCTCTGAA CTGACCCAAGACCCGGCGGTGTCGGTCGCCCTTGGTCAGACTGTGCGGACTACCTGTCAG GGGGACGCGCTGCGCTCGTACTACGCTTCATGGTACCAGCAGAAGCCCGGACAGGCACCT ATGCTGGTCATCTACGGAAAGAATAACCGCCCATCCGGCATCCCGGATCGCTTCTCGGAT TCGGACAGCGGCGACACCGCATCCCTGACGATCACTGGAGCGCAGGCCGAGGATGAAGCC GACTACTACTGCAATTCCCGAGATTCAAGCGGCTACCCTGTGTTTGGGACCGGAACTAAG GTCACCGTCCTG | 85 |
| M16 (na) | GAAGTGCAACTCGTGGAATCTGGTGGAGGACTTGTGCAACCTGGAAGATCGTTGAGACTC TCATGTGCTGCCTCCGGGTTCACCTTTGACGACTACGCCATGCACTGGGTGCGCCAGGCA CCAGGAAAGGGTCTGGAGTGGGTTTCGGGTATCTCGTGGAACTCCGGGAGCACTGGCTAC GCTGATTCGGTGAAAGGCCGGTTTACCATCTCCCGAGACAATGCGAAGAATTCCCTCTAT CTGCAGATGAACAGCCTCCGGGCCGAGGATACTGCCCTGTACTACTGCGCCAAGGATAGC TCATCATGGTACGGAGGTGGATCGGCTTTCGATATCTGGGGCCAGGGCACGATGGTCACC GTGTCCTCGGGGGCGGAGGCTCCGGGGAGGAGGTAGCGGAGGAGGAGGATCGAGCTCA GAGTTGACTCAAGAACCCGCAGTGTCCGTGGCACTGGGCAAACCGTCAGGATCACTTGC CAGGGAGACAGCCTGAGGTCGTACTACGCGTCCTGGTACCAGAGAGCCGGGACAGGCC CCGGTCCTGGTCATTTTCGGACGCTCAAGACGCCCATCGGGCATCCCGGACCGGTTCAGC GGAAGCTCCTCGGGAAACACCGCGTCACTTATCATTACCGGCGCACAGGCTGAGGACG AAGCGGATTACTACTGCAACTCCCGCGACAATACTGCCAACCATTACGTGTTCGGGACCG GAACGAAACTGACTGTCCTG | 86 |
| M17 (na) | GAAGTTCAATTGGTGGAATCTGGAGGAGGACTTGTGCAACCCGGTAGATCTCTGAGACTG TCCTGTGCGGCATCGGGATTCACCTTCGACGACTACGCTATGCACTGGGTGAGACAAGCC CCTGGAAAAGGACTGGAGTGGGTGTCAGGCATCTCCTGGAATAGCGGGTCCACTGGATAC GCCGATTCGGTCAAGGGTCGCTTCACCATTTCCCGGGACAATGCCAAGAACTCCCTGTAC CTTCAAATGAACTCCCTCCGGGCCGAGGATACCGCCCTACTACTGCGCCAAAGACAGC TCGTCATGGTATGGCGGAGGGTCGGCATTTGACATCTGGGGACAGGGAACTATGGTGACT GTGTCATCAGGAGGCGGCGAAGCGGCGGCGGCGGGTCCGGCGGAGGAGGTCGTCCAGC GAACTCACCCAAGATCCAGCAGTGAGCGTCGCGCTGGGCCAGACCGTCAGGATCACGTGC | 87 |

TABLE 2-continued

Antigen binding domains that bind to mesothelin
(aa - amino acids, na - nucleic acid
that encodes the corresponding polypeptide)

| Name | Sequence | SEQ ID NO: |
|---|---|---|
|  | CAGGGAGATTCACTGCGCTCATACTACGCGTCCTGGTACCAGCAGAAGCCGGGGCAGGCC<br>CCGGTCCTCGTGATCTACGGAAAGAACAACCGCCCGTCGGGTATCCCAGACCGCTTTTCG<br>GGTAGCTCCAGCGGAAATACGGCTAGCCTGACCATCACTGGAGCACAGGCTGAGGATGAA<br>GCGGACTACTACTGCAATTCGCGGGGCTCATCGGGGAACCATTACGTGTTCGGAACTGGT<br>ACCAAGGTGACTGTCCTG |  |
| M18 (na) | CAAGTGCAGCTCGTTCAATCAGGCGGAGGACTCGTTCAACCAGGAGGATCATTGCGACTC<br>TCATGTGCGGCCTCTGGATTCACGTTTAGCTCATATTGGATGCACTGGGTGCGGCAGGCG<br>CCGGGGAAAGGTCTGGTGTGGGTCAGCCGCATCAACTCAGACGGCTCCTCGACTTCGTAC<br>GCCGACTCCGTGAAGGGACGCTTTACCATTTCCCGCGACAACGCCAAGAATACCCTTTAC<br>CTTCAGATGAACTCCCTCCGCGCTGAGGATACCGCCGTGTACTACTGCGTGAGGACTGGC<br>TGGGTCGGCAGCTACTACTACTACATGGACGTGTGGGCAAAGGAACTACTGTCACCGTG<br>TCAAGCGGCGGTGGAGGTTCCGGCGGGGAGGATCGGGGGGGGCGGATCGGGTGGCGGA<br>GGATCGGAGATCGTGTTGACCCAGTCGCCGGGAACCCTGTCGCTGTCGCCTGGGGAGAGA<br>GCAACTCTGTCCTGCCGGGCTTCCCAGTCGGTGTCGAGCAATTACCTGGCATGGTACCAA<br>CAGAAGCCGGGACAGCCGCCACGCCTGCTGATCTATGACGTGTCAACTCGGGCAACTGGA<br>ATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTG<br>GACGTTCGGACAAGGAACCAAGGTCGAAATCAAG | 88 |
| M19 (na) | CAAGTGCAATTGGTTCAATCAGGAGGAGGAGTCGTGCAGCCCGGAAGATCGTTGAGACTG<br>TCATGTGCCGCGAGCGGCTTTACTTTCTCAAGCTACGGAATGCATTGGGTGCGACAGGCT<br>CCGGGAAAAGGACTGGAATGGGTCGCAGTGATCTCATACGACGGCTCGAACAAGTACTAC<br>GCCGACTCCGTCAAGGGTCGGTTCACGATTTCGCGCGATAATTCCAAGAACACTCTGTAC<br>CTCCAAATGAACAGCCTCCGGGCAGAGGACACCGCCGTCTACTACTGCGCTAAGGGATAC<br>TCGCGCTACTACTACTATGGAATGGATGTGTGGGGCCAGGGAACTACCGTGACGGTGTCG<br>TCCGGCGGCGGTGGGTCGGGCGGAGGCGGATCAGGTGGAGGTGGAAGCGGAGGAGGAGGG<br>AGCGAAATCGTCATGACTCAGTCCCCTGCTACCCTTTCTCTGTCGCCGGGAGAAAGAGCC<br>ATCCTGAGCTGCCGGGCCTCCCAGAGCGTGTACACCAAATACCTGGGATGGTACCAGCAG<br>AAGCCGGGGCAGGCACCAAGGCTCCTGATCTACGATGCGTCCACCCGCGCGACTGGTATC<br>CCAGACCGCTTTTCCGGCTCGGGGTCAGGGACTGACTTCACCCTTACTATCAATCGGCTC<br>GAGCCTGAGGATTTCGCCGTGTATTACTGCCAGCACTACGGAGGGTCCCCGCTGATTACC<br>TTCGGCCAAGGCACCAAAGTGGACATCAAG | 89 |
| M20 (na) | CAAGTGCAACTTGTTCAATCAGGAGGAGGACTCGTTCAACCCGGAGGATCACTGCGACTC<br>TCATGTGCAGCGTCGGGGTTCACCTTCTCCAGCTACGCAATGTCCTGGGTGCGCCAAGCC<br>CCTGGAAAAGGCCTGGAGTGGGTGTCGGCCATCTCTGGGAGCGGGGGATCAACTTACTAC<br>GCTGACTCCGTCAAGGGCCGCTTTACCATCTCCCGGGACAACAGCAAGAACACTCTCTAT<br>CTCCAGATGAACTCGCTGAGAGCCGAAGATACCGCTGTCTACTACTGCGCGAAGAGAGAA<br>GCTGCCGCAGGGCACGATTGGTACTTCGACTTGTGGGGCAGGGGCACCCTTGTGACCGTG<br>TCCTCCGGTGGAGGCGGATCAGGAGGTGGGGATCGGGTGGAGGAGGAAGCGGAGGCGGC<br>GGTTCGGACATTCGCGTCACCCAGTCACCGAGCTCCCTCAGCGCATCGGTGGGCGACCGG<br>GTCACTATCACTTGCCGGGCGTCCCAGTCGATCTCATCGTATCTGAATTGGTACCAGCAG<br>AAACCGGGAAAGGCGCCGAAGCTGTTGATCTACGCTGCCAGCTCCCTGCAGTCGGGTGTG<br>CCATCACGCTTTTCCGGCTCGGGATCGGGAACCGATTTCACTCTGACGATCTCTAGCCTG<br>CAGCCAGAAGATTTCGCCACTTACTACTGCCAGCAGTCCTACAGCATCCCTCTGACTTTC<br>GGACAAGGGACGAAAGTGGAGATTAAG | 90 |
| M21 (na) | CAAGTCCAACTCGTTCAGTCATGGGCAGAAGTCAAGAAACCCGGTGCAAGCGTCAAAGTG<br>TCGTGTAAGGCCTCCGGCTACACTTTCACTTCCTACTACATGCACTGGGTGCGCCAAGCC<br>CCGGGACAGGGCCTTGAATGGATGGGCATCATCAACCCATCAGGAGGTTCCACGAGCTAC<br>GCGCAGAAGTTCCAGGGGAGAGTGACGATGACTAGAGATACCTCCACGAGCACCGTCTAC<br>ATGGAGCTGTCGAATCTGCGGTCAGAGGACACTGCTGTGTATTACTGCGCGCGCTCCCCG<br>CGGGTGACCACTGGCTACTTTGACTACTGGGGACAAGGGACCCTGGTGACCGTCAGCTCG<br>GGAGGCGGAGGATCGGGAGGTGGAGGGTCCGGTGGAGGCGGCTCTGGAGGAGGCGGGTC<br>GGACATTCAATTGACCCAGAGCCCATCCACCCTCTCAGCCTCGGTGGGGATAGGGTGAC<br>TATCACTTGCCGGGCCTCCCAGTCAATTTCCAGCTGGCTGGCTTGGTACCAGCAAAAGCC<br>TGGAAAGGCACCGAAGCTCCTGATCTACAAGGCCTCATCTCTGGAATCAGGAGTGCCTTC<br>GCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGG<br>AGGTACCCGCCTCGAAATCAAA | 91 |
| M22 (na) | CAAGTCCAACTCGTCCAGTCCGGTGCAGAAGTCAGAAGGCCAGGAGCAAGCGTGAAGATC<br>TCGTGTAGAGCGTCAGGAGACACCAGCACTCGCCATTACATCCATGGCTGCGCCAGGCT<br>CCGGGCCAAGGGCCGGAGTGGATGGGTGTGATCAACCCGACTACGGGACCGGCTACCGGA<br>AGCCCTGCGTACGCACAGATGCTGCAGGGACGGGTGACTATGACCCGCGATACTAGCACT<br>AGGACCGTGTACATGGAACTCCGCTCGTTGCGGTTCGAAGATACCGCCGTCTACTACTGC<br>GCCCGGTCCGTGGTGGGCCGAAGCGCCCCTTACTACTTCGATTACTGGGGACAGGGCACT<br>CTGGTGACCGTTAGCTCCGGTGGGGAGGCTCGGGTGGAGGCGGATCGGGAGGAGGAGGC<br>AGCGGTGGAGGGGGATCGGACATTCAGATGACCCAGTCACCCTCCTCCCTCTCAGCCTCG<br>GTCGGGGACCGGGTGACCATTACGTGCAGAGCCTCACAAGGGATCTCGGACTACTCCGCC<br>TGGTACCAGCAGAAACCGGGAAAGCGCCAAAGCTCCTGATCTACGCCGCGAGCACCCTG<br>CAATCAGGAGTGCCATCGCGCTTTTCTGGATCGGGCTCAGGGACTGACTTCACGCTGACT | 92 |

TABLE 2-continued

Antigen binding domains that bind to mesothelin
(aa - amino acids, na - nucleic acid
that encodes the corresponding polypeptide)

| Name | Sequence | SEQ ID NO: |
|---|---|---|
|  | ATCTCCTACCTTCAGTCCGAGGATTTCGCTACCTACTACTGCCAACAGTATTACTCCTAT<br>CCCCTGACCTTTGGCGGAGGCACTAAGGTGGACATCAAG |  |
| M23 (na) | CAAGTCCAACTCCAGCAATCGGGAGCAGAAGTCAAGAAACCAGGCGCATCGGTGAAAGTG<br>TCGTGTAAGGCGTCAGGGTACACCTTCACCAACTACTATATGCACTGGGTGCGCCAGGCT<br>CCAGGCCAGGGGTTGGAGTGGATGGGGATCATCAATCCGTCAGGTGGCTACACCACTTAC<br>GCTCAGAAGTTCCAGGGACGCCTCACTATGACTCGCGATACTAGCACCTCCACGGTGTAC<br>ATGGAACTGTCATCGCTGAGGTCCGAAGATACCGCCGTCTACTACTGCGCACGGATCAGA<br>TCCTGCGGAGGAGATTGTTACTACTTTGACAACTGGGGACAGGGCACCCTTGTTACTGTG<br>TCATCGGGAGGAGGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAG<br>AGTGACCATCACTTGCCGGGCGTCCGAGAACGTCAATATCTGGCTGGCCTGGTACCAGCA<br>AAAGCCTGGAAAAGCCCCGAAGCTGCTCATCTATAAGTCATCCAGCCTGGCGTCTGGTGT<br>GCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTT<br>TGGAGGTGGAACCAAGGTGGACATCAAG | 93 |
| M24 (na) | CAAATCACTCTGAAAGAATCTGGACCGGCCCTGGTTAAGCCGACTCAAACGCTCACCCTT<br>ACTTGCACCTTCAGCGGATTCTCACTCAGCACTGCTGGTGTGCACGTCGGATGGATTAGA<br>CAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGG<br>TGGTGCTCTCAATGACCAATATGCAGCCGGAGGACACCGCTACGTACTACTGCGCACTGC<br>AAGGATTTGACGGCTACGAGGCTAACTGGGGACCAGGTACTCTGGTCACCGTGAGCTCCG<br>GCGGGGGAGGATCAGGCGGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTA<br>TCACTTGCCGGGCCAGCCGCGGCATCTCCTCCGCACTGGCGTGGTACCAGCAGAAGCCTG<br>GAAAACCGCCAAAGCTCCTGATCTATGATGCCTCCAGCCTGGAGTCAGGTGTCCCCAGCC<br>GCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAG<br>GGACGAAGGTGGACATCAAG | 94 |
| Ss1 (na) | caagtccagctccagcagtcgggcccagagttggagaagcctggggcgagcgtgaagat<br>ctcatgcaaagcctcaggctactccttactggatacacgatgaattgggtgaaacagt<br>cgcatggaaagtcactggaatggatcggtctgattacgccctacaacggcgcctccagc<br>tacaaccagaagttcagggaaaggcgacccttactgtcgacaagtcgtcaagcaccgc<br>ctacatggacctcctgtccctgacctccgaagatagcgcggtctactttgtgcacgcg<br>gaggttacgatggacggggattcgactactggggccagggaaccactgtcaccgtgtcg<br>agcggaggcggagggagcggaggaggaggcagcggaggtggagggtcggatatcgaact<br>cactcagtccccagcaatcatgtccgcttcaccgggagaaaaggtgaccatgacttgct<br>cggcctcctcgtccgtgtcatacatgcactggtaccaacaaaaatcggggacctcccct<br>aagagatggatctacgataccagcaaactggcttcaggcgtgccgggacgcttctcggg<br>ttcggggagcggaaattcgtattcgttgaccatttcgtccgtggaagccgaggacgacg<br>caacttattactgccaacagtggtcaggctacccgctcactttcggagccggcactaag<br>ctggagatc | 95 |

The sequences of the CDR sequences of the scFv domains of the mesothelin antigen binding domains provided in Table 2 are shown in Table 3 for the heavy chain variable domains and in Table 4 for the light chain variable domains.

TABLE 3

Amino acid sequences for the heavy chain
(HC) CDR1, CDR2, and CDR3
regions of human anti-mesothelin scFvs

| Descrip. | HC-CDR1 | SEQ ID NO: | HC-CDR2 | SEQ ID NO: | HC-CDR3 | SEQ ID NO: |
|---|---|---|---|---|---|---|
| M1 | GYTFTGYYMH | 275 | RINPNSGGTNYAQKFQG | 295 | GRYYGMDV | 317 |
| M2 | GYTFTGYYMH | 275 | WINPNSGGTNYAQKFQG | 296 | DLRRTVVTPRAYYGMDV | 318 |
| M3 | GYTFTGYYMH | 275 | WINPNSGGTNYAQKFQG | 296 | GEWDGSYYDY | 319 |
| M4 | GFTFSSYWMH | 276 | RINTDGSTTTYADSVEG | 297 | GHWAV | 320 |
| M5 | GYTFTDYYMH | 277 | WINPNSGGTNYAQKFQG | 296 | GWDFDY | 321 |
| M6 | GYTFTSYYMH | 278 | IINPSGGSTSYAQKFQ | 297 | YRLIAVAGDYYYGMDV | 322 |

TABLE 3-continued

Amino acid sequences for the heavy chain
(HC) CDR1, CDR2, and CDR3
regions of human anti-mesothelin scFvs

| Descrip. | HC-CDR1 | SEQ ID NO: | HC-CDR2 | SEQ ID NO: | HC-CDR3 | SEQ ID NO: |
|---|---|---|---|---|---|---|
| M7  | GFTFSSYAMH   | 279 | VISYDGSNKYYADSVKG   | 298 | WKVSSSSPAFDY  | 323 |
| M8  | GYPFTGYSLH   | 280 | WINPNSGGTNYAQKFQG   | 299 | DHYGGNSLFY    | 324 |
| M9  | GYTFTSYYMH   | 281 | IINPSGGSTGYAQKFQG   | 300 | GGYSSSSDAFDI  | 325 |
| M10 | GYTFTSYGIS   | 282 | WISAYNGNTNYAQKLQ    | 301 | VAGGIYYYYGMDV | 326 |
| M11 | GYTFTGYYMH   | 283 | WINPNSGGTNYAQNFQG   | 302 | GWDFDY        | 327 |
| M12 | GYTFTGYYMH   | 283 | RINPNSGGTNYAQKFQG   | 303 | TTTSYAFDI     | 328 |
| M13 | GFIFSDYYMG   | 284 | YIGRSGSSMYYADSVKG   | 304 | SPVVAATEDFQH  | 329 |
| M14 | GFTFRGYYIH   | 285 | IINPSGGSRAYAQKFQG   | 305 | TASCGGDCYYLDY | 330 |
| M15 | GFTFDDYAMH   | 286 | GISWNSGSIGYADSVK    | 306 | DGSSSWSWGYFDY | 331 |
| M16 | GFTFDDYAMH   | 286 | GISWNSGSTGYADSVKG   | 307 | DSSSWYGGGSAFDI| 332 |
| M17 | GFTFDDYAMH   | 286 | GISWNSGSTGYADSVKG   | 308 | DSSSWYGGGSAFDI| 333 |
| M18 | GFTFSSYWMH   | 287 | RINSDGSSTSYADSVKG   | 309 | TGWVGSYYYYMDV | 334 |
| M19 | GFTFSSYGMH   | 288 | VISYDGSNKYYADSVKG   | 310 | GYSRYYYYGMDV  | 335 |
| M20 | GFTFSSYAMS   | 289 | AISGSGGSTYYADSVKG   | 311 | REAAAGHDWYFDL | 336 |
| M21 | GYTFTSYYMH   | 290 | IINPSGGSTSYAQKFQG   | 312 | SPRVTTGYFDY   | 337 |
| M22 | GDTSTRHYIH   | 291 | VINPTTGPATGSPAYAQMLQG | 313 | SVVGRSAPYYFDY | 338 |
| M23 | GYTFTNYYMH   | 292 | IINPSGGYTTYAQKFQG   | 314 | IRSCGGDCYYFDN | 339 |
| M24 | GFSLSTAGVHVG | 293 | LISWADDKRYRPSLRS    | 315 | QGFDGYEAN     | 340 |
| Ss1 | GYSFTGYTMN   | 294 | LITPYNGASSYNQKFRG   | 316 | GGYDGRGFDY    | 341 |

TABLE 4

Amino acid sequences for the light chain
(LC) CDR1, CDR2, and CDR3
regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M1  | RASQSVSSNFA      | 342 | DASNRAT | 367 | HQRSNWLYT | 392 |
| M2  | QASQDISNSLN      | 343 | DASTLET | 368 | QQHDNLPLT | 393 |
| M3  | RASQSINTYLN      | 344 | AASSLQS | 369 | QQSFSPLT  | 394 |
| M4  | RASQSISDRLA      | 345 | KASSLES | 370 | QQYGHLPMYT| 395 |
| M5  | RASQSIRYYLS      | 346 | TASILQN | 371 | LQTYTTPD  | 396 |
| M6  | RASQGVGRWLA      | 347 | AASTLQS | 372 | QQANSFPLT | 397 |
| M7  | RASQSVYTKYLG     | 348 | DASTRAT | 373 | QHYGGSPLIT| 398 |
| M8  | RASQDSGTWLA      | 349 | DASTLED | 374 | QQYNSYPLT | 399 |
| M9  | RASQDISSALA      | 350 | DASSLES | 375 | QQFSSYPLT | 400 |
| M10 | KSSHSVLYNRNNKNYLA| 351 | WASTRKS | 376 | QQTQTFPLT | 401 |
| M11 | RASQSIRYYLS      | 352 | TASILQN | 377 | LQTYTTPD  | 402 |

TABLE 4-continued

Amino acid sequences for the light chain
(LC) CDR1, CDR2, and CDR3
regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M12 | RASQSISTWLA | 353 | KASTLES | 378 | QQYNTYSPYT | 403 |
| M13 | RASQSVTSNYLA | 354 | GASTRAT | 379 | QQYGSAPVT | 404 |
| M14 | RASENVNIWLA | 355 | KSSSLAS | 380 | QQYQSYPLT | 405 |
| M15 | QGDALRSYYAS | 356 | GKNNRPS | 381 | NSRDSSGYPV | 406 |
| M16 | QGDSLRSYYAS | 357 | GRSRRPS | 382 | NSRDNTANHYV | 407 |
| M17 | QGDSLRSYYAS | 358 | GKNNRPS | 383 | NSRGSSGNHYV | 408 |
| M18 | RASQSVSSNYLA | 359 | DVSTRAT | 384 | QQRSNWPPWT | 409 |
| M19 | RASQSVYTKYLG | 360 | DASTRAT | 385 | QHYGGSPLIT | 410 |
| M20 | RASQSISSYLN | 361 | AASSLQS | 386 | QQSYSIPLT | 411 |
| M21 | RASQSISSWLA | 362 | KASSLES | 387 | QQYSSYPLT | 412 |
| M22 | RASQGISDYS | 363 | AASTLQS | 388 | QQYYSYPLT | 413 |
| M23 | RASENVNIWLA | 364 | KSSSLAS | 389 | QQYQSYPLT | 414 |
| M24 | RASRGISSALA | 365 | DASSLES | 390 | QQSYSTPWT | 415 |
| Ss1 | SASSSVSYMH | 366 | DTSKLAS | 391 | QQWSGYPLT | 416 |

In one embodiment, the mesothelin binding domain comprises one or more (e.g., all three) light chain complementary determining region 1 (LC CDR1), light chain complementary determining region 2 (LC CDR2), and light chain complementary determining region 3 (LC CDR3) of a mesothelin binding domain described herein, e.g., provided in Table 2 or 4, and/or one or more (e.g., all three) heavy chain complementary determining region 1 (HC CDR1), heavy chain complementary determining region 2 (HC CDR2), and heavy chain complementary determining region 3 (HC CDR3) of a mesothelin binding domain described herein, e.g., provided in Table 2 or 3. In one embodiment, the mesothelin binding domain comprises one, two, or all of LC CDR1, LC CDR2, and LC CDR3 of any amino acid sequences as provided in Table 4; and one, two or three of all of HC CDR1, HC CDR2 and HC CDR3, of any amino acid acid sequences as provided in Table 3.

In one embodiment, the mesothelin binding domain comprises a light chain variable region described herein (e.g., in Table 2) and/or a heavy chain variable region described herein (e.g., in Table 2). In one embodiment, the mesothelin binding domain is a scFv comprising a light chain and a heavy chain of an amino acid sequence listed in Table 2. In an embodiment, the mesothelin binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 2, or a sequence with 95-99% identity with an amino acid sequence provided in Table 2; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 2, or a sequence with 95-99% identity to an amino acid sequence provided in Table 2.

In one embodiment, the mesothelin binding domain comprises an amino acid sequence selected from a group consisting of SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67, SEQ ID NO: 68; SEQ ID NO: 69; and SEQ ID NO: 70; or an amino acid sequence having at least one, two or three modifications (e.g., substitutions, e.g., conservative substitutions) but not more than 30, 20 or 10 modifications (e.g., substitutions, e.g., conservative substitutions) to any of the aforesaid sequences; or a sequence with 95-99% identity to any of the aforesaid sequences. In one embodiment, the mesothelin binding domain is a scFv, and a light chain variable region comprising an amino acid sequence described herein, e.g., in Table 2, is attached to a heavy chain variable region comprising an amino acid sequence described herein, e.g., in Table 2, via a linker, e.g., a linker described herein. In one embodiment, the mesothelin binding domain includes a (Gly4-Ser)n linker, wherein n is 1, 2, 3, 4, 5, or 6, preferably 4 (SEQ ID NO: 417). The light chain variable region and heavy chain variable region of a scFv can be, e.g., in any of the following orientations: light chain variable region-linker-heavy chain variable region or heavy chain variable region-linker-light chain variable region.

In one embodiment, the antigen binding domain of a CAR described herein, e.g., a nonconditional or a conditional CAR, binds to Folate receptor alpha. In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484. In one embodiment, the antigen binding domain that binds to FRa is provided in Table 5. The antigen binding domain sequences provided in Table 5 include a VL and a VH, attached by a linker comprising SEQ ID NO: 30.

TABLE 5

Sequences for antigen binding domains that bind FRa (aa- amino acids, na- nucleic acid that encodes the corresponding polypeptide)

MOv19 scFv (AA)
(SEQ ID NO: 96)
SRAAQPAMAQVQLQQSGAELVKPGASVKISCKASGYSFTGYFMNWVKQSHGKSLEWIGRI

HPYDGDTFYNQNFKDKATLTVDKSSNTAHMELLSLTSEDFAVYYCTRYDGSRAMDYWGQG

TTVTVSSGGGGSGGGGSGGGGSDIELTQSPASLAVSLGQRAIISCKASQSVSFAGTSLMH

WYHQKPGQQPKLLIYRASNLEAGVPTRFSGSGSKTDFTLNIHPVEEEDAATYYCQQSREY

PYTFGGGTKLEIKRAA

MOv19 scFv (NA)
(SEQ ID NO: 97)
```
tctagagcgg cccagccggc catggcccag gtgcagctgc agcagtctgg agctgagctg   60
gtgaagcctg ggcttcagt  gaagatatcc tgcaaggctt ctggttactc atttactggc  120
tactttatga actgggtgaa gcagagccat ggaaagagcc ttgagtggat tggacgtatt  180
catccttacg atggtgatac tttctacaac cagaacttca aggacaaggc cacattgact  240
gtagacaaat cctctaacac agcccacatg agctcctga  gcctgacatc tgaggacttt  300
gcagtctatt attgtacaag atacgacggt agtcgggcta tggactactg gggccaaggg  360
accacggtca ccgtctcctc aggtggaggc ggttcaggcg gaggtggctc tggcggtggc  420
ggatcggaca tcgagctcac tcagtctcca gcttctttgg ctgtgtctct agggcagagg  480
gccatcatct cctgcaaggc cagccaaagt gtcagttttg ctggtactag tttaatgcac  540
tggtaccacc agaaaccagg acagcaaccc aaactcctca tctatcgtgc atccaaccta  600
gaagctgggg ttcctaccag gtttagtggc agtgggtcta gacagactt  cacccctcaat  660
atccatcctg tggaggagga ggatgctgca acctattact gtcagcaaag tagggaatat  720
ccgtacacgt tcggaggggg gacaaagttg gaaataaaac gggcggcc               768
```

C4 scFv (AA)
(SEQ ID NO: 98)
QLVESGGGLVQPGRSLRLSCTTSGFTFGDYAMIWARQAPGKGLEWVSSISSSSSYTYYAD

SVKGRFTISRDNAKNSLYLQMNSLRAEDTAVYYCARERYDEWSGMDVWGKGTTVTVSSGG

GGSGGGGSGGSAQSALTQPASVSGSPGQSITISCTGTSSDVGSYNLVSWYQQHPGKAPKL

MIYEGSKRPSGVSNRFSGSKSGNAASLTISGLQAEDEADYYCQSYDSSLSVVEGGGTKLT

VLG

C4 scFv (NA)
(SEQ ID NO: 99)
```
cagctggtgg agtctggggg aggcttggta cagccagggc ggtccctgag actctcctgc   60
acaacttctg gattcacttt tggtgattat gctatgatct gggcccgcca ggctccaggg  120
aaggggctgg agtgggtctc atccattagt agtagtagta gttacatata ctacgcagac  180
tcagtgaagg gccgattcac catctccaga gacaacgcca agaactcact gtatctgcaa  240
atgaacagcc tgagagccga ggacacggct gtgtattact gtgcgagaga acgatacgat  300
ttttggagtg gaatggacgt ctggggcaaa gggaccacgg tcaccgtctc gagtggtgga  360
ggcggttcag gcggaggtgg ctctggcggt agtgcacagt ctgccctgac tcagcctgcc  420
```

TABLE 5-continued

Sequences for antigen binding domains that
bind FRa (aa- amino acids, na- nucleic
acid that encodes the corresponding polypeptide)

```
tccgtgtctg ggtctcctgg acagtcgatc accatctcct gcactggaac cagcagtgat  480
gttgggagtt ataaccttgt ctcctggtac caacagcacc caggcaaagc ccccaaactc  540
atgatttatg agggcagtaa gcggccctca ggggtttcta atcgcttctc tggctccaag  600
tctggcaacg cggcctccct gacaatctct gggctccagg ctgaggacga ggctgattat  660
tactgccagt cctatgacag cagcctgagt gtggtattcg gcggagggac caagctgacc  720
gtcctaggt                                                          729
```

In one embodiment, the FRa binding domain comprises one or more (e.g., all three) light chain complementary determining region 1 (LC CDR1), light chain complementary determining region 2 (LC CDR2), and light chain complementary determining region 3 (LC CDR3) of a FRa binding domain described herein, e.g., provided in Table 5, and/or one or more (e.g., all three) heavy chain complementary determining region 1 (HC CDR1), heavy chain complementary determining region 2 (HC CDR2), and heavy chain complementary determining region 3 (HC CDR3) of a mesothelin binding domain described herein, e.g., provided in Table 5. In one embodiment, the mesothelin binding domain comprises one, two, or all of LC CDR1, LC CDR2, and LC CDR3 of any amino acid sequences as provided in Table 5; and one, two or three of all of HC CDR1, HC CDR2 and HC CDR3, of any amino acid sequences as provided in Table 5.

In one embodiment, the FRa binding domain comprises a light chain variable region described herein (e.g., in Table 5) and/or a heavy chain variable region described herein (e.g., in Table 5). In one embodiment, the FRa binding domain is a scFv comprising a light chain and a heavy chain of an amino acid sequence listed in Table 5. In an embodiment, the mesothelin binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 5, or a sequence with 95-99% identity with an amino acid sequence provided in Table 5; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 5, or a sequence with 95-99% identity to an amino acid sequence provided in Table 5.

In one embodiment, the FRa binding domain comprises an amino acid sequence of SEQ ID NO: 96 or SEQ ID NO: 98; or an amino acid sequence having at least one, two or three modifications (e.g., substitutions, e.g., conservative substitutions) but not more than 30, 20 or 10 modifications (e.g., substitutions, e.g., conservative substitutions) to any of the aforesaid sequences; or a sequence with 95-99% identity to any of the aforesaid sequences. In one embodiment, the mesothelin binding domain is a scFv, and a light chain variable region comprising an amino acid sequence described herein, e.g., in Table 5, is attached to a heavy chain variable region comprising an amino acid sequence described herein, e.g., in Table 5, via a linker, e.g., a linker described herein.

In one embodiment, an antigen binding domain against ERBB2 (Her2/neu) is an antigen binding portion, e.g., CDRs, of the antibody trastuzumab, or pertuzumab.

In one embodiment, an antigen binding domain against EGFRvIII is an antigen binding portion, e.g., CDRs, of the antibody described in US 2014/0322275, which is hereby incorporated by reference in its entirety.

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008, Blood 112(4): 1329-37; Tai et al., 2007, Blood. 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD).

In one embodiment, an antigen binding domain against CD33 is an antigen binding portion, e.g., CDRs, of an antibody described in, e.g., Bross et al., Clin Cancer Res 7(6):1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014).

In one embodiment, an antigen binding domain against GD2 is an antigen binding portion, e.g., CDRs, of an antibody described in, e.g., Mujoo et al., Cancer Res. 47(4):1098-1104 (1987); Cheung et al., Cancer Res 45(6): 2642-2649 (1985), Cheung et al., J Clin Oncol 5(9):1430-1440 (1987), Cheung et al., J Clin Oncol 16(9):3053-3060 (1998), Handgretinger et al., Cancer Immunol Immunother 35(3):199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment, an antigen binding domain against BCMA is an antigen binding portion, e.g., CDRs, of an antibody described in, e.g., WO2012163805, WO200112812, and WO2003062401.

In one embodiment, an antigen binding domain against Tn antigen is an antigen binding portion, e.g., CDRs, of an antibody described in, e.g., U.S. Pat. No. 8,440,798, Brooks et al., PNAS 107(22):10056-10061 (2010), and Stone et al., OncoImmunology 1(6):863-873 (2012).

In one embodiment, an antigen binding domain against PSMA is an antigen binding portion, e.g., CDRs, of an antibody described in, e.g., Parker et al., Protein Expr Purif 89(2):136-145 (2013), US 20110268656 (J591 ScFv); Frigerio et al, European J Cancer 49(9):2223-2232 (2013) (scFvD2B); WO 2006125481 (mAbs 3/A12, 3/E7 and 3/F11) and single chain antibody fragments (scFv A5 and D7).

In one embodiment, an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922, U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAP5), US Pat. Publication No. 2009/0304718; sibrotuzumab (see e.g., Hofheinz et al., Oncology Research and Treatment 26(1), 2003); and Tran et al., J Exp Med 210(6):1125-1135 (2013).

In one embodiment, an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122 (20): 3461-3472 (2013).

In one embodiment, an antigen binding domain against CEA is an antigen binding portion, e.g., CDRs, of an antibody described in, e.g., Chmielewski et al., Gastoenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion, e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in, e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. Nos. 7,253,263; 8,207, 308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11Ra is an antigen binding portion, e.g., CDRs, of an antibody available from Abcam (cat #ab55262) or Novus Biologicals (cat #EPR5446). In another embodiment, an antigen binding domain again IL-11Ra is a peptide, see, e.g., Huang et al., Cancer Res 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013 (2013), article ID 839831 (scFv CS-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC10 scFv).

In one embodiment, an antigen binding domain against CD24 is an antigen binding portion, e.g., CDRs, of an antibody described in, e.g., Maliar et al., Gastroenterology 143(5):1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signaling), or other commercially available antibodies.

In one embodiment, an antigen binding domain against CD20 is an antigen binding portion, e.g., CDRs, of the antibody Rituximab, Ofatumumab, Ocrelizumab, Veltuzumab, or GA101.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B: MAB5324 (EMD Millipore) In one embodiment, an antigen binding domain against Ephrin B2 is an antigen binding portion, e.g., CDRs, of an antibody described in, e.g., Abengozar et al., Blood 119(19):4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995.

In one embodiment, an antigen binding domain against CAIX is an antigen binding portion, e.g., CDRs, of the antibody clone 303123 (R&D Systems).

In one embodiment, an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment, an antigen binding domain against tyrosinase is an antigen binding portion, e.g., CDRs, of an antibody described in, e.g., U.S. Pat. No. 5,843,674; or US19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., US20100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1):e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion, e.g., CDRs, of an antibody described in, e.g., U.S. Pat. Nos. 8,603,466; 8,501,415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009); or an antibody from R&D:MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against plysialic acid is an antigen binding portion, e.g., CDRs, of an antibody described in, e.g., Nagae et al., J Biol Chem 288(47):33784-33796 (2013).

In one embodiment, an antigen binding domain against PLAC1 is an antigen binding portion, e.g., CDRs, of an antibody described in, e.g., Ghods et al., Biotechnol Appl Biochem 2013 doi:10.1002/bab.1177.

In one embodiment, an antigen binding domain against GloboH is an antigen binding portion of the antibody VK9; or an antibody described in, e.g., Kudryashov V et al, Glycoconj J. 15(3):243-9 (1998), Lou et al., Proc Natl Acad Sci USA 111(7):2482-2487 (2014); MBr1: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176):176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR-like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signaling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment, an antigen binding domain against TRP-2 is an antigen binding portion, e.g., CDRs, of an antibody described in, e.g., Wang et al, J Exp Med. 184(6): 2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment, an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences)

In one embodiment, an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and coworkers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530, 101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a VH4_4-59 germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a VK3_1.25 germline sequence. In one embodiment, the framework region can comprise, one, two, three, four or five modifications, e.g., substitutions, e.g., from the amino acid at the corresponding murine sequence.

In some aspects, the portion of a CAR composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human a cancer associated antigen as described herein. In some embodiments, a humanized antibody or antibody fragment may have improved affinity and/or specificity of binding to human a cancer associated antigen as described herein.

In one aspect, the antigen binding domain of the invention is characterized by particular functional features or properties of an antibody or antibody fragment. For example, in one aspect, the portion of a CAR composition of the invention that comprises an antigen binding domain specifically binds a tumor antigen as described herein.

In one aspect, the anti-cancer associated antigen as described herein binding domain is a fragment, e.g., a single chain variable fragment (scFv). In one aspect, the anti-cancer associated antigen as described herein binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a cancer associated antigen as described herein protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as (Gly$_4$Ser)n, where n is a positive integer equal to or greater than 1, 2, 3, 4, 5, 6, 7, 8, 9 or 10 (SEQ ID NO:28). In one embodiment, the linker can be (Gly$_4$Ser)$_4$ (SEQ ID NO:29) or (Gly$_4$Ser)$_3$ (SEQ ID NO:30). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellular, however, a fragment of such antigen (peptide) is presented on the surface of the cancer cells by MHC.

In one embodiment, the antigen binding domain of a cancer associated antigen described herein, e.g., scFv, comprises at least one mutation arising from the humanization process such that the mutated scFv confers improved stability to the CAR construct. In another embodiment, the antigen binding domain of a cancer associated antigen described herein, e.g., scFv, comprises at least 1, 2, 3, 4, 5, 6, 7, 8, 9, 10 mutations arising from the humanization process such that the mutated scFv confers improved stability to the CAR construct.

In one aspect, the antigen binding domain of the CAR comprises an amino acid sequence that is homologous to an antigen binding domain amino acid sequence described herein, and the antigen binding domain retains the desired functional properties of the antigen binding domain described herein.

In one specific aspect, the CAR composition of the invention comprises an antibody fragment. In a further aspect, the antibody fragment comprises a scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, the antibody fragment comprises a scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein. For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an antigen binding domain to a cancer associated antigen described herein, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the antigen binding domain to the cancer associated antigen described herein, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, a CAR, e.g., a conditional CAR or a nonconditional CAR, can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used, e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect, the transmembrane domain is capable of signaling to the intracellular domain(s) whenever the CAR has bound to a target. A transmembrane domain of particular use in this invention may include at least the transmembrane domain(s) of, e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:4.

In one aspect, the hinge or spacer comprises an IgG4 hinge. For example, in one embodiment, the hinge or spacer comprises a hinge of the amino acid sequence SEQ ID NO:6.

In some embodiments, the hinge or spacer comprises a hinge encoded by a nucleotide sequence SEQ ID NO:7.

In one aspect, the hinge or spacer comprises an IgD hinge. For example, in one embodiment, the hinge or spacer comprises a hinge of the amino acid sequence SEQ ID NO:8.

In some embodiments, the hinge or spacer comprises a hinge encoded by a nucleotide sequence of SEQ ID NO:9.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic signaling region of the CAR. A glycine-serine doublet provides a particularly suitable linker. For example, in one aspect, the linker comprises the amino acid sequence of GGGGSGGGGS (SEQ ID NO: 10). In some embodiments, the linker is encoded by a nucleotide sequence of GGTGGCGGAGGTTCTGGAGGTGGAGGTTCC (SEQ ID NO:23).

In one aspect, the hinge or spacer comprises a KIR2DS2 hinge and portions thereof.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary cytoplasmic signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon R1b), CD3 gamma, CD3 delta, CD3 epsilon, CD5, CD22, CD79a, CD79b, CD278 (also known as "ICOS"), FcεRI, CD66d, DAP10, and DAP12. In one embodiment, a CAR of the invention comprises an intracellular signaling domain, e.g., a primary signaling domain of CD3-zeta, e.g., a CD3-zeta sequence described herein.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32. The intracellular domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1 (also known as PD1), ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. For example, CD27 costimulation has been demonstrated to enhance expansion, effector function, and survival of human CART cells in vitro and augments human T cell persistence and antitumor activity in vivo (Song et al. Blood. 2012; 119(3): 696-706).

The intracellular signaling domains within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling domains. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 14. In one aspect, the signaling domain of CD3-zeta is a signaling domain of SEQ ID NO: 18 (mutant CD3-zeta) or SEQ ID NO: 20 (wild type human CD3-zeta).

In one aspect, the intracellular is designed to comprise the signaling domain of CD3-zeta and the signaling domain of 4-1BB. In one aspect, the signaling domain of 4-1BB comprises an amino acid sequence of SEQ ID NO: 14. In one aspect, the signaling domain of 4-1BB is encoded by a nucleic acid sequence of SEQ ID NO: 15.

In one aspect, the intracellular signaling domain is designed to comprise the signaling domain of CD3-zeta and the signaling domain of CD27. In one aspect, the signaling domain of CD27 comprises an amino acid sequence of SEQ ID NO: 16. In one aspect, the signalling domain of CD27 is encoded by a nucleic acid sequence of SEQ ID NO: 17.

In one aspect, the intracellular is designed to comprise the signaling domain of CD3-zeta and the signaling domain of CD28. In one aspect, the signaling domain of CD28 comprises an amino acid sequence of SEQ ID NO: 44. In one aspect, the signaling domain of CD28 is encoded by a nucleic acid sequence of SEQ ID NO: 45.

In one aspect, the intracellular is designed to comprise the signaling domain of CD3-zeta and the signaling domain of ICOS. In one aspect, the signaling domain of ICOS comprises an amino acid sequence of SEQ ID NO: 40. In one aspect, the signaling domain of ICOS is encoded by a nucleic acid sequence of SEQ ID NO: 41.

Expression of Multiple CARs

In one aspect, the CAR-expressing cell described herein comprises a first CAR, e.g., a conditional CAR, and a second CAR, e.g., a nonconditional CAR. In one embodiment, the first CAR comprises an antigen binding domain to a different target than the antigen binding domain of the second CAR (e.g., a target other than a cancer associated antigen described herein or a different cancer associated antigen described herein). In one embodiment, the second CAR includes an antigen binding domain to a target expressed the same cancer cell type as the cancer associated antigen. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27, ICOS or OX-40, onto the first CAR, and the primary signaling domain, e.g., CD3 zeta, on the second CAR can limit the CAR activity to cells where both targets are expressed. In one embodiment, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In one embodiment, the CAR-expressing cell further comprises an XCAR described herein and an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

In one embodiment, when the CAR-expressing cell comprises two or more different CARs, e.g., a nonconditional CAR or a conditional CAR, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising a antigen binding domains that minimize such interactions, as well as methods of making and using such cells and nucleic acids. In an embodiment the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is a scFv, and the other is not a scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

In some embodiments, the antigen binding domain of one of said first CAR said second CAR comprises an scFv, and the other comprises a single VH domain, e.g., a camelid, shark, or lamprey single VH domain, or a single VH domain derived from a human or mouse sequence. In some embodiments, the antigen binding domain of one of said first CAR said second CAR comprises an scFv, and the other comprises a nanobody. In some embodiments, the antigen binding domain of one of said first CAR said second CAR comprises an scFv, and the other comprises a camelid VHH domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CAR.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), fused to a transmembrane domain and intracellular signaling domains such as 41BB and CD3 zeta (also referred to herein as a PD1 CAR). In one embodiment, the PD1 CAR, when used in combinations with a XCAR described herein, improves the persistence of the T cell. In one embodiment, the CAR is a PD1 CAR comprising the extracellular domain of PD1, e.g., SEQ ID NO: 24, and as indicated as underlined in SEQ ID NO: 39. In one embodiment, the PD1 CAR comprises the amino acid sequence of SEQ ID NO:39. In one embodiment, the PD1 CAR comprises the amino acid sequence provided in SEQ ID NO:26.

In one embodiment, the agent comprises a nucleic acid sequence encoding the PD1 CAR, e.g., the PD1 CAR described herein. In one embodiment, the nucleic acid sequence for the PD1 CAR comprises SEQ ID NO: 27, with the PD1 ECD underlined.

In another aspect, the present invention provides a population of CAR-expressing cells, e.g., CART cells or CAR-expressing NK cells. In some embodiments, the population of CAR-expressing cells comprises a mixture of cells expressing different CARs. For example, in one embodiment, the population of CAR-expressing cells can include a first cell expressing a CAR having an antigen binding domain to a cancer associated antigen described herein, and a second cell expressing a CAR having a different antigen binding domain, e.g., an antigen binding domain to a different cancer associated antigen described herein, e.g., an antigen binding domain to a cancer associated antigen described herein that differs from the cancer associated antigen bound by the antigen binding domain of the CAR expressed by the first cell. As another example, the population of CAR-expressing cells can include a first cell expressing a CAR that includes an antigen binding domain to a cancer associated antigen described herein, and a second cell expressing a CAR that includes an antigen binding domain to a target other than a cancer associated antigen as described herein. In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an antigen binding domain to a cancer associated antigen described herein, and a second cell expressing another agent, e.g., an agent which enhances the activity of a CAR-expressing cell. For example, in one embodiment, the agent can be an agent which inhibits an inhibitory molecule. Inhibitory molecules, e.g., PD-1, can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these, and a second polypeptide which is an intracellular signaling domain described herein (e.g., comprising a costimulatory domain (e.g., 41BB, CD27, OX40, ICOS or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells, e.g., CART cells, e.g., a mixture of cells expressing different CARs, in combination with another agent, e.g., a kinase inhibitor, such as a kinase inhibitor described herein. In another aspect, the present invention provides methods comprising administering a population of cells wherein at least one cell in the population expresses a CAR having an antigen binding domain of a cancer associated antigen described herein, and a second cell expressing another agent, e.g., an agent which enhances the activity of a CAR-expressing cell, in combination with another agent, e.g., a kinase inhibitor, such as a kinase inhibitor described herein.

Exemplary CAR Molecules

Exemplary CAR molecules that bind to mesothelin are provided in Table 6. The CAR molecules in Table 6 comprise a mesothelin antigen binding domain, e.g., an amino acid sequence of any mesothelin antigen binding domain provided in Table 2. The leader sequence is in bold and underlined, CDRs are underlined, and the linker sequence between the heavy and light chain of the antigen binding region is shaded in grey. Amino acid and nucleic acid sequences are provided.

TABLE 6

Exemplary mesothelin CAR molecules (aa—amino acids; na—nucleic acid encoding the corresponding polypeptide)

| Name | Sequence | SEQ ID NO: |
|---|---|---|
| M1 CAR (aa) | MALPVTALLLPLALLLHAARPQVQLQQSGAEVKKPGASVKVSCKASGYTFTGYYMHWVRQ APGQGLEWMGRINPNSGGTNYAQKFQGRVTMTRDTSISTAYMELSRLRSEDTAVYYCARG RYYGMDVWGQGTMVTVSSGGGGSGGGGSGGGGSGGGGSEIVLTQSPATLSLSPGERATIS CRASQSVSSNFAWYQQRPGQAPRLLIYDASNRATGIPPRFSGSGSGTDFTLTISSLEPED FAAYYCHQRSNWLYTFGQGTKVDIKTTTPAPRPPTPAPTIASQPLSLRPEACRPAAGGAV HTRGLDFACDIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVLDKRRGRDPE MGGKPRRKNPQEGLYNELQKDKMAEAYSEIGMKGERRRGKGHDGLYQGLSTATKDTYDAL HMQALPPR | 100 |
| M2 CAR (aa) | MALPVTALLLPLALLLHAARPQVQLVQSGAEVKKPGASVKVSCKASGYTFTGYYMHWVRQ APGQGLEWMGWINPNSGGTNYAQKFQGRVTMTRDTSISTAYMELSRLRSDDTAVYYCARD LRRTVVTPRAYYGMDVWGQGTTVTVSSGGGGSGGGGSGGGGSGGGGSDIQLTQSPSTLSA SVGDRVTITCQASQDISNSLNWYQQKAGKAPKLLIYDASTLETGVPSRFSGSGSGTDFSF TISSLQPEDIATYYCQQHDNLPLTFGQGTKVEIKTTTPAPRPPTPAPTIASQPLSLRPEA CRPAAGGAVHTRGLDFACDIYIWAPLAGTCGVLLLSLVITLYCKRGRKKLLYIFKQPFMR PVQTTQEEDGCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGHDGLYQGLST ATKDTYDALHMQALPPR | 101 |
| M3 CAR (aa) | MALPVTALLLPLALLLHAARPQVQLVQSGAEVKKPGAPVKVSCKASGYTFTGYYMHWVRQ APGQGLEWMGWINPNSGGTNYAQKFQGRVTMTRDTSISTAYMELSRLRSDDTAVYYCARG EWDGSYYYDYWGQGTLVTVSSGGGGSGGGGSGGGGSGGGGSDIVLTQTPSSLSASVGDRV TITCRASQSINTYLNWYQHKPGKAPKLLIYAASSLQSGVPSRFSGSGSGTDFTLTISSLQ | 102 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | PEDFATYYCQQSFSPLTFGGGTKLEIKTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR | |
| M4 CAR (aa) | MALPVTALLLPLALLLHAARPQVQLVESGGGLVQPGGSLRLSCAASGFTFSSYWMHWVRQ VPGKGLVWVSRINTDGSTTTYADSVEGRFTISRDNAKNTLYLQMNSLRDDDTAVYYCVGG HWAVWGQGTTVTVSSGGGGSGGGGSGGGGSGGGGSDIQMTQSPSTLSASVGDRVTITCRA SQSISDRLAWYQQKPGKAPKLLIYKASSLESGVPSRFSGSGSGTEFTLTISSLQPDDFAV YYCQQYGHLPMYTFGQGTKVEIKTTTPAPRPPTPAPTIASQPLSLRPEACRPAAGGAVHT RGLDFACDIYIWAPLAGTCGVLLLSLVITLYCKRGRKKLLYIFKQPFMRPVQTTQEEDGC SCRFPEEEEGGCELRVKFSRSADAPAYKQGQNQLYNELNLGRREEYDVLDKRRGRDPEMG GKPRRKNPQEGLYNELQKDKMAEAYSEIGMKGERRRGKGHDGLYQGLSTATKDTYDALHM QALPPR | 103 |
| M5 CAR (aa) | MALPVTALLLPLALLLHAARPQVQLVQSGAEVEKPGASVKVSCKASGYTFTDYYMHWVRQ APGQGLEWMGWINPNSGGTNYAQKFQGRVTMTRDTSISTAYMELSRLRSDDTAVYYCASG WDFDYWGQGTLVTVSSGGGGSGGGGSGGGGSGGGGSDIVMTQSPSSLSASVGDRVTITCR ASQSIRYYLSWYQQKPGKAPKLLIYTASILQNGVPSRFSGSGSGTDFTLTISSLQPEDFA TYYCLQTYTTPDFGPGTKVEIKTTTPAPRPPTPAPTIASQPLSLRPEACRPAAGGAVHTR GLDFACDIYIWAPLAGTCGVLLLSLVITLYCKRGRKKLLYIFKQPFMRPVQTTQEEDGCS CRFPEEEEGGCELRVKFSRSADAPAYKQGQNQLYNELNLGRREEYDVLDKRRGRDPEMGG KPRRKNPQEGLYNELQKDKMAEAYSEIGMKGERRRGKGHDGLYQGLSTATKDTYDALHMQ ALPPR | 104 |
| M6 CAR (aa) | MALPVTALLLPLALLLHAARPQVQLVQSGAEVKKPGASVKVSCKASGYTFTSYYMHWVRQ APGQGLEWMGIINPSGGSTSYAQKFQGRVTMTRDTSTSTVYMELSSLRSEDTAVYYCARY RLIAVAGDYYYGMDVWGQGTMVTVSSGGGGSGGGGSGGGGSGGGGSGGGGSDIQMTQSPSSVSA SVGDRVTITCRASQGVGRWLAWYQQKPGTAPKLLIYAASTLQSGVPSRFSGSGSGTDFTL TINNLQPEDFATYYCQQANSFPLTFGGGTRLEIKTTTPAPRPPTPAPTIASQPLSLRPEA CRPAAGGAVHTRGLDFACDIYIWAPLAGTCGVLLLSLVITLYCKRGRKKLLYIFKQPFMR PVQTTQEEDGCSCRFPEEEEGGCELRVKFSRSADAPAYKQGQNQLYNELNLGRREEYDVL | 105 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | DKRRGRDPEMGGKPRRKNPQEGLYNELQKDKMAEAYSEIGMKGERRRGKGHDGLYQGLST ATKDTYDALHMQALPPR | |
| M7 CAR (aa) | MALPVTALLLPLALLLHAARPQVQLVQSGGGVVQPGRSLRLSCAASGFTFSSYAMHWVRQ APGKGLEWVAVISYDGSNKYYADSVKGRFTISRDNSKNTLYLQMNSLRAEDTAVYYCARW KVSSSSPAFDYWGQGTLVTVSSGGGGSGGGGSGGGGSGGGGSGGGGSEIVLTQSPATLSLSPGER AILSCRASQSVYTKYLGWYQQKPGQAPRLLIYDASTRATGIPDRFSGSGSGTDFTLTINR LEPEDFAVYYCQHYGGSPLITFGQGTRLEIKTTTPAPRPPTPAPTIASQPLSLRPEACRP AAGGAVHTRGLDFACDIYIWAPLAGTCGVLLLSLVITLYCKRGRKKLLYIFKQPFMRPVQ TTQEEDGCSCRFPEEEEGGCELRVKFSRSADAPAYKQGQNQLYNELNLGRREEYDVLDKR RGRDPEMGGKPRRKNPQEGLYNELQKDKMAEAYSEIGMKGERRRGKGHDGLYQGLSTATK DTYDALHMQALPPR | 106 |
| M8 CAR (aa) | MALPVTALLLPLALLLHAARPQVQLQQSGAEVKKPGASVKVSCKTSGYPFTGYSLHWVRQ APGQGLEWMGWINPNSGGTNYAQKFQGRVTMTRDTSISTAYMELSRLRSDDTAVYYCARD HYGGNSLFYWGQGTLVTVSSGGGGSGGGGSGGGGSGGGGSGGGGSDIQLTQSQSSISASVGDTVS ITCRASQDSGTWLAWYQQKPGKAPNLLMYDASTLEDGVPSRFSGSASGTEFTLYVNRLQP EDSATYYCQQYNSYPLTFGGGTKVDIKTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR | 107 |
| M9 CAR (aa) | MALPVTALLLPLALLLHAARPQVQLVQSGAEVKKPGASVEVSCKASGYTFTSYYMHWVRQ APGQGLEWMGIINPSGGSTGYAQKFQGRVTMTRDTSTSTVHMELSSLRSEDTAVYYCARG GYSSSSDAFDIWGQGTMVTVSSGGGGSGGGGSGGGGSGGGGSGGGGSDIQMTQSPPSLSASVGDR VTITCRASQDISSALAWYQQKPGTPPKLLIYDASSLESGVPSRFSGSGSGTDFTLTISSL QPEDFATYYCQQFSSYPLTFGGGTRLEIKTTTPAPRPPTPAPTIASQPLSLRPEACRPAA GGAVHTRGLDFACDIYIWAPLAGTCGVLLLSLVITLYCKRGRKKLLYIFKQPFMRPVQTT QEEDGCSCRFPEEEEGGCELRVKFSRSADAPAYKQGQNQLYNELNLGRREEYDVLDKRRG RDPEMGGKPRRKNPQEGLYNELQKDKMAEAYSEIGMKGERRRGKGHDGLYQGLSTATKDT YDALHMQALPPR | 108 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| M10 CAR (aa) | MALPVTALLLPLALLLHAARPQVQLVQSGAEVKKPGASVKVSCKASGYTFTSYGISWVRQ APGQGLEWMGWISAYNGNTNYAQKLQGRVTMTTDTSTSTAYMELRSLRSDDTAVYYCARV AGGIYYYYGMDVWGQGTTITVSSGGGGSGGGGSGGGGSGGGGSDIVMTQTPDSLAVSLGE RATISCKSSHSVLYNRNNKNYLAWYQQKPGQPPKLLFYWASTRKSGVPDRFSGSGSGTDF TLTISSLQPEDFATYFCQQTQTFPLTFGQGTRLEINTTTPAPRPPTPAPTIASQPLSLRP EACRPAAGGAVHTRGLDFACDIYIWAPLAGTCGVLLLSLVITLYCKRGRKKLLYIFKQPF MRPVQTTQEEDGCSCRFPEEEEGGCELRVKFSRSADAPAYKQGQNQLYNELNLGRREEYD VLDKRRGRDPEMGGKPRRKNPQEGLYNELQKDKMAEAYSEIGMKGERRRGKHDGLYQGL STATKDTYDALHMQALPPR | 109 |
| M11 CAR (aa) | MALPVTALLLPLALLLHAARPQVQLQQSGAEVKKPGASVKVSCKASGYTFTGYYMHWVRQ APGQGLEWMGWINPNSGGTNYAQNFQGRVTMTRDTSISTAYMELRRLRSDDTAVYYCASG WDFDYWGQGTLVTVSSGGGGSGGGGSGGGGSGGGGSDIRMTQSPSSLSASVGDRVTITCR ASQSIRYYLSWYQQKPGKAPKLLIYTASILQNGVPSRFSGSGSGTDFTLTISSLQPEDFA TYYCLQTYTTPDFGPGTKVEIKTTTPAPRPPTPAPTIASQPLSLRPEACRPAAGGAVHTR GLDFACDIYIWAPLAGTCGVLLLSLVITLYCKRGRKKLLYIFKQPFMRPVQTTQEEDGCS CRFPEEEEGGCELRVKFSRSADAPAYKQGQNQLYNELNLGRREEYDVLDKRRGRDPEMGG KPRRKNPQEGLYNELQKDKMAEAYSEIGMKGERRRGKHDGLYQGLSTATKDTYDALHMQ ALPPR | 110 |
| M12 CAR (aa) | MALPVTALLLPLALLLHAARPQVQLVQSGAEVKKPGASVKVSCKASGYTFTGYYMHWVRQ APGQGLEWMGRINPNSGGTNYAQKFQGRVTMTTDTSTSTAYMELRSLRSDDTAVYYCART TTSYAFDIWGQGTMVTVSSGGGGSGGGGSGGGGSGGGGSDIQLTQSPSTLSASVGDRVTI TCRASQSISTWLAWYQQKPGKAPNLLIYKASTLESGVPSRFSGSGSGTEFTLTISSLQPD DFATYYCQQYNTYSPYTFGQGTKLEIKTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKHDGLYQGLSTATKDTYD ALHMQALPPR | 111 |
| M13 CAR (aa) | MALPVTALLLPLALLLHAARPQVQLVQSGGGLVKPGGSLRLSCEASGFIFSDYYMGWIRQ APGKGLEWVSYIGRSGSSMYYADSVKGRFTFSRDNAKNSLYLQMNSLRAEDTAVYYVAAS PVVAATEDFQHWGQGTLVTVSSGGGGSGGGGSGGGGSGGGGSDIVMTQTPATLSLSPGER | 112 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | ATLSC<u>RASQSVTSNYLA</u>WYQQKPGQAPRLLLF<u>GASTRAT</u>GIPDRFSGSGSTDFTLTINR | |
| | LEPEDFAMYYC<u>QQYGSAPVT</u>FGQGTKLEIKTTTPAPRPPTPAPTIASQPLSLRPEACRPA | |
| | AGGAVHTRGLDFACDIYIWAPLAGTCGVLLLSLVITLYCKRGRKKLLYIFKQPFMRPVQT | |
| | TQEEDGCSCRFPEEEEGGCELRVKFSRSADAPAYKQGQNQLYNELNLGRREEYDVLDKRR | |
| | GRDPEMGGKPRRKNPQEGLYNELQKDKMAEAYSEIGMKGERRRGKHDGLYQGLSTATKD | |
| | TYDALHMQALPPR | |
| M14 CAR (aa) | MALPVTALLLPLALLLHAARPQVQLVQSGAEVRAPGASVKISCKASG<u>FTFRGYYIH</u>WVRQ | 113 |
| | APGQGLEWMG<u>IINPSGGSRAYAQKFQG</u>RVTMTRDTSTSTVYMELSSLRSDDTAMYYC<u>ART</u> | |
| | <u>ASCGGDCYYLDY</u>WGQGTLVTVSS<u>GGGGSGGGGSGGGGSGGGGS</u>SDIQMTQSPPTLSASVGD | |
| | RVTITC<u>RASENVNIW</u>LAWYQQKPGKAPKLLIY<u>KSSSLAS</u>GVPSRFSGSGSGAEFTLTISS | |
| | LQPDDFATYYC<u>QQYQSYPLT</u>FGGGTKVDIKTTTPAPRPPTPAPTIASQOLSLRPEACRPA | |
| | AGGAVHTRGLDFACDIYIWAPLAGTCGVLLLSLVITLYCKRGRKKLLYIFKQPFMRPVQT | |
| | TQEEDGCSCRFPEEEEGGCELRVKFSRSADAPAYKQGQNQLYNELNLGRREEYDVLDKRR | |
| | GRDPEMGGKPRRKNPQEGLYNELQKDKMAEAYSEIGMKGERRRGKHDGLYQGLSTATKD | |
| | TYDALHMQALPPR | |
| M15 CAR (aa) | MALPVTALLLPLALLLHAARPQVQLVQSGGGLVQPGRSLRLSCAASG<u>FTFDDYAMH</u>WVRQ | 114 |
| | APGKGLEWVS<u>GISWNSGSIGYADSVKFR</u>FTISRDNAKNSLYLQMNSLRAEDTAVYYCAK<u>D</u> | |
| | <u>GSSSWSWGYFDY</u>WGQGTLVTVSS<u>GGGGSGGGGSGGGGSGGGGS</u>SSELTQDPAVSVALGQTVRTTC | |
| | <u>QGDALRSYYAS</u>WYQQKPGQAPMLVIY<u>GKNNRPS</u>GIPDRFSGSDSGDTASLTITGAQAEDE | |
| | ADYYC<u>NSRDSSGYPV</u>FGTGTKVTVLTTTPAPRPPTPAPTIASQPLSLRPEACRPAAGGAV | |
| | HTRGLDFACDIYIWAPLAGTCGVLLLSLVITLYCKRGRKKLLYIFKQPFMRPVQTTQEED | |
| | GCSCRFPEEEEGGCELRVKFSRSADAPAYKQGQNQLYNELNLGRREEYDVLDKRRGRDPE | |
| | MGGKPRRKNPQEGLYNELQKDKMAEAYSEIGMKGERRRGKHDGLYQGLSTATKDTYDAL | |
| | HMQALPPR | |
| M16 CAR (aa) | MALPVTALLLPLALLLHAARPEVQLVESGGGLVQPGRSLRLSCAASG<u>FTFDDYAMH</u>WVRQ | 115 |
| | APGKGLEWVS<u>GISWNSGSTGYADSVKGR</u>FTISRDNAKNSLYLQMNSLRAEDTALYYCAK<u>D</u> | |
| | <u>SSSWYGGGSAFDI</u>WGQGTMVTVSS<u>GGGGSGGGGSGGGGSGGGGS</u>SSELTQEPAVSVALGQTVRIT | |
| | C<u>QGDSLRSYYAS</u>WYQQKPGQAPVLVIF<u>GRSRRPS</u>GIPDRFSGSSSGNTASLIITGAQAED | |
| | EADYYC<u>NSRDNTANHYV</u>FGTGTKLTVLTTTPAPRPPTPAPTIASQPLSLRPEACRPAAGG | |
| | AVHTRGLDFACDIYIWAPLAGTCGVLLLSLVITLYCKRGRKKLLYIFKQPFMRPVQTTQE | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | EDGCSCRFPEEEEGGCELRVKFSRSADAPAYKQGQNQLYNELNLGRREEYDVLDKRRGRD | |
| | PEMGGKPRRKNPQEGLYNELQKDKMAEAYSEIGMKGERRRGKGHDGLYQGLSTATKDTYD | |
| | ALHMQALPPR | |
| M17 CAR (aa) | MALPVTALLLPLALLLHAARPEVQLVESGGGLVQPGRSLRLSCAASGFTFDDYAMHWVRQ | 116 |
| | APGKGLEWVSGISWNSGSTGYADSVKGRFTISRDNAKNSLYLQMNSLRAEDTALYYCAKD | |
| | SSSWYGGGSAFDIWGQGTMVTVSSGGGGSGGGGSGGGGSSSELTQDPAVSVALGQTVRIT | |
| | CQGDSLRSYYASWYQQKPGQAPVLVIYGKNNRPSGIPDRFSGSSSGNTASLTITGAQAED | |
| | EADYYCNSRGSSGNHYVFGTGTKVTVLTTTPAPRPPTPAPTIASQPLSLRPEACRPAAGG | |
| | AVHTRGLDFACDIYIWAPLAGTCGVLLLSLVITLYCKRGRKKLLYIFKQPFMRPVQTTQE | |
| | EDGCSCRFPEEEEGGCELRVKFSRSADAPAYKQGQNQLYNELNLGRREEYDVLDKRRGRD | |
| | PEMGGKPRRKNPQEGLYNELQKDLMAEAYSEIGMKGERRRGKGHDGLYQGLSTATKDTYD | |
| | ALHMQALPPR | |
| M18 CAR (aa) | MALPVTALLLPLALLLHAARPQVQLVQSGGGLVQPGGSLRLSCAASGFTFSSYWMHWVRQ | 117 |
| | APGKGLVWVSRINSDGSSTSYADSVKGRFTISRDNAKNTLYLQMNSLRAEDTAVYYCVRT | |
| | GWVGSYYYYMDVWGKGTTVTVSSGGGGSGGGGSGGGGSGGGGSEIVLTQSPGTLSLSPGE | |
| | RATLSCRASQSVSSNYLAWYQQKPGQPPRLLIYDVSTRATGIPARFSGGGSGTDFTLTIS | |
| | SLEPEDFAVYYCQQRSNWPPWTFGQGTKVEIKTTTPAPRPPTPAPTIASQPLSLRPEACR | |
| | PAAGGAVHTRGLDFACDIYIWAPLAGTCGVLLLSLVITLYCKRGRKKLLYIFKQPFMRPV | |
| | QTTQEEDGCSCRFPEEEEGGCELRVKFSRSADAPAYKQGQNQLYNELNLGRREEYDVLDK | |
| | RRGRDPEMGGKPRRKNPQEGLYNELQKDKMAEAYSEIGMKGERRRGKGHDGLYQGLSTAT | |
| | KDTYDALHMQALPPR | |
| M19 CAR (aa) | MALPVTALLLPLALLLHAARPQVQLVQSGGGVVQPGRSLRLSCAASGFTFSSYGMHWVRQ | 118 |
| | APGKGLEWVAVISYDGSNKYYADSVKGRFTISRDNSKNTLYLQMNSLRAEDTAVYYCAKG | |
| | YSRYYYYGMDVWGQGTTVTVSSGGGGSGGGGSGGGGSGGGGSEIVMTQSPATLSLSPGER | |
| | AILSCRASQSVYTKYLGWYQQKPGQAPRLLIYDASTRATGIPDRFSGSGSGTDFTLTINR | |
| | LEPEDFAVYYCQHYGGSPLITFGQGTKVDIKTTTPAPRPPTPAPTIASQPLSLRPEACRP | |
| | AAGGAVHTRGLDFACDIYIWAPLAGTCGVLLLSLVITLYCKRGRKKLLYIFKQPFMRPVQ | |
| | TTQEEDGCSCRFPEEEEGGCELRVKFSRSADAPAYKQGQNQLYNELNLGRREEYDVLDKR | |
| | RGRDPEMGGKPRRKNPQEGLYNELQKDKMAEAYSEIGMKGERRRGKGHDGLYQGLSTATK | |
| | DTYDALHMQALPPR | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| M20 CAR (aa) | MALPVTALLLPLALLLHAARPQVQLVQSGGGLVQPGGSLRLSCAASG<u>FTFSSYAMS</u>WVRQ APGKGLEWVS<u>AISGSGGSTYYADSVKG</u>RFTISRDNSKNTLYLQMNSLRAEDTAVYYCAK<u>R EAAAGHDWYFDL</u>WGRGTLVTVSS<u>GGGGSGGGGSGGGGSGGGGS</u>DIRVTQSPSSLSASVGD RVTITC<u>RASQSISSYLN</u>WYQQKPGKAPKLLIY<u>AASSLQS</u>GVPSRFSGSGSGTDFTLTISS LQPEDFATYYC<u>QQSYSIPLT</u>FGQGTKVEIKTTTPAPRPPTPAPTIASQPLSLRPEACRPA AGGAVHTRGLDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRREEYDVLDKRR GRDPEMGGKPRRKNPQEGLYNELQKDMAEAYSEIGMKGERRRGKGHDGLYQGLSTATKD TYDALHMQALPPR | 119 |
| M21 CAR (aa) | MALPVTALLLPLALLLHAARPQVQLVQSWAEVKKPGASVKVSCKASG<u>YTFTSYYMH</u>WVRQ APGQGLEWMG<u>IINPSGGSTSYAQKFQG</u>RVTMTRDTSTSTVYMELSNLRSEDTAVYYCARS <u>PRVTTGYFDY</u>WGQGTLVTVSS<u>GGGGSGGGGSGGGGSGGGGS</u>DIQLTQSPSTLSASVGDRV TITC<u>RASQSISSWLA</u>WYQQKPGKAPKLLIY<u>KASSLES</u>GVPSRFSGSGSGTEFTLTISSLQ PDDFATYYCQQ<u>YSSYPLT</u>FGGGTRLEIKTTTPAPRPPTPAPTIASQPLSLSPEACRPAAG GAVHTRGLDFACDIYIWAPLAGTCGVLLLSLVITLYCKRGRKKLLYIFKQPFMRPVQTTQ EEDGCSCRFPEEEEGGCELRVKFSRSADAPAYKQGQNQLYNELNLGRREEYDVLDKRRGR DPEMGGKPRRKNPQEGLYNELQKDMAEAYSEIGMKGERRRGKGHDGLYQGLSTATKDTY DALHMQALPPR | 120 |
| M22 CAR (aa) | MALPVTALLLPLALLLHAARPQVQLVQSGAEVRRPGASVKISCKASG<u>DTSTRHYIH</u>WLRQ APGQGPEWMG<u>VINPTTGPATGSPAYAQMLQG</u>RVTMTRDTSTRTVYMELRSLRFEDTAVYY CARS<u>VVGRSAPYYFDY</u>WGQGTLVTVSS<u>GGGGSGGGGSGGGGSGGGGS</u>DIQMTQSPSSLSA SVGDRVTITC<u>RASQGISDYSA</u>WYQQKPGKAPKLLIY<u>AASTLQS</u>GVPSRFSGSGSGTDFTL TISYLQSEDFATYYC<u>QQYYSYPLT</u>FGGGTKVDIKTTTPAPRPPTPAPTIASQPLSLRPEA CRPAAGGAVHTRGLDFACDIYIWAPLAGTCGVLLLSLVITLYCKRGRKKLLYIFKQPFMR PVQTTQEEDGCSCRFPEEEEGGCELRVKFSRSADAPAYKQGQNQLYNELNLGRREEYDVL DKRRGRDPEMGGKPRRKNPQEGLYNELQKDMAEAYSEIGMKGERRRGKGHDGLYQGLST ATKDTYDALHMQALPPR | 121 |
| M23 CAR (aa) | MALPVTALLLPLALLLHAARPQVQLQQSGAEVKKPGASVKVSCKASG<u>YTFTNYYMH</u>WVRQ APGQGLEWMG<u>IINPSGGYTTYAQKFQG</u>RLTMTRDTSTSTVYMELSSLRSEDTAVYYCARI <u>RSCGGDCYYFDN</u>WGQGTLVTVSS<u>GGGGSGGGGSGGGGSGGGGS</u>DIQLTQSPSTLSASVGD | 122 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | RVTITC<u>RASENVNIWLA</u>WYQQKPGKAPKLLIY<u>KSSSLAS</u>GVPSRFSGSGSGAEFTLTISS | |
| | LQPDDFATYYC<u>QQYQSYPLT</u>FGGGTKVDIKTTTPAPRPPTPAPTIASQPLSLRPEACRPA | |
| | AGGAVHTRGLDFACDIYIWAPLAGTCGVLLLSLVITLYCKRGRKKLLYIFKQPFMRPVQT | |
| | TQEEDGCSCRFPEEEEGGCELRVKFSRSADAPAYKQGQNQLYNELNLGRREEYDVLDKRR | |
| | GRDPEMGGKPRRKNPQEGLYNELQKDKMAEAYSEIGMKGERRRGKGHDGLYQGLSTATKD | |
| | TYDALHMQALPPR | |
| M24 CAR (aa) | MALPVTALLLPLALLLHAARPQITLKESGPALVKPTQTLTLTCTFSG<u>FSLSTAGVHVGWI</u> | 123 |
| | RQPPGKALEWLA<u>LISWADDKRYRPSLRS</u>RLDITRVTSKDQVVLSMTNMQPEDTATYYCAL | |
| | <u>QGFDGYEAN</u>WGPGTLVTVSS<u>GGGGSGGGGSGGGGSGGGGS</u>DIVMTQSPSSLSASAGDRVT | |
| | ITC<u>RASRGISSALA</u>WYQQKPGKPPKLLIY<u>DASSLES</u>GVP[SRFSGSGSGTDFTLTIDSLEP | |
| | EDFATYYC<u>QQSYSTPWT</u>FGQGTKVDIKTTTPAPRPPTPAPTIASQPLSLRPEACRPAAGG | |
| | AVHTRGLDFACDIYIWAPLAGTCGVLLLSLVITLYCKRGRKKLLYIFKQPFMRPVQTTQE | |
| | EDGCSCRFPEEEEGGCELRVKFSRSADAPAYKQGQNQLYNELNLGRREEYDVLDKRRGRD | |
| | PEMGGKPRRKNPQEGLYNELQKDKMAEAYSEIGMKGERRRGKGHDGLYQGLSTATKDTYD | |
| | ALHMQALPPR | |
| SS1 CAR (aa) | MALPVTALLLPLALLLHAARPQVQLQQSGPELEKPGASVKISCKASG<u>YSFTGYTMN</u>WVK | 124 |
| | QSHGKSLEWIG<u>LITPYNGASSYNQKFR</u>GKATLTVDKSSSTAYMDLLSLTSEDSAVYFCA | |
| | R<u>GGYDGRGFDY</u>WGQGTTVTVSS<u>GGGGSGGGGSGGGGS</u>DIELTQSPAIMSASPGEKVTMT | |
| | C<u>SASSSVSYMH</u>WYQQKSGTSPKRWIY<u>DTSKLAS</u>GVPGRFSGSGSGNSYSLTISSVEAED | |
| | DATYYC<u>QQWSGYPLT</u>FGAGTKLEITTTPAPRPPTPAPTIASQPLSLRPEACRPAAGGAV | |
| | HTRGLDFACDIYIWAPLAGTCGVLLLSLVITLYCKRGRKKLLYIFKQPFMRPVQTTQEE | |
| | DGCSCRFPEEEEGGCELRVKFSRSADAPA | |
| M1 CAR (na) | ATGGCCCTCCCTGTCACCGCCCTGCTGCTTCCGCTGGCTCTTCTGCTCCACGCCGCTCGGCC | 125 |
| | CCAAGTCCAACTGCAGCAGTCAGGAGCGGAAGTGAAGAAACCAGGAGCGTCAGTCAAAGTGT | |
| | CGTGCAAGGCTAGCGGCTACACCTTCACCGGCTACTACATGCACTGGGTTCGACAGGCTCCA | |
| | GGGCAGGGTCTGGAGTGGATGGGCCGCATCAACCCCGAATTCCGGTGGGACTAACTACGCCCA | |
| | GAAGTTCCAGGGAAGAGTGACCATGACTAGGGACACGTCGATCAGCACTGCGTACATGGAAC | |
| | TGAGCCGCCTGCGGTCCGAGGATACTGCCGTCTACTACTGCGCACGCGGAAGGTACTATGGA | |
| | ATGGACGTGTGGGGCCAAGGGACTATGGTGACTGTGAGCTCGGGAGGGGGAGGCTCCGGTGG | |
| | CGGGGGATCAGGAGGAGGAGGATCAGGGGGAGGAGGTTCCGAAATTGTCCTCACCCAGAGCC | |
| | CGGCAACCCTCTCACTTTCCCGGGAGAGCGCGCAACCATCTCTTGCCGGGCTAGCCAATCC | |
| | GTGTCGTCCAATTTCGCCTGGTACCAGCAACGGCCGGGACAAGCCCCTAGACTCCTGATCTA | |

TABLE 6-continued

Exemplary mesothelin CAR molecules (aa-amino acids; na-nucleic acid encoding the corresponding polypeptide)

| Name | Sequence | SEQ ID NO: |
|---|---|---|
| | CGACGCCAGCAACAGAGCGACTGGAATTCCTCCACGCTTTTCGGGATCAGGCTCCGGTACCG | |
| | ACTTCACCCTGACTATCTCGTCGCTCGAACCCGAGGATTTCGCCGCCTACTACTGTCATCAG | |
| | CGGTCGAACTGGTTGTATACGTTTGGCCAGGGCACCAAGGTGGATATCAAGACCACTACCCC | |
| | AGCACCGAGGCCACCCACCCCGGCTCCTACCATCGCCTCCCAGCCTCTGTCCCTGCGTCCGG | |
| | AGGCATGTAGACCCGCAGCTGGTGGGCCGTGCATACCCGGGGTCTTGACTTCGCCTGCGAT | |
| | ATCTACATTTGGGCCCCTCTGGCTGGTACTTGCGGGGTCCTGCTGCTTTCACTCGTGATCAC | |
| | TCTTTACTGTAAGCGCGGTCGGAAGAAGCTGCTGTACATCTTTAAGCAACCCTTCATGAGGC | |
| | CTGTGCAGACTACTCAAGAGGAGGACGGCTGTTCATGCCGGTTCCCAGAGGAGGAGGAAGGC | |
| | GGCTGCGAACTGCGCGTGAAATTCAGCCGCAGCGCAGATGCTCCAGCCTACAAGCAGGGGCA | |
| | GAACCAGCTCTACAACGAACTCAATCTTGGTCGGAGAGAGGAGTACGACGTGCTGGACAAGC | |
| | GGAGAGGACGGGACCCAGAAATGGGCGGGAAGCCGCGCAGAAAGAATCCCCAAGAGGGCCTG | |
| | TACAACGAGCTCCAAAAGGATAAGATGGCAGAAGCCTATAGCGAGATTGGTATGAAAGGGGA | |
| | ACGCAGAAGAGGCAAAGGCCACGACGGACTGTACCAGGGACTCAGCACCGCCACCAAGGACA | |
| | CCTATGACGCTCTTCACATGCAGGCCCTGCCGCCTCGG | |
| M2 CAR (na) | ATGGCCCTCCCTGTCACCGCCCTGCTGCTTCCGCTGGCTCTTCTGCTCCACGCCGCTCGGCC | 126 |
| | CCAAGTCCAACTCGTCCAGTCAGGAGCAGAAGTCAAGAAACCAGGTGCTAGCGTGAAAGTGT | |
| | CGTGCAAGGCGTCGGGATACACTTTCACCGGATACTACATGCACTGGGTCCGCCAGGCCCCC | |
| | GGACAAGGACTGGAATGGATGGGCTGGATCAACCCGAATAGCGGGGAACTAATTACGCCCA | |
| | GAAGTTTCAGGGACGAGTGACCATGACCCGCGATACCTCTATCTCGACCGCCTACATGGAGC | |
| | TCTCCAGACTGCGCTCCGACGATACTGCAGTGTACTACTGCGCCCGGGACCTGAGGCGGACT | |
| | GTGGTTACTCCTCGCGCCTATTATGGCATGGACGTGTGGGGCCAAGGAACTACTGTGACTGT | |
| | GAGCTCGGGAGGCGGTGGGTCAGGCGGAGGAGGGTCGGGCGGTGGTGGCTCGGGAGGGGGAG | |
| | GAAGCGACATTCAACTTACGCAGAGCCCGTCAACCCTGTCAGCGTCAGTGGGAGATCGGGTG | |
| | ACCATCACGTGTCAGGCCAGCCAGGATATCTCCAACTCGCTCAACTGGTACCAGCAAAAGGC | |
| | GGGTAAAGCTCCGAAGCTGCTGATCTACGACGCTTCCACCCTCGAGACTGGAGTCCCATCCA | |
| | GATTTTCCGGGTCAGGAAGCGGCACCGATTTCTCCTTCACCATTTCGTCCTTGCAACCGGAG | |
| | GACATCGCAACCTACTACTGCCAGCAGCATGACAACTTGCCTCTGACGTTCGGGCAGGGCAC | |
| | CAAGGTGGAAATCAAGACCACTACCCCAGCACCGAGGCCACCCACCCCGGCTCCTACCATCG | |
| | CCTCCCAGCCTCTGTCCCTGCGTCCGGAGGCATGTAGACCCGCAGCTGGTGGGCCGTGCAT | |
| | ACCCGGGGTCTTGACTTCGCCTGCGATATCTACATTTGGGCCCCTCTGGCTGGTACTTGCGG | |
| | GGTCCTGCTGCTTTCACTCGTGATCACTCTTTACTGTAAGCGCGGTCGGAAGAAGCTGCTGT | |
| | ACATCTTTAAGCAACCCTTCATGAGGCCTGTGCAGACTACTCAAGAGGAGGACGGCTGTTCA | |
| | TGCCGGTTCCCAGAGGAGGAGGAAGGCGGCTGCGAACTGCGCGTGAAATTCAGCCGCAGCGC | |
| | AGATGCTCCAGCCTACAAGCAGGGGCAGAACCAGCTCTACAACGAACTCAATCTTGGTCGGA | |
| | GAGAGGAGTACGACGTGCTGGACAAGCGGAGAGGACGGGACCCAGAAATGGGCGGGAAGCCG | |
| | CGCAGAAAGAATCCCCAAGAGGGCCTGTACAACGAGCTCCAAAAGGATAAGATGGCAGAA | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | GCCTATAGCGAGATTGGTATGAAAGGGGAACGCAGAAGAGGCAAAGGCCACGACGGACTGTA | |
| | CCAGGGACTCAGCACCGCCACCAAGGACACCTATGACGCTCTTCACATGCAGGCCCTGCCGC | |
| | CTCGG | |
| M3 CAR (na) | ATGGCCCTCCCTGTCACCGCCCTGCTGCTTCCGCTGGCTCTTCTGCTCCACGCCGCTCGGCC CCAAGTCCAACTCGTCCAATCAGGAGCGGAAGTCAAAAAGCCCGGAGCTCCAGTGAAAGTGT CATGCAAGGCCTCCGGCTACACCTTCACCGGTTACTATATGCACTGGGTGCGGCAGGCCCCG GGCCAGGGGTTGGAATGGATGGGATGGATCAATCCAAACTCGGGTGGGACTAACTACGCCCA GAAGTTCCAAGGACGGGTGACCATGACTAGGGACACCTCGATCTCCACCGCATACATGGAGC TTAGCAGACTCCGCTCCGACGATACCGCAGTCTACTATTGCGCGCGGGGAGAGTGGGACGGA TCGTACTACTACGATTACTGGGGCCAGGGAACTCTGGTGACTGTTTCCTCGGGTGGAGGAGG TTCAGGCGGAGGCGGCTCGGGCGGGGAGGATCTGGAGGAGGAGGGTCCGACATTGTGCTGA CCCAAACTCCTTCGTCCCTGTCGGCCAGCGTGGGCGACCGCGTGACGATTACGTGCAGAGCT AGCCAATCCATCAATACTTACCTCAACTGGTACCAGCATAAGCCGGGGAAAGCACCAAAGCT GCTGATCTACGCCGCCTCATCCTTGCAGAGCGGTGTGCCTTCACGCTTTAGCGGATCGGGAT CGGGAACGGATTTCACCCTGACTATCAGCTCCCTCCAGCCGGAGGATTTTGCGACCTACTAC TGTCAGCAGAGCTTCTCACCGCTGACTTTCGGCGGCGGGACCAAGCTGGAAATCAAGACCAC TACCCCAGCACCGAGGCCACCCACCCCGGCTCCTACCATCGCCTCCCAGCCTCTGTCCCTGC GTCCGGAGGCATGTAGACCCGCAGCTGGTGGGCCGTGCATACCCGGGGTCTTGACTTCGCC TGCGATATCTACATTTGGGCCCCTCTGGCTGGTACTTGCGGGGTCCTGCTGCTTTCACTCGT GATCACTCTTTACTGTAAGCGCGGTCGGAAGAAGCTGCTGTACATCTTTAAGCAACCCTTCA TGAGGCCTGTGCAGACTACTCAAGAGGAGGACGGCTGTTCATGCCGGTTCCCAGAGGAGGAG GAAGGCGGCTGCGAACTGCGCGTGAAATTCAGCCGCAGCGCAGATGCTCCAGCCTACAAGCA GGGGCAGAACCAGCTCTACAACGAACTCAATCTTGGTCGGAGAGAGGAGTACGACGTGCTGG ACAAGCGGAGAGGACGGGACCCAGAAATGGGCGGGAAGCCGCGCAGAAAGAATCCCCAAGAG GGCCTGTACAACGAGCTCCAAAAGGATAAGATGGCAGAAGCCTATAGCGAGATTGGTATGAA AGGGGAACGCAGAAGAGGCAAAGGCCACGACGGACTGTACCAGGGACTCAGCACCGCCACCA AGGACACCTATGACGCTCTTCACATGCAGGCCCTGCCGCCTCGG | 127 |
| M4 CAR (na) | ATGGCCCTCCCTGTCACCGCCCTGCTGCTTCCGCTGGCTCTTCTGCTCCACGCCGCTCGGCC CCAAGTGCAACTCGTTGAATCAGGTGGAGGTTTGGTGCAACCCGGAGGATCTCTCAGACTGT CGTGTGCGGCGTCCGGGTTCACCTTTTCGTCCTACTGGATGCACTGGGTGCGCCAGGTGCCG GGAAAAGGACTGGTGTGGGTGTCCAGAATCAACACCGACGGGTCAACGACTACCTACGCAGA TAGCGTGGAAGGTCGGTTCACCATTTCGCGGGACAACGCTAAAAACACTCTGTACCTTCAGA TGAATTCACTGCGCGATGACGACACCGCAGTCTACTACTGCGTCGGTGGACACTGGGCGGTC TGGGGACAGGGAACTACGGTGACTGTGTCCAGCGGCGGGGAGGAAGCGGCGGAGGGGGAG CGGAGGCGGAGGATCAGGAGGAGGCGGCTCCGATATCCAGATGACCCAGTCGCCATCGACCC TCTCCGCTAGCGTGGGGGATAGGGTCACTATCACTTGCCGAGCCAGCCAATCCATTAGCGAC | 128 |

TABLE 6-continued

Exemplary mesothelin CAR molecules (aa-amino acids; na-nucleic acid encoding the corresponding polypeptide)

| Name | Sequence | SEQ ID NO: |
|---|---|---|
| | CGGCTTGCCTGGTACCAACAGAAACCTGGAAAGGCCCCGAAGCTGCTCATCTACAAGGCCTC | |
| | GTCACTGGAGTCGGGAGTCCCGTCCCGCTTTTCCGGCTCGGGCTCAGGCACCGAGTTCACTC | |
| | TGACCATCTCGAGCCTGCAGCCGGACGATTTCGCCGTGTATTACTGCCAGCAATACGGACAT | |
| | CTCCCAATGTACACGTTCGGTCAGGGCACCAAGGTCGAAATCAAGACCACTACCCCAGCACC | |
| | GAGGCCACCCACCCCGGCTCCTACCATCGCCTCCCAGCCTCTGTCCCTGCGTCCGGAGGCAT | |
| | GTAGACCCGCAGCTGGTGGGGCCGTGCATACCCGGGGTCTTGACTTCGCCTGCGATATCTAC | |
| | ATTTGGGCCCCTCTGGCTGGTACTTGCGGGGTCCTGCTGCTTTCACTCGTGATCACTCTTTA | |
| | CTGTAAGCGCGGTCGGAAGAAGCTGCTGTACATCTTTAAGCAACCCTTCATGAGGCCTGTGC | |
| | AGACTACTCAAGAGGAGGACGGCTGTTCATGCCGGTTCCCAGAGGAGGAGGAAGGCGGCTGC | |
| | GAACTGCGCGTGAAATTCAGCCGCAGCGCAGATGCTCCAGCCTACAAGCAGGGGCAGAACCA | |
| | GCTCTACAACGAACTCAATCTTGGTCGGAGAGAGGAGTACGACGTGCTGGACAAGCGGAGAG | |
| | GACGGGACCCAGAAATGGGCGGGAAGCCGCGCAGAAAGAATCCCCAAGAGGGCCTGTACAAC | |
| | GAGCTCCAAAAGGATAAGATGGCAGAAGCCTATAGCGAGATTGGTATGAAAGGGGAACGCAG | |
| | AAGAGGCAAAGGCCACGACGGACTGTACCAGGGACTCAGCACCGCCACCAAGGACACCTATG | |
| | ACGCTCTTCACATGCAGGCCCTGCCGCCTCGG | |
| M5 CAR (na) | ATGGCCCTCCCTGTCACCGCCCTGCTGCTTCCGCTGGCTCTTCTGCTCCACGCCGCTCGGCC | 129 |
| | CCAAGTCCAACTCGTTCAATCAGGCGCAGAAGTCGAAAAGCCCGGAGCATCAGTCAAAGTCT | |
| | CTTGCAAGGCTTCCGGCTACACCTTCACGGACTACTACATGCACTGGGTGCGCCAGGCTCCA | |
| | GGCCAGGGACTGGAGTGGATGGGATGGATCAACCCGAATTCCGGGGGAACTAACTACGCCCA | |
| | GAAGTTTCAGGGCCGGGTGACTATGACTCGCGATACCTCGATCTCGACTGCGTACATGGAGC | |
| | TCAGCCGCCTCCGGTCGGACGATACCGCCGTGTACTATTGTGCGTCGGGATGGGACTTCGAC | |
| | TACTGGGGGCAGGGCACTCTGGTCACTGTGTCAAGCGGAGGAGGTGGATCAGGTGGAGGTGG | |
| | AAGCGGGGGAGGAGGTTCCGGCGGCGGAGGATCAGATATCGTGATGACGCAATCGCCTTCCT | |
| | CGTTGTCCGCATCCGTGGGAGACAGGGTGACCATTACTTGCAGAGCGTCCCAGTCCATTCGG | |
| | TACTACCTGTCGTGGTACCAGCAGAAGCCGGGGAAAGCCCCAAAACTGCTTATCTATACTGC | |
| | CTCGATCCTCCAAAACGGCGTGCCATCAAGATTCAGCGGTTCGGGCAGCGGGACCGACTTTA | |
| | CCCTGACTATCAGCAGCCTGCAGCCGGAAGATTTCGCCACGTACTACTGCCTGCAAACCTAC | |
| | ACCACCCCGGACTTCGGACCTGGAACCAAGGTGGAGATCAAGACCACTACCCCAGCACCGAG | |
| | GCCACCCACCCCGGCTCCTACCATCGCCTCCCAGCCTCTGTCCCTGCGTCCGGAGGCATGTA | |
| | GACCCGCAGCTGGTGGGGCCGTGCATACCCGGGGTCTTGACTTCGCCTGCGATATCTACATT | |
| | TGGGCCCCTCTGGCTGGTACTTGCGGGGTCCTGCTGCTTTCACTCGTGATCACTCTTTACTG | |
| | TAAGCGCGGTCGGAAGAAGCTGCTGTACATCTTTAAGCAACCCTTCATGAGGCCTGTGCAGA | |
| | CTACTCAAGAGGAGGACGGCTGTTCATGCCGGTTCCCAGAGGAGGAGGAAGGCGGCTGCGAA | |
| | CTGCGCGTGAAATTCAGCCGCAGCGCAGATGCTCCAGCCTACAAGCAGGGGCAGAACCAGCT | |
| | CTACAACGAACTCAATCTTGGTCGGAGAGAGGAGTACGACGTGCTGGACAAGCGGAGAGGAC | |
| | GGGACCCAGAAATGGGCGGGAAGCCGCGCAGAAAGAATCCCCAAGAGGGCCTGTACAACGAG | |
| | CTCCAAAAGGATAAGATGGCAGAAGCCTATAGCGAGATTGGTATGAAAGGGGAACGCAGAAG | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | AGGCAAAGGCCACGACGGACTGTACCAGGGACTCAGCACCGCCACCAAGGACACCTATGACG | |
| | CTCTTCACATGCAGGCCCTGCCGCCTCGG | |
| M6 CAR (na) | ATGGCCCTCCCTGTCACCGCCCTGCTGCTTCCGCTGGCTCTTCTGCTCCACGCCGCTCGGCC | 130 |
| | CCAAGTGCAACTCGTCCAGTCAGGTGCAGAAGTGAAGAAACCCGGAGCGTCAGTCAAAGTGT | |
| | CATGCAAGGCGTCAGGCTACACCTTCACCAGCTACTACATGCACTGGGTGCGGCAGGCCCCA | |
| | GGCCAAGGCTTGGAGTGGATGGGAATCATTAACCCGTCAGGAGGCTCCACCTCCTACGCCCA | |
| | GAAGTTTCAGGGAAGAGTGACGATGACTCGGGATACGTCGACCTCGACCGTGTACATGGAAC | |
| | TGAGCTCGCTGCGCTCCGAGGACACTGCTGTGTACTACTGCGCACGGTACAGACTCATTGCC | |
| | GTGGCAGGAGACTACTACTACTATGGCATGGACGTCTGGGGCAGGGCACTATGGTCACTGT | |
| | GTCGTCCGGCGGAGGAGGCTCGGGTGGAGGAGGTAGCGGAGGAGGGGAAGCGGAGGGGGGG | |
| | GCTCCGATATCCAGATGACTCAGTCGCCTTCCTCCGTGTCGGCCTCGGTTGGAGATCGCGTC | |
| | ACCATCACTTGTCGAGCTTCCCAAGGAGTCGGTAGGTGGCTGGCGTGGTACCAGCAAAAGCC | |
| | GGGAACTGCCCCGAAGCTCCTGATCTACGCGGCTAGCACCCTGCAGTCGGGAGTGCCATCCC | |
| | GCTTCAGCGGATCTGGGTCAGGTACCGACTTCACCCTTACGATCAACAATCTCCAGCCGGAG | |
| | GACTTTGCCACCTATTACTGCAACAGGCCAACAGCTTCCCTCTGACTTTCGGAGGGGGCAC | |
| | TCGCCTGGAAATCAAGACCACTACCCCAGCACCGAGGCCACCCACCCCGGCTCCTACCATCG | |
| | CCTCCCAGCCTCTGTCCCTGCGTCCGGAGGCATGTAGACCCGCAGCTGGTGGGGCCGTGCAT | |
| | ACCCGGGGTCTTGACTTCGCCTGCGATATCTACATTTGGGCCCCTCTGGCTGGTACTTGCGG | |
| | GGTCCTGCTGCTTTCACTCGTGATCACTCTTTACTGTAAGCGCGGTCGGAAGAAGCTGCTGT | |
| | ACATCTTTAAGCAACCCTTCATGAGGCCTGTGCAGACTACTCAAGAGGAGGACGGCTGTTCA | |
| | TGCCGGTTCCCAGAGGAGGAGGAAGGCGGCTGCGAACTGCGCGTGAAATTCAGCCGCAGCGC | |
| | AGATGCTCCAGCCTACAAGCAGGGGCAGAACCAGCTCTACAACGAACTCAATCTTGGTCGGA | |
| | GAGAGGAGTACGACGTGCTGGACAAGCGGAGAGGACGGGACCCAGAAATGGGCGGGAAGCCG | |
| | CGCAGAAAGAATCCCCAAGAGGGCCTGTACAACGAGCTCCAAAAGGATAAGATGGCAGAAGC | |
| | CTATAGCGAGATTGGTATGAAAGGGAACGCAGAAGAGGCAAAGGCCACGACGGACTGTACC | |
| | AGGGACTCAGCACCGCCACCAAGGACACCTATGACGCTCTTCACATGCAGGCCCTGCCGCCT | |
| | CGG | |
| M7 CAR (na) | ATGGCCCTCCCTGTCACCGCCCTGCTGCTTCCGCTGGCTCTTCTGCTCCACGCCGCTCGGCC | 131 |
| | CCAAGTGCAATTGGTTCAATCAGGAGGAGGAGTGGTGCAACCTGGAAGATCTCTCAGACTGT | |
| | CGTGTGCGGCATCGGGATTCACTTTCTCATCATACGCAATGCACTGGGTCCGCCAGGCCCCG | |
| | GGCAAAGGCTTGGAATGGGTGGCGGTCATTTCATACGACGGCTCGAACAAGTACTACGCTGA | |
| | CAGCGTGAAGGGACGCTTTACTATTTCCCGGGACAATTCGAAGAACACTCTGTACCTCCAGA | |
| | TGAACTCCCTTAGGGCTGAGGACACCGCCGTCTACTACTGCGCACGCTGGAAAGTGTCGTCC | |
| | AGCTCCCCAGCTTTTGACTACTGGGGACAGGGAACCCTTGTGACCGTGTCGTCCGGTGGAGG | |
| | GGGAAGCGGCGGAGGGGGATCAGGTGGCGGCGGATCGGGAGGCGGGGGATCAGAAATCGTGC | |
| | TGACTCAGTCCCCGGCCACGCTGTCTCTCAGCCCGGGAGAGAGAGCGATCCTGTCCTGCCGC | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | GCCTCGCAGAGCGTGTACACTAAGTACCTGGGGTGGTACCAGCAGAAACCGGGTCAAGCGCC | |
| | TCGGCTGCTGATCTACGATGCCTCCACCCGGGCCACCGGAATCCCCGATCGGTTCTCCGGCA | |
| | GCGGCTCGGGAACTGATTTCACGCTGACCATCAATCGCCTGGAGCCGGAAGATTTCGCCGTC | |
| | TATTACTGCCAGCATTACGGCGGGAGCCCACTCATCACCTTCGGTCAAGGAACCCGACTCGA | |
| | AATCAAGACCACTACCCCAGCACCGAGGCCACCCACCCCGGCTCCTACCATCGCCTCCCAGC | |
| | CTCTGTCCCTGCGTCCGGAGGCATGTAGACCCGCAGCTGGTGGGGCCGTGCATACCCGGGGT | |
| | CTTGACTTCGCCTGCGATATCTACATTTGGGCCCCTCTGGCTGGTACTTGCGGGGTCCTGCT | |
| | GCTTTCACTCGTGATCACTCTTTACTGTAAGCGCGGTCGGAAGAAGCTGCTGTACATCTTTA | |
| | AGCAACCCTTCATGAGGCCTGTGCAGACTACTCAAGAGGAGGACGGCTGTTCATGCCGGTTC | |
| | CCAGAGGAGGAGGAAGGCGGCTGCGAACTGCGCGTGAAATTCAGCCGCAGCGCAGATGCTCC | |
| | AGCCTACAAGCAGGGGCAGAACCAGCTCTACAACGAACTCAATCTTGGTCGGAGAGAGGAGT | |
| | ACGACGTGCTGGACAAGCGGAGAGGACGGGACCCAGAAATGGGCGGGAAGCCGCGCAGAAAG | |
| | AATCCCCAAGAGGGCCTGTACAACGAGCTCCAAAAGGATAAGATGGCAGAAGCCTATAGCGA | |
| | GATTGGTATGAAAGGGGAACGCAGAAGAGGCAAAGGCCACGACGGACTGTACCAGGGACTCA | |
| | GCACCGCCACCAAGGACACCTATGACGCTCTTCACATGCAGGCCCTGCCGCCTCGG | |
| M8 CAR (na) | ATGGCCCTCCCTGTCACCGCCCTGCTGCTTCCGCTGGCTCTTCTGCTCCACGCCGCTCGGCC | 132 |
| | CCAAGTCCAACTCCAGCAGTCAGGTGCAGAAGTCAAAAAGCCAGGAGCATCCGTGAAGGTTT | |
| | CGTGCAAGACTTCCGGCTACCCTTTTACCGGGTACTCCCTCCATTGGGTGAGACAAGCACCG | |
| | GGCCAGGGACTGGAGTGGATGGGATGGATCAACCCAAATTCGGGCGGCACCAACTATGCGCA | |
| | GAAGTTCCAGGGACGGGTGACCATGACTCGCGACACTTCGATCTCCACTGCCTACATGGAGC | |
| | TGTCCCGCTTGAGATCTGACGACACGGCCGTCTACTACTGCGCCCGGGATCACTACGGAGGT | |
| | AATTCGCTGTTCTACTGGGGGCAGGGAACCCTTGTGACTGTGTCCTCGGGTGGTGGAGGGTC | |
| | AGGAGGCGGAGGCTCAGGGGGAGGAGGTAGCGGAGGAGGCGGATCAGACATCCAACTGACCC | |
| | AGTCACCATCCTCCATCTCGGCTAGCGTCGGAGACACCGTGTCGATTACTTGTAGGGCCTCC | |
| | CAAGACTCAGGGACGTGGCTGGCGTGGTATCAGCAAAAACCGGGCAAAGCTCCGAACCTGTT | |
| | GATGTACGACGCCAGCACCCTCGAAGATGGAGTGCCTAGCCGCTTCAGCGGAAGCGCCTCGG | |
| | GCACTGAATTCACGCTGACTGTGAATCGGCTCCAGCCGGAGGATTCGGCGACCTACTACTGC | |
| | CAGCAGTACAACAGCTACCCCCTGACCTTTGGAGGCGGGACCAAGGTGGATATCAAGACCAC | |
| | TACCCCAGCACCGAGGCCACCCACCCCGGCTCCTACCATCGCCTCCCAGCCTCTGTCCCTGC | |
| | GTCCGGAGGCATGTAGACCCGCAGCTGGTGGGGCCGTGCATACCCGGGGTCTTGACTTCGCC | |
| | TGCGATATCTACATTTGGGCCCCTCTGGCTGGTACTTGCGGGGTCCTGCTGCTTTCACTCGT | |
| | GATCACTCTTTACTGTAAGCGCGGTCGGAAGAAGCTGCTGTACATCTTTAAGCAACCCTTCA | |
| | TGAGGCCTGTGCAGACTACTCAAGAGGAGGACGGCTGTTCATGCCGGTTCCCAGAGGAGGAG | |
| | GAAGGCGGCTGCGAACTGCGCGTGAAATTCAGCCGCAGCGCAGATGCTCCAGCCTACAAGCA | |
| | GGGGCAGAACCAGCTCTACAACGAACTCAATCTTGGTCGGAGAGAGGAGTACGACGTGCTGG | |
| | ACAAGCGGAGAGGACGGGACCCAGAAATGGGCGGGAAGCCGCGCAGAAAGAATCCCCAAGAG | |
| | GGCCTGTACAACGAGCTCCAAAAGGATAAGATGGCAGAAGCCTATAGCGAGATTGGTATGAA | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | AGGGGAACGCAGAAGAGGCAAAGGCCACGACGGACTGTACCAGGGACTCAGCACCGCCACCA | |
| | AGGACACCTATGACGCTCTTCACATGCAGGCCCTGCCGCCTCGG | |
| M9 CAR (na) | ATGGCCCTCCCTGTCACCGCCCTGCTGCTTCCGCTGGCTCTTCTGCTCCACGCCGCTCGGCC CCAAGTGCAACTCGTCCAGTCAGGTGCAGAAGTGAAGAAACCAGGAGCGTCCGTCGAAGTGT CGTGTAAGGCGTCCGGCTACACTTTCACCTCGTACTACATGCACTGGGTGCGGCAGGCCCCG GGACAAGGCCTCGAATGGATGGGAATCATCAACCCGAGCGGAGGCTCGACTGGTTACGCCCA GAAGTTCCAGGGAAGGGTGACGATGACCCGCGATACCTCGACTTCGACCGTTCATATGGAGC TCTCGTCCCTGCGGAGCGAGGACACTGCTGTCTACTATTGCGCGCGGGGAGGATACTCTAGC TCCTCCGATGCATTTGACATTTGGGGCCAGGGAACTATGGTGACCGTGTCATCAGGCGGAGG TGGATCAGGAGGAGGAGGGTCGGGAGGGGGAGGCAGCGGCGGGGGTGGGTCGGACATTCAGA TGACGCAGTCCCCTCCTAGCCTGAGCGCCTCGGTGGGTGACAGAGTGACCATCACTTGCAGA GCCTCGCAAGACATCTCCTCCGCATTGGCTTGGTACCAGCAAAAGCCGGGCACTCCGCCGAA ACTGCTCATCTACGATGCCTCCTCACTGGAGTCAGGAGTCCCATCTCGCTTCTCGGGGTCAG GAAGCGGCACCGATTTTACCCTTACCATCTCCAGCCTGCAGCCCGAGGACTTCGCCACGTAC TACTGCCAACAGTTCAGCTCCTACCCACTGACCTTCGGGGCGGAACTCGCCTGGAAATCAA GACCACTACCCCAGCACCGAGGCCACCCACCCCGGCTCCTACCATCGCCTCCCAGCCTCTGT CCCTGCGTCCGGAGGCATGTAGACCCGCAGCTGGTGGGCCGTGCATACCCGGGGTCTTGAC TTCGCCTGCGATATCTACATTTGGGCCCCTCTGGCTGGTACTTGCGGGGTCCTGCTGCTTTC ACTCGTGATCACTCTTTACTGTAAGCGCGGTCGGAAGAAGCTGCTGTACATCTTTAAGCAAC CCTTCATGAGGCCTGTGCAGACTACTCAAGAGGAGGACGGCTGTTCATGCCGGTTCCCAGAG GAGGAGGAAGGCGGCTGCGAACTGCGCGTGAAATTCAGCCGCAGCGCAGATGCTCCAGCCTA CAAGCAGGGGCAGAACCAGCTCTACAACGAACTCAATCTTGGTCGGAGAGAGGAGTACGACG TGCTGGACAAGCGGAGAGGACGGGACCCAGAAATGGGCGGGAAGCCGCGCAGAAAGAATCCC CAAGAGGGCCTGTACAACGAGCTCCAAAAGGATAAGATGGCAGAAGCCTATAGCGAGATTGG TATGAAAGGGAACGCAGAAGAGGCAAAGGCCACGACGGACTGTACCAGGGACTCAGCACCG CCACCAAGGACACCTATGACGCTCTTCACATGCAGGCCCTGCCGCCTCGG | 133 |
| M10 CAR (na) | ATGGCCCTCCCTGTCACCGCCCTGCTGCTTCCGCTGGCTCTTCTGCTCCACGCCGCTCGGCC CCAAGTGCAACTCGTCCAGAGCGGAGCAGAAGTCAAGAAGCCAGGAGCGTCAGTGAAAGTGT CATGCAAGGCCAGCGGCTATACCTTTACTTCGTATGGGATCTCCTGGGTGCGGCAGGCACCG GGCCAAGGACTGGAGTGGATGGGATGGATCTCAGCCTACAACGGTAACACCAACTACGCCCA GAAGCTGCAAGGACGCGTGACCATGACTACTGATACGAGCACCTCCACTGCCTACATGGAAT TGCGGTCCCTTCGGTCGGACGATACTGCTGTGTACTACTGCGCAAGAGTCGCCGGAGGGATC TACTACTACTACGGCATGGACGTCTGGGGACAGGGAACCACCATTACGGTGTCGAGCGGAGG GGGAGGCTCGGGGGGAGGAGGAAGCGGAGGTGGCGGCTCCGGGGGCGGCGGATCGGACATTG TGATGACCCAGACTCCTGACTCCCTGGCTGTTTCGTTGGGAGAGCGCGCGACTATCTCGTGT AAGTCCAGCCACTCAGTCCTGTACAATCGCAATAACAAGAACTACCTCGCGTGGTACCAGCA | 134 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | AAAACCGGGTCAGCCGCCTAAACTCCTGTTCTACTGGGCCTCCACCAGAAAGAGCGGGGTGC | |
| | CAGATCGATTCTCTGGATCAGGATCAGGTACCGACTTTACGCTGACCATCTCGTCCCTGCAG | |
| | CCGGAGGATTTCGCGACTTACTTCTGCCAGCAGACTCAGACTTTCCCCCTCACCTTCGGTCA | |
| | AGGCACCAGGCTGGAAATCAATACCACTACCCCAGCACCGAGGCCACCCACCCCGGCTCCTA | |
| | CCATCGCCTCCCAGCCTCTGTCCCTGCGTCCGGAGGCATGTAGACCCGCAGCTGGTGGGGCC | |
| | GTGCATACCCGGGGTCTTGACTTCGCCTGCGATATCTACATTTGGGCCCCTCTGGCTGGTAC | |
| | TTGCGGGGTCCTGCTGCTTTCACTCGTGATCACTCTTTACTGTAAGCGCGGTCGGAAGAAGC | |
| | TGCTGTACATCTTTAAGCAACCCTTCATGAGGCCTGTGCAGACTACTCAAGAGGAGGACGGC | |
| | TGTTCATGCCGGTTCCCAGAGGAGGAGGAAGGCGGCTGCGAACTGCGCGTGAAATTCAGCCG | |
| | CAGCGCAGATGCTCCAGCCTACAAGCAGGGGCAGAACCAGCTCTACAACGAACTCAATCTTG | |
| | GTCGGAGAGAGGAGTACGACGTGCTGGACAAGCGGAGAGGACGGGACCCAGAAATGGGCGGG | |
| | AAGCCGCGCAGAAAGAATCCCCAAGAGGGCCTGTACAACGAGCTCCAAAAGGATAAGATG | |
| | GCAGAAGCCTATAGCGAGATTGGTATGAAAGGGGAACGCAGAAGAGGCAAAGGCCACGACGG | |
| | ACTGTACCAGGGACTCAGCACCGCCACCAAGGACACCTATGACGCTCTTCACATGCAGGCCC | |
| | TGCCGCCTCGG | |
| M11 CAR (na) | ATGGCCCTCCCTGTCACCGCCCTGCTGCTTCCGCTGGCTCTTCTGCTCCACGCCGCTCGGCC | 135 |
| | CCAAGTCCAATTGCAGCAGAGCGGAGCAGAAGTGAAGAAGCCAGGAGCGTCAGTCAAAGTGT | |
| | CGTGTAAGGCGTCAGGATACACCTTCACGGGATACTACATGCACTGGGTGCGCCAGGCCCCG | |
| | GGCCAAGGACTCGAGTGGATGGGCTGGATCAACCCTAACTCTGGAGGCACCAACTACGCCCA | |
| | GAATTTCCAAGGCAGAGTGACCATGACCCGGGACACCTCCATCTCGACTGCCTATATGGAAC | |
| | TGCGGCGGCTGCGCTCGGACGATACTGCTGTGTATTACTGCGCCAGCGGCTGGGACTTTGAC | |
| | TACTGGGGACAGGGTACTCTGGTGACTGTTTCCTCGGGAGGAGGCGGATCGGGTGGAGGAGG | |
| | TAGCGGGGGAGGGGGGTCGGGAGGCGGAGGCAGCGATATTCGCATGACTCAATCGCCGTCCT | |
| | CCCTGAGCGCTAGCGTGGGAGATCGAGTCACCATCACTTGCAGAGCGTCACAGTCGATTCGC | |
| | TACTACCTGTCCTGGTACCAGCAGAAACCGGGAAAGGCACCAAAGCTTCTGATCTACACGGC | |
| | CTCCATCCTGCAAAATGGTGTCCCATCAAGGTTCTCCGGGTCAGGGAGCGGCACTGACTTCA | |
| | CTCTCACCATCTCCTCACTCCAGCCCGAGGACTTTGCAACCTACTACTGCTCCAGACGTAC | |
| | ACCACCCCGGATTTCGGTCCTGGAACCAAGGTGGAAATCAAAACCACTACCCCAGCACCGAG | |
| | GCCACCCACCCCGGCTCCTACCATCGCCTCCCAGCCTCTGTCCCTGCGTCCGGAGGCATGTA | |
| | GACCCGCAGCTGGTGGGGCCGTGCATACCCGGGGTCTTGACTTCGCCTGCGATATCTACATT | |
| | TGGGCCCCTCTGGCTGGTACTTGCGGGGTCCTGCTGCTTTCACTCGTGATCACTCTTTACTG | |
| | TAAGCGCGGTCGGAAGAAGCTGCTGTACATCTTTAAGCAACCCTTCATGAGGCCTGTGCAGA | |
| | CTACTCAAGAGGAGGACGGCTGTTCATGCCGGTTCCCAGAGGAGGAGGAAGGCGGCTGCGAA | |
| | CTGCGCGTGAAATTCAGCCGCAGCGCAGATGCTCCAGCCTACAAGCAGGGGCAGAACCAGCT | |
| | CTACAACGAACTCAATCTTGGTCGGAGAGAGGAGTACGACGTGCTGGACAAGCGGAGAGGAC | |
| | GGGACCCAGAAATGGGCGGGAAGCCGCGCAGAAAGAATCCCCAAGAGGGCCTGTACAACGAG | |
| | CTCCAAAAGGATAAGATGGCAGAAGCCTATAGCGAGATTGGTATGAAAGGGGAACGCAGAAG | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | AGGCAAAGGCCACGACGGACTGTACCAGGGACTCAGCACCGCCACCAAGGACACCTATGACG | |
| | CTCTTCACATGCAGGCCCTGCCGCCTCGG | |
| M12 CAR (na) | ATGGCCCTCCCTGTCACCGCCCTGCTGCTTCCGCTGGCTCTTCTGCTCCACGCCGCTCGGCC CCAAGTCCAACTCGTCAAAGCGGAGCAGAAGTCAAAAAGCCAGGAGCGTCGGTGAAAGTGT CTTGCAAAGCCAGCGGCTACACCTTCACGGGTTACTACATGCACTGGGTGCGCCAGGCGCCG GGCCAGGGGCTGGAGTGGATGGGCCGGATTAACCCTAACAGCGGGGGAACTAATTACGCTCA GAAGTTCCAGGGTAGAGTCACCATGACTACGGACACTTCCACTTCCACCGCCTATATGGAAC TGCGCTCCCTCCGCTCAGATGATACTGCCGTGTATTACTGCGCGCGGACTACCACGTCATAC GCATTTGACATCTGGGGCCAGGGAACTATGGTGACCGTGAGCTCGGGCGGAGGCGGTTCAGG GGGAGGAGGAAGCGGAGGAGGAGGATCGGGAGGAGGTGGCTCCGATATCCAGCTGACTCAGT CCCCGAGCACCCTGTCGGCGTCGGTGGGGACAGGGTTACCATCACCTGTAGAGCTTCCCAA TCCATTTCGACTTGGCTGGCCTGGTACCAGCAAAAGCCGGGAAAGGCCCTAATTTGCTTAT CTACAAGGCATCGACCCTCGAAAGCGGTGTGCCCTCCCGGTTTTCGGGATCAGGATCAGGGA CCGAGTTCACCCTGACCATCTCATCCCTCCAGCCGGACGACTTCGCCACTTACTACTGCCAG CAGTACAACACCTACTCGCCATACACTTTCGGCCAAGGCACCAAGCTGGAGATCAAGACCAC TACCCCAGCACCGAGGCCACCCACCCCGGCTCCTACCATCGCCTCCCAGCCTCTGTCCCTGC GTCCGGAGGCATGTAGACCCGCAGCTGGTGGGGCCGTGCATACCCGGGGTCTTGACTTCGCC TGCGATATCTACATTTGGGCCCCTCTGGCTGGTACTTGCGGGGTCCTGCTGCTTTCACTCGT GATCACTCTTTACTGTAAGCGCGGTCGGAAGAAGCTGCTGTACATCTTTAAGCAACCCTTCA TGAGGCCTGTGCAGACTACTCAAGAGGAGGACGGCTGTTCATGCCGGTTCCCAGAGGAGGAG GAAGGCGGCTGCGAACTGCGCGTGAAATTCAGCCGCAGCGCAGATGCTCCAGCCTACAAGCA GGGGCAGAACCAGCTCTACAACGAACTCAATCTTGGTCGGAGAGAGGAGTACGACGTGCTGG ACAAGCGGAGAGGACGGGACCCAGAAATGGGCGGGAAGCCGCGCAGAAAGAATCCCCAAGAG GGCCTGTACAACGAGCTCCAAAAGGATAAGATGGCAGAAGCCTATAGCGAGATTGGTATGAA AGGGGAACGCAGAAGAGGCAAAGGCCACGACGGACTGTACCAGGGACTCAGCACCGCCACCA AGGACACCTATGACGCTCTTCACATGCAGGCCCTGCCGCCTCGG | 136 |
| M13 CAR (na) | ATGGCCCTCCCTGTCACCGCCCTGCTGCTTCCGCTGGCTCTTCTGCTCCACGCCGCTCGGCC CCAAGTTCAACTCGTGCAATCAGGTGGAGGACTCGTCAAACCCGGAGGATCATTGAGACTGT CATGCGAAGCGAGCGGTTTTATCTTCTCCGATTACTATATGGGATGGATTCGGCAGGCCCCG GGAAAGGGACTCGAATGGGTGTCATACATCGGAAGGTCAGGCTCGTCCATGTACTACGCAGA CTCGGTGAAAGGCAGATTCACCTTTAGCCGGGACAACGCCAAGAATTCCCTCTACTTGCAGA TGAACAGCCTGCGAGCCGAGGATACTGCTGTCTACTACTGTGCCGCGTCGCCGGTGGTGGCA GCTACTGAAGATTTCCAGCACTGGGGACAGGGAACTCTGGTCACGGTGTCGAGCGGTGGGGG CGGAAGCGGAGGCGGAGGATCGGGCGGCGGAGGTTCGGGGGGGGGAGGGTCTGACATCGTGA TGACCCAAACCCCAGCCACCCTGAGCCTCTCCCCTGGAGAGCGCGCGACTCTTTCGTGCCGC GCTTCCCAGTCAGTGACCAGCAATTACTTGGCTTGGTACCAACAGAAGCCGGGACAGGCGCC | 137 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | ACGGCTGCTGCTTTTTGGTGCCAGCACTCGCGCCACCGGAATCCCGGATCGCTTCTCGGGCT | |
| | CAGGGTCCGGGACGGACTTCACCCTGACTATCAACCGGCTGGAACCTGAGGACTTCGCGATG | |
| | TACTACTGCCAGCAGTACGGCTCCGCACCAGTCACTTTCGGACAAGGCACCAAGCTGGAGAT | |
| | CAAGACCACTACCCCAGCACCGAGGCCACCCACCCCGGCTCCTACCATCGCCTCCCAGCCTC | |
| | TGTCCCTGCGTCCGGAGGCATGTAGACCCGCAGCTGGTGGGCCGTGCATACCCGGGGTCTT | |
| | GACTTCGCCTGCGATATCTACATTTGGGCCCCTCTGGCTGGTACTTGCGGGGTCCTGCTGCT | |
| | TTCACTCGTGATCACTCTTTACTGTAAGCGCGGTCGGAAGAAGCTGCTGTACATCTTTAAGC | |
| | AACCCTTCATGAGGCCTGTGCAGACTACTCAAGAGGAGGACGGCTGTTCATGCCGGTTCCCA | |
| | GAGGAGGAGGAAGGCGGCTGCGAACTGCGCGTGAAATTCAGCCGCAGCGCAGATGCTCCAGC | |
| | CTACAAGCAGGGGCAGAACCAGCTCTACAACGAACTCAATCTTGGTCGGAGAGAGGAGTACG | |
| | ACGTGCTGGACAAGCGGAGAGGACGGGACCCAGAAATGGGCGGGAAGCCGCGCAGAAAGAAT | |
| | CCCCAAGAGGGCCTGTACAACGAGCTCCAAAAGGATAAGATGGCAGAAGCCTATAGCGAGAT | |
| | TGGTATGAAAGGGGAACGCAGAAGAGGCAAAGGCCACGACGGACTGTACCAGGGACTCAGCA | |
| | CCGCCACCAAGGACACCTATGACGCTCTTCACATGCAGGCCCTGCCGCCTCGG | |
| M14 CAR (na) | ATGGCCCTCCCTGTCACCGCCCTGCTGCTTCCGCTGGCTCTTCTGCTCCACGCCGCTCGGCC | 138 |
| | CCAAGTCCAACTCGTCCAGTCGGGAGCAGAAGTTAGAGCACCAGGAGCGTCAGTGAAAATCT | |
| | CATGCAAGGCCTCGGGCTTCACGTTCCGCGGATACTACATCCACTGGGTGCGCCAAGCCCCG | |
| | GGTCAGGGATTGGAGTGGATGGGAATCATTAACCCATCAGGAGGGAGCCGGGCTTACGCGCA | |
| | GAAGTTCCAGGGACGCGTCACTATGACCCGAGATACTTCCACCTCGACTGTGTACATGGAAC | |
| | TCTCGTCCCTGAGGTCCGACGACACTGCGATGTATTACTGTGCTCGGACTGCCAGCTGCGGT | |
| | GGGGACTGTTACTACCTCGATTACTGGGGCCAGGGAACTCTGGTGACCGTGTCCAGCGGAGG | |
| | TGGCGGGTCAGGGGGTGGCGGAAGCGGAGGCGGCGGTTCAGGCGGAGGAGGCTCGGACATCC | |
| | AAATGACGCAATCGCCGCCTACCCTGAGCGCTTCCGTGGGAGATCGGGTGACCATTACTTGC | |
| | AGAGCATCCGAGAACGTCAATATCTGGCTGGCCTGGTACCAACAGAAGCCGGGGAAGGCCCC | |
| | TAAACTGCTGATCTACAAGTCGAGCAGCCTTGCCTCTGGAGTGCCCTCCCGCTTCTCGGGCT | |
| | CGGGATCAGGAGCGGAATTCACCCTCACCATCTCCTCCCTGCAGCCAGATGACTTTGCCACC | |
| | TACTACTGCCAGCAGTACCAGAGCTATCCGTTGACCTTTGGGGAGGCACTAAAGTGGACAT | |
| | CAAGACCACTACCCCAGCACCGAGGCCACCCACCCCGGCTCCTACCATCGCCTCCCAGCCTC | |
| | TGTCCCTGCGTCCGGAGGCATGTAGACCCGCAGCTGGTGGGCCGTGCATACCCGGGGTCTT | |
| | GACTTCGCCTGCGATATCTACATTTGGGCCCCTCTGGCTGGTACTTGCGGGGTCCTGCTGCT | |
| | TTCACTCGTGATCACTCTTTACTGTAAGCGCGGTCGGAAGAAGCTGCTGTACATCTTTAAGC | |
| | AACCCTTCATGAGGCCTGTGCAGACTACTCAAGAGGAGGACGGCTGTTCATGCCGGTTCCCA | |
| | GAGGAGGAGGAAGGCGGCTGCGAACTGCGCGTGAAATTCAGCCGCAGCGCAGATGCTCCAGC | |
| | CTACAAGCAGGGGCAGAACCAGCTCTACAACGAACTCAATCTTGGTCGGAGAGAGGAGTACG | |
| | ACGTGCTGGACAAGCGGAGAGGACGGGACCCAGAAATGGGCGGGAAGCCGCGCAGAAAGAAT | |
| | CCCCAAGAGGGCCTGTACAACGAGCTCCAAAAGGATAAGATGGCAGAAGCCTATAGCGAGAT | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | TGGTATGAAAGGGGAACGCAGAAGAGGCAAAGGCCACGACGGACTGTACCAGGGACTCAGCA | |
| | CCGCCACCAAGGACACCTATGACGCTCTTCACATGCAGGCCCTGCCGCCTCGG | |
| M15 CAR (na) | ATGGCCCTCCCTGTCACCGCCCTGCTGCTTCCGCTGGCTCTTCTGCTCCACGCCGCTCGGCC CCAAGTTCAACTCGTTCAATCAGGTGGAGGACTCGTGCAACCAGGAAGATCACTCAGACTCA GCTGCGCCGCGTCGGGATTCACTTTCGATGACTACGCAATGCACTGGGTGCGGCAGGCCCCG GGCAAAGGACTGGAATGGGTGAGCGGAATTAGCTGGAACTCGGGGTCCATCGGGTACGCCGA CTCGGTGAAGGGACGCTTTACGATCTCCCGGGACAATGCCAAGAACTCCCTGTATTTGCAGA TGAACTCCTTGAGGGCTGAGGACACCGCCGTGTACTACTGCGCTAAAGATGGATCATCGTCC TGGTCCTGGGGATACTTCGATTACTGGGGCCAGGGCACTCTGGTGACCGTGTCGTCAGGCGG TGGAGGGTCGGCGGAGGAGGTAGCGGAGGCGGAGGGAGCAGCTCTGAACTGACCCAAGACC CGGCGGTGTCGGTCGCCCTTGGTCAGACTGTGCGGACTACCTGTCAGGGGACGCGCTGCGC TCGTACTACGCTTCATGGTACCAGCAGAAGCCCGACAGGCACCTATGCTGGTCATCTACGG AAAGAATAACCGCCCATCCGGCATCCCGGATCGCTTCTCGGGTTCGGACAGCGGCGACACCG CATCCCTGACGATCACTGGAGCGCAGGCCGAGGATGAAGCCGACTACTACTGCAATTCCCGA GATTCAAGCGGCTACCCTGTGTTTGGGACCGGAACTAAGGTCACCGTCCTGACCACTACCCC AGCACCGAGGCCACCCACCCCGGCTCCTACCATCGCCTCCCAGCCTCTGTCCCTGCGTCCGG AGGCATGTAGACCCGCAGCTGGTGGGGCCGTGCATACCCGGGGTCTTGACTTCGCCTGCGAT ATCTACATTTGGGCCCCTCTGGCTGGTACTTGCGGGGTCCTGCTGCTTTCACTCGTGATCAC TCTTTACTGTAAGCGCGGTCGGAAGAAGCTGCTGTACATCTTTAAGCAACCCTTCATGAGGC CTGTGCAGACTACTCAAGAGGAGGACGGCTGTTCATGCCGGTTCCCAGAGGAGGAGGAAGGC GGCTGCGAACTGCGCGTGAAATTCAGCCGCAGCGCAGATGCTCCAGCCTACAAGCAGGGGCA GAACCAGCTCTACAACGAACTCAATCTTGGTCGGAGAGAGGAGTACGACGTGCTGGACAAGC GGAGAGGACGGGACCCAGAAATGGGCGGGAAGCCGCGCAGAAAGAATCCCCAAGAGGGCCTG TACAACGAGCTCCAAAAGGATAAGATGGCAGAAGCCTATAGCGAGATTGGTATGAAAGGGGA ACGCAGAAGAGGCAAAGGCCACGACGGACTGTACCAGGGACTCAGCACCGCCACCAAGGACA CCTATGACGCTCTTCACATGCAGGCCCTGCCGCCTCGG | 139 |
| M16 CAR (na) | ATGGCCCTCCCTGTCACCGCCCTGCTGCTTCCGCTGGCTCTTCTGCTCCACGCCGCTCGGCC CGAAGTGCAACTCGTGGAATCTGGTGGAGGACTTGTGCAACCTGGAAGATCGTTGAGACTCT CATGTGCTGCCTCCGGGTTCACCTTTGACGACTACGCCATGCACTGGGTGCGCCAGGCACCA GGAAAGGGTCTGGAGTGGGTTTCGGGTATCTCGTGGAACTCCGGGAGCACTGGCTACGCTGA TTCGGTGAAAGGCCGGTTTACCATCTCCCGAGACAATGCGAAGAATTCCCTCTATCTGCAGA TGAACAGCCTCCGGGCCGAGGATACTGCCCTGTACTACTGCGCCAAGGATAGCTCATCATGG TACGAGGTGGATCGGCTTTCGATATCTGGGGCCAGGGCACGATGGTCACCGTGTCCTCGGG GGGCGGAGGCTCCGGGGGAGGAGGTAGCGGAGGAGGAGGATCGAGCTCAGAGTTGACTCAAG AACCCGCAGTGTCCGTGGCACTGGGCCAAACCGTCAGGATCACTTGCCAGGGAGACAGCCTG AGGTCGTACTACGCGTCCTGGTACCAGCAGAAGCCGGGACAGGCCCCGGTCCTGGTCATTTT | 140 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | CGGACGCTCAAGACGCCCATCGGGCATCCCGGACCGGTTCAGCGGAAGCTCCTCGGGAAACA | |
| | CCGCGTCACTTATCATTACCGGCGCACAGGCTGAGGACGAAGCGGATTACTACTGCAACTCC | |
| | CGCGACAATACTGCCAACCATTACGTGTTCGGGACCGGAACGAAACTGACTGTCCTGACCAC | |
| | TACCCCAGCACCGAGGCCACCCACCCCGGCTCCTACCATCGCCTCCCAGCCTCTGTCCCTGC | |
| | GTCCGGAGGCATGTAGACCCGCAGCTGGTGGGCCGTGCATACCCGGGGTCTTGACTTCGCC | |
| | TGCGATATCTACATTTGGGCCCCTCTGGCTGGTACTTGCGGGGTCCTGCTGCTTTCACTCGT | |
| | GATCACTCTTTACTGTAAGCGCGGTCGGAAGAAGCTGCTGTACATCTTTAAGCAACCCTTCA | |
| | TGAGGCCTGTGCAGACTACTCAAGAGGAGGACGGCTGTTCATGCCGGTTCCCAGAGGAGGAG | |
| | GAAGGCGGCTGCGAACTGCGCGTGAAATTCAGCCGCAGCGCAGATGCTCCAGCCTACAAGCA | |
| | GGGGCAGAACCAGCTCTACAACGAACTCAATCTTGGTCGGAGAGAGGAGTACGACGTGCTGG | |
| | ACAAGCGGAGAGGACGGGACCCAGAAATGGGCGGGAAGCCGCGCAGAAAGAATCCCCAAGAG | |
| | GGCCTGTACAACGAGCTCCAAAAGGATAAGATGGCAGAAGCCTATAGCGAGATTGGTATGAA | |
| | AGGGAACGCAGAAGAGGCAAAGGCCACGACGGACTGTACCAGGGACTCAGCACCGCCACCA | |
| | AGGACACCTATGACGCTCTTCACATGCAGGCCCTGCCGCCTCGG | |
| M17 CAR (na) | ATGGCCCTCCCTGTCACCGCCCTGCTGCTTCCGCTGGCTCTTCTGCTCCACGCCGCTCGGCC | 141 |
| | CGAAGTTCAATTGGTGGAATCTGGAGGAGGACTTGTGCAACCCGGTAGATCTCTGAGACTGT | |
| | CCTGTGCGGCATCGGGATTCACCTTCGACGACTACGCTATGCACTGGGTGAGACAAGCCCCT | |
| | GGAAAAGGACTGGAGTGGGTGTCAGGCATCTCCTGGAATAGCGGGTCCACTGGATACGCCGA | |
| | TTCGGTCAAGGGTCGCTTCACCATTTCCCGGGACAATGCCAAGAACTCCCTGTACCTTCAAA | |
| | TGAACTCCCTCCGGGCCGAGGATACCGCCCTCTACTACTGCGCCAAAGACAGCTCGTCATGG | |
| | TATGGCGGAGGGTCGGCATTTGACATCTGGGGACAGGGAACTATGGTGACTGTGTCATCAGG | |
| | AGGCGGCGGAAGCGGCGGCGGCGGGTCCGGCGGAGGAGGGTCGTCCAGCGAACTCACCCAAG | |
| | ATCCAGCAGTGAGCGTCGCGCTGGGCCAGACCGTCAGGATCACGTGCCAGGGAGATTCACTG | |
| | CGCTCATACTACGCGTCCTGGTACCAGCAGAAGCCGGGGCAGGCCCCGGTCCTCGTGATCTA | |
| | CGGAAAGAACAACCGCCCGTCGGGTATCCCAGACCGCTTTTCGGGTAGCTCCAGCGGAAATA | |
| | CGGCTAGCCTGACCATCACTGGAGCACAGGCTGAGGATGAAGCGGACTACTACTGCAATTCG | |
| | CGGGGCTCATCGGGGAACCATTACGTGTTCGGAACTGGTACCAAGGTGACTGTCCTGACCAC | |
| | TACCCCAGCACCGAGGCCACCCACCCCGGCTCCTACCATCGCCTCCCAGCCTCTGTCCCTGC | |
| | GTCCGGAGGCATGTAGACCCGCAGCTGGTGGGCCGTGCATACCCGGGGTCTTGACTTCGCC | |
| | TGCGATATCTACATTTGGGCCCCTCTGGCTGGTACTTGCGGGGTCCTGCTGCTTTCACTCGT | |
| | GATCACTCTTTACTGTAAGCGCGGTCGGAAGAAGCTGCTGTACATCTTTAAGCAACCCTTCA | |
| | TGAGGCCTGTGCAGACTACTCAAGAGGAGGACGGCTGTTCATGCCGGTTCCCAGAGGAGGAG | |
| | GAAGGCGGCTGCGAACTGCGCGTGAAATTCAGCCGCAGCGCAGATGCTCCAGCCTACAAGCA | |
| | GGGGCAGAACCAGCTCTACAACGAACTCAATCTTGGTCGGAGAGAGGAGTACGACGTGCTGG | |
| | ACAAGCGGAGAGGACGGGACCCAGAAATGGGCGGGAAGCCGCGCAGAAAGAATCCCCAAGAG | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | GGCCTGTACAACGAGCTCCAAAAGGATAAGATGGCAGAAGCCTATAGCGAGATTGGTATGAA | |
| | AGGGGAACGCAGAAGAGGCAAAGGCCACGACGGACTGTACCAGGGACTCAGCACCGCCACCA | |
| | AGGACACCTATGACGCTCTTCACATGCAGGCCCTGCCGCCTCGG | |
| M18 CAR (na) | ATGGCCCTCCCTGTCACCGCCCTGCTGCTTCCGCTGGCTCTTCTGCTCCACGCCGCTCGGCC | 142 |
| | CCAAGTGCAGCTCGTTCAATCAGGCGGAGGACTCGTTCAACCAGGAGGATCATTGCGACTCT | |
| | CATGTGCGGCCTCTGGATTCACGTTTAGCTCATATTGGATGCACTGGGTGCGGCAGGCGCCG | |
| | GGGAAAGGTCTGGTGTGGGTCAGCCGCATCAACTCAGACGGCTCCTCGACTTCGTACGCCGA | |
| | CTCCGTGAAGGGACGCTTTACCATTTCCCGCGACAACGCCAAGAATACCCTTTACCTTCAGA | |
| | TGAACTCCCTCCGCGCTGAGGATACCGCCGTGTACTACTGCGTGAGGACTGGCTGGGTCGGC | |
| | AGCTACTACTACTACATGGACGTGTGGGGCAAAGGAACTACTGTCACCGTGTCAAGCGGCGG | |
| | TGGAGGTTCCGGCGGGGAGGATCGGGGGGGGCGGATCGGGTGGCGGAGGATCGGAGATCG | |
| | TGTTGACCCAGTCGCCGGGAACCCTGTCGCTGTCGCCTGGGGAGAGAGCAACTCTGTCCTGC | |
| | CGGGCTTCCCAGTCGGTGTCGAGCAATTACCTGGCATGGTACCAACAGAAGCCGGGACAGCC | |
| | GCCACGCCTGCTGATCTATGACGTGTCAACTCGGGCAACTGGAATCCCTGCGCGGTTCAGCG | |
| | GCGGAGGGAGCGGTACCGATTTCACCCTGACTATTTCCTCCCTCGAACCAGAAGATTTCGCC | |
| | GTCTACTACTGCCAGCAGAGAAGCAACTGGCCGCCCTGGACGTTCGGACAAGGAACCAAGGT | |
| | CGAAATCAAGACCACTACCCCAGCACCGAGGCCACCCACCCCGGCTCCTACCATCGCCTCCC | |
| | AGCCTCTGTCCCTGCGTCCGGAGGCATGTAGACCCGCAGCTGGTGGGCCGTGCATACCCGG | |
| | GGTCTTGACTTCGCCTGCGATATCTACATTTGGGCCCCTCTGGCTGGTACTTGCGGGGTCCT | |
| | GCTGCTTTCACTCGTGATCACTCTTTACTGTAAGCGCGGTCGGAAGAAGCTGCTGTACATCT | |
| | TTAAGCAACCCTTCATGAGGCCTGTGCAGACTACTCAAGAGGAGGACGGCTGTTCATGCCGG | |
| | TTCCCAGAGGAGGAGGAAGGCGGCTGCGAACTGCGCGTGAAATTCAGCCGCAGCGCAGATGC | |
| | TCCAGCCTACAAGCAGGGGCAGAACCAGCTCTACAACGAACTCAATCTTGGTCGGAGAGAGG | |
| | AGTACGACGTGCTGGACAAGCGGAGAGGACGGGACCCAGAAATGGGCGGGAAGCCGCGCAGA | |
| | AAGAATCCCCAAGAGGGCCTGTACAACGAGCTCCAAAAGGATAAGATGGCAGAAGCCTATAG | |
| | CGAGATTGGTATGAAAGGGGAACGCAGAAGAGGCAAAGGCCACGACGGACTGTACCAGGGAC | |
| | TCAGCACCGCCACCAAGGACACCTATGACGCTCTTCACATGCAGGCCCTGCCGCCTCGG | |
| M19 CAR (na) | ATGGCCCTCCCTGTCACCGCCCTGCTGCTTCCGCTGGCTCTTCTGCTCCACGCCGCTCGGCC | 143 |
| | CCAAGTGCAATTGGTTCAATCAGGAGGAGGAGTCGTGCAGCCCGGAAGATCGTTGAGACTGT | |
| | CATGTGCCGCGAGCGGCTTTACTTTCTCAAGCTACGGAATGCATTGGGTGCGACAGGCTCCG | |
| | GGAAAAGGACTGGAATGGGTCGCAGTGATCTCATACGACGGCTCGAACAAGTACTACGCCGA | |
| | CTCCGTCAAGGGTCGGTTCACGATTTCGCGCGATAATTCCAAGAACACTCTGTACCTCCAAA | |
| | TGAACAGCCTCCGGGCAGAGGACACCGCCGTCTACTACTGCGCTAAGGGATACTCGCGCTAC | |
| | TACTACTATGGAATGGATGTGTGGGGCCAGGGAACTACCGTGACGGTGTCGTCCGGCGGCGG | |
| | TGGGTCGGGCGGAGGCGGATCAGGTGGAGGTGGAAGCGGAGGAGGAGGGAGCGAAATCGTCA | |
| | TGACTCAGTCCCCTGCTACCCTTTCTCTGTCGCCGGGAGAAAGAGCCATCCTGAGCTGCCGG |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | GCCTCCCAGAGCGTGTACACCAAATACCTGGGATGGTACCAGCAGAAGCCGGGGCAGGCACC | |
| | AAGGCTCCTGATCTACGATGCGTCCACCCGCGCGACTGGTATCCCAGACCGCTTTTCCGGCT | |
| | CGGGGTCAGGGACTGACTTCACCCTTACTATCAATCGGCTCGAGCCTGAGGATTTCGCCGTG | |
| | TATTACTGCCAGCACTACGAGGGTCCCCGCTGATTACCTTCGGCCAAGGCACCAAAGTGGA | |
| | CATCAAGACCACTACCCCAGCACCGAGGCCACCCACCCCGGCTCCTACCATCGCCTCCCAGC | |
| | CTCTGTCCCTGCGTCCGGAGGCATGTAGACCCGCAGCTGGTGGGCCGTGCATACCCGGGGT | |
| | CTTGACTTCGCCTGCGATATCTACATTTGGGCCCCTCTGGCTGGTACTTGCGGGGTCCTGCT | |
| | GCTTTCACTCGTGATCACTCTTTACTGTAAGCGCGGTCGGAAGAAGCTGCTGTACATCTTTA | |
| | AGCAACCCTTCATGAGGCCTGTGCAGACTACTCAAGAGGAGGACGGCTGTTCATGCCGGTTC | |
| | CCAGAGGAGGAGGAAGGCGGCTGCGAACTGCGCGTGAAATTCAGCCGCAGCGCAGATGCTCC | |
| | AGCCTACAAGCAGGGGCAGAACCAGCTCTACAACGAACTCAATCTTGGTCGGAGAGAGGAGT | |
| | ACGACGTGCTGGACAAGCGGAGAGGACGGGACCCAGAAATGGGCGGGAAGCCGCGCAGAAAG | |
| | AATCCCCAAGAGGGCCTGTACAACGAGCTCCAAAAGGATAAGATGGCAGAAGCCTATAGCGA | |
| | GATTGGTATGAAAGGGGAACGCAGAAGAGGCAAAGGCCACGACGGACTGTACCAGGGACTCA | |
| | GCACCGCCACCAAGGACACCTATGACGCTCTTCACATGCAGGCCCTGCCGCCTCGG | |
| M20 CAR (na) | ATGGCCCTCCCTGTCACCGCCCTGCTGCTTCCGCTGGCTCTTCTGCTCCACGCCGCTCGGCC | 144 |
| | CCAAGTGCAACTTGTTCAATCAGGAGGAGGACTCGTTCAACCCGGAGGATCACTGCGACTCT | |
| | CATGTGCAGCGTCGGGGTTCACCTTCTCCAGCTACGCAATGTCCTGGGTGCGCCAAGCCCCT | |
| | GGAAAAGGCCTGGAGTGGGTGTCGGCCATCTCTGGGAGCGGGGGATCAACTTACTACGCTGA | |
| | CTCCGTCAAGGGCCGCTTTACCATCTCCCGGGACAACAGCAAGAACACTCTCTATCTCCAGA | |
| | TGAACTCGCTGAGAGCCGAAGATACCGCTGTCTACTACTGCGCGAAGAGAGAAGCTGCCGCA | |
| | GGGCACGATTGGTACTTCGACTTGTGGGCAGGGCACCCTTGTGACCGTGTCCTCCGGTGG | |
| | AGGCGGATCAGGAGGTGGGGATCGGGTGGAGGAGGAAGCGGAGGCGGCGGTTCGGACATTC | |
| | GCGTCACCCAGTCACCGAGCTCCCTCAGCGCATCGGTGGGCGACCGGGTCACTATCACTTGC | |
| | CGGGCGTCCCAGTCGATCTCATCGTATCTGAATTGGTACCAGCAGAAACCGGGAAAGGCGCC | |
| | GAAGCTGTTGATCTACGCTGCCAGCTCCCTGCAGTCGGGTGTGCCATCACGCTTTTCCGGCT | |
| | CGGGATCGGGAACCGATTTCACTCTGACGATCTCTAGCCTGCAGCCAGAAGATTTCGCCACT | |
| | TACTACTGCCAGCAGTCCTACAGCATCCCTCTGACTTTCGGACAAGGGACGAAAGTGGAGAT | |
| | TAAGACCACTACCCCAGCACCGAGGCCACCCACCCCGGCTCCTACCATCGCCTCCCAGCCTC | |
| | TGTCCCTGCGTCCGGAGGCATGTAGACCCGCAGCTGGTGGGCCGTGCATACCCGGGGTCTT | |
| | GACTTCGCCTGCGATATCTACATTTGGGCCCCTCTGGCTGGTACTTGCGGGGTCCTGCTGCT | |
| | TTCACTCGTGATCACTCTTTACTGTAAGCGCGGTCGGAAGAAGCTGCTGTACATCTTTAAGC | |
| | AACCCTTCATGAGGCCTGTGCAGACTACTCAAGAGGAGGACGGCTGTTCATGCCGGTTCCCA | |
| | GAGGAGGAGGAAGGCGGCTGCGAACTGCGCGTGAAATTCAGCCGCAGCGCAGATGCTCCAGC | |
| | CTACAAGCAGGGGCAGAACCAGCTCTACAACGAACTCAATCTTGGTCGGAGAGAGGAGTACG | |
| | ACGTGCTGGACAAGCGGAGAGGACGGGACCCAGAAATGGGCGGGAAGCCGCGCAGAAAGAAT | |
| | CCCCAAGAGGGCCTGTACAACGAGCTCCAAAAGGATAAGATGGCAGAAGCCTATAGCGAGAT | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | TGGTATGAAAGGGGAACGCAGAAGAGGCAAAGGCCACGACGGACTGTACCAGGGACTCAGCA | |
| | CCGCCACCAAGGACACCTATGACGCTCTTCACATGCAGGCCCTGCCGCCTCGG | |
| M21 CAR (na) | ATGGCCCTCCCTGTCACCGCCCTGCTGCTTCCGCTGGCTCTTCTGCTCCACGCCGCTCGGCC | 145 |
| | CCAAGTCCAACTCGTTCAGTCATGGGCAGAAGTCAAGAAACCCGGTGCAAGCGTCAAAGTGT | |
| | CGTGTAAGGCCTCCGGCTACACTTTCACTTCCTACTACATGCACTGGGTGCGCCAAGCCCCG | |
| | GGACAGGGCCTTGAATGGATGGGCATCATCAACCCATCAGGAGGTTCCACGAGCTACGCGCA | |
| | GAAGTTCCAGGGGAGAGTGACGATGACTAGAGATACCTCCACGAGCACCGTCTACATGGAGC | |
| | TGTCGAATCTGCGGTCAGAGGACACTGCTGTGTATTACTGCGCGCGCTCCCCGCGGGTGACC | |
| | ACTGGCTACTTTGACTACTGGGGACAAGGGACCCTGGTGACCGTCAGCTCGGGAGGCGGAGG | |
| | ATCGGGAGGTGGAGGGTCCGGTGGAGGCGGCTCTGGAGGAGGCGGGTCGGACATTCAATTGA | |
| | CCCAGAGCCCATCCACCCTCTCAGCCTCGGTGGGGATAGGGTGACTATCACTTGCCGGGCC | |
| | TCCCAGTCAATTTCCAGCTGGCTGGCTTGGTACCAGCAAAAGCCTGGAAAGGCACCGAAGCT | |
| | CCTGATCTACAAGGCCTCATCTCTGGAATCAGGAGTGCCTTCGCGCTTCAGCGGAAGCGGCT | |
| | CGGGAACTGAGTTTACCCTGACCATCTCGAGCCTGCAGCCAGATGACTTCGCGACCTATTAC | |
| | TGCCAGCAGTACTCGTCCTACCCGTTGACTTTCGGAGGAGGTACCCGCCTCGAAATCAAAAC | |
| | CACTACCCCAGCACCGAGGCCACCCACCCCGGCTCCTACCATCGCCTCCCAGCCTCTGTCCC | |
| | TGCGTCCGGAGGCATGTAGACCCGCAGCTGGTGGGCCGTGCATACCCGGGGTCTTGACTTC | |
| | GCCTGCGATATCTACATTTGGGCCCCTCTGGCTGGTACTTGCGGGGTCCTGCTGCTTTCACT | |
| | CGTGATCACTCTTTACTGTAAGCGCGGTCGGAAGAAGCTGCTGTACATCTTTAAGCAACCCT | |
| | TCATGAGGCCTGTGCAGACTACTCAAGAGGAGGACGGCTGTTCATGCCGGTTCCCAGAGGAG | |
| | GAGGAAGGCGGCTGCGAACTGCGCGTGAAATTCAGCCGCAGCGCAGATGCTCCAGCCTACAA | |
| | GCAGGGGCAGAACCAGCTCTACAACGAACTCAATCTTGGTCGGAGAGAGGAGTACGACGTGC | |
| | TGGACAAGCGGAGAGGACGGGACCCAGAAATGGGCGGAAGCCGCGCAGAAAGAATCCCCAA | |
| | GAGGGCCTGTACAACGAGCTCCAAAAGGATAAGATGGCAGAAGCCTATAGCGAGATTGGTAT | |
| | GAAAGGGGAACGCAGAAGAGGCAAAGGCCACGACGGACTGTACCAGGGACTCAGCACCGCCA | |
| | CCAAGGACACCTATGACGCTCTTCACATGCAGGCCCTGCCGCCTCGG | |
| M22 CAR (na) | ATGGCCCTCCCTGTCACCGCCCTGCTGCTTCCGCTGGCTCTTCTGCTCCACGCCGCTCGGCC | 146 |
| | CCAAGTCCAACTCGTCCAGTCCGGTGCAGAAGTCAGAAGGCCAGGAGCAAGCGTGAAGATCT | |
| | CGTGTAGAGCGTCAGGAGACACCAGCACTCGCCATTACATCCACTGGCTGCGCCAGGCTCCG | |
| | GGCCAAGGGCCGGAGTGGATGGGTGTGATCAACCCGACTACGGGACCGGCTACCGGAAGCCC | |
| | TGCGTACGCACAGATGCTGCAGGGACGGGTGACTATGACCCGCGATACTAGCACTAGGACCG | |
| | TGTACATGGAACTCCGCTCGTTGCGGTTCGAAGATACCGCCGTCTACTACTGCGCCCGGTCC | |
| | GTGGTGGGCCGAAGCGCCCCTTACTACTTCGATTACTGGGGACAGGGCACTCTGGTGACCGT | |
| | TAGCTCCGGTGGGGAGGCTCGGGTGGAGGCGGATCGGGAGGAGGAGGCAGCGGTGGAGGGG | |
| | GATCGGACATTCAGATGACCCAGTCACCCTCCTCCCTCTCAGCCTCGGTCGGGACCGGGTG | |
| | ACCATTACGTGCAGAGCCTCACAAGGGATCTCGGACTACTCCGCCTGGTACCAGCAGAAACC | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | GGGAAAAGCGCCAAAGCTCCTGATCTACGCCGCGAGCACCCTGCAATCAGGAGTGCCATCGC | |
| | GCTTTTCTGGATCGGGCTCAGGGACTGACTTCACGCTGACTATCTCCTACCTTCAGTCCGAG | |
| | GATTTCGCTACCTACTACTGCCAACAGTATTACTCCTATCCCCTGACCTTTGGCGGAGGCAC | |
| | TAAGGTGGACATCAAGACCACTACCCCAGCACCGAGGCCACCCACCCCGGCTCCTACCATCG | |
| | CCTCCCAGCCTCTGTCCCTGCGTCCGGAGGCATGTAGACCCGCAGCTGGTGGGCCGTGCAT | |
| | ACCCGGGGTCTTGACTTCGCCTGCGATATCTACATTTGGGCCCCTCTGGCTGGTACTTGCGG | |
| | GGTCCTGCTGCTTTCACTCGTGATCACTCTTTACTGTAAGCGCGGTCGGAAGAAGCTGCTGT | |
| | ACATCTTTAAGCAACCCTTCATGAGGCCTGTGCAGACTACTCAAGAGGAGGACGGCTGTTCA | |
| | TGCCGGTTCCCAGAGGAGGAGGAAGGCGGCTGCGAACTGCGCGTGAAATTCAGCCGCAGCGC | |
| | AGATGCTCCAGCCTACAAGCAGGGGCAGAACCAGCTCTACAACGAACTCAATCTTGGTCGGA | |
| | GAGAGGAGTACGACGTGCTGGACAAGCGGAGAGGACGGGACCCAGAAATGGGCGGGAAGCCG | |
| | CGCAGAAAGAATCCCCAAGAGGGCCTGTACAACGAGCTCCAAAAGGATAAGATGGCAGAAGC | |
| | CTATAGCGAGATTGGTATGAAAGGGGAACGCAGAAGAGGCAAAGGCCACGACGGACTGTACC | |
| | AGGGACTCAGCACCGCCACCAAGGACACCTATGACGCTCTTCACATGCAGGCCCTGCCGCCT | |
| | CGG | |
| M23 CAR (na) | ATGGCCCTCCCTGTCACCGCCCTGCTGCTTCCGCTGGCTCTTCTGCTCCACGCCGCTCGGCC | 147 |
| | CCAAGTCCAACTCCAGCAATCGGGAGCAGAAGTCAAGAAACCAGGCGCATCGGTGAAAGTGT | |
| | CGTGTAAGGCGTCAGGGTACACCTTCACCAACTACTATATGCACTGGGTGCGCCAGGCTCCA | |
| | GGCCAGGGGTTGGAGTGGATGGGGATCATCAATCCGTCAGGTGGCTACACCACTTACGCTCA | |
| | GAAGTTCCAGGGACGCCTCACTATGACTCGCGATACTAGCACCTCCACGGTGTACATGGAAC | |
| | TGTCATCGCTGAGGTCCGAAGATACCGCCGTCTACTACTGCGCACGGATCAGATCCTGCGGA | |
| | GGAGATTGTTACTACTTTGACAACTGGGGACAGGGCACCCTTGTTACTGTGTCATCGGGAGG | |
| | AGGGGGAAGCGGAGGAGGTGGATCAGGCGGCGGTGGCAGCGGGGGCGGAGGATCGGACATTC | |
| | AGCTGACTCAGTCCCCCTCCACTTTGTCGGCCAGCGTGGGAGACAGAGTGACCATCACTTGC | |
| | CGGGCGTCCGAGAACGTCAATATCTGGCTGGCCTGGTACCAGCAAAAGCCTGGAAAAGCCCC | |
| | GAAGCTGCTCATCTATAAGTCATCCAGCCTGGCGTCTGGTGTGCCGTCGCGGTTCTCCGGCA | |
| | GCGGGAGCGGAGCCGAGTTCACTCTCACCATTTCGAGCCTTCAACCGGACGATTTCGCCACC | |
| | TACTACTGCCAGCAGTACCAATCCTACCCTCTGACGTTTGGAGGTGGAACCAAGGTGGACAT | |
| | CAAGACCACTACCCCAGCACCGAGGCCACCCACCCCGGCTCCTACCATCGCCTCCCAGCCTC | |
| | TGTCCCTGCGTCCGGAGGCATGTAGACCCGCAGCTGGTGGGCCGTGCATACCCGGGGTCTT | |
| | GACTTCGCCTGCGATATCTACATTTGGGCCCCTCTGGCTGGTACTTGCGGGGTCCTGCTGCT | |
| | TTCACTCGTGATCACTCTTTACTGTAAGCGCGGTCGGAAGAAGCTGCTGTACATCTTTAAGC | |
| | AACCCTTCATGAGGCCTGTGCAGACTACTCAAGAGGAGGACGGCTGTTCATGCCGGTTCCCA | |
| | GAGGAGGAGGAAGGCGGCTGCGAACTGCGCGTGAAATTCAGCCGCAGCGCAGATGCTCCAGC | |
| | CTACAAGCAGGGGCAGAACCAGCTCTACAACGAACTCAATCTTGGTCGGAGAGAGGAGTACG | |
| | ACGTGCTGGACAAGCGGAGAGGACGGGACCCAGAAATGGGCGGGAAGCCGCGCAGAAAGAAT | |
| | CCCCAAGAGGGCCTGTACAACGAGCTCCAAAAGGATAAGATGGCAGAAGCCTATAGCGAGAT | |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | TGGTATGAAAGGGGAACGCAGAAGAGGCAAAGGCCACGACGGACTGTACCAGGGACTCAGCA | |
| | CCGCCACCAAGGACACCTATGACGCTCTTCACATGCAGGCCCTGCCGCCTCGG | |
| M24 CAR (na) | ATGGCCCTCCCTGTCACCGCCCTGCTGCTTCCGCTGGCTCTTCTGCTCCACGCCGCTCGGCC<br>CCAAATCACTCTGAAAGAATCTGGACCGGCCCTGGTTAAGCCGACTCAAACGCTCACCCTTA<br>CTTGCACCTTCAGCGGATTCTCACTCAGCACTGCTGGTGTGCACGTCGGATGGATTAGACAG<br>CCGCCTGGAAAGGCCCTGGAATGGCTCGCCCTCATCTCCTGGGCCGATGACAAGAGATACAG<br>GCCCTCGCTTCGATCCCGGTTGGACATTACCCGGGTGACCTCGAAAGATCAGGTGGTGCTCT<br>CAATGACCAATATGCAGCCGGAGGACACCGCTACGTACTACTGCGCACTGCAAGGATTTGAC<br>GGCTACGAGGCTAACTGGGGACCAGGTACTCTGGTCACCGTGAGCTCCGGCGGGGAGGATC<br>AGGCGGGGGGGGGTCAGGAGGCGGAGGCTCCGGTGGAGGAGGATCGGATATCGTCATGACCC<br>AGTCCCCAAGCTCGCTGAGCGCGTCAGCGGGCGACCGCGTGACTATCACTTGCCGGGCCAGC<br>CGCGGCATCTCCTCCGCACTGGCGTGGTACCAGCAGAAGCCTGGAAAACCGCCAAAGCTCCT<br>GATCTATGATGCCTCCAGCCTGGAGTCAGGTGTCCCCAGCCGCTTCTCGGGTTCGGGCTCGG<br>GAACCGACTTCACTTTGACCATCGACTCGCTGGAACCGGAAGATTTCGCAACCTACTACTGT<br>CAGCAGTCCTACTCGACCCCTTGGACTTTTGGACAAGGGACGAAGGTGGACATCAAGACCAC<br>TACCCCAGCACCGAGGCCACCCACCCCGGCTCCTACCATCGCCTCCCAGCCTCTGTCCCTGC<br>GTCCGGAGGCATGTAGACCCGCAGCTGGTGGGGCCGTGCATACCCGGGGTCTTGACTTCGCC<br>TGCGATATCTACATTTGGGCCCCTCTGGCTGGTACTTGCGGGGTCCTGCTGCTTTCACTCGT<br>GATCACTCTTTACTGTAAGCGCGGTCGGAAGAAGCTGCTGTACATCTTTAAGCAACCCTTCA<br>TGAGGCCTGTGCAGACTACTCAAGAGGAGGACGGCTGTTCATGCCGGTTCCCAGAGGAGGAG<br>GAAGGCGGCTGCGAACTGCGCGTGAAATTCAGCCGCAGCGCAGATGCTCCAGCCTACAAGCA<br>GGGGCAGAACCAGCTCTACAACGAACTCAATCTTGGTCGGAGAGAGGAGTACGACGTGCTGG<br>ACAAGCGGAGAGGACGGGACCCAGAAATGGGCGGGAAGCCGCGCAGAAAGAATCCCCAAGAG<br>GGCCTGTACAACGAGCTCCAAAAGGATAAGATGGCAGAAGCCTATAGCGAGATTGGTATGAA<br>AGGGGAACGCAGAAGAGGCAAAGGCCACGACGGACTGTACCAGGGACTCAGCACCGCCACCA<br>AGGACACCTATGACGCTCTTCACATGCAGGCCCTGCCGCCTCGG | 148 |
| Ss1 CAR (na) | atggccctccctgtcaccgccctgctgcttccgctggctcttctgctccacgccgctcg<br>gccccaagtccagctccagcagtcgggcccagagttggagaagcctggggcgagcgtga<br>agatctcatgcaaagcctcaggctactccttactggatacacgatgaattgggtgaaa<br>cagtcgcatggaaagtcactggaatggatcggtctgattacgccctacaacggcgcctc<br>cagctacaaccagaagttcaggggaaaggcgacccttactgtcgacaagtcgtcaagca<br>ccgcctacatggacctcctgtccctgacctccgaagatagcgcggtctacttttgtgca<br>cgcggaggttacgatggacggggattcgactactggggccagggaaccactgtcaccgt<br>gtcgagcggaggcggagggagcggaggaggaggcagcggaggtggagggtcggatatcg<br>aactcactcagtccccagcaatcatgtccgcttcaccgggagaaaaggtgaccatgact<br>tgctcggcctcctcgtccgtgtcatacatgcactggtaccaacaaaaatcggggacctc | 149 |

TABLE 6-continued

Exemplary mesothelin CAR molecules (aa—amino acids; na—nucleic acid encoding the corresponding polypeptide)

| Name | Sequence | SEQ ID NO: |
|---|---|---|
| | ccctaagagatggatctacgataccagcaaactggcttcaggcgtgccgggacgcttct | |
| | cgggttcggggagcggaaattcgtattcgttgaccatttcgtccgtggaagccgaggac | |
| | gacgcaacttattactgccaacagtggtcaggctaccgctcactttcggagccggcac | |
| | taagctggagatcaccactacccagcaccgaggccacccacccggctcctaccatcg | |
| | cctcccagcctctgtccctgcgtccggaggcatgtagacccgcagctggtggggccgtg | |
| | catacccggggtcttgacttcgcctgcgatatctacatttgggcccctctggctggtac | |
| | ttgcggggtcctgctgctttcactcgtgatcactctttactgtaagcgcggtcggaaga | |
| | agctgctgtacatctttaagcaaccccttcatgaggcctgtgcagactactcaagaggag | |
| | gacggctgttcatgccggttcccagaggaggaggaaggcggctgcgaactgcgcgtgaa | |
| | attcagccgcagcgcagatgctccagcc | |

In one embodiment, the CAR molecule comprises (e.g., consists of) an amino acid sequence as provided in Table 11 and Table 2 of International Publication No. WO2015/090230, filed Dec. 19, 2014; incorporated herein by reference. In one embodiment, the CAR molecule comprises (e.g., consists of) an amino acid sequence of SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, or SEQ ID NO: 124; or an amino acid sequence having at least one, two, three, four, five, 10, 15, 20 or 30 modifications (e.g., substitutions, e.g., conservative substitutions) but not more than 60, 50, or 40 modifications (e.g., substitutions, e.g., conservative substitutions) of an amino acid sequence of SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, or SEQ ID NO: 124; or an amino acid sequence having 85%, 90%, 95%, 96%, 97%, 98%, 99% identity to an amino acid sequence of SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, or SEQ ID NO: 124.

Exemplary CAR molecules that bind to Folate receptor alpha (FRa) are provided in Table 7. The CAR molecules in Table 7 comprise a FRa antigen binding domain, e.g., an amino acid sequence or nucleic acid sequence of any mesothelin antigen binding domain provided in Table 5.

TABLE 7

Exemplary FRa CAR molecules (aa- amino acids; na- nucleic acid encoding the corresponding polypeptide)

MOv19-4-1BB-CD3zeta CAR (AA)

(SEQ ID NO: 150)

MALPVTALLLPLALLLHAARPGSSRAAQPAMAQVQLQQSGAELVKPGASVKISCKASGYS

FTGYFMNWVKQSHGKSLEWIGRIHPYDGDTFYNQNFKDKATLTVDKSSNTAHMELLSLTS

EDFAVYYCTRYDGSRAMDYWGQGTTVTVSSGGGGSGGGGSGGGGSDIELTQSPASLAVSL

GQRAIISCKASQSVSFAGTSLMHWYHQKPGQQPKLLIYRASNLEAGVPTRFSGSGSKTDF

TLNIHPVEEEDAATYYCQQSREYPYTFGGGTKLEIKRAAASTTTPAPRPPTPAPTIASQP

LSLRPEACRPAAGGAVHTRGLDFACDIYIWAPLAGTCGVLLLSLVITLYCKRGRKKLLYI

TABLE 7-continued

Exemplary FRa CAR molecules
(aa- amino acids; na- nucleic acid encoding the
corresponding polypeptide)

FKQPFMRPVQTTQEEDGCSCRFPEEEEGGCELRVKFSRSADAPAYKQGQNQLYNELNLGR

REEYDVLDKRRGRDPEMGGKPRRKNPQEGLYNELQKDKMAEAYSEIGMKGERRRGKGHDG

LYQGLSTATKDTYDALHMQALPPR

MOv19-4-1BB-CD3zeta CAR (NA)

(SEQ ID NO: 151)

```
atggccttac cagtgaccgc cttgctcctg ccgctggcct tgctgctcca cgccgccagg   60
ccgggatcct ctagagcggc ccagccggcc atggcccagg tgcagctgca gcagtctgga  120
gctgagctgg tgaagcctgg ggcttcagtg aagatatcct gcaaggcttc tggttactca  180
tttactggct actttatgaa ctgggtgaag cagagccatg gaaagagcct gagtggatt   240
ggacgtattc atccttacga tggtgatact ttctacaacc agaacttcaa ggacaaggcc  300
acattgactg tagacaaatc ctctaacaca gcccacatgg agctcctgag cctgacatct  360
gaggactttg cagtctatta ttgtacaaga tacgacggta gtcgggctat ggactactgg  420
ggccaaggga ccacggtcac cgtctcctca ggtggaggcg gttcaggcgg aggtggctct  480
ggcggtggcg gatcggacat cgagctcact cagtctccag cttctttggc tgtgtctcta  540
gggcagaggg ccatcatctc ctgcaaggcc agccaaagtg tcagttttgc tggtactagt  600
ttaatgcact ggtaccacca gaaaccagga cagcaaccca aactcctcat ctatcgtgca  660
tccaacctag aagctggggt tcctaccagg tttagtggca gtgggtctaa gacagacttc  720
accctcaata tccatcctgt ggaggaggag gatgctgcaa cctattactg tcagcaaagt  780
agggaatatc cgtacacgtt cggaggggg acaaagttgg aaataaaacg gcggccgct   840
agcaccacga cgccagcgcc gcgaccacca acaccggcgc ccaccatcgc gtcgcagccc  900
ctgtccctgc gcccagaggc gtgccggcca gcggcgggg gcgcagtgca cacgagggg   960
ctggacttcg cctgtgatat ctacatctgg gcgcccttgg ccgggacttg tggggtcctt 1020
ctcctgtcac tggttatcac cctttactgc aaacggggca gaaagaaact cctgtatata 1080
ttcaaacaac catttatgag accagtacaa actactcaag aggaagatgg ctgtagctgc 1140
cgatttccag aagaagaaga aggaggatgt gaactgagag tgaagttcag caggagcgca 1200
gacgcccccg cgtacaagca gggccagaac cagctctata cgagctcaa tctaggacga 1260
agagaggagt acgatgtttt ggacaagaga cgtggccggg accctgagat gggggggaaag 1320
ccgagaagga agaaccctca ggaaggcctg tacaatgaac tgcagaaaga taagatggcg 1380
gaggcctaca gtgagattgg gatgaaaggc gagcgccgga ggggcaaggg cacgatggc   1440
ctttaccagg gtctcagtac agccaccaag gacacctacg acgcccttca catgcaggcc 1500
ctgcccctc gctaagtcga ctcgacaatc aacctctgga ttacaaaatt tgtgaaagat 1560
tgactggtat tcttaactat gttgctcctt ttacgctatg tggatacgct gctttaatgc 1620
ctttgtatca tgctattgct tcccgtatgg ctttcatttt ctcctccttg tataaatcct 1680
ggttgctgtc tctttatgag gagttgtggc ccgttgtcag caacgtggc gtggtgtgca  1740
ctgtgtttgc tgacgcaacc cccactggtt ggggcattgc caccacctgt cagctccttt 1800
ccgggacttt cgctttcccc ctccctattg ccacggcgga actcatcgcc gcctgccttg 1860
cccgctgctg gacaggggct cggctgttgg gcactgacaa ttccgtggtg ttgtcgggga 1920
agctgacgtc ctttccatgg ctgctcgcct gtgttgccac ctggattctg cgcggacgt  1980
ccttctgcta cgtcccttcg ccctcaatc cagcggacct tccttcccgc ggcctgctgc 2040
```

TABLE 7-continued

Exemplary FRa CAR molecules
(aa- amino acids; na- nucleic acid encoding the
corresponding polypeptide)

```
cggctctgcg gcctcttccg cgtcttcgcc ttcgccctca gacgagtcgg atctcccttt    2100
gggccgcctc cccgcctgga attcgagctc ggtacctta  agaccaatga cttacaaggc    2160
agctgtagat cttagccact ttttaaaaga aaaggggga  ctggaagggc taattcactc    2220
ccaacgaaga caagatctgc tttttgcttg tactgggtct ctctggttag accagatctg    2280
agcctgggag ctctctggct aactagggaa cccactgctt aagcctcaat aaagcttgcc    2340
ttgagtgctt caagtagtgt gtgcccgtct gttgtgtgac tctggtaact agagatccct    2400
cagacccttt tagtcagtgt ggaaaatctc tagcagtagt agttcatgtc atcttattat    2460
tcagtattta aacttgcaa  agaaatgaat atcagagagt gagaggaact tgtttattgc    2520
agcttataat ggttacaaat aaagcaatag catcacaaat ttcacaaata aagcattttt    2580
ttcactgcat tctagttgtg gtttgtccaa actcatcaat gtatcttatc atgtctggct    2640
ctagctatcc cgcccctaac tccgcccagt tccgcccatt ctccgcccca tggctgacta    2700 attttttta  tttatgcaga ggccgaggcc gcctcggcct ctgagctatt ccagaagtag    2760
tgaggaggct tttttggagg cctaggcttt tgcgtcgaga cgtacccaat cgccctata    2820 gtgagtcgta ttacgcgcgc tcactggccg tcgttttaca acgtcgtgac tgggaaaacc    2880
ctggcgttac ccaacttaat cgccttgcag cacatccccc tttcgccagc tggcgtaata    2940
gcgaagaggc ccgcaccgat cgcccttccc aacagttgcg cagcctgaat ggcgaatggc    3000
gcgacgcgcc ctgtagcggc gcattaagcg cggcgggtgt ggtggttacg cgcagcgtga    3060
ccgctacact tgccagcgcc ctagcgcccg ctcctttcgc tttcttccct tcctttctcg    3120
ccacgttcgc cggctttccc cgtcaagctc taaatcgggg gctccctta  gggttccgat    3180 ttagtgcttt acggcacctc gaccccaaaa aacttgatta gggtgatggt tcacgtagtg    3240
ggccatcgcc ctgatagacg gttttttcgcc ctttgacgtt ggagtccacg ttctttaata   3300
gtggactctt gttccaaact ggaacaacac tcaaccctat ctcggtctat tcttttgatt    3360
tataagggat tttgccgatt tcggcctatt ggttaaaaaa tgagctgatt taacaaaaat    3420
ttaacgcgaa ttttaacaaa atattaacgt ttacaatttc caggtggca  ctttcgggg    3480 aaatgtgcgc ggaaccccta tttgtttatt tttctaaata cattcaaata tgtatccgct    3540
catgagacaa taaccctgat aaatgcttca ataatattga aaaggaaga  gtatgagtat    3600 tcaacatttc cgtgtcgccc ttattccctt ttttgcggca ttttgccttc ctgtttttgc    3660
tcacccagaa acgctggtga agtaaaaga  tgctgaagat cagttgggtg cacgagtggg    3720
ttacatcgaa ctggatctca acagcggtaa gatccttgag agttttcgcc ccgaagaacg    3780
ttttccaatg atgagcactt ttaaagttct gctatgtggc gcggtattat cccgtattga    3840
cgccgggcaa gagcaactcg gtcgccgcat acactattct cagaatgact tggttgagta    3900
ctcaccagtc acagaaaagc atcttacgga tggcatgaca gtaagagaat tatgcagtgc    3960
tgccataacc atgagtgata acactgcggc caacttactt ctgacaacga tcggaggacc    4020
gaaggagcta accgcttttt tgcacaacat ggggatcat  gtaactcgcc ttgatcgttg    4080
ggaaccggag ctgaatgaag ccataccaaa cgacgagcgt gacaccacga tgcctgtagc    4140
aatggcaaca acgttgcgca aactattaac tggcgaacta cttactctag cttcccggca    4200
acaattaata gactggatgg aggcggataa agttgcagga ccacttctgc gctcggccct    4260
tccggctggc tggtttattg ctgataaatc tggagccggt gagcgtgggt ctcgcggtat    4320
```

TABLE 7-continued

Exemplary FRa CAR molecules
(aa- amino acids; na- nucleic acid encoding the
corresponding polypeptide)

```
cattgcagca ctggggccag atggtaagcc ctcccgtatc gtagttatct acacgacggg   4380
gagtcaggca actatggatg aacgaaatag acagatcgct gagataggtg cctcactgat   4440
taagcattgg taactgtcag accaagttta ctcatatata ctttagattg atttaaaact   4500
tcatttttaa tttaaaagga tctaggtgaa gatccttttt gataatctca tgaccaaaat   4560
cccttaacgt gagttttcgt tccactgagc gtcagacccc gtagaaaaga tcaaaggatc   4620
ttcttgagat cctttttttc tgcgcgtaat ctgctgcttg caaacaaaaa aaccaccgct   4680
accagcggtg gtttgtttgc cggatcaaga gctaccaact cttttccga aggtaactgg   4740 cttcagcaga gcgcagatac caaatactgt ccttctagtg tagccgtagt taggccacca   4800
cttcaagaac tctgtagcac cgcctacata cctcgctctg ctaatcctgt taccagtggc   4860
tgctgccagt ggcgataagt cgtgtcttac cgggttggac tcaagacgat agttaccgga   4920
taaggcgcag cggtcgggct gaacggggggt tcgtgcaca cagcccagct tggagcgaac   4980
gacctacacc gaactgagat acctacagcg tgagctatga gaaagcgcca cgcttcccga   5040
agggagaaag gcggacaggt atccggtaag cggcagggtc ggaacaggag agcgcacgag   5100
ggagcttcca gggggaaacg cctggtatct ttatagtcct gtcgggtttc gccacctctg   5160
acttgagcgt cgatttttgt gatgctcgtc agggggggcgg agcctatgga aaaacgccag   5220
caacgcggcc ttttttacggt tcctggcctt ttgctggcct tttgctcaca tgttctttcc   5280
tgcgttatcc cctgattctg tggataaccg tattaccgcc tttgagtgag ctgataccgc   5340
tcgccgcagc cgaacgaccg agcgcagcga gtcagtgagc gaggaagcgg aagagcgccc   5400
aatacgcaaa ccgcctctcc ccgcgcgttg gccgattcat taatgcagct ggcacgacag   5460
gtttcccgac tggaaagcgg gcagtgagcg caacgcaatt aatgtgagtt agctcactca   5520
ttaggcaccc caggctttac actttatgct tccggctcgt atgttgtgtg gaattgtgag   5580
cggataacaa tttcacacag gaaacagcta tgaccatgat tacgccaagc gcgcaattaa   5640
ccctcactaa agggaacaaa agctggagct gcaagcttaa tgtagtctta tgcaatactc   5700
ttgtagtctt gcaacatggt aacgatgagt tagcaacatg ccttacaagg agagaaaaag   5760
caccgtgcat gccgattggt ggaagtaagg tggtacgatc gtgccttatt aggaaggcaa   5820
cagacgggtc tgacatggat tggacgaacc actgaattgc cgcattgcag agatattgta   5880
tttaagtgcc tagctcgata caataaacgg gtctctctgg ttagaccaga tctgagcctg   5940
ggagctctct ggctaactag gaacccact gcttaagcct caataaagct tgccttgagt   6000
gcttcaagta gtgtgtgccc gtctgttgtg tgactctggt aactagagat ccctcagacc   6060
cttttagtca gtgtggaaaa tctctagcag tggcgcccga acaggacct gaaagcgaaa   6120 gggaaaccag agctctctcg acgcaggact cggcttgctg aagcgcgcac ggcaagaggc   6180
gaggggcggc gactggtgag tacgccaaaa attttgacta gcggaggcta aaggagaga   6240 gatgggtgcg agagcgtcag tattaagcgg gggagaatta gatcgcgatg ggaaaaaatt   6300
cggttaaggc caggggggaaa gaaaaaatat aaattaaaac atatagtatg ggcaagcagg   6360
gagctagaac gattcgcagt taatcctggc ctgttagaaa catcagaagg ctgtagacaa   6420
atactgggac agctacaacc atcccttcag acaggatcag aagaacttag atcattatat   6480
aatacagtag caaccctcta ttgtgtgcat caaaggatag agataaaaga caccaaggaa   6540
gctttagaca agatagagga agagcaaaac aaaagtaaga ccaccgcaca gcaagcggcc   6600
```

TABLE 7-continued

Exemplary FRa CAR molecules
(aa- amino acids; na- nucleic acid encoding the
corresponding polypeptide)

```
gctgatcttc agacctggag gaggagatat gagggacaat tggagaagtg aattatataa 6660
atataaagta gtaaaaattg aaccattagg agtagcaccc accaaggcaa agagaagagt 6720
ggtgcagaga gaaaaaagag cagtgggaat aggagctttg ttccttgggt tcttgggagc 6780
agcaggaagc actatgggcg cagcctcaat gacgctgacg gtacaggcca gacaattatt 6840
gtctggtata gtgcagcagc agaacaattt gctgagggct attgaggcgc aacagcatct 6900
gttgcaactc acagtctggg gcatcaagca gctccaggca agaatcctgg ctgtggaaag 6960
atacctaaag gatcaacagc tcctggggat ttggggttgc tctggaaaac tcatttgcac 7020
cactgctgtg ccttggaatg ctagttggag taataaatct ctggaacaga ttggaatcac 7080
acgacctgga tggagtggga cagagaaatt aacaattaca caagcttaat acactcctta 7140
attgaagaat cgcaaaacca gcaagaaaag aatgaacaag aattattgga attagataaa 7200
tgggcaagtt tgtggaattg gtttaacata acaaattggc tgtggtatat aaaattattc 7260
ataatgatag taggaggctt ggtaggttta agaatagttt ttgctgtact ttctatagtg 7320
aatagagtta ggcagggata ttcaccatta tcgtttcaga cccacctccc aaccccgagg 7380
ggacccgaca ggcccgaagg aatagaagaa gaaggtggag agagacag agacagatcc 7440 attcgattag tgaacggatc tcgacggtat cgattagact gtagcccagg aatatggcag 7500
ctagattgta cacatttaga aggaaaagtt atcttggtag cagttcatgt agccagtgga 7560
tatatagaag cagaagtaat tccagcagag acagggcaag aaacagcata cttcctctta 7620
aaattagcag gaagatggcc agtaaaaaca gtacatacag acaatggcag caatttcacc 7680
agtactacag ttaaggccgc ctgttggtgg gcggggatca agcaggaatt tggcattccc 7740
tacaatcccc aaagtcaagg agtaatagaa tctatgaata aagaattaaa gaaaattata 7800
ggacaggtaa gagatcaggc tgaacatctt aagacagcag tacaaatggc agtattcatc 7860
cacaatttta aaagaaaagg ggggattggg ggtacagtg caggggaaag aatagtagac 7920
ataatagcaa cagacataca aactaaagaa ttacaaaaac aaattacaaa aattcaaaat 7980
tttcgggttt attacaggga cagcagagat ccagtttggc tgcatacgcg tcgtgaggct 8040
ccggtgcccg tcagtgggca gagcgcacat cgcccacagt ccccgagaag ttggggggag 8100
gggtcggcaa ttgaaccggt gcctagagaa ggtggcgcgg ggtaaactgg gaaagtgatg 8160
tcgtgtactg gctccgcctt tttcccgagg gtgggggaga accgtatata agtgcagtag 8220
tcgccgtgaa cgttcttttt cgcaacgggt ttgccgccag aacacaggta agtgccgtgt 8280
gtggttcccg cgggcctggc ctctttacgg gttatggccc ttgcgtgcct tgaattactt 8340
ccacctggct gcagtacgtg attcttgatc ccgagcttcg ggttggaagt gggtgggaga 8400
gttcgaggcc ttgcgcttaa ggagccccct cgcctcgtgc ttgagttgag gcctggcctg 8460
ggcgctgggg ccgccgcgtg cgaatctggt ggcaccttcg cgcctgtctc gctgctttcg 8520
ataagtctct agccatttaa aattttttgat gacctgctgc gacgcttttt ttctggcaag 8580
atagtcttgt aaatgcgggc caagatctgc acactggtat ttcggttttt ggggccgcgg 8640
gcggcgacgg ggcccgtgcg tcccagcgca catgttcggc gaggcgggc ctgcgagcgc 8700 ggccaccgag aatcggacgg gggtagtctc aagctggccg gcctgctctg gtgcctggcc 8760
tcgcgccgcc gtgtatcgcc ccgccctggg cggcaaggct ggcccggtcg caccagttg 8820 cgtgagcgga aagatggccg cttcccggcc ctgctgcagg gagctcaaaa tggaggacgc 8880
```

TABLE 7-continued

Exemplary FRa CAR molecules
(aa- amino acids; na- nucleic acid encoding the
corresponding polypeptide)

```
ggcgctcggg agagcgggcg ggtgagtcac ccacacaaag gaaaagggcc tttccgtcct  8940
cagccgtcgc ttcatgtgac tccacggagt accgggcgcc gtccaggcac ctcgattagt  9000
tctcgagctt ttggagtacg tcgtctttag gttgggggga ggggttttat gcgatggagt  9060
ttccccacac tgagtgggtg gagactgaag ttaggccagc ttggcacttg atgtaattct  9120
ccttggaatt tgccctttt gagtttggat cttggttcat tctcaagcct cagacagtgg  9180
ttcaaagttt ttttcttcca tttcaggtgt cgtgagctag ctctagag                9228
```

C4scFv-4-1BB-CD3zeta CAR (AA)
(SEQ ID NO: 152)

MALPVTALLLPLALLLHAARPGSQLVESGGGLVQPGRSLRLSCTTSGFTFGDYAMIWARQ

APGKGLEWVSSISSSSSYTYYADSVKGRFTISRDNAKNSLYLQMNSLRAEDTAVYYCARE

RYDFWSGMDVWGKGTTVTVSSGGGGSGGGGSGGSAQSALTQPASVSGSPGQSITISCTGT

SSDVGSYNLVSWYQQHPGKAPKLMIYEGSKRPSGVSNRFSGSKSGNAASLTISGLQAEDE

ADYYCQSYDSSLSVVEGGGTKLTVLGASTTTPAPRPPTPAPTIASQPLSLRPEACRPAAG

GAVHTRGLDFACDIYIWAPLAGTCGVLLLSLVITLYCKRGRKKLLYIFKQPFMRPVQTTQ

EEDGCSCRFPEEEEGGCELRVKFSRSADAPAYKQGQNQLYNELNLGRREEYDVLDKRRGR

DPEMGGKPRRKNPQEGLYNELQKDKMAEAYSEIGMKGERRRGKGHDGLYQGLSTATKDTY

DALHMQALPPR

C4scFv-4-1BB-CD3zeta CAR (AA)
(SEQ ID NO: 153)

```
atggccttac cagtgaccgc cttgctcctg ccgctggcct tgctgctcca cgccgccagg    60
ccgggatccc agctggtgga gtctggggga ggcttggtac agccagggcg gtccctgaga   120
ctctcctgca caacttctgg attcactttt ggtgattatg ctatgatctg gccccgccag   180
gctccaggga aggggctgga gtgggtctca tccattagta gtagtagtag ttacatatac   240
tacgcagact cagtgaaggg ccgattcacc atctccagag acaacgccaa gaactcactg   300
tatctgcaaa tgaacagcct gagagccgag gacacggctg tgtattactg tgcgagagaa   360
cgatacgatt tttggagtgg aatggacgtc tggggcaaag gaccacggt caccgtctcg   420 agtggtggag gcggttcagg cggaggtggc tctggcggta gtgcacagtc tgccctgact   480
cagcctgcct ccgtgtctgg gtctcctgga cagtcgatca ccatctcctg cactggaacc   540
agcagtgatg ttgggagtta taaccttgtc tcctggtacc aacagcaccc aggcaaagcc   600
cccaaactca tgatttatga gggcagtaag cggccctcag gggtttctaa tcgcttctct   660
ggctccaagt ctggcaacgc ggcctccctg acaatctctg gctccaggc tgaggacgag   720 gctgattatt actgccagtc ctatgacagc agcctgagtg tggtattcgg cggagggacc   780
aagctgaccg tcctaggtgc tagcaccacg acgccagcgc cgcgaccacc aacaccggcg   840
cccaccatcg cgtcgcagcc cctgtccctg cgcccagagg cgtgccgcc agcggcgggg   900 ggcgcagtgc acacgagggg gctggacttc gcctgtgata tctacatctg ggcgcccttg   960
gccgggactt gtgggtcctt ctcctgtca ctggttatca cccttactg caaacggggc  1020 agaaagaaac tcctgtatat attcaaacaa ccatttatga ccagtacaa actactcaa   1080 gaggaagatg gctgtagctg ccgatttcca gaagaagaag aaggaggatg tgaactgaga  1140
gtgaagttca gcaggagcgc agacgccccc gcgtacaagc agggccagaa ccagctctat  1200
aacgagctca atctaggacg aagagaggag tacgatgttt tggacaagag acgtggccgg  1260
```

TABLE 7-continued

Exemplary FRa CAR molecules
(aa- amino acids; na- nucleic acid encoding the
corresponding polypeptide)

```
gaccctgaga tgggggggaaa gccgagaagg aagaaccctc aggaaggcct gtacaatgaa  1320
ctgcagaaag ataagatggc ggaggcctac agtgagattg ggatgaaagg cgagcgccgg  1380
aggggcaagg ggcacgatgg cctttaccag ggtctcagta cagccaccaa ggacacctac  1440 gacgccttc acatgcaggc cctgcccct cgctaagtcg actcgacaat caacctctgg  1500
attacaaaat ttgtgaaaga ttgactggta ttcttaacta tgttgctcct tttacgctat  1560
gtggatacgc tgctttaatg cctttgtatc atgctattgc ttcccgtatg gctttcattt  1620
tctcctcctt gtataaatcc tggttgctgt ctctttatga ggagttgtgg cccgttgtca  1680
ggcaacgtgg cgtggtgtgc actgtgtttg ctgacgcaac ccccactggt tggggcattg  1740
ccaccacctg tcagctcctt tccgggactt tcgctttccc cctccctatt gccacggcgg  1800
aactcatcgc cgcctgcctt gcccgctgct ggacaggggc tcggctgttg ggcactgaca  1860
attccgtggt gttgtcgggg aagctgacgt cctttccatg gctgctcgcc tgtgttgcca  1920
cctggattct gcgcgggacg tccttctgct acgtcccttc ggccctcaat ccagcggacc  1980
ttccttcccg cggcctgctg ccggctctgc ggcctcttcc gcgtcttcgc cttcgccctc  2040
agacgagtcg gatctcccctt tgggccgcct ccccgcctgg aattcgagct cggtacctttt  2100 aagaccaatg acttacaagg cagctgtaga tcttagccac ttttttaaaag aaaagggggg  2160 actggaaggg ctaattcact cccaacgaag acaagatctg cttttttgctt gtactgggtc  2220 tctctggtta gaccagatct gagcctggga gctctctggc taactaggga acccactgct  2280
taagcctcaa taaagcttgc cttgagtgct tcaagtagtg tgtgcccgtc tgttgtgtga  2340
ctctggtaac tagagatccc tcagacccctt ttagtcagtg tggaaaatct ctagcagtag  2400
tagttcatgt catcttatta ttcagtattt ataacttgca aagaaatgaa tatcagagag  2460
tgagaggaac ttgtttattg cagcttataa tggttacaaa taaagcaata gcatcacaaa  2520
tttcacaaat aaagcatttt tttcactgca ttctagttgt ggtttgtcca aactcatcaa  2580
tgtatcttat catgtctggc tctagctatc ccgcccctaa ctccgcccag ttccgcccat  2640
tctccgcccc atggctgact aattttttttt atttatgcag aggccgaggc cgcctcggcc  2700
tctgagctat tccagaagta gtgaggaggc ttttttggag gcctaggctt ttgcgtcgag  2760
acgtacccaa ttcgccctat agtgagtcgt attacgcgcg ctcactggcc gtcgttttac  2820
aacgtcgtga ctgggaaaac cctggcgtta cccaacttaa tcgccttgca gcacatcccc  2880
ctttcgccag ctggcgtaat agcgaagagg cccgcaccga tcgcccttcc caacagttgc  2940
gcagcctgaa tggcgaatgg cgcgacgcgc cctgtagcgg cgcattaagc gcggcgggtg  3000
tggtggttac gcgcagcgtg accgctacac ttgccagcgc cctagcgccc gctcctttcg  3060
ctttcttccc ttcctttctc gccacgttcg ccggctttcc ccgtcaagct ctaaatcggg  3120
ggctcccttt agggttccga tttagtgctt tacggcacct cgaccccaaa aaacttgatt  3180
agggtgatgg ttcacgtagt gggccatcgc cctgatagac ggtttttcgc cctttgacgt  3240
tggagtccac gttctttaat agtggactct tgttccaaac tggaacaaca ctcaaccccta  3300 tctcggtcta ttcttttgat ttataaggga ttttgccgat ttcggcctat tggttaaaaa  3360
atgagctgat ttaacaaaaa tttaacgcga attttaacaa aatattaacg tttacaattt  3420
cccaggtggc acttttcggg gaaatgtgcg cggaaccccct atttgtttat ttttctaaat  3480
acattcaaat atgtatccgc tcatgagaca ataaccctga taaatgcttc aataatattg  3540
```

TABLE 7-continued

Exemplary FRa CAR molecules
(aa- amino acids; na- nucleic acid encoding the
corresponding polypeptide)

```
aaaaaggaag agtatgagta ttcaacattt ccgtgtcgcc cttattccct tttttgcggc  3600
attttgcctt cctgtttttg ctcacccaga aacgctggtg aaagtaaaag atgctgaaga  3660
tcagttgggt gcacgagtgg gttacatcga actggatctc aacagcggta agatccttga  3720
gagttttcgc cccgaagaac gttttccaat gatgagcact tttaaagttc tgctatgtgg  3780
cgcggtatta tcccgtattg acgccgggca agagcaactc ggtcgccgca tacactattc  3840
tcagaatgac ttggttgagt actcaccagt cacagaaaag catcttacgg atggcatgac  3900
agtaagagaa ttatgcagtg ctgccataac catgagtgat aacactgcgg ccaacttact  3960
tctgacaacg atcggaggac cgaaggagct aaccgctttt ttgcacaaca tgggggatca  4020
tgtaactcgc cttgatcgtt gggaaccgga gctgaatgaa gccataccaa acgacgagcg  4080
tgacaccacg atgcctgtag caatggcaac aacgttgcgc aaactattaa ctggcgaact  4140
acttactcta gcttcccggc aacaattaat agactggatg gaggcggata agttgcagg  4200 accacttctg cgctcggccc ttccggctgg ctggtttatt gctgataaat ctggagccgg  4260
tgagcgtggg tctcgcggta tcattgcagc actggggcca gatggtaagc cctcccgtat  4320
cgtagttatc tacacgacgg ggagtcaggc aactatggat gaacgaaata gacagatcgc  4380
tgagataggt gcctcactga ttaagcattg gtaactgtca gaccaagttt actcatatat  4440
actttagatt gatttaaaac ttcatttta atttaaaagg atctaggtga agatccttt  4500 tgataatctc atgaccaaaa tcccttaacg tgagttttcg ttccactgag cgtcagaccc  4560
cgtagaaaag atcaaaggat cttcttgaga tcctttttt ctgcgcgtaa tctgctgctt  4620
gcaaacaaaa aaaccaccgc taccagcggt ggtttgtttg ccggatcaag agctaccaac  4680 tcttttccg aaggtaactg gcttcagcag agcgcagata ccaaatactg tccttctagt  4740
gtagccgtag ttaggccacc acttcaagaa ctctgtagca ccgcctacat acctcgctct  4800
gctaatcctg ttaccagtgg ctgctgccag tggcgataag tcgtgtctta ccgggttgga  4860
ctcaagacga tagttaccgg ataaggcgca gcggtcgggc tgaacggggg gttcgtgcac  4920
acagcccagc ttggagcgaa cgacctacac cgaactgaga tacctacagc gtgagctatg  4980
agaaagcgcc acgcttcccg aagggagaaa ggcggacagg tatccggtaa gcggcagggt  5040
cggaacagga gagcgcacga gggagcttcc agggggaaac gcctggtatc tttatagtcc  5100
tgtcgggttt cgccacctct gacttgagcg tcgatttttg tgatgctcgt caggggggcg  5160
gagcctatgg aaaaacgcca gcaacgcggc cttttacgg ttcctggcct tttgctggcc  5220
ttttgctcac atgttctttc ctgcgttatc ccctgattct gtggataacc gtattaccgc  5280
ctttgagtga gctgataccg ctcgccgcag ccgaacgacc gagcgcagcg agtcagtgag  5340
cgaggaagcg gaagagcgcc caatacgcaa accgcctctc cccgcgcgtt ggccgattca  5400
ttaatgcagc tggcacgaca ggtttcccga ctggaaagcg ggcagtgagc gcaacgcaat  5460
taatgtgagt tagctcactc attaggcacc ccaggcttta cactttatgc ttccggctcg  5520
tatgttgtgt ggaattgtga gcggataaca atttcacaca ggaaacagct atgaccatga  5580
ttacgccaag cgcgcaatta accctcacta agggaacaa agctggagc tgcaagctta  5640 atgtagtctt atgcaatact cttgtagtct tgcaacatgg taacgatgag ttagcaacat  5700
gccttacaag gagagaaaaa gcaccgtgca tgccgattgg tggaagtaag gtggtacgat  5760
cgtgccttat taggaaggca acagacgggt ctgacatgga ttggacgaac cactgaattg  5820
```

TABLE 7-continued

Exemplary FRa CAR molecules
(aa- amino acids; na- nucleic acid encoding the
corresponding polypeptide)

```
ccgcattgca gagatattgt atttaagtgc ctagctcgat acaataaacg ggtctctctg   5880
gttagaccag atctgagcct gggagctctc tggctaacta gggaacccac tgcttaagcc   5940
tcaataaagc ttgccttgag tgcttcaagt agtgtgtgcc cgtctgttgt gtgactctgg   6000
taactagaga tccctcagac ccttttagtc agtgtggaaa atctctagca gtggcgcccg   6060
aacagggacc tgaaagcgaa agggaaacca gagctctctc gacgcaggac tcggcttgct   6120
gaagcgcgca cggcaagagg cgaggggcgg cgactggtga gtacgccaaa aattttgact   6180
agcggaggct agaaggagag agatgggtgc gagagcgtca gtattaagcg gggagaatt    6240 agatcgcgat gggaaaaaat tcggttaagg ccaggggga agaaaaata taaattaaaa     6300 catatagtat gggcaagcag ggagctagaa cgattcgcag ttaatcctgg cctgttagaa   6360
acatcagaag gctgtagaca atactggga cagctacaac catcccttca gacaggatca    6420
gaagaactta gatcattata taatacagta gcaaccctct attgtgtgca tcaaaggata   6480
gagataaaag acaccaagga agctttagac aagatagagg aagagcaaaa caaaagtaag   6540
accaccgcac agcaagcggc cgctgatctt cagacctgga ggaggagata tgagggacaa   6600
ttggagaagt gaattatata aatataaagt agtaaaaatt gaaccattag gagtagcacc   6660
caccaaggca aagagaagag tggtgcagag agaaaaaaga gcagtgggaa taggagcttt   6720
gttccttggg ttcttgggag cagcaggaag cactatgggc gcagcctcaa tgacgctgac   6780
ggtacaggcc agacaattat tgtctggtat agtgcagcag cagaacaatt tgctgagggc   6840
tattgaggcg caacagcatc tgttgcaact cacagtctgg ggcatcaagc agctccaggc   6900
aagaatcctg gctgtggaaa gatacctaaa ggatcaacag ctcctgggga tttggggttg   6960
ctctggaaaa ctcatttgca ccactgctgt gccttggaat gctagttgga gtaataaatc   7020 tctgaacag attggaatca cacgacctgg atggagtggg acagagaaat taacaattac   7080
acaagcttaa tacactcctt aattgaagaa tcgcaaaacc agcaagaaaa gaatgaacaa   7140
gaattattgg aattagataa atgggcaagt ttgtggaatt ggtttaacat aacaaattgg   7200
ctgtggtata taaaattatt cataatgata gtaggaggct tggtaggttt aagaatagtt   7260
tttgctgtac tttctatagt gaatagagtt aggcagggat attcaccatt atcgtttcag   7320
acccacctcc caaccccgag gggacccgac aggcccgaag gaatagaaga agaaggtgga   7380
gagagagaca gagacagatc cattcgatta gtgaacggat ctcgacggta tcgattagac   7440
tgtagcccag gaatatggca gctagattgt acacatttag aaggaaaagt tatcttggta   7500
gcagttcatg tagccagtgg atatatagaa gcagaagtaa ttccagcaga gacagggcaa   7560
gaaacagcat acttcctctt aaaattagca ggaagatggc cagtaaaaac agtacataca   7620
gacaatggca gcaatttcac cagtactaca gttaaggccg cctgttggtg gcggggatc    7680 aagcaggaat ttggcattcc ctacaatccc caaagtcaag gagtaataga atctatgaat   7740
aaagaattaa agaaaattat aggacaggta agagatcagg ctgaacatct taagacagca   7800
gtacaaatgg cagtattcat ccacaatttt aaaagaaaag gggggattgg ggggtacagt   7860
gcaggggaaa gaatagtaga cataatagca acagacatac aaactaaaga attacaaaaa   7920
caaattacaa aaattcaaaa ttttcgggtt tattacaggg acagcagaga tccagtttgg   7980
ctgcatacgc gtcgtgaggc tccggtgccc gtcagtgggc agagcgcaca tcgcccacag   8040
tccccgagaa gttgggggga ggggtcggca attgaaccgg tgcctagaga aggtggcgcg   8100
```

TABLE 7-continued

Exemplary FRa CAR molecules
(aa- amino acids; na- nucleic acid encoding the
corresponding polypeptide)

```
gggtaaactg ggaaagtgat gtcgtgtact ggctccgcct tttcccgag ggtggggag  8160 aaccgtatat aagtgcagta gtcgccgtga acgttctttt tcgcaacggg tttgccgcca  8220
gaacacaggt aagtgccgtg tgtggttccc gcgggcctgg cctctttacg ggttatggcc  8280
cttgcgtgcc ttgaattact tccacctggc tgcagtacgt gattcttgat cccgagcttc  8340
gggttggaag tgggtgggag agttcgaggc cttgcgctta aggagcccct tcgcctcgtg  8400
cttgagttga ggcctggcct gggcgctggg gccgccgcgt gcgaatctgg tggcaccttc  8460
gcgcctgtct cgctgctttc gataagtctc tagccattta aaattttga tgacctgctg  8520 cgacgctttt tttctggcaa gatagtcttg taaatgcggg ccaagatctg cacactggta  8580
tttcggtttt tggggccgcg ggcggcgacg gggcccgtgc gtcccagcgc acatgttcgg  8640
cgaggcgggg cctgcgagcg cggccaccga gaatcggacg ggggtagtct caagctggcc  8700
ggcctgctct ggtgcctggc ctcgcgccgc cgtgtatcgc cccgccctgg gcggcaaggc  8760
tggcccggtc ggcaccagtt gcgtgagcgg aaagatggcc gcttcccggc cctgctgcag  8820
ggagctcaaa atggaggacg cggcgctcgg gagagcgggc gggtgagtca cccacacaaa  8880
ggaaaagggc ctttccgtcc tcagccgtcg cttcatgtga ctccacggag taccgggcgc  8940
cgtccaggca cctcgattag ttctcgagct tttggagtac gtcgtcttta ggttggggg  9000 aggggtttta tgcgatggag tttccccaca ctgagtgggt ggagactgaa gttaggccag  9060
cttggcactt gatgtaattc tccttggaat ttgcccttt tgagtttgga tcttggttca  9120
ttctcaagcc tcagacagtg gttcaaagtt tttttcttcc atttcaggtg tcgtgagcta  9180
gctctagag                                                           9189
```

In one embodiment, the CAR molecule comprises (e.g., consists of) an amino acid sequence of SEQ ID NO: 150 or SEQ ID NO: 152; or an amino acid sequence having at least one, two, three, four, five, 10, 15, 20 or 30 modifications (e.g., substitutions, e.g., conservative substitutions) but not more than 60, 50, or 40 modifications (e.g., substitutions, e.g., conservative substitutions) of an amino acid sequence of SEQ ID NO: 150 or SEQ ID NO: 152; or an amino acid sequence having 85%, 90%, 95%, 96%, 97%, 98%, 99% identity to an amino acid sequence of SEQ ID NO: 150 or SEQ ID NO: 152.

Natural Killer Cell Receptor (NKR) CARs

In an embodiment, the CAR molecule described herein, e.g., the nonconditional CAR or the conditional CAR, comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Split CAR

In some embodiments, the CAR-expressing cell described herein, uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes the tumor antigen or B cell antigen described herein, e.g., comprises an antigen binding domain described herein, and the second antigen binding domain recognizes a second antigen, e.g., a second tumor antigen or a second B cell antigen described herein.

Strategies for Regulating Chimeric Antigen Receptors

There are many ways CAR activities can be regulated. In some embodiments, a regulatable CAR (RCAR) where the CAR activity can be controlled is desirable to optimize the safety and efficacy of a CAR therapy. For example, inducing apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or complement-induced cell death. For example, CAR expressing cells described herein may also express a receptor capable of being targeted by an antibody or antibody fragment. Examples of such receptors include EpCAM, VEGFR, integrins (e.g., integrins αvβ3, α4, αI¾β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/ CD40L, CD195/CCR5, CD319/SLAMF7, and EGFR, and truncated versions thereof (e.g., versions preserving one or more extracellular epitopes but lacking one or more regions within the cytoplasmic domain).

For example, a CAR-expressing cell described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8) 853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g, ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In other embodiments, a CAR-expressing cell described herein may also express a target protein recognized by the T cell depleting agent. In one embodiment, the target protein is CD20 and the T cell depleting agent is an anti-CD20 antibody, e.g., rituximab. In such embodiment, the T cell depleting agent is administered once it is desirable to reduce or eliminate the CAR-expressing cell, e.g., to mitigate the CAR induced toxicity. In other embodiments, the T cell depleting agent is an anti-CD52 antibody, e.g., alemtuzumab.

In other embodiments, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain. Additional description and exemplary configurations of such regulatable CARs are provided herein and in International Publication No. WO 2015/090229, hereby incorporated by reference in its entirety.

Co-Expression of CAR with a Costimulatory Molecule

In another example, in one embodiment, the agent which enhances the activity of a CAR-expressing cell can be a costimulatory molecule or costimulatory molecule ligand. Examples of costimulatory molecules include MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, e.g., as described herein. Examples of costimulatory molecule ligands include CD80, CD86, CD40L, ICOSL, CD70, OX40L, 4-1BBL, GITRL, and LIGHT. In embodiments, the costimulatory molecule ligand is a ligand for a costimulatory molecule different from the costimulatory molecule domain of the CAR. In embodiments, the costimulatory molecule ligand is a ligand for a costimulatory molecule that is the same as the costimulatory molecule domain of the CAR. In an embodiment, the costimulatory molecule ligand is 4-1BBL. In an embodiment, the costimulatory ligand is CD80 or CD86. In an embodiment, the costimulatory molecule ligand is CD70. In embodiments, a CAR-expressing immune effector cell described herein can be further engineered to express one or more additional costimulatory molecules or costimulatory molecule ligands.

Co-Expression of CAR with a Chemokine Receptor

In embodiments, the CAR-expressing cell described herein further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., J Immunother. 2010 October; 33(8): 780-8 and Kershaw et al., Hum Gene Ther. 2002 Nov. 1; 13(16):1971-80). Thus, without wishing to be bound by theory, it is believed that chemokine receptors expressed in CAR-expressing cells that recognize chemokines secreted by tumors, e.g., solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell described herein include a CXC chemokine receptor (e.g., CXCR1, CXCR2, CXCR3, CXCR4, CXCR5, CXCR6, or CXCR7), a CC chemokine receptor (e.g., CCR1, CCR2, CCR3, CCR4, CCR5, CCR6, CCR7, CCR8, CCR9, CCR10, or CCR11), a CX3C chemokine receptor (e.g., CX3CR1), a XC chemokine receptor (e.g., XCR1), or a chemokine-binding fragment thereof. In one embodiment, the chemokine receptor molecule to be expressed with a CAR described herein is selected based on the chemokine(s) secreted by the tumor. In one embodiment, the CAR-expressing cell described herein further comprises, e.g., expresses, a CCR2b receptor or a CXCR2 receptor. In an embodiment, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

Nucleic Acid Constructs

The present invention also provides nucleic acid molecules encoding one or more CAR constructs described herein. The present invention also provides nucleic acid molecules encoding agents that enhance the immune response of an immune effector cell. In such embodiments, the nucleic acid construct comprises an activation-conditional control region operably linked to the sequence encoding an agent that enhances the immune response of an immune effector cell. In other embodiments, a nucleic acid sequence encoding a CAR as described herein operably linked to a nucleic acid sequence comprising a constitutive promoter and an agent that enhances the immune response of an effector cell operably linked to an activation-conditional control region are found on the same nucleic acid molecule, e.g., a vector, e.g., a bicistronic lentiviral vector.

In embodiments, nucleic acid molecule described herein comprises an activation-conditional control region operably linked to a nucleic acid sequence encoding any of the agents that enhance an immune response described herein, e.g., an agent that comprises one or more of the following characteristics: 1) targets an additional tumor antigen, e.g., a different tumor antigen targeted by the constitutively expressed CAR; 2) inhibits the expression or activity of an inhibitory molecule (e.g., a checkpoint inhibitor); and/or 3) activates the expression and/or secretion of a component that enhances immune response or immune effector cell activation. Exemplary agents that enhance the immune response of the non-conditional CAR-expressing cell are further described in the section entitled "Conditional Expression of Immune-Response Enhancers".

In one aspect, the nucleic acid molecule is provided as a DNA construct.

Accordingly, in one aspect, the invention pertains to a nucleic acid molecule encoding a chimeric antigen receptor (CAR), wherein the CAR comprises an antigen binding domain that binds to a tumor antigen described herein, a transmembrane domain (e.g., a transmembrane domain described herein), and an intracellular signaling domain (e.g., an intracellular signaling domain described herein) comprising a stimulatory domain, e.g., a costimulatory signaling domain (e.g., a costimulatory signaling domain described herein) and/or a primary signaling domain (e.g., a primary signaling domain described herein, e.g., a zeta chain described herein).

In one embodiment, the transmembrane domain is transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp. In one embodiment, the nucleic acid molecule further comprises a nucleic acid sequence that encodes a transmembrane domain comprising a sequence of SEQ ID NO: 12, or a sequence with 95-99% identity thereof. In one embodiment, the nucleic acid molecule further comprises a transmembrane domain comprising a nucleic acid sequence of SEQ ID NO: 13, or a sequence with 95-99% identity thereof. In one embodiment, the antigen binding domain is connected to the transmembrane domain by a hinge region, e.g., a hinge described herein. In one embodiment, the hinge region comprises SEQ ID NO:4 or SEQ ID NO:6 or SEQ ID NO:8 or SEQ ID NO:10, or a sequence with 95-99% identity thereof. In one embodiment, the hinge region comprises the nucleic acid sequence comprising SEQ ID NO: 5, SEQ ID NO: 7, SEQ ID NO: 9, or SEQ ID NO: 11, or a sequence with 95-99% identity thereof.

In one embodiment, the isolated nucleic acid molecule further comprises a nucleic acid sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18), ICOS (CD278), and 4-1BB (CD137). Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/ RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp. In one embodiment, the intracellular signaling domain comprises a functional signaling domain selected from 4-1BB, CD27, ICOS, or CD28, and a functional signaling domain of CD3 zeta. In one embodiment, the intracellular signaling domain comprises the sequence of SEQ ID NO: 14, SEQ ID NO:16, SEQ ID NO: 40, or SEQ ID NO: 44, or a sequence with 95-99% identity thereof, and the sequence of SEQ ID NO: 18 or SEQ ID NO:20, or a sequence with 95-99% identity thereof, wherein the sequences comprising the intracellular signaling domain are expressed in the same frame and as a single polypeptide chain. In one embodiment, the intracellular signaling domain comprises the nucleic acid sequence of SEQ ID NO: 15, SEQ ID NO:17, SEQ ID NO: 41, or SEQ ID NO: 45, or a nucleic acid sequence with 95-99% identity thereof, and the nucleic acid sequence of SEQ ID NO: 19 or SEQ ID NO:21, or a nucleic acid sequence with 95-99% identity thereof.

In another aspect, the invention pertains to an isolated nucleic acid molecule encoding a CAR construct comprising a leader sequence of SEQ ID NO: 2, a scFv domain as described herein, a hinge region of SEQ ID NO:4 or SEQ ID NO:6 or SEQ ID NO:8 or SEQ ID NO:10 (or a sequence with 95-99% identity thereof), a transmembrane domain having a sequence of SEQ ID NO: 12 (or a sequence with 95-99% identity thereof), a 4-1BB costimulatory domain having a sequence of SEQ ID NO: 14, a CD27 costimulatory domain having a sequence of SEQ ID NO: 16 (or a sequence with 95-99% identity thereof), an ICOS costimulatory domain having a sequence of SEQ ID NO:40 (or a sequence with 95-99% identity thereof), and a CD28 costimulatory domain having a sequence of SEQ ID NO:44 (or a sequence with 95-99% identity thereof), and a CD3 zeta stimulatory domain having a sequence of SEQ ID NO: 18 or SEQ ID NO:20 (or a sequence with 95-99% identity thereof).

In another aspect, the invention pertains to a nucleic acid molecule encoding a chimeric antigen receptor (CAR) molecule that comprises an antigen binding domain, a transmembrane domain, and an intracellular signaling domain comprising a stimulatory domain, and wherein said antigen binding domain binds to a tumor antigen selected from a group consisting of: CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, SSEA-4, CD20, Folate receptor alpha, ERBB2 (Her2/ neu), MUC1, EGFR, NCAM, Prostase, PRSS21, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/ MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In one embodiment, the nucleic acid molecule comprises a sequence encoding a mesothelin CAR. In one embodiment, the nucleic acid molecule comprises a nucleic acid sequence encoding a mesothelin CAR comprising an amino acid sequence having at least one, two or three modifications but not more than 30, 20 or 10 modifications to any amino acid sequence in Table 6, e.g., SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, or SEQ ID NO: 124. In one embodiment, the nucleic acid molecule comprises a nucleic acid sequence encoding a mesothelin CAR comprising an amino acid sequence with 95-99% identity to any amino acid sequence in Table 6, e.g., SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, or SEQ ID NO: 124. In one embodiment, the nucleic acid molecule comprises a nucleic acid sequence encoding a mesothelin CAR comprising the amino acid sequence, e.g., as provided in Table 6, e.g., SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, or SEQ ID NO: 124.

In one embodiment, the nucleic acid molecule comprises a nucleic acid sequence with 95-99% identity to a nucleic acid sequence, e.g., a mesothelin CAR, in Table 6, e.g., SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, or SEQ ID NO: 149. In one embodiment, the nucleic acid molecule comprises a nucleic acid sequence, e.g., a mesothelin CAR, e.g., as provided in Table 6, e.g., SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO:

134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, or SEQ ID NO: 149.

In one embodiment, the nucleic acid molecule comprises a sequence encoding a FRa CAR. In one embodiment, the nucleic acid molecule comprises a nucleic acid sequence encoding a FRa CAR comprising an amino acid sequence having at least one, two or three modifications but not more than 30, 20 or 10 modifications to any amino acid sequence in Table 7, e.g., SEQ ID NO: 150 or SEQ ID NO: 152. In one embodiment, the nucleic acid molecule comprises a nucleic acid sequence encoding a FRa CAR comprising an amino acid sequence with 95-99% identity to any amino acid sequence in Table 7, e.g., SEQ ID NO: 150 or SEQ ID NO: 152. In one embodiment, the nucleic acid molecule comprises a nucleic acid sequence encoding a FRa CAR comprising the amino acid sequence, e.g., as provided in Table 7, e.g., SEQ ID NO: 150 or SEQ ID NO: 152.

In one embodiment, the nucleic acid molecule comprises a nucleic acid sequence with 95-99% identity to a nucleic acid sequence, e.g., a FRa CAR, in Table 7, e.g., SEQ ID NO: 151 or SEQ ID NO: 153. In one embodiment, the nucleic acid molecule comprises a nucleic acid sequence, e.g, a FRa CAR, e.g., as provided in Table 7, e.g., SEQ ID NO: 151 or SEQ ID NO: 153.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In one embodiment, the vector comprising the nucleic acid encoding the desired CAR of the invention is a DNA, a RNA, a plasmid, an adenoviral vector, a lentivirus vector, or a retrovirus vector. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural genes such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, CRISPR, CAS9, and zinc finger nucleases. See, e.g., June et al. 2009 Nature Reviews Immunology 9.10: 704-716, incorporated herein by reference in its entirety.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR encoding nucleic acid molecule in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from nucleic acid molecules cloned into a lentiviral vector. See, e.g., Milone et al., Mol. Ther. 17(8): 1453-1464 (2009). In one aspect, the EF1a promoter comprises the sequence provided as SEQ ID NO:1.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1 Ovian leukemia virus promoter, an Epstein-Barr virus immediate early promoter, a Rous sarcoma virus promoter, as well as human gene promoters such as, but not limited to, the actin promoter, the myosin promoter, the elongation factor-1 operatively linked provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below.

WT PGK Promoter (SEQ ID NO: 154)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTGTGGGGCGGAGGGCGTGGCGGGGAAGGGCC

GGCGACGAGAGCCGCGCGGGACGACTCGTCGGCGATAACCGGTGTCGGG

TAGCGCCAGCCGCGCGACGGTAACGAGGGACCGCGACAGGCAGACGCTC

CCATGATCACTCTGCACGCCGAAGGCAAATAGTGCAGGCCGTGCGGCGC

TTGGCGTTCCTTGGAAGGGCTGAATCCCCGCCTCGTCCTTCGCAGCGGC

CCCCCGGGTGTTCCCATCGCCGCTTCTAGGCCCACTGCGACGCTTGCCT

GCACTTCTTACACGCTCTGGGTCCCAGCCGCGGCGACGCAAAGGGCTT

GGTGCGGGTCTCGTCGGCGCAGGGACGCGTTTGGGTCCCGACGGAACCT

TTTCCGCGTTGGGGTTGGGGCACCATAAGCT

Exemplary Truncated PGK Promoters:

PGK100:
(SEQ ID NO: 155)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTG

PGK200:
(SEQ ID NO: 156)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTGTGGGGCGGAGGGCGTGGCGGGGAAGGGCC

GGCGACGAGAGCCGCGCGGGACGACTCGTCGGCGATAACCGGTGTCGGG

TAGCGCCAGCCGCGCGACGGTAACG

PGK300:
(SEQ ID NO: 157)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTGTGGGGCGGAGGGCGTGGCGGGGAAGGGCC

GGCGACGAGAGCCGCGCGGGACGACTCGTCGGCGATAACCGGTGTCGGG

TAGCGCCAGCCGCGCGACGGTAACGAGGGACCGCGACAGGCAGACGCTC

CCATGATCACTCTGCACGCCGAAGGCAAATAGTGCAGGCCGTGCGGCGC

TTGGCGTTCCTTGGAAGGGCTGAATCCCCG

PGK400:
(SEQ ID NO: 158)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTGTGGGGCGGAGGGCGTGGCGGGGAAGGGCC

GGCGACGAGAGCCGCGCGGGACGACTCGTCGGCGATAACCGGTGTCGGG

TAGCGCCAGCCGCGCGACGGTAACGAGGGACCGCGACAGGCAGACGCTC

CCATGATCACTCTGCACGCCGAAGGCAAATAGTGCAGGCCGTGCGGCGC

TTGGCGTTCCTTGGAAGGGCTGAATCCCCGCCTCGTCCTTCGCAGCGGC

CCCCCGGGTGTTCCCATCGCCGCTTCTAGGCCCACTGCGACGCTTGCCT

GCACTTCTTACACGCTCTGGGTCCCAGCCG

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In such embodiments, the two or more nucleic acid sequences, e.g., encoding a mesothelin CAR described herein and a second CAR or other polypeptide, are encoded by a single nucleic molecule in the same frame and as a single polypeptide chain. In one embodiment, the two or more polypeptides can be separated by one or more peptide cleavage sites (e.g., an auto-cleavage site or a substrate for an intracellular protease). Examples of peptide cleavage sites include the following, wherein the GSG residues are optional:

```
T2A:
                                             (SEQ ID NO: 159)
(GSG) E G R G S L L T C G D V E E N P G P

P2A:
                                             (SEQ ID NO: 160)
(GSG) A T N F S L L K Q A G D V E E N P G P

E2A:
                                             (SEQ ID NO: 161)
(GSG) Q C T N Y A L L K L A G D V E S N P G P

F2A:
                                             (SEQ ID NO: 162)
(GSG) V K Q T L N F D L L K L A G D V E S N P G P
```

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or a NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian immune effector cells (e.g., T cells, NK cells). In one aspect, the mammalian T cell is a human T cell. In one aspect, the mammalian NK cell is a human NK cell.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:35). RNA so produced can efficiently transfect different kinds of cells. In one aspect, the template includes sequences for the CAR.

In one aspect the mesothelin CAR is encoded by a messenger RNA (mRNA). In one aspect the mRNA encoding the mesothelin CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. The term "substantially complementary" refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. The term "upstream" refers to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. The term "downstream" refers to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 33).

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein, e.g., a nonconditional CAR or a conditional CAR, into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1 (2011):R14-20; Singh et al. Cancer Res. 15 (2008):2961-2971; Huang et al. Mol. Ther. 16 (2008):580-589; Grabundzija et al. Mol. Ther. 18 (2010):1200-1209; Kebriaei et al. Blood. 122.21 (2013): 166; Williams. Molecular Therapy 16.9 (2008):1515-16;

Bell et al. Nat. Protoc. 2.12 (2007):3153-65; and Ding et al. Cell. 122.3 (2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3 (2013): 1829-47; and Singh et al. Cancer Res. 68.8 (2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Sources of Cells

Prior to expansion and genetic modification, e.g., to express a CAR described herein, a source of cells, e.g., T cell or NK cells, can be obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present disclosure, any number of T cell lines available in the art, may be used. In certain aspects of the present disclosure, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi: 10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD1 b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD1b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1 \times 10^5$/ml to $1 \times 10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present disclosure.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present disclosure, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR Immune Effector Cells

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class I and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

Expression systems for siRNA and shRNAs, and exemplary shRNAs, are described, e.g., in paragraphs 649 and 650 of International Publication WO2015/142675, filed Mar. 13, 2015, which is incorporated by reference in its entirety.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein.

A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

The CRISPR/Cas system, and uses thereof, are described, e.g., in paragraphs 651-658 of International Publication WO2015/142675, filed Mar. 13, 2015, which is incorporated by reference in its entirety.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

TALENs, and uses thereof, are described, e.g., in paragraphs 659-665 of International Publication WO2015/142675, filed Mar. 13, 2015, which is incorporated by reference in its entirety.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

ZFNs, and uses thereof, are described, e.g., in paragraphs 666-671 of International Publication WO2015/142675, filed Mar. 13, 2015, which is incorporated by reference in its entirety.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

(SEQ ID NO: 163)
MPRAPRCRAVRSLLRSHYREVLPLATFVRRLGPQGWRLVQRGDPAAF

RALVAQCLVCVPWDARPPPAAPSFRQVSCLKELVARVLQRLCERGAK

NVLAFGFALLDGARGGPPEAFTTSVRSYLPNTVTDALRGSGAWGLLL

RRVGDDVLVHLLARCALFVLVAPSCAYQVCGPPLYQLGAATQARPPP

HASGPRRRLGCERAWNHSVREAGVPLGLPAPGARRRGGSASRSLPLP

KRPRRGAAPEPERTPVGQGSWAHPGRTRGPSDRGFCVVSPARPAEEA

TSLEGALSGTRHSHPSVGRQHHAGPPSTSRPPRPWDTPCPPVYAETK

HFLYSSGDKEQLRPSFLLSSLRPSLTGARRLVETIFLGSRPWMPGTP

RRLPRLPQRYWQMRPLFLELLGNHAQCPYGVLLKTHCPLRAAVTPAA

GVCAREKPQGSVAAPEEEDTDPRRLVQLLRQHSSPWQVYGFVRACLR

RLVPPGLWGSRHNERRFLRNTKKFISLGKHAKLSLQELTWKMSVRGC

AWLRRSPGVGCVPAAEHRLREEILAKFLHWLMSVYVVELLRSFFYVT

ETTFQKNRLFFYRKSVWSKLQSIGIRQHLKRVQLRELSEAEVRQHRE

ARPALLTSRLRFIPKPDGLRPIVNMDYVVGARTFRREKRAERLTSRV

KALFSVLNYERARRPGLLGASVLGLDDIHRAWRTFVLRVRAQDPPPE

LYFVKVDVTGAYDTIPQDRLTEVIASIIKPQNTYCVRRYAVVQKAAH

GHVRKAFKSHVSTLTDLQPYMRQFVAHLQETSPLRDAVVIEQSSSLN

EASSGLFDVFLRFMCHHAVRIRGKSYVQCQGIPQGSILSTLLCSLCY

GDMENKLFAGIRRDGLLLRLVDDFLLVTPHLTHAKTFLRTLVRGVPE

YGCVVNLRKTVVNFPVEDEALGGTAFVQMPAHGLFPWCGLLLDTRTL

EVQSDYSSYARTSIRASLTFNRGFKAGRNMRRKLFGVLRLKCHSLFL

DLQVNSLQTVCTNIYKILLLQAYRFHACVLQLPFHQQVWKNPTFFLR

VISDTASLCYSILKAKNAGMSLGAKGAAGPLPSEAVQWLCHQAFLLK

LTRHRVTYVPLLGSLRTAQTQLSRKLPGTTLTALEAAANPALPSDFK

TILD

In an embodiment, the hTERT has a sequence at least 80%, 85%, 90%, 95%, 96%, 97%, 98%, or 99% identical to the sequence of SEQ ID NO: 163. In an embodiment, the hTERT has a sequence of SEQ ID NO: 163. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

(SEQ ID NO: 164)

```
   1  caggcagcgt ggtcctgctg cgcacgtggg aagccctggc cccggccacc cccgcgatgc
  61  cgcgcgctcc ccgctgccga gccgtgcgct ccctgctgcg cagccactac cgcgaggtgc
 121  tgccgctggc cacgttcgtg cggcgcctgg ggccccaggg ctggcggctg gtgcagcgcg
 181  gggacccggc ggctttccgc cgcgctggtgg cccagtgcct ggtgtgcgtg ccctgggacg
 241  cacggccgcc ccccgccgcc ccctccttcc gccaggtgtc ctgcctgaag agctggtgg
 301  cccgagtgct gcagaggctg tgcgagcgcg cgcgaagaa cgtgctggcc ttcggcttcg
 361  cgctgctgga cggggcccgc gggggccccc ccgaggcctt caccaccagc gtgcgcagct
 421  acctgcccaa cacggtgacc gacgcactgc ggggagcgg ggcgtggggg ctgctgttgc
 481  gccgcgtggg cgacgacgtg ctggttcacc tgctggcacg ctgcgcgctc tttgtgctgg
 541  tggctcccag ctgcgcctac caggtgtgcg ggccgccgct gtaccagctc ggcgctgcca
 601  ctcaggcccg ccccccgcca cacgctagtg accccgaag cgtctggga tgcgaacggg
 661  cctggaacca tagcgtcagg gaggccgggg tcccctggg cctgccagcc ccgggtgcga
 721  ggaggcgcgg gggcagtgcc agccgaagtc tgccgttgcc caagaggccc aggcgtggcg
 781  ctgccccctga gccggagcgg acgcccgttg ggcaggggtc ctgggcccac ccgggcagga
 841  cgcgtggacc gagtgaccgt ggtttctgtg tggtgtcacc tgccagaccc gccgaagaag
 901  ccacctcttt ggagggtgcg ctctctggca cgcgccactc ccacccatcc gtgggccgcc
 961  agcaccacgc gggccccca tccacatcgc ggccaccacg tccctgggac acgccttgtc
1021  cccggtgta cgccgagacc aagcacttcc tctactcctc aggcgacaag gagcagctgc
1081  ggccctcctt cctactcagc tctctgaggc ccagcctgac tggcgctcgg aggctcgtgg
1141  agaccatctt tctgggttcc aggccctgga tgccaggggac tccccgcagg ttgccccgcc
1201  tgccccagcg ctactggcaa atgcggcccc tgtttctgga gctgcttggg aaccacgcgc
1261  agtgccccta cggggtgctc ctcaagacgc actgcccgct cgagctgcg gtcacccag
1321  cagccggtgt ctgtgcccgg gagaagcccc agggctctgt ggcggccccc gaggaggagg
1381  acacagaccc ccgtcgcctg gtgcagctgc tccgccagca cagcagcccc tggcaggtgt
1441  acggcttcgt gcgggcctgc ctgcgccggc tggtgccccc aggcctctgg ggctccaggc
1501  acaacgaacg ccgcttcctc aggaacacca agaagttcat ctccctgggg aagcatgcca
1561  agctctcgct gcaggagctg acgtggaaga tgagcgtgcg gggctgcgct tggctgcgca
1621  ggagcccagg ggttggctgt gttccggccg cagagcaccg tctgcgtgag gagatcctgg
1681  ccaagttcct gcactggctg atgagtgtgt acgtcgtcga gctgctcagg tctttctttt
1741  atgtcacgga gaccacgttt caaaagaaca ggctctttt ctaccggaag agtgtctgga
1801  gcaagttgca aagcattgga atcagacagc acttgaagag ggtgcagctg cggagctgt
1861  cggaagcaga ggtcaggcag catcgggaag ccaggcccgc cctgctgacg tccagactcc
1921  gcttcatccc caagcctgac gggctgcggc cgattgtgaa catggactac gtcgtgggag
1981  ccagaacgtt ccgcagagaa aagagggccg agcgtctcac ctcgagggtg aaggcactgt
2041  tcagcgtgct caactacgag cgggcgcggc gccccggcct cctgggcgcc tctgtgctgg
2101  gcctggacga tatccacagg gcctggcgca ccttcgtgct gcgtgtgcgg gcccaggacc
2161  cgccgcctga gctgtacttt gtcaaggtgg atgtgacggg cgcgtacgac accatccccc
2221  aggacaggct cacggaggtc atcgccagca tcatcaaacc ccagaacacg tactgcgtgc
2281  gtcggtatgc cgtggtccag aaggccgccc atgggcacgt ccgcaaggcc ttcaagagcc
2341  acgtctctac cttgacagac ctccagccgt acatgcgaca gttcgtggct cacctgcagg
```

-continued

```
2401  agaccagccc gctgagggat gccgtcgtca tcgagcagag ctcctccctg aatgaggcca
2461  gcagtggcct cttcgacgtc ttcctacgct tcatgtgcca ccacgccgtg cgcatcaggg
2521  gcaagtccta cgtccagtgc caggggatcc cgcagggctc catcctctcc acgctgctct
2581  gcagcctgtg ctacggcgac atggagaaca agctgtttgc ggggattcgg cgggacgggc
2641  tgctcctgcg tttggtggat gatttcttgt tggtgacacc tcacctcacc cacgcgaaaa
2701  ccttcctcag gaccctggtc cgaggtgtcc ctgagtatgg ctgcgtggtg aacttgcgga
2761  agacagtggt gaacttccct gtagaagacg aggccctggg tggcacggct tttgttcaga
2821  tgccggccca cggcctattc ccctggtgcg gcctgctgct ggatacccgg accctggagg
2881  tgcagagcga ctactccagc tatgcccgga cctccatcag agccagtctc accttcaacc
2941  gcggcttcaa ggctgggagg aacatgcgtc gcaaactctt tgggtcttg cggctgaagt
3001  gtcacagcct gtttctggat ttgcaggtga acagcctcca gacggtgtgc accaacatct
3061  acaagatcct cctgctgcag gcgtacaggt ttcacgcatg tgtgctgcag ctcccatttc
3121  atcagcaagt ttggaagaac cccacatttt tcctgcgcgt catctctgac acggcctccc
3181  tctgctactc catcctgaaa gccaagaacg cagggatgtc gctggggcc aagggcgccg
3241  ccggccctct gccctccgag gccgtgcagt ggctgtgcca ccaagcattc ctgctcaagc
3301  tgactcgaca ccgtgtcacc tacgtgccac tcctggggtc actcaggaca gcccagacgc
3361  agctgagtcg gaagctcccg gggacgacgc tgactgccct ggaggccgca gccaacccgg
3421  cactgccctc agacttcaag accatcctgg actgatggcc acccgcccac agccaggccg
3481  agagcagaca ccagcagccc tgtcacgccg ggctctacgt cccagggagg gaggggcggc
3541  ccacacccag gcccgcaccg ctgggagtct gaggcctgag tgagtgtttg gccgaggcct
3601  gcatgtccgg ctgaaggctg agtgtccggc tgaggcctga gcgagtgtcc agccaagggc
3661  tgagtgtcca gcacacctgc cgtcttcact tccccacagg ctggcgctcg gctccacccc
3721  agggccagct tttcctcacc aggagcccgg cttccactcc ccacatagga atagtccatc
3781  cccagattcg ccattgttca cccctcgccc tgccctcctt tgccttccac cccaccatc
3841  caggtggaga ccctgagaag gaccctggga gctctgggaa tttggagtga ccaaaggtgt
3901  gccctgtaca caggcgagga ccctgcacct ggatgggggt ccctgtgggt caaattgggg
3961  ggaggtgctg tgggagtaaa atactgaata tatgagtttt tcagttttga aaaaaaaaaa
4021  aaaaaaa
```

In an embodiment, the hTERT is encoded by a nucleic acid having a sequence at least 80%, 85%, 90%, 95%, 96, 97%, 98%, or 99% identical to the sequence of SEQ ID NO: 164. In an embodiment, the hTERT is encoded by a nucleic acid of SEQ ID NO: 164.

Activation and Expansion of Immune Effector Cells (e.g., T Cells)

Immune effector cells, such as T cells or NK cells, may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells, e.g., T cells or NK cells, may be expanded by contact with a surface having attached thereto an agent that stimulates a CD3/TCR complex associated signal and a ligand that stimulates a costimulatory molecule on the surface of the immune effector cells, e.g., T cells or NK cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present disclosure.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present disclosure, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type. In one aspect, the most typical ratios for use are in the neighborhood of 1:1, 2:1 and 3:1 on the first day.

In further aspects of the present disclosure, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CAR-expressing cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CAR-expressing cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CAR-expressing cell described herein, expanded for 5 days show at least a one, two, three, four, five, tenfold or more increase in pg/ml of proinflammatory cytokine production, e.g., IFN-γ and/or GM-CSF levels, as compared to the same cells expanded in culture for 9 days under the same culture conditions.

In one aspect of the present disclosure, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

In one embodiment, the cells are cultured (e.g., expanded, simulated, and/or transduced) in media comprising serum. The serum may be, e.g., human AB serum (hAB). In some embodiments, the hAB serum is present at about 2%, about 5%, about 2-3%, about 3-4%, about 4-5%, or about 2-5%. 2% and 5% serum are each suitable levels that allow for many fold expansion of T cells. Furthermore, as shown in Smith et al., "Ex vivo expansion of human T cells for adoptive immunotherapy using the novel Xeno-free CTS Immune Cell Serum Replacement" Clinical & Translational Immunology (2015) 4, e31; doi: 10.1038/cti.2014.31, medium containing 2% human AB serum is suitable for ex vivo expansion of T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some embodiments, cells transduced with a nucleic acid encoding a CAR, e.g., a CAR described herein, can be selected for administration based upon, e.g., protein expression levels of one or more of CCL20, GM-CSF, IFNγ, IL-10, IL-13, IL-17a, IL-2, IL-21, IL-4, IL-5, IL-6, IL-9, TNFα and/or combinations thereof. In some embodiments, cells transduced with a nucleic acid encoding a CAR, e.g., a CAR described herein, can be selected for administration based upon, e.g., protein expression levels of CCL20, IL-17a, IL-6 and combinations thereof.

CAR Activity Assays

Once a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a cars of the present invention are described in further detail below.

Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of CD4$^+$ and CD8$^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-t chain. The same T cell subsets are used for SDS-PAGE analysis under non-reducing conditions to permit evaluation of covalent dimer formation.

In vitro expansion of CAR$^+$ T cells following antigen stimulation can be measured by flow cytometry. For example, a mixture of CD4$^+$ and CD8$^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4$^+$ and/or CD8$^+$ T cell subsets by flow cytometry. See, e.g., Milone et al., Molecular Therapy 17(8): 1453-1464 (2009). Alternatively, a mixture of CD4$^+$ and CD8$^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associated antigen as described herein$^+$ K562 cells (K562 expressing a cancer associated antigen as described herein), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. GFP$^+$ T cells are enumerated by flow cytometry using bead-based counting. See, e.g., Milone et al., Molecular Therapy 17(8): 1453-1464 (2009).

Sustained CAR$^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with αCD3/αCD28 coated magnetic beads on day 0, and transduction with the indicated CAR on day 1.

Animal models can also be used to measure a CART activity. For example, xenograft model using human a cancer associated antigen described herein-specific CAR$^+$ T cells to treat a primary human pre-B ALL in immunodeficient mice can be used. See, e.g., Milone et al., Molecular Therapy 17(8): 1453-1464 (2009). Very briefly, after establishment of ALL, mice are randomized as to treatment groups. Different numbers of a cancer associated antigen-specific CAR engineered T cells are coinjected at a 1:1 ratio into NOD-SCID-γ$^{-/-}$ mice bearing B-ALL. The number of copies of a cancer associated antigen-specific CAR vector in spleen DNA from mice is evaluated at various times following T cell injection. Animals are assessed for leukemia at weekly intervals. Peripheral blood a cancer associate antigen as described herein$^+$ B-ALL blast cell counts are measured in mice that are injected with a cancer associated antigen described herein-ζ CAR$^+$ T cells or mock-transduced T cells. Survival curves for the groups are compared using the log-rank test. In addition, absolute peripheral blood CD4$^+$ and CD8$^+$ T cell counts 4 weeks following T cell injection in NOD-SCID-γ$^{-/-}$ mice can also be analyzed. Mice are injected with leukemic cells and 3 weeks later are injected with T cells engineered to express CAR by a bicistronic lentiviral vector that encodes the CAR linked to eGFP. T cells are normalized to 45-50% input GFP$^+$ T cells by mixing with mock-transduced cells prior to injection, and confirmed by flow cytometry. Animals are assessed for leukemia at 1-week intervals. Survival curves for the CAR$^+$ T cell groups are compared using the log-rank test.

Dose dependent CAR treatment response can be evaluated. See, e.g., Milone et al., Molecular Therapy 17(8): 1453-1464 (2009). For example, peripheral blood is obtained 35-70 days after establishing leukemia in mice injected on day 21 with CAR T cells, an equivalent number of mock-transduced T cells, or no T cells. Mice from each group are randomly bled for determination of peripheral blood a cancer associate antigen as described herein$^+$ ALL blast counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing a cancer associated antigen described herein (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8$^+$ T cell expansion ex vivo. T cells are enumerated in cultures using CountBright™ fluorescent beads (Invitrogen, Carlsbad, Calif.) and flow cytometry as described by the manufacturer. CAR$^+$ T cells are identified by GFP expression using T cells that are engineered with eGFP-2A linked CAR-expressing lentiviral vectors. For CAR+ T cells not expressing GFP, the CAR+ T cells are detected with biotinylated recombinant a cancer associate antigen as described herein protein and a secondary avidin-PE conjugate. CD4+ and CD8+ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (K562 lines and primary pro-B-ALL cells) are loaded with 51Cr (as NaCrO4, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/$\gamma c^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of CAR+ T cells in Nalm-6 xenograft model can be measured as the following: NSG mice are injected with Nalm-6 transduced to stably express firefly luciferase, followed by a single tail-vein injection of T cells electroporated with cars of the present invention 7 days later. Animals are imaged at various time points post injection. For example, photon-density heat maps of firefly luciferasepositive leukemia in representative mice at day 5 (2 days before treatment) and day 8 (24 hr post CAR+ PBLs) can be generated.

Other assays, including those described in the Example section herein as well as those that are known in the art can also be used to evaluate the CARs described herein.

Therapeutic Application

In one aspect, the invention provides methods for treating a disease associated with expression of a cancer associated antigen described herein.

In one aspect, the present invention provides methods of treating cancer by providing to the subject in need thereof immune effector cells (e.g., T cells, NK cells) that are engineered to express an XCAR, wherein X represents a tumor antigen as described herein, and wherein the cancer cells express said X tumor antigen. In one embodiment, the immune effector cell that constitutively expresses an XCAR is further engineered to conditionally express an agent that enhances the anti-cancer immune response, e.g., another CAR, an inhibitor of a checkpoint inhibitor (or inhibitory molecule described herein), or a cytokine. In one embodiment, the conditionally expressed agent comprises an XCAR.

In one aspect, the present invention provides methods of treating cancer by providing to the subject in need thereof immune effector cells (e.g., T cells, NK cells) that are engineered to express a XCAR described herein, e.g., a conditional XCAR or a nonconditional XCAR, wherein the cancer cells express X. In one embodiment, X is expressed on both normal cells and cancers cells, but is expressed at lower levels on normal cells. In one embodiment, the method further comprises selecting a CAR that binds X with an affinity that allows the XCAR to bind and kill the cancer cells expressing X but less than 30%, 25%, 20%, 15%, 10%, 5% or less of the normal cells expressing X are killed, e.g., as determined by an assay described herein. For example, the assay described in the Examples described herein can be used or a killing assay such as flow cytometry based on Cr51 CTL. In one embodiment, the selected CAR has an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the selected antigen binding domain has a binding affinity that is at least five-fold, 10-fold, 20-fold, 30-fold, 50-fold, 100-fold or 1,000-fold less than a reference antibody, e.g., an antibody described herein.

In embodiments, the present invention provides methods of treating by providing to the subject in need thereof immune effector cells that are engineered to express the CARs that bind to a cancer associated antigen described herein, wherein the CAR is a nonconditional CAR or a conditional CAR.

In one aspect, the present invention provides methods of treating cancer by providing to the subject in need thereof immune effector cells (e.g., T cells, NK cells) that are engineered to express a mesothelinCAR, wherein the cancer cells express mesothelin. In one embodiment, the cancer to be treated is mesothelioma, pancreatic cancer, or ovarian cancer, or other solid tumors.

In one aspect, the present invention provides methods of treating cancer by providing to the subject in need thereof immune effector cells (e.g., T cells, NK cells) that are engineered to express an EGFRvIIICAR, wherein the cancer cells express EGFRvIII. In one embodiment, the cancer to be treated is glioblastoma.

In one aspect, the present invention provides methods of treating cancer by providing to the subject in need thereof immune effector cells (e.g., T cells, NK cells) that are engineered to express a Folate receptor alphaCAR, wherein the cancer cells express folate receptor alpha. In one embodiment, the cancer to be treated is ovarian cancer, NSCLC, endometrial cancer, renal cancer, or other solid tumors.

In one aspect, the present invention provides methods of treating cancer by providing to the subject in need thereof immune effector cells (e.g., T cells, NK cells) that are engineered to express an ERBB2CAR, wherein the cancer cells express ERBB2 (Her2/neu). In one embodiment, the cancer to be treated is breast cancer, gastric cancer, colorectal cancer, lung cancer, or other solid tumors.

In one aspect, the present invention provides methods of treating cancer by providing to the subject in need thereof immune effector cells (e.g., T cells, NK cells) that are engineered to express an IL-13Ra2CAR, wherein the cancer cells express IL-13Ra2. In one embodiment, the cancer to be treated is glioblastoma.

In one aspect, the present invention provides methods of treating cancer by providing to the subject in need thereof immune effector cells (e.g., T cells, NK cells) that are engineered to express an EphA2CAR, wherein the cancer cells express EphA2. In one embodiment, the cancer to be treated is GBM.

In one aspect, the present invention provides methods of treating cancer by providing to the subject in need thereof immune effector cells (e.g., T cells, NK cells) that are engineered to express an EGFRCAR, wherein the cancer cells express EGFR. In one embodiment, the cancer to be treated is glioblastoma, SCLC (small cell lung cancer), SCCHN (squamous cell carcinoma of the head and neck), NSCLC, or other solid tumors.

In one embodiment, the present invention provides methods of treating cancer by providing to the subject in need thereof immune effector cells (e.g., T cells, NK cells) that are engineered to express CD19 CAR, wherein the cancer cells express CD19. In one embodiment, the cancer to be treated is ALL (acute lymphoblastic leukemia), CLL (chronic lymphocytic leukemia), DLBCL (diffuse large B-cell lymphoma), MCL (Mantle cell lymphoma, or MM (multiple myeloma).

In one aspect, the present invention provides methods of treating cancer by providing to the subject in need thereof immune effector cells (e.g., T cells, NK cells) that are engineered to express a CD123CAR, wherein the cancer cells express CD123. In one embodiment, the cancer to be treated is AML.

In one aspect, the present invention provides methods of treating cancer by providing to the subject in need thereof immune effector cells (e.g., T cells, NK cells) that are engineered to express a CD22CAR, wherein the cancer cells express CD22. In one embodiment, the cancer to be treated is B cell malignancies.

In one aspect, the present invention provides methods of treating cancer by providing to the subject in need thereof immune effector cells (e.g., T cells, NK cells) that are engineered to express a CS-1CAR, wherein the cancer cells express CS-1. In one embodiment, the cancer to be treated is multiple myeloma.

In one aspect, the present invention provides methods of treating cancer by providing to the subject in need thereof immune effector cells (e.g., T cells, NK cells) that are engineered to express a CLL-1CAR, wherein the cancer cells express CLL-1. In one embodiment, the cancer to be treated is AML.

In one aspect, the present invention provides methods of treating cancer by providing to the subject in need thereof immune effector cells (e.g., T cells, NK cells) that are engineered to express a CD33CAR, wherein the cancer cells express CD33. In one embodiment, the cancer to be treated is AML.

In one aspect, the present invention provides methods of treating cancer by providing to the subject in need thereof immune effector cells (e.g., T cells, NK cells) that are engineered to express a GD2CAR, wherein the cancer cells express GD2. In one embodiment, the cancer to be treated is neuroblastoma.

In one aspect, the present invention provides methods of treating cancer by providing to the subject in need thereof immune effector cells (e.g., T cells, NK cells) that are engineered to express a BCMACAR, wherein the cancer cells express BCMA. In one embodiment, the cancer to be treated is multiple myeloma.

In one aspect, the present invention provides methods of treating cancer by providing to the subject in need thereof immune effector cells (e.g., T cells, NK cells) that are engineered to express a TnCAR, wherein the cancer cells express Tn antigen. In one embodiment, the cancer to be treated is ovarian cancer.

In one aspect, the present invention provides methods of treating cancer by providing to the subject in need thereof immune effector cells (e.g., T cells, NK cells) that are engineered to express a PSMACAR, wherein the cancer cells express PSMA. In one embodiment, the cancer to be treated is prostate cancer.

In one aspect, the present invention provides methods of treating cancer by providing to the subject in need thereof immune effector cells (e.g., T cells, NK cells) that are engineered to express a ROR1CAR, wherein the cancer cells express ROR1. In one embodiment, the cancer to be treated is B cell malignancies.

In one aspect, the present invention provides methods of treating cancer by providing to the subject in need thereof immune effector cells (e.g., T cells, NK cells) that are engineered to express a FLT3 CAR, wherein the cancer cells express FLT3. In one embodiment, the cancer to be treated is AML.

In one aspect, the present invention provides methods of treating cancer by providing to the subject in need thereof immune effector cells (e.g., T cells, NK cells) that are engineered to express a TAG72CAR, wherein the cancer cells express TAG72. In one embodiment, the cancer to be treated is gastrointestinal cancer.

In one aspect, the present invention provides methods of treating cancer by providing to the subject in need thereof immune effector cells (e.g., T cells, NK cells) that are engineered to express a CD38CAR, wherein the cancer cells express CD38. In one embodiment, the cancer to be treated is multiple myeloma.

In one aspect, the present invention provides methods of treating cancer by providing to the subject in need thereof immune effector cells (e.g., T cells, NK cells) that are engineered to express a CD44v6CAR, wherein the cancer cells express CD44v6. In one embodiment, the cancer to be treated is cervical cancer, AML, or MM.

In one aspect, the present invention provides methods of treating cancer by providing to the subject in need thereof immune effector cells (e.g., T cells, NK cells) that are engineered to express a CEACAR, wherein the cancer cells express CEA. In one embodiment, the cancer to be treated is gastrointestinal cancer, or pancreatic cancer.

In one aspect, the present invention provides methods of treating cancer by providing to the subject in need thereof immune effector cells (e.g., T cells, NK cells) that are engineered to express an EPCAMCAR, wherein the cancer cells express EPCAM. In one embodiment, the cancer to be treated is gastrointestinal cancer.

In one aspect, the present invention provides methods of treating cancer by providing to the subject in need thereof immune effector cells (e.g., T cells, NK cells) that are engineered to express a B7H3CAR, wherein the cancer cells express B7H3.

In one aspect, the present invention provides methods of treating cancer by providing to the subject in need thereof immune effector cells (e.g., T cells, NK cells) that are engineered to express a KITCAR, wherein the cancer cells express KIT. In one embodiment, the cancer to be treated is gastrointestinal cancer.

In one aspect, the present invention provides methods of treating cancer by providing to the subject in need thereof immune effector cells (e.g., T cells, NK cells) that are engineered to express a PRSS21CAR, wherein the cancer cells express PRSS21. In one embodiment, the cancer to be treated is selected from ovarian, pancreatic, lung and breast cancer.

In one aspect, the present invention provides methods of treating cancer by providing to the subject in need thereof immune effector cells (e.g., T cells, NK cells) that are engineered to express a CD30CAR, wherein the cancer cells express CD30. In one embodiment, the cancer to be treated is lymphomas, or leukemias.

In one aspect, the present invention provides methods of treating cancer by providing to the subject in need thereof immune effector cells (e.g., T cells, NK cells) that are engineered to express a GD3CAR, wherein the cancer cells express GD3. In one embodiment, the cancer to be treated is melanoma.

In one aspect, the present invention provides methods of treating cancer by providing to the subject in need thereof immune effector cells (e.g., T cells, NK cells) that are engineered to express a CD171CAR, wherein the cancer cells express CD171. In one embodiment, the cancer to be treated is neuroblastoma, ovarian cancer, melanoma, breast cancer, pancreatic cancer, colon cancers, or NSCLC (non-small cell lung cancer).

In one aspect, the present invention provides methods of treating cancer by providing to the subject in need thereof immune effector cells (e.g., T cells, NK cells) that are engineered to express an IL-11RaCAR, wherein the cancer cells express IL-11Ra. In one embodiment, the cancer to be treated is osteosarcoma.

In one aspect, the present invention provides methods of treating cancer by providing to the subject in need thereof immune effector cells (e.g., T cells, NK cells) that are engineered to express a PSCACAR, wherein the cancer cells express PSCA. In one embodiment, the cancer to be treated is prostate cancer.

In one aspect, the present invention provides methods of treating cancer by providing to the subject in need thereof immune effector cells (e.g., T cells, NK cells) that are engineered to express a VEGFR2CAR, wherein the cancer cells express VEGFR2. In one embodiment, the cancer to be treated is a solid tumor.

In one aspect, the present invention provides methods of treating cancer by providing to the subject in need thereof immune effector cells (e.g., T cells, NK cells) that are engineered to express a LewisYCAR, wherein the cancer cells express LewisY. In one embodiment, the cancer to be treated is ovarian cancer, or AML.

In one aspect, the present invention provides methods of treating cancer by providing to the subject in need thereof immune effector cells (e.g., T cells, NK cells) that are engineered to express a CD24CAR, wherein the cancer cells express CD24. In one embodiment, the cancer to be treated is pancreatic cancer.

In one aspect, the present invention provides methods of treating cancer by providing to the subject in need thereof immune effector cells (e.g., T cells, NK cells) that are engineered to express a PDGFR-betaCAR, wherein the cancer cells express PDGFR-beta. In one embodiment, the cancer to be treated is breast cancer, prostate cancer, GIST (gastrointestinal stromal tumor), CML, DFSP (dermatofibrosarcoma protuberans), or glioma.

In one aspect, the present invention provides methods of treating cancer by providing to the subject in need thereof immune effector cells (e.g., T cells, NK cells) that are engineered to express a SSEA-4CAR, wherein the cancer cells express SSEA-4. In one embodiment, the cancer to be treated is glioblastoma, breast cancer, lung cancer, or stem cell cancer.

In one aspect, the present invention provides methods of treating cancer by providing to the subject in need thereof immune effector cells (e.g., T cells, NK cells) that are engineered to express a CD20CAR, wherein the cancer cells express CD20. In one embodiment, the cancer to be treated is B cell malignancies.

In one aspect, the present invention provides methods of treating cancer by providing to the subject in need thereof immune effector cells (e.g., T cells, NK cells) that are engineered to express a MUC1CAR, wherein the cancer cells express MUC1. In one embodiment, the cancer to be treated is breast cancer, lung cancer, or other solid tumors.

In one aspect, the present invention provides methods of treating cancer by providing to the subject in need thereof immune effector cells (e.g., T cells, NK cells) that are engineered to express a NCAMCAR, wherein the cancer cells express NCAM. In one embodiment, the cancer to be treated is neuroblastoma, or other solid tumors.

In one aspect, the present invention provides methods of treating cancer by providing to the subject in need thereof immune effector cells (e.g., T cells, NK cells) that are engineered to express a CAIXCAR, wherein the cancer cells express CAIX. In one embodiment, the cancer to be treated is renal cancer, CRC, cervical cancer, or other solid tumors.

In one aspect, the present invention provides methods of treating cancer by providing to the subject in need thereof immune effector cells (e.g., T cells, NK cells) that are engineered to express a GD3CAR, wherein the cancer cells express GD3. In one embodiment, the cancer to be treated is melanoma.

In one aspect, the present invention provides methods of treating cancer by providing to the subject in need thereof immune effector cells (e.g., T cells, NK cells) that are engineered to express a Fucosyl GM1CAR, wherein the cancer cells express Fucosyl GM.

In one aspect, the present invention provides methods of treating cancer by providing to the subject in need thereof immune effector cells (e.g., T cells, NK cells) that are engineered to express a sLeCAR, wherein the cancer cells express sLe. In one embodiment, the cancer to be treated is NSCLC, or AML.

In one aspect, the present invention provides methods of treating cancer by providing to the subject in need thereof immune effector cells (e.g., T cells, NK cells) that are engineered to express a GM3CAR, wherein the cancer cells express GM3.

In one aspect, the present invention provides methods of treating cancer by providing to the subject in need thereof immune effector cells (e.g., T cells, NK cells) that are engineered to express a TGS5CAR, wherein the cancer cells express TGS5.

In one aspect, the present invention provides methods of treating cancer by providing to the subject in need thereof immune effector cells (e.g., T cells, NK cells) that are engineered to express a HMWMAACAR, wherein the cancer cells express HMWMAA. In one embodiment, the cancer to be treated is melanoma, glioblastoma, or breast cancer.

In one aspect, the present invention provides methods of treating cancer by providing to the subject in need thereof immune effector cells (e.g., T cells, NK cells) that are engineered to express an o-acetyl-GD2CAR, wherein the cancer cells express o-acetyl-GD2. In one embodiment, the cancer to be treated is neuroblastoma, or melanoma.

In one aspect, the present invention provides methods of treating cancer by providing to the subject in need thereof immune effector cells (e.g., T cells, NK cells) that are engineered to express a CD19CAR, wherein the cancer cells express CD19. In one embodiment, the cancer to be treated is a hematological cancer. In one embodiment, the cancer to be treated is selected from the group consisting of chronic lymphocytic leukemia (CLL), mantle cell lymphoma (MCL), multiple myeloma, acute lymphoid leukemia (ALL), Hodgkin lymphoma, B-cell acute lymphoid leukemia (BALL), T-cell acute lymphoid leukemia (TALL), small lymphocytic leukemia (SLL), B cell prolymphocytic leukemia, blastic plasmacytoid dendritic cell neoplasm, Burkitt's lymphoma, diffuse large B cell lymphoma (DLBCL), DLBCL associated with chronic inflammation, follicular lymphoma, pediatric follicular lymphoma, hairy cell leukemia, small cell- or a large cell-follicular lymphoma, malignant lymphoproliferative conditions, MALT lymphoma (extranodal marginal zone lymphoma of mucosa-associated lymphoid tissue), Marginal zone lymphoma, myelodysplasia and myelodysplastic syndrome, non-Hodgkin lymphoma, plasmablastic lymphoma, plasmacytoid dendritic cell neoplasm, Waldenstrom macroglobulinemia, splenic marginal zone lymphoma, splenic lymphoma/leukemia, splenic diffuse red pulp small B-cell lymphoma, hairy cell leukemia-variant, lymphoplasmacytic lymphoma, a heavy chain disease, plasma cell myeloma, solitary plasmocytoma of bone, extraosseous plasmocytoma, nodal marginal zone lymphoma, pediatric nodal marginal zone lymphoma, primary cutaneous follicle center lymphoma, lymphomatoid granulomatosis, primary mediastinal (thymic) large B-cell lymphoma, intravascular large B-cell lymphoma, ALK+ large B-cell lymphoma, large B-cell lymphoma arising in HHV8-associated multicentric Castleman disease, primary effusion lymphoma, B-cell lymphoma, or unclassifiable lymphoma.

In one aspect, the present invention provides methods of treating cancer by providing to the subject in need thereof immune effector cells (e.g., T cells, NK cells) that are engineered to express a TEM1/CD248CAR, wherein the cancer cells express TEM1/CD248. In one embodiment, the cancer to be treated is a solid tumor.

In one aspect, the present invention provides methods of treating cancer by providing to the subject in need thereof immune effector cells (e.g., T cells, NK cells) that are engineered to express a TEM7RCAR, wherein the cancer cells express TEM7R. In one embodiment, the cancer to be treated is solid tumor.

In one aspect, the present invention provides methods of treating cancer by providing to the subject in need thereof immune effector cells (e.g., T cells, NK cells) that are engineered to express a CLDN6CAR, wherein the cancer cells express CLDN6. In one embodiment, the cancer to be treated is ovarian cancer, lung cancer, or breast cancer.

In one aspect, the present invention provides methods of treating cancer by providing to the subject in need thereof immune effector cells (e.g., T cells, NK cells) that are engineered to express a TSHRCAR, wherein the cancer cells express TSHR. In one embodiment, the cancer to be treated is thyroid cancer, or multiple myeloma.

In one aspect, the present invention provides methods of treating cancer by providing to the subject in need thereof immune effector cells (e.g., T cells, NK cells) that are engineered to express a GPRC5DCAR, wherein the cancer cells express GPRC5D. In one embodiment, the cancer to be treated is multiple myeloma.

In one aspect, the present invention provides methods of treating cancer by providing to the subject in need thereof immune effector cells (e.g., T cells, NK cells) that are engineered to express a CXORF61CAR, wherein the cancer cells express CXORF61.

In one aspect, the present invention provides methods of treating cancer by providing to the subject in need thereof immune effector cells (e.g., T cells, NK cells) that are engineered to express a CD97CAR, wherein the cancer cells express CD97. In one embodiment, the cancer to be treated is B cell malignancies, gastric cancer, pancreatic cancer, esophageal cancer, glioblastoma, breast cancer, or colorectal cancer.

In one aspect, the present invention provides methods of treating cancer by providing to the subject in need thereof immune effector cells (e.g., T cells, NK cells) that are engineered to express a CD179aCAR, wherein the cancer cells express CD179a. In one embodiment, the cancer to be treated is B cell malignancies.

In one aspect, the present invention provides methods of treating cancer by providing to the subject in need thereof immune effector cells (e.g., T cells, NK cells) that are engineered to express an ALK CAR, wherein the cancer cells express ALK. In one embodiment, the cancer to be treated is NSCLC, ALCL (anaplastic large cell lymphoma), IMT (inflammatory myofibroblastic tumor), or neuroblastoma.

In one aspect, the present invention provides methods of treating cancer by providing to the subject in need thereof immune effector cells (e.g., T cells, NK cells) that are engineered to express a Plysialic acid CAR, wherein the cancer cells express Plysialic acid. In one embodiment, the cancer to be treated is small cell lung cancer.

In one aspect, the present invention provides methods of treating cancer by providing to the subject in need thereof immune effector cells (e.g., T cells, NK cells) that are engineered to express a PLAC1CAR, wherein the cancer cells express PLAC1. In one embodiment, the cancer to be treated is HCC (hepatocellular carcinoma).

In one aspect, the present invention provides methods of treating cancer by providing to the subject in need thereof immune effector cells (e.g., T cells, NK cells) that are engineered to express a GloboHCAR, wherein the cancer cells express GloboH. In one embodiment, the cancer to be treated is ovarian cancer, gastric cancer, prostate cancer, lung cancer, breast cancer, or pancreatic cancer.

In one aspect, the present invention provides methods of treating cancer by providing to the subject in need thereof immune effector cells (e.g., T cells, NK cells) that are engineered to express a NY-BR-1CAR, wherein the cancer cells express NY-BR-1. In one embodiment, the cancer to be treated is breast cancer.

In one aspect, the present invention provides methods of treating cancer by providing to the subject in need thereof immune effector cells (e.g., T cells, NK cells) that are engineered to express a UPK2CAR, wherein the cancer cells express UPK2. In one embodiment, the cancer to be treated is bladder cancer.

In one aspect, the present invention provides methods of treating cancer by providing to the subject in need thereof immune effector cells (e.g., T cells, NK cells) that are engineered to express a HAVCR1CAR, wherein the cancer cells express HAVCR1. In one embodiment, the cancer to be treated is renal cancer.

In one aspect, the present invention provides methods of treating cancer by providing to the subject in need thereof immune effector cells (e.g., T cells, NK cells) that are engineered to express a ADRB3CAR, wherein the cancer cells express ADRB3. In one embodiment, the cancer to be treated is Ewing sarcoma.

In one aspect, the present invention provides methods of treating cancer by providing to the subject in need thereof immune effector cells (e.g., T cells, NK cells) that are engineered to express a PANX3CAR, wherein the cancer cells express PANX3. In one embodiment, the cancer to be treated is osteosarcoma.

In one aspect, the present invention provides methods of treating cancer by providing to the subject in need thereof immune effector cells (e.g., T cells, NK cells) that are engineered to express a GPR20CAR, wherein the cancer cells express GPR20. In one embodiment, the cancer to be treated is GIST.

In one aspect, the present invention provides methods of treating cancer by providing to the subject in need thereof immune effector cells (e.g., T cells, NK cells) that are engineered to express a LY6KCAR, wherein the cancer cells express LY6K. In one embodiment, the cancer to be treated is breast cancer, lung cancer, ovary cancer, or cervix cancer.

In one aspect, the present invention provides methods of treating cancer by providing to the subject in need thereof immune effector cells (e.g., T cells, NK cells) that are engineered to express a OR51E2CAR, wherein the cancer cells express OR51E2. In one embodiment, the cancer to be treated is prostate cancer.

In one aspect, the present invention provides methods of treating cancer by providing to the subject in need thereof immune effector cells (e.g., T cells, NK cells) that are engineered to express a TARPCAR, wherein the cancer cells express TARP. In one embodiment, the cancer to be treated is prostate cancer.

In one aspect, the present invention provides methods of treating cancer by providing to the subject in need thereof immune effector cells (e.g., T cells, NK cells) that are engineered to express a WT1CAR, wherein the cancer cells express WT1.

In one aspect, the present invention provides methods of treating cancer by providing to the subject in need thereof immune effector cells (e.g., T cells, NK cells) that are engineered to express a NY-ESO-1CAR, wherein the cancer cells express NY-ESO-1.

In one aspect, the present invention provides methods of treating cancer by providing to the subject in need thereof immune effector cells (e.g., T cells, NK cells) that are engineered to express a LAGE-1a CAR, wherein the cancer cells express LAGE-1a.

In one aspect, the present invention provides methods of treating cancer by providing to the subject in need thereof immune effector cells (e.g., T cells, NK cells) that are engineered to express a MAGE-A1CAR, wherein the cancer cells express MAGE-A1. In one embodiment, the cancer to be treated is melanoma.

In one aspect, the present invention provides methods of treating cancer by providing to the subject in need thereof immune effector cells (e.g., T cells, NK cells) that are engineered to express a MAGE A1CAR, wherein the cancer cells express MAGE A1.

In one aspect, the present invention provides methods of treating cancer by providing to the subject in need thereof immune effector cells (e.g., T cells, NK cells) that are engineered to express a ETV6-AML CAR, wherein the cancer cells express ETV6-AML.

In one aspect, the present invention provides methods of treating cancer by providing to the subject in need thereof immune effector cells (e.g., T cells, NK cells) that are engineered to express a sperm protein 17 CAR, wherein the cancer cells express sperm protein 17. In one embodiment, the cancer to be treated is ovarian cancer, HCC, or NSCLC.

In one aspect, the present invention provides methods of treating cancer by providing to the subject in need thereof immune effector cells (e.g., T cells, NK cells) that are engineered to express a XAGE1CAR, wherein the cancer cells express XAGE1. In one embodiment, the cancer to be treated is Ewings, or rhabdo cancer.

In one aspect, the present invention provides methods of treating cancer by providing to the subject in need thereof immune effector cells (e.g., T cells, NK cells) that are engineered to express a Tie 2 CAR, wherein the cancer cells express Tie 2. In one embodiment, the cancer to be treated is a solid tumor.

In one aspect, the present invention provides methods of treating cancer by providing to the subject in need thereof immune effector cells (e.g., T cells, NK cells) that are engineered to express a MAD-CT-1CAR, wherein the cancer cells express MAD-CT-1. In one embodiment, the cancer to be treated is prostate cancer, or melanoma.

In one aspect, the present invention provides methods of treating cancer by providing to the subject in need thereof immune effector cells (e.g., T cells, NK cells) that are engineered to express a MAD-CT-2CAR, wherein the cancer cells express MAD-CT-2. In one embodiment, the cancer to be treated is prostate cancer, melanoma.

In one aspect, the present invention provides methods of treating cancer by providing to the subject in need thereof immune effector cells (e.g., T cells, NK cells) that are engineered to express a Fos-related antigen 1 CAR, wherein the cancer cells express Fos-related antigen 1. In one embodiment, the cancer to be treated is glioma, squamous cell cancer, or pancreatic cancer.

In one aspect, the present invention provides methods of treating cancer by providing to the subject in need thereof immune effector cells (e.g., T cells, NK cells) that are engineered to express a p53CAR, wherein the cancer cells express p53.

In one aspect, the present invention provides methods of treating cancer by providing to the subject in need thereof immune effector cells (e.g., T cells, NK cells) that are engineered to express a prostein CAR, wherein the cancer cells express prostein.

In one aspect, the present invention provides methods of treating cancer by providing to the subject in need thereof immune effector cells (e.g., T cells, NK cells) that are engineered to express a survivin and telomerase CAR, wherein the cancer cells express survivin and telomerase.

In one aspect, the present invention provides methods of treating cancer by providing to the subject in need thereof immune effector cells (e.g., T cells, NK cells) that are engineered to express a PCTA-1/Galectin 8 CAR, wherein the cancer cells express PCTA-1/Galectin 8.

In one aspect, the present invention provides methods of treating cancer by providing to the subject in need thereof immune effector cells (e.g., T cells, NK cells) that are engineered to express a MelanA/MART1CAR, wherein the cancer cells express MelanA/MART1.

In one aspect, the present invention provides methods of treating cancer by providing to the subject in need thereof immune effector cells (e.g., T cells, NK cells) that are engineered to express a Ras mutant CAR, wherein the cancer cells express Ras mutant.

In one aspect, the present invention provides methods of treating cancer by providing to the subject in need thereof immune effector cells (e.g., T cells, NK cells) that are engineered to express a p53 mutant CAR, wherein the cancer cells express p53 mutant.

In one aspect, the present invention provides methods of treating cancer by providing to the subject in need thereof immune effector cells (e.g., T cells, NK cells) that are engineered to express a hTERT CAR, wherein the cancer cells express hTERT.

In one aspect, the present invention provides methods of treating cancer by providing to the subject in need thereof immune effector cells (e.g., T cells, NK cells) that are engineered to express a sarcoma translocation breakpoints CAR, wherein the cancer cells express sarcoma translocation breakpoints. In one embodiment, the cancer to be treated is sarcoma.

In one aspect, the present invention provides methods of treating cancer by providing to the subject in need thereof immune effector cells (e.g., T cells, NK cells) that are engineered to express a ML-IAP CAR, wherein the cancer cells express ML-IAP. In one embodiment, the cancer to be treated is melanoma.

In one aspect, the present invention provides methods of treating cancer by providing to the subject in need thereof immune effector cells (e.g., T cells, NK cells) that are engineered to express an ERGCAR, wherein the cancer cells express ERG (TMPRSS2 ETS fusion gene).

In one aspect, the present invention provides methods of treating cancer by providing to the subject in need thereof immune effector cells (e.g., T cells, NK cells) that are engineered to express a NA17CAR, wherein the cancer cells express NA17. In one embodiment, the cancer to be treated is melanoma.

In one aspect, the present invention provides methods of treating cancer by providing to the subject in need thereof immune effector cells (e.g., T cells, NK cells) that are engineered to express a PAX3CAR, wherein the cancer cells express PAX3. In one embodiment, the cancer to be treated is alveolar rhabdomyosarcoma.

In one aspect, the present invention provides methods of treating cancer by providing to the subject in need thereof immune effector cells (e.g., T cells, NK cells) that are engineered to express an androgen receptor CAR, wherein the cancer cells express androgen receptor. In one embodiment, the cancer to be treated is metastatic prostate cancer.

In one aspect, the present invention provides methods of treating cancer by providing to the subject in need thereof immune effector cells (e.g., T cells, NK cells) that are engineered to express a Cyclin B1CAR, wherein the cancer cells express Cyclin B1.

In one aspect, the present invention provides methods of treating cancer by providing to the subject in need thereof immune effector cells (e.g., T cells, NK cells) that are engineered to express a MYCNCAR, wherein the cancer cells express MYCN.

In one aspect, the present invention provides methods of treating cancer by providing to the subject in need thereof immune effector cells (e.g., T cells, NK cells) that are engineered to express a RhoC CAR, wherein the cancer cells express RhoC.

In one aspect, the present invention provides methods of treating cancer by providing to the subject in need thereof immune effector cells (e.g., T cells, NK cells) that are engineered to express a TRP-2CAR, wherein the cancer cells express TRP-2. In one embodiment, the cancer to be treated is melanoma.

In one aspect, the present invention provides methods of treating cancer by providing to the subject in need thereof immune effector cells (e.g., T cells, NK cells) that are engineered to express a CYP1B1CAR, wherein the cancer cells express CYP1B1. In one embodiment, the cancer to be treated is breast cancer, colon cancer, lung cancer, esophagus cancer, skin cancer, lymph node cancer, brain cancer, or testis cancer.

In one aspect, the present invention provides methods of treating cancer by providing to the subject in need thereof immune effector cells (e.g., T cells, NK cells) that are engineered to express a BORIS CAR, wherein the cancer cells express BORIS. In one embodiment, the cancer to be treated is lung cancer.

In one aspect, the present invention provides methods of treating cancer by providing to the subject in need thereof immune effector cells (e.g., T cells, NK cells) that are engineered to express a SART3CAR, wherein the cancer cells express SART3 In one aspect, the present invention provides methods of treating cancer by providing to the subject in need thereof immune effector cells (e.g., T cells, NK cells) that are engineered to express a PAX5CAR, wherein the cancer cells express PAX5.

In one aspect, the present invention provides methods of treating cancer by providing to the subject in need thereof immune effector cells (e.g., T cells, NK cells) that are engineered to express a OY-TES1CAR, wherein the cancer cells express OY-TES1.

In one aspect, the present invention provides methods of treating cancer by providing to the subject in need thereof immune effector cells (e.g., T cells, NK cells) that are engineered to express a LCK CAR, wherein the cancer cells express LCK.

In one aspect, the present invention provides methods of treating cancer by providing to the subject in need thereof immune effector cells (e.g., T cells, NK cells) that are engineered to express a AKAP-4CAR, wherein the cancer cells express AKAP-4.

In one aspect, the present invention provides methods of treating cancer by providing to the subject in need thereof immune effector cells (e.g., T cells, NK cells) that are engineered to express a SSX2CAR, wherein the cancer cells express SSX2.

In one aspect, the present invention provides methods of treating cancer by providing to the subject in need thereof immune effector cells (e.g., T cells, NK cells) that are engineered to express a RAGE-1CAR, wherein the cancer cells express RAGE-1. In one embodiment, the cancer to be treated is RCC (renal cell cancer), or other solid tumors.

In one aspect, the present invention provides methods of treating cancer by providing to the subject in need thereof immune effector cells (e.g., T cells, NK cells) that are engineered to express a human telomerase reverse transcriptase CAR, wherein the cancer cells express human telomerase reverse transcriptase. In one embodiment, the cancer to be treated is solid tumors.

In one aspect, the present invention provides methods of treating cancer by providing to the subject in need thereof immune effector cells (e.g., T cells, NK cells) that are engineered to express a RU1CAR, wherein the cancer cells express RU1.

In one aspect, the present invention provides methods of treating cancer by providing to the subject in need thereof immune effector cells (e.g., T cells, NK cells) that are engineered to express a RU2CAR, wherein the cancer cells express RU2.

In one aspect, the present invention provides methods of treating cancer by providing to the subject in need thereof immune effector cells (e.g., T cells, NK cells) that are engineered to express an intestinal carboxyl esterase CAR, wherein the cancer cells express intestinal carboxyl esterase. In one embodiment, the cancer to be treated is thyroid cancer, RCC, CRC (colorectal cancer), breast cancer, or other solid tumors.

In one aspect, the present invention provides methods of treating cancer by providing to the subject in need thereof immune effector cells (e.g., T cells, NK cells) that are engineered to express a Prostase CAR, wherein the cancer cells express Prostase.

In one aspect, the present invention provides methods of treating cancer by providing to the subject in need thereof immune effector cells (e.g., T cells, NK cells) that are engineered to express a PAPCAR, wherein the cancer cells express PAP.

In one aspect, the present invention provides methods of treating cancer by providing to the subject in need thereof immune effector cells (e.g., T cells, NK cells) that are engineered to express an IGF-I receptor CAR, wherein the cancer cells express IGF-I receptor.

In one aspect, the present invention provides methods of treating cancer by providing to the subject in need thereof immune effector cells (e.g., T cells, NK cells) that are engineered to express a gp100 CAR, wherein the cancer cells express gp100.

In one aspect, the present invention provides methods of treating cancer by providing to the subject in need thereof immune effector cells (e.g., T cells, NK cells) that are engineered to express a bcr-abl CAR, wherein the cancer cells express bcr-abl.

In one aspect, the present invention provides methods of treating cancer by providing to the subject in need thereof immune effector cells (e.g., T cells, NK cells) that are engineered to express a tyrosinase CAR, wherein the cancer cells express tyrosinase.

In one aspect, the present invention provides methods of treating cancer by providing to the subject in need thereof immune effector cells (e.g., T cells, NK cells) that are engineered to express a Fucosyl GM1CAR, wherein the cancer cells express Fucosyl GM1.

In one aspect, the present invention provides methods of treating cancer by providing to the subject in need thereof immune effector cells (e.g., T cells, NK cells) that are engineered to express a mut hsp70-2CAR, wherein the cancer cells express mut hsp70-2. In one embodiment, the cancer to be treated is melanoma.

In one aspect, the present invention provides methods of treating cancer by providing to the subject in need thereof immune effector cells (e.g., T cells, NK cells) that are engineered to express a CD79a CAR, wherein the cancer cells express CD79a.

In one aspect, the present invention provides methods of treating cancer by providing to the subject in need thereof immune effector cells (e.g., T cells, NK cells) that are engineered to express a CD79b CAR, wherein the cancer cells express CD79b.

In one aspect, the present invention provides methods of treating cancer by providing to the subject in need thereof immune effector cells (e.g., T cells, NK cells) that are engineered to express a CD72 CAR, wherein the cancer cells express CD72.

In one aspect, the present invention provides methods of treating cancer by providing to the subject in need thereof immune effector cells (e.g., T cells, NK cells) that are engineered to express a LAIR1 CAR, wherein the cancer cells express LAIR1.

In one aspect, the present invention provides methods of treating cancer by providing to the subject in need thereof immune effector cells (e.g., T cells, NK cells) that are engineered to express a FCAR CAR, wherein the cancer cells express FCAR.

In one aspect, the present invention provides methods of treating cancer by providing to the subject in need thereof immune effector cells (e.g., T cells, NK cells) that are engineered to express a LILRA2 CAR, wherein the cancer cells express LILRA2.

In one aspect, the present invention provides methods of treating cancer by providing to the subject in need thereof immune effector cells (e.g., T cells, NK cells) that are engineered to express a CD300LF CAR, wherein the cancer cells express CD300LF.

In one aspect, the present invention provides methods of treating cancer by providing to the subject in need thereof immune effector cells (e.g., T cells, NK cells) that are engineered to express a CLEC12A CAR, wherein the cancer cells express CLEC12A.

In one aspect, the present invention provides methods of treating cancer by providing to the subject in need thereof immune effector cells (e.g., T cells, NK cells) that are engineered to express a BST2 CAR, wherein the cancer cells express BST2.

In one aspect, the present invention provides methods of treating cancer by providing to the subject in need thereof immune effector cells (e.g., T cells, NK cells) that are engineered to express an EMR2 CAR, wherein the cancer cells express EMR2.

In one aspect, the present invention provides methods of treating cancer by providing to the subject in need thereof immune effector cells (e.g., T cells, NK cells) that are engineered to express a LY75 CAR, wherein the cancer cells express LY75.

In one aspect, the present invention provides methods of treating cancer by providing to the subject in need thereof immune effector cells (e.g., T cells, NK cells) that are engineered to express a GPC3 CAR, wherein the cancer cells express GPC3.

In one aspect, the present invention provides methods of treating cancer by providing to the subject in need thereof immune effector cells (e.g., T cells, NK cells) that are engineered to express a FCRL5 CAR, wherein the cancer cells express FCRL5.

In one aspect, the present invention provides methods of treating cancer by providing to the subject in need thereof immune effector cells (e.g., T cells, NK cells) that are engineered to express an IGLL1 CAR, wherein the cancer cells express IGLL1.

In one aspect, the present invention relates to treatment of a subject in vivo using an PD1 CAR such that growth of cancerous tumors is inhibited. A PD1 CAR may be used alone to inhibit the growth of cancerous tumors. Alternatively, PD1 CAR may be used in conjunction with other CARs, immunogenic agents, standard cancer treatments, or other antibodies. In one embodiment, the subject is treated with a PD1 CAR and an XCAR described herein. In an embodiment, a PD1 CAR is used in conjunction with another CAR, e.g., a CAR described herein, and a kinase inhibitor, e.g., a kinase inhibitor described herein.

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. As used herein, the term "cancer" is meant to include all types of cancerous growths or oncogenic processes, metastatic tissues or malignantly transformed cells, tissues, or organs, irrespective of histopathologic type or stage of invasiveness.

In one embodiment, the methods and compositions described herein for treating a subject having a solid tumor.

Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) Int. Immunol. 17:133-144) can be effected using the antibody molecules described herein.

In an embodiment, the methods and compositions described herein can be used to be treat a disease associated with mesothelin expression. In an embodiment, the methods and compositions described herein can be used to treat ovarian cancer, e.g., epithelial ovarian cancer, serous ovarian cancer, or metatastic ovarian cancer.

Exemplary cancers whose growth can be inhibited include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the molecules described herein.

In one aspect, the invention pertains to a vector comprising a CAR operably linked to a control region, e.g., comprising a constitutive promoter, for expression in mammalian immune effector cells (e.g., T cells, NK cells). In one aspect, the invention provides a recombinant immune effector cell expressing a CAR of the present invention for use in treating cancer expressing a cancer associated antigen as described herein. In one aspect, CAR-expressing cells of the invention is capable of contacting a tumor cell with at least one cancer associated antigen expressed on its surface such that the CAR-expressing cell targets the cancer cell and growth of the cancer is inhibited. Upon binding of the constitutively expressed CAR (nonconditional CAR) to the cancer associated antigen expressed on the cancer cell, expression of a conditional agent that enhances anti-cancer immune response is induced.

In one aspect, the invention pertains to a method of inhibiting growth of a cancer, comprising contacting the cancer cell with a CAR-expressing cell of the present invention such that the CART is activated in response to the antigen and targets the cancer cell, wherein the growth of the tumor is inhibited.

In one aspect, the invention pertains to a method of treating cancer in a subject. The method comprises administering to the subject CAR-expressing cell of the present invention such that the cancer is treated in the subject. In one aspect, the cancer associated with expression of a cancer associated antigen as described herein is a solid tumor. In one aspect, the cancer associated with expression of a cancer associate antigen as described herein is a hematological cancer.

In one aspect, the hematological cancer is a leukemia or a lymphoma. In one aspect, a cancer associated with expression of a cancer associate antigen as described herein includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of a cancer associate antigen as described herein include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with a cancer associate antigen as described herein expression include, but not limited to, e.g., atypical and/or non-classical cancers, malignancies, precancerous conditions or proliferative diseases associated with expression of a cancer associate antigen as described herein.

In some embodiments, a cancer that can be treated with CAR-expressing cell of the present invention is multiple myeloma. Multiple myeloma is a cancer of the blood, characterized by accumulation of a plasma cell clone in the bone marrow. Current therapies for multiple myeloma include, but are not limited to, treatment with lenalidomide, which is an analog of thalidomide. Lenalidomide has activities which include anti-tumor activity, angiogenesis inhibition, and immunomodulation. Generally, myeloma cells are thought to be negative for a cancer associate antigen as described herein expression by flow cytometry. Thus, in some embodiments, a CD19 CAR, e.g., as described herein, may be used to target myeloma cells. In some embodiments, cars of the present invention therapy can be used in combination with one or more additional therapies, e.g., lenalidomide treatment.

The invention includes a type of cellular therapy where immune effector cells (e.g., T cells, NK cells) are genetically modified to express a chimeric antigen receptor (CAR) and the CAR-expressing T cell or NK cell is infused to a recipient in need thereof. The infused cell is able to kill tumor cells in the recipient. Unlike antibody therapies, CAR-modified immune effector cells (e.g., T cells, NK cells) are able to replicate in vivo resulting in long-term persistence that can lead to sustained tumor control. In various aspects, the immune effector cells (e.g., T cells, NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell or NK cell to the patient.

The invention also includes a type of cellular therapy where immune effector cells (e.g., T cells, NK cells) are modified, e.g., by in vitro transcribed RNA, to transiently express a chimeric antigen receptor (CAR) and the CAR T cell or NK cell is infused to a recipient in need thereof. The infused cell is able to kill tumor cells in the recipient. Thus, in various aspects, the immune effector cells (e.g., T cells, NK cells) administered to the patient, is present for less than one month, e.g., three weeks, two weeks, one week, after administration of the T cell or NK cell to the patient.

Without wishing to be bound by any particular theory, the anti-tumor immunity response elicited by the CAR-modified immune effector cells (e.g., T cells, NK cells) may be an active or a passive immune response, or alternatively may be due to a direct vs indirect immune response. In one aspect, the CAR transduced immune effector cells (e.g., T cells, NK cells) exhibit specific proinflammatory cytokine secretion and potent cytolytic activity in response to human cancer cells expressing the a cancer associate antigen as described herein, resist soluble a cancer associate antigen as described herein inhibition, mediate bystander killing and mediate regression of an established human tumor. For example, antigen-less tumor cells within a heterogeneous field of a cancer associate antigen as described herein-expressing tumor may be susceptible to indirect destruction by a cancer associate antigen as described herein-redirected immune effector cells (e.g., T cells, NK cells) that has previously reacted against adjacent antigen-positive cancer cells.

In one aspect, the fully-human CAR-modified immune effector cells (e.g., T cells, NK cells) of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of immune effector cells (e.g., T cells, NK cells) comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells (e.g., T cells, NK cells) of the invention are used in the treatment of diseases, disorders and conditions associated with expression of a cancer associate antigen as described herein. In certain aspects, the cells of the invention are used in the treatment of patients at risk for developing diseases, disorders and conditions associated with expression of a cancer associate antigen as described herein. Thus, the present invention provides methods for the treatment or prevention of diseases, disorders and conditions associated with expression of a cancer associate antigen as described herein comprising administering to a subject in need thereof, a therapeutically effective amount of the CAR-modified immune effector cells (e.g., T cells, NK cells) of the invention.

In one aspect the CAR-expressing cells of the inventions may be used to treat a proliferative disease such as a cancer or malignancy or is a precancerous condition such as a myelodysplasia, a myelodysplastic syndrome or a preleukemia. Further a disease associated with a cancer associate antigen as described herein expression include, but not limited to, e.g., atypical and/or non-classical cancers, malignancies, precancerous conditions or proliferative diseases expressing a cancer associated antigen as described herein. Non-cancer related indications associated with expression of a cancer associate antigen as described herein include, but are not limited to, e.g., autoimmune disease, (e.g., lupus), inflammatory disorders (allergy and asthma) and transplantation.

The CAR-modified immune effector cells (e.g., T cells, NK cells) of the present invention may be administered either alone, or as a pharmaceutical composition in combination with diluents and/or with other components such as IL-2 or other cytokines or cell populations.

The present invention also provides methods for inhibiting the proliferation or reducing a cancer associated antigen as described herein-expressing cell population, the methods comprising contacting a population of cells comprising a cancer associated antigen as described herein-expressing cell with a CAR-expressing T cell or NK cell of the invention that binds to the a cancer associate antigen as described herein-expressing cell. In a specific aspect, the present invention provides methods for inhibiting the proliferation or reducing the population of cancer cells expressing a cancer associated antigen as described herein, the methods comprising contacting a cancer associate antigen as described herein-expressing cancer cell population with a CAR-expressing T cell or NK cell of the invention that binds to a cancer associated antigen as described herein-expressing cell. In one aspect, the present invention provides methods for inhibiting the proliferation or reducing the population of cancer cells expressing a cancer associated antigen as described herein, the methods comprising contacting a cancer associated antigen as described herein-expressing cancer cell population with a CAR-expressing T cell or NK cell of the invention that binds to a cancer associated antigen as described herein-expressing cell. In certain aspects, a CAR-expressing T cell or NK cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with a cancer associated antigen as described herein-expressing cells relative to a negative control.

The present invention also provides methods for preventing, treating and/or managing a disease associated with a cancer associated antigen as described herein-expressing cells (e.g., a hematologic cancer, a solid cancer, or atypical cancer expressing a cancer associated antigen as described herein), the methods comprising administering to a subject in need a CAR T cell or NK cell of the invention that binds to a cancer associated antigen as described herein-expressing cell. In one aspect, the subject is a human. Non-limiting examples of disorders associated with a cancer associated antigen as described herein-expressing cells include autoimmune disorders (such as lupus), inflammatory disorders (such as allergies and asthma) and cancers (such as hematological cancers or atypical cancers expressing a cancer associated antigen as described herein).

The present invention also provides methods for preventing, treating and/or managing a disease associated with a cancer associated antigen as described herein-expressing cells, the methods comprising administering to a subject in need a CAR T cell or NK cell of the invention that binds to a cancer associated antigen as described herein-expressing cell. In one aspect, the subject is a human.

The present invention provides methods for preventing relapse of cancer associated with a cancer associated antigen as described herein-expressing cells, the methods comprising administering to a subject in need thereof a CAR-expressing T cell or NK cell of the invention that binds to a cancer associated antigen as described herein-expressing cell. In one aspect, the methods comprise administering to the subject in need thereof an effective amount of a CAR-expressing T cell or NK cell described herein that binds to a cancer associated antigen as described herein-expressing cell in combination with an effective amount of another therapy.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, a CAR-expressing cell described herein can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.0$^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 264), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, a CAR-expressing cell described herein is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, a CAR-expressing cell described herein is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 mg/m$^2$ (e.g., about 300-325, 325-350, 350-375, 375-400, 400-425, or 425-450 mg/m$^2$), e.g., intravenously. In embodiments, bendamustine is administered at a dosage of about 75-125 mg/m2 (e.g., 75-100 or 100-125 mg/m$^2$, e.g., about 90 mg/m$^2$), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1 (2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s53111 lbl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 mg/m$^2$ to 750 mg/m$^2$, e.g., about 150-175 mg/m$^2$, 175-200 mg/m$^2$, 200-225 mg/m$^2$, 225-250 mg/m$^2$, 250-300 mg/m$^2$, 300-325 mg/m$^2$, 325-350 mg/m$^2$, 350-375 mg/m$^2$, 375-400 mg/m$^2$, 400-425 mg/m$^2$, 425-450 mg/m$^2$, 450-475 mg/m$^2$, 475-500 mg/m$^2$, 500-525 mg/m$^2$, 525-550 mg/m$^2$, 550-575 mg/m$^2$, 575-600 mg/m$^2$, 600-625 mg/m$^2$, 625-650 mg/m$^2$, 650-675 mg/m$^2$, or 675-700 mg/m$^2$, where m$^2$ indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgGκ human monoclonal antibody with a molecular weight of approximately 149 kDa. For example, ofatumumab is generated using transgenic mouse and hybridoma technology and is expressed and purified from a recombinant murine cell line (NS0). See, e.g., www.accessdata.fda.gov/drugsatfda_docs/label/2009/125326lbl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378 (2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5) (2010):747-55.

In some cases, the anti-CD20 antibody comprises GA101. GA101 (also called obinutuzumab or RO5072759) is a humanized and glyco-engineered anti-CD20 monoclonal antibody. See, e.g., Robak. Curr. Opin. Investig. Drugs. 10.6 (2009):588-96; Clinical Trial Identifier Numbers: NCT01995669, NCT01889797, NCT02229422, and NCT01414205; and www.accessdata.fda.gov/drugsatfda_docs/label/2013/125486s000lbl.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1 (2011):13-25; and Forero-Torres et al. Clin Cancer Res. 18.5 (2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1 (2011):13-25; and Casulo et al. Clin Immunol. 154.1 (2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1 (2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

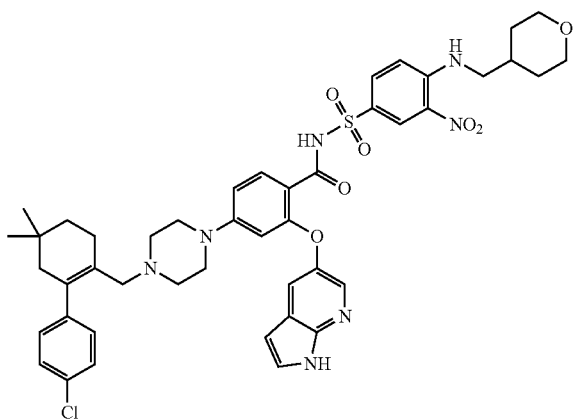 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously, e.g., monthly.

In some embodiments, a CAR-expressing cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B fibronectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3 (2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18 (2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220); ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129); VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759); Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661); CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intra-arterial, intravenous, intramuscular, intrathecal, or intraperitoneal injection. In embodiments, an oncolytic virus described herein is administered intratumorally, transdermally, transmucosally, orally, intranasally, or via pulmonary administration.

In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse.

In one embodiment, cells expressing a CAR described herein are administered to a subject in combination with a molecule targeting GITR and/or modulating GITR functions, such as a GITR agonist and/or a GITR antibody that depletes regulatory T cells (Tregs). In one embodiment, the GITR binding molecules and/or molecules modulating GITR functions (e.g., GITR agonist and/or Treg depleting GITR antibodies) are administered prior to the CAR-expressing cell. For example, in one embodiment, the GITR agonist can be administered prior to apheresis of the cells. In one embodiment, the subject has CLL. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells. In one embodiment, the subject has CLL.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells. In one embodiment, the subject has CLL.

In one embodiment, a CAR expressing cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102.

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl] amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In embodiments, a CAR-expressing cell described herein is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

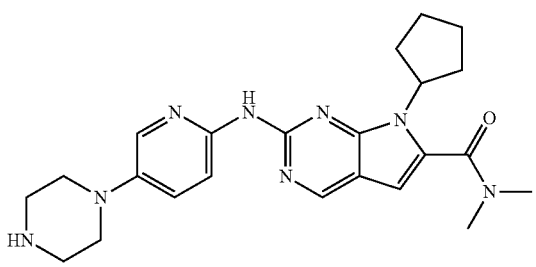 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

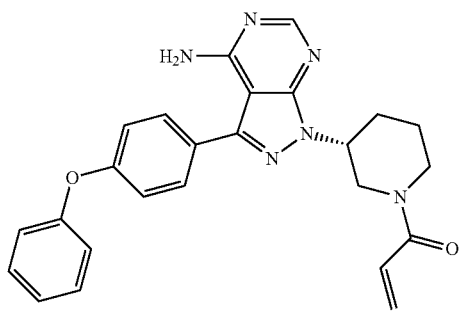 [SMILES: C=CC(=O)N1CCC[C@@H](n2nc(-c3ccc(Oc4ccccc4)cc3)c3c(N)ncnc32)C1]

In embodiments, the subject has CLL, mantle cell lymphoma (MCL), or small lymphocytic lymphoma (SLL). For example, the subject has a deletion in the short arm of chromosome 17 (del(17p), e.g., in a leukemic cell). In other examples, the subject does not have a del(17p). In embodiments, the subject has relapsed CLL or SLL, e.g., the subject has previously been administered a cancer therapy (e.g., previously been administered one, two, three, or four prior cancer therapies). In embodiments, the subject has refractory CLL or SLL. In other embodiments, the subject has follicular lymphoma, e.g., relapse or refractory follicular lymphoma. In some embodiments, ibrutinib is administered at a dosage of about 300-600 mg/day (e.g., about 300-350, 350-400, 400-450, 450-500, 500-550, or 550-600 mg/day, e.g., about 420 mg/day or about 560 mg/day), e.g., orally. In embodiments, the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of ibrutinib are administered.

In some embodiments, ibrutinib is administered in combination with rituximab. See, e.g., Burger et al. (2013) Ibrutinib In Combination With Rituximab (iR) Is Well Tolerated and Induces a High Rate Of Durable Remissions In Patients With High-Risk Chronic Lymphocytic Leukemia (CLL): New, Updated Results Of a Phase II Trial In 40 Patients, Abstract 675 presented at 55th ASH Annual Meeting and Exposition, New Orleans, La. 7-10 December Without being bound by theory, it is thought that the addition of ibrutinib enhances the T cell proliferative response and may shift T cells from a T-helper-2 (Th2) to T-helper-1 (Th1) phenotype. Th1 and Th2 are phenotypes of helper T cells, with Th1 versus Th2 directing different immune response pathways. A Th1 phenotype is associated with proinflammatory responses, e.g., for killing cells, such as intracellular pathogens/viruses or cancerous cells, or perpetuating autoimmune responses. A Th2 phenotype is associated with eosinophil accumulation and anti-inflammatory responses.

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

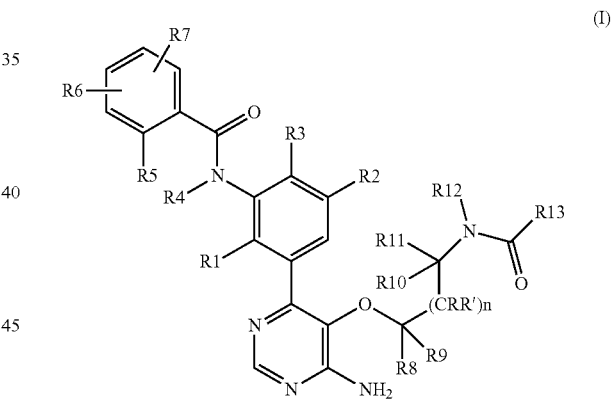

wherein,
R1 is hydrogen, C1-C6 alkyl optionally substituted by hydroxy;
R2 is hydrogen or halogen;
R3 is hydrogen or halogen;
R4 is hydrogen;
R5 is hydrogen or halogen;
or R4 and R5 are attached to each other and stand for a bond, —CH2-, —CH2-CH2-, —CH═CH—, —CH═CH—CH2-; —CH2-CH═CH—; or —CH2-CH2-CH2-;
R6 and R7 stand independently from each other for H, C1-C6 alkyl optionally substituted by hydroxyl, C3-C6 cycloalkyl optionally substituted by halogen or hydroxy, or halogen;
R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylacrylamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)

methanol (AZD8055); 2-amino-8-[trans-4-(2-hydroxyethoxy)cyclohexyl]-6-(6-methoxy-3-pyridinyl)-4-methylpyrido[2,3-d]pyrimidin-7(8H)-one (PF04691502); and N²-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 264), inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d]pyrimidine.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d]pyrimidine.

In embodiments, a CAR-expressing cell described herein is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

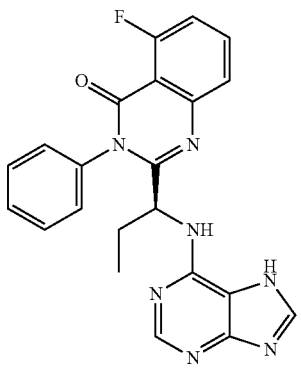 [SMILES: CC[C@H](Nc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

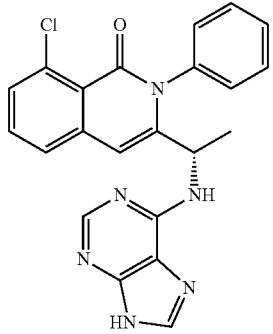 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgV$_H$) gene. In other embodiments, the subject does not comprise a leukemic cell comprising a mutation in the immunoglobulin heavy-chain variable-region (IgV$_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 mg/m² (e.g., 350-375, 375-400, 400-425, 425-450, 450-475, or 475-500 mg/m²), e.g., intravenously.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-N²-[2-isopropoxy-5-methyl-4-(4-piperidinyl)phenyl]-N⁴-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-N²-{4-[4-(dimethylamino)-1-piperidinyl]-2-methoxyphenyl}-N⁴-[2-(dimethylphosphoryl)phenyl]-2,4-pyrimidinediamine. The chemical name of entrectinib is N-(5-(3,5-difluorobenzyl)-1H-indazol-3-yl)-4-(4-methylpiperazin-1-yl)-2-(((tetrahydro-2H-pyran-4-yl)amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present disclosure may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

In embodiments, a CAR-expressing cell described herein is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255)

In embodiments, a CAR-expressing cell described herein is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19 (2013): 1264-72. The structure of BLZ945 is shown below.

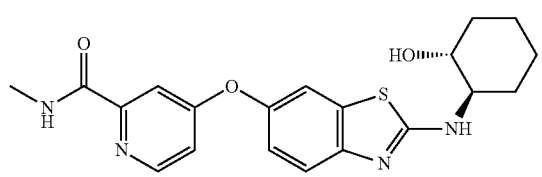 [SMILES: CNC(=O)c1cc(Oc2ccc3nc(N[C@@H]4CCCC[C@H]4O)sc3c2)ccn1]

In embodiments, a CAR-expressing cell described herein is administered to a subject in combination with an agent that inhibits or reduces the activity of immunosuppressive plasma cells. Immunosuppressive plasma cells have been shown to impede T cell-dependent immunogenic chemotherapy, such as oxaliplatin (Shalapour et al., Nature 2015, 521:94-101). In an embodiment, immunosuppressive plasma cells can express one or more of IgA, interleukin (IL)-10, and PD-L1. In an embodiment, the agent is a CD19 CAR-expressing cell or a BCMA CAR-expressing cell.

In some embodiments, a CAR-expressing cell described herein is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In embodiments, a subject having a disease described herein, e.g., a hematological disorder, e.g., AML or MDS, is administered a CAR-expressing cell described herein in combination with an agent, e.g., cytotoxic or chemotherapy agent, a biologic therapy (e.g., antibody, e.g., monoclonal antibody, or cellular therapy), or an inhibitor (e.g., kinase inhibitor). In embodiments, the subject is administered a CAR-expressing cell described herein in combination with a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. CPX-351 is a liposomal formulation comprising cytarabine and daunorubicin at a 5:1 molar ratio. In embodiments, the subject is administered a CAR-expressing cell described herein in combination with a hypomethylating agent, e.g., a DNA methyltransferase inhibitor, e.g., azacitidine or decitabine. In embodiments, the subject is administered a CAR-expressing cell described herein in combination with a biologic therapy, e.g., an antibody or cellular therapy, e.g., 225Ac-lintuzumab (Actimab-A; Actinium Pharmaceuticals), IPH2102 (Innate Pharma/Bristol Myers Squibb), SGN-CD33A (Seattle Genetics), or gemtuzumab ozogamicin (Mylotarg; Pfizer). SGN-CD33A is an antibody-drug conjugate (ADC) comprising a pyrrolobenzodiazepine dimer that is attached to an anti-CD33 antibody. Actimab-A is an anti-CD33 antibody (lintuzumab) labeled with actinium. IPH2102 is a monoclonal antibody that targets killer immunoglobulin-like receptors (KIRs). In embodiments, the subject is administered a CAR-expressing cell described herein in combination a FLT3 inhibitor, e.g., sorafenib (Bayer), midostaurin (Novartis), quizartinib (Daiichi Sankyo), crenolanib (Arog Pharmaceuticals), PLX3397 (Daiichi Sankyo), AKN-028 (Akinion Pharmaceuticals), or ASP2215 (Astellas). In embodiments, the subject is administered a CAR-expressing cell described herein in combination with an isocitrate dehydrogenase (IDH) inhibitor, e.g., AG-221 (Celgene/Agios) or AG-120 (Agios/Celgene). In embodiments, the subject is administered a CAR-expressing cell described herein in combination with a cell cycle regulator, e.g., inhibitor of polo-like kinase 1 (Plk1), e.g., volasertib (Boehringer Ingelheim); or an inhibitor of cyclin-dependent kinase 9 (Cdk9), e.g., alvocidib (Tolero Pharmaceuticals/Sanofi Aventis). In embodiments, the subject is administered a CAR-expressing cell described herein in combination with a B cell receptor signaling network inhibitor, e.g., an inhibitor of B-cell lymphoma 2 (Bcl-2), e.g., venetoclax (Abbvie/Roche); or an inhibitor of Bruton's tyrosine kinase (Btk), e.g., ibrutinib (Pharmacyclics/Johnson & Johnson Janssen Pharmaceutical). In embodiments, the subject is administered a CAR-expressing cell described herein in combination with an inhibitor of M1 aminopeptidase, e.g., tosedostat (CTI Bio-Pharma/Vernalis); an inhibitor of histone deacetylase (HDAC), e.g., pracinostat (MEI Pharma); a multi-kinase inhibitor, e.g., rigosertib (Onconova Therapeutics/Baxter/SymBio); or a peptidic CXCR4 inverse agonist, e.g., BL-8040 (BioLineRx).

In another embodiment, the subjects receive an infusion of the CAR-expressing cell, compositions of the present disclosure prior to transplantation, e.g., allogeneic stem cell transplant, of cells. In a preferred embodiment, CAR expressing cells transiently express a CAR, e.g., by electroporation of an mRNA encoding a CAR, whereby the expression of the CAR is terminated prior to infusion of donor stem cells to avoid engraftment failure.

Some patients may experience allergic reactions to the compounds of the present disclosure and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present disclosure and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present disclosure, can be prepared and administered as described in the art, such as in the documents cited above.

In one embodiment, the present disclosure provides pharmaceutical compositions comprising at least one compound of the present disclosure (e.g., a compound of the present disclosure) or a pharmaceutically acceptable salt thereof together with a pharmaceutically acceptable carrier suitable for administration to a human or animal subject, either alone or together with other anti-cancer agents.

In one embodiment, the present disclosure provides methods of treating human or animal subjects suffering from a cellular proliferative disease, such as cancer. The present disclosure provides methods of treating a human or animal subject in need of such treatment, comprising administering to the subject a therapeutically effective amount of a compound of the present disclosure (e.g., a compound of the present disclosure) or a pharmaceutically acceptable salt thereof, either alone or in combination with other anti-cancer agents.

In particular, compositions will either be formulated together as a combination therapeutic or administered separately.

In combination therapy, the compound of the present disclosure and other anti-cancer agent(s) may be administered either simultaneously, concurrently or sequentially with no specific time limits, wherein such administration provides therapeutically effective levels of the two compounds in the body of the patient.

In a preferred embodiment, the compound of the present disclosure and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present disclosure and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present disclosure, kits that include one or more compound of the present disclosure and a combination partner as disclosed herein are provided. Representative kits include (a) a compound of the present disclosure or a pharmaceutically acceptable salt thereof, (b) at least one combination partner, e.g., as indicated above, whereby such kit may comprise a package insert or other labeling including directions for administration.

A compound of the present disclosure may also be used to advantage in combination with known therapeutic processes, for example, the administration of hormones or especially radiation. A compound of the present disclosure may in particular be used as a radiosensitizer, especially for the treatment of tumors which exhibit poor sensitivity to radiotherapy.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others.

In some embodiments, the subject is administered a vasopressor, such as, e.g., norepinephrine, dopamine, phenylephrine, epinephrine, vasopressin, or a combination thereof.

In an embodiment, the subject can be administered an antipyretic agent. In an embodiment, the subject can be administered an analgesic agent.

Inhibitors of Checkpoint Inhibitors

In one embodiment, the subject can be administered an agent which enhances the activity or fitness of a CAR-expressing cell. For example, in one embodiment, the agent can be an agent which inhibits a molecule that modulates or regulates, e.g., inhibits, immune response of an immune effector cell, e.g., T cell function. In some embodiments, the molecule that modulates or regulates immune response of an immune effector cell, e.g., T cell function, is an inhibitory molecule, also known as a checkpoint inhibitor. Inhibitory molecules, also referred to herein as checkpoint inhibitors, e.g., Programmed Death 1 (PD-1), can, in some embodiments, decrease the ability of a CAR-expressing cell to mount an immune effector response. Examples of inhibitory molecules include PD-1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of a molecule that modulates or regulates, e.g., inhibits, T cell function, e.g., by inhibition at the DNA, RNA or protein level, can optimize a CAR-expressing cell performance. In embodiments, an agent, e.g., an inhibitory nucleic acid, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CAR-expressing cell. In an embodiment, the inhibitor is an shRNA.

In an embodiment, the agent that modulates or regulates, e.g., inhibits, T-cell function is inhibited within a CAR-expressing cell. In these embodiments, a dsRNA molecule that inhibits expression of a molecule that modulates or regulates, e.g., inhibits, T-cell function is linked to the nucleic acid that encodes a component, e.g., all of the components, of the CAR. In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. Configurations of exemplary vectors for expressing a component, e.g., all of the components, of the CAR with a dsRNA molecule that inhibits expression of the molecule that modulates or regulates, e.g., inhibits, T-cell function, is provided, e.g., in FIG. 47 of International Publication WO2015/090230, filed Dec. 19, 2014, which is herein incorporated by reference.

Examples of dsRNA molecules useful for inhibiting expression of a molecule that modulates or regulates, e.g., inhibits, T-cell function, wherein the molecule that modulates or regulates, e.g., inhibits, T-cell function is PD-1 include RNAi agents that target PD-1 are also provided in the section titled "Conditional Expression of Immune-Response Enhancers", in the subsection titled "Agents that Inhibit a Checkpoint Inhibitor". Additional description of such molecules is as described, e.g., in paragraph [00489] and Tables 16 and 17 of International Publication WO2015/090230, filed Dec. 19, 2014, which is incorporated by reference in its entirety.

In one embodiment, the agent that modulates or regulates, e.g., inhibits, T-cell function can be, e.g., an antibody or antibody fragment that binds to an inhibitory molecule. For example, the agent can be an antibody or antibody fragment that binds to PD-1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present disclosure described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/ Roche) is a human Fc optimized IgG1 monoclonal antibody that binds to PD-L. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

In one embodiment, the anti-PD-1 antibody or fragment thereof is an anti-PD-1 antibody molecule as described in US 2015/0210769, entitled "Antibody Molecules to PD-1 and Uses Thereof," incorporated by reference in its entirety. In one embodiment, the anti-PD-1 antibody molecule includes at least one, two, three, four, five or six CDRs (or collectively all of the CDRs) from a heavy and light chain variable region from an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1, or a sequence substantially identical (e.g., at least 80%, 85%, 90%, 92%, 95%, 97%, 98%, 99% or higher identical) to any of the aforesaid sequences; or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/ 0210769, or encoded by the nucleotide sequence in Table 1; or a sequence substantially identical (e.g., at least 80%, 85%, 90%, 92%, 95%, 97%, 98%, 99% or higher identical) to any of the aforesaid sequences.

TIM3 (T cell immunoglobulin-3) also negatively regulates T cell function, particularly in IFN-g-secreting CD4+T helper 1 and CD8+T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In one embodiment, the anti-TIM3 antibody or fragment thereof is an anti-TIM3 antibody molecule as described in US 2015/0218274, entitled "Antibody Molecules to TIM3 and Uses Thereof," incorporated by reference in its entirety. In one embodiment, the anti-TIM3 antibody molecule includes at least one, two, three, four, five or six CDRs (or collectively all of the CDRs) from a heavy and light chain variable region from an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-TIM3 antibody molecule comprises at least one, two, three or four variable regions from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal-.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. J Immunol. 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BM S-986016 (Bristol-Myers Squib) is a monoclonal antibody that targets LAG3. IMP701 (Immutep) is an antagonist LAG3 antibody and IMP731 (Immutep and GlaxoSrnithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO02010/019570.

In one embodiment, the anti-LAG3 antibody or fragment thereof is an anti-LAG3 antibody molecule as described in US 2015/0259420, entitled "Antibody Molecules to LAG3 and Uses Thereof," incorporated by reference in its entirety. In one embodiment, the anti-LAG3 antibody molecule includes at least one, two, three, four, five or six CDRs (or collectively all of the CDRs) from a heavy and light chain variable region from an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420; or encoded by the nucleotide sequence in Table 1; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-LAG3 antibody molecule comprises at least one, two, three or four variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420; or encoded by the nucleotide sequence in Tables 1; or a sequence substantially identical (e.g., at least 80%, 85%, 90%, 92%, 95%, 97%, 98%, 99% or higher identical) to any of the aforesaid sequences.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express a CAR of the present disclosure.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CAR-expressing T cells. The cytokine can be administered simultaneously or concurrently with the CAR-expressing T cells, e.g., administered on the same day. The cytokine may be prepared in the same pharmaceutical composition as the CAR-expressing T cells, or may be prepared in a separate pharmaceutical composition. Alternatively, the cytokine can be administered shortly after administration of the CAR-expressing T cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing T cells, or the first day of the cytokine dosing regimen can be 1 day, 2 days, 3 days, 4 days, 5 days, 6 days, or 7 days after administration of the CAR-expressing T cells. In one embodiment, on the first day, the CAR-expressing T cells are administered to the subject, and on the second day, a cytokine is administered once a day for the next 7 days. In a preferred embodiment, the cytokine to be administered in combination with CAR-expressing T cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CART therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CART therapy can be administered a cytokine. Administration of the cytokine to the subject that has sub-optimal response to the CART therapy improves CART efficacy or anti-tumor activity. In a preferred embodiment, the cytokine administered after administration of CAR-expressing cells is IL-7.

Combination with a Low Dose of an mTOR Inhibitor

In one embodiment, the cells expressing a CAR molecule, e.g., a CAR molecule described herein, are administered in combination with a low, immune enhancing dose of an mTOR inhibitor.

In another embodiment, administration of a low, immune enhancing, dose of an mTOR inhibitor results in increased or prolonged proliferation of CAR-expressing cells, e.g., in culture or in a subject, e.g., as compared to non-treated CAR-expressing cells or a non-treated subject. In embodiments, increased proliferation is associated with in an increase in the number of CAR-expressing cells. Methods for measuring increased or prolonged proliferation are described in Examples 4 and 5. In another embodiment, administration of a low, immune enhancing, dose of an mTOR inhibitor results in increased killing of cancer cells by CAR-expressing cells, e.g., in culture or in a subject, e.g., as compared to non-treated CAR-expressing cells or a non-treated subject. In embodiments, increased killing of cancer cells is associated with in a decrease in tumor volume.

In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

(A)

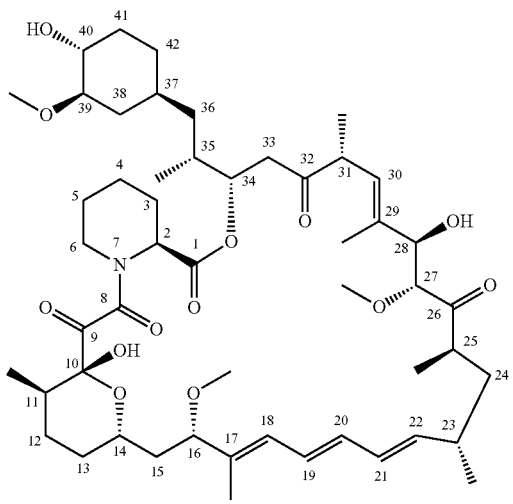

Other suitable rapamycin analogs include, but are not limited to, RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone, sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669).b Other examples of allosteric mTor inhibitors include zotarolimus (ABT578) and umirolimus as described in US2005/0101624 the contents of which are incorporated by reference. Other suitable mTOR inhibitors are described in paragraphs 946 to 964 of International Publication WO2015/142675, filed Mar. 13, 2015, which is incorporated by reference in its entirety. Low, immune enhancing doses of an mTOR inhibitor, suitable levels of mTOR inhibition associated with low doses of an mTOR inhibitor, methods for detecting the level of mTOR inhibition, and suitable pharmaceutical compositions thereof are further described in paragraphs 936 to 945 and 965 to 1003 of International Publication WO2015/142675, filed Mar. 13, 2015, which is incorporated by reference in its entirety.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis*, *Candida albicans*, *Escherichia coli*, *Haemophilus influenza*, *Neisseria meningitides*, *Pseudomonas aeruginosa*, *Staphylococcus aureus*, *Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the immune effector cells (e.g., T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells (e.g., T cells, NK cells) to a subject and then subsequently redraw blood (or have an apheresis performed), activate immune effector cells (e.g., T cells, NK cells) therefrom according to the present invention, and reinfuse the patient with these activated and expanded immune effector cells (e.g., T cells, NK cells). This process can be carried out multiple times every few weeks. In certain aspects, immune effector cells (e.g., T cells, NK cells) can be activated from blood draws of from 10 cc to 400 cc. In certain aspects, immune effector cells (e.g., T cells, NK cells) are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of immune effector cells (e.g., T cells, NK cells) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into immune effector cells (e.g., T cells, NK cells), e.g., using in vitro transcription, and the subject (e.g., human) receives an initial administration of CAR immune effector cells (e.g., T cells, NK cells) of the invention, and one or more subsequent administrations of the CAR immune effector cells (e.g., T cells, NK cells) of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR immune effector cells (e.g., T cells, NK cells) of the invention are administered to the subject (e.g., human) per week, e.g., 2, 3, or 4 administrations of the CAR immune effector cells (e.g., T cells, NK cells) of the invention are administered per week. In one embodiment, the subject (e.g., human subject) receives more than one administration of the CAR immune effector cells (e.g., T cells, NK cells) per week (e.g., 2, 3 or 4 administrations per week) (also referred to herein as a cycle), followed by a week of no CAR immune effector cells (e.g., T cells, NK cells) administrations, and then one or more additional administration of the CAR immune effector cells (e.g., T cells, NK cells) (e.g., more than one administration of the CAR immune effector cells (e.g., T cells, NK cells) per week) is administered to the subject. In another embodiment, the subject (e.g., human subject) receives more than one cycle of CAR immune effector cells (e.g., T cells, NK cells), and the time between each cycle is less than 10, 9, 8, 7, 6, 5, 4, or 3 days. In one embodiment, the CAR immune effector cells (e.g., T cells, NK cells) are administered every other day for 3 administrations per week. In one embodiment, the CAR immune effector cells (e.g., T cells, NK cells) of the invention are administered for at least two, three, four, five, six, seven, eight or more weeks.

In some embodiments, a dose of CAR-expressing cells described herein comprises about $1 \times 10^6$, $1.1 \times 10^6$, $2 \times 10^6$, $3.6 \times 10^6$, $5 \times 10^6$, $1 \times 10^7$, $1.8 \times 10^7$, $2 \times 10^7$, $5 \times 10^7$, $1 \times 10^8$, $2 \times 10^8$, $3 \times 10^8$, or $5 \times 10^8$ cells/kg. In some embodiments, a dose of CAR cells comprises at least about $1 \times 10^6$, $1.1 \times 10^6$, $2 \times 10^6$, $3.6 \times 10^6$, $5 \times 10^6$, $1 \times 10^7$, $1.8 \times 10^7$, $2 \times 10^7$, $5 \times 10^7$, $1 \times 10^8$, $2 \times 10^8$, $3 \times 10^8$, or $5 \times 10^8$ cells/kg. In some embodiments, a dose of CAR cells comprises up to about $1 \times 10^6$, $1.1 \times 10^6$, $2 \times 10^6$, $3.6 \times 10^6$, $5 \times 10^6$, $1 \times 10^7$, $1.8 \times 10^7$, $2 \times 10^7$, $5 \times 10^7$, $1 \times 10^8$, $2 \times 10^8$, $3 \times 10^8$, or $5 \times 10^8$ cells/kg. In some embodiments, a dose of CAR cells comprises about $1.1 \times 10^6$-$1.8 \times 10^7$ cells/kg. In some embodiments, a dose of CAR cells comprises about $1 \times 10^7$, $2 \times 10^7$, $5 \times 10^7$, $1 \times 10^8$, $2 \times 10^8$, $3 \times 10^8$, $5 \times 10^8$, $1 \times 10^9$, $2 \times 10^9$, or $5 \times 10^9$ cells. In some embodiments, a dose of CAR cells comprises at least about $1 \times 10^7$, $2 \times 10^7$, $5 \times 10^7$, $1 \times 10^8$, $2 \times 10^8$, $3 \times 10^8$, $5 \times 10^8$, $1 \times 10^9$, $2 \times 10^9$, or $5 \times 10^9$ cells. In some embodiments, a dose of CAR cells comprises up to about $1 \times 10^7$, $2 \times 10^7$, $5 \times 10^7$, $1 \times 10^8$, $2 \times 10^8$, $3 \times 10^8$, $5 \times 10^8$, $1 \times 10^9$, $2 \times 10^9$, or $5 \times 10^9$ cells.

In some embodiments, a dose of CAR cells comprises up to about $1 \times 10^7$, $1.5 \times 10^7$, $2 \times 10^7$, $2.5 \times 10^7$, $3 \times 10^7$, $3.5 \times 10^7$, $4 \times 10^7$, $5 \times 10^7$, $1 \times 10^8$, $1.5 \times 10^8$, $2 \times 10^8$, $2.5 \times 10^8$, $3 \times 10^8$, $3.5 \times 10^8$, $4 \times 10^8$, $5 \times 10^8$, $1 \times 10^9$, $2 \times 10^9$, or $5 \times 10^9$ cells. In some embodiments, a dose of CAR cells comprises up to about $1$-$3 \times 10^7$ to $1$-$3 \times 10^8$. In some embodiments, the subject is administered about $1$-$3 \times 10^7$ of mesothelin CAR-expressing cells. In other embodiments, the subject is administered about $1$-$3 \times 10^8$ of mesothelin-CAR-expressing cells.

In one aspect, CAR-expressing cells are generated using lentiviral viral vectors, such as lentivirus. CAR-expressing cells generated that way will have stable CAR expression.

In one aspect, CAR-expressing cells transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the immune effector cell, e.g., T cell or NK cell, by electroporation.

A potential issue that can arise in patients being treated using transiently expressing CAR immune effector cells (e.g., T cells, NK cells) (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CAR-expressing cells, e.g., T cells or NK cells, infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: A Camelid Single VHH Domain-Based CAR can be Expressed on a T Cell Surface in Combination with a scFv-Based CAR without Appreciable Receptor Interaction Material and Method:

Jurkat T cells expressing GFP under an NFAT-dependent promoter (NF-GFP) were transduced with either a mesothelin-specific activating CAR (SS1-CAR), CD19-specific activating (19-CAR) or a CAR generated using a camelid VHH domain specific to EGFR (VHH-CAR). Following transduction with the activating CAR, the cells were then transduced with an additional inhibitory CAR recognizing CD19 (19-PD1) to generate cells co-expressing both the activating and inhibitory CAR (SS1+19PD1, 19+19PD1 or VHH+19PD1). The transduced Jurkat T cells were co-cultured for 24 hours with different cell lines that are either 1) devoid of all target antigens (K562), 2) express mesothelin (K-meso), CD19 (K-19) or EGFR (A431) only, 3) express a combination of EGFR and mesothelin (A431-mesothelin) or CD19 (A431-CD19) or 4) express a combination of CD19 and mesothelin (K-19/meso). Additional conditions that include either no stimulator cells (no stim) or K562 with 1 ug/mL of OKT3 (OKT3) were also included as negative and positive controls for NFAT activation, respectively. GFP expression, as a marker of NFAT activation, was assessed by flow cytometry.

Result:

Camels and related species (e.g. Llama) naturally produce antibodies that have a single heavy-chain like variable domain. This domain, known as a camelid VHH domain, has evolved to exist without pairing to a light chain variable domain. It was found that the possibility that two heterologous scFv molecules can dissociate and re-associate with one another when displayed on the surface of a cell as demonstrated by the disruption in scFv binding to cognate ligand during receptor co-expression. The present example showed the expected reduced interaction between a scFv CAR displayed on the surface of a cell in combination with a VHH domain-based CAR. It was found that coexpression of two scFv-based CARs (SS1-z activating CAR and CD19-PD1 inhibitory CAR) on the surface of a Jurkat leads to the inability of the activating CAR (SS1-z) to recognize its cognate ligand on the target cell and trigger T cell activation despite the absence of the inhibitory receptor's ligand. This is consistent with the observed reduced ligand binding on the surface. In contrast, the coexpression of the same inhibitory CAR (CD19-PD1) with a camelid VHH-based activating CAR (VHH-z) has no impact on the ability of the VHH-based activating CAR to recognize its cognate ligand. These data support the model that a VHH-based activating CAR can be expressed with an scFv-based CAR without significant interaction between the receptors due to the reduced ability of the scFv and VHH domains to interact.

Example 2: CART Targeting Folate Receptor-Alpha Expressing Tumor

Folate receptor a (FRA) is over expressed in approximately 90% of ovarian carcinomas, as well as in cancers of the endometrium, kidney, breast, lung, pancreas, colorectal cancer and mesothelioma, and its expression is not affected by prior administration of chemotherapy (see, e.g., Despierre et al., *Gynecol Oncol* 130, 192-199 (2013)). In normal tissues, FRA expression is null or low and restricted to the apical surface of polarized epithelial cells (Kelemen et al., *International journal of cancer* 119, 243-250 (2006)), where it appears to be inaccessible to circulating anti-FR drugs.

CAR-T cell therapy in oncology was first tested in ovarian cancer, where administration of T cells engineered to express an anti-FRA CAR composed of the murine MOv18 scFv and a CD3z endodomain was shown to be feasible but did not induce tumor regression due to the poor persistence of the gene-modified T cells (Kershaw et al, *Clin Cancer Res* 12, 6106-6115 (2006)).

In this example, we constructed a fully human anti-FRA C4 CAR to reduce the risk of potential CAR transgene immunogenicity. Although the binding affinity of the human C4 Fab fragment ($2\times10^7$ M$^{-1}$) is approximately five-fold less than that of the high affinity murine MOv19 antibody (Figini, M. et al. (1998) *Cancer Res* 58, 991-996), it retains its specificity for FRA and its K(d) of <$10^8$ M$^{-1}$ is predicted to confer exclusive activation of CAR upon encounter with tumor cells bearing high amounts of surface FRA. The targeting domain is linked to a combined intracellular CD27 and CD3z signaling chain to further enhance the efficacy of this receptor (referred to hereafter as "C4-27z"). In addition, the C4-27z CAR has reduced activity against normal cells bearing low level antigen and decreases the potential risk of on-antigen, off-tumor toxicity. These results lead to fully human C4 CAR T cell therapy for the safe and effective treatment of a wide spectrum of FRA-expressing malignancies.

Material and Methods

Cell Lines.

Lentivirus packaging was performed in the immortalized normal fetal renal 293T cell line purchased from ATCC. Human cell lines used in immune based assays include the established human ovarian cancer cell lines SKOV3, A1847, OVCAR2, OVCAR3, OVCAR4, OVCAR5, A2780, A2008, C30, and PEO-1. The human lymphoid cell lines SUP-T1 was used for lentivirus titer analysis. For bioluminescence assays, target cancer cell lines were transfected to express firefly luciferase (fLuc). The mouse malignant mesothelioma cell line, AE17 (kindly provided by Steven Albelda, University of Pennsylvania) was used as negative control. All cell lines were maintained in R10 medium: RPMI-1640 supplemented with 10% heat inactivated FBS, 100 U/mL penicillin, 100 mg/mL streptomycin sulfate, 10 mmol/L HEPES).

CAR Construction and Lentivirus Production.

The pHEN2 plasmid containing the anti-FRa C4/AFRA4 scFv kindly provided by Dr. Silvana Canevari (Figini, M. et al. (1998) *Cancer Res* 58, 991-996) was used as a template for PCR amplification of a 729-bp C4 fragment using the following primers: 5'-ata ggatcccagctggtggagtctggggaggc-3' (SEQ ID NO: 263) (BamHI is underlined) and 5'-ata gctagcacctaggacggtcagcttggtccc-3' (SEQ ID NO: 264) (NheI is underlined). Third generation self-inactivating lentiviral expression vectors pELNS previously described were digested with BamHI and NheI and gel purified. The digested PCR products were then inserted into the pELNS vector containing CD3z or CD27-CD3z T cell signaling domains in which transgene expression is driven by the elongation factor-1α (EF-1α) promoter. The resulting construct was designated pELNS-C4-z or C4-27z. High-titer replication-defective lentiviral vectors were produced and concentrated as previously described in Parry, R. V., et al. (2003) *The Journal of Immunology* 171, 166-174. Briefly, 293T cells were seeded in 150 cm$^2$ flask and transfected using Express In (Open Biosystems) according to manufacturer's instructions. Fifteen micrograms of FR-specific CAR transgene plasmid were cotransfected with 7 ug pVSV-G (VSV glycoprotein expression plasmid), 18 ug pRSV.REV (Rev expression plasmid) and 18 ug pMDLg/p.RRE (Gag/Pol expression plasmid) with 174 ul Express In (1 ug/ul) per flask. Supernatants were collected at 24 h and 48 h after transfection, concentrated 10-fold by ultracentrifugation for 2 hours at 28,000 rpm with a Beckman SW32Ti rotor (Beckman Coulter). The viruses were aliquoted into tubes and stored at −80° C. until ready to use for tittering or experiments. All lentiviruses used in the experiments were from concentrated stocks.

Determination of Lentiviral Titer.

Titers of concentrated lentiviral vectors encoding FRA CAR were determined by serially (3-fold) diluting vector preparations in R10 medium and transduce SUP-T1 cells. Briefly, SUP-T1 cells (20,000 cells/100 ul/well) were seeded in a single well of a 96-well plate and 50 ul 3-fold diluted vector supernatant was transferred and incubated overnight. The next day, feed the cells with 100 ul pre-warmed R10 medium. Two days post transduction, vector titers were determined by flow cytometry applying standard flow cytometric methods for analysis of CAR expression. The titers (transducing units [TU]=(% positive/100)×2E4×20× dilution. All the experiments were repeated at least three times and average titers obtained from the experiments were used for data analysis.

Human T Cells and Transfection.

Primary human CD4+ and CD8+ T cells, purchased from the Human Immunology Core at University of Pennsylvania, were isolated from healthy volunteer donors following leukapheresis by negative selection. All specimens were collected under a protocol approved by a University Institutional Review Board, and written informed consent was obtained from each donor. T cells were cultured in R10 medium and stimulated with anti-CD3 and anti-CD28 monoclonal antibodies (mAb)-coated beads (Invitrogen). Eighteen to 24 hours after activation, human T cells were transduced using a spinoculation procedure. Briefly, $0.5\times10^6$ T cells were infected with a multiplicity of infection (MOI) of 2 and 5 of concentrated C4-27z and MOv19-27z vector, respectively. Mixtures of cells and vectors were centrifuged at room temperature for 90 min (2,500 rpm) in a table-top centrifuge (Sorvall ST 40). Human recombinant interleukin-2 (IL-2; Novartis) was added every 2-3 days to a 100 IU/mL final concentration and a cell density of $0.5\times10^6$ to $1\times10^6$ cells/mL was maintained. Once engineered T-cell cultures appeared to rest down, as determined by both decreased growth kinetics and cell-sizing determined using the Multisizer 3 Coulter Counter (Beckman Coulter), the T cells were used for functional analysis.

Flow Cytometric Analysis.

The following monoclonal antibodies were used for phenotypic analysis: APC-Cy7 anti-human CD3; FITC antihuman CD4; APC anti-human CD8; PE-anti-human CD45; PE anti-human CD137. 7-Aminoactinomycin D (7-AAD) was used for viability staining. All monoclonal antibodies were purchased from BD Biosciences. In T cell transfer experiments, peripheral blood was obtained via retro-orbital bleeding and stained for the presence of human CD45, CD4, and CD8 T cells. After gating on the human CD45+ population, the CD4+ and CD8+ subsets were quantified using TruCount tubes (BD Biosciences) with known numbers of fluorescent beads as described in the manufacturer's instructions. Tumor cell surface expression of FRa was performed using MOv18 mAb followed by APC-labeled goat anti mouse Ab. T cell surface expression of the both C4 and MOv19 CAR was evaluated using biotin-labeled recombinant FRa protein (R&D Systems, Inc) followed by Streptavidin-APC (eBioscience, Inc.) or biotin-labeled rabbit anti-human IgG and goat anti-Mouse IgG F(ab')$_2$ fragment followed by Streptavidin-APC, respectively. For intracellular cytokine staining, cells were stimulated in culture medium containing phosphomolybdic acid (PMA) (30 ng/mL) (Sigma-Aldrich), ionomycin (500 ng/mL) (Sigma-Aldrich), and monensin (GolgiStop) (1 μL/mL) (BD Biosciences) in a cell incubator with 10% CO2 at 37° C. for 4 h. To determine cytokine production in CAR T cells, cells were cocultured with $FR^{pos}$ ovarian cancer cells for 5 h. After surface markers were stained, cells were fixed and permeabilized using Cytofix/Cytoperm and Perm/Wash buffer (BD Biosciences) according to the manufacturer's instructions. Then cells were stained with fluorescence-conjugated cytokine antibodies including PE anti-human IFN-γ, Pacific blue anti-human TNF-α or FITC anti-human IL-2 before analysis. Flow cytometry was performed with a BD FACSCanto II flow cytometer (BD Biosciences) and flow cytometric data were analyzed with FlowJo version 7.2.5 software (Tree Star, Ashland, Oreg.).

Cytokine Release Assays.

Cytokine release assays were performed by coculture of $1\times10^5$ T cells with $1\times10^5$ target cells per well in triplicate in 96-well flat bottom plates in a 200 ul volume of R10 medium. After 20-24 hours, coculture supernatants were assayed for presence of IFN-γ using an ELISA Kit, according to manufacturer's instructions (Biolegend, San Diego, Calif.). Values represent the mean of triplicate wells.

Cytotoxicity Assays.

For the cell-based bioluminescence assays, $5\times10^4$ firefly Luciferase (fLuc)-expressing tumor cells were cultured with R10 media in the presence of different ratios of transduced T cells with the use of a 96-well Microplate (BD Biosciences). After incubation for ~20 hours at 37° C., each well was filled with 50 uL of DPBS resuspended with 1 ul of D-luciferin (0.015 g/mL) and imaged with the Xenogen IVIS Spectrum. Percent tumor cell viability was calculated as the mean luminescence of the experimental sample minus background divided by the mean luminescence of the input number of target cells used in the assay minus background times 100. All data are represented as a mean of triplicate wells.

CAR T cells ($5\times10^5$) were cocultured with $5\times10^5$ $FR^{pos}$ A1847 cancer cells or $FR^{neg}$AE17 cells in 1 ml in 24-well plate. GolgiStop (BD Biosciences) was added after coculture. Cells were then cultured for an additional 4 h. Cultures were stained for MOv19 or C4 scFv, followed by CD3 and CD8. Permeabilized cells were then stained intracellularly for IFN-g, TNF-a, and IL-2 production. T cells were gated on CD3 and CD8 expression and further analyzed for cytokine expression using a Boolean gate platform to assess all of the possible patterns of cytokine responses.

Xenograft Model of Ovarian Cancer.

All animals were obtained from the Stem Cell and Xenograft Core of the Abramson Cancer Center, University of Pennsylvania. Six to 12-week-old NOD/SCID/γ-chain−/− (NSG) mice were bred, treated and maintained under pathogen-free conditions in-house under University of Pennsylvania IACUC approved protocols. For an established ovarian cancer model, 6 to 12-week-old female NSG mice were inoculated s.c. with $3\times10^6$ SKOV3 fLuc+ cells on the flank on day 0. After tumors become palpable at about 1 month, human primary T cell (CD4+ and CD8+ T cells used were mixed at 1:1 ratio) were activated, and transduced as described above. After 2 weeks T cell expansion, when the tumor burden was ~200-300 mm$^3$, mice were treated with T cells. The route, dose, and timing of T-cell injections is indicated in the individual figure legends. Tumor dimensions were measured with calipers, and tumor volumes calculated using the formula V=½(length×width$^2$), where length is greatest longitudinal diameter and width is greatest transverse diameter. Animals were imaged prior to T cell transfer and about every week thereafter to evaluate tumor growth. Photon emission from fLuc+ cells was quantified using the "Living Image" software (Xenogen) for all in vivo experiments. Tumors were resected immediately after euthanasia approximately 40 days after first T cell dose for size measurement and immunohistochemistry.

For the intraperitoneal model of ovarian cancer, NSG mice were injected i.p. with $5\times10^6$ SKOV3 fLuc+ cells. Twenty days after peritoneal inoculation, mice bearing well-established SKOV3 tumors were divided into groups and treated. Mice were sacrificed and necropsied when the mice became distressed and moribund. To monitor the extent of tumor progression, the mice were imaged weekly or biweekly and body weights of the mice were measured. In all models, 4-5 mice were randomized per group prior to treatment.

Bioluminescence Imaging.

Tumor growth was also monitored by Bioluminescent imaging (BLI). BLI was done using Xenogen IVIS imaging system and the photons emitted from fLuc-expressing cells within the animal body were quantified using Living Image software (Xenogen). Briefly, mice bearing SKOV3 fLuc+ tumor cells were injected intraperitoneally with D-luciferin (150 mg/kg stock, 100 µL of D-luciferin per 10 grams of mouse body weight) suspended in PBS and imaged under isoflurane anesthesia after 5-10 minutes. A pseudocolor image representing light intensity (blue, least intense; red, most intense) was generated using Living Image. BLI findings were confirmed at necropsy.

Statistical Analysis.

The data are reported as means and SD. Statistical analysis was performed by the use of 2-way repeated-measures ANOVA for the tumor burden (tumor volume, photon counts). Student t test was used to evaluate differences in absolute numbers of transferred T cells, cytokine secretion, and specific cytolysis. GraphPad Prism 5.0 (GraphPad Software) was used for the statistical calculations. $P<0.05$ was considered significant.

Results

1. Enhanced Function of the Human C4 CAR Compared to Murine MOv19 CAR In Vitro

Figure 34A:
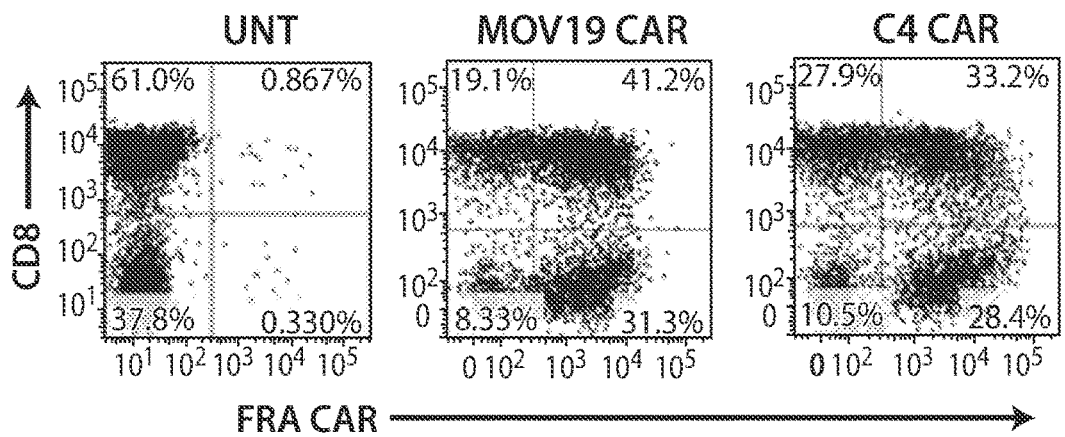
FIGS. 34A, 34B, 34C, 34D, and 34E. Comparison of anti-tumor activity of FR-specific C4 and MOv19 CARs with CD27 costimulatory endodomain in vitro.
Figure 37A:
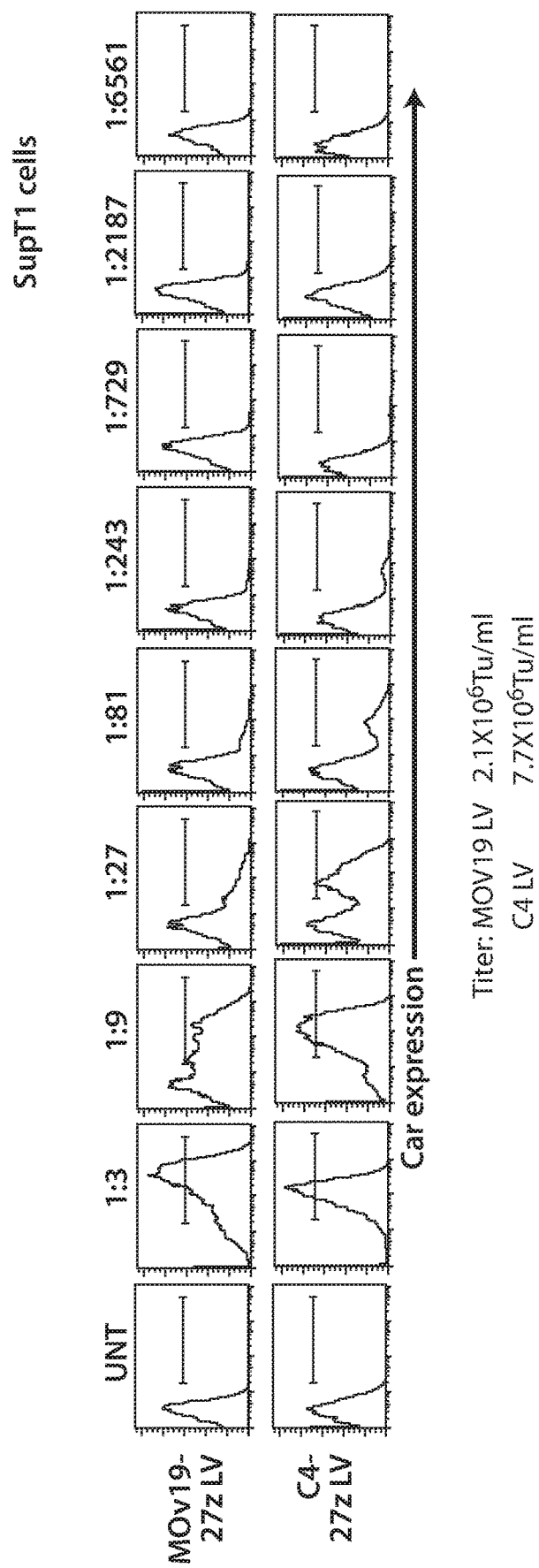
FIGS. 37A and 37B. Fully human C4 CAR is expressed and detected on T cell surface.
Figure 37B:
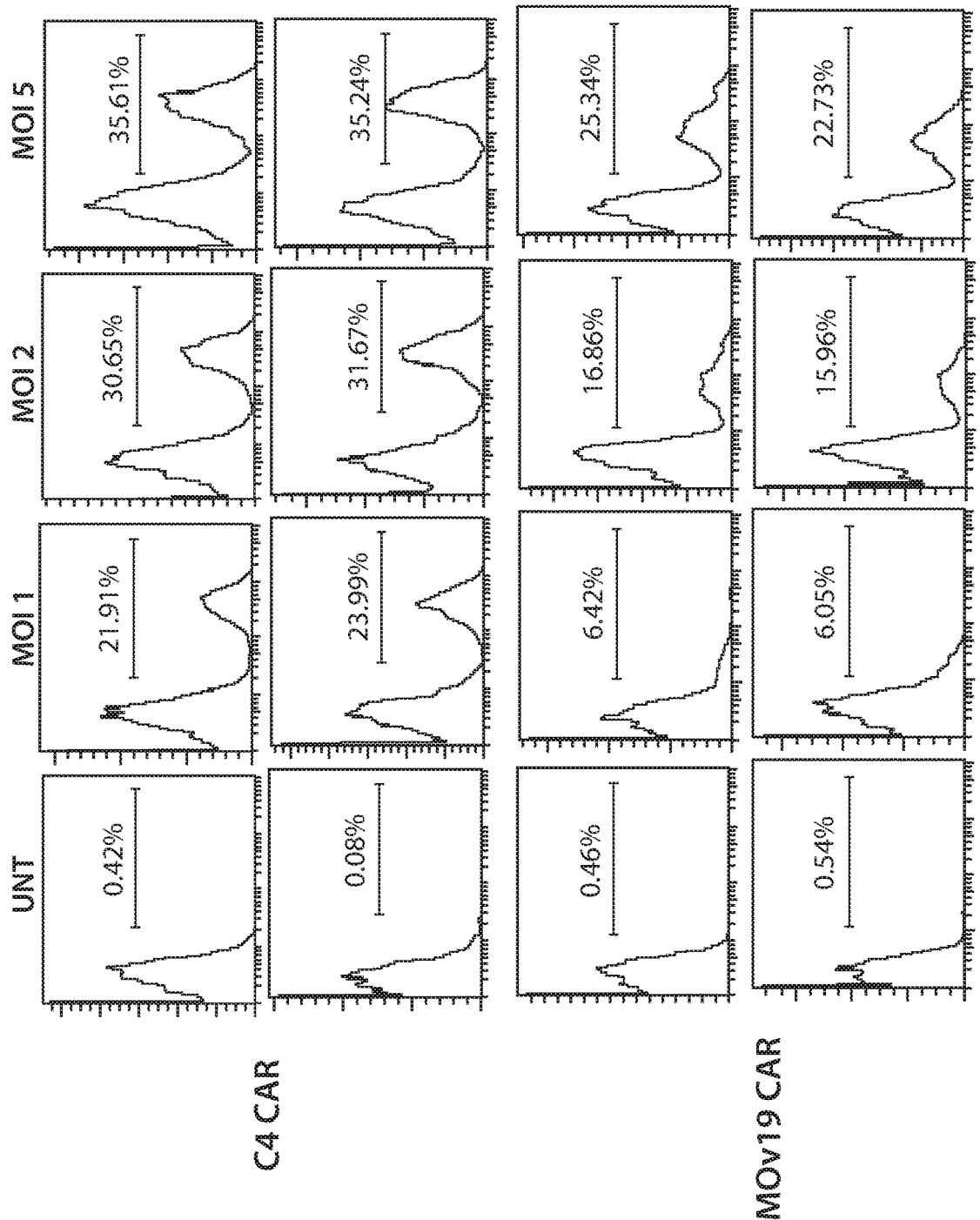

Using the production and concentration protocols described above, we found that the C4 CAR-encoding lentivirus has a higher effective titer than the murine MOv19 CAR, possibly the result of more efficient expression of the human scFv on human T cells (FIG. 37a). Indeed, we observed a multiplicity of infection (MOI) of C4 CAR lentivirus as low as 1 is sufficient to infect >20% human T cells, while the MOv19 CAR lentivirus required a MOI of 5 (FIG. 37b). Thus, for the following experiments, T cells were infected with a MOI of 2 and 5 of concentrated C4-27z and MOv19-27z vector, respectively, and both C4 and MOv19 CAR surface expression on T cells were detected via recombinant FRA protein staining (FIG. 34a).

Figure 34B:
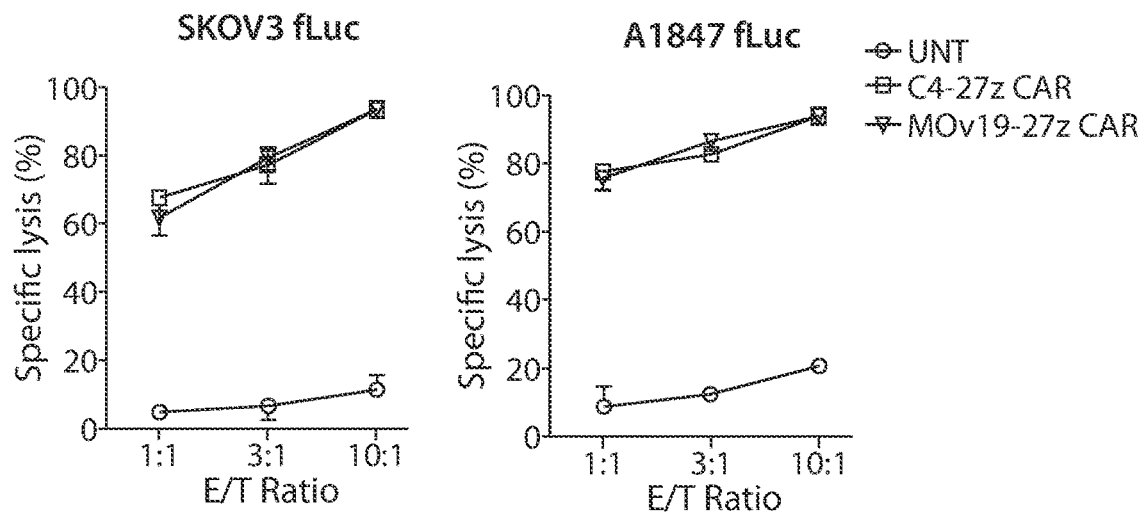
Figure 34C:
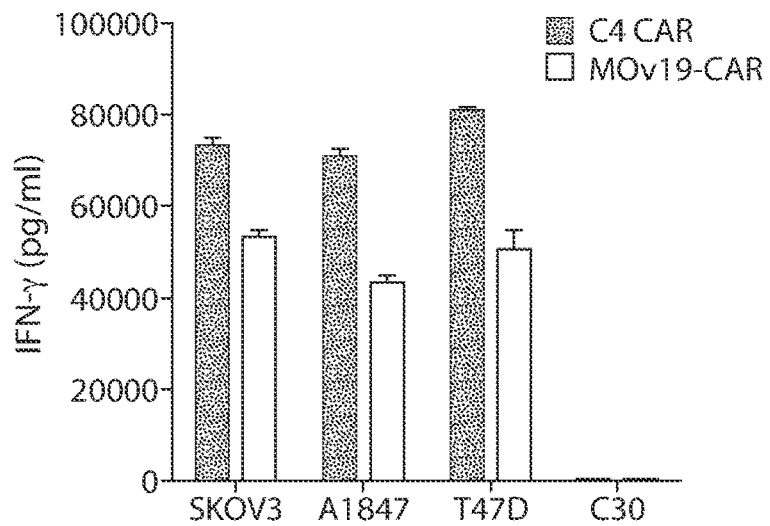
Figure 34D:
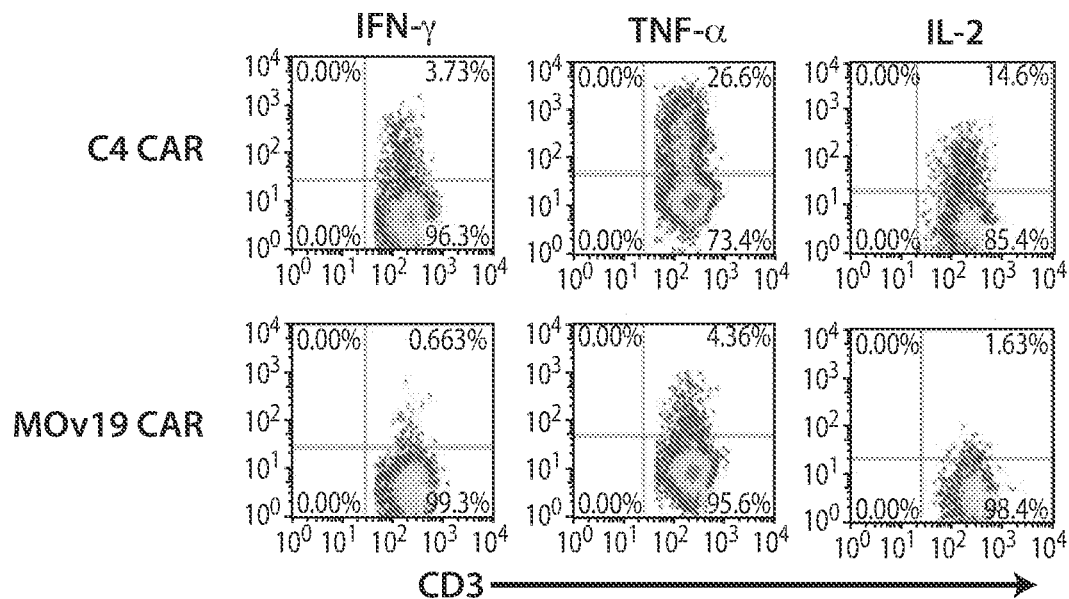
Figure 38A:
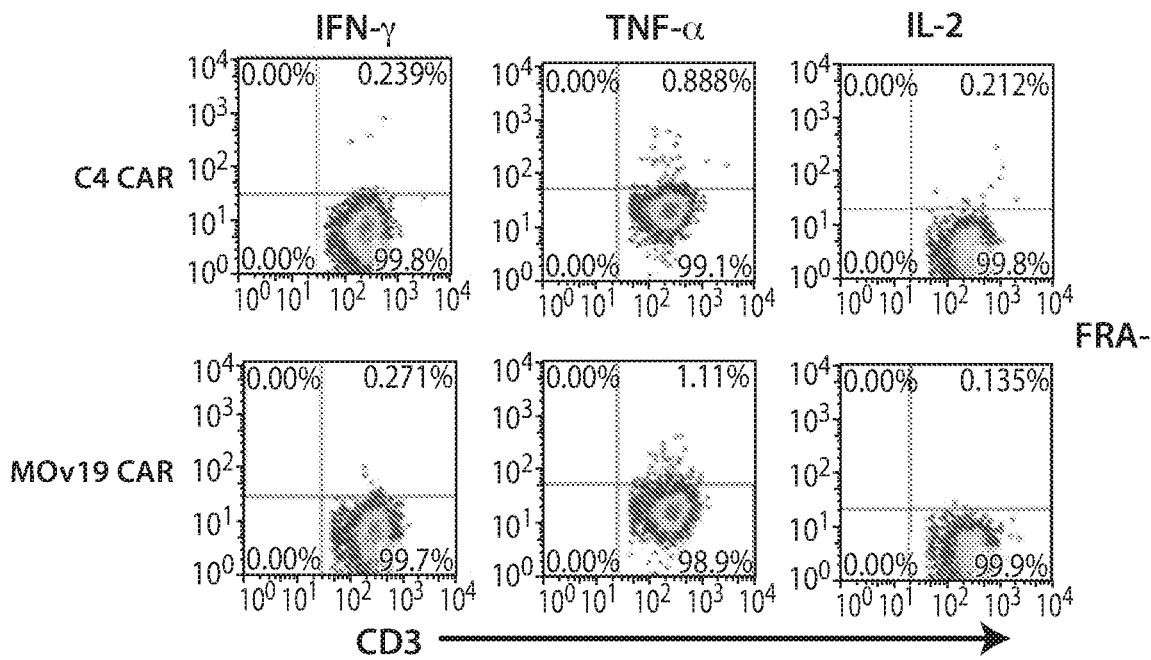
FIGS. 38A, 38B, and 38C. Untransduced T cells were stimulated with FRA+ SKOV3 cells and C4 or MOv19 CAR T cells (FIG. 38A) were stimulated with FRA-C30 cells for 5-hour in the presence of Golgi inhibitor and analyzed by flow cytometry for intracellular IFN-g, TNF-a and IL-2, as compared to untreated cells (FIG. 38B). FRA expression is shown in FIG. 38C.
Figure 38B:
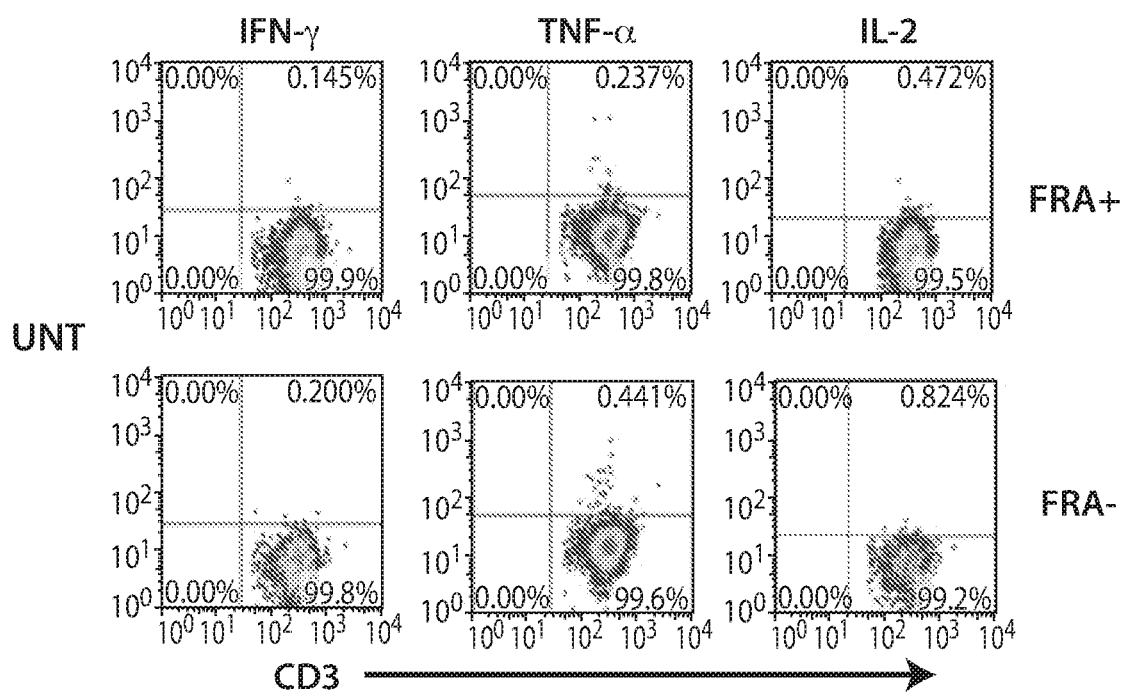
Figure 38C:
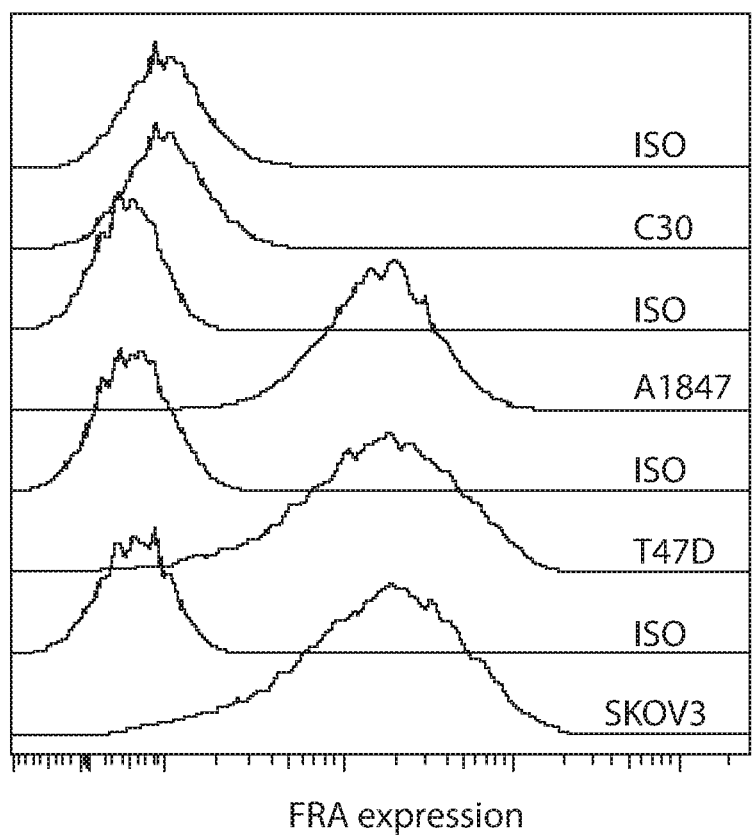

ScFvs used for CAR construction require a minimal antigen affinity to achieve activation threshold for the engineered T cell, however, higher affinity scFvs do not necessarily induce a more potent activation of CAR T cells than low affinity scFvs. Since the binding affinity of the human C4 Fab fragment ($2\times10^7$ $M^{-1}$) is approximately five-fold weaker than that of the murine MOv19, we examined whether the lower affinity of the C4 scFv used to construct the fully human C4 CAR might influence redirected T-cell function via comparison to the MOv19 CAR containing a higher affinity anti-FRA scFv. T cells modified to express either the C4-27z or MOv19-27z CAR specifically lysed $FRA^{pos}$ SKOV3 and A1847 tumor cells with approximately equivalent efficiency in overnight co-cultures (FIG. 34b). However, in vitro cytokine production analysis showed that MOv19-27z CAR T cells secreted significantly less IFN-γ than C4 CAR T cells at an equivalent 1:1 E:T ratio after overnight co-culture (FIG. 34c). This result was validated by 5-hour intracellular cytokine production assays. Representative fluorescence activated cell sorter (FACS) plots of 5-hour intracellular cytokine expression by tumor-activated CAR T cells show that both C4 and MOv19 CAR T cells produce IFN-γ, TNF-α and IL-2 cytokines when incubated overnight with $FRA^{pos}$ SKOV3 ovarian cancer cells, but MOv19 CAR T cells produced less of these cytokines than C4 CAR T cells (FIG. 34d). The frequency of C4 CAR T cells expressing cytokine was 5.6-fold higher for IFN-γ, 6.1-fold for higher TNF-α and 9-fold higher for IL-2, than that observed in MOv19 CAR T cells in vitro. Untransduced T cells cocultured with $FRA^{pos}$ or FRA-negative cancer cells, or CAR T cells cocultured with FRA-negative cancer cells, did not produced proinflammatory cytokines (FIG. 38).

Figure 39A:
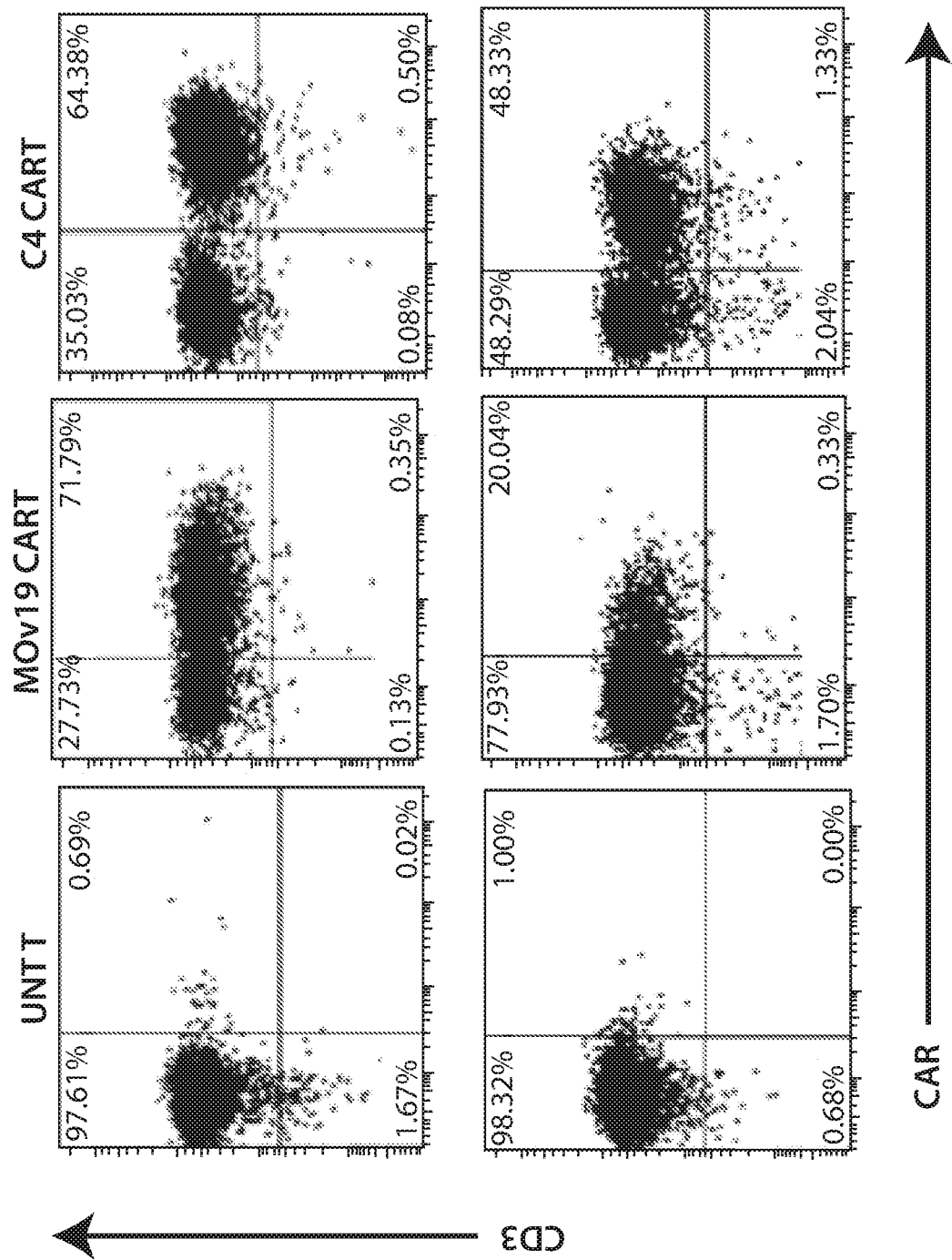
FIGS. 39A, 39B, and 39C. CAR down-modulation may impair the antitumor activity of MOv19 CAR but not C4 CAR. C4 and MOv19 CAR T cells were stimulated with SKOV3 or C30 cells for 5-hour in the presence of Golgi inhibitor and analyzed by flow cytometry for T cell surface of CAR expression and intracellular IFN-g, TNF-α and IL-2.
Figure 39B:
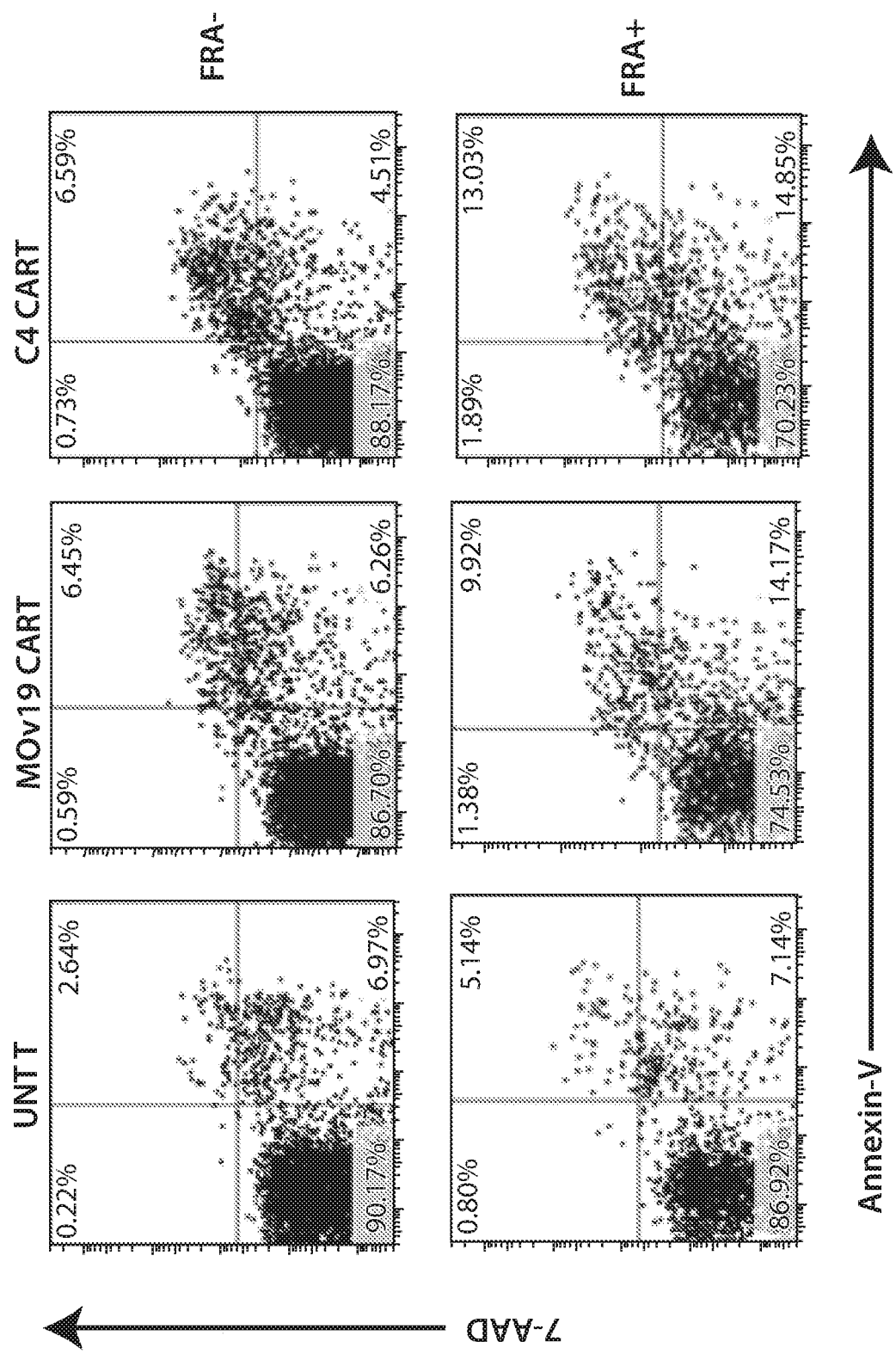
Figure 39C:
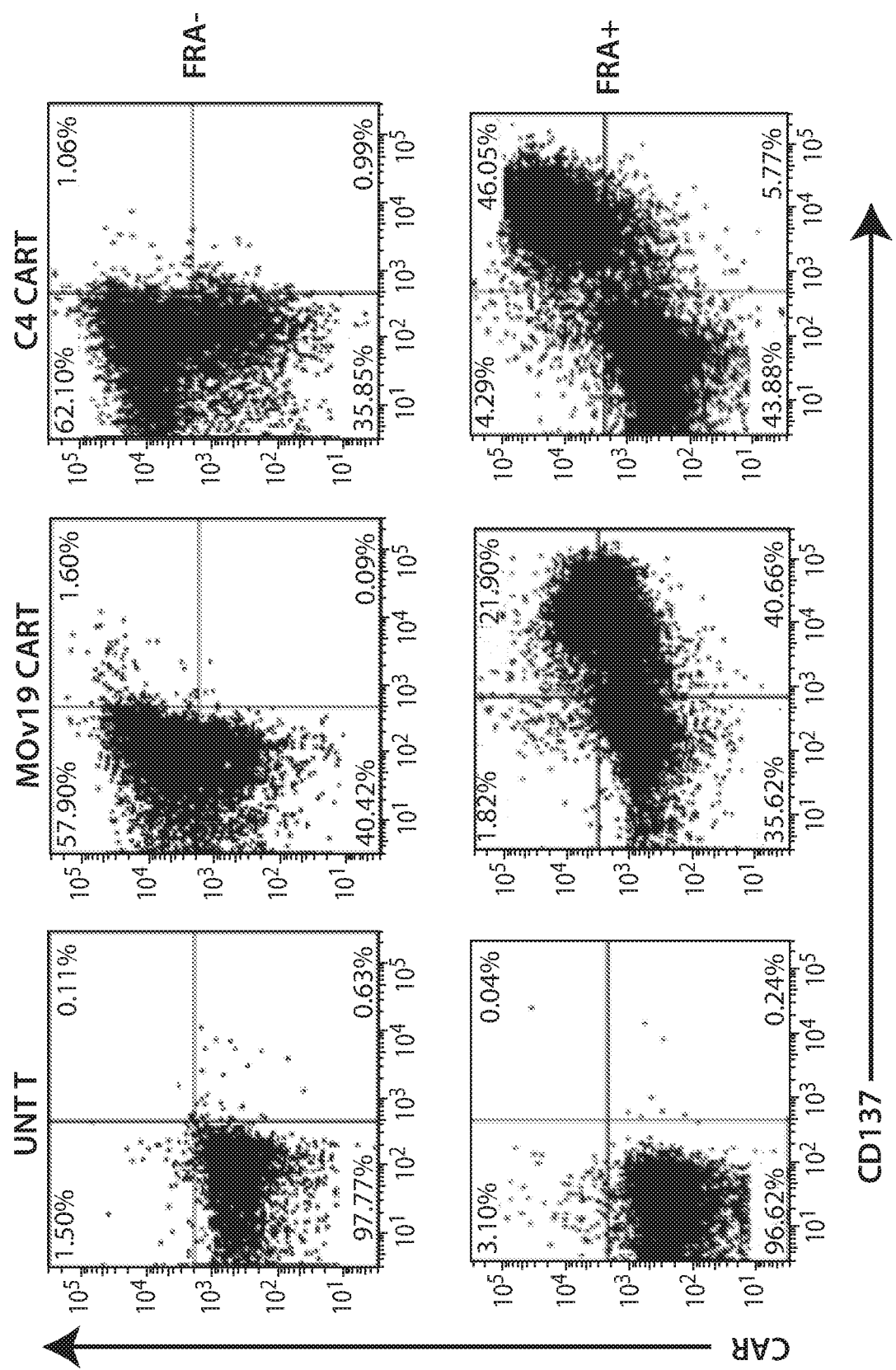

The results in vitro suggested that C4 CAR T cells with an intermediate affinity for FRA may be functionally superior to MOv19 CAR T cells with a higher affinity scFv. To understand the mechanisms accounting for reduced function by high affinity MOv19 CAR T cells, we carefully analyzed CAR expression on T cells after co-incubation with antigen-expressing tumor cells. Stimulation with SKOV3 cancer cells, which express a high level of FRA, induced a rapid and marked down-modulation of surface MOv19 CAR expression following antigen engagement (FIG. 39). Five hours after exposure to tumor cells, MOv19 CAR frequency was rapidly down-modulated from about 65% of T cells to ~1%. This finding was also confirmed by using $FRA^{pos}$ A1847 cells and breast cancer cell line T47D, which also express high levels of FRA (data not shown). By comparison, the C4 CAR was not markedly down-modulated (FIG. 39). Intracellular cytokine expression analysis showed that T cells with maintained C4 CAR surface expression produced IFN-γ, TNF-α and IL-2, while cytokine production was exclusively detected in the CAR-negative fraction of the MOv19 group, indicating that CAR down-modulation and cytokine production had occurred following antigen encounter.

There was a similar frequency of Annexin V+/7-AAD+ as measured by apoptosis staining in T cells modified with C4 compared with MOv19-CARs after stimulation with SKOV3 cells, respectively. CARs with CD28 domain had lower AICD compared with 4-1BB (R12: 16.4%/18.4% vs. 2A2 38.1%/39.6%).

Figure 34E:
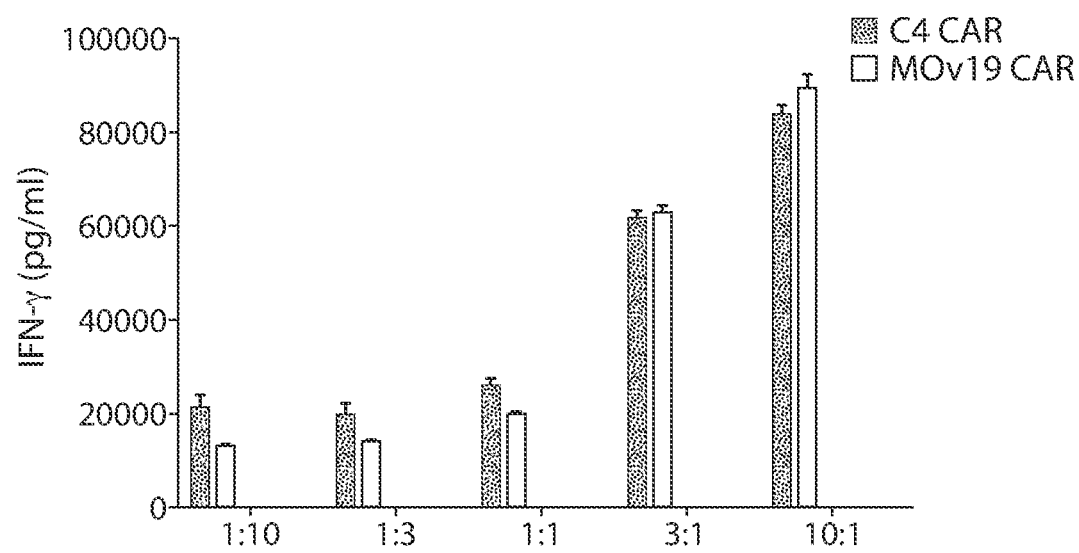
Figures 1, 40:
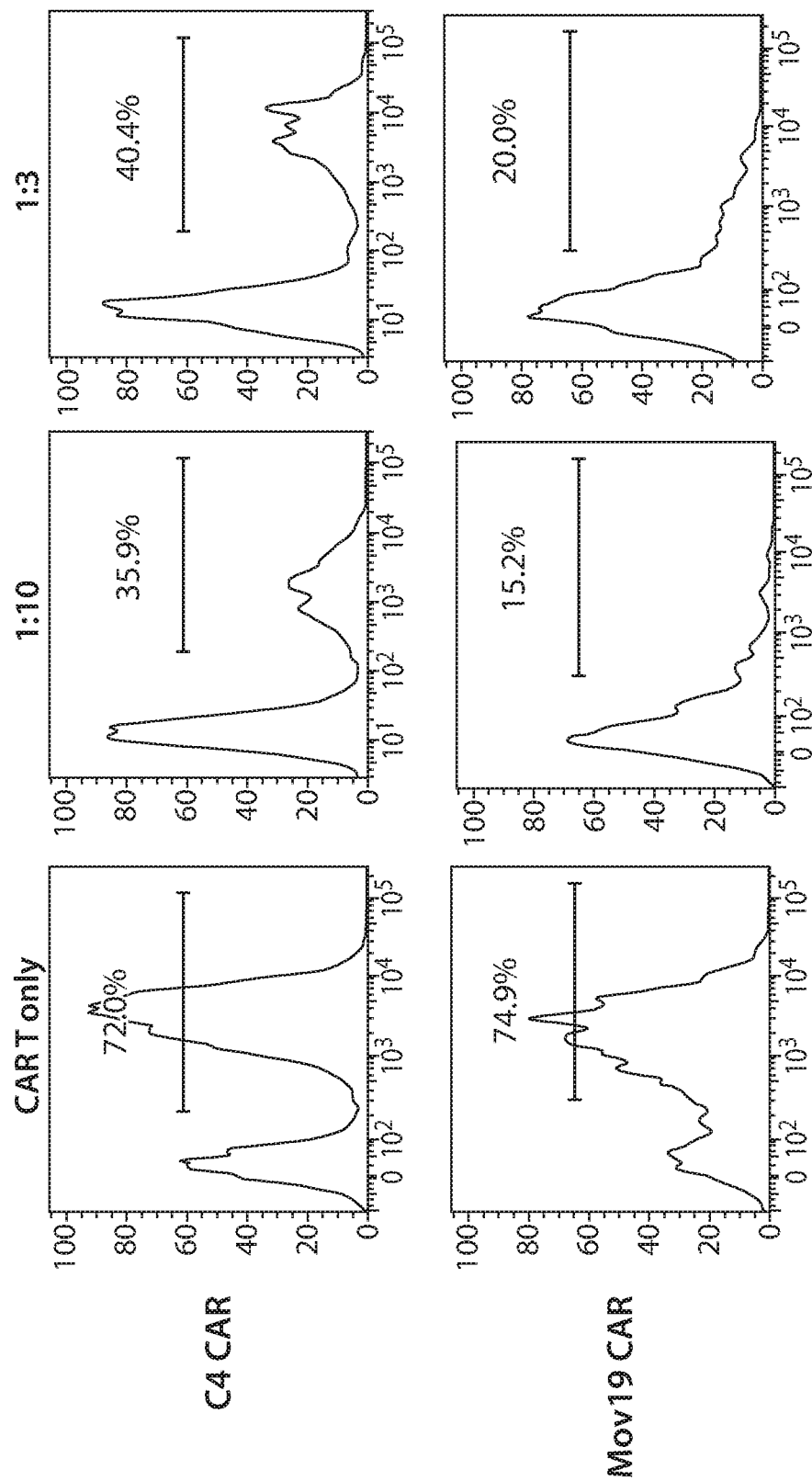
FIG. 40. Flow cytometry analysis of CAR expression changes after overnight co-culture with FRA+ tumor cells (at 1:10, 1:3, 1:1, 3:1 and 10:1 ratios).
Figures 2, 40:
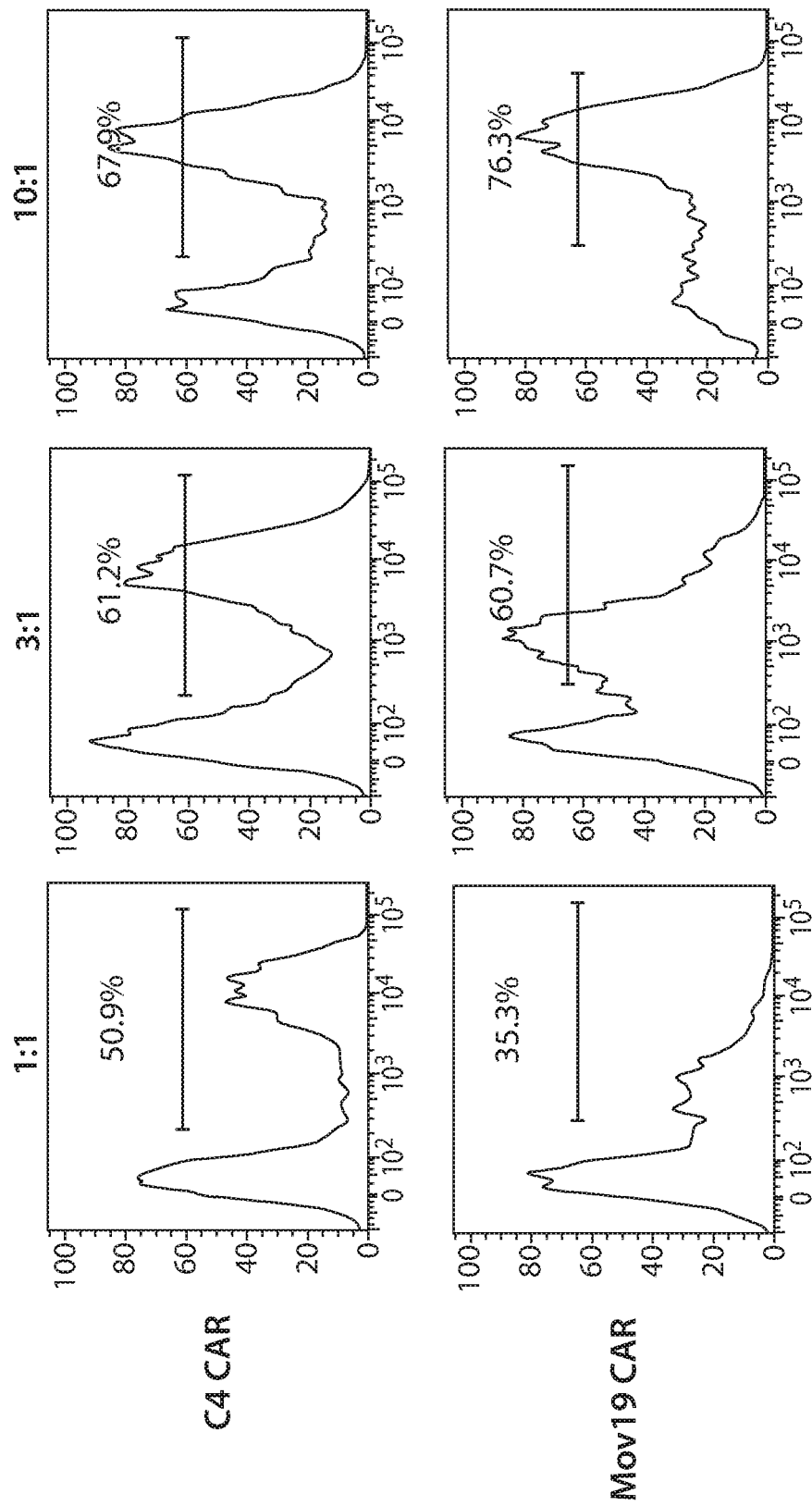

Overall avidity between CAR and target molecule may account for this observed difference in CAR expression. We evaluated the impact of T cell to target cell ratio on relative CAR expression by C4 or MOv19 CAR T cells following co-culture with SKOV3 cells. At lower E:T ratios of 1:10, 1:3 and 1:1, MOv19 CAR T cells showed a marked, dose-dependent down-modulation in CAR expression compared with C4 CAR, which maintained ~50% of initial CAR expression at the lowest E:T ratio tested. However, at high E:T ratios of 3:1 and 10:1 where tumor antigen is more limiting, T cells bearing either C4 or MOv19 CAR maintained high CAR expression (FIG. 40). Consistent with changes in CAR expression after antigen stimulation, C4 CAR T cells released more IFN-γ than MOv19 CAR T cells at E:T ratios of 1:10, 1:3 and 1:1, but similar amounts at E:T ratios of 3:1 and 10:1 (FIG. 34e). Thus, CAR down-modulation occurs in an antigen dose-dependent fashion with anti-FRA CAR T cells bearing the high affinity MOv19 scFv being more sensitive to low antigen level.

2. Comparable Antitumor Activity of C4 and MOv19 CAR T Cells In Vivo

Figure 35A:
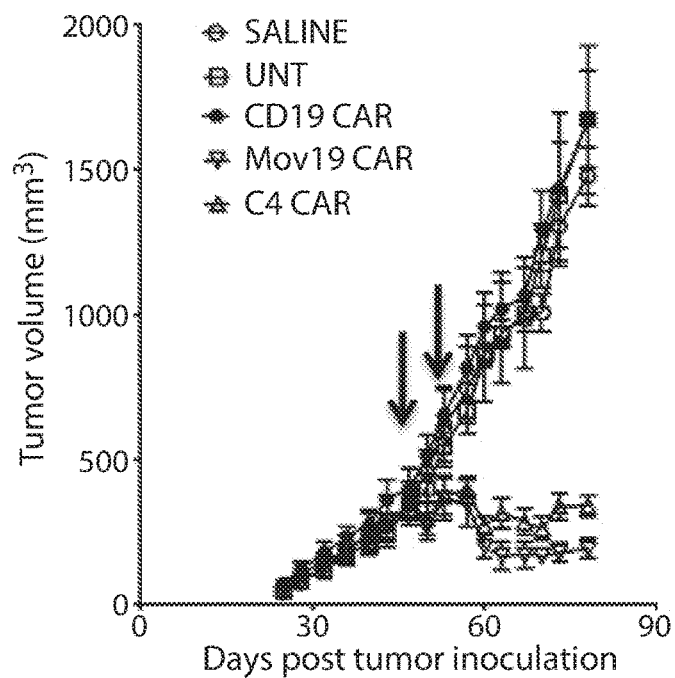
FIGS. 35A, 35B, 35C, and 35D. Antitumor activity of C4-CAR T cells is comparable to MOv19 CAR T cells.
Figure 35B:
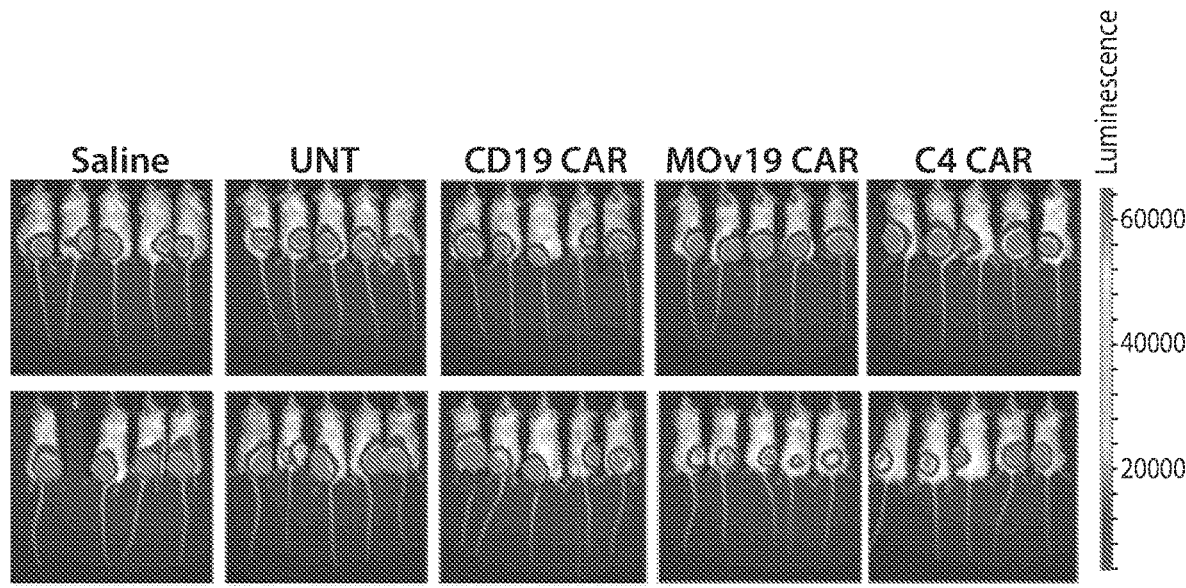
Figure 35C:
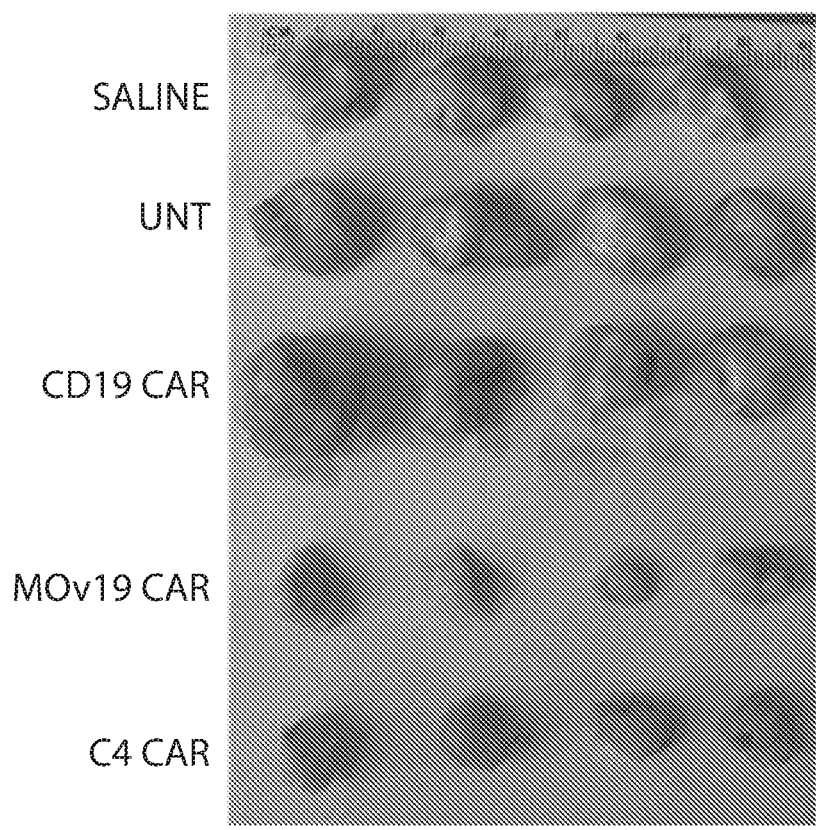
Figure 35D:
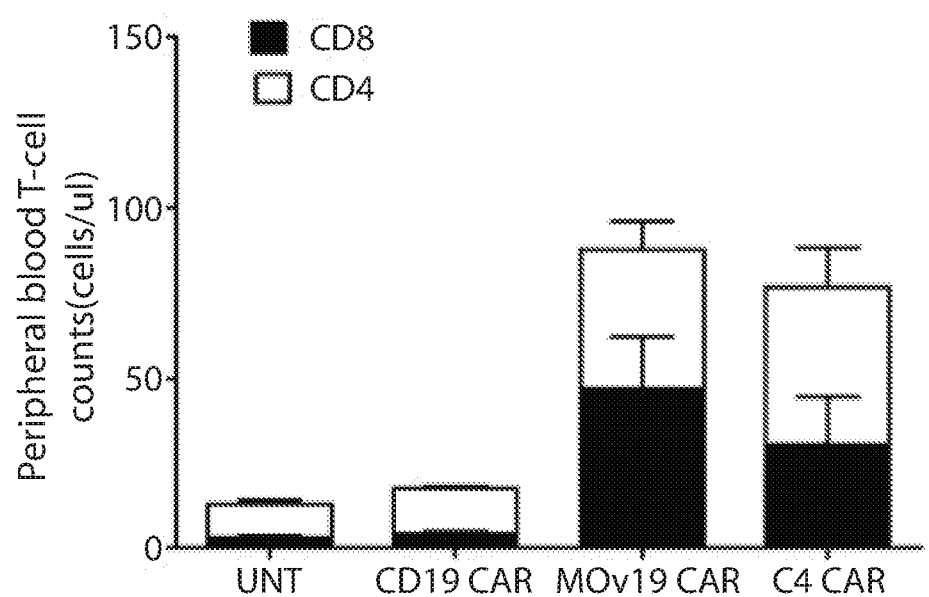

To compare the antitumor capacity of C4 CAR T cells with MOv19 CAR T cells in vivo, NSG mice with large, established subcutaneous SKOV3 tumors (~300 $mm^3$) received intravenous injections of $10^7$ CAR+ T cells on days 40 and 47 post-tumor inoculation. Tumors in animals treated with saline, untransduced T cells or CD19-27z CAR T cells continued to grow rapidly. In contrast, mice receiving C4-27z or MOv19-27z CAR T cells experienced tumor regression (p<0.0001), compared with all 3 control groups at the latest evaluated time point. The antitumor activity of MOv19-27z CAR T cells appeared slightly better than that of C4-27z CAR T cells, but not at a significant level (p=0.058; FIG. 35a). BLI of tumor xenografts before and 3 weeks after T cells injection showed progressive growth of tumors in all animals receiving control T cells but not in CAR T cells groups (FIG. 35b). Tumor BLI results were consistent with the size of resected residual tumors (FIG. 35c). Next, we analyzed the persistence of transferred T-cells in the peripheral blood 3 weeks following adoptive transfer and detected higher numbers of CD4+ and CD8+ T cells in mice treated with both the C4 and MOv19 CAR T cells groups compared with the UNT and CD19-27z CAR T cells treatment group (FIG. 35d), suggesting that tumor antigen recognition drives the survival of the adoptively transferred T cells in vivo. These results demonstrated that the anti-tumor activity of C4 CAR are comparable to MOv19 CAR which was well described previously (see, e.g., Song et al., *Blood* 119, 696-706 (2012); Song et al., *Cancer Res* 71, 4617-4627 (2011)) and confirm that the C4 CAR, despite its decreased affinity, is suitable for in vivo application.

Figure 36A:
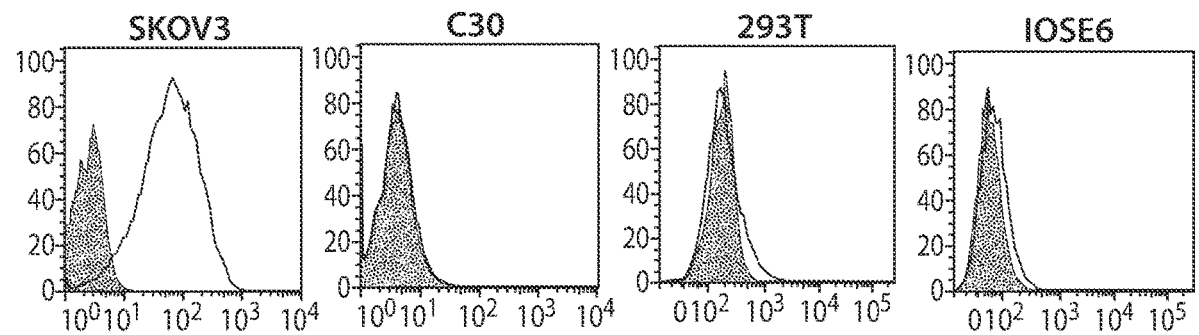
FIGS. 36A, 36B, and 36C. C4 CAR T cells showed minimal cytotoxic activity in vitro.
Figure 36B:
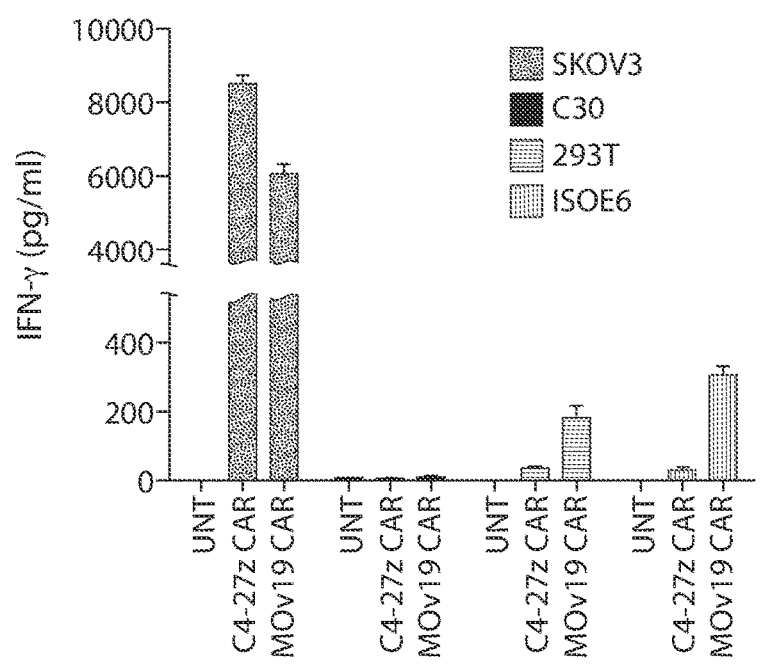
Figures 1, 36C:
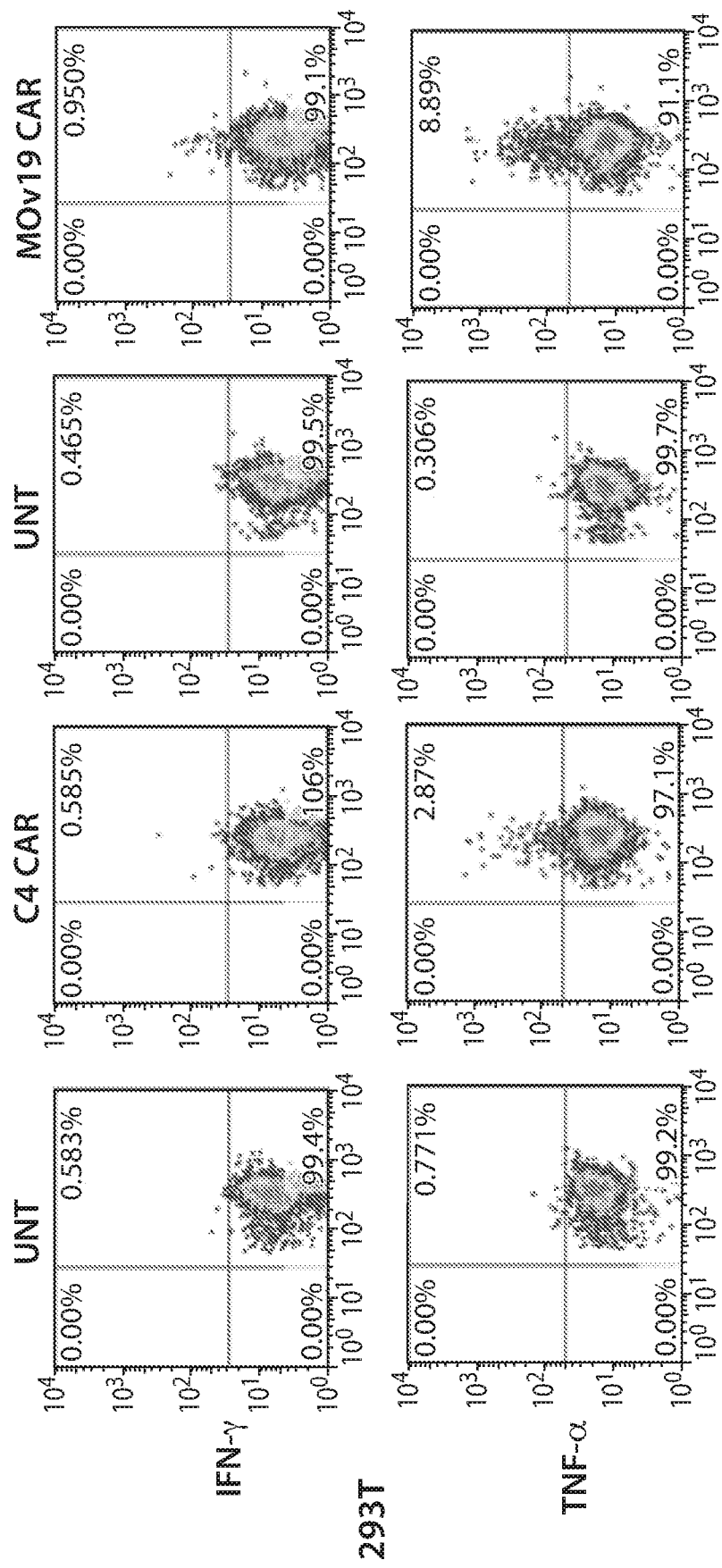
Figures 2, 36C:
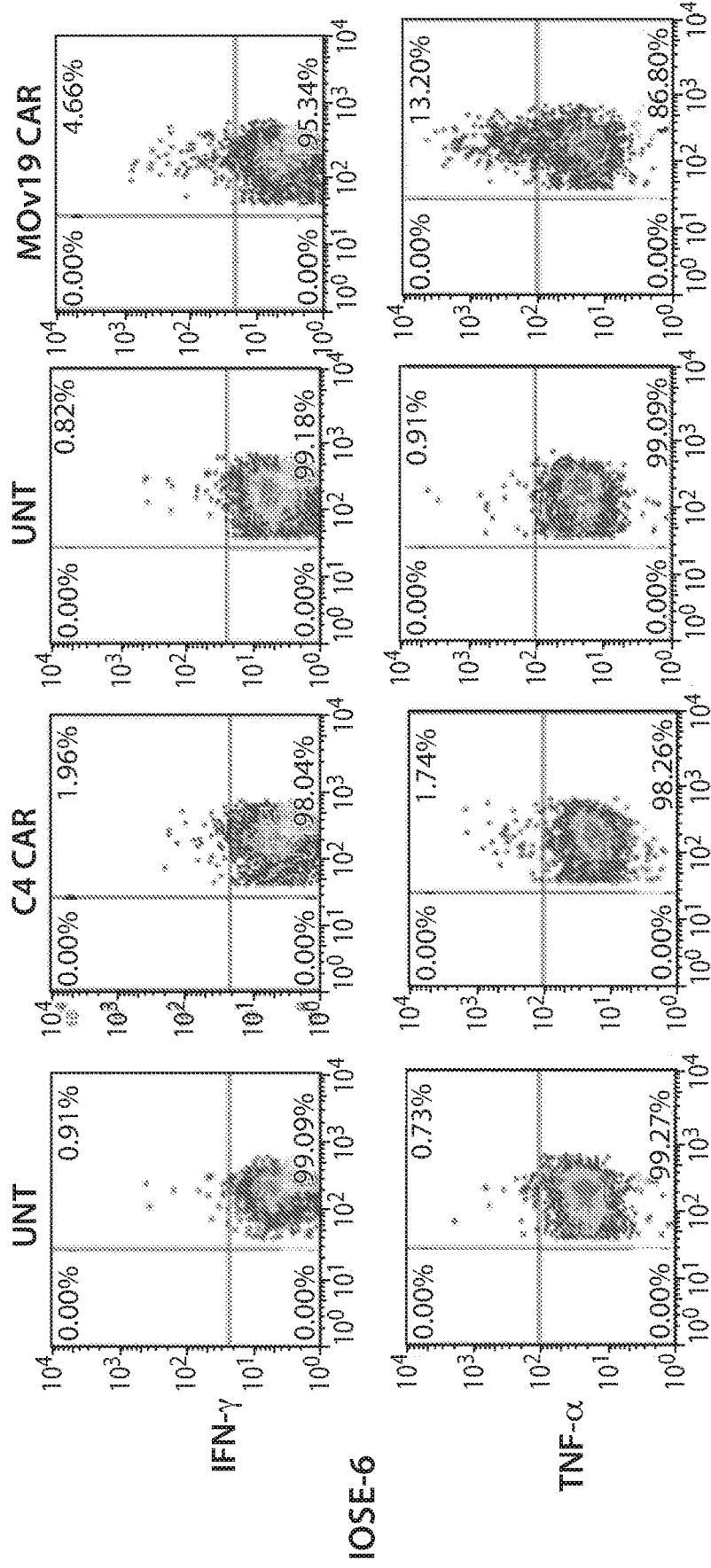

3. Anti-FRA CAR with Lower Affinity May Decrease the Risk of "On-Target" Toxicity On-target toxicities have been observed in clinical trials with CAR T-cells specific for tumor associated antigens that are expressed at low levels on normal cells, and a critical issue to be addressed is whether CARs with higher affinity may increase the risk of toxicity. To investigate the functional effect of primary human T cells modified with C4 CAR and MOv19 CAR on normal cells expressing low levels of FRA, we analyzed cytokine production of C4 CAR and MOv19 CAR T-cells after co-culture with human embryonic kidney 293T cells or normal epithelial ovarian cell line IOSE 6, which express low but detectable levels of FRA, and $FRA^{pos}$ SKOV3 cells (FIG. 36a). C4 and MOv19 CAR T cells responded against SKOV3 with greater activity observed again from C4 CAR T cells. However, greater IFN-γ cytokine production was observed from the MOv19 CAR T cells in response to low antigen expressing cells, suggesting that MOv19 CAR T cells are more functionally avid and sensitive to low antigen (FIG. 36b). Similar to what we observed in overnight IFN-γ release assays, 5-hour intracellular cytokine secretion assays showed that more MOv19 CAR T cells produced IFN-γ and TNF-α in response to low antigen on normal cells (FIG. 36c), which is one primary proposed contributors to the "on-target" cytokine storm, as compared with C4 CAR T cells. These data suggest that the new described C4 CAR may have a more appropriate affinity for the delivery of safe and effective engineered T cell therapy.

Conclusion:

The decreased affinity of the fully human C4 scFv selected for designing a CAR could affect T-cell recognition. However, a direct comparison of cytokine production after tumor engagement by T cells modified with the C4 and MOv19 CARs showed that the C4 CAR with lower affinity was superior at an E/T ratio of 1:1. It may be due to the rapid internalization of MOv19 CAR with higher affinity encountering with high levels of antigen. When we increase the E/T ratios, the anti-tumor activity of C4 CAR T cells is comparable to MOv19 CAR T cells. To further compare the antitumor activity in vivo, we found that T cells expressing the high-affinity MOv19 CAR mediated slightly superior activity in vivo compared with the C4 CAR. However, this difference is not statistically significant, suggesting that the affinity of C4 CAR is adequate for in vivo application.

Possible on-target, off-tumor toxicities resulting from the expression of TAAs on normal tissues need to be considered in the application of CAR approach. The development of high affinity CAR or TCR with great anti-tumor activity can lead to severe toxicity. Our study showed that C4 CAR T cells release minimal cytokine compared with MOv19 CAR T cells when encountering with normal cells expressing low levels of FRA. Thus, the relative lower affinity C4 CAR could decrease the risk of on-target toxicity, while the higher affinity MOv19 CAR could increase this risk in vivo.

Example 3: Decreasing the Affinity of CAR Increases Therapeutic Efficacy

Adoptive cell therapy (ACT) with CAR engineered T cells can target and kill widespread malignant cells thereby inducing durable clinical responses in treating some hematopoietic malignancies (Kochenderfer, J. N., et al. (2010) *Blood* 116:4099-4102; Porter, D. L., et al. (2011) *N Engl J Med* 365:725-733; and Brentjens, R. J., et al. (2013) *Sci Transl Med* 5:177ra138). However, many commonly targeted tumor antigens are also expressed by healthy tissues and on target off tumor toxicity from T cell-mediated destruction of normal tissue has limited the development and adoption of this otherwise promising type of cancer therapy. Recent reports on severe adverse events associated with treatment of cancer patients with CAR- or TCR-engineered T lymphocytes further illustrate the critical importance of target selection for safe and efficient therapy (Lamers et al., 2006, *J Clin Oncol.* 24:e20; Parkhurst et al., 2011, *Molecular therapy: the journal of the American Society of Gene Therapy.* 19:620-6; Morgan et al., 2013, *J Immunotherapy.* 36:133-151; Linette et al., 2013, *Blood.* 122:863-71). In specific, the targeting of ErbB2 (Her2/neu or CD340) with high affinity CARTs led to serious toxicity due to target recognition on normal cardiopulmonary tissue (Morgan et al., 2013, *Mol Therapy.* 18:843-851), and similarly, the presence of relatively high levels of EGFR in healthy skin leads to dose-limiting skin toxicity (Perez-Soler et al., 2010, *J Clin Oncol.* 23:5235-46).

Selecting highly tissue-restricted antigens, cancer testis antigens, mutated gene products or viral proteins as targets could significantly improve the safety profile of using CART cells. However, none of these antigens is present with high frequency in common cancers, constitutively expressed exclusively by malignant cells, functionally important for tumor growth, and targetable with CART. Most of the top-ranked target antigens that could be targeted by CART are expressed in potentially important normal tissues, such as ErbB2, EGFR, MUC1, PSMA, and GD2 (Cheever et al., 2009, *Clinical Cancer Research.* 15:5323-37). Current strategies for generating CARs consist of selecting scFv with high affinity, as previous studies have shown that the activation threshold inversely correlated with the affinity of the scFv (Chmielewski et al., 2004, *J Clin Oncol.* 173:7647-53; and Hudecek et al., 2013, *Clinical Cancer Research.* 19:3153-64. Studies indicate that the costimulatory domain of CARs does not influence the activation threshold (Chmielewski et al., 2011, *Gene Therapy.* 18:62-72). After TCR stimulation there is a narrow window of affinity for optimal T cell activation, and increasing the affinity of the TCRs does not necessarily improve treatment efficacy (Zhong et al., 2013, *Proc Natl Acad Sci USA.* 110:6973-8 and Schmid et al., 2010, *J Immunol.* 184:4936-46).

In this example, it was determined whether equipping T cells with high affinity scFv may limit the utility of CARs, due to poor discrimination of the CART for tumors and normal tissues that express the same antigen at lower levels. It was also determined whether fine-tuning the affinity of the scFv could increase the ability of CART cells to discriminate tumors from normal tissues expressing the same antigen at lower levels. CARs with affinities against two validated targets, ErbB2 and EGFR, which are amplified or overexpressed in variety of cancers but are also expressed, at lower levels by normal tissues, were tested extensively against multiple tumor lines, as well as primary cell lines from normal tissues and organs. It was found that decreasing the affinity of the scFv could significantly increase the therapeutic index of CARs while maintaining robust antitumor efficacy.

The following materials and methods were used in the experiments described in this example:

Cell Lines and Primary Human Lymphocytes

SK-BR3, SK-OV3, BT-474, MCF7, MDA231, MDA468, HCC2281, MDA-361, MDA-453, HCC-1419, HCC-1569, UACC-812, LnCap, MDA-175, MCF-10A, HCC38 and HG261 cell lines were purchased from American Type Culture Collection and cultured as instructed. Seven primary cell lines (keratinocytes, osteoblast, renal epithelial, pulmonary artery endothelial cells, pulmonary artery smooth muscle, neural progenitor, CD34+ enriched PBMC) were obtained from Promocell and cultured according to their protocols. Primary lymphocytes were isolated from normal donors by the University of Pennsylvania Human Immunology Core and cultured in R10 medium (RPMI 1640 supplemented with 10% fetal calf serum; Invitrogen). Primary lymphocytes were stimulated with microbeads coated with CD3 and CD28 stimulatory antibodies (Life Technologies, Grand Island, N.Y., Catalog) as described (Barrett et al., 2009, Proc Nat Acad Sci USA, 106:3360). T cells were cryopreserved at day 10 in a solution of 90% fetal calf serum and 10% dimethylsulfoxide (DMSO) at $1 \times 10^8$ cells/vial.

Generation of CAR Constructs for mRNA Electroporation and Lentiviral Transduction.

CAR scFv domains against ErbB2 or EGFR were synthesised and/or amplified by PCR, based on sequencing information provided by the relevant publications (Carter et al., 1992, Proc Nat Acad Sci USA, 89:4285; Zhou et al., 2007, J Mol Bio, 371:934), linked to CD8 transmembrane domain and 4-1BB and CD3Z intracellular signaling domains, and subcloned into pGEM.64A RNA based vector (Zhao et al., 2010, Cancer Res, 70:9053) or pTRPE lentiviral vectors (Carpenito et al., 2009, Proc Nat Acad Sci USA, 106:3360.

Biacore Assay

Biotinylated ErbB2 was mobilized to a streptavidin coated sensor chip at a density of 200 RU. Binding affinity of the parental 4D5 antibody (Carter et al., 1992, Proc Nat Acad Sci USA, 89:4285) were compared to recombinant scFv. The purity and atomic mass of the scFv were verified by liquid chromatography-mass spectrometry. ScFv samples were serial diluted 3-fold and injected over the chip at a constant flow rate. Association and dissociation rates of the protein complex were monitored for 270 s and 400 s, respectively. Double referencing was performed against a blank immobilized flow cell and a buffer blank and the data was fit using a 1:1 Langmuir model or steady state affinity where appropriate with the Biacore T200 evaluation software.

mRNA In Vitro Transcription and T Cell Electroporation

T7 mScript systems kit (CellScript) was used to generate IVT RNA. CD3/CD28 bead stimulated T cells were electroporated with IVT RNA using BTX EM830 (Harvard Apparatus BTX) as previously described (Zhao et al., 2010, Cancer Res, 70:9053). Briefly, T cells were washed three times and resuspended in OPTI-MEM (Invitrogen) at a final concentration of $1-3 \times 10^8$ cells/ml. Subsequently, 0.1 ml of cells were mixed with 10 ug IVT RNA (or as indicated) and electroporated in a 2 mm cuvette.

Flow Cytometry Analysis

Antibodies were obtained from the following suppliers: anti-human CD3 (BD Biosciences, 555335), anti-human CD8 (BD Biosciences 555366), anti-human CD107a (BD Biosciences 555801), anti-human CD137 (BD Biosciences 555956). Cell surface expression of ErbB2 was detected by biotinylated anti-ErbB2 Affibody (Abcam, ab31890), and EGFR by FITC conjugated anti-EGFR affibody (Abcam, ab81872). ErbB2, EGFR and CD19 specific CAR T cell expression were detected by ErbB2-Fc fusion protein (R&D system, 1129-ER), EGFR-Fc fusion protein and biotin-labeled polyclonal goat anti-mouse F(ab)2 antibodies (Jackson Immunoresearch, 115-066-072) respectively, incubated at 4° C. for 25 minutes and washed twice (PBS with 2% FBS). Samples were then stained with PE-conjugated anti-human IgG Fc Ab (eBioscience, 12-4998-82) or phycoerythrin-labeled streptavidin (eBioscience, 17-4317-82), incubated at 4° C. for 25 minutes and washed once. Flow cytometry acquisition was performed on either a BD FacsCalibur or Accuri C6 Cytometer (BD Biosciences). Analysis was performed using FlowJo software (Treestar).

ELISA Assays

Target cells were washed and suspended at $1 \times 10^6$ cells/ml in R10 medium (RPMI 1640 supplemented with 10% fetal calf serum; Invitrogen). 100 ul each target cell type were added in duplicate to a 96 well round bottom plate (Corning). Effector T cells were washed, and resuspended at $1 \times 10^6$ cells/ml in R10 medium and then 100 ul of T cells were combined with target cells in the indicated wells. In addition, wells containing T cells alone were prepared. The plates were incubated at 37° C. for 18 to 20 hours. After the incubation, supernatant was harvested and subjected to an ELISA assay (eBioscience, 88-7316-77; 88-7025-77).

CD107a Staining

Cells were plated at an E:T of 1:1 ($1 \times 10^5$ effectors: $1 \times 10^5$ targets) in 160 µl of complete RPMI medium in a 96 well plate. 20 µl of phycoerythrin-labeled anti-CD107a Ab (BD Biosciences, 555801) was added and the plate was incubated at 37° C. for 1 hour before adding Golgi Stop (2 ul Golgi Stop in 3 ml RPMI medium, 20 ul/well; BD Biosciences, 51-2092KZ) and incubating for another 2.5 hours. Then 5 µl FITC-anti-CD8 and 5 ul APC-anti-CD3 were added and incubated at 37° C. for 30 min. After incubation, the samples were washed with FACS buffer and analyzed by flow cytometry.

CFSE Based T Cells Proliferation Assay

Resting CD4 T cells were washed and suspended at a concentration of $1 \times 10^7$ cells/ml in PBS. Then 120 ul CFSE working solution (25 µM CFSE) was added to $1 \times 10^7$ cells for 3.5 min at 25° C. The labeling was stopped with 5% FBS (in PBS), washed twice with 5% FBS and cultured in R10 with 10 IU/ml IL2. After overnight culture, the CFSE labeled T cells were electroporated with different affinity ErbB2 CAR RNA. Two to four hours after electroporation, T cells were suspended at concentration of $1 \times 10^6$/ml in R10 medium (with 10 IU/ml IL2). Tumor or K562 cell lines were irradiated and suspended at $1 \times 10^6$/mL in R10 medium. Cells were plated at an E:T of 1:1 ($5 \times 10^5$ effectors: $5 \times 10^5$ targets)

in 1 ml of complete RPMI medium in a 48 well plate. T cells were then counted and fed every 2 days from day 3. CFSE dilution was monitored by flow cytometry at day 3, day 5 and day 7.

Luciferase Based CTL Assay.

Nalm6-CBG tumor cells were generated and employed in a modified version of a luciferase based CTL assay as follows: Click beetle green luciferase (CBG) was cloned into the pELNS vector, packaged into lentivirus, transduced into NALM6 tumor cells and sorted for CBG expression. Resulting Nalm6-CBG cells were washed and resuspended at 1×10$^5$ cells/ml in R10 medium, and 100 ul of CBG-labeled cells were incubated with different ratios of T cells (e.g. 30:1, 15:1, etc) overnight at 37° C. 100 □l of the mixture was transferred to a 96 well white luminometer-plate, 100 ul of substrate was added and the luminescence was immediately determined.

Mouse Xenograft Studies

Studies were performed as previously described with certain modifications (Barrett et al., 2011, *Human Gene Therapy*, 22:1575; and Carpenito et al., 2009, PNAS, 106: 336). Briefly, 6-10 week old NOD scid gamma (NSG) mice were injected subcutaneously with 1×10$^6$ PC3-CBG tumors cells on the right flank at day 0 and the same mice were given SK-OV3-CBG tumor cells (5×10$^6$ cells/mouse, s.c.) on the left flank at day 5. The mice were treated with T cells via the tail vein at day 23 post PC3-CBG tumor inoculation such that both tumors were approximately 200 mm$^3$ in volume. Lentivirally transduced T cells were given at 1×10$^7$ cells/mouse (10M), or 3×10$^6$ cells/mouse (3M). RNA electroporated T cells were given at 5×10$^7$ cells/mouse for the 1st treatment, followed by 3 treatments at days 26, 30 and 33 in the dose of 1×10$^7$ RNA electroporated T cells/mouse.

Results

Figures 1, 4:
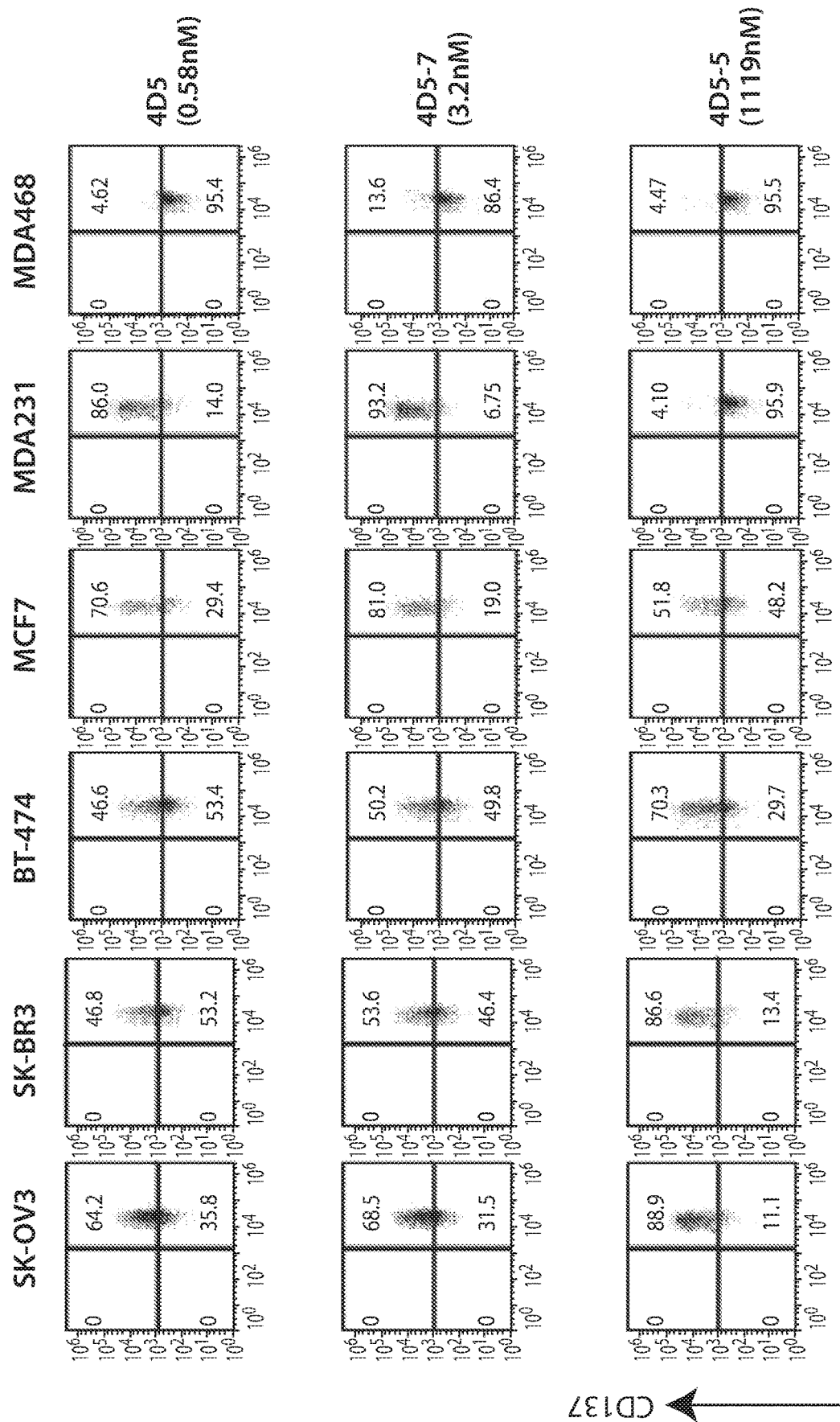
FIG. 4. The induction of CD137 (4-1BB) expression on CAR T cells after stimulation by tumor cells was measured. One day after electroporation the various CAR T cells ($K_D$, nM) were co-cultured with the indicated tumor cell lines and CD137 expression was measured after 24 hr.
Figures 2, 4:
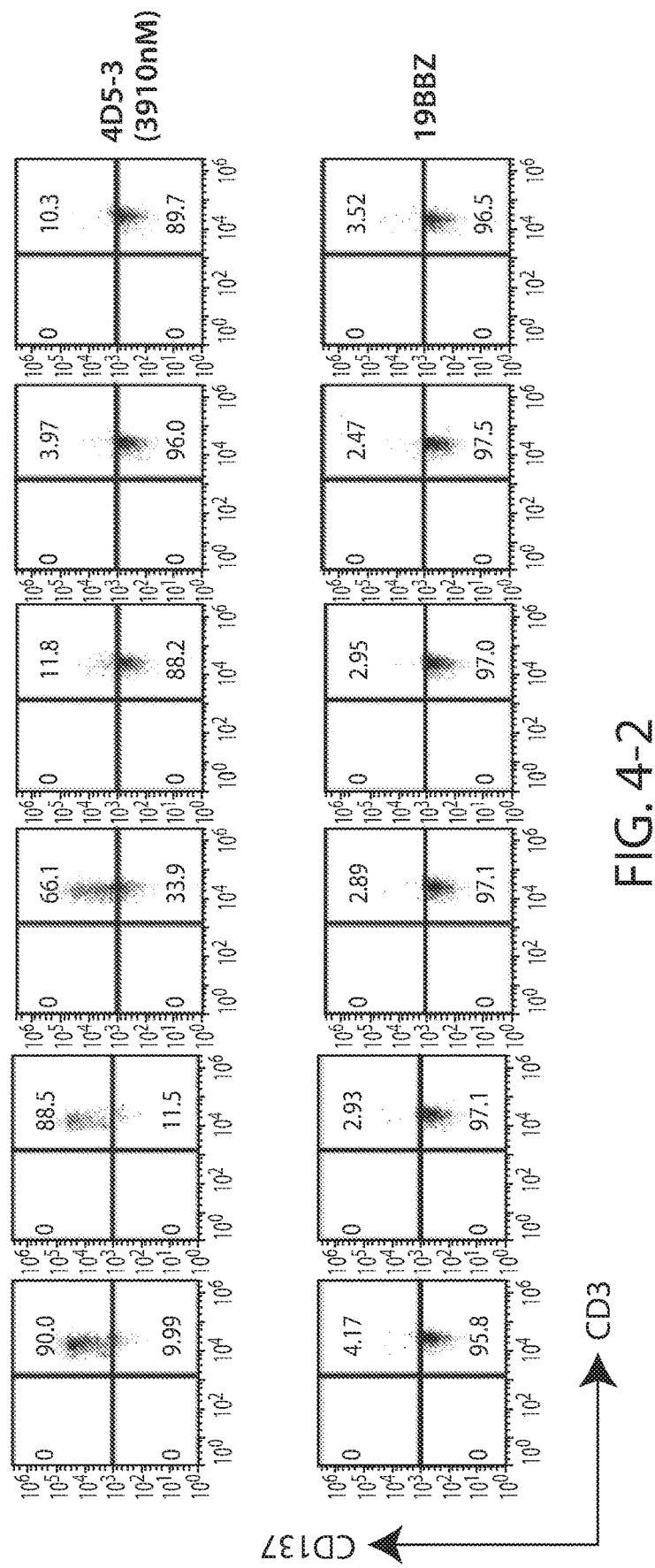

Lowering the Affinity of the Anti-ErbB2 scFv Improves the Therapeutic Index of ErbB2 CAR T Cells In Vitro A panel of tumor lines with a wide range of ErbB2 expression as measured by flow cytometry was compiled (FIG. 1). SK-OV3 (ovarian cancer), SK-BR3 (breast cancer), BT-474 (breast cancer) over-express ErbB2, while EM-Meso (mesothelioma), MCF7 (breast cancer), 293T (embryonic kidney 293 cell), A549 (lung cancer), 624mel (melanoma), PC3 (prostate cancer), MDA231 (breast cancer) express ErbB2 at lower levels and ErbB2 was not detected in MDA468 (breast cancer). ErbB2 mRNA levels were also measured by real time PCR and there was a strong correlation between the two techniques (FIG. 2).

A panel of ErbB2 CARs was constructed making use scFv derived from the published mutations of the parental 4D5 antibody (Carter et al. (1992) *Proc Natl Acad Sci USA* 89:4285-4289). The sequences encoding the CARs against ErbB2 are provided in Table 10.

TABLE 10

Nucleic acid sequences encoding CARs against ErbB2

| CAR Designation | Nucleic Acid Sequence | SEQ ID NO: |
|---|---|---|
| 4D5-BZZ | atg gac ttc cag gtt cag atc ttt tcg ttc ctg ctg atc agc gcc tct gtt atc atg tcg cgc ggc gac atc cag atg acc cag tcc cct tcc tcc ctc tct gcc tct gtg gga gac cgc gtt acc atc aca tgc cga gct tcc cag gac gtg aac aca gcc gtg gcc tgg tac cag cag aag ccc ggg aag gca ccc aaa ctc ctc atc tac tcc gcc tcc ttc cta tac agt ggc gtg cct tcc cga ttc tcc ggc tcc agg agt ggc acg gac ttt acg ctc acc att agt agc ctg cag ccc gaa gac ttc gcg acc tac tat tgt cag caa cac tac acg acg cca cca act ttc ggc cag ggt acc aag gtc gag att aag cga acc ggc agt acc agt ggg tct ggc aag ccc ggc agc ggc gag gga tcc gag gtc cag ctg gtc gag tcc ggc ggg ggc ctg gtg cag ccg ggc ggc tcg ctg agg tta tct tgc gcc gcc agt ggc ttc aac atc aag gat act tac atc cac tgg gtg agg cag gct ccg ggc aag ggc ctg gaa tgg gtg gct agg atc tac cct act aac ggg tac aca cgc tac gca gat tcg gtg aaa ggc cgc ttc act atc tcc gcc gac acc tcg aag aac act gct tac ctg cag atg aac tcc ctc agg gcc gaa gat act gca gtc tac tac tgc tcc cgc tgg ggt ggg gac ggc ttc tac gcc atg gac gtg tgg ggt cag ggc act cta gtt aca gtg tca tcc acc acg acg cca gcg ccg cga cca cca aca ccg gcg ccc acc atc gcg tcg cag ccc ctg tcc ctg cgc cca gag gcg tgc cgg cca gcg gcg ggg ggc gca gtg cac acg agg ggg ctg gac ttc gcc tgt gat atc tac atc tgg gcg ccc ttg gcc ggg act tgt ggg gtc ctt ctc ctg tca ctg gtt atc acc ctt tac tgc aaa cgg ggc aga aag aaa ctc ctg tat ata ttc aaa caa cca ttt atg aga cca gta caa act act caa gag gaa gat ggc tgt agc tgc cga ttt cca gaa gaa gaa gaa gga gga tgt gaa ctg aga gtg aag ttc agc agg agc gca gac gcc ccc gcg tac aag cag ggc cag aac cag ctc tat aac gag ctc aat cta gga cga aga gag gag tac gac gtt ttg gac aag aga cgt ggc cgg gac cct gag atg ggg gga aag ccg aga agg aag aac cct cag gaa ggc ctg tac aat gaa ctg cag aaa gat aag atg gcg gag gcc tac agt gag att ggg atg aaa ggc gag cgc cgg agg ggc aag ggg cac gat ggc ctt tac cag ggt ctc agt aca gcc acc aag gac acc tac gac gcc ctt cac atg cag gcc ctg ccc cct cgc taa | 265 |
| 4D5-1-BBZ | atg gac ttc cag gtt cag atc ttt tcg ttc ctg ctg atc agc gcc tct gtt atc atg tcg cgc ggc gac atc cag atg acc cag tcc cct tcc tcc ctc tct gcc tct gtg gga gac cgc gtt acc atc aca tgc cga gct tcc cag gac gtg aac aca gcc gtg gcc tgg tac cag cag aag ccc ggg aag gca ccc aaa ctc ctc atc tac tcc gcc tcc ttc cta gag agt ggc gtg cct tcc cga ttc tcc ggc tcc agt ggc acg gac ttt acg ctc acc att agt agc ctg cag ccc gaa gac ttc gcg acc tac tat tgt cag caa cac tac acg acg cca cca act ttc ggc cag ggt acc aag gtc gag att aag cga acc ggc agt acc agt ggg tct ggc aag ccc ggc agc ggc gag gga tcc gag gtc cag ctg gtc gag tcc ggc ggg ggc ctg gtg cag ccg ggc ggc tcg ctg agg tta tct tgc gcc gcc agt ggc ttc aac atc aag gat act tac atc cac tgg gtg agg cag gct ccg ggc aag ggc ctg gaa tgg gtg gct agg atc tac cct act aac ggg tac aca cgc tac gca gat tcg gtg aaa ggc cgc ttc act atc tcc agg gac gac tcg aag aac act ctg tac ctg cag atg aac tcc ctc agg gcc gaa gat act gca | 266 |

TABLE 10-continued

Nucleic acid sequences encoding CARs against ErbB2

| CAR Designation | Nucleic Acid Sequence | SEQ ID NO: |
|---|---|---|
| | gtc tac tac tgc gcc cgc tgg ggt ggg gac ggc ttc gta gcc atg gac gtg tgg<br>ggt cag ggc act cta gtt aca gtg tca tcc acc acg acg cca gcg ccg cga cca<br>cca aca ccg gcg ccc acc atc gcg tcg cag ccc ctg tcc ctg cgc cca gag gcg<br>tgc cgg cca gcg gcg ggg ggc gca gtg cac acg agg ggg ctg gac ttc gcc tgt<br>gat atc tac atc tgg gcg ccc ttg gcc ggg act tgt ggg gtc ctt ctc ctg tca ctg<br>gtt atc acc ctt tac tgc aaa cgg ggc aga aag aaa ctc ctg tat ata ttc aaa<br>caa cca ttt atg aga cca gta caa act act caa gag gaa gat ggc tgt agc tgc<br>cga ttt cca gaa gaa gaa gaa gga gga tgt gaa ctg aga atg gac ttc cag gtt<br>cag atc ttt tcg ttc ctg ctg atc agc gcc tct gtt atc atg tcg cgc ggc gac atc<br>cag atg acc cag tcc cct tcc tcc ctc tct gcc tct gtg gga gac cgc gtt acc atc<br>aca tgc cga gct tcc cag gac gtg aac aca gcc gtg gcc tgg tac cag cag aag<br>ccc ggg aag gca ccc aaa ctc ctc atc tac tcc gcc tcc ttc cta gag agt ggc<br>gtg cct tcc cga ttc tcc ggc tcc ggc agt ggc acg gac ttt acg ctc acc att agt<br>agc ctg cag ccc gaa gac ttc gcg acc tac tat tgt cag caa cac tac acg acg<br>cca cca act ttc ggc cag ggt acc aag gtc gag att aag cga acc ggc agt acc<br>agt ggg tct ggc aag ccc ggc agc ggc gag gga tcc gag gtc cag ctg gtc gag<br>tcc ggc ggg ggc ctg gtg cag ccg ggc ggc tcg ctg agg tta tct tgc gcc gcc<br>agt ggc ttc aac atc aag gat act tac atc cac tgg gtg agg cag gct ccg ggc<br>aag ggc ctg gaa tgg gtg gct agg atc tac cct act aac ggg tac aca cgc tac<br>gca gat tcg gtg aaa ggc cgc ttc act atc tcc agg gac acc tcg aag aac act<br>ctg tac ctg cag atg aac tcc ctc agg gcc gaa gat act gca gtc tac tac tgc<br>gcc cgc tgg ggt ggg gac ggc ttc gta gcc atg gac gtg tgg ggt cag ggc act<br>cta gtt aca gtg tca tcc gtg aag ttc agc agg agc gca gac gcc ccc gcg tac<br>aag cag ggc cag aac cag ctc tat aac gag ctc aat cta gga cga aga gag gag<br>tac gac gtt ttg gac aag aga cgt ggc cgg gac cct gag atg ggg gga aag ccg<br>aga agg aag aac cct cag gaa ggc ctg tac aat gaa ctg cag aaa gat aag atg<br>gcg gag gcc tac agt gag att ggg atg aaa ggc gag cgc cgg agg ggc aag ggg<br>cac gat ggc ctt tac cag ggt ctc agt aca gcc acc aag gac acc tac gac gcc<br>ctt cac atg cag gcc ctg ccc cct cgc taa | |
| 4D5-3-BBZ | acc acg acg cca gcg ccg cga cca cca aca ccg gcg ccc acc atc gcg tcg cag<br>ccc ctg tcc ctg cgc cca gag gcg tgc cgg cca gcg gcg ggg ggc gca gtg cac<br>acg agg ggg ctg gac ttc gcc tgt gat atc tac atc tgg gcg ccc ttg gcc ggg<br>act tgt ggg gtc ctt ctc ctg tca ctg gtt atc acc ctt tac tgc aaa cgg ggc aga<br>aag aaa ctc ctg tat ata ttc aaa caa cca ttt atg aga cca gta caa act act<br>caa gag gaa gat ggc tgt agc tgc cga ttt cca gaa gaa gaa gaa gga gga<br>tgt gaa ctg aga atg gac ttc cag gtt cag atc ttt tcg ttc ctg ctg atc agc gcc tct gtt atc atg tcg cgc ggc gac<br>atc cag atg acc cag tcc cct tcc tcc ctc tct gcc tct gtg gga gac cgc gtt acc<br>atc aca tgc cga gct tcc cag gac gtg aac aca gcc gtg gcc tgg tac cag cag<br>aag ccc ggg aag gca ccc aaa ctc ctc atc tac tcc gcc tcc ttc cta gag agt<br>ggc gtg cct tcc cga ttc tcc ggc tcc ggc agt ggc acg gac ttt acg ctc acc att<br>agt agc ctg cag ccc gaa gac ttc gcg acc tac tat tgt cag caa cac tac acg<br>acg cca cca act ttc ggc cag ggt acc aag gtc gag att aag cga acc ggc agt<br>acc agt ggg tct ggc aag ccc ggc agc ggc gag gga tcc gag gtc cag ctg gtc<br>gag tcc ggc ggg ggc ctg gtg cag ccg ggc ggc tcg ctg agg tta tct tgc gcc<br>gcc agt ggc ttc aac atc aag gat act tac atc cac tgg gtg agg cag gct ccg<br>ggc aag ggc ctg gaa tgg gtg gct agg atc tac cct act aac ggg tac aca cgc<br>tac gca gat tcg gtg aaa ggc cgc ttc act atc tcc agg gac acc tcg aag aac<br>act ctg tac ctg cag atg aac tcc ctc agg gcc gaa gat act gca gtc tac tac<br>tgc tcc cgc tgg ggt ggg gac ggc ttc gta gcc atg gac gtg tgg ggt cag ggc<br>act cta gtt aca gtg tca tcc gaa gga gga tgt gaa ctg aga atg aag ttc agc<br>agg agc gca gac gcc ccc gcg tac aag cag ggc cag aac cag ctc tat aac gag<br>ctc aat cta gga cga aga gag gag tac gac gtt ttg gac aag aga cgt ggc cgg<br>gac cct gag atg ggg gga aag ccg aga agg aag aac cct cag gaa ggc ctg tac<br>aat gaa ctg cag aaa gat aag atg gcg gag gcc tac agt gag att ggg atg aaa<br>ggc gag cgc cgg agg ggc aag ggg cac gat ggc ctt tac cag ggt ctc agt aca<br>gcc acc aag gac acc tac gac gcc ctt cac atg cag gcc ctg ccc cct cgc taa | 267 |
| 4D5-5-BBZ | atg gac ttc cag gtt cag atc ttt tcg ttc ctg ctg atc agc gcc tct gtt atc atg<br>tcg cgc ggc gac atc cag atg acc cag tcc cct tcc tcc ctc tct gcc tct gtg gga<br>gac cgc gtt acc atc aca tgc cga gct tcc cag gac gtg aac aca gcc gtg gcc<br>tgg tac cag cag aag ccc ggg aag gca ccc aaa ctc ctc atc tac tcc gcc tcc<br>ttc cta gag agt ggc gtg cct tcc cga ttc tcc ggc tcc agg agt ggc acg gac ttt<br>acg ctc acc att agt agc ctg cag ccc gaa gac ttc gcg acc tac tat tgt cag<br>caa cac tac acg acg cca cca act ttc ggc cag ggt acc aag gtc gag att aag<br>cga acc ggc agt acc agt ggg tct ggc aag ccc ggc agc ggc gag gga tcc gag<br>gtc cag ctg gtc gag tcc ggc ggg ggc ctg gtg cag ccg ggc ggc tcg ctg agg<br>tta tct tgc gcc gcc agt ggc ttc aac atc aag gat act tac atc cac tgg gtg agg<br>cag gct ccg ggc aag ggc ctg gaa tgg gtg gct agg atc tac cct act aac ggg<br>tac aca cgc tac gca gat tcg gtg aaa ggc cgc ttc act atc tcc gcc gac acc<br>tcg aag aac act gct tac ctg cag atg aac tcc ctc agg gcc gaa gat act gca<br>gtc tac tac tgc tcc cgc tgg ggt ggg gac ggc ttc gta gcc atg gac gtg tgg<br>ggt cag ggc act cta gtt aca gtg tca tcc acc acg acg cca gcg ccg cga cca<br>cca aca ccg gcg ccc acc atc gcg tcg cag ccc ctg tcc ctg cgc cca gag gcg | 268 |

TABLE 10-continued

Nucleic acid sequences encoding CARs against ErbB2

| CAR Designation | Nucleic Acid Sequence | SEQ ID NO: |
|---|---|---|
|  | tgc cgg cca gcg gcg ggg ggc gca gtg cac acg agg ggg ctg gac ttc gcc tgt<br>gat atc tac atc tgg gcg ccc ttg gcc ggg act tgt ggg gtc ctt ctc ctg tca ctg<br>gtt atc acc ctt tac tgc aaa cgg ggc aga aag aaa ctc ctg tat ata ttc aaa<br>caa cca ttt atg aga cca gta caa act act caa gag gaa gat ggc tgt agc tgc<br>cga ttt cca gaa gaa gaa gaa gga gga tgt gaa ctg aga gtg aag ttc agc agg<br>agc gca gac gcc ccc gcg tac aag cag ggc cag aac cag ctc tat aac gag ctc<br>aat cta gga cga aga gag gag tac gac gtt ttg gac aag aga cgt ggc cgg gac<br>cct gag atg ggg gga aag ccg aga agg aag aac cct cag gaa ggc ctg tac aat<br>gaa ctg cag aaa gat aag atg gcg gag gcc tac agt gag att ggg atg aaa ggc<br>gag cgc cgg agg ggc aag ggg cac gat ggc ctt tac cag ggt ctc agt aca gcc<br>acc aag gac acc tac gac gcc ctt cac atg cag gcc ctg ccc cct cgc taa |  |
| 4D5-7-BBZ | atg gac ttc cag gtt cag atc ttt tcg ttc ctg ctg atc agc gcc tct gtt atc atg<br>tcg cgc ggc gac atc cag atg acc cag tcc cct tcc tcc ctc tct gcc tct gtg gga<br>gac cgc gtt acc atc aca tgc cga gct tcc cag gac gtg aac aca gcc gtg gcc<br>tgg tac cag cag aag ccc ggg aag gca ccc aaa ctc ctc atc tac tcc gcc tcc<br>ttc cta gag agt ggc gtg cct tcc cga ttc tcc ggc tcc agg agt ggc acg gac ttt<br>acg ctc acc att agt agc ctg cag ccc gaa gac ttc gcg acc tac tat tgt cag<br>caa cac tac acg acg cca cca act ttc ggc cag ggt acc aag gtc gag att aag<br>cga acc ggc agt acc agt ggg tct ggc aag ccc ggc agc ggc gag gga tcc gag<br>gtc cag ctg gtc gag tcc ggc ggg ggc ctg gtg cag ccg ggc ggc tcg ctg agg<br>tta tct tgc gcc gcc agt ggc ttc aac atc aag gat act tac atc cac tgg gtg agg<br>cag gct ccg ggc aag ggc ctg gaa tgg gtg gct agg atc tac cct act aac ggg<br>tac aca cgc tac gca gat tcg gtg aaa ggc cgc ttc act atc tcc gcc gac acc<br>tcg aag aac act gct tac ctg cag atg aac tcc ctc agg gcc gaa gat act gca<br>gtc tac acc acg acg cca gcg ccg cga cca cca aca ccg gcg ccc acc atc gcg<br>tcg cag ccc ctg tcc ctg cgc cca gag gcg tgc cgg cca gcg gcg ggg ggc gca<br>gtg cac acg agg ggg ctg gac ttc gcc tgt gat atc tac atc tgg gcg ccc ttg<br>gcc ggg act tgt ggg gtc ctt ctc ctg tca ctg gtt atc acc ctt tac tgc aaa cgg<br>ggc aga aag aaa ctc ctg tat ata ttc aaa caa cca ttt atg aga cca gta caa<br>act act caa gag gaa gat ggc tgt agc tgc cga ttt cca gaa gaa gaa gaa gga<br>gga tgt gaa ctg aga gtg aag ttc agc agg agc gca gac gcc ccc gcg tac aag<br>cag ggc cag aac cag ctc tat aac gag ctc aat cta gga cga aga gag gag tac<br>gac gtt ttg gac aag aga cgt ggc cgg gac cct gag atg ggg gga aag ccg aga<br>agg aag aac cct cag gaa ggc ctg tac aat gaa ctg cag aaa gat aag atg gcg<br>gag gcc tac agt gag att ggg atg aaa ggc gag cgc cgg agg ggc aag ggg cac<br>gat ggc ctt tac cag ggt ctc agt aca gcc acc aag gac acc tac gac gcc ctt<br>cac atg cag gcc ctg ccc cct cgc taa | 269 |

The monovalent affinities of the ErbB2 scFvs varied by approximately 3 orders of magnitude (Table 9), in contrast to the corresponding mutant antibodies that retained binding affinities within 10-fold of each other (Carter, P., et al. 1992).

TABLE 11

Comparison of measured affinities of the wild type 4D5 and mutated antibody with the corresponding scFv

| Sample | Mutation | Antibody KD (nM) | scFv KD (nM) |
|---|---|---|---|
| 4D5 | Wild Type | 0.3 | 0.58 |
| 4D5-7 | 1 in CDR2 | 0.62 | 3.2 |
| 4D5-5 | 1 in CDR3, 1 in CDR2 | 1.1 | 1119 |
| 4D5-3 | 1 in framework, 1 in CDR3, 1 in CDR2 | 4.4 | 3910 |

Figure 3:
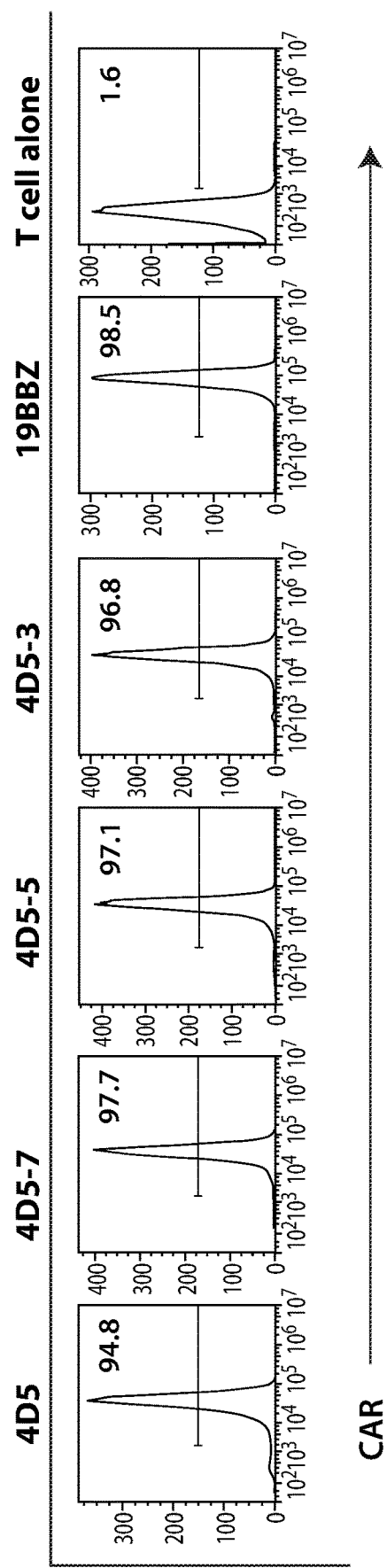
FIG. 3. FACS analysis of affinity-tuned CAR expression in mRNA electroporated T cells. T cells were electroporated with indicated CAR mRNA and one day after the electroporation, the CAR expression was detected using an anti-mouse IgG Fab antibody (for CD19-BBZ) or ErbB2-Fc (for ErbB2-BBZ CARs). T cells without electroporation were used as a negative control.
Figure 5:
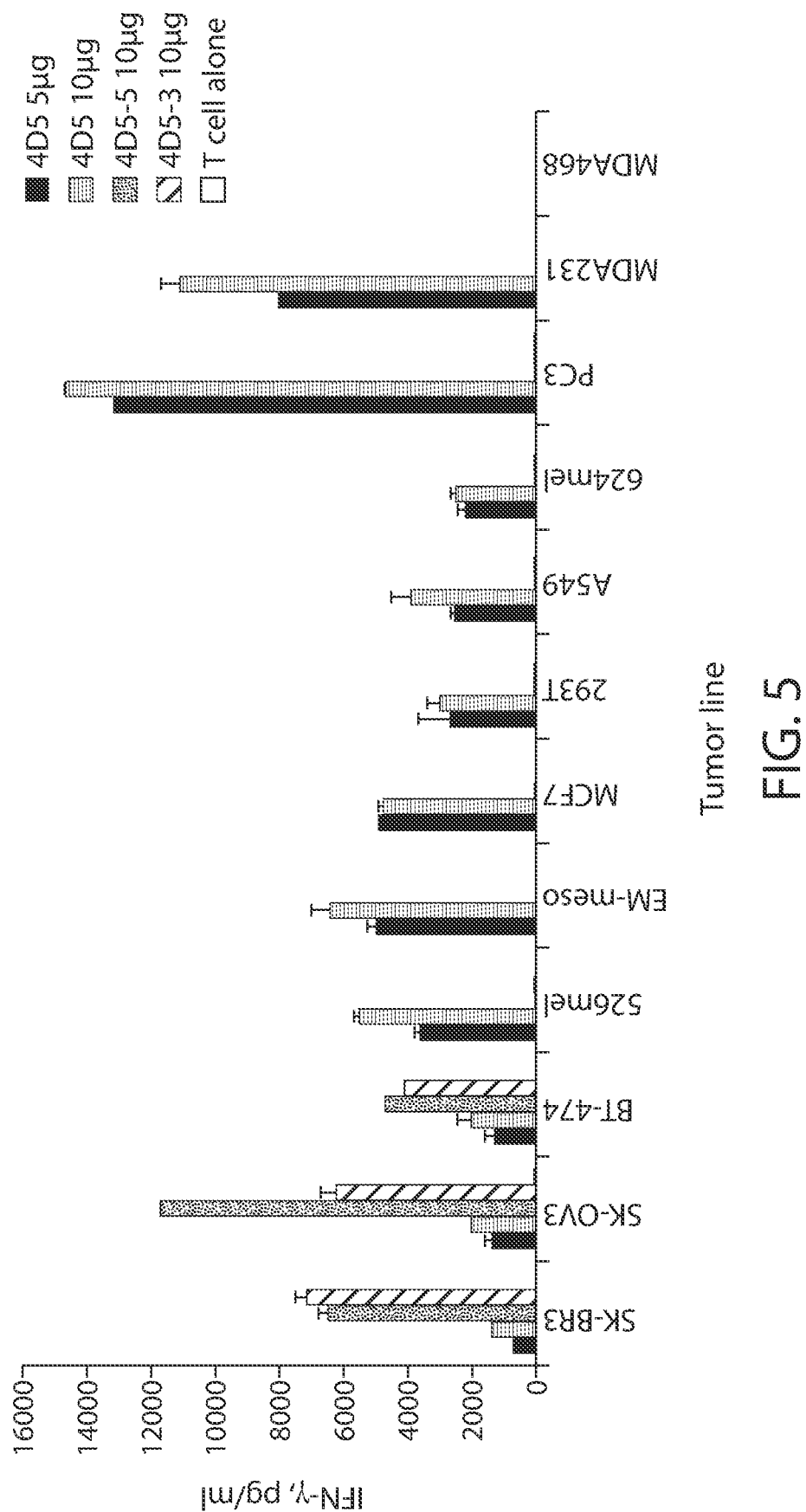
FIG. 5. Cytokine secretion was measured (ELISA) in culture supernatants. T cells were electroporated with 5 ug or 10 ug affinity-tuned ErbB2 CAR mRNA as indicated. One day after the electroporation, the CAR T cells were co-cultured with indicated tumor cell lines for 24 h. Bar chart shows results from a representative experiment (values represent the average±SD of duplicates) for IFN-gamma.
Figure 6:
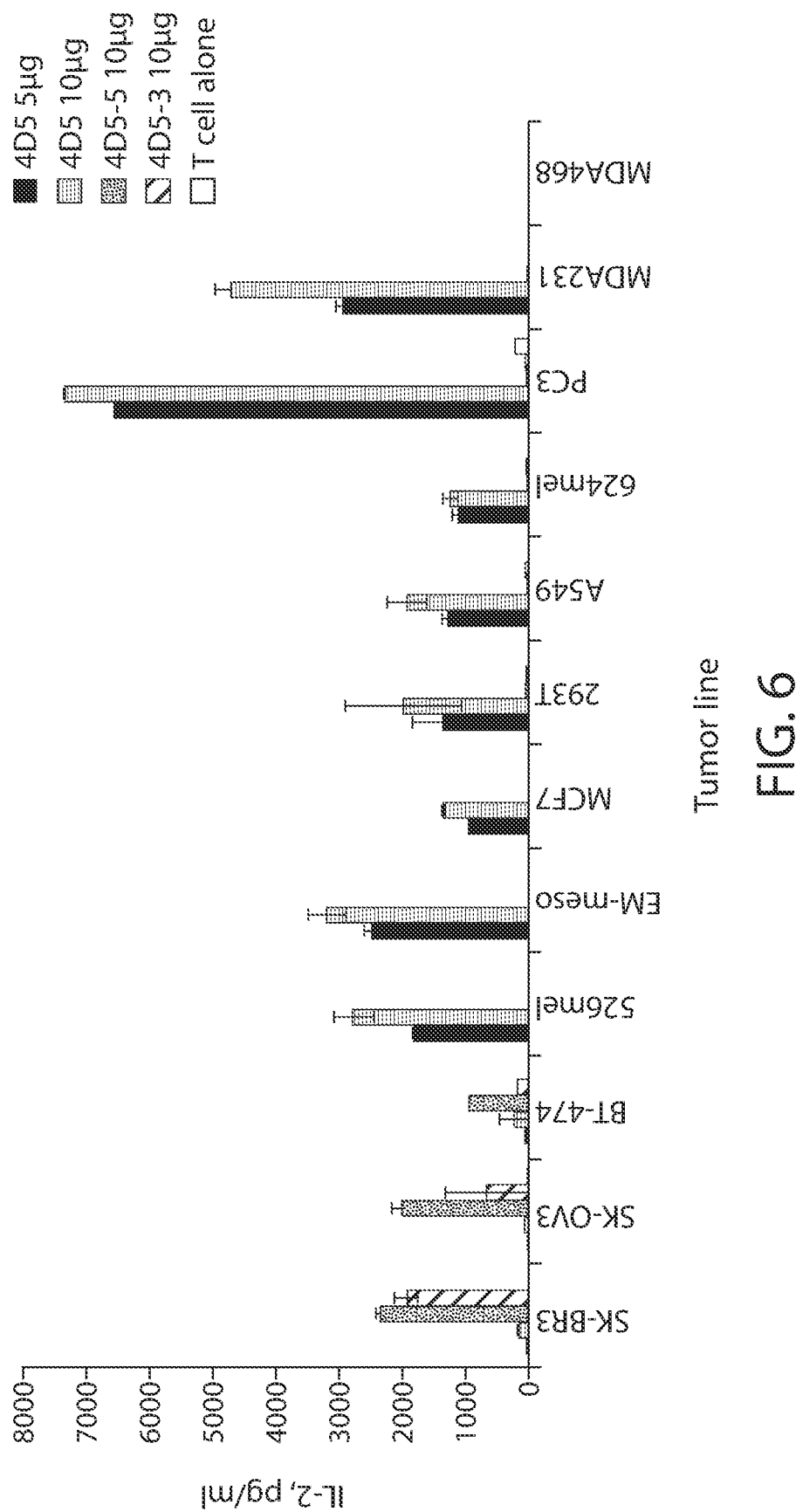
FIG. 6. Cytokine secretion was measured (ELISA) in culture supernatants. T cells were electroporated with 5 ug or 10 ug affinity-tuned ErbB2 CAR mRNA as indicated. One day after the electroporation, the CAR T cells were co-cultured with indicated tumor cell lines for 24 h. Bar chart shows results from a representative experiment (values represent the average±SD of duplicates) for IL-2.
Figure 7:
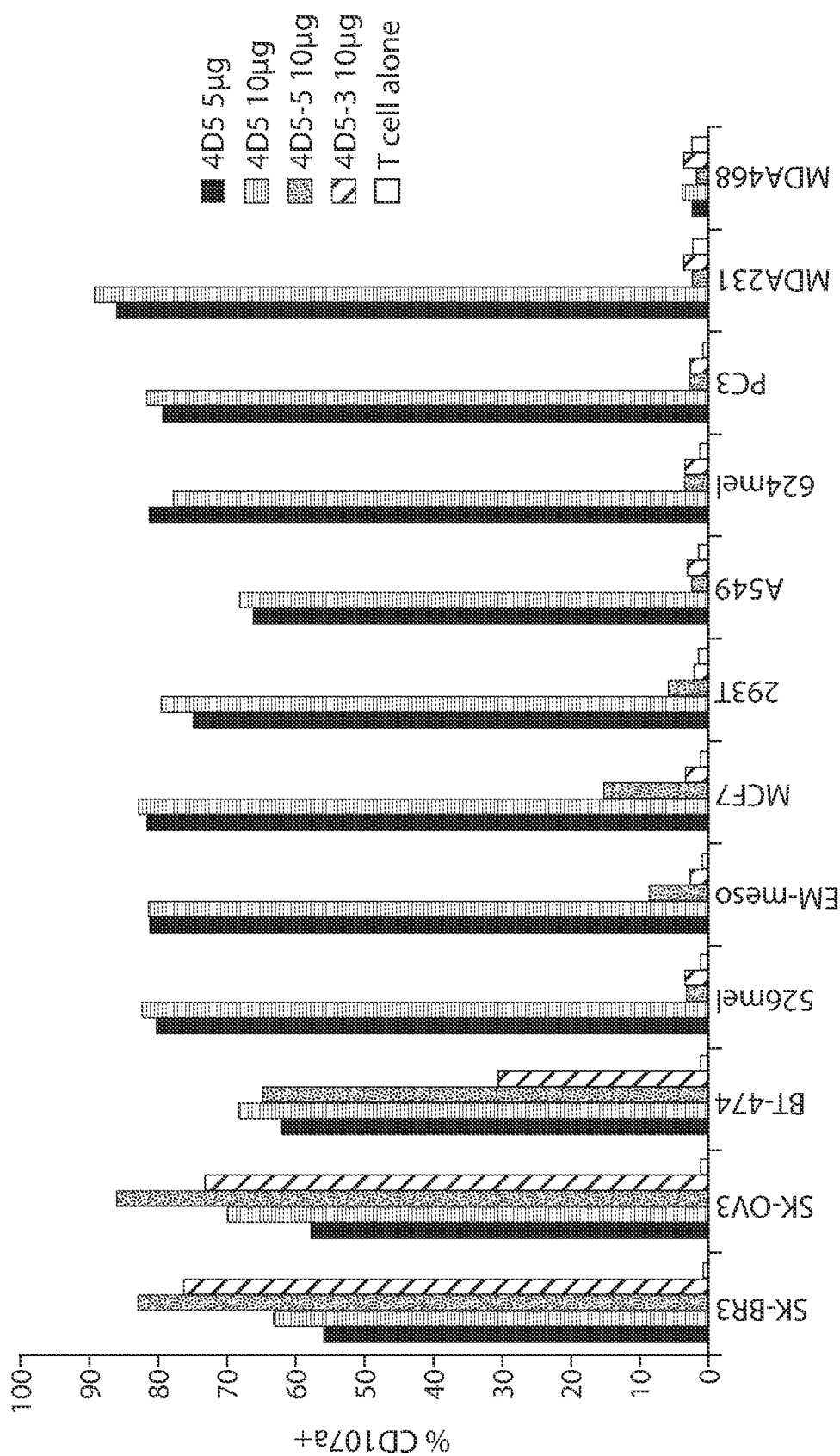
FIG. 7. CD107a up-regulation on CAR T cells stimulated by tumors. T cells were electroporated with 5 ug or 10 ug ErbB2 CAR mRNAs encoding the indicated scFv and one day later the CAR T cells were co-cultured with the indicated cell line for 4 hr CD107a expression was measured by gating on CD3+CD8+ cells.
Figure 8:
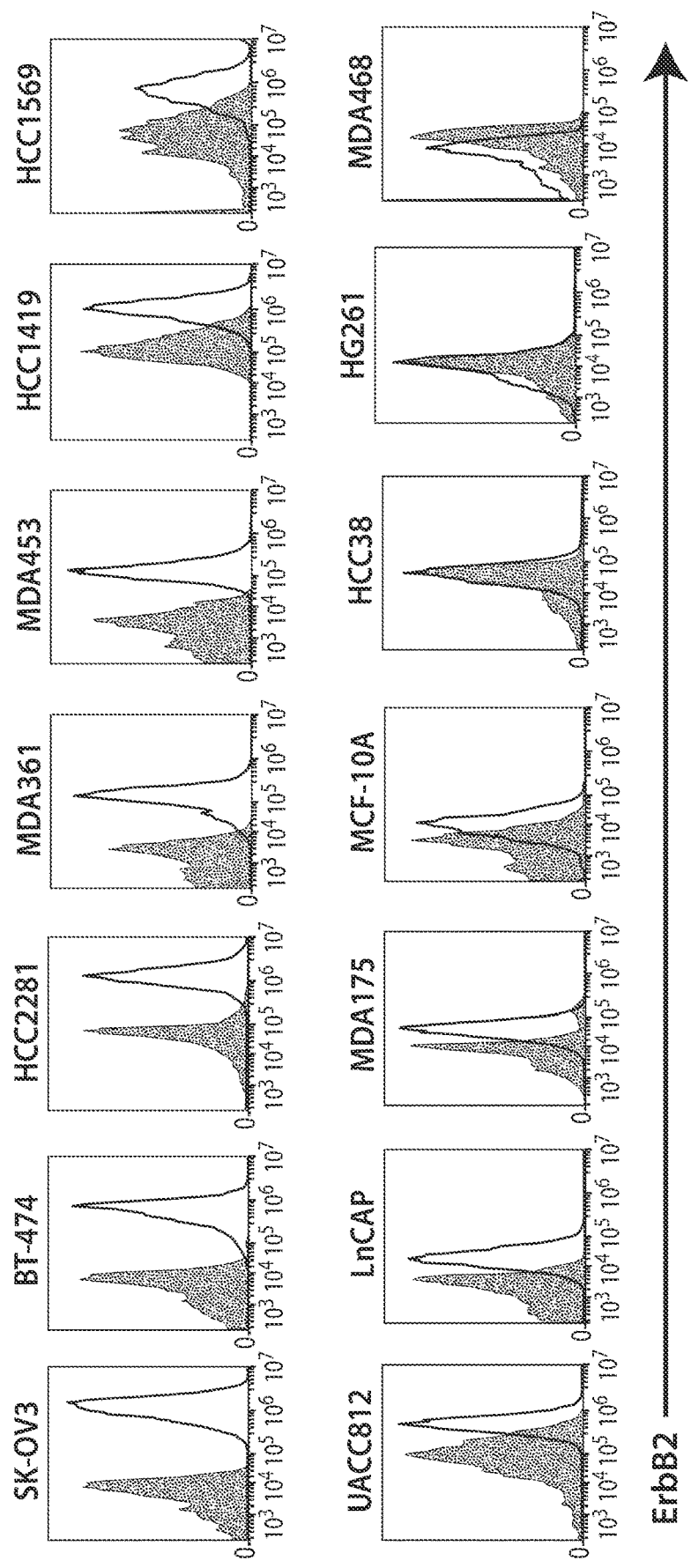
FIG. 8. Additional tumor cell lines were examined for ErbB2 expression by flow cytometry using Biotin-ErbB2 Affibody (streptavidin-PE) staining (open histograms). The same cells stained only with Streptavidin-PE were used as negative control (grey histograms).
Figure 9:
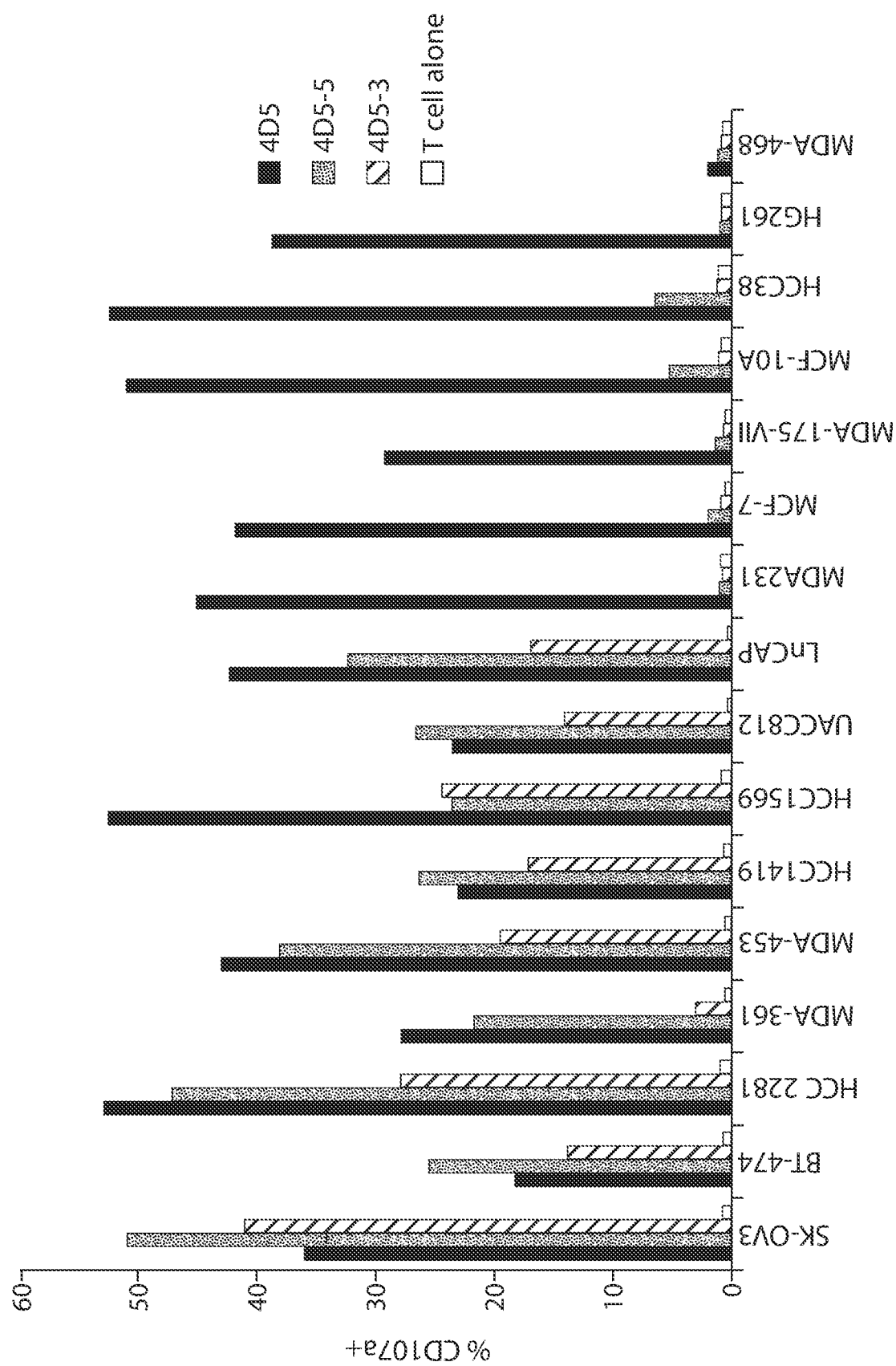
FIG. 9. T cells electroporated with ErbB2 CAR mRNA were stimulated with tumor lines tested in C. SK-OK3, BT-474, HCC2281, MDA-361, MDA-453, HCC-1419, HCC-1569, UACC-812 and LnCap were reported to be ErbB2 amplified tumors, while MDA-175, MCF-10A, HCC38, HG261 were reported to be ErbB2 low or negative cell lines. After 4 h stimulation, CD107a on the T cells were monitored by flow cytometry staining and the % cells expressing CD107a plotted.

CARs were constructed by linking the various scFv to the CD8 alpha hinge and transmembrane domain followed by the 4-1BB and CD3ζ intracellular signaling domains. The CARs were expressed by lentiviral vector technology or by cloning into an RNA-based vector (Zhao et al., 2010, Cancer Res, 70:9053). After production of mRNA by in vitro transcription and electroporation into T cells, the surface expression of the panel of affinity-modified ErbB2 RNA CARs was similar (FIG. 3). To compare recognition thresholds, the panel of ErbB2 CAR T cells was stimulated with ErbB2 high expressing (SK-BR3, SK-OV3 and BT-474) or low expressing tumor cell lines (MCF7, 293T, A549, 624Mel, PC3, MDA231 and MDA468) and T cell activation was assessed by upregulation of CD137 (4-1BB; FIG. 4), secretion of IFN-γ (FIG. 5) and IL-2 (FIG. 6) and induction of surface CD107a expression (FIG. 7). T cells expressing a CD19-specific CAR served as control for allogeneic reactivity. Lower affinity CAR T cells (4D5-5 and 4D5-3) were strongly reactive to tumors with amplified ErbB2 expression and exhibited undetectable or low reactivity to the tumor lines that expressed ErbB2 at lower levels. In contrast, higher affinity CAR T cells (4D5 and 4D5-7) showed strong reactivity to tumor lines expressing high and low levels of ErbB2, as evidenced by CD137 up-regulation, cytokine secretion and CD107a translocation. These results were extended by assaying additional ErbB2-expressing cell lines (FIGS. 8 and 9). Interestingly, higher affinity CAR T cells secreted greater levels of IFN-γ and IL-2 when exposed to targets expressing low levels of ErbB2, while lower affinity CAR T cells secreted more cytokines when exposed to cells expressing high levels of target (FIGS. 5 and 6). As expected, the CD19-BBζ CAR was not reactive against ErbB2-expressing cell lines. In summary, higher affinity 4D5-BBζ T cells recognized all the ErbB2 expressing lines tested, whereas CARs with lower affinity scFvs, 4D5-5-BBζ or 4D5-3-BBζ, were highly reactive to all tumor lines with overexpressed ErbB2, but displayed negligible reactivity to cell lines expressing low or undetectable levels of ErbB2.

ErbB2 CARs with Lower Affinity scFvs Discriminate Between Tumor Cells Expressing Low and High Levels of ErbB2.

Figures 1, 10:
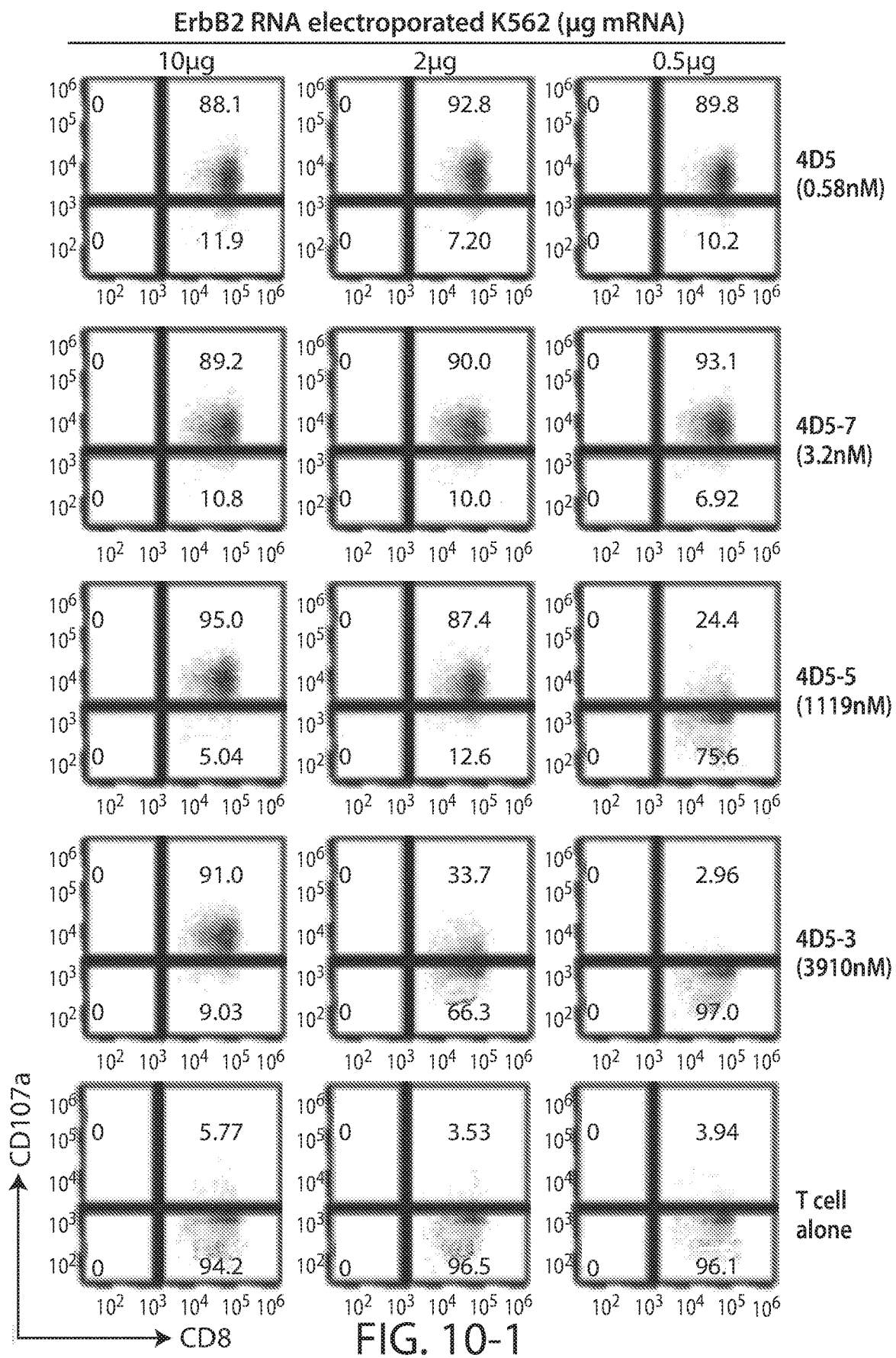
FIG. 10. Recognition of K562 cells were electroporated with indicated amounts of ErbB2 mRNA and CAR T cells expressing the indicated scFv ($K_D$, nM) were co-cultured with target for 4 h and the % CD107a expression was quantified on CD3+CD8+ cells.
Figures 2, 10:
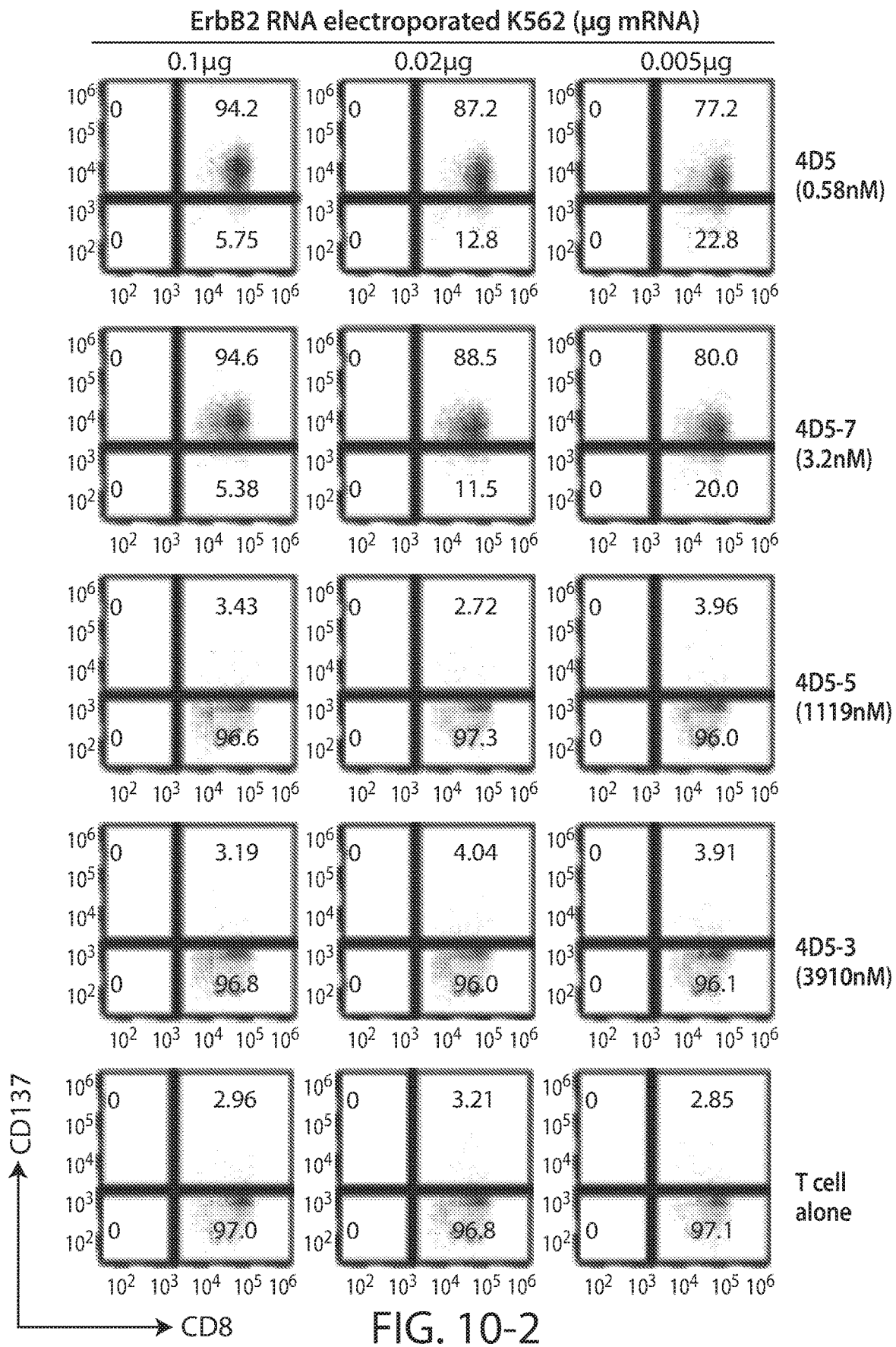
Figures 3, 10:
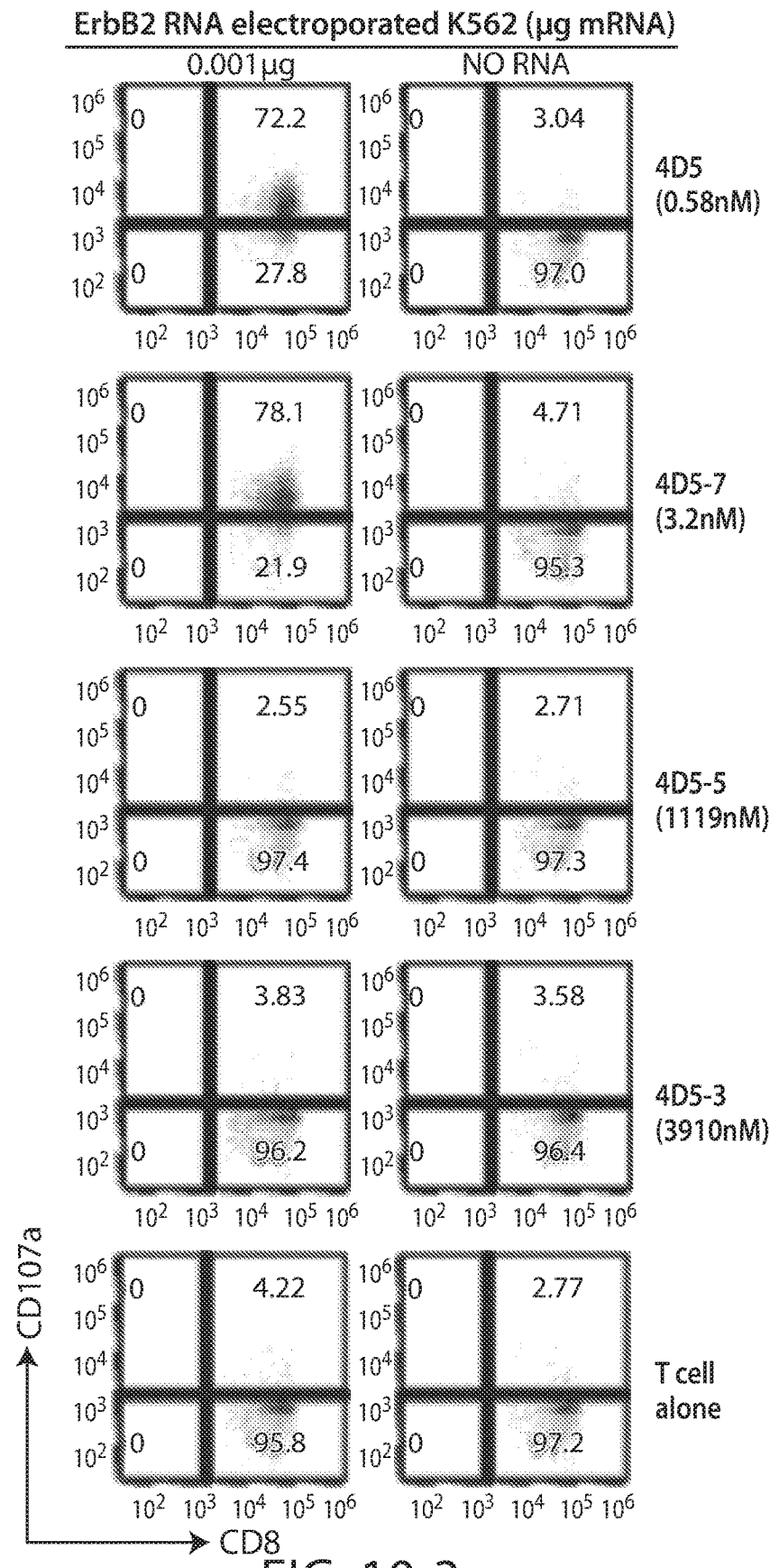
Figure 11A:
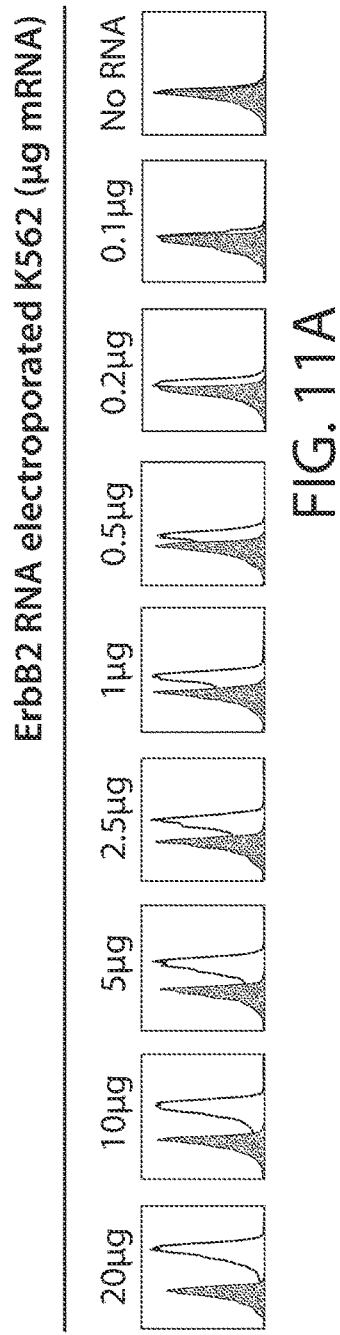
FIG. 11A. ErbB2 expression in K562 cells after electroporation. K562 cells were electroporated with the indicated amount of ErbB2 mRNA and staining indicates cells with ErbB2 expression (open histogram); cells incubated with secondary antibody alone indicates background (grey histogram).
Figure 11B:
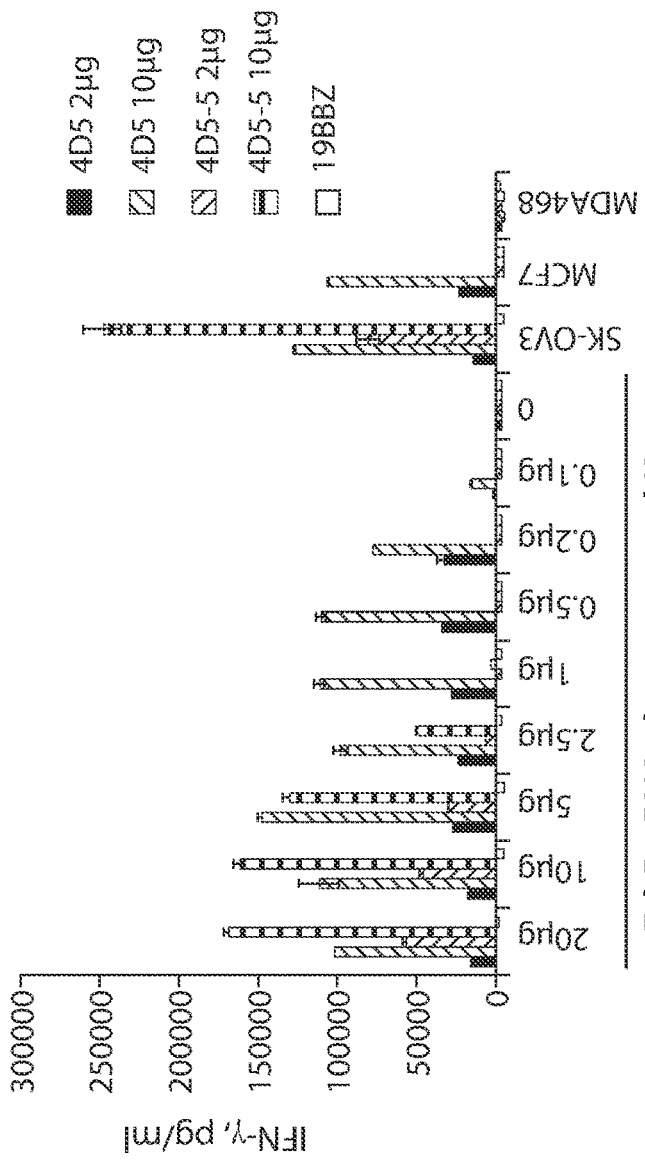
FIG. 11B. IFN-gamma secretion by the panel of ErbB2 CART cells stimulated by ErbB2 mRNA electroporated K562 cells. K562 cells were electroporated with 2 ug or 10 ug ErbB2 CAR mRNA as indicated. CAR T cells were co-cultured with indicted K562 targets and IFN-gamma secretion was measured by ELISA after 24 hrs.
Figure 12:
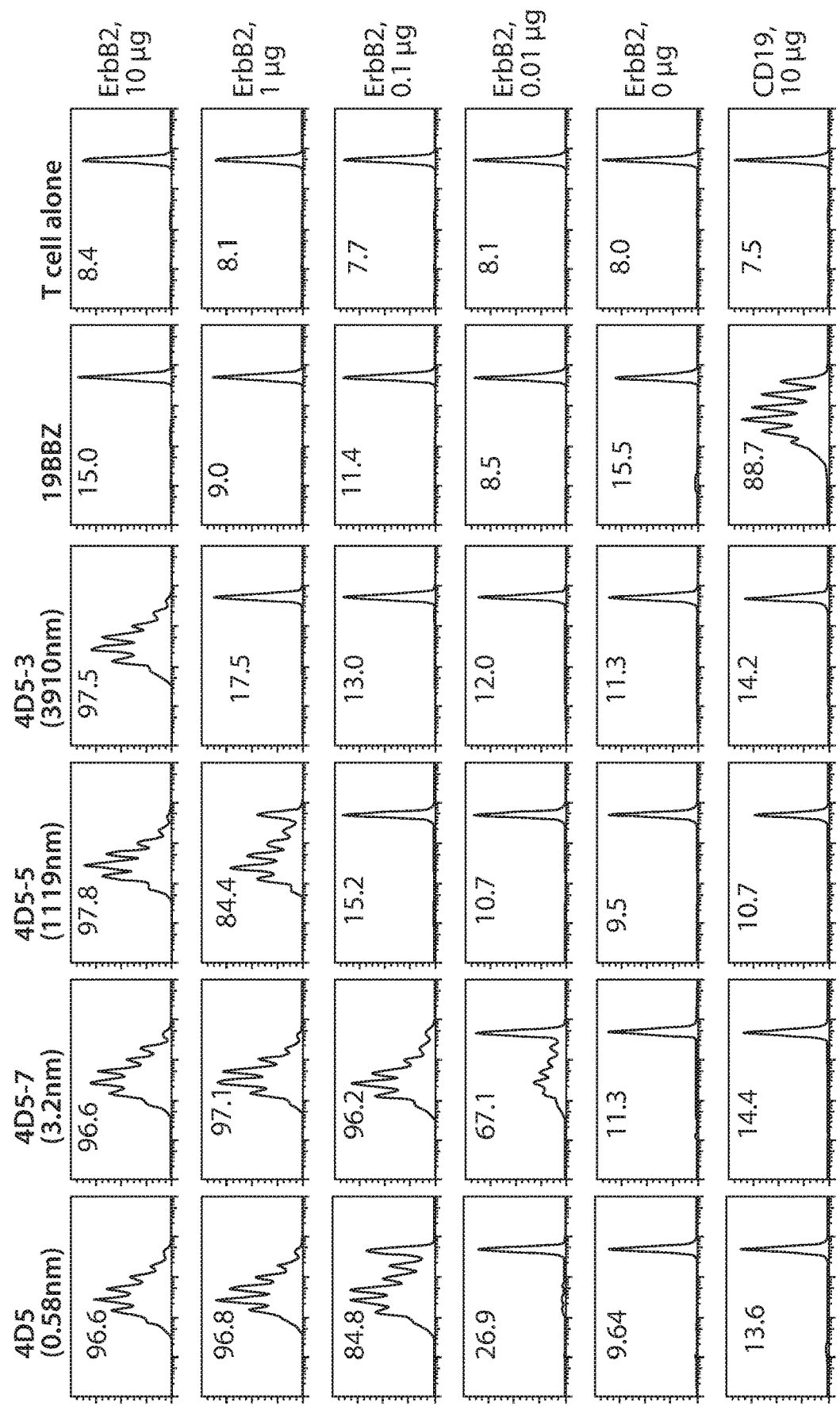
FIG. 12. Proliferation of the panel of affinity-tuned CAR T cells after stimulation by ErbB2 mRNA electroporated K562 cells. Resting T cells were labeled with CFSE and electroporated with 10 ug CAR mRNA. K562 cells were electroporated with the indicated 9 amount of ErbB2 mRNA or control CD19 mRNA (19BBBZ). The T cells and irradiated targets were cultured (1:1 ratio) for 7 days and CFSE dilution measured by flow cytometry (CD3 gated); the % divided T cells is shown.

To exclude any tumor-specific effects that might contribute to the above results, the activity of the panel of ErbB2-BBζ CAR T cells was assayed against a single tumor line expressing varying levels of ErbB2 (K562 cells electroporated with varying amounts of ErbB2 RNA). In agreement, it was observed that T cells expressing higher affinity scFvs (4D5 and 4D5-7) recognized K562 cells electroporated with ErbB2 RNA at doses as low as 0.001 μg, which is 100 fold lower than the flow cytometrically detectable level of 0.1 μg mRNA (FIGS. 10, 11A, and 11B). In contrast the CARs with lower affinity scFvs (4D5-5 and 4D5-3) only recognized K562 electroporated ErbB2 RNA at doses of 0.5 μg (4D5-5; 10) or higher, indicating that CAR T cell sensitivity was decreased by 2000-(4D5-3) to 500-fold (4D5-5) compared to the high affinity 4D5 CAR T cells. Moreover, the antigen dose associated reactivity observed with lower affinity ErbB2 CARs (4D5-5 and 4D5-3; FIGS. 11A and 11B), was confirmed by performing a CFSE-based proliferation assay (FIG. 12). Interestingly, decreasing the CAR RNA dose 5 fold (from 10 μg RNA/100 μl T cells to 2 μg RNA/100 μl T cells), further increased the antigen recognition threshold of the T cells with lower and high affinity CARs as assessed by cytokine secretion, suggesting that fine tuning of CAR density on the surface of the T cells is an important variable, or that doses above 2 μg of mRNA may have some toxicity on overall T cell activity.

Figure 13A:
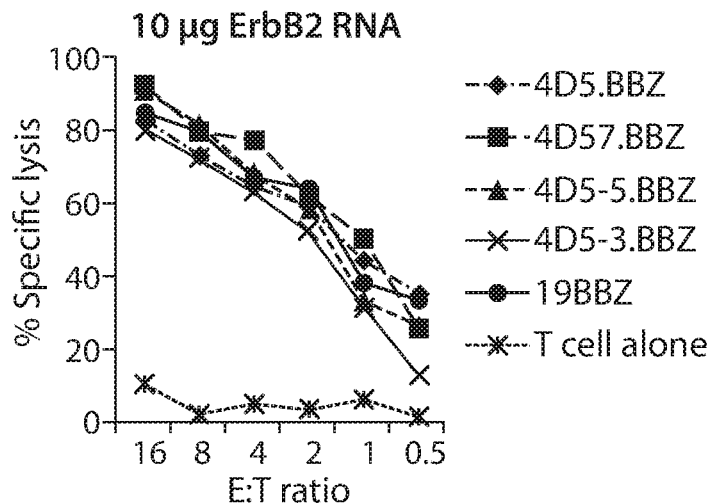
FIGS. 13A, 13B, and 13C. The cytotoxicity of the panel of CAR T cells against ErbB2 mRNA electroporated Nalm6-CBG target cells was measured. T cells were electroporated with ErbB2 or CD19 CAR mRNA as indicated. CD19+ve Nalm6-CBG (click beetle green) target cells were electroporated with ErbB2 mRNA at the indicated dose: 10 μg ErbB2 RNA (FIG. 13A); 1 μg ErbB2 RNA (FIG. 13B); and 0.1 μg ErbB2 RNA (FIG. 13C). One day after the electroporation, the CAR T cells were co-cultured with Nalm6-CBG cells at indicated E:T ratio and % specific lysis calculated after 8 hr.
Figure 13B:
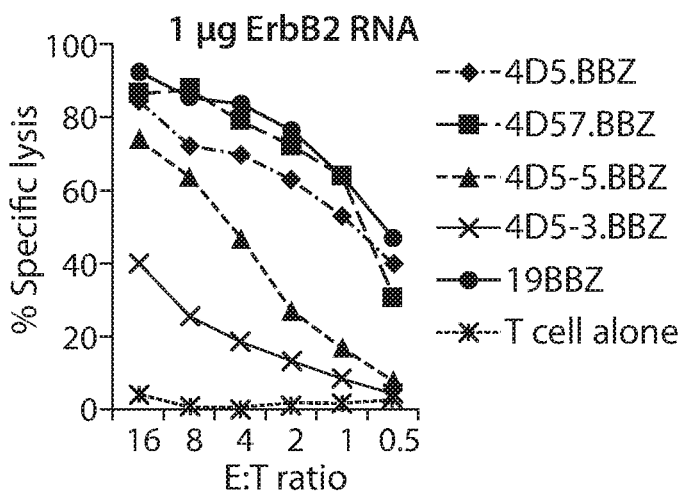
Figure 13C:
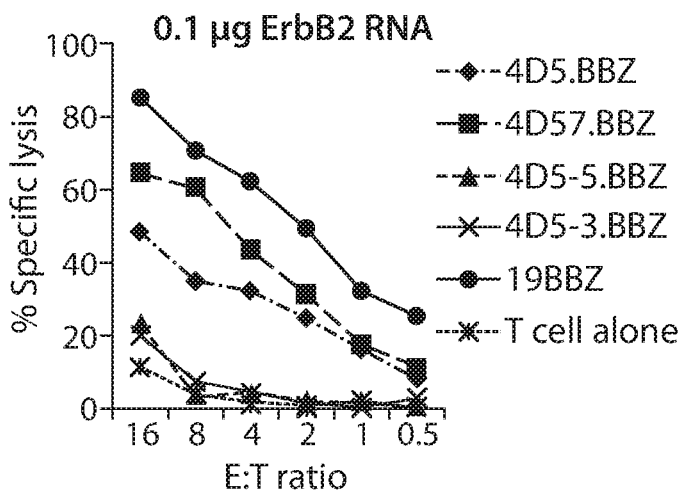

A luciferase based cytolytic T cell (CTL) assay was used to determine whether T cells with affinity decreased CARs could maintain potent killing activity against ErbB2 over expressing targets while sparing cells expressing lower ErbB2 levels. When Nalm6 target cells were transfected with 10 μg ErbB2 RNA, T cells with either higher or lower affinity ErbB2 CARs effectively lysed target cells (FIG. 13A). CARs with higher affinity scFv (4D5 and 4D5-7) exhibit potent lytic activity against target cells transfected with 1 μg ErbB2 RNA, but lower affinity scFvs (4D5-5 and 4D5-3) showed decreased killing activity (FIG. 13B). Finally, only CARs with higher affinity scFvs were able to kill target cells expressing very low amounts of target after electroporation with 0.1 μg ErbB2 RNA (FIG. 13C). Since Nalm6 is a CD19 positive cell line, CART 19 maintained cytolytic activity independent of levels of transfected ErbB2 RNA. These data indicate that that fine-tuning the affinity of ErbB2 CAR T cells enhances discrimination of ErbB2 over-expressing tumor from tumor cells that have low or undetectable levels of ErbB2 expression.

Affinity Decreased ErbB2 CAR T Cells Fail to Recognize Physiological Levels of ErbB2

Figure 14:
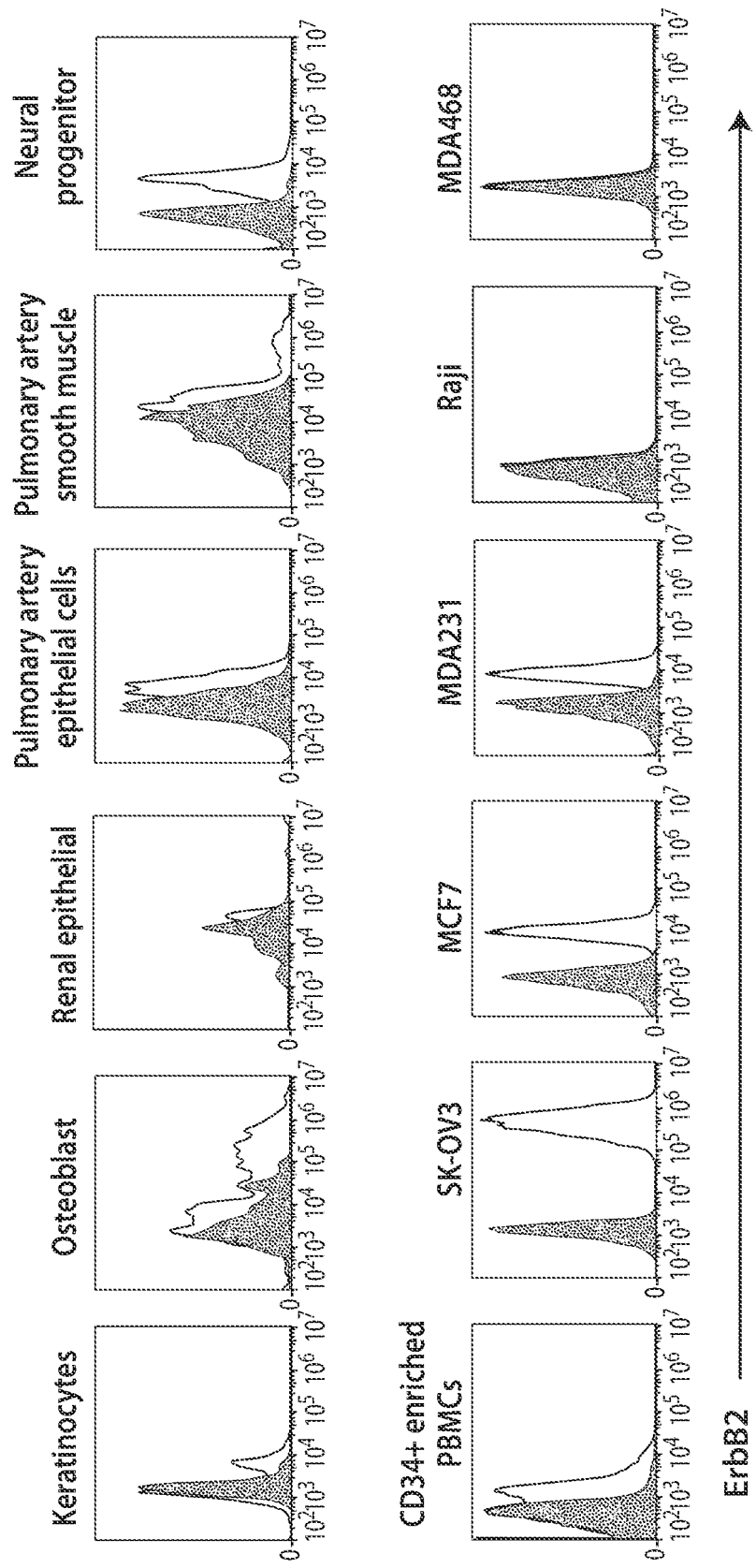
FIG. 14. ErbB2 expression in the indicated primary cell lines. The primary cell lines were stained using anti-ErBb2 Affibody-biotin and detected using streptavidin-allophycocyanin (APC) (open histograms); cells stained with APC only were used as control (grey histograms).
Figure 15:
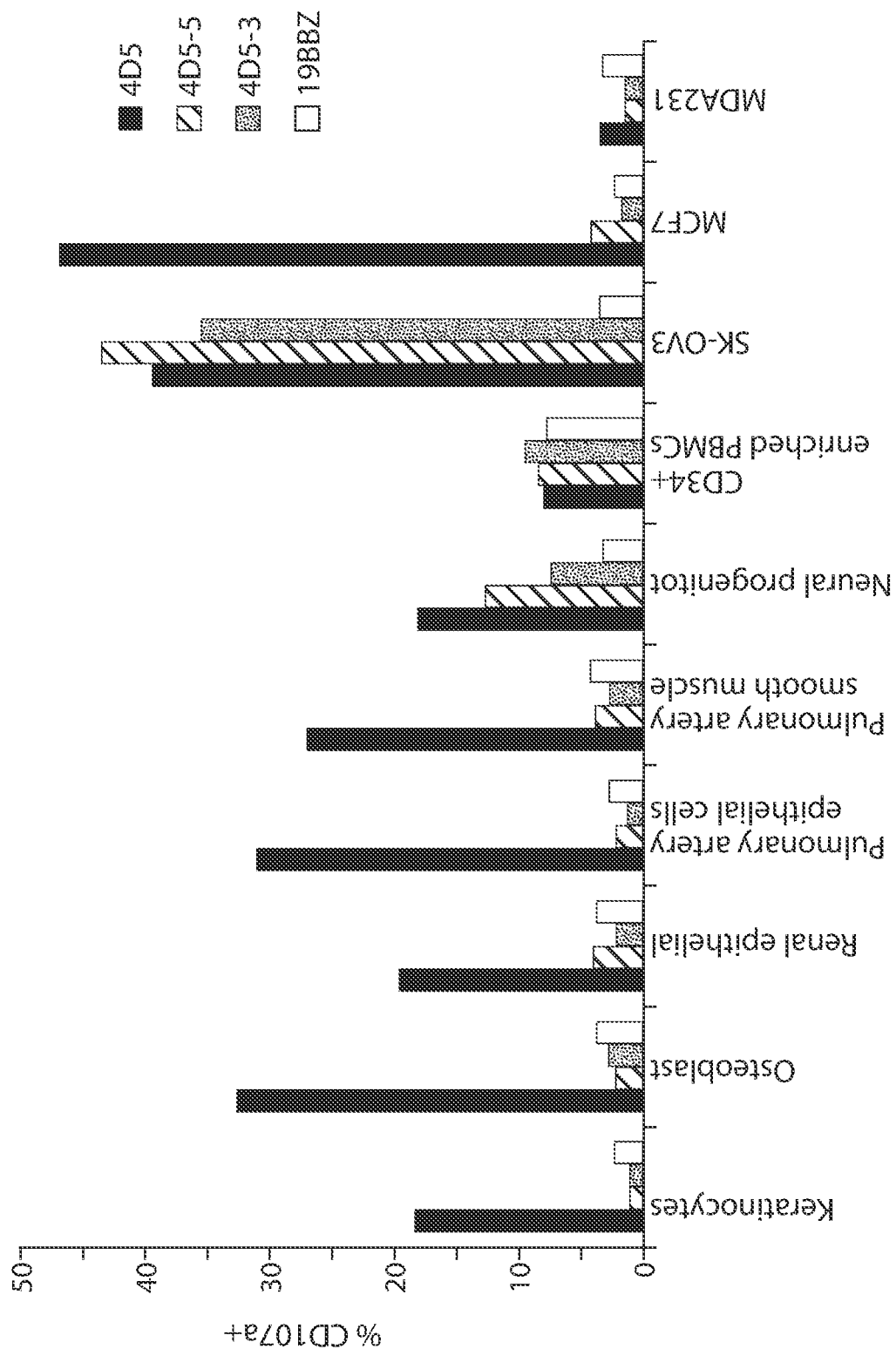
FIG. 15. Selective targeting of ErbB2 on primary cell lines. The panel of CAR T cells was stimulated with the indicted primary cell lines for 4 h and the % of CAR T cells expressing CD107a was measured by gating on CD3+CD8+ cells.

Given the previous serious adverse event which occurred upon administration of the high affinity ErbB2 CAR that incorporated the scFv from the parental 4D5 trastuzumab antibody (Morgan et al., 2010, *Mol Therapy*, 18:843), it is of paramount importance to evaluate potential reactivity of the reduced affinity ErbB2 CAR T cells to physiological levels of ErbB2 expression. To address this, seven primary cell lines isolated from different organs were tested for ErbB2 expression. Most of the primary lines had detectable levels of surface ErbB2, with the neural progenitor line expressing the highest levels of ErbB2 (FIG. 14). T cells expressing the high affinity 4D5 CAR were strongly reactive to all primary lines tested, as evidenced by levels of CD107a up-regulation (FIG. 15). However, T cells expressing the affinity decreased ErbB2 CARs 4D5-5 and 4D5-3 exhibited no reactivity to the primary lines with the exception of weak reactivity to the neural progenitor line. These results were confirmed by analysis of a larger panel of cell lines that had low or undetectable levels of ErbB2 by flow cytometry (FIGS. 8 and 9).

Figure 16A:
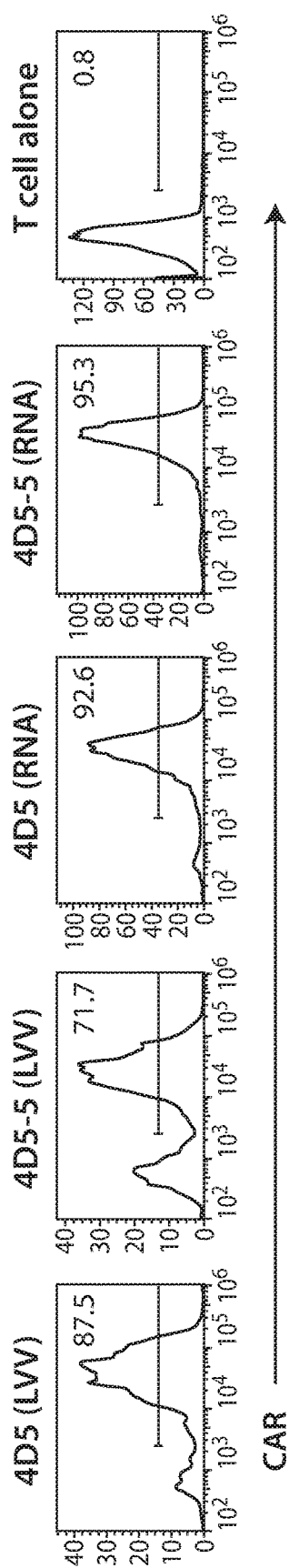
FIGS. 16A, 16B, and 16C. T cells were modified with high (4D5) or low (4D5-5) affinity ErbB2 CAR using lentiviral transduction (LVV) or mRNA electroporation (RNA) as indicated. The % CAR expression and brightness was measured using ErbB2-Fc (FIG. 16A). ErbB2 expression on a panel of tumor lines and K562 cells electroporated with ErbB2 mRNA was detected by flow cytometry (FIGS. 16B and 16C); percentage cells+ cells and (MFI) shown for K562 cells.
Figure 16B:
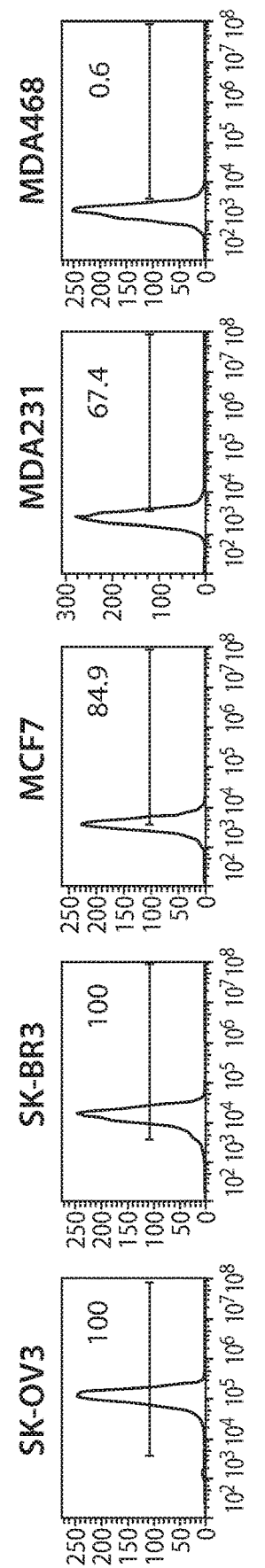
Figure 16C:
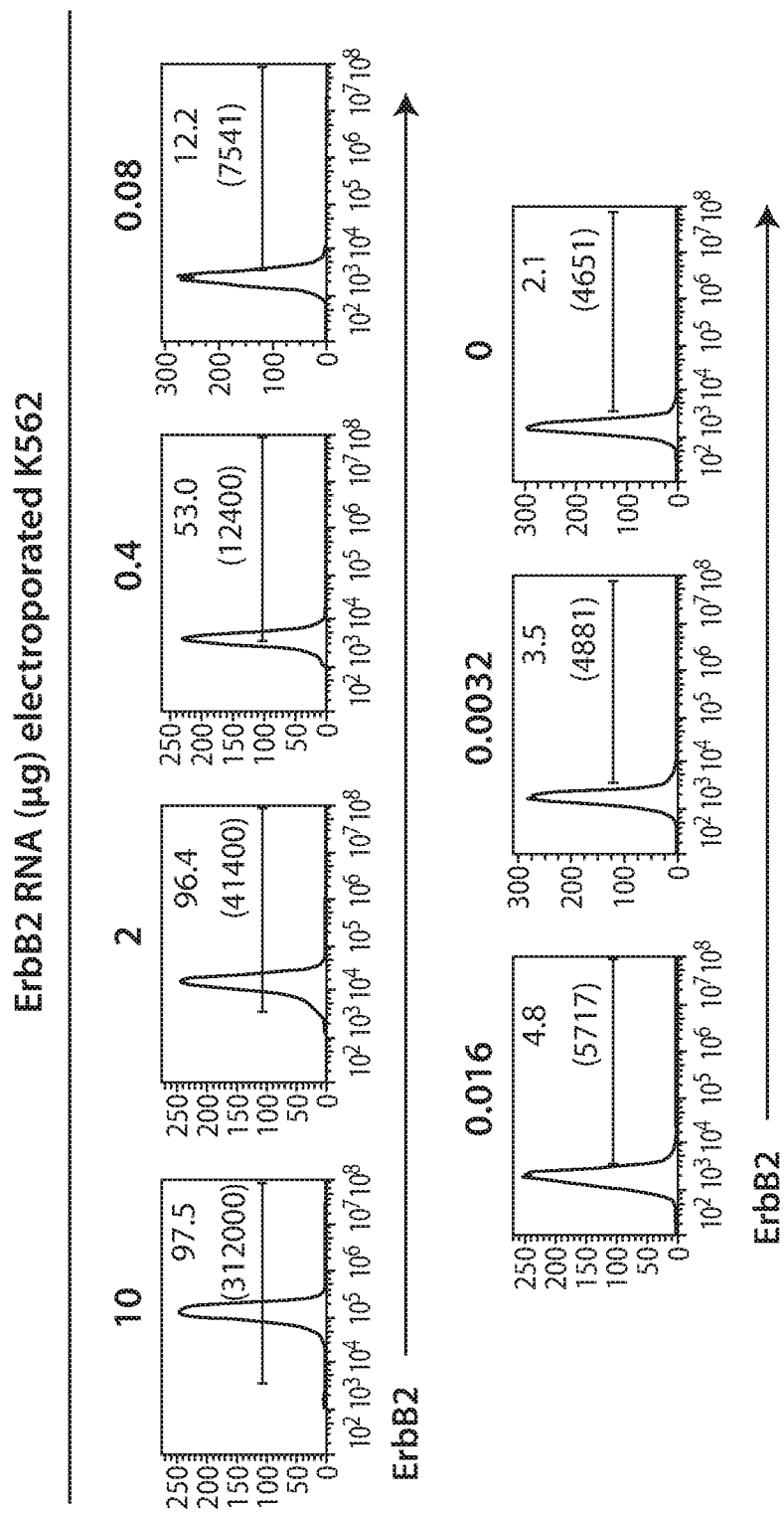
Figures 1, 17:
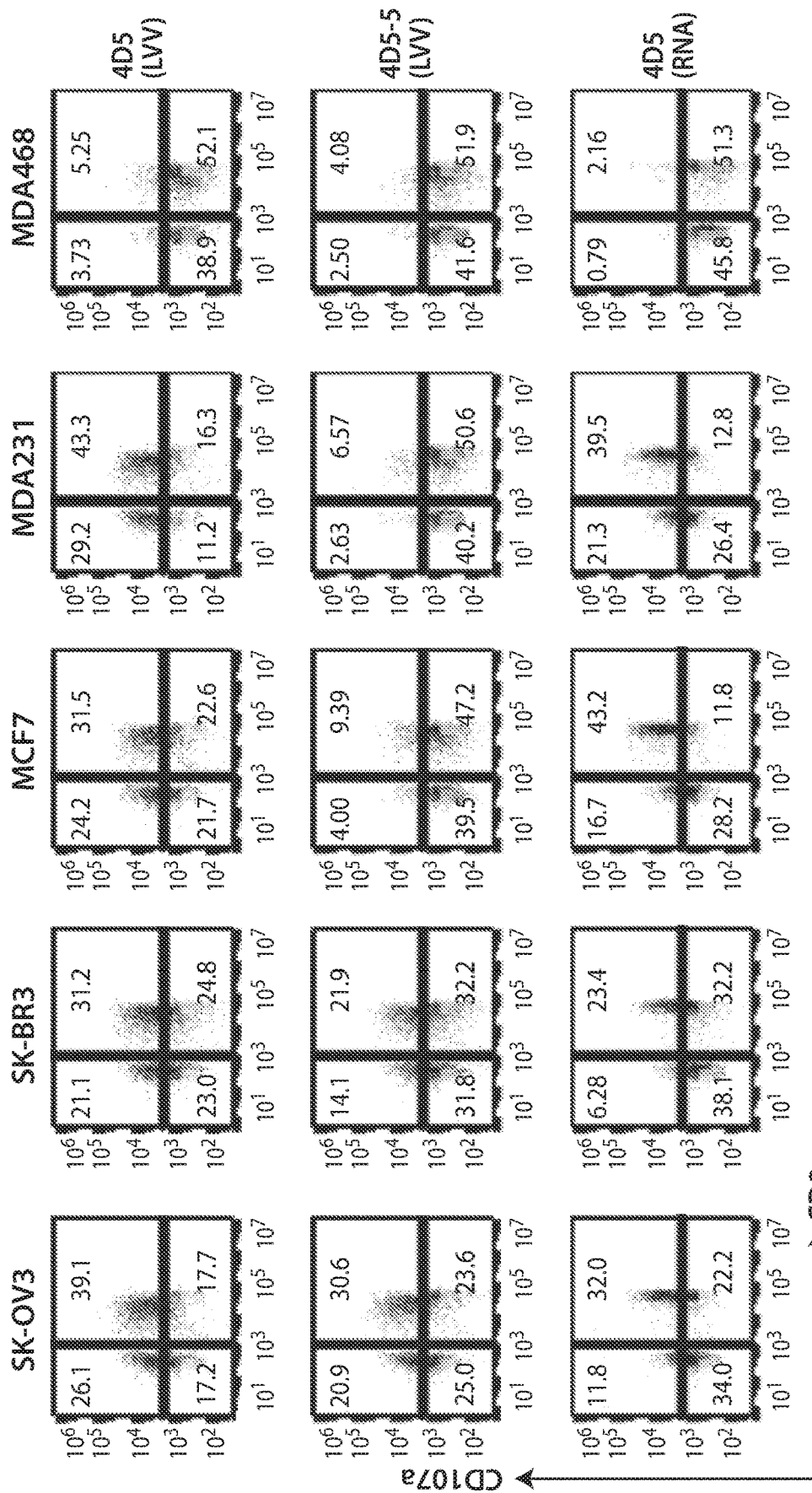
FIG. 17. CAR T cell recognition of the indicated tumor lines. CD107a up-regulation was measured on lentiviral transduced or mRNA electroporated CAR T cells after 4 hr stimulation with indicated tumor lines (gated on CD3+ cells).
Figures 2, 17:
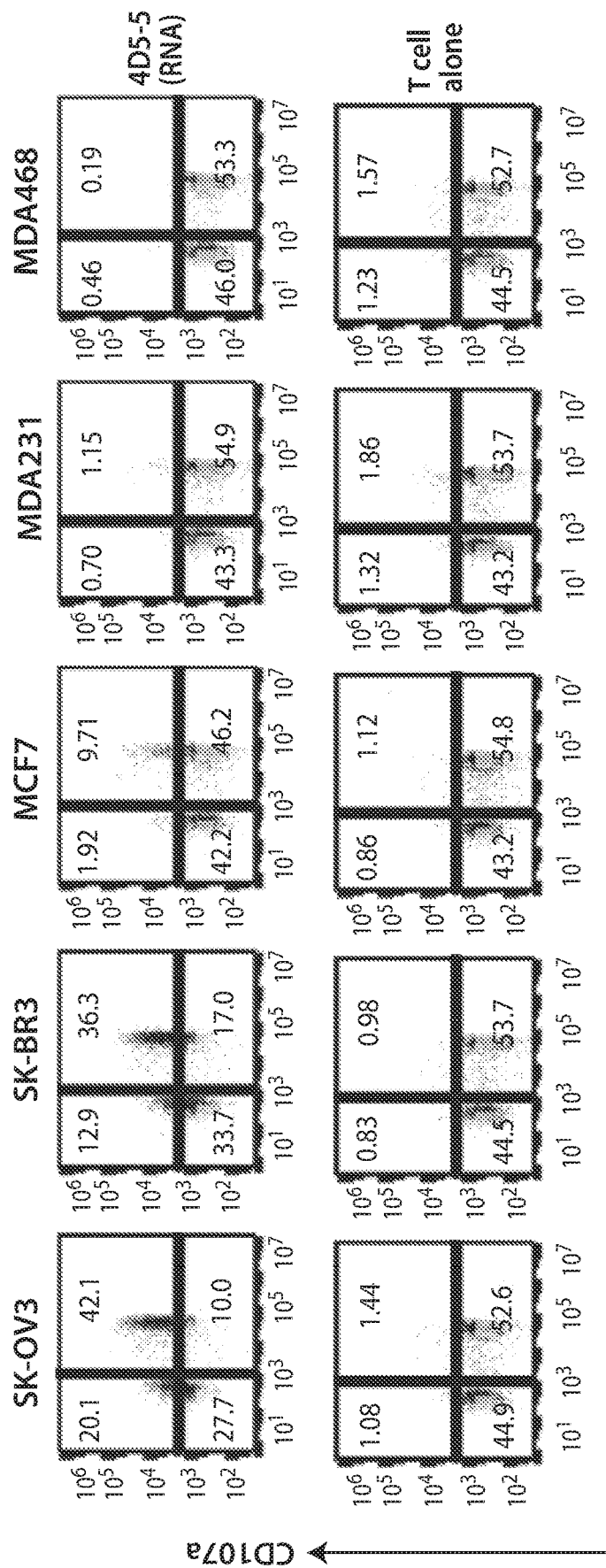
Figures 1, 18:
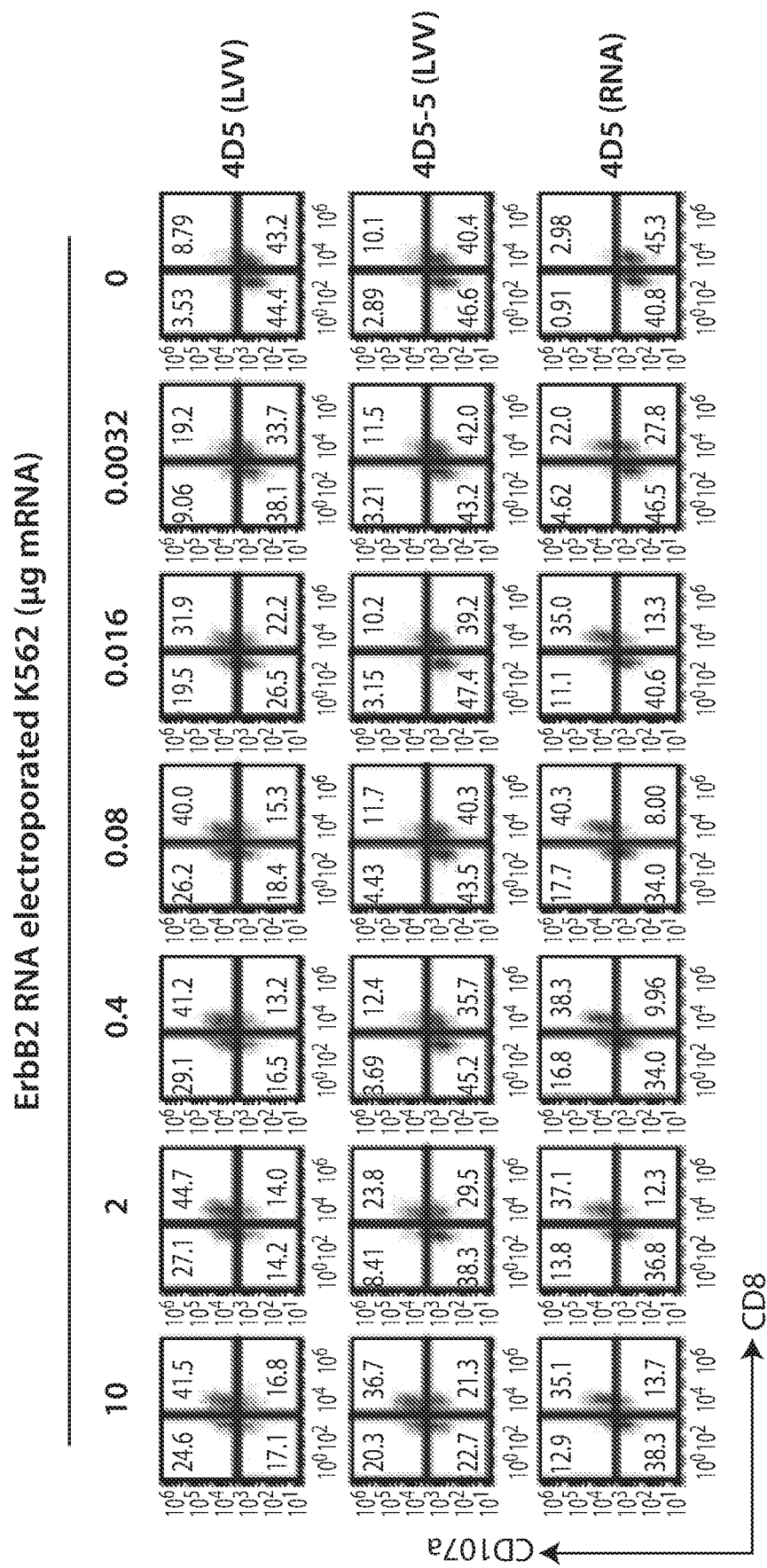
FIG. 18. CAR T cell recognition of the K562 cells electroporated with the indicated amounts of ErbB2 mRNA. Induction of CD107a expression was measured on lentiviral transduced or mRNA electroporated CAR T cells after 4 hr stimulation with ErbB2 electroporated K562 cells by gating on CD3+ cells.
Figures 2, 18:
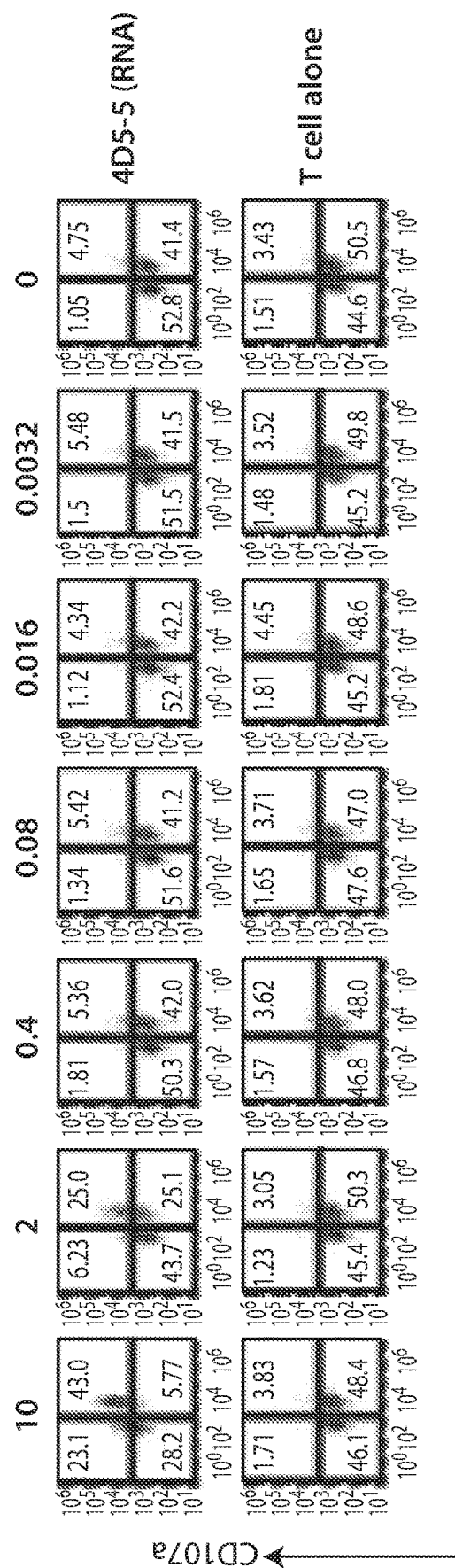
Figures 1, 19:
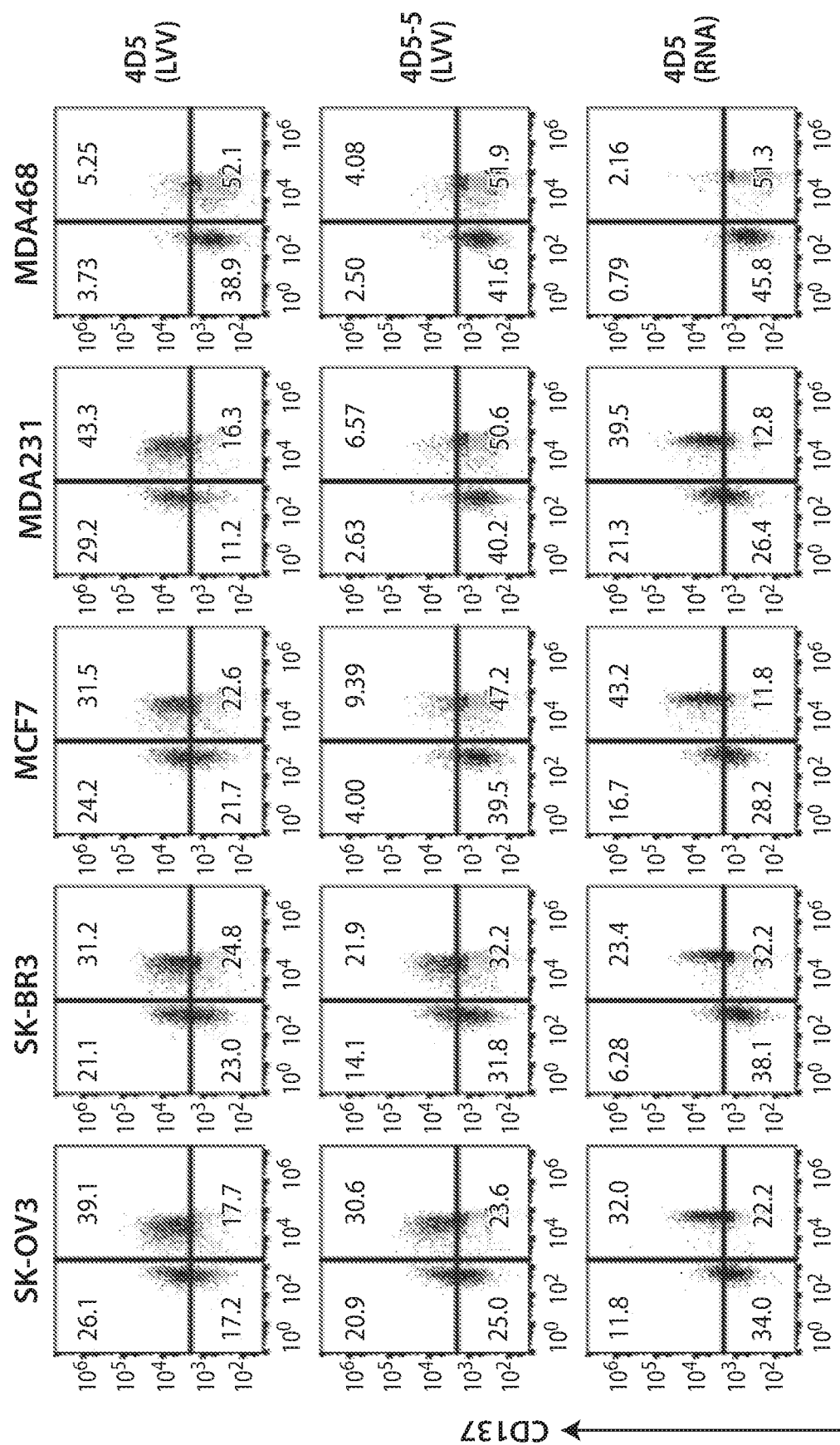
FIG. 19. ErbB2 target dependent upregulation of CD107a on lentiviral transduced or mRNA electroporated T cells. T cells as shown in main text FIG. 4A were stimulated 4 hr with tumor cell lines expressing ErbB2 at levels varying from over-expressed to low levels. CD107a up-regulation was detected by flow cytometry (CD3+ gated).
Figures 2, 19:
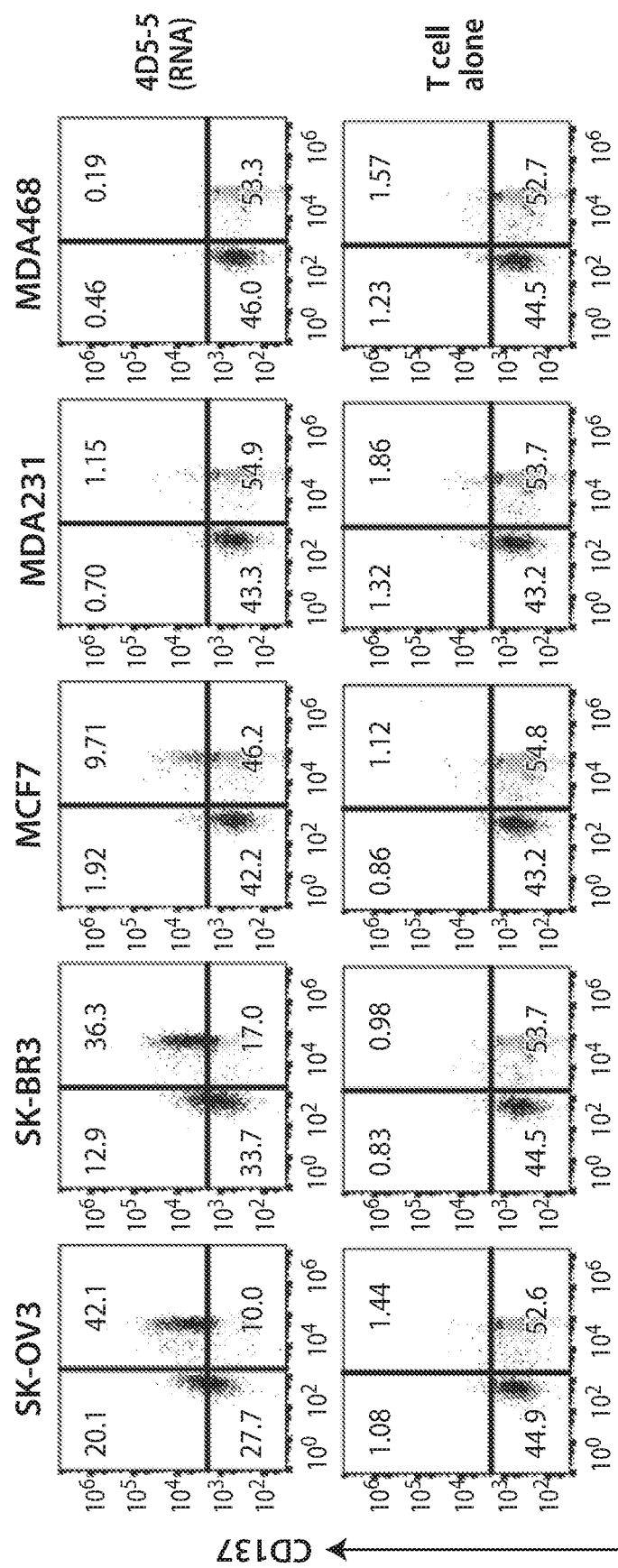
Figure 20:
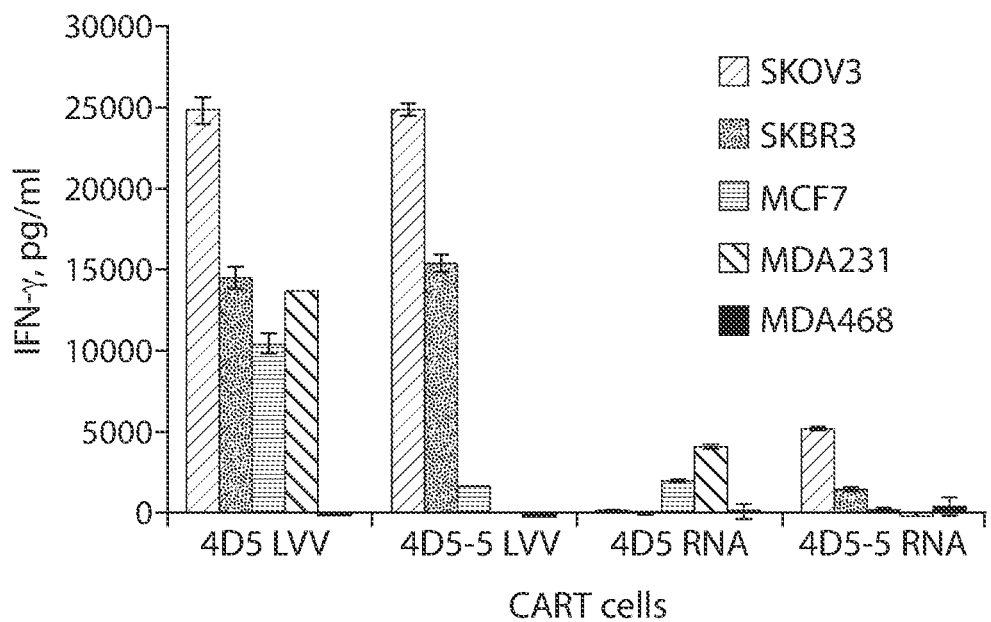
FIG. 20. IFN-gamma secretion by lentiviral transduced or RNA electroporated CAR T cells was measured by ELISA after 18 hr.
Figure 21:
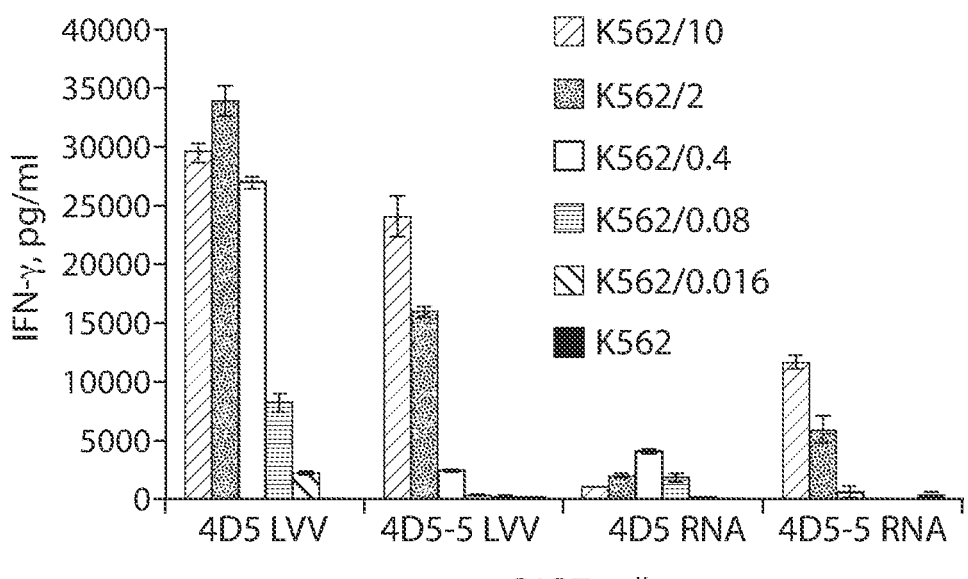
FIG. 21. IFN-gamma production by CAR T cells measured 18 hr after stimulation with K562 cells electroporated with indicated amount of ErbB2 mRNA.

Comparable Effects with Affinity-Tuned ErbB2 CARs Expressed Using Lentiviral Transduction or RNA Electroporation To establish comparability between T cells permanently expressing CARs by lentiviral transduction with mRNA electroporated CAR T cells, the panel of affinity-tuned CARs was expressed in T cells from the same normal donor using either lentiviral transduction or mRNA electroporation (FIG. 16A). T cells were stimulated with tumor cell lines (FIG. 16B), or K562 cells, expressing varying amounts of ErbB2 (FIG. 16C). CAR T cell recognition and activation was monitored by CD107a upregulation (FIGS. 17 and 18), CD137 upregulation (FIG. 19) and IFN-γ secretion (FIGS. 20 and 21). In agreement with the previous ErbB2 mRNA CAR T cell results, T cells that constitutively expressed high affinity CARs showed strong reactivity to all cell lines expressing ErbB2; no correlation was observed between antigen expression levels and T cell-activity. In contrast, T cells with low affinity CARs expressed by lentiviral technology demonstrated a robust correlation between target antigen expression and activation (FIGS. 17, 18, 20, and 21). These results confirm that the sensitivity of ErbB2 antigen recognition is dependent on scFv affinity using both mRNA electroporated and lentiviral transduced CAR T cells.

Affinity Decreased ErbB2 CAR T Cells Eliminate Tumor In Vivo and Ignore Tissues Expressing Physiological Levels of ErbB2

Figure 22:
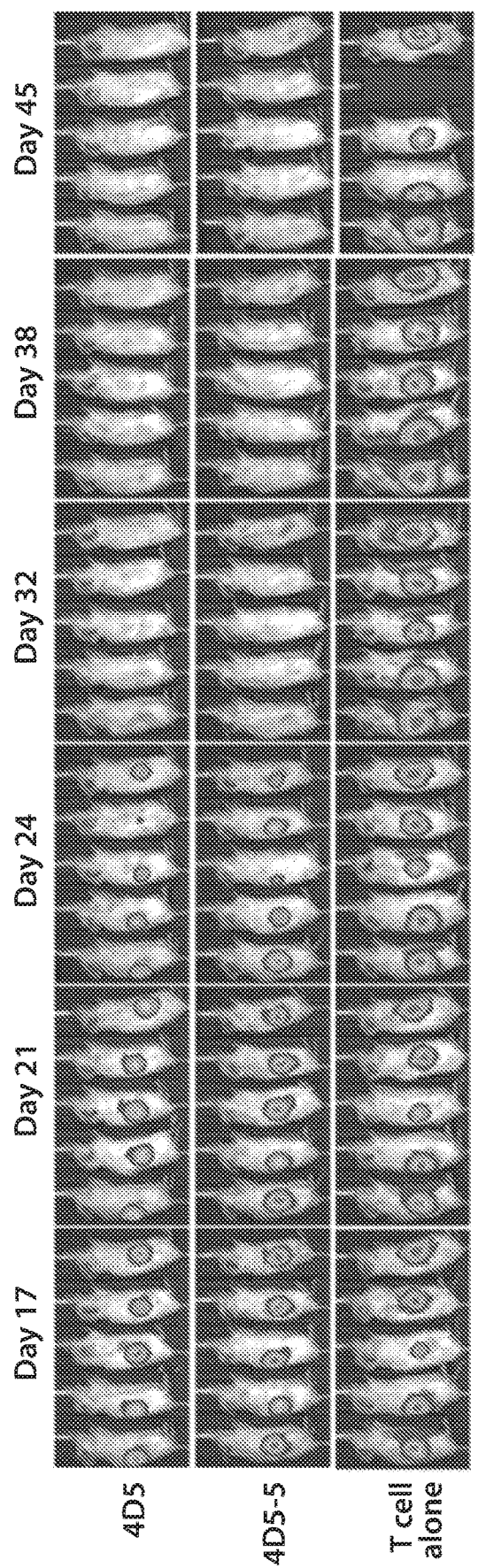
FIG. 22. Regression of advanced vascularized tumors in mice treated by affinity tuned ErbB2 CAR T cells. Flank tumors were established by injection of $5 \times 10^6$ SK-OV3-CBG (s.c.) in NOD-SCID-γ−/− (NSG) mice (n=5). Eighteen days after tumor inoculation, mice were randomized to equalize tumor burden and treated with $1 \times 10^7$ lentivirally transduced T cells expressing either higher affinity (4D5.BBZ) or lower affinity (4D5-5.BBZ) CAR. Mice treated with non-transduced T cells (T Cell Alone) served as controls. Animals were imaged at the indicated time points post tumor inoculation.

To extend the above in vitro results, a series of experiments were conducted in NSG mice with advanced vascularized tumor xenografts. Based on data above in FIG. 1, the human ovarian cancer cell line SK-OV3 was selected as a representative ErbB2 over-expressing tumor and PC3, a human prostate cancer line, was chosen to model normal tissue ErbB2 levels. The antitumor efficacy of ErbB2 CAR T cells expressing either the high affinity 4D5 scFv or the low affinity 45D-5 scFv in NSG mice was compared with day 18 established flank SK-OV3 tumors (FIG. 22). Serial bioluminescence imaging revealed that both the high and low affinity CAR T cells resulted in the rapid elimination of the tumors.

Figure 23:
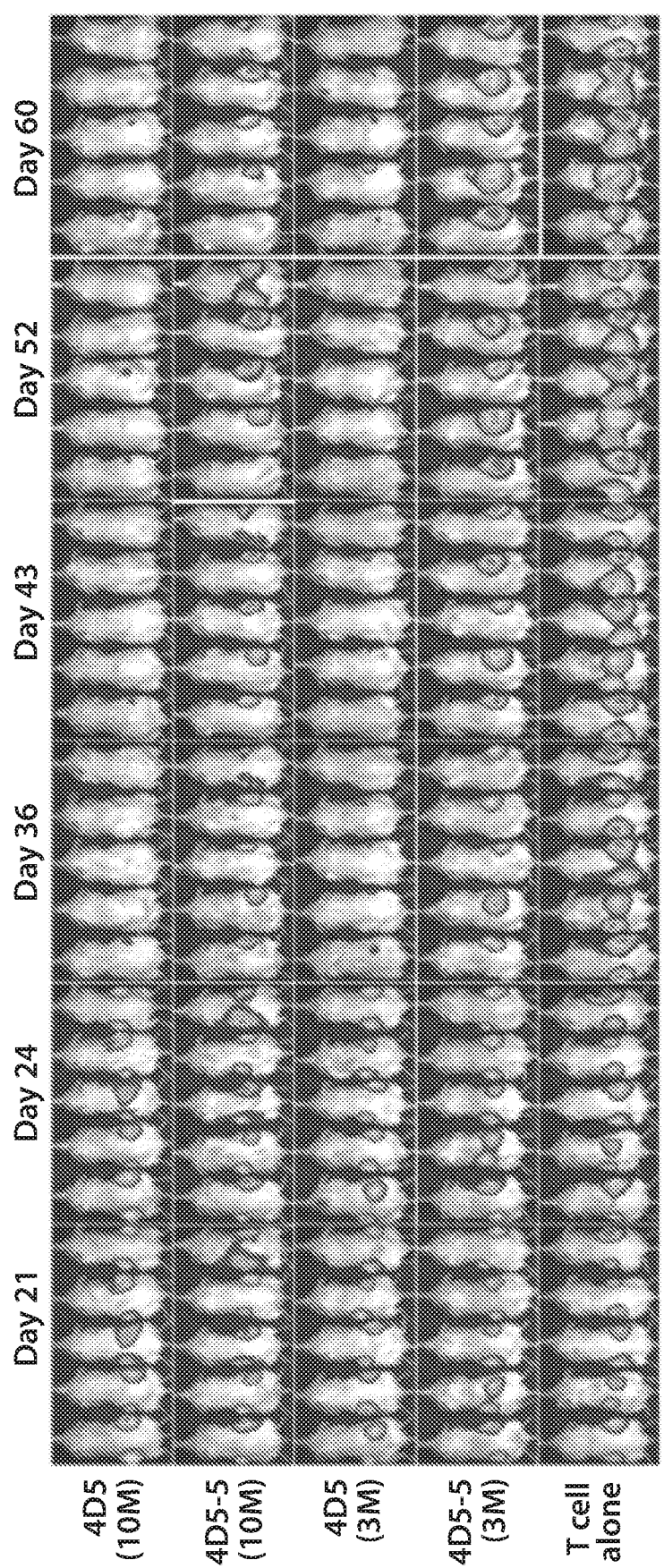
FIG. 23. In vivo discrimination of high ErbB2 (SK-OV3) and low ErbB2 (PC3) expressing tumors by affinity tuned CARs. T cells modified with different affinity ErbB2 CARs by lentiviral transduction were tested in dual-tumor engrafted NSG mice. Mice were implanted with PC3-CBG tumor cells (1e6 cells/mouse, s.c.) on the right flank on day 0. On day 5 the same mice were given SK-OV3-CBG tumor cells (5e6 cells/mouse, s.c.) on the left flank. The mice were treated with T cells (i.v.) on at day 23 after PC3 tumor inoculation. CAR T cells were given as a single injection of 10e6/mouse (10M), or 3e6/mouse (3M) as indicted. Mice treated with non-transduced T cells served as control. Animals were imaged at the indicated time post PC3 tumor inoculation.
Figure 24:
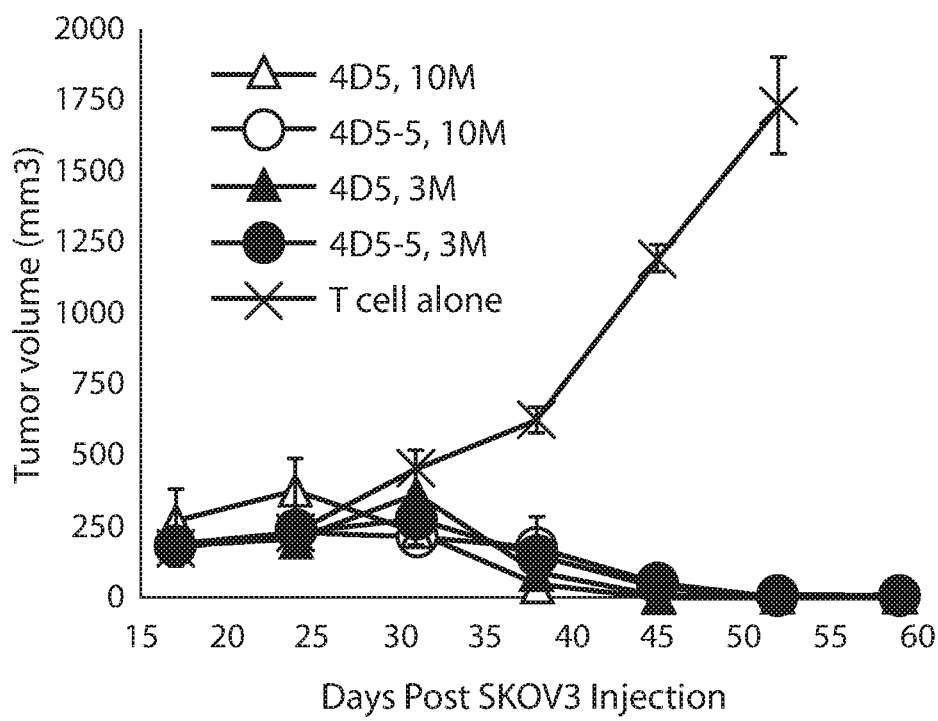
FIG. 24. SK-OV3 tumor size in dual-tumor grafted NSG mice treated with the indicated affinity tuned ErbB2 CARs. SK-OV3 tumor sizes were measured over time (days, x-axis), and the tumor volume was calculated and plotted ($mm^3$, y-axis).
Figure 25:
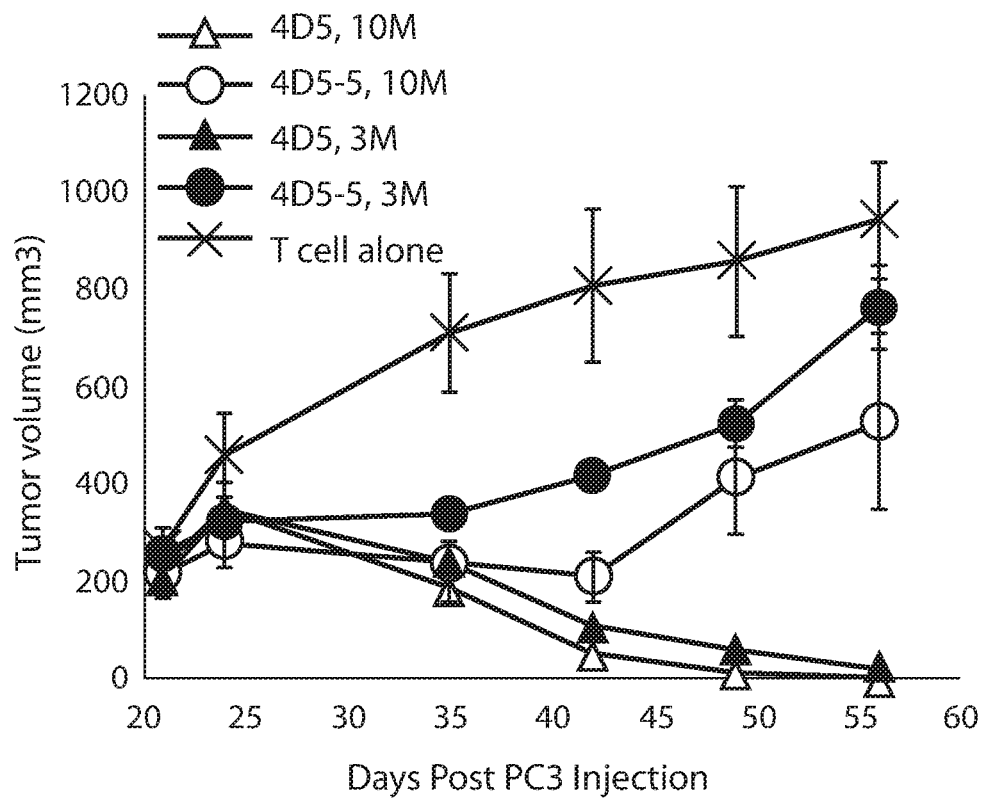
FIG. 25. PC3 tumor sizes in the dual-tumor grafted NSG mice treated with the indicated affinity tuned ErbB2 CARs. PC3 tumor sizes were measured over time (days, x-axis), and the tumor volume was calculated and plotted ($mm^3$, y-axis).

To further evaluate the therapeutic index of the low affinity ErbB2 CAR T cells in vivo, a mouse model was designed to simultaneously compare the efficacy and normal tissue toxicity of the high affinity (4D5:BBζ) and low affinity (4D5-5:BBζ) ErbB2 CARs. SK-OV3 and PC3 tumor cell lines were injected subcutaneously into opposite flanks of the same NSG mouse and T cells were administered when tumor volumes reached approximately 200 mm$^3$. Mice were injected (i.v.) with either $3 \times 10^6$ or $1 \times 10^7$ CAR T cells on day 22 and serial bioluminescence imaging and tumor size assessments were conducted. Mice treated with either dose of the CAR T cells exhibited nearly complete regression of the ErbB2 overexpressing SK-OV3 tumor (FIGS. 23, 24, and 25). In addition, almost complete regression of the PC3 tumor expressing ErbB2 at low levels on the opposite flank was also seen for the mice treated with high affinity 4D5-based CAR T cells. In contrast, the progressive tumor growth of PC3 was observed in the mice treated with low affinity 4D5-5-based CAR T cells, indicating that whereas the lower affinity CAR T cells were efficacious against ErbB2 overexpressing tumor, they show limited or no detectable reactivity against cells expressing ErbB2 at physiological levels. Moreover, the selective tumor elimination was observed in mice treated at both high and low doses of CAR T cells. The above effects were not due to allorecognition because progressive tumor growth of both tumors was observed in mice treated with mock transduced T cells.

Affinity-Tuning of scFv Increases the Therapeutic Index of EGFR CAR T Cells

To test the broader applicability the strategy to fine tune the affinity of the scFv, we evaluated a panel of EGFR CARs. EGFR:BBz CARs were constructed from scFvs derived from the parental human anti-EGFR antibody C10 (Heitner et al., 2001, *J Immunol Methods*, 248:17-30. The nucleic acid sequences encoding the EGFR CARs are provided in Table 12.

TABLE 12

Nucleic Acid Sequences of Exemplary EGFR CARs

| CAR designation | Nucleic Acid Sequence | SEQ. ID NO: |
|---|---|---|
| C10-BBZ | atg ggt tgg tcg tgc att atc ctc ttc ctc gtc gca acc gct acc ggc gtt cac tcg gat tac aag gat gac gac gac aaa gag gta cag ctg gtg cag agc ggg gcc gag gtt aag aag ccc ggg tct tcc gta aag gtg tcc tgc aag gcc tcg ggg ggc aca ttc tca tcg tac gca ata tcg tgg gtg cgg cag gcc ccc ggg cag ggg ctg gaa tgg atg ggc gga att atc cca atc ttc ggg acc gcc aac tat gcc cag aag ttt cag ggt cgt gtg acc att act gcc gac gag tcc acc agt acg gcc tac atg gag ctg agt agt ctg cgt agc gag gat act gcc gtt tat tat tgc gcc cgg gaa gag gga ccg tac tgc tcg tcg acc tca tgt tac ggc gcc ttc gac atc tgg ggc caa ggc acc ctg gtg acg gtg tcc tcc ggt ggt ggc gga agt ggc ggc ggg ggg tcc ggc ggg ggc ggt tca cag tcc gtc ctg acc cag gat ccc gcg gtg tcg gtc gcg ctg ggt cag aca gta aag ata aca tgc cag ggc gat tct ctg cgc agt tat ttc gcc tcg tgg tac cag cag aaa ccc ggc cag gct cct acc ctt gtt atg tac gcg cgc aat gac aga ccc gcg ggc gtg ccc gac cgc ttc tcc ggc tca aag agc ggg acc tcc gcc tcc ctg gcc atc tcc ggg ctc cag tct gag gat gag gcc gat tac tac tgc gct gct tgg gac gac tcc ctc aat ggc tat ctg ttt ggc gca ggc aca aag ctg acc gtg ctc acc acg acg cca gcg ccg cga cca cca aca ccg gcg ccc acc atc gcg tcg cag ccc ctg tcc ctg cgc cca gag gcg tgc cgg cca gcg gcg ggg ggc gca gtg cac acg agg ggg ctg gac ttc gcc tgt gat atc tac atc tgg gcg ccc ttg gcc ggg act tgt ggg gtc ctt ctc ctg tca ctg gtt atc acc ctt tac tgc aaa cgg ggc aga aag aaa ctc ctg tat ata ttc aaa caa cca ttt atg aga cca gta caa act act caa gag gaa gat ggc tgt agc tgc cga ttt cca gaa gaa gaa gaa gga gga tgt gaa ctg aga gtg aag ttc agc agg agc gca gac gcc ccc gcg tac aag cag ggc cag aac cag ctc tat aac gag ctc aat cta gga cga aga gag gag tac gac gtt ttg gac aag aga cgt ggc cgg gac cct gag atg ggg gga aag ccg aga agg aag aac cct cag gaa ggc ctg tac aat gaa ctg cag aaa gat aag atg gcg gag gcc tac agt gag att ggg atg aaa ggc gag cgc cgg agg ggc aag ggg cac gat ggc ctt tac cag ggt ctc agt aca gcc acc aag gac acc tac gac gcc ctt cac atg cag gcc ctg ccc cct cgc taa | 270 |
| 2224-BBZ | atg ggt tgg tcg tgc att atc ctc ttc ctc gtc gca acc gct acc ggc gtt cac tcg gat tac aag gat gac gac gac aaa gag gta cag ctg gtg cag agc ggg gcc gag gtt aag aag ccc ggg tct tcc gta aag gtg tcc tgc aag gcc tcg ggg ggc aca ttc tca tcg tac gca ata ggt tgg gtg cgg cag gcc ccc ggg cag ggg ctg gaa tgg atg ggc gga att atc cca atc ttc ggg atc gcc aac tat gcc cag aag ttt cag ggt cgt gtg acc att act gcc gac gag tcc acc agt agt gcc tac atg gag ctg agt agt ctg cgt agc gag gat act gcc gtt tat tat tgc gcc cgg gaa gag gga ccg tac tgc tcg tcg acc tca tgt tac gca gcc ttc gac atc tgg ggc caa ggc acc ctg gtg acg gtg tcc tcc ggt ggt ggc gga agt ggc ggc ggg ggg tcc ggc ggg ggc ggt tca cag tcc gtc ctg acc cag gat ccc gcg gtg tcg gtc gcg ctg ggt cag aca gta aag ata aca tgc cag ggc gat tct ctg cgc agt tat ttc gcc tcg tgg tac cag cag aaa ccc ggc cag gct cct acc ctt gtt atg tac gcg cgc aat gac aga ccc gcg ggc gtg ccc gac cgc ttc tcc ggc tca aag agc ggg acc tcc gcc tcc ctg gcc atc tcc ggg ctc cag ccc gag gat gag gcc gat tac tac tgc gct gct tgg gac gac tcc ctc aat ggc tat ctg ttt ggc gca ggc aca aag ctg acc gtg ctc acc acg acg cca gcg ccg cga cca cca aca ccg gcg ccc acc atc gcg tcg cag ccc ctg tcc ctg cgc cca gag gcg tgc cgg cca gcg gcg ggg ggc gca gtg cac acg agg ggg ctg gac ttc gcc tgt gat atc tac atc tgg gcg ccc ttg gcc ggg act tgt ggg gtc ctt ctc ctg tca ctg gtt atc acc ctt tac tgc aaa cgg ggc aga aag aaa ctc ctg tat ata ttc aaa caa cca ttt atg aga cca gta caa act act caa gag gaa gat ggc tgt agc tgc cga ttt cca gaa gaa gaa gaa gga gga tgt gaa ctg aga gtg aag ttc agc agg agc gca gac gcc ccc gcg tac aag cag ggc cag aac cag ctc tat aac gag ctc aat cta gga cga aga gag gag tac gac gtt ttg gac aag aga cgt ggc cgg gac cct gag atg ggg gga aag ccg aga agg aag aac cct cag gaa ggc ctg tac aat gaa ctg cag aaa gat aag atg gcg gag gcc tac agt gag att ggg atg aaa ggc gag cgc cgg agg ggc aag ggg cac gat ggc ctt tac cag ggt ctc agt aca gcc acc aag gac acc tac gac gcc ctt cac atg cag gcc ctg ccc cct cgc taa | 171 |
| 3524-BBZ | atg ggt tgg tcg tgc att atc ctc ttc ctc gtc gca acc gct acc ggc gtt cac tcg gat tac aag gat gac gac gac aaa gag gta cag ctg gtg cag agc ggg gcc gag gtt aag aag ccc ggg tct tcc gta aag gtg tcc tgc aag gcc tcg ggg ggc aca ttc tca tcg tac gca ata tcg tgg gtg cgg cag gcc ccc ggg cag ggg ctg gaa tgg | 272 |

TABLE 12-continued

Nucleic Acid Sequences of Exemplary EGFR CARs

| CAR designation | Nucleic Acid Sequence | SEQ. ID NO: |
|---|---|---|
| | gtc ggc gga att atc cca atc ttc ggg acc gcc aac tat gcc cag aag ttt cag ggt<br>cgt gtg aag att act gcc gac gag tcc gca agt acg gcc tac atg gag ctg agt<br>agt ctg cgt agc gag gat act gcc gtt tat tat tgc gcc cgg gaa gag gga ccg tac<br>tgc tcg tcg acc tca tgt tac gca gcc ttc gac atc tgg ggc caa ggc acc ctg gtg<br>acg gtg tcc tcc ggt ggt ggc gga agt ggc ggc ggg ggg tcc ggc ggg ggc ggt<br>tca cag tcc gtc ctg acc cag gat ccc gcg gtg tcg gtc gcg ctg ggt cag aca gta<br>aag ata aca tgc cag ggc gat tct ctg cgc agt tat ctg gcc tcg tgg tac cag cag<br>aaa ccc ggc cag gct cct acc ctt gtt acc tac gcg cgc aat gac aga ccc gcg<br>ggc gtg ccc gac cgc ttc tcc ggc tca aag agc ggg acc tcc gcc tcc ctg gcc atc<br>tcc ggg ctc cag tct gag gat gag gcc gat tac tac tgc gct gct tgg gac gac tcc<br>ctc aat ggc tat ctg ttt ggc gca ggc aca aag ctg acc gtg ctc acc acg cca<br>gcg ccg cga cca cca aca ccg gcg ccc acc atc gcg tcg cag ccc ctg tcc ctg<br>cgc cca gag gcg tgc cgg cca gcg gcg ggg ggc gca gtg cac acg agg ggg ctg<br>gac ttc gcc tgt gat atc tac atc tgg gcg ccc ttg gcc ggg act tgt ggg gtc ctt<br>ctc ctg tca ctg gtt atc acc ctt tac tgc aaa cgg ggc aga aag aaa ctc ctg tat<br>ata ttc aaa caa cca ttt atg aga cca gta caa act act caa gag gaa gat ggc<br>tgt agc tgc cga ttt cca gaa gaa gaa gaa gga gga tgt gaa ctg aga gtg aag<br>ttc agc agg agc gca gac gcc ccc gcg tac aag cag ggc cag aac cag ctc tat<br>aac gag ctc aat cta cga cga aga gag gag tac gac gtt ttg gac aag aga cgt<br>ggc cgg gac cct gag atg ggg gga aag ccg aga agg aag aac cct cag gaa ggc<br>ctg tac aat gaa ctg cag aaa gat aag atg gcg gag gcc tac agt gag att ggg<br>atg aaa ggc gag cgc cgg agg ggc aag ggg cac gat ggc ctt tac cag ggt ctc<br>agt aca gcc acc aag gac acc tac gac gcc ctt cac atg cag gcc ctg ccc cct<br>cgc taa | |
| P3-5BBZ | atg ggt tgg tcg tgc att atc ctc ttc ctc gtc gca acc gct acc ggc gtt cac tcg<br>gat tac aag gat gac gac gac aaa gag gta cag ctg gtg cag agc ggg gcc gag<br>gtt aag aag ccc ggg tct tcc gta aag gtg tcc tgc aag gcc tcg ggg gc aca ttc<br>tca tcg tac gca ata tcg tgg gtg cgg cag gcc ccc ggg cag ggg ctg gaa tgg<br>gtc ggc gga att atc cca atc ttc ggg acc gcc aac tat gcc cag aag ttt cag ggt<br>cgt gtg aag att act gcc gac gag tcc gca agt acg gcc tac atg gag ctg agt<br>agt ctg cgt agc gag gat act gcc gtt tat tat tgc gcc cgg gaa gag gga ccg tac<br>tgc tcg tcg acc tca tgt tac ggc gcc ttc gac atc tgg ggc caa ggc acc ctg gtg<br>acg gtg tcc tcc ggt ggt ggc gga agt ggc ggc ggg ggg tcc ggc ggg ggc ggt<br>tca cag tcc gtc ctg acc cag gat ccc gcg gtg tcg gtc gcg ctg ggt cag aca gta<br>aag ata aca tgc cag ggc gat tct ctg cgc agt tat ctg gcc tcg tgg tac cag cag<br>aaa ccc ggc cag gct cct acc ctt gtt acc tac gcg cgc aat gac aga ccc gcg<br>ggc gtg ccc gac cgc ttc tcc ggc tca aag agc ggg acc tcc gcc tcc ctg gcc atc<br>tcc ggg ctc cag tct gag gat gag gcc gat tac tac tgc gct gct tgg gac gac tcc<br>ctc aat ggc tat ctg ttt ggc gca ggc aca aag ctg acc gtg ctc acc acg cca<br>gcg ccg cga cca cca aca ccg gcg ccc acc atc gcg tcg cag ccc ctg tcc ctg<br>cgc cca gag gcg tgc cgg cca gcg gcg ggg ggc gca gtg cac acg agg ggg ctg<br>gac ttc gcc tgt gat atc tac atc tgg gcg ccc ttg gcc ggg act tgt ggg gtc ctt<br>ctc ctg tca ctg gtt atc acc ctt tac tgc aaa cgg ggc aga aag aaa ctc ctg tat<br>ata ttc aaa caa cca ttt atg aga cca gta caa act act caa gag gaa gat ggc<br>tgt agc tgc cga ttt cca gaa gaa gaa gaa gga gga tgt gaa ctg aga gtg aag<br>ttc agc agg agc gca gac gcc ccc gcg tac aag cag ggc cag aac cag ctc tat<br>aac gag ctc aat cta gga cga aga gag gag tac gac gtt ttg gac aag aga cgt<br>ggc cgg gac cct gag atg ggg gga aag ccg aga agg aag aac cct cag gaa ggc<br>ctg tac aat gaa ctg cag aaa gat aag atg gcg gag gcc tac agt gag att ggg<br>atg aaa ggc gag cgc cgg agg ggc aag ggg cac gat ggc ctt tac cag ggt ctc<br>agt aca gcc acc aag gac acc tac gac gcc ctt cac atg cag gcc ctg ccc cct<br>cgc taa | 273 |
| P2-4BBZ | atg ggt tgg tcg tgc att atc ctc ttc ctc gtc gca acc gct acc ggc gtt cac tcg<br>gat tac aag gat gac gac gac aaa gag gta cag ctg gtg cag agc ggg gcc gag<br>gtt aag aag ccc ggg tct tcc gta aag gtg tcc tgc aag gcc tcg ggg gc aca ttc<br>tca tcg tac gca ata tcg tgg gtg cgg cag gcc ccc ggg cag ggg ctg gaa tgg<br>atg ggc gga att atc cca atc ttc ggg acc gcc aac tat gcc cag aag ttt cag ggt<br>cgt gtg acc att act gcc gac gag tcc acc agt acg gcc tac atg gag ctg agt agt<br>ctg cgt agc gag gat act gcc gtt tat tat tgc gcc cgg gaa gag gga ccg tac tgc<br>tcg tcg acc tca tgt tac gca gcc ttc gac atc tgg ggc caa ggc acc ctg gtg acg<br>gtg tcc tcc ggt ggt ggc gga agt ggc ggc ggg ggg tcc ggc ggg ggc ggt tca<br>cag tcc gtc ctg acc cag gat ccc gcg gca tcg gtc gcg ctg ggt cag aca gta<br>aag ata aca tgc cag ggc gat tct ctg cgc agt tat ttc tcg tgg tac cag cag<br>aaa ccc ggc cag gct cct acc ctt gtt atg tac gcg cgc aat gac aga ccc gcg<br>ggc gtg ccc gac cgc ttc tcc ggc tca aag agc ggg acc tcc gcc tcc ctg gcc atc<br>tcc ggg ctc cag tct gag gat gag gcc gat tac tac tgc gct gct tgg gac gac tcc<br>ctc aat ggc tat ctg ttt ggc gca ggc aca aag ctg acc gtg ctc acc acg cca<br>gcg ccg cga cca cca aca ccg gcg ccc acc atc gcg tcg cag ccc ctg tcc ctg<br>cgc cca gag gcg tgc cgg cca gcg gcg ggg ggc gca gtg cac acg agg ggg ctg<br>gac ttc gcc tgt gat atc tac atc tgg gcg ccc ttg gcc ggg act tgt ggg gtc ctt<br>ctc ctg tca ctg gtt atc acc ctt tac tgc aaa cgg ggc aga aag aaa ctc ctg tat<br>ata ttc aaa caa cca ttt atg aga cca gta caa act act caa gag gaa gat ggc | 274 |

TABLE 12-continued

Nucleic Acid Sequences of Exemplary EGFR CARs

| CAR designation | Nucleic Acid Sequence | SEQ. ID NO: |
|---|---|---|
| | tgt agc tgc cga ttt cca gaa gaa gaa gaa gga gga tgt gaa ctg aga gtg aag<br>ttc agc agg agc gca gac gcc ccc gcg tac aag cag ggc cag aac cag ctc tat<br>aac gag ctc aat cta gga cga aga gag gag tac gac gtt ttg gac aag aga cgt<br>ggc cgg gac cct gag atg ggg gga aag ccg aga agg aag aac cct cag gaa ggc<br>ctg tac aat gaa ctg cag aaa gat aag atg gcg gag gcc tac agt gag att ggg<br>atg aaa ggc gag cgc cgg agg ggc aag ggg cac gat ggc ctt tac cag ggt ctc<br>agt aca gcc acc aag gac acc tac gac gcc ctt cac atg cag gcc ctg ccc cct<br>cgc taa | |

Figure 26A:
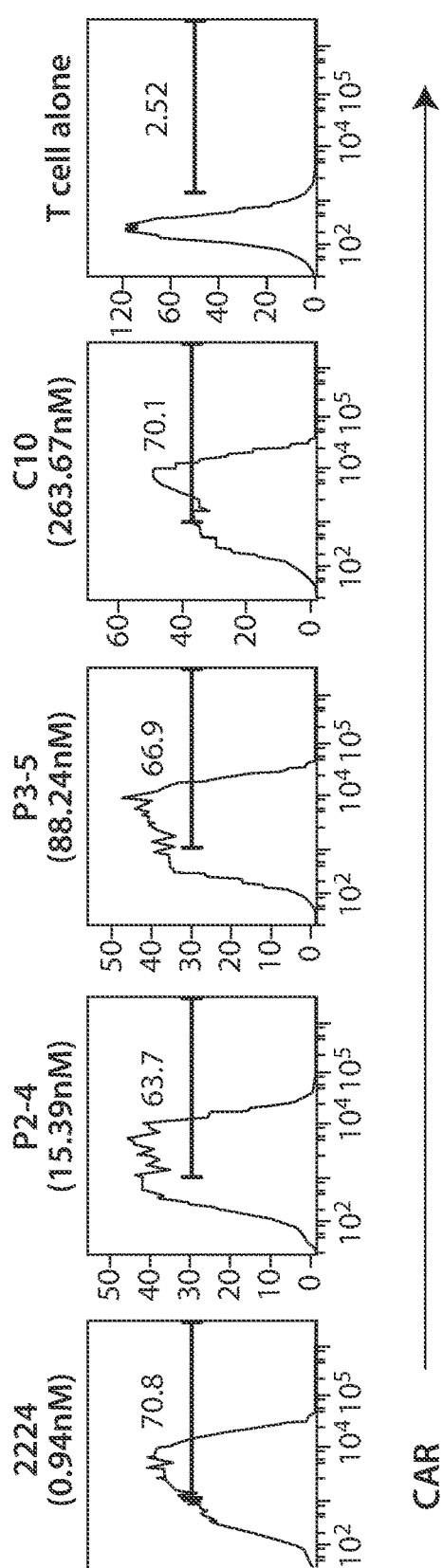
FIGS. 26A and 26B. CAR expression on T cells electroporated with EGFR CAR mRNA were stained by an anti-human IgG Fab and detected by flow cytometry staining (FIG. 26A); the affinity of the scFv is indicated (nM). Tumor lines (FIG. 26B) were stained with anti-EGFR Affibody-FITC (open histograms), the same cells were stained with mouse IgG1-FITC as isotype control (grey histograms).
Figure 26B:
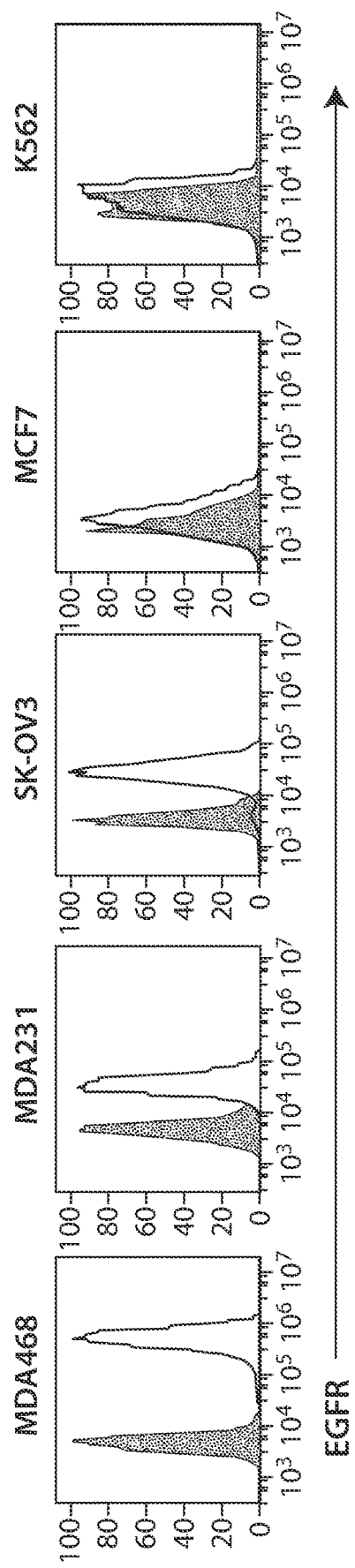
Figure 27:
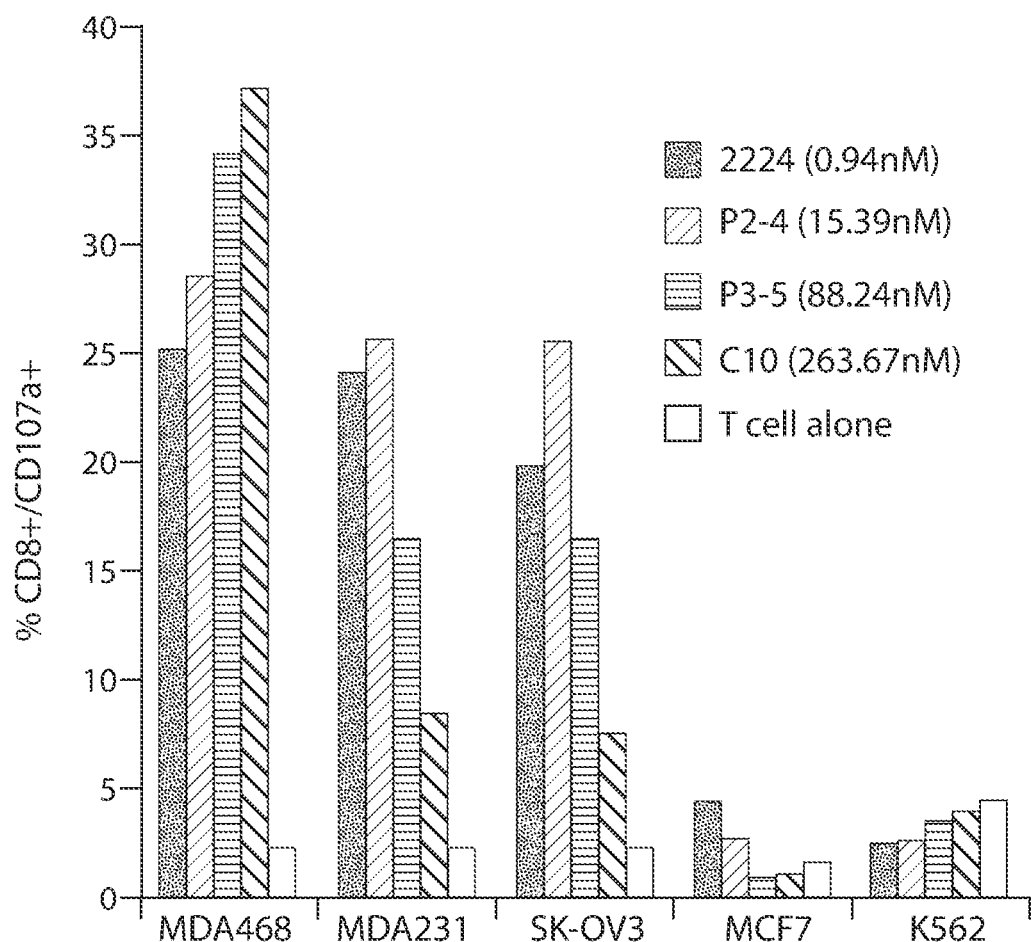
FIG. 27. EGFR CAR recognition sensitivity is correlated with affinity. A panel of EGFR CAR T cells with the indicated affinity of the scFv (KD, nM) was stimulated with the panel of tumors expressing EGFR at the density shown in FIG. 26B. After 4 h stimulation, CD107a up-regulation on the CAR T cells was detected by gating on CD3+ cells.

The monovalent affinities of the panel of EGFR-specific scFvs varied over a range of approximately 300-fold (Zhoe et al., 2007, *J Mol Biol*, 371:934). The 2224, P2-4, P3-5 and C10 scFvs were cloned into an RNA-based vector and in vitro transcribed for T cell mRNA electroporation. Levels of CAR surface expression were assayed and found to be similar among the EGFR constructs (FIG. 26A). To compare reactivities of the panel of EGFR CARs, CAR T cells were stimulated with EGFR-expressing tumor cell lines that have a broad range of EGFR expression at the cell surface (FIG. 26B). CAR T cell activation was evaluated by levels of CD107a up-regulation; the data is summarized in FIG. 27. Higher affinity EGFR CARs (2224:BB and P2-4:BBζ) responded to all EGFR positive tumor lines (MDA468, MDA231 and SK-OV3) regardless of EGFR expression levels (FIG. 27). However, the reactivity exhibited by lower affinity EGFR CARs (P3-5.BBZ and C10.BBZ) against EGFR-expressing tumor lines did correlate with the levels of EGFR expression. Furthermore, lower affinity EGFR CARs displayed more potent reactivity to the EGFR overexpressing tumor, MDA468, than the higher affinity EGFR CARs, while provoking a much weaker response to EGFR low expressing cells (FIG. 27). None of the EGFR CAR T cells reacted to the EGFR negative tumor line K562.

Figure 28:
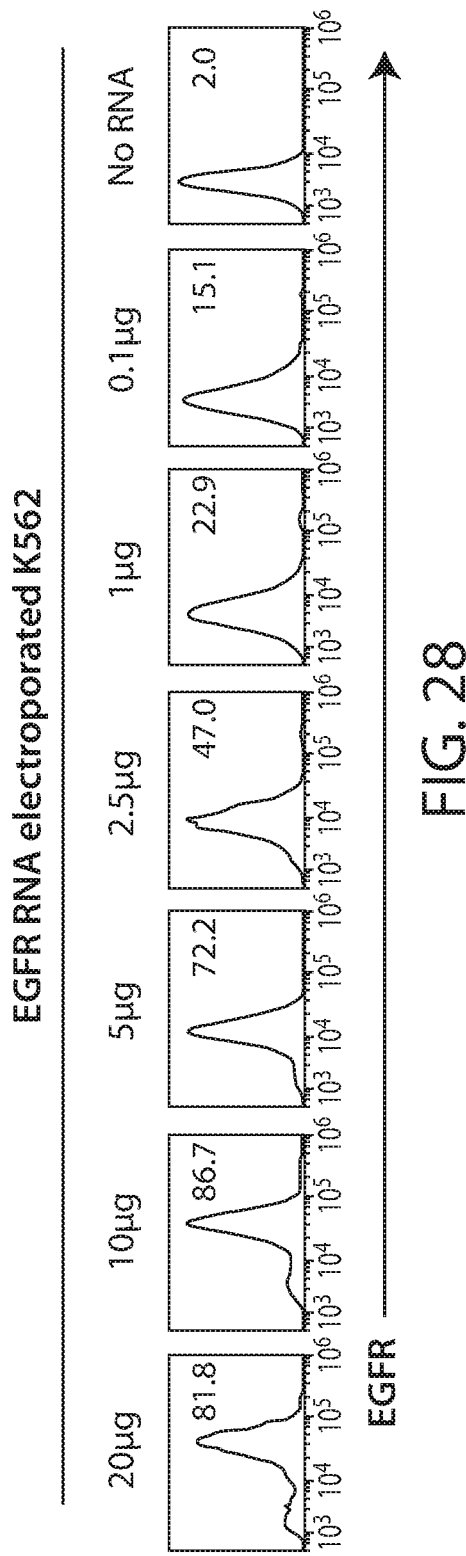
FIG. 28. ErbB2 expression in K562 cells electroporated with the indicated amount of EGFR mRNA. EGFR expression was detected using anti-EGFR Affibody-FITC staining 14 h post electroporation.
Figure 29:
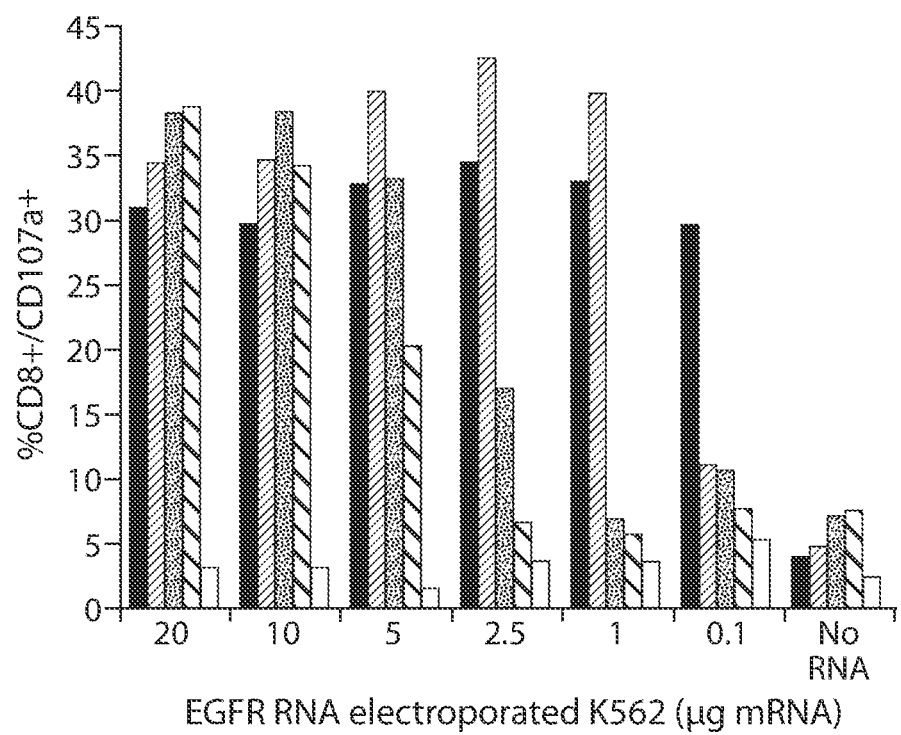
FIG. 29. EGFR CAR recognition sensitivity is correlated with affinity. T cells were electroporated with the panel of EGFR CARs with different affinities as indicated and stimulated with K562 electroporated with EGFR mRNA at different levels as shown in FIG. 30. After 4 hr stimulation, CD107a expression on CAR T cells was measured by gating on CD3+ cells.

To confirm that the level of response was related to scFv affinity and the level of EGFR expression, and to exclude tumor-specific effects, the panel of EGFR CAR T cells was co-cultured with K562 cells expressing varying levels of EGFR after electroporation with EGFR mRNA (FIG. 28). The higher affinity EGFR CARs did not discriminate between target cells with different levels of EGFR expression (FIG. 29). For example, T cells expressing CAR 2224 responded equally well to K562 cells electroporated with a 200-fold difference in EGFR mRNA (0.1 μg to 20 μg). However in agreement with the above ErbB2 CAR results, the lower affinity EGFR CARs (P3-5 and C10) exhibited a high correlation between T cell responses and EGFR expression levels; data are summarized in FIG. 29.

Figure 30:
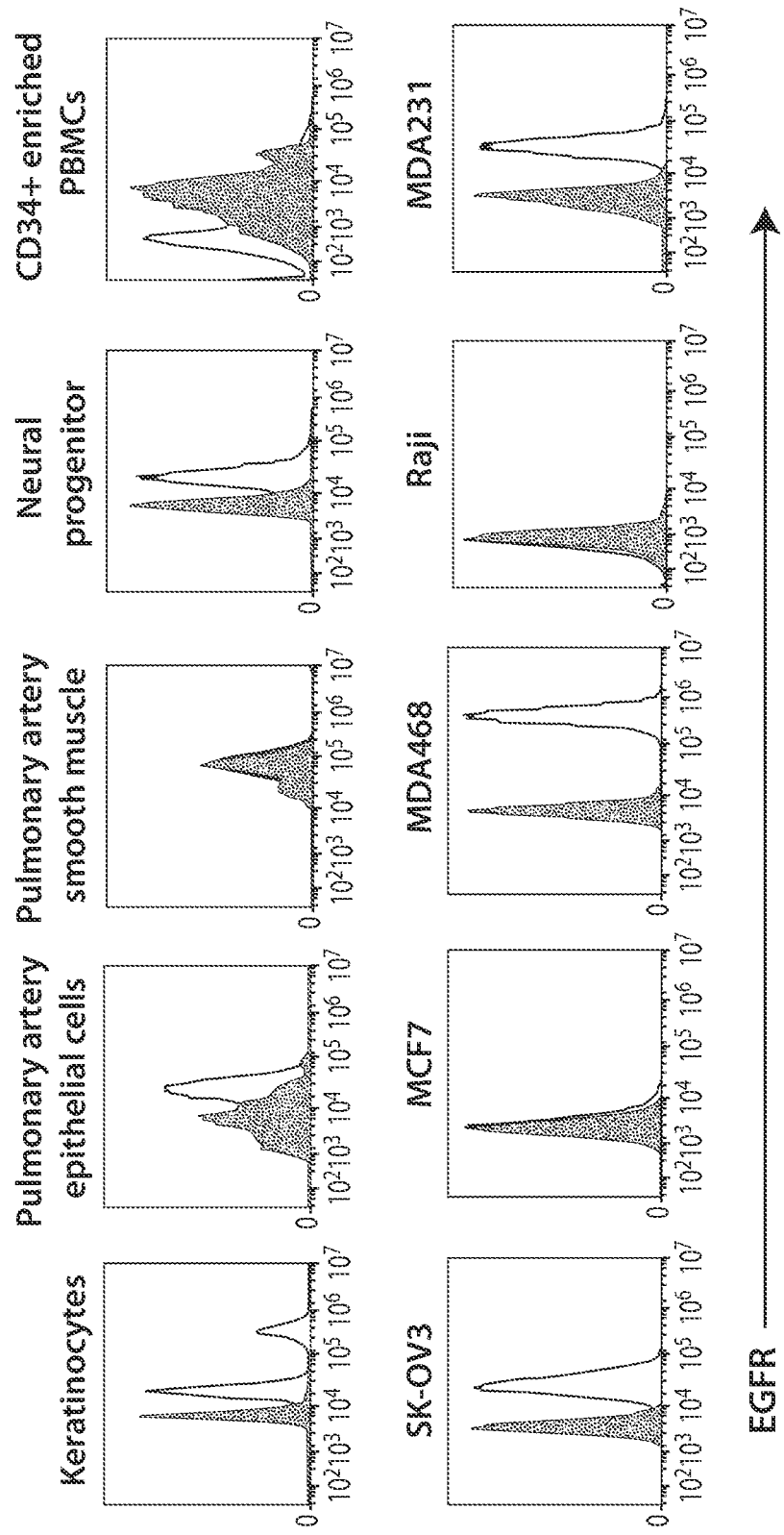
FIG. 30. Affinity dependent recognition of primary cell lines and tumor cells using affinity-tuned EGFR CARs. T cells were electroporated with the indicated EGFR CAR mRNA. One day after electroporation, the CAR T cells were stimulated with the panel of cells for 4 hr and the induction CD107a expression on the CAR T cells was quantified (CD3+ gated).
Figure 31:
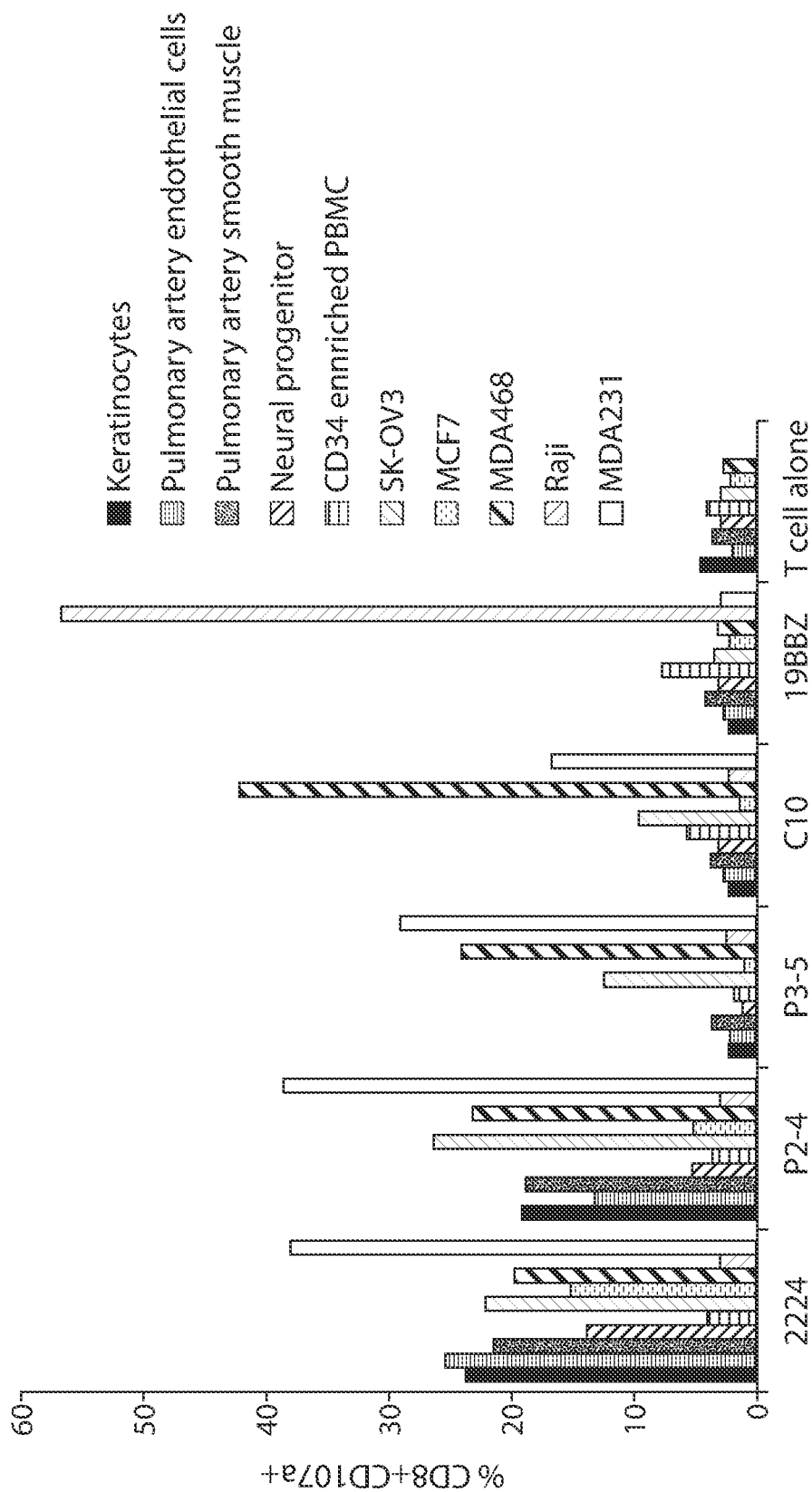
FIG. 31. Differential recognition of primary cell lines by T cells modified with affinity-tuned EGFR CARs. The percentage of CD8+CD107a+ double positive cells was plotted.
Figure 32:
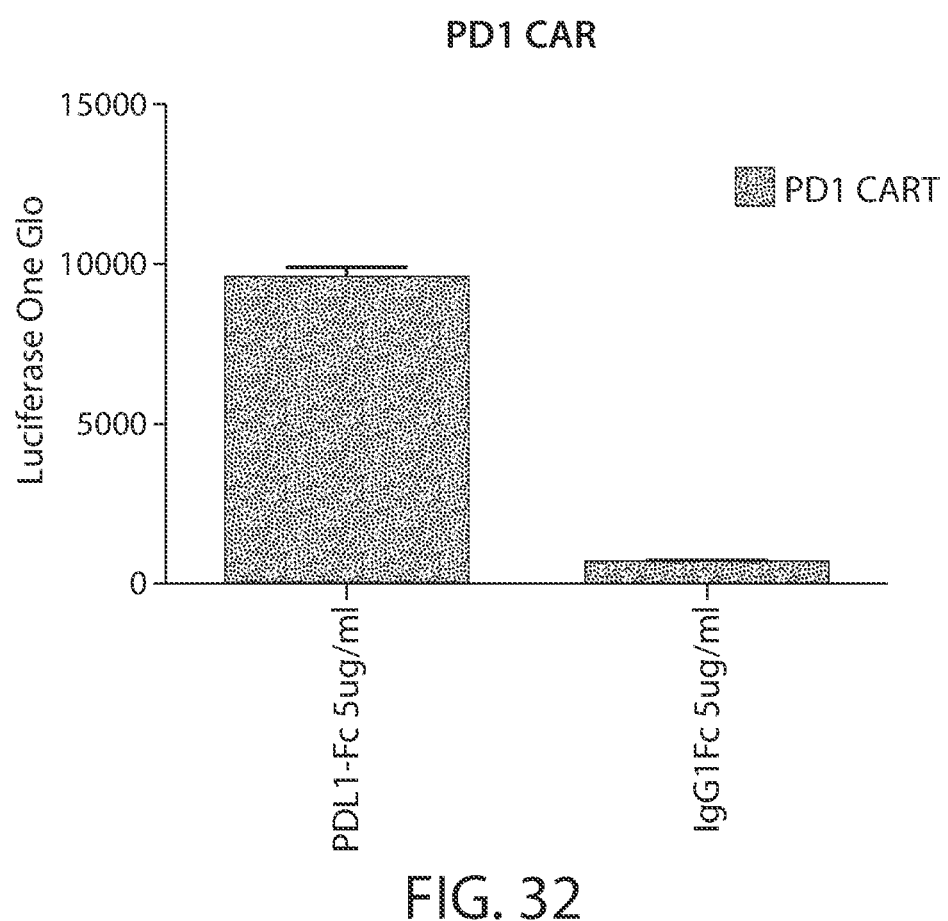
FIG. 32. depicts NFAT inducible promoter driven luciferase activity of a PD1 CAR as compared to the control treatment by IgG1-Fc.
Figure 33A:
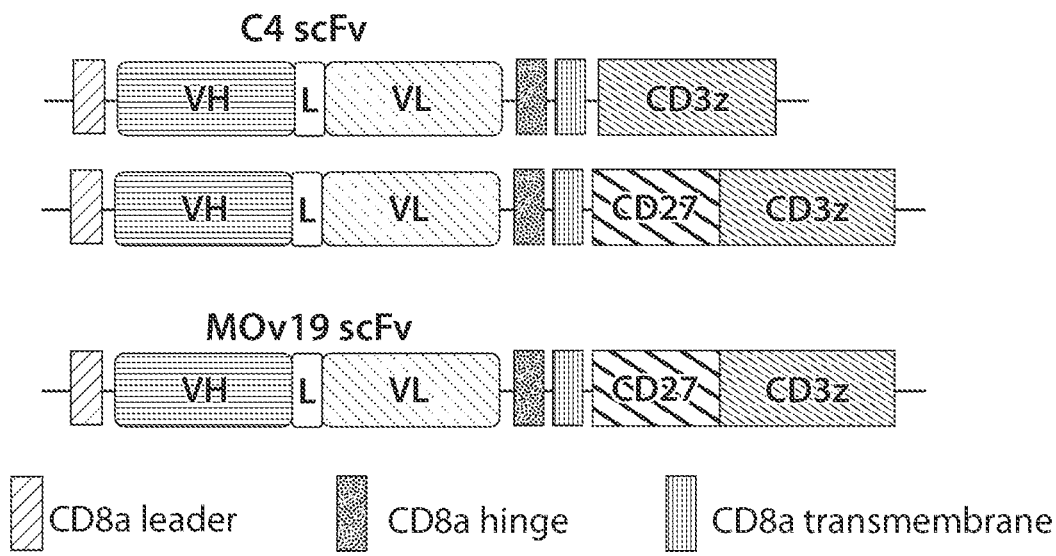
FIGS. 33A and 33B. Generation of folate receptor alpha (FRA)-specific fully human chimeric antigen receptor (CAR) T cells.
Figure 33B:
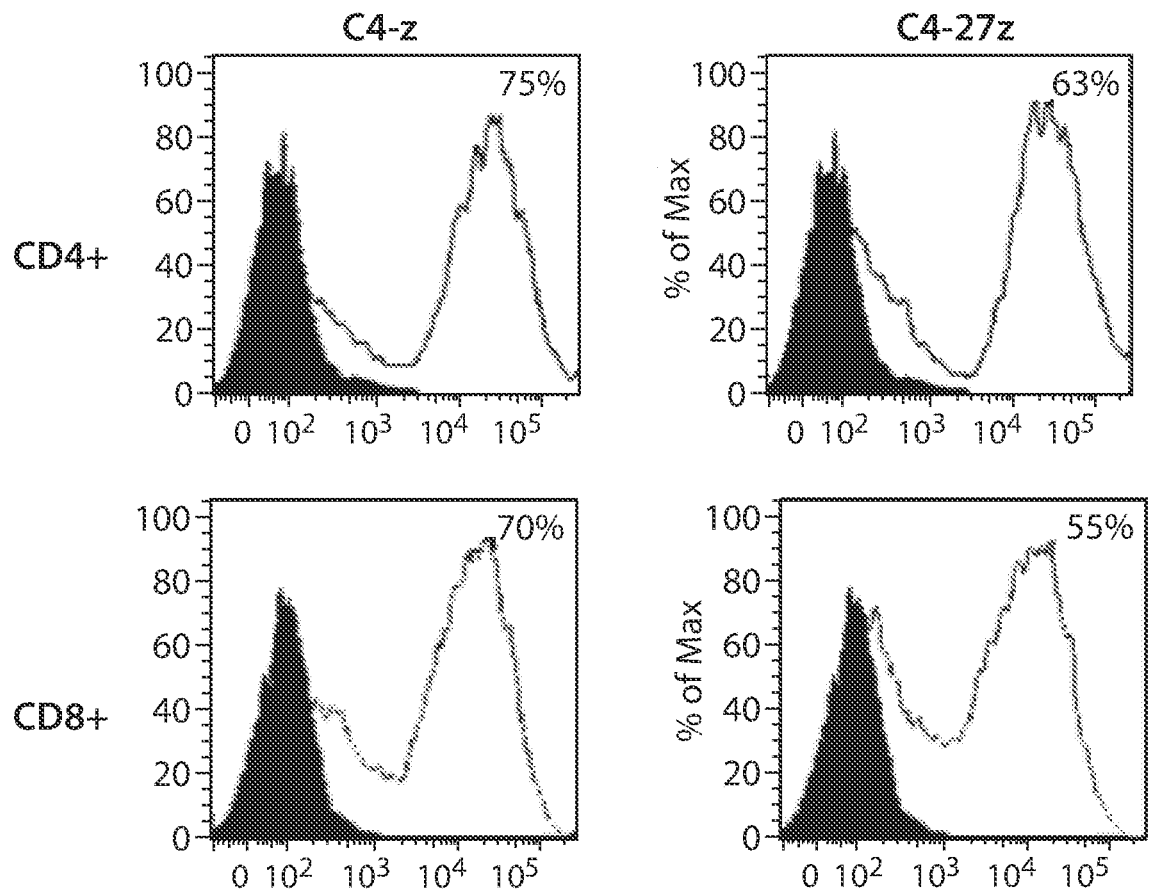

To confirm the increased safety profile of the lower affinity EGFR CARs, we tested the reactivities of EGFR CARs against primary cells derived from different organs. Five primary cell lines and five tumor cell lines were tested for both surface levels of EGFR (FIG. 30) and ability to trigger CAR T cell reactivity (FIG. 31). Three of the primary cell lines examined express detectable levels of EGFR and two did not (pulmonary artery smooth muscle and PBMC). Two of the tumor cell lines (MCF7 and Raji) did not express detectable EGFR on the cell surface. Comparing EGFR CAR T cells to CD19 CAR T cells, T cells with higher EGFR affinity CARs (2224 and P2-4) reacted to all the primary lines tested and all of the tumors except Raji (FIG. 31). However, T cells with the affinity decreased EGFR CAR T cells P3-5 and C10 were not reactive to any of the five primary cells tested (FIG. 31). CD19 specific CAR T cells reacted to the CD19+ line Raji, and to PBMCs, presumably to the B cells in PBMC, but did not respond to any of the tumor lines or other primary cell lines. These data demonstrate that affinity tuning of scFv can increase the therapeutic index for CAR T cells that target either ErbB2 or EGFR.

Discussion

The efficacy of CAR T cells is dictated in part by the differential expression of the target antigen in tumor versus normal tissue. The results described above demonstrate that CARs with known severe on-target toxicities can be reengineered by affinity tuning, retaining potent in vivo efficacy while eliminating or reducing toxicity. In particular, the 4D5 CAR based on trastuzumab had lethal toxicity (Morgan et al., 2010, *Mol Ther*, 18:843), due to recognition of physiological levels of ErbB2 expressed in cardiopulmonary tissues (Press et al., 1990, *Oncogene*, 5:953). It was shown that by reducing the $K_D$ of scFv employed in CAR T cells by 2- to 3-log, a substantial improvement in the therapeutic index was demonstrated for ErbB2 and EGFR CAR T cells. CAR T cells with lower affinity scFv showed equally robust anti-tumor activity against ErbB2 overexpressing tumors as compared to the high affinity CARs, but displayed little reactivity against physiological levels of ErbB2.

CARs specific for the B cell lineage antigens CD19 and CD20 have been tested by a variety of groups and have displayed potent efficacy in B cell malignancies (Maus et al., 2014, *Blood*, 123:2625). However in solid tumors, with the exception of tumor-specific isoforms such as EGFRviii (Morgan et al., 2012, *Human Gene Therapy*), on-target toxicity is anticipated to be a severe limitation for CAR T cells. This limitation is expected to be more serious with CARs than with antibody therapies using intact antibodies or antibody drug conjugates, due to the lower limit of target sensitivity for CAR T cells compared to antibody based therapies that differs by several orders of magnitude. The present studies using target cells electroporated with ErbB2 or EGFR mRNA are consistent with previous studies indicating that CAR T cells can recognize tumor cells with ~100 targets per cell (Stone et al., 2012, *Oncoimmunology*, 1:863). In contrast, amplification of ErbB2 occurs in approximately 20% to 25% of primary human breast cancers and typically results in overexpression of ErbB2 protein at >1 million copies per cell (Robertson et al., 1996, *Cancer Res*, 56:3823; and Vogel et al., 2002, *J Clin Oncol*, 20:719). At present, available data indicate that cancer cells do not lose ErbB2 expression when they become refractory to ErbB2 directed therapies (Ritter et al., 2007, *Clin Cancer Res*, 13:4909).

These findings support previous work from Chmielewski (Chmielewski et al., 2004, J Immunol, 173:7647), suggesting that the high affinity CARs exhibit less discrimination between target cells with high or low target expression levels. However, the present results differ from Chmielewski and coworkers in that none of the higher affinity CARs (with $K_D$ ranging from 15 pM to 16 nM) in their report were reactive to cells with low level expression of ErbB2 and their lower affinity CAR that only recognized tumors with amplified ErbB2 showed a substantial reduction in T cell efficacy compared to the higher affinity CARs. In contrast, it was found that the ErbB2 CAR using the 4DF5 scFv with $K_D$ at 0.3 nM was strongly reactive to keratinocytes and even to cell lines transfected with extremely low amounts ErbB2 mRNA that were 100 times below detectable levels, while affinity-tuned CAR T cells retained reactivity to ErbB2 amplified tumors that was at least as potent as the high affinity CAR, both in vitro and in aggressive mouse tumor models. Some variables that may explain these differences include the use of different scFvs (C5.6 versus 4D5) that may recognize different epitopes, distinct CAR signaling domain configuration (zeta alone versus 4-1BB-zeta), and different gene transfer approaches (retroviral transduction versus RNA electroporation or lentiviral transduction) that affect CAR surface expression levels on the T cells. Together, this suggests that each of these factors should be considered when selecting the affinity of a CAR in relevant clinical situations.

The findings described in this example also demonstrated the importance of selecting the right affinity for a CAR targeting a particular tumor-associated antigen (TAA). The in vitro and in vivo results were consistent with each other, demonstrating that CARs having lower affinity was at least as potent as the high affinity CAR (for both lentivirally-transduced and RNA-electroporated CAR T cells), but had minimal impact on cells that had low expression of a TAA (ErbB2), representing normal tissue. In contrast, CARs with high affinity were more reactive to the low-expressing TAA cells representing normal tissue. Thus, CARs with high affinity may not be preferred for cancers where the TAA is also expressed in normal tissue, as these results demonstrate that CARs with high affinity may also target normal tissues and therefore would result in adverse side effects. Taken together, these results indicate that the affinity of the CARs must be considered with respect to the nature of the cancer (e.g., whether the TAA is expressed only in cancer cells or whether the TAA is expressed higher in cancer cells, but is also expressed at a low level in normal tissue) for potency and safety reasons.

The advent of more potent adoptive transfer strategies has prompted a reassessment of targets previously considered as safe using weaker immunotherapeutic strategies (Hinrichs et al., 2013, *Nature Biotechnology*, 31:999). Strategies to maximize the therapeutic index of CAR T cells include target selection, CAR design, cell manufacturing and gene transfer techniques. In addition to affinity tuning, other strategies being developed to manage on-target toxicity include the use of dual CAR T cell approaches (Kloss et al., 2013, *Nat Biotech*, 31:999; and Lanitis et al., 2013, *Cancer Immunol Res*, 1:43), conditional deletion and suicide systems (Di Stasi et al., 2011, *NEJM*, 365:1673; and Wang et al., 2011, *Blood*, 118:1255), and repeated infusions of T cells having mRNA CARs that have transient expression and self limiting toxicity (Beatty et al., 2014, *Cancer Immunol Res*, 2:112).

These results demonstrate that affinity-tuning can increase the therapeutic index for ErbB2 and EGFR. In addition to scFv affinity, other variables that require examination to increase the therapeutic index for other targets include the location of the target epitope, the length of the hinge and the nature of the signaling domain (Hudecek et al., 2013, *Clin Cancer Res*, 15:5323; and Guedan et al., 2014, *Blood*, 124:1070).

In summary, ErbB2 and EGFR have previously been considered as undruggable targets for CAR T cells. Given that dysregulation of the expression of ErbB2 and EGFR occurs frequently in multiple human carcinomas including breast, glioblastoma, lung, pancreatic, ovarian, head and neck squamous cell cancer and colon cancer, these findings have considerable clinical importance. This affinity-tuning strategy has the potential not only to improve the safety profile and clinical outcome of CARs directed against validated targets but also to expand the landscape to targets not previously druggable with CAR T cells because of on-target toxicities. More generally, these findings suggest that affinity-tuning suggests that safer and more potent CARs can be designed by employing affinity-decreased scFvs for a variety of common carcinomas.

Example 4: Mesothelin CAR Efficacy

A CAR lentiviral construct was designed to express murine anti-mesothelin SS1 scFv with signaling domains comprised of TCRζ and CD28 or 4-1BB costimulatory signaling domains, e.g., SS1 scFV with TCRζ (SS1-Zeta), SS1 scFv with 4-1BB and TCRζ (SS1-BBz), SS1 scFv with CD28 and TCRζ (SS1-CD28z), or SS1 scFv with 4-1BB, CD28, and TCRζ (SS1-CD28BBz). T cells were transduced routinely with high efficiency (>75%) by using the EF1α promoter which drives constitutive surface expression of the CAR.

In vitro, T cells expressing anti-mesothelin CARs efficiently and specifically kill tumor cell lines transduced with mesothelin, as well as primary mesothelin-positive tumors isolated from patients with chemotherapy-resistant tumors (Carpenito et al., *Proc Natl Acad Sci USA*, 2009, 106:3360-5) and various PDA cell lines.

Figure 41:
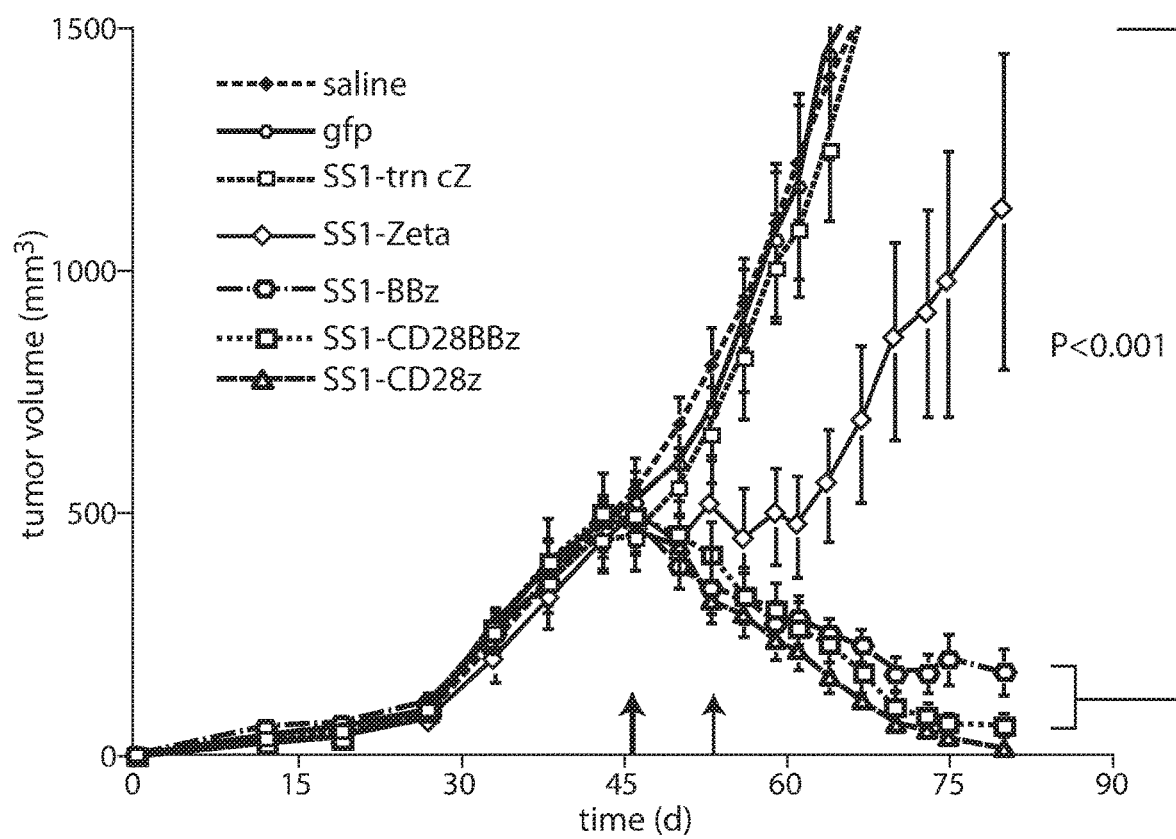
FIG. 41. Antitumor activity of SS1 CAR T cells in a xenograft mouse model. Human mesothelioma tumor cells were established in the flanks of NOD/SCID mice, forming tumors of about 500 mm$^3$ before receiving two intra-tumoral injections of 10×10$^6$ SS1 CAR T cells, or GFP (solid square, black solid line) or saline control (solid diamond, dashed line). Different CAR constructs containing the SS1 antigen binding domain were used: SS1-tmcZ (SS1 and control signaling domain) (open square, gray line); SS1-zeta (SS1 and TCRzeta), or GFP (solid square, black solid line) or saline control (solid diamond, dashed line). Different CAR constructs containing the SS1 antigen binding domain were used: SS1-tmcZ (SS1 and control signaling domain) (open square, gray line); SS1-zetBB signaling domain) (open square, grey solid line). Student-Newman-Keuls multiple comparison was performed: p<0.001 for control groups compared to SS1 CAR T cells expressing CARs with CD28z, 41BBz, and CD28BBz.

To test the potential efficacy of anti-mesothelin CARs in vivo, mesothelin positive tumor cells from a patient were injected into the flanks of mice, and the tumor was permitted to grow for 45 days until it had reached a very large size. At this point, mice were injected intratumorally with the different CAR constructs: SS1-Zeta, SS1-BBz, SS1-CD28z, or SS1-CD28BBz (n=8 per group). As shown in FIG. 41, mice receiving mock, GFP or TCRζ truncated CARs had continued tumor growth and required sacrifice. In contrast, the groups of mice that were administered CARs with costimulatory domains (SS1-BBz, SS1-CD28Z, SS1-CD28BBz) had a striking tumor regression (See, e.g., Carpenito et al., *Proc Natl Acad Sci USA*, 2009, 106:3360-5). The results from these experiments indicate that anti-mesothelin CAR therapy has strong antitumor activity.

Example 5: Mesothelin CAR Therapy in Clinical Trials

Several clinical trials are in progress testing mRNA anti-mesothelin CARs, lentiviral anti-mesothelin CARs, and retroviral anti-mesothelin CARs. The first-in-human trial of SS1 CART-meso cells using mRNA electroporation (EP) to provide transient CAR expression was conducted (Beatty et al., *Cancer Immunol Res*. 2014; 2:112-120). Adoptive transfer of mRNA CART-meso cells was feasible and safe without overt evidence of off-tumor, on-target toxicity against normal tissues in six patients treated. Similar to preclinical findings (Zhao et al., *Cancer Res.* 2010, 70:9053-9061), CART-meso cells persisted transiently within the peripheral blood after intravenous administration and migrated to primary and metastatic tumor sites. Importantly, clinical and laboratory evidence of antitumor activity was identified in a subset of patients with one patient experiencing the disappearance of cancer cells in ascitic fluid as well as a reduction in liver and subcutaneous lesions. In some patients, CART-meso cells elicited an endogenous anti-tumor immune response seen by the development of novel tumor-specific antibodies, consistent with epitope spreading (Beatty et al., *Cancer Immunol Res.* 2014; 2:112-120). Manageable cytokine-release syndrome was observed in most patients. One patient had an SAE due to anaphylaxis upon re-exposure to the same CART-meso cell product, as reported and was attributed to an immune response to the murine-derived scFv component of the CAR. The allergic-type immune response was thought to occur because of the prolonged time in between infusions that this patient uniquely experienced.

Figure 42:
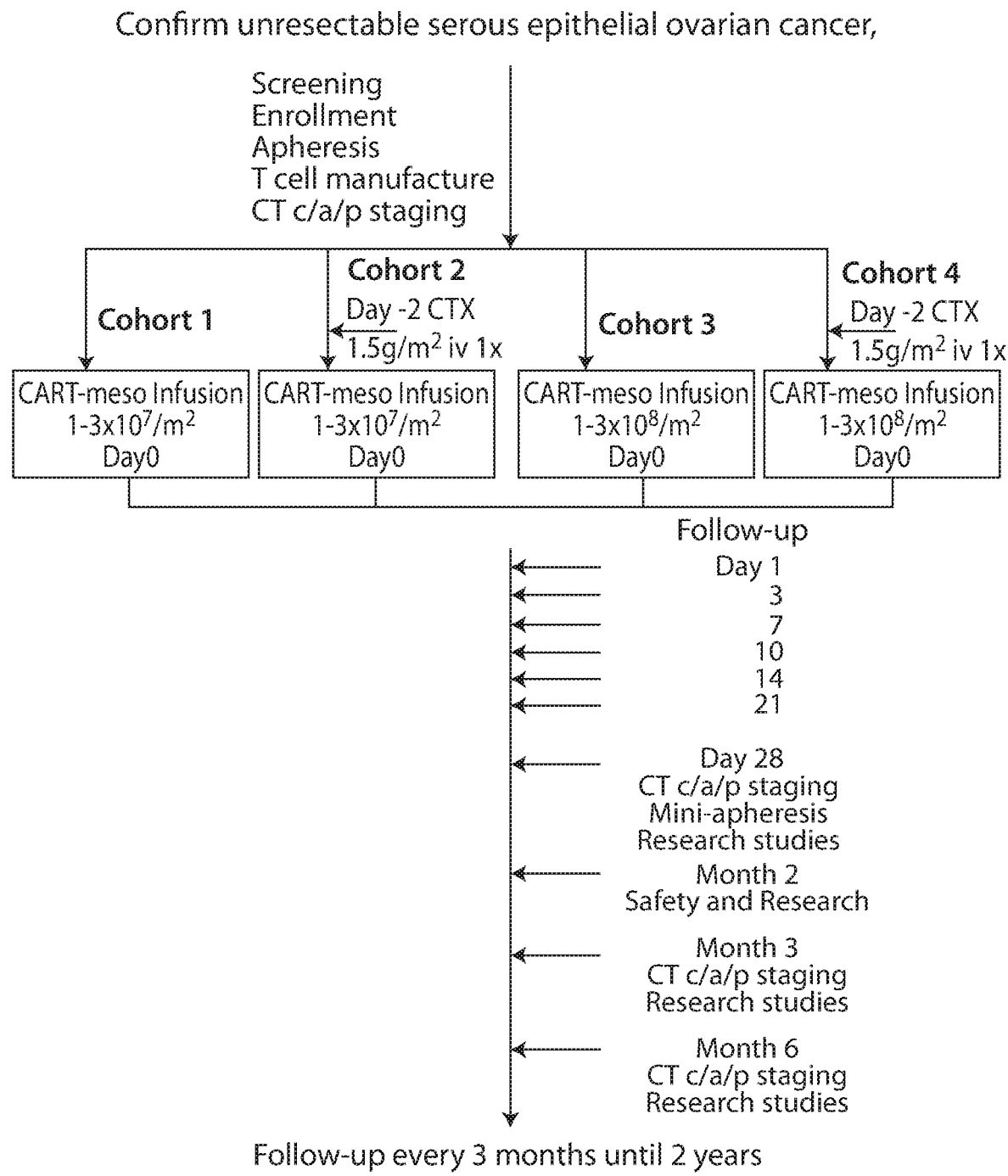
FIG. 42. Study schema for phase I trail of lentivirally transduced meso CAR cells in recurrent serous epithelial ovarian cancer.

An additional clinical trial will evaluate the safety and feasibility of meso-CART cells engineered with lentivirus in patients with metastatic epithelial ovarian cancer. Patients will be administered lentivirally-transduced meso-CAR T cells with and without lymphodepeleting cyclophosphamide (CTX) in a 4 cohort, 3+3 dose escalation design. The study population will include women with serous epithelial ovarian cancer who have progressed after at least one prior regiment of standard systemic therapy and must have ECOG 0-1 performance status and >3 month expected survival. The details of the treatment and study schema are provided in FIG. 42. Secondary objectives are to evaluate the clinical anti-tumor effect by standard criteria (RECIST and immune-related response criteria) and assess progression free survival (PFS) and overall survival (OS).

Figure 43:
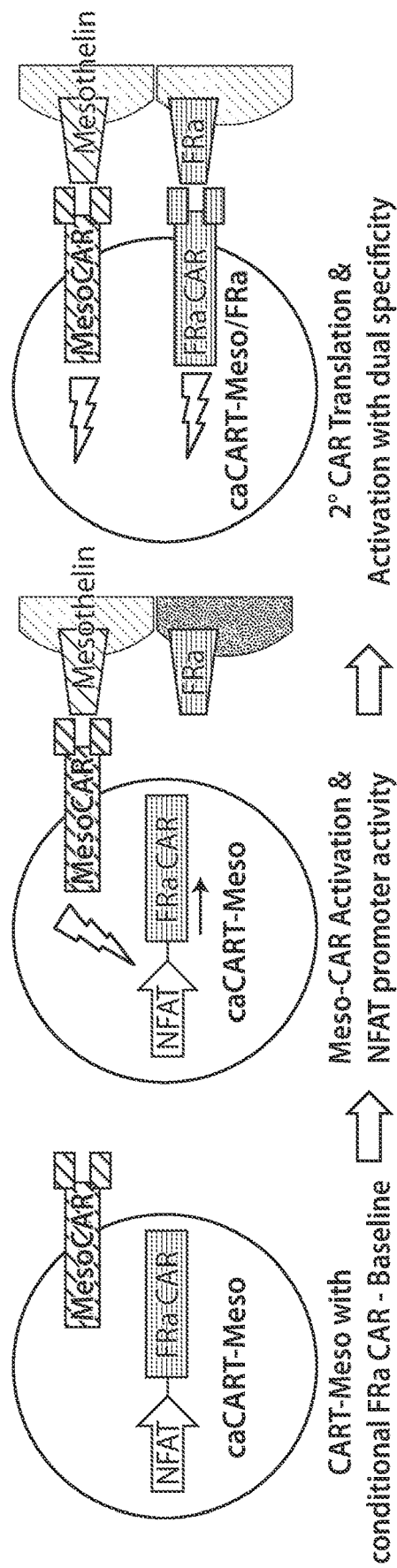
FIG. 43. Activation-induced expression of a second agent to broaden the antigen-specific response and limit immune escape. Meso-CAR T cells engineered for NFAT promoter driven transgene expression upregulates a second agent, such as a CAR that targets folate receptor alpha (FRa CAR) upon encounter with mesothelin antigen in the tumor microenvironment, resulting in the killing of mesothelin-deficient FRa+ ovarian cancer cells.
Figure 44:
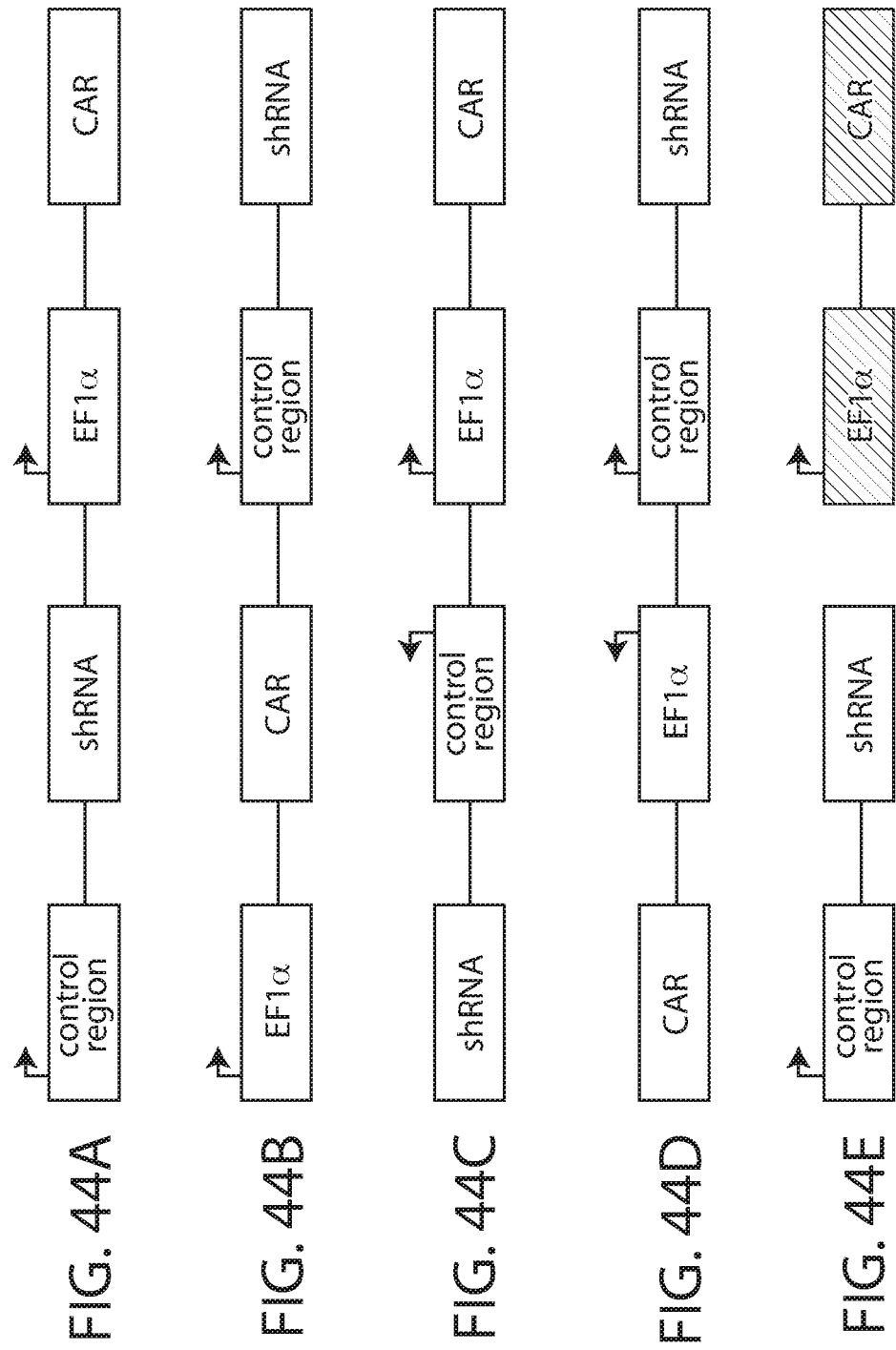
FIGS. 44A, 44B, 44C, 44D, and 44E. Schematic diagram depicting different vector constructs comprising different configurations of a CAR and a shRNA, e.g., an shRNA for targeting an inhibitory molecule.

Example 6: Generation and Analysis of CAR-Expressing Cells Specific to Multiple Tumor Antigens In this example, immune effector cells are conditionally converted into multi-specificity cytotoxic T cells upon antigen encounter in vivo, resulting in bispecific immune effector cells expressing two chimeric receptors, e.g., targeting two different tumor antigens. Here, the immune effector cells, e.g., T cells, comprise a nucleic acid encoding a mesoCAR under the control of an EF1alpha promoter and a nucleic acid encoding a second entity, such as a folate receptor alpha CAR (FRa CAR), a HER2-specific TCR, or GFP (control), under the control of an NFAT-inducible control region. The NFAT-inducible control region comprises multiple NFAT binding sites, e.g. 3 or 6, and a minimal IL-2 promoter. The nucleic acids encoding the mesoCAR and the second agent are on the same vector, such as a bicistronic lentiviral vector. Alternatively, the cells can be lentivirally cotransduced, simultaneously or sequentially, with multiple vectors, e.g., where each vector encodes a mesoCAR and the second agent. The T cells constitutively express meso-CAR, and upon recognition of mesothelin, e.g., on mesothelin-expressing tumor cells, the meso-CAR T cells are activated. T cell activation triggers NFAT expression, which induces expression of the second entity, e.g., the FRa CAR, the HER2 specific TCR, or GFP (FIG. 43).

To test ex vivo activation and conditional expression of the T cells expressing mesoCAR and a second agent as described above, the T cells described above are incubated with mesothelin-expressing cells (e.g., mesothelin-positive ovarian cancer cells) or cells that do not express mesothelin (e.g., mesothelin-negative ovarian cancer cells). Flow cytometry will be used to measure the expression of meso-CAR and FRa CAR or HER2 specific TCR. Tagged recombinant proteins or peptide-specific HLA tetramers are used to determine the baseline expression of the CARs and/or TCR. GFP expression serves to determine the level of baseline and activation-induced promoter activity, and as a negative control for secondary antigen specificity. Subsequent analysis of the T cells expressing mesoCAR and a second agent as described above include flow cytometry assays to determine the kinetics and duration of the activation-induced expression of the second agent, e.g., the FRa CAR, HER2-specific TCR, or GFP.

Additional assays are performed to evaluate the functional capacity of the immune effector cells after encountering mesothelin. Antigen specific cytokine production is tested using multiplex assays. Antigen-specific proliferation is assessed by CFSE-dilution. Targeted cytotoxicity is assessed using Cr-release assays, as well as relative comparability to conventional meso-CAR T cells.

The mesothelin-activated CART cells will then be tested for redirected T cell function in response to secondary stimulation with cancer cells expressing Meso+/FRa− and Meso−/Fra+, or Meso+/Her2− and Meso−/Her2+ cancer cells to determine the degree to which they maintain specificity for their primary target (meso) and acquire specificity for the secondary target (FRa). The immune-based assays described above are used, e.g., multiplex assay to determine antigen specific cytokine production, CFSE-dilution to determine antigen specific proliferation, and Cr-release assays to determine cytotoxicity.

Preclinical evaluation of the CART cells is conducted in NSG mice harboring heterogeneous ovarian cancers comprising Meso+/FRa− and Meso−/Fra+, or Meso+/Her2− and Meso−/Her2+ cancer cells. For example, Meso+/FRa− and Meso−/Fra+, or Meso+/Her2− and Meso−/Her2+ cancer cells ovarian cancer cells (or mixtures thereof) are injected into the flanks of mice and allowed to grow to a sufficient size. CART cells are injected, e.g., intratumorally or intravenously, and tumor progression, size, and overall health of the mice are monitored.

Example 7: Low Dose RAD001 Stimulates CART Proliferation in a Cell Culture Model The effect of low doses of RAD001 on CAR T cell proliferation in vitro was evaluated by co-culturing CART-expressing cells with target cells in the presence of different concentrations of RAD001.

Materials and Methods

Generation of CAR-Transduced T Cells

A humanized, anti-human CD19 CAR (huCART19) lentiviral transfer vector was used to produce the genomic material packaged into VSVg pseudotyped lentiviral particles. The amino acid and nucleotide sequence of the humanized anti-human CD19 CAR (huCART19) is CAR 1, ID 104875 described in PCT publication, WO2014/153270, filed Mar. 15, 2014, and is designated SEQ ID NOs. 85 and 31 therein.

Lentiviral transfer vector DNA is mixed with the three packaging components VSVg env, gag/pol and rev in combination with lipofectamine reagent to transfect Lenti-X 293T cells. Medium is changed after 24 h and 30 h thereafter, the virus-containing media is collected, filtered and stored at −80° C. CARTs are generated by transduction of fresh or frozen naïve T cells obtained by negative magnetic selection of healthy donor blood or leukopak. T cells are activated by incubation with anti-CD3/anti-CD28 beads for 24 h, after which viral supernatant or concentrated virus (MOI=2 or 10, respectively) is added to the cultures. The modified T cells are allowed to expand for about 10 days. The percentage of cells transduced (expressing the CARs on the cell surface) and the level of CAR expression (relative fluorescence intensity, Geo Mean) are determined by flow cytometric analysis between days 7 and 9. The combination of slowing growth rate and T cell size approaching ~350 fL determines the state for T cells to be cryopreserved for later analysis.

Evaluating Proliferation of CARTs

To evaluate the functionality of CARTs, the T cells are thawed and counted, and viability is assessed by Cellometer. The number of CAR-positive cells in each culture is normalized using non-transduced T cells (UTD). The impact of RAD001 on CARTs was tested in titrations with RAD001, starting at 50 nM. The target cell line used in all co-culture experiments is Nalm-6, a human pre-B cell acute lymphoblastic leukemia (ALL) cell line expressing CD19 and transduced to express luciferase.

For measuring the proliferation of CARTs, T cells are cultured with target cells at a ratio of 1:1. The assay is run for 4 days, when cells are stained for CD3, CD4, CD8 and CAR expression. The number of T cells is assessed by flow cytometry using counting beads as reference.

Results

Figure 45:
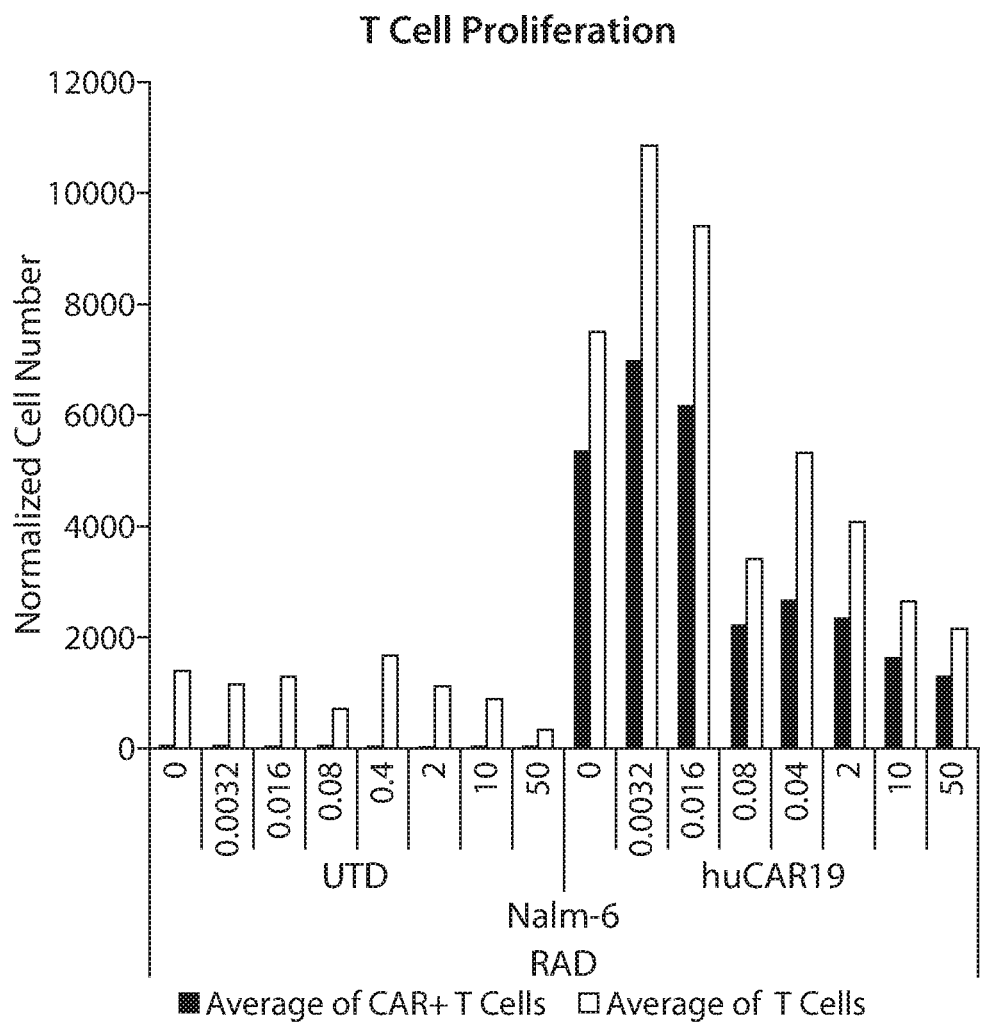
FIG. 45. Graph showing that the proliferation of CAR-expressing, transduced T cells is enhanced by low doses of RAD001 in a cell culture system. CARTs were co-cultured with Nalm-6 cells in the presence of different concentrations of RAD001. The number of CAR-positive CD3-positive T cells (black) and total T cells (gray) was assessed after 4 days of co-culture.

The proliferative capacity of CART cells was tested in a 4 day co-culture assay. The number of CAR-positive CD3-positive T cells (dark bars) and total CD3-positive T cells (light bars) was assessed after culturing the CAR-transduced and non-transduced T cells with Nalm-6 (FIG. 45). huCART19 cells expanded when cultured in the presence of less than 0.016 nM of RAD001, and to a lesser extent at higher concentrations of the compound. Importantly, both at 0.0032 and 0.016 nM RAD001 the proliferation was higher than observed without the addition of RAD001. The non-transduced T cells (UTD) did not show detectable expansion.

Example 8: Low Dose RAD001 Stimulates CART Expansion In Vivo

This example evaluates the ability of huCAR19 cells to proliferate in vivo with different concentrations of RAD001.
Materials and Methods:
NALM6-Luc Cells:

The NALM6 human acute lymphoblastic leukemia (ALL) cell line was developed from the peripheral blood of a patient with relapsed ALL. The cells were then tagged with firefly luciferase. These suspension cells grow in RPMI supplemented with 10% heat inactivated fetal bovine serum.

Mice:

6 week old NSG (NOD.Cg-Prkdc$^{scid}$Il2rg$^{tm1Wjl}$/SzJ) mice were received from the Jackson Laboratory (stock number 005557).

Tumor Implantation:

NALM6-luc cells were grown and expanded in vitro in RPMI supplemented with 10% heat inactivated fetal bovine serum. The cells were then transferred to a 15 ml conical tube and washed twice with cold sterile PBS. NALM6-luc cells were then counted and resuspended at a concentration of 10×10$^6$ cells per milliliter of PBS. The cells were placed on ice and immediately (within one hour) implanted in the mice. NALM6-luc cells were injected intravenously via the tail vein in a 100 µl volume, for a total of 1×10$^6$ cells per mouse.

CAR T Cell Dosing:

Mice were administered 5×10$^6$ CAR T cells 7 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of 50×10$^6$ CAR T cells per ml of cold PBS and kept on ice until the mice were dosed. The mice were injected intravenously via the tail vein with 100 µl of the CAR T cells for a dose of 5×10$^6$ CAR T cells per mouse. Eight mice per group were treated either with 100 µl of PBS alone (PBS), or humanized CD19 CAR T cells.

RAD001 Dosing:

A concentrated micro-emulsion of 50 mg equal to 1 mg RAD001 was formulated and then resuspended in D5W (dextrose 5% in water) at the time of dosing. Mice were orally dosed daily (via oral gavage) with 200 µl of the desired doses of RAD001. PK analysis: Mice were dosed daily with RAD001 starting 7 days post tumor implantation. Dosing groups were as follows: 0.3 mg/kg, 1 mg/kg, 3 mg/kg, and 10 mg/kg. Mice were bled on days 0 and 14 following the first and last dose of RAD001, at the following time points for PK analysis: 15 minutes, 30 minutes, 1 hour, 2 hours, 4 hours, 8 hours, 12 hours, and 24 hours.

Results

Figure 46:
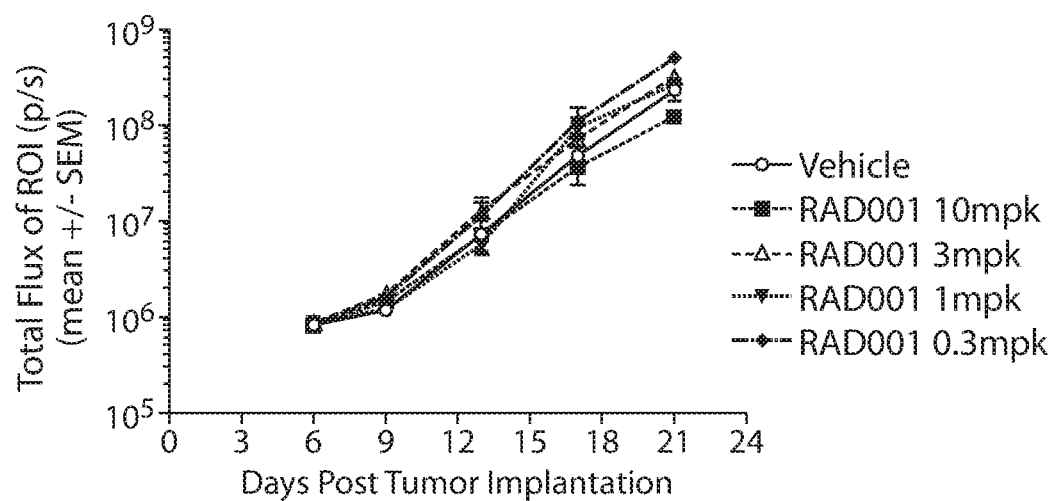
FIG. 46. Graph depicting tumor growth measurements of NALM6-luc cells with daily RAD001 dosing at 0.3, 1, 3, and 10 mg/kg (mpk) or vehicle dosing. Circles denote the vehicle; squares denote the 10 mg/kg dose of RAD001; triangles denote the 3 mg/kg dose of RAD001, inverted triangles denote the 1 mg/kg dose of RAD001; and diamonds denote the 0.3 mg/kg dose of RAD001.
Figure 47A:
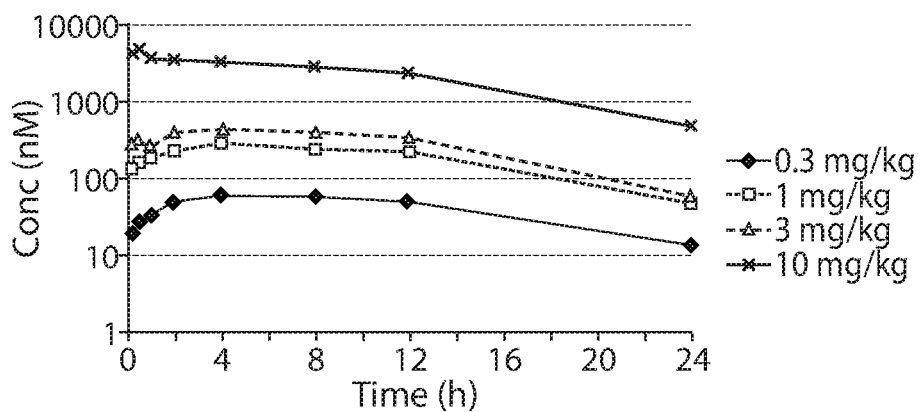
FIGS. 47A and 47B. Graphs show pharmacokinetic curves showing the amount of RAD001 in the blood of NSG mice with NALM6 tumors.
Figure 47B:
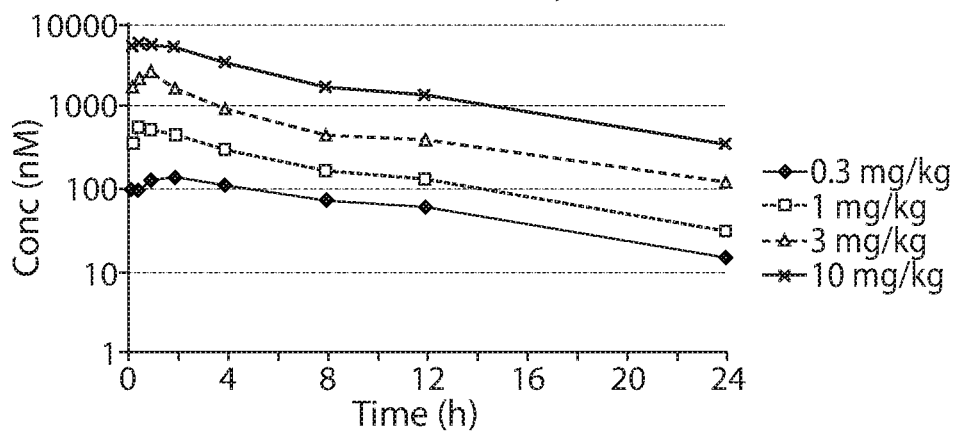

The expansion and pharmacokinetics of RAD001 was tested in NSG mice with NALM6-luc tumors. Daily oral dosing of RAD001 alone did not have an impact on the growth of NALM6-luc tumors (FIG. 46). The pharmacokinetic analysis of RAD001 shows that it is fairly stable in the blood of tumor bearing mice (FIGS. 47A and 47B). Both the day 0 and day 14 PK analyses show that the RAD001 concentrations in the blood is above 10 nm even 24 hours after dosing at the lowest dose tested (0.3 mg/kg).

Based on these doses, huCAR19 CAR T cells were dosed with and without RAD001 to determine the proliferative ability of these cells. The highest dose used was 3 mg/kg based on the levels of RAD001 in the blood 24 hours after dosing. As the concentration of RAD001 was above 10 nM 24 hours after the final dose of RAD001, several lower doses of RAD001 were used in the in vivo study with CAR T cells. The CAR T cells were dosed IV one day prior to the start of the daily oral RAD001 dosing. Mice were monitored via FACS for T cell expansion.

Figure 48A:
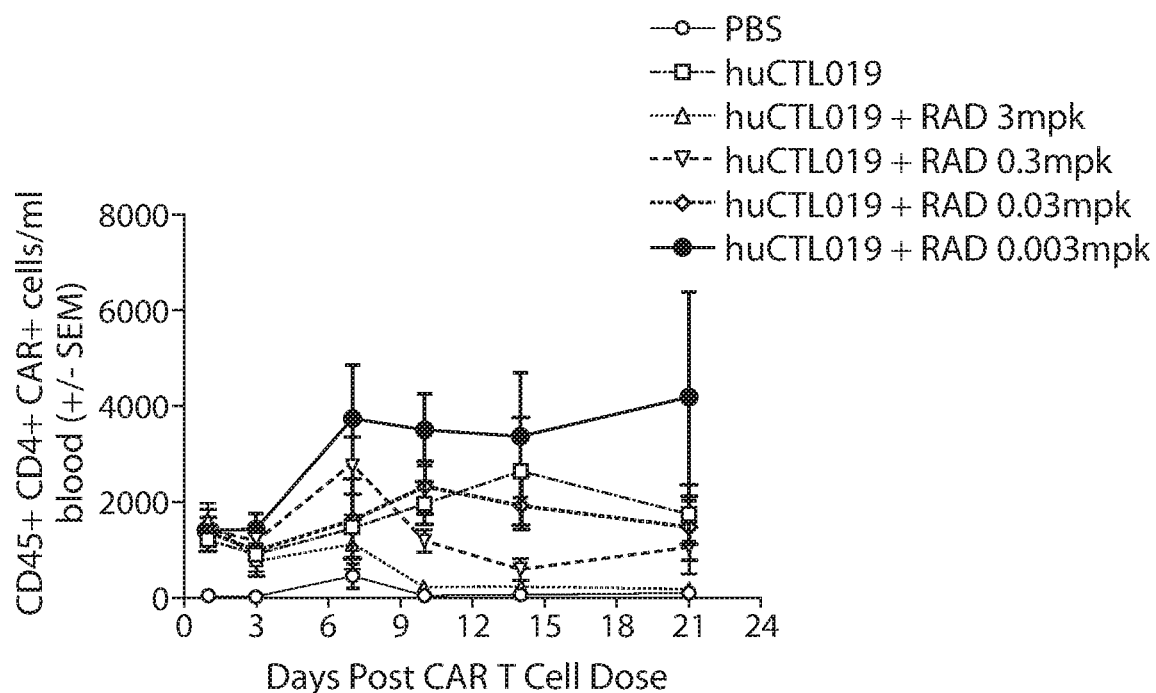
FIGS. 48A and 48B. Graphs shows in vivo proliferation of humanized CD19 CART cells with and without RAD001 dosing. Low doses of RAD001 (0.003 mg/kg) daily lead to an enhancement in CAR T cell proliferation, above the normal level of huCAR19 proliferation.
Figure 48B:
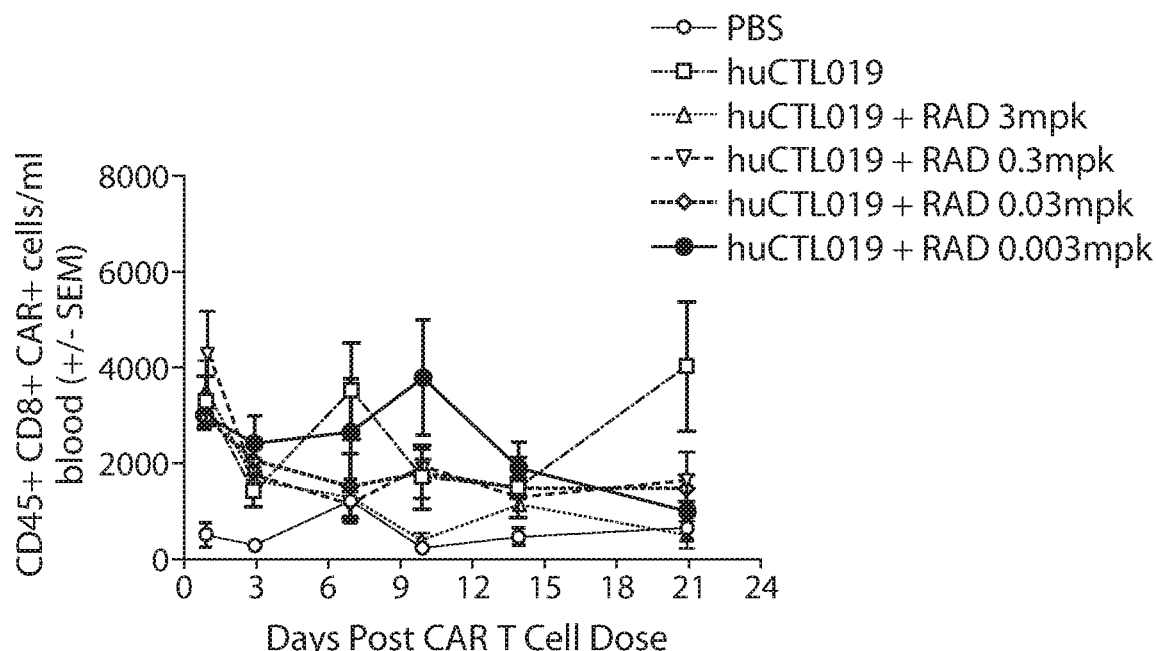

The lowest doses of RAD001 show an enhanced proliferation of the CAR T cells (FIG. 48A). This enhanced proliferation is more evident and prolonged with the CD4$^+$ CAR T cells (FIG. 48A) than the CD8$^+$ CAR T cells (FIG. 48B). However, with the CD8$^+$ CAR T cells, enhanced proliferation can be seen at early time points following the CAR T cell dose. In embodiments, a RNA CART cell can also be used in combination with checkpoint inhibitors.

Without further description, it is believed that one of ordinary skill in the art can, using the preceding description and the following illustrative examples, make and utilize the compounds of the present disclosure and practice the claimed methods. The following working examples specifically point out various aspects of the present disclosure, and are not to be construed as limiting in any way the remainder of the disclosure.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:
1. An isolated nucleic acid, comprising:
   (a) a nucleic acid sequence encoding a polypeptide that enhances the immune response against a target cell, or a cancer cell, and wherein the polypeptide is a first chimeric antigen receptor (first CAR) that binds a first antigen, wherein the first CAR comprises an antigen binding domain, a transmembrane domain, and an intracellular signaling domain;
   (b) a first activation-conditional control region operatively linked to (a), wherein the activation-conditional control region comprises a nucleic acid sequence that induces expression of (a) upon immune effector cell activation, and wherein the nucleic acid sequence comprises a promoter chosen from a nuclear factor of activated T cells (NFAT) promoter, an NF-kB promoter, an IL-2 promoter, or an IL-2 receptor (IL-2R) promoter;
   (c) a nucleic acid sequence encoding a second CAR that binds a second antigen comprising an antigen binding domain, a transmembrane domain, and an intracellular signaling domain; and
   (d) a second control region operatively linked to (c), wherein the second control region is other than an activation-conditional control region, and wherein, the second control region comprises a constitutive control region.

2. The isolated nucleic acid of claim 1, wherein the second control region comprises an elongation factor 1 alpha (EF1a) control region.

3. The isolated nucleic acid of claim 1, wherein the antigen binding domain of the first CAR and/or the second CAR binds to mesothelin, EGFRvIII, TSHR, CD19, CD123, CD22, CD30, CD171, CS-1, CLL-1, CD33, GD2, GD3, BCMA, Tn Ag, prostate specific membrane antigen (PSMA), ROR1, FLT3, FAP, TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha (FRa), ERBB2 (Her2/neu), MUC1, epidermal growth factor receptor (EGFR), NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

4. The isolated nucleic acid of claim 3, wherein the antigen binding domain of the first and/or second CAR binds to mesothelin, Folate receptor alpha (FRa), or ErbB2 (Her2/neu).

5. The isolated nucleic acid of claim 4, wherein the antigen binding domain of the first or second CAR binds to mesothelin and comprises:
   (i) a light chain complementarity determining region 1 (LC CDR1), a light chain complementarity determining region 2 (LC CDR2), and a light chain complementarity determining region 3 (LC CDR3) of a mesothelin binding domain in Table 2; and a heavy chain complementarity determining region 1 (HC CDR1), a heavy chain complementarity determining region 2 (HC CDR2), and a heavy chain complementarity determining region 3 (HC CDR3) of a mesothelin binding domain in Table 2;
   (ii) the LC CDR1, LC CDR2, and LC CDR3 of the LC CDR sequences listed in Table 4; and the HC CDR1, HC CDR2, and HC CDR3 of the HC CDR sequences listed in Table 3;
   (iii) SEQ ID NO: 51, SEQ ID NO: 57, SEQ ID NO: 70, SEQ ID NO: 46, SEQ ID NO: 47, SEQ ID NO: 48, SEQ ID NO: 49, SEQ ID NO: 50, SEQ ID NO: 52, SEQ ID NO: 53, SEQ ID NO: 54, SEQ ID NO: 55, SEQ ID NO: 56, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, or SEQ ID NO: 69; or
   (iv) an amino acid sequence with at least 95-99% homology to SEQ ID NO: 51, SEQ ID NO: 57, SEQ ID NO: 70, SEQ ID NO: 46, SEQ ID NO: 47, SEQ ID NO: 48, SEQ ID NO: 49, SEQ ID NO: 50, SEQ ID NO: 52, SEQ ID NO: 53, SEQ ID NO: 54, SEQ ID NO: 55, SEQ ID NO: 56, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, or SEQ ID NO: 69.

6. The isolated nucleic acid of claim 1, wherein:
   the first antigen and the second antigen are co-expressed on the cancer cell;
   the first antigen is expressed on a first population of cancer cells and the second antigen is expressed on a second population of cancer cells; or the second antigen is expressed on the cancer cell and the first antigen is not expressed on the cancer cell.

7. The isolated nucleic acid of claim 1, wherein the antigen binding domain of the first CAR and/or the second CAR binds to Folate receptor alpha (FRa), ERBB2 (Her2/neu), EphA2, IL-13Ra2, epidermal growth factor receptor (EGFR), or Mesothelin.

8. The isolated nucleic acid of claim 1, wherein:
   the second antigen is EGFRvIII; and the first antigen is EGFR or a variant thereof; EphA2; ErbB2 (Her2/neu); or IL-13Ra2; or
   the second antigen is mesothelin; and the first antigen is FRa or ErbB2 (Her2/neu).

9. The isolated nucleic acid of claim 1, wherein the antigen binding domain of the first CAR binds to FRa and comprises:
   (i) a light chain complementarity determining region 1 (LC CDR1), a light chain complementarity determining region 2 (LC CDR2), and a light chain complementarity determining region 3 (LC CDR3) of a FRa binding domain in SEQ ID NO: 96 or SEQ ID NO: 98; and a heavy chain complementarity determining region 1 (HC CDR1), a heavy chain complementarity determining region 2 (HC CDR2), and a heavy chain complementarity determining region 3 (HC CDR3) of a FRa binding domain in SEQ ID NO: 96 or SEQ ID NO: 98

(ii) the amino acid sequence of SEQ ID NO: 96 or SEQ ID NO: 98; or (iii) an amino acid sequence with at least 95% identity SEQ ID NO: 96 or SEQ ID NO: 98.

10. The isolated nucleic acid of claim 1, wherein the transmembrane domain of the first and/or second CAR comprises:

(i) a transmembrane domain of: alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 or CD154;

(ii) a transmembrane domain of SEQ ID NO: 12; or (iii) a transmembrane domain that comprises an amino acid sequence with at least 95% identity to SEQ ID NO:12.

11. The isolated nucleic acid of claim 1, wherein the antigen binding domain of the first and/or second CAR is connected to the transmembrane domain of the corresponding CAR by a hinge region, the hinge region comprising SEQ ID NO:4 or an amino acid sequence with at least 95% identity to SEQ ID NO:4.

12. The isolated nucleic acid of claim 1, wherein the intracellular signaling domain of the first and/or second CAR comprises a costimulatory signaling domain comprising:

(i) a signaling domain obtained from a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, ICAM-1, LFA-1 (CD11a/CD18), 4-1BB (CD137), B7-H3, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, or CD19a;

(ii) SEQ ID NO:14; or (iii) an amino acid sequence with at least 95% identity to SEQ ID NO:14.

13. The isolated nucleic acid of claim 1, wherein the intracellular signaling domain comprises:

(i) a signaling domain of 4-1BB and/or signaling domain of CD3 zeta;

(ii) SEQ ID NO: 14 and/or SEQ ID NO:18 or SEQ ID NO:20;

(iii) an amino acid sequence with at least 95% identity to SEQ ID NO:14 and/or SEQ ID NO:18 or SEQ ID NO:20; or (iv) SEQ ID NO:14, and SEQ ID NO:18 or SEQ ID NO:20, wherein the amino acid sequences comprising the intracellular signaling domain are expressed in the same frame and as a single polypeptide chain.

14. The isolated nucleic acid of claim 1, wherein the first CAR comprises:

(i) an amino acid sequence in SEQ ID NO: 150, or SEQ ID NO: 152;

(ii) an amino acid sequence with 95-99% identity to an amino acid sequence in SEQ ID NO: 150, or SEQ ID NO: 152;

(iii) an amino acid sequence encoded by a nucleic acid sequence in, SEQ ID NO: 151, or SEQ ID NO: 153; or (iv) an amino acid sequence encoded by a nucleic acid sequence with at least 95% identity to a nucleic acid sequence in SEQ ID NO: 151, or SEQ ID NO: 153.

15. The isolated nucleic acid of claim 1, wherein the second CAR comprises:

(i) SEQ ID NO: 104, SEQ ID NO: 110, SEQ ID NO: 124, SEQ ID NO: 100, SEQ ID NO: 101, SEQ ID NO: 102, SEQ ID NO: 103, SEQ ID NO: 105, SEQ ID NO: 106, SEQ ID NO: 107, SEQ ID NO: 108, SEQ ID NO: 109, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123;

(ii) an amino acid sequence at least 95% identity to SEQ ID NO: 104, SEQ ID NO: 110, SEQ ID NO: 124, SEQ ID NO: 100, SEQ ID NO: 101, SEQ ID NO: 102, SEQ ID NO: 103, SEQ ID NO: 105, SEQ ID NO: 106, SEQ ID NO: 107, SEQ ID NO: 108, SEQ ID NO: 109, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123;

(iii) an amino acid sequence encoded by SEQ ID NO: 129, SEQ ID NO: 135, SEQ ID NO: 149, SEQ ID NO: 125, SEQ ID NO: 126, SEQ ID NO: 127, SEQ ID NO: 128, SEQ ID NO: 130, SEQ ID NO: 131, SEQ ID NO: 132, SEQ ID NO: 133, SEQ ID NO: 134, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, or SEQ ID NO: 148; or (iv) an amino acid sequence encoded by a nucleic acid sequence with at least 95% identity to SEQ ID NO: 129, SEQ ID NO: 135, SEQ ID NO: 149, SEQ ID NO: 125, SEQ ID NO: 126, SEQ ID NO: 127, SEQ ID NO: 128, SEQ ID NO: 130, SEQ ID NO: 131, SEQ ID NO: 132, SEQ ID NO: 133, SEQ ID NO: 134, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, or SEQ ID NO: 148.

16. The isolated nucleic acid of claim 1, further comprising:

(e) a nucleic acid sequence encoding a third CAR; and/or, (f) a second activation-conditional control region operatively linked to (e).

17. The isolated nucleic acid of claim 1, wherein the activation-conditional control region comprises:

(i) one or more NFAT binding sites; or (ii) one or more of GGAAA, GGGACT, or SEQ ID NO: 261.

18. The nucleic acid of claim 1, wherein the second control region is a constitutive control region, wherein the constitutive control region comprises a constitutive promoter, an EF1alpha promoter, or SEQ ID NO: 1.

19. The isolated nucleic acid of claim 1, wherein:
(i) (a) and (b) are disposed on a single nucleic acid molecule, a viral vector, or a lentiviral vector; or (c) and (d) are disposed on a single nucleic acid molecule, a viral vector, or a lentiviral vector;
(ii) (a), (b), (c) and (d) are all disposed on a single nucleic acid molecule, a viral vector, or a lentiviral vector;
(iii) the isolated nucleic acid comprises a bicistronic viral vector or a bicistronic lentiviral vector; or
(iv) (a) is translated as a first RNA, and (c) is translated as a second RNA.

20. The isolated nucleic acid of claim 1, wherein:
(i) (a) is disposed on a first nucleic acid molecule, a first viral vector, or a first lentiviral vector; and (c) is disposed on a second nucleic acid molecule, a second viral vector, or a second lentiviral vector; or
(ii) (a) and (b) are disposed on a first nucleic acid molecule, a first viral vector, or a first lentiviral vector; and (c) and (d) are disposed on a second nucleic acid molecule, a second viral vector, or a second lentiviral vector.

21. A vector system comprising one or more vectors, comprising the isolated nucleic acid of claim 1.

22. A cell, or an immune effector cell, comprising the isolated nucleic acid of claim 1.

23. The cell of claim 22, wherein the cell is a human cell, a T cell, or an NK cell.

24. A method of making a chimeric antigen receptor (CAR) cell, comprising introducing into a cell, the isolated nucleic acid of claim 1, thereby making the CAR cell.

25. The method of claim 24, wherein the cell is a human cell, a T cell or an NK cell.

26. The isolated nucleic acid of claim 4, wherein the mesothelin binding domain comprises a nucleic acid sequence encoding the LC CDR1 of SEQ ID NO: 346, LC CDR2 of SEQ ID NO: 371, or LC CDR3 of SEQ ID NO: 396, and HC CDR1 of SEQ ID NO: 277, HC CDR2 of SEQ ID NO: 296, and HC CDR3 of SEQ ID NO: 321.

27. The isolated nucleic acid of claim 4, wherein the mesothelin binding domain comprises a nucleic acid sequence encoding SEQ ID NO: 51 or an amino acid sequence with at least 95% identity thereto.

28. The isolated nucleic acid of claim 1, wherein the second CAR comprises a nucleic acid sequence encoding SEQ ID NO: 104 or an amino acid sequence with at least 95% identity thereto.

29. An isolated nucleic acid, comprising:
(a) a nucleic acid sequence encoding a chimeric antigen receptor (first CAR) that binds to a first antigen comprising an antigen binding domain, a transmembrane domain, and an intracellular signaling domain;
(b) a first activation-conditional control region operatively linked to (a), wherein the activation-conditional control region comprises a nucleic acid sequence that induces expression of (a) upon immune effector cell activation, and wherein the nucleic acid sequence comprises a promoter chosen from a nuclear factor of activated T cells (NFAT) promoter, an NF-kB promoter, an IL-2 promoter, or an IL-2 receptor (IL-2R) promoter;
(c) a nucleic acid sequence encoding a second CAR that binds to a second antigen comprising an antigen binding domain, a transmembrane domain, and an intracellular signaling domain; and
(d) a second control region operatively linked to (c), wherein the second control region is other than an activation-conditional control region, and comprises a constitutive control region.

30. The isolated nucleic acid of claim 1, wherein the activation-conditional control region comprises SEQ ID NO: 262.

31. The isolated nucleic acid of claim 1, wherein the intracellular domain of the first CAR comprises a first costimulatory signaling domain and/or a first primary signaling domain; and wherein the intracellular domain of the second CAR comprises a second costimulatory domain and/or a second primary signaling domain.

32. The isolated nucleic acid of claim 29, wherein the intracellular domain of the first CAR comprises a first costimulatory signaling domain and/or a first primary signaling domain; and wherein the intracellular domain of the second CAR comprises a second costimulatory domain and/or a second primary signaling domain.

33. An isolated nucleic acid, comprising:
(a) a nucleic acid sequence encoding a polypeptide that enhances the immune response against a target cell, or a cancer cell, and wherein the polypeptide is a first chimeric antigen receptor (first CAR) that binds a first antigen, wherein the first CAR comprises an antigen binding domain, a transmembrane domain, and an intracellular signaling domain;
(b) a first activation-conditional control region operatively linked to (a), wherein the activation-conditional control region comprises one or more NFAT binding sites and a nucleic acid sequence that induces expression of (a) upon immune effector cell activation;
(c) a nucleic acid sequence encoding a second CAR that binds a second antigen comprising an antigen binding domain, a transmembrane domain, and an intracellular signaling domain; and
(d) a second control region operatively linked to (c), wherein the second control region is other than an activation-conditional control region, and wherein, the second control region comprises a constitutive control region.

34. The isolated nucleic acid of claim 33, wherein the activation-conditional control region comprises one or more of GGAAA, GGGACT, or SEQ ID NO: 261.

35. An isolated nucleic acid, comprising:
(a) a nucleic acid sequence encoding a polypeptide that enhances the immune response against a target cell, or a cancer cell, and wherein the polypeptide is a first chimeric antigen receptor (first CAR) that binds a first antigen, wherein the first CAR comprises an antigen binding domain, a transmembrane domain, and an intracellular signaling domain;
(b) a first activation-conditional control region operatively linked to (a), wherein the activation-conditional control region comprises the nucleic acid sequence of SEQ ID NO: 262 that induces expression of (a) upon immune effector cell activation;
(c) a nucleic acid sequence encoding a second CAR that binds a second antigen comprising an antigen binding domain, a transmembrane domain, and an intracellular signaling domain; and
(d) a second control region operatively linked to (c), wherein the second control region is other than an activation-conditional control region, and wherein, the second control region comprises a constitutive control region.

* * * * *

UNITED STATES PATENT AND TRADEMARK OFFICE
CERTIFICATE OF CORRECTION

Page 1 of 1

PATENT NO.       : 11,161,907 B2
APPLICATION NO.  : 15/548202
DATED            : November 2, 2021
INVENTOR(S)      : June et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Twenty-fourth Day of January, 2023

Katherine Kelly Vidal
*Director of the United States Patent and Trademark Office*